(12) United States Patent
Chen et al.

(10) Patent No.: US 12,116,619 B2
(45) Date of Patent: Oct. 15, 2024

(54) CRISPR MEDIATED IN VIVO MODELING AND GENETIC SCREENING OF TUMOR GROWTH AND METASTASIS

(71) Applicants: The Broad Institute, Inc., Cambridge, MA (US); Massachusetts Institute of Technology, Cambridge, MA (US)

(72) Inventors: Sidi Chen, Milford, CT (US); Randall Jeffrey Platt, Basel (CH); Neville Espi Sanjana, New York, NY (US); Phillip A. Sharp, Newton, MA (US); Feng Zhang, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/640,103

(22) Filed: Jun. 30, 2017

(65) Prior Publication Data

US 2018/0112255 A1    Apr. 26, 2018

Related U.S. Application Data

(63) Continuation-in-part of application No. PCT/US2015/000194, filed on Dec. 23, 2015.

(60) Provisional application No. 62/098,285, filed on Dec. 30, 2014.

(51) Int. Cl.
| | | |
|---|---|---|
| C12Q 1/6809 | (2018.01) | |
| C12N 9/22 | (2006.01) | |
| C12N 9/96 | (2006.01) | |
| C12N 15/11 | (2006.01) | |
| C12Q 1/6886 | (2018.01) | |

(52) U.S. Cl.
CPC .......... *C12Q 1/6809* (2013.01); *C12N 9/22* (2013.01); *C12N 9/96* (2013.01); *C12N 15/11* (2013.01); *C12Q 1/6886* (2013.01); *C12N 2310/20* (2017.05); *C12N 2320/12* (2013.01); *C12Q 2600/118* (2013.01); *C12Q 2600/136* (2013.01)

(58) Field of Classification Search
None
See application file for complete search history.

(56) References Cited

U.S. PATENT DOCUMENTS

| | | | |
|---|---|---|---|
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 8,999,641 B2 | 4/2015 | Zhang et al. | |
| 11,124,796 B2 * | 9/2021 | Sharp | C12N 15/85 |
| 2011/0265198 A1 | 10/2011 | Gregory et al. | |
| 2012/0017290 A1 | 1/2012 | Cui et al. | |
| 2013/0236946 A1 | 9/2013 | Gouble | |
| 2014/0170753 A1 | 6/2014 | Zhang | |
| 2014/0179006 A1 | 6/2014 | Zhang | |
| 2014/0179770 A1 | 6/2014 | Zhang et al. | |
| 2014/0186843 A1 | 7/2014 | Zhang et al. | |
| 2014/0186919 A1 | 7/2014 | Zhang et al. | |
| 2014/0186958 A1 | 7/2014 | Zhang et al. | |
| 2014/0189896 A1 | 7/2014 | Zhang et al. | |
| 2014/0227787 A1 | 8/2014 | Zhang | |
| 2014/0234972 A1 | 8/2014 | Zhang | |
| 2014/0242664 A1 | 8/2014 | Zhang et al. | |
| 2014/0242699 A1 | 8/2014 | Zhang | |
| 2014/0242700 A1 | 8/2014 | Zhang et al. | |

(Continued)

FOREIGN PATENT DOCUMENTS

| | | |
|---|---|---|
| EP | 2771468 B1 | 2/2015 |
| EP | 2784162 B1 | 4/2015 |

(Continued)

OTHER PUBLICATIONS

Sanjana et al., "Genome-Scale CRISPR-Cas9 Screening in Human Cells" 22(Supplement 1) Molecular Therapy S123-S124 Abstract 321 (May 2014).*

(Continued)

*Primary Examiner* — Nancy J Leith

(74) *Attorney, Agent, or Firm* — F. Brent Nix, Esq.; Johnson, Marcou, Isaacs & Nix, LLC; Christopher D. Southgate, Esq.

(57) ABSTRACT

The present invention relates to in vivo methods for modeling tumor formation and/or tumor evolution comprising the use of eukaryotic cells in which one or more genetic target locus has been altered by the CRISPR/Cas system, and which cells are transplanted in non-human eukaryote as a model system for tumor formation and tumor evolution. In particular in vivo genetic screening methods for identifying genes involved in tumorigenesis and metastasis are disclosed. The invention further relates to kits and components for practicing the methods, as well as materials obtainable by the methods, in particular tumor and metastasis samples and cells or cell lines derived therefrom. The invention also relates to diagnostic and therapeutic methods derived from the information obtained in the modeling methods.

18 Claims, 132 Drawing Sheets

(3 of 132 Drawing Sheet(s) Filed in Color)

Specification includes a Sequence Listing.

(56) References Cited

U.S. PATENT DOCUMENTS

| | | |
|---|---|---|
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0031134 A1 | 1/2015 | Zhang et al. |
| 2015/0184139 A1 | 7/2015 | Zhang et al. |

FOREIGN PATENT DOCUMENTS

| | | |
|---|---|---|
| EP | 2764103 B1 | 8/2015 |
| WO | 2014018423 A2 | 1/2014 |
| WO | 2014093595 A1 | 6/2014 |
| WO | 2014093622 A2 | 6/2014 |
| WO | 2014093635 A1 | 6/2014 |
| WO | 2014093655 A2 | 6/2014 |
| WO | 2014093661 A2 | 6/2014 |
| WO | 2014093694 A1 | 6/2014 |
| WO | 2014093701 A1 | 6/2014 |
| WO | 2014093709 A1 | 6/2014 |
| WO | 2014093712 A1 | 6/2014 |
| WO | 2014093718 A1 | 6/2014 |
| WO | 2014/204723 A1 | 12/2014 |
| WO | 2014/204727 A1 | 12/2014 |
| WO | 2014204724 A1 | 12/2014 |
| WO | 2014204725 A1 | 12/2014 |
| WO | 2014204726 A1 | 12/2014 |
| WO | 2014204728 A1 | 12/2014 |
| WO | 2014204729 A1 | 12/2014 |
| WO | 2015065964 A1 | 5/2015 |
| WO | 2015089351 A1 | 6/2015 |
| WO | 2015089354 A1 | 6/2015 |
| WO | 2015089364 A9 | 6/2015 |
| WO | 2015089419 A2 | 6/2015 |
| WO | 2015089427 A1 | 6/2015 |
| WO | 2015089462 A1 | 6/2015 |
| WO | 2015089465 A1 | 6/2015 |
| WO | 2015089473 A1 | 6/2015 |
| WO | 2015089486 A2 | 6/2015 |
| WO | 2016028682 A1 | 2/2016 |
| WO | 2016049163 A2 | 3/2016 |
| WO | 2016049258 A2 | 3/2016 |

OTHER PUBLICATIONS

Sorek et al., "CRISPR-Mediated Adaptive Immune Systems in Bacteria and Archaea" 82 Annual Review of Biochemistry 237-266 (2013).*

Koonin et al., "Diversity, classification and evolution of CRISPR-Cas systems" 37 Current Opinion in Microbiology 67-78 (2017).*

Yoo et al., "Mutational analysis of tumour suprressor gene NF2 in common solid cancers and acute leukaemias" 44(1) Pathology 29-32 (Year: 2012).*

Marsit et al., "PTEN expression in non-small-cell lung cancer: evaluating its relation to tumor characteristics, allelic loss, and epigenetic alteration" 36 Human Pathology 768-776 (Year: 2005).*

Zhang et al., "Comparison of the inhibitory effects of three transcriptional variants of CDKN2A in human lung cancer cell line A549" 29 Journal of Experimental & Clinical Cancer Research 74 1-8 (Year: 2010).*

Alloush et al. "TRIM Proteins in Therapeutic Membrane Repair of Muscular Dystrophy" 70(7) JAMA Neurology 928-931 (Year: 2013).*

Cheng et al., "MiR-152 suppresses the proliferation and invasion of NSCLC cells by inhibiting FGF2" 46 (Experimental & Molecular Medicine e112 1-9 (Year: 2014).*

Wang et al., "Cell-Free MicroRNA Expression Profiles in Malignant Effusion Associated with Patient Survival in Non-Small Cell Lung Cancer" 7(8) PLoS ONE e43268 1-7 (Year: 2012).*

T. Wang, et al., Genetic Screens in Human Cells Using the CRISPR-Cas9 System, Science (Dec. 12, 2013) vol. 343, No. 6166, p. 80-84.

O. Shalem, et al., Genome-Scale CRISPR-Cas9 Knockout Screening in Human Cells, Science (Dec. 12, 2013) vol. 343, No. 6166, p. 84-87.

Platt, Randall J., et al., CRISPR-Cas9 Knockin Mice for Genome Editing and Cancer Modeling, Cell, Cell Press US (Sep. 25, 2014) vol. 159, No. 2, p. 440-455.

Wen, Xue, et al., CRISPR-Mediated Direct Mutation of Cancer Genes in the Mouse Liver, Nature (Aug. 6, 2014) vol. 514, No. 7522, p. 380-384.

Chen, Sidi, et al., Genome-Wide CRISPR Screen in a Mouse Model of Tumor Growth and Metastasis, Cell (Mar. 12, 2015) vol. 160, No. 6, p. 1246-1260.

Cong, Le et al., "Multiplex Genome Engineering Using CRISPR/Cas Systems", Science, pp. 819-823, Feb. 15, 2013.

Jiang, Wenyan et al., "CRISPR-assisted editing of bacterial genomes", Nat Biotechnology, vol. 31, No. 3, pp. 233-239, Mar. 2013.

Wang, Haoyi et al., "One-Step Generation of Mice Carrying Mutations in Multiple Genes by CRISPR/Cas-Mediated Genome Engineering", Cell, vol. 153, pp. 910-918, May 9, 2013.

Konermann, Silvana et al., "Optical control of mammalian endogenous transcription and epigenetic states", Nature, vol. 500, pp. 472-476, Aug. 22, 2013.

Ran, F.A. et al., "Double nicking by RNA-guided CRISPR Cas9 for enhanced genome editing specificity", Cell, vol. 154, No. 6, pp. 1-18, Available in PMC: Sep. 12, 2014.

Ran, F.A. et al., "Genome engineering using the CRISPR-Cas9 system", Nature Protocos, vol. 8, No. 11, pp. 2281-2308, 2013.

Hsu, P.D. et al., "DNA targeting specificity of rNA-guided Cas9 nucleases", Nature Biotechnology Letters, vol. 31, No. 9, pp. 827-834, Sep. 2013.

Hsu, P.D. et al., "Development and Applications of CRISPR-Cas9 for Genome Engineering", Cell, Leading Edge Review, vol. 157, pp. 1262-1278, Jun. 5, 2014.

Koike-Yusa, Hiroko et al., "Genome-wide recessive genetic screening in mammalian cells with a lentiviral CRISPR-guide RNA library", Nature Biotechnology, vol. 32, No. 3, pp. 267-273, Mar. 2014.

Nishimasu, Hiroshi et al., "Crystal Structure of Cas9 in Complex with Guide RNA and Target DNA", Cell, vol. 156, pp. 935-949, Feb. 27, 2014.

Kaina, Bernd et al., "MGMT: Key node in the battle against genotoxicity, carcinogenicity and apoptosis induced by alkylating agents", Science Direct, DNA Repair, vol. 6, pp. 1079-1099, Published online: May 7, 2007.

Wu, Xuebing et al., "Genome-wide binding of the crisPr endonuclease cas9 in mammalian cells", Nature Biotechnology Letters, pp. 1-9, Published online: Apr. 20, 2014.

Jesien-Lewandowicz et al., "High incidence of MGMT promoter methylation in primary glioblastomas without correlation with TP53 gene mutations", Cancer Genetics and Cytogenetics, vol. 188, pp. 77-82, 2009.

Doench, J.G. et al., "Rational design of highly active sgRNAs for CRISPR-Cas9-mediated gene inactivation", Nat Biotechnology, vol. 32, No. 12, pp. 1262-1267, Dec. 2014.

Swiech, Lukasz et al., "In vivo interrogation of gene function in the mammalian brain using CRISPR-Cas9", Nat. Biotechnology, vol. 33, No. 1, pp. 102-106, Jan. 2015.

Konermann, Silvana et al., "Genome-scale transcriptional activation by an engineered CRISPR-Cas9 complex", Nature, vol. 517, No. 7536, pp. 583-588, Jan. 29, 2015.

Zetche, Bernd et al., "A Split Cas9 Architecture for Inducible Genome Editing and Transcription Modulation", Nat. Biotechnology, vol. 33, No. 2, pp. 139-142, Feb. 2015.

Tsai, Shengdar et al., "Dimeric CRISPR RNA-guided FokI nucleases for highly specific genome editing", Nature Biology, vol. 32, No. 6, pp. 569-576, Jun. 2014.

Ran, F.A. et al., "In vivo genome editing using *Staphylococcus aureus* Cas9", Nature, vol. 520, No. 7546, pp. 186-191, Apr. 9, 2015.

Shalem, Ophir et al., "High-throughput functional genomics using CRISPR-Cas9", Nature Reviews, vol. 16, pp. 299-311, May 2015.

Xu, Han et al., "Sequence determinants of improved CRISPR sgRNA design", Genome Research, pp. 1147-1157, 2015.

(56) References Cited

OTHER PUBLICATIONS

Parnas, Oren et al., "A genome-wide CRISPR screen in primary immune cells to dissect regulatory networks", Cell, vol. 162, No. 3, pp. 675-686, Jul. 30, 2015.
Ramanan, Vyas et al., "CRISPR/Cas9 cleavage of viral DNA efficiently suppresses hepatitis B virus", Scientific Reports, pp. 1-9, Published: Jun. 2, 2015.
Nishimasu, Hiroshi et al., "Crystal Structure of *Staphylococcus aureus* Cas9", Cell, vol. 162, pp. 1113-11126, Aug. 27, 2015.
Canver, Matthew et al., "BCL11A enhancer dissection by Cas9-mediated in situ saturating mutagenesis", Nature, vol. 527, No. 7577, pp. 192-197, Nov. 12, 2015.
Zetsche, Bernd et al., "Cpf1 is a single RNA-guided endonuclease of a Class 2 CRISPR-Cas system", Cell, vol. 163, No. 3, pp. 759-771, Oct. 22, 2015.
Shmakov, Sergey et al., "Discovery and Functional Characterization of Diverse Class 2 CRISPR-Cas Systems", Molecular Cell, vol. 60, No. 3, pp. 385-397, Nov. 5, 2015.
Slaymaker, I.M. et al., "Rationally engineered Cas9 nucleases with improved specificity", Science, aad5227, pp. 1-7, Dec. 1, 2015.
Karginov, F.V., "The CRISPR System: Small RNA-Guided Defense in Bacteria and Archaea", Molecular Cell, vol. 37, No. 1, pp. 7-19, Jan. 15, 2010.
Van Embden, J.D., "Genetic Variation and Evolutionary Origin of the Direct Repeat Locus of Mycobacterium tuberculosis Complex Bacteria," Journal of Bacteriology, vol. 182, No. 9, pp. 2393-2401, May 2000.
Jansen, Ruud et al., "Identification of genes that are associated with DNA repeats in prokaryotes", Molecular Microbiology, vol. 43, pp. 1565-1575, Apr. 25, 2002.
Mojica, F.J.M. et al., "Intervening Sequences of Regularly Spaced Prokaryotic Repeats Derive from Foreign Genetic Elements", Journal of Molecular Evolution, vol. 60, Issue 2, pp. 174-182, Feb. 2005.
Chen, Sidi et al., "Global microRNA depletion suppresses tumor angiogenesis", Genes & Development, vol. 28, pp. 1054-1067, Revised version accepted: Apr. 10, 2014.
Cheng, Z. et al., "MiR-152 suppresses the proliferation and invasion of NSCLC cells by inhibiting FGF2", Experimental & Molecular Medicine, vol. 49, No. 9, e112, pp. 1-9, Sep. 2014.
Deltcheva, Elitza et al., "CRISPR RNA maturation by trans-encoded small RNA and host factor RNase III", Nature, vol. 471, No. 7340, pp. 602-607, Mar. 31, 2011.
Gasiunas, G. et al., "Cas9-crRNA ribonucleoprotein complex mediates specific DNA cleavage for adaptive immunity in bacteria", Proceedings of the National Academy of Sciences of the United States of America, pp. E2579-E2586, Sep. 4, 2012.
Gilbert, L.A., "Genome-Scale CRISPR-Mediated Control of Gene Repression and Activation", Cell, vol. 159, pp. 647-661, Oct. 23, 2014.
Hegi, M.E. et al., "MGMT gene silencing and benefit from temozolomide in glioblastoma", The New England Journal of Medicine, vol. 352, Issue 10, pp. 997-1003, Mar. 10, 2005.
Huang, S. et al., "MED12 Controls the Response to Multiple Cancer Drugs through Regulation of TGF-b Receptor Signaling", Cell, vol. 151, pp. 937-950, Nov. 21, 2012.
Iwasaki, M. et al., "BAG3 Regulates Motility and Adhesion of Epithelial Cancer Cells", The Journal of Cancer Research, vol. 67, No. 21, pp. 10252-10259, Nov. 1, 2007.
Jackson, E.L. et al., "Analysis of lung tumor initiation and progression using conditional expression of oncogenic K-ras", Genes & Development, vol. 15, pp. 3243-3248, 2001.
Jinek, Martin et al., "A Programmable Dual-RNA-Guided DNA Endonuclease in Adaptive Bacterial Immunity", Science, vol. 337, pp. 816-821, Aug. 17, 2012.
Kaczmarczyk, G. et al., "Cytological examination of pleural cavity lavage accompanied by the study of gene promoter hypermethylation of p16 and O6-methylguanine-DNA-methyltransferase genes in diagnostics of non-small cell lung cancer metastatic changes into pleura", Contemporary Oncology, vol. 16, No. 4, pp. 322-327, 2012.

Kumar, M.S. et al., "Dicer1 functions as a haploinsufficient tumor suppressor", Genes & Development, vol. 23, pp. 2700-2704, 2009.
Lawrence, M.S. et al., "Discovery and saturation analysis of cancer genes across 21 tumour types", Nature, vol. 505, pp. 495-503, Jan. 23, 2014.
Mali, P. et al., "RNA-Guided Human Genome Engineering via Cas9", Science, vol. 339, pp. 823-826, Feb. 15, 2013.
McClatchey, A.I. et al., "Mice heterozygous for a mutation at the Nf2 tumor suppressor locus develop a range of highly metastatic tumors", Genes & Development, vol. 12, pp. 1121-1133, 1998.
Molenaar, R.J. et al., "The combination of IDH1 mutations and MGMT methylation status predicts survival in glioblastoma better than either IDH1 or MGMT alone", Neuro-Oncology, vol. 16, No. 9, pp. 1263-1273, 2014.
Naba, A. et al., "Extracellular matrix signatures of human mammary carcinoma identify novel metastasis promoters", eLife, Cell biology | Human biology and medicine, e01308, vol. 3, pp. 1-23, Published: Mar. 11, 2014.
Naba, A. et al., "Extracellular matrix signatures of human primary metastatic colon cancers and their metastases to liver", BMC Cancer, vol. 14, No. 518, 2014.
Nguyen, D.X. et al., "WNT/TCF Signaling through LEF1 and HOXB9 Mediates Lung Adenocarcinoma Metastasis", Cell, vol. 138, pp. 51-62, Jul. 10, 2009.
Nissen, L.J. et al., "Angiogenic factors FGF2 and PDGF-BB synergistically promote murine tumor neovascularization and metastasis", The Journal of Clinical Investigation, vol. 117, No. 10, pp. 2766-2777, Oct. 2007.
Pylayeva-Gupta, Y. et al., "RAS oncogenes: weaving a tumorigenic web", Nat Rev Cancer, vol. 11, No. 11, pp. 761-774, Apr. 22, 2013.
Sanjana, N.E. et al., "Improved vectors and genome-wide libraries for CRISPR screening", Nature Methods, vol. 11, No. 8, pp. 783-784, Aug. 2014.
Schiano, C. et al., "Involvement of Mediator complex in malignancy", Biochimica et Biophysica Acta 1845, pp. 66-83, 2014.
Shackelford, D.B. et al., "The LKB1-AMPK pathway: metabolism and growth control in tumour suppression", Nature Reviews Cancer, vol. 9, pp. 563-575, Aug. 2009.
Schramek, D. et al., "Direct in Vivo RNAi Screen Unveils Myosin IIa as a Tumor Suppressor of Squamous Cell Carcinomas", Science, vol. 343, pp. 309-313, Jan. 17, 2014.
Shao, D.D. et al., "KRAS and YAP1 Converge to Regulate EMT and Tumor Survival", Cell, vol. 158, pp. 171-184, Jul. 3, 2014.
Tang, J.T. et al., "MicroRNA 345, a methylation-sensitive microRNA is involved in cell proliferation and invasion in human colorectal cancer", Carcinogenesis, vol. 32, No. 8, pp. 1207-1215, 2011.
Tano, K. et al., "Isolation and structural characterization of acDNA clone encoding the human DNA repair protein for 06-alkylguanine", Proc. Natl.Acad. Sci. USA, vol. 87, pp. 686-690, Jan. 1990.
Teo, A.K. et al., "The Modified Human DNA Repair Enzyme O6-Methylguanine-DNA Methyltransferase Is a Negative Regulator of Estrogen Receptor-Mediated Transcription upon Alkylation DNA Damage", Molecular and Cellular Biology, vol. 21, No. 20, p. 7105-7114, Oct. 2001.
Valiente, M. et al., "Serpins Promote Cancer Cell Survival and Vascular Co-Option in Brain Metastasis", Cell, vol. 156, pp. 1002-10016, Feb. 27, 2014.
Whittaker, S.R. et al., "A Genome-Scale RNA Interference Screen Implicates NF1 Loss in Resistance to RAF Inhibition", Cancer Discovery, vol. 3, American Association for Cancer Research, pp. 350-362, Published Online First Jan. 3, 2013.
Winslow, M.M. et al., "Suppression of Lung Adenocarcinoma Progression by Nkx2-1", Nature, vol. 473, No. 7345, pp. 101-104, 2011.
Ji, Hongbin et al., "LKB1 modulates lung cancer differentiation and metastasis", Nature, vol. 448, pp. 807-810, Aug. 16, 2007.
Johnson, Leisa et al. "Somatic activation of the K-ras oncogene causes early onset lung cancer in mice", Nature, vol. 410, pp. 1111-1116, Apr. 26, 2001.

* cited by examiner

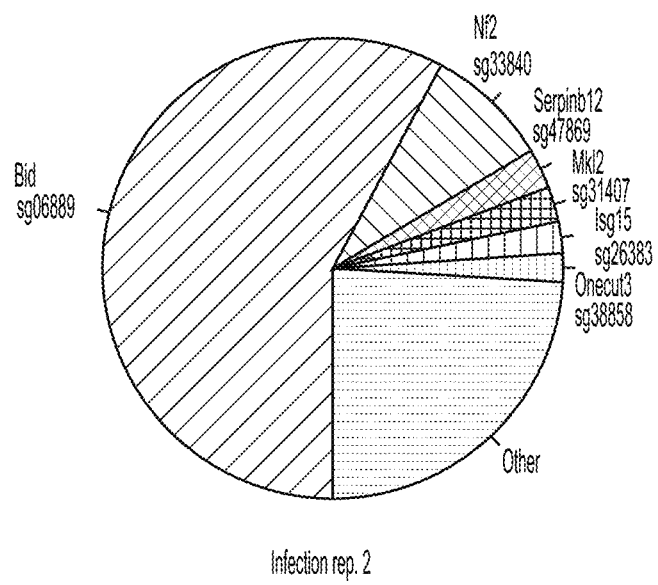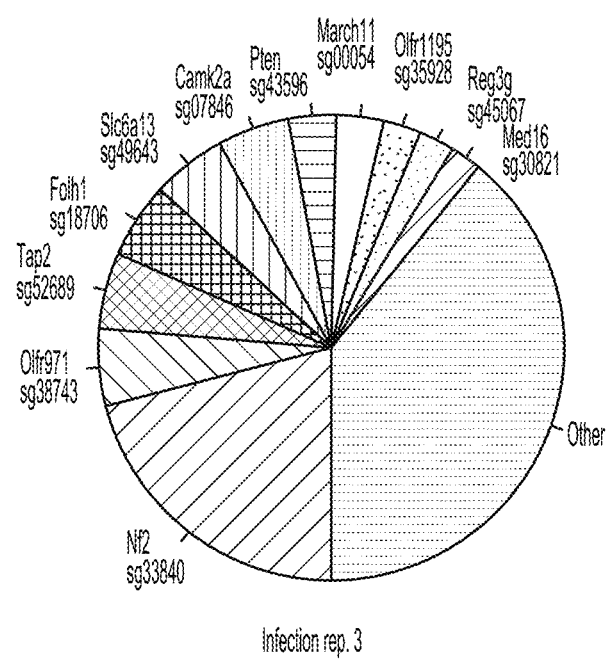
FIG. 3A
CONTINUED

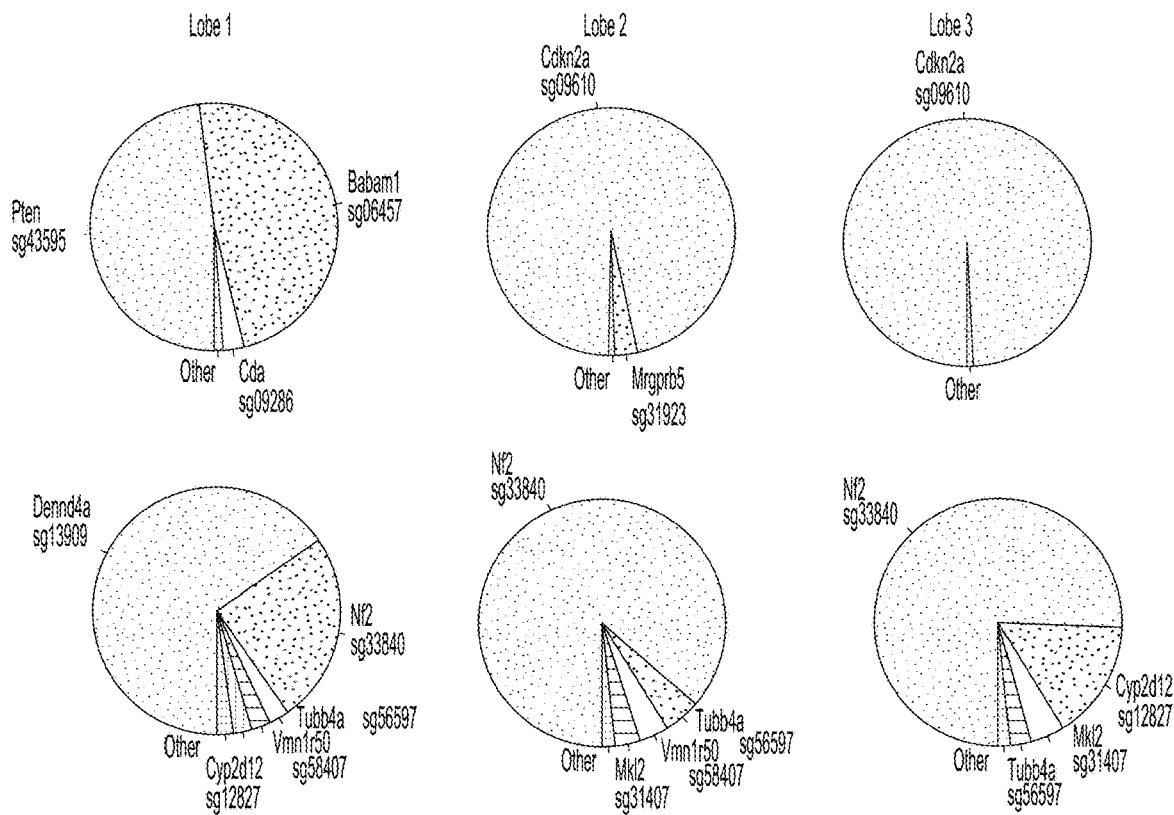
FIG. 4A
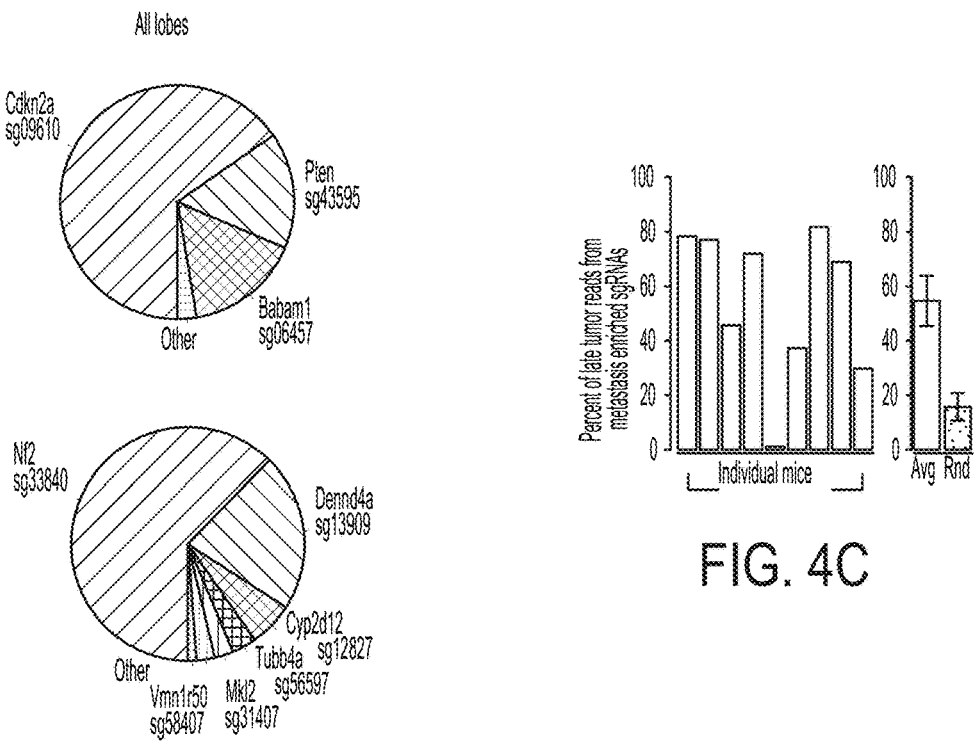
FIG. 4B
FIG. 4C

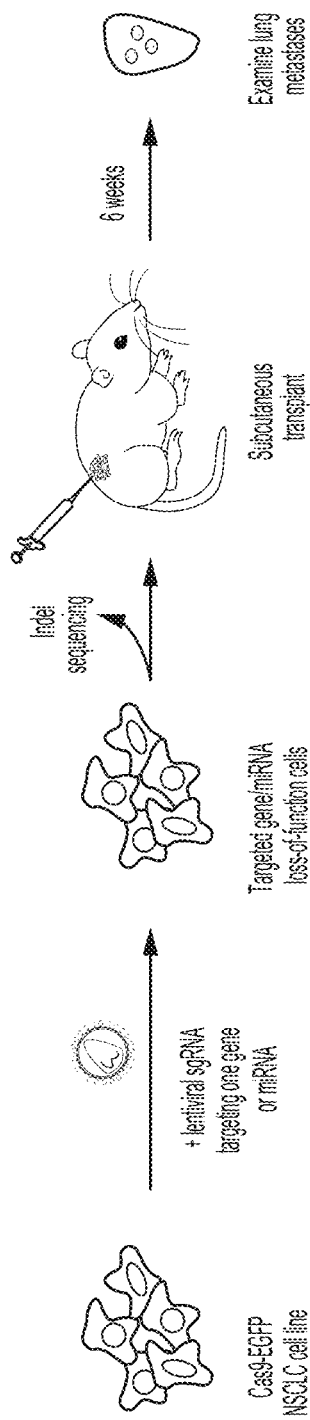
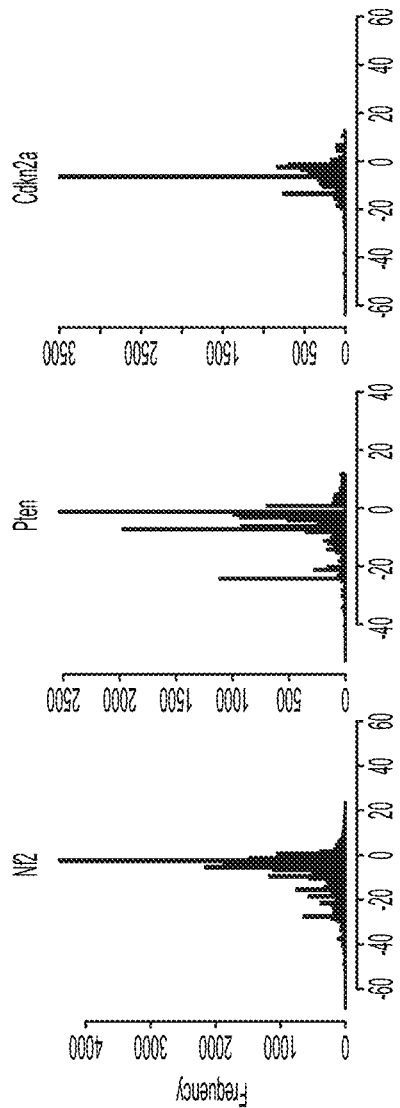
FIG. 5A
FIG. 5B

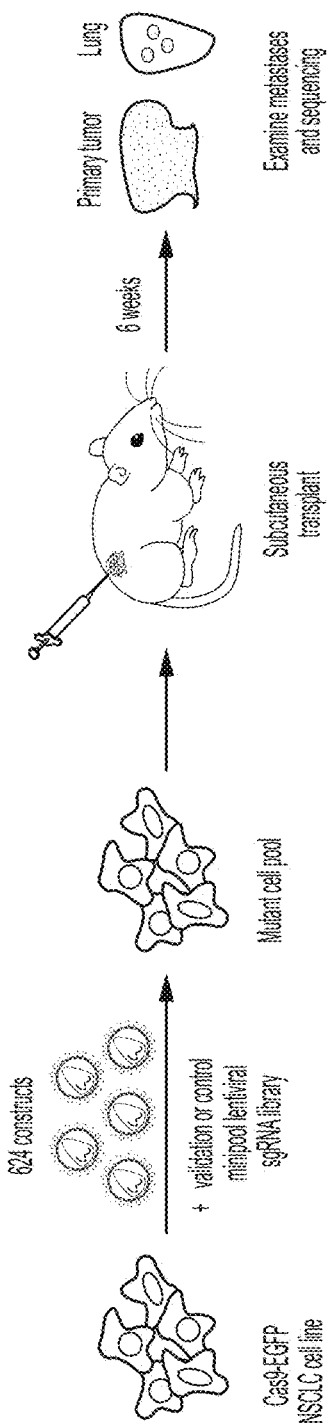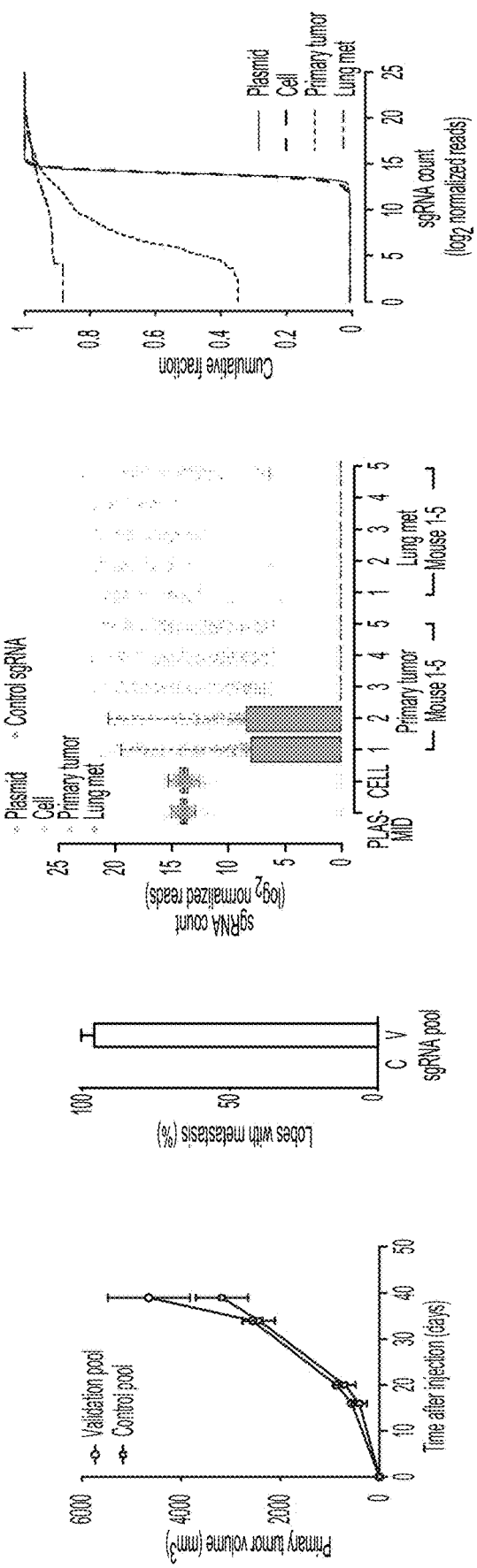
FIG. 6A
FIG. 6B
FIG. 6C
FIG. 6D
FIG. 6E

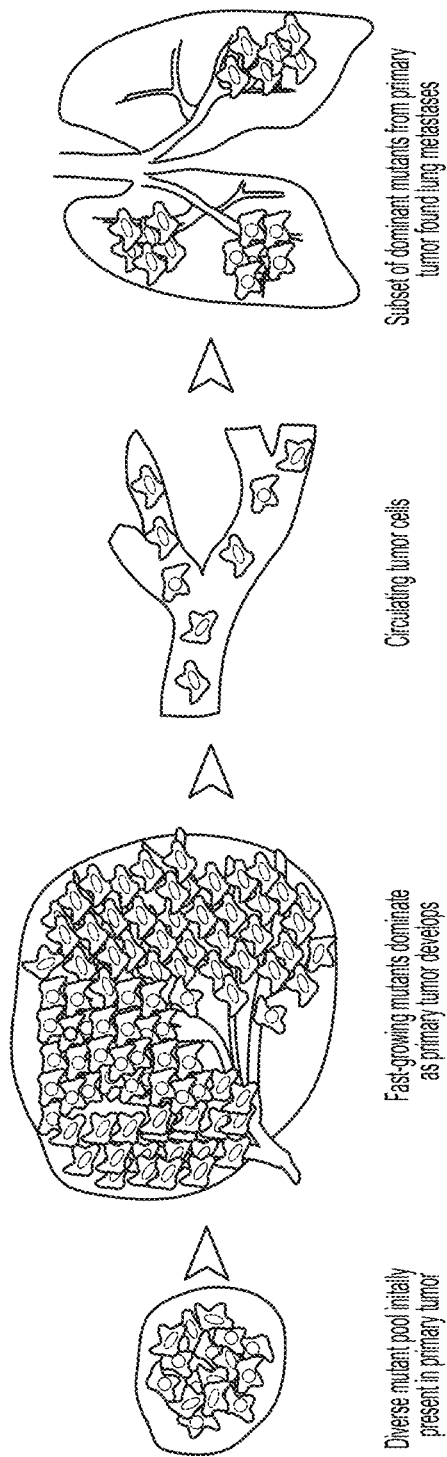
FIG. 7E
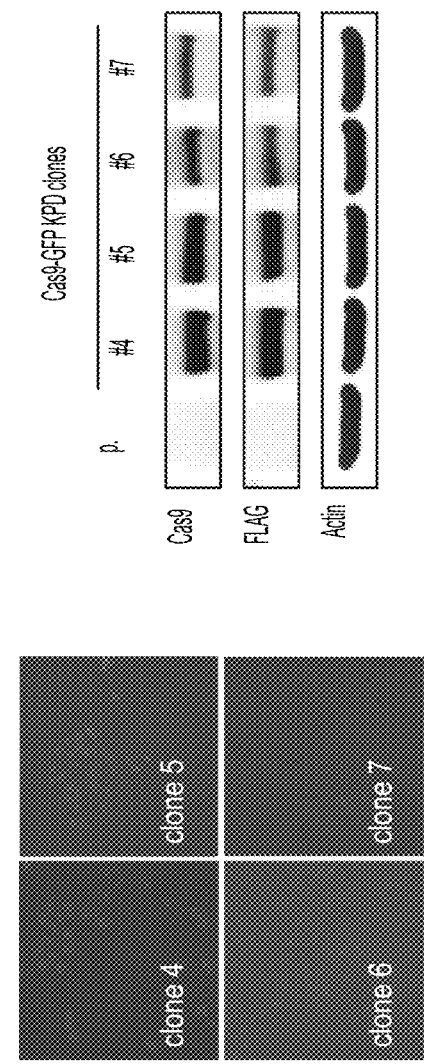
FIG. 8B
FIG. 8A

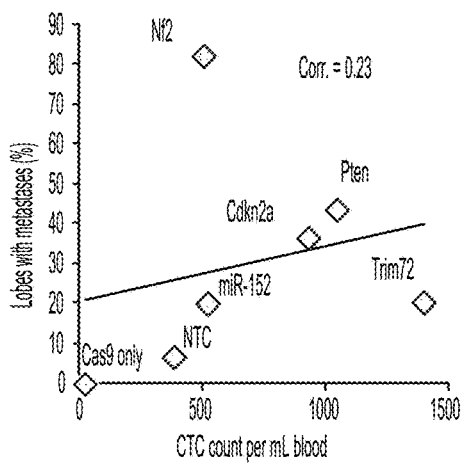
FIG. 13G
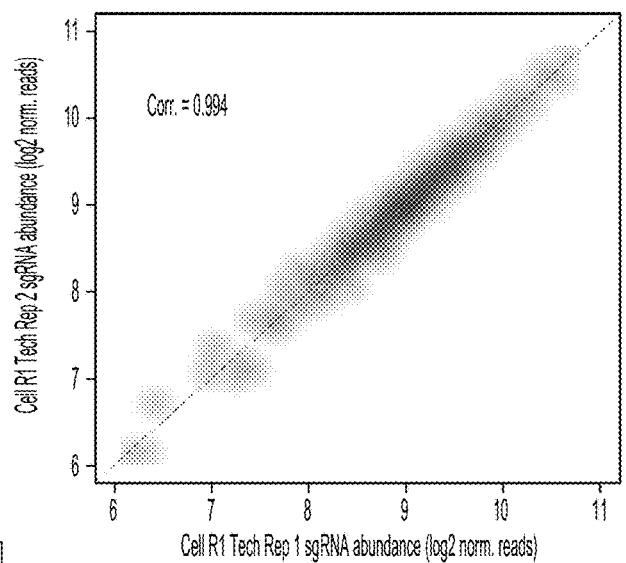
FIG. 14A
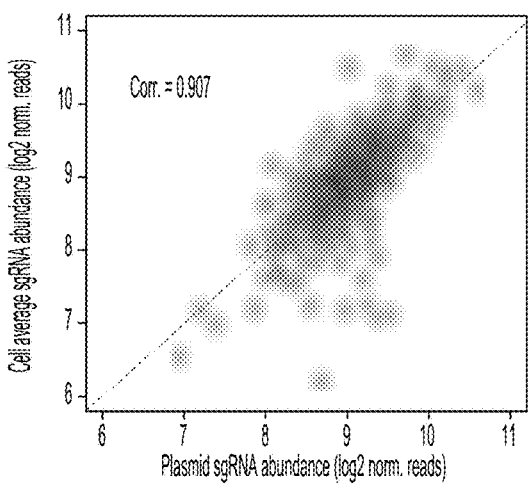
FIG. 14B
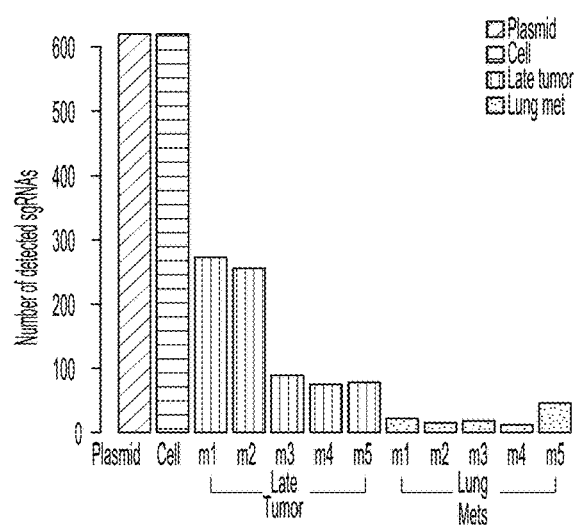
FIG. 14C
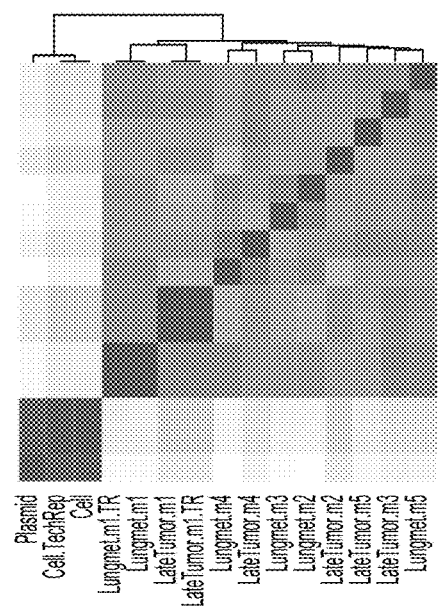
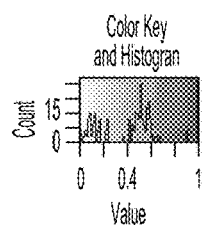
FIG. 14D

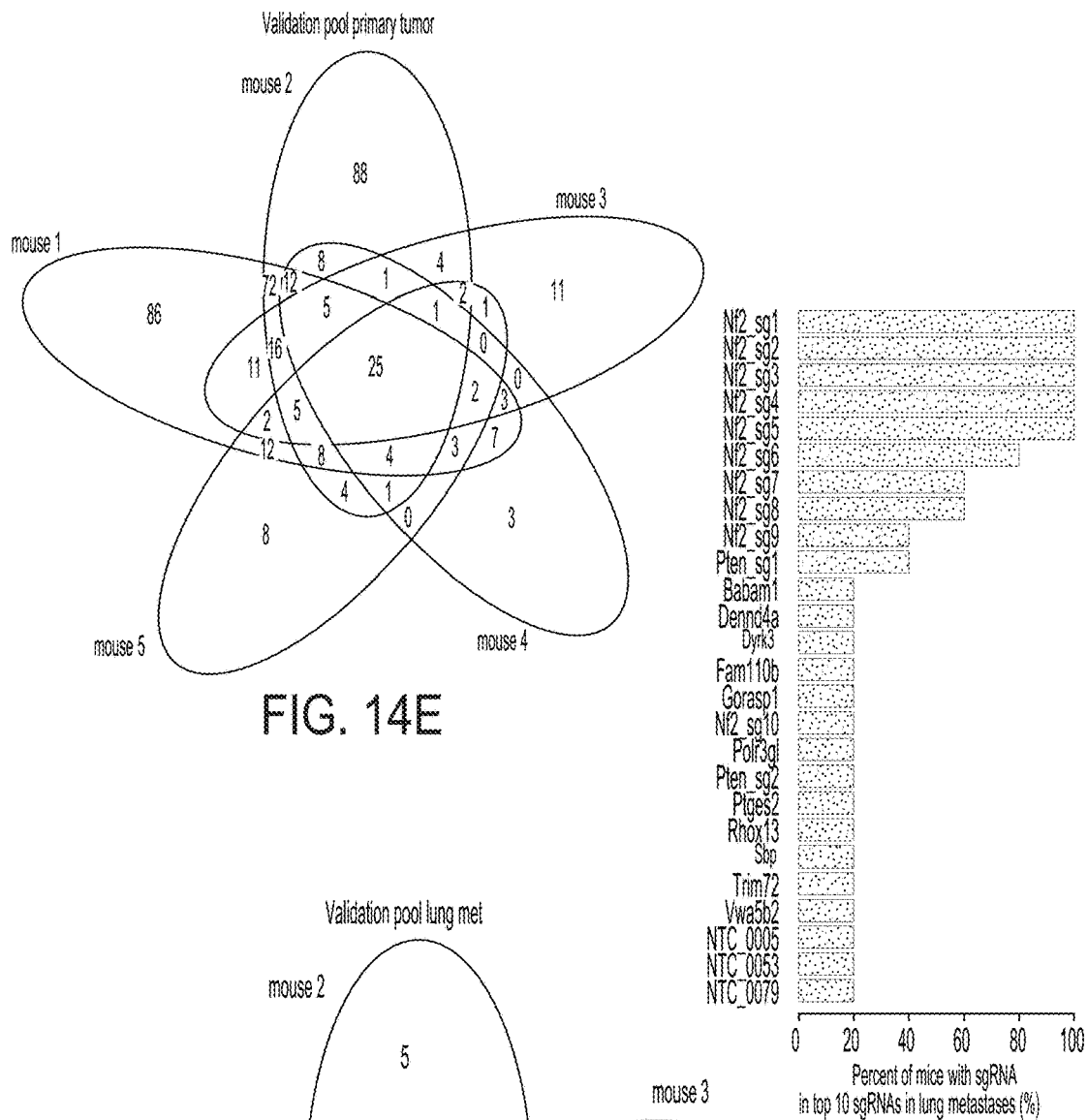
FIG. 14E
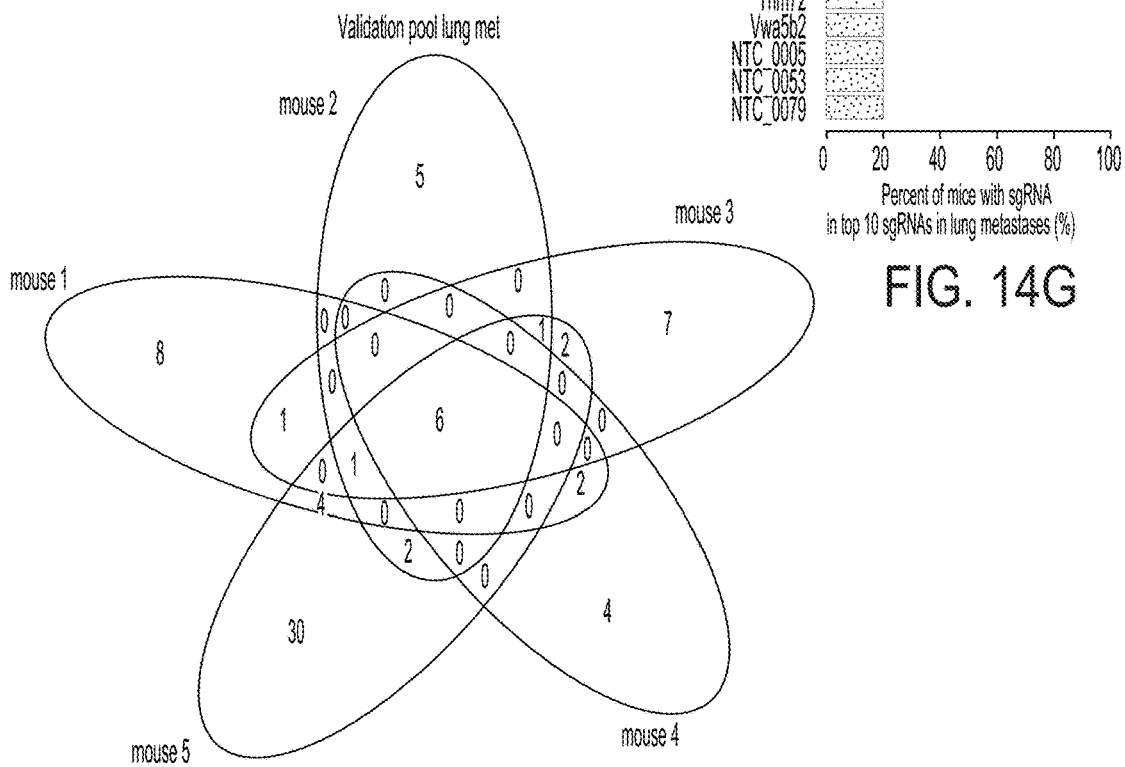
FIG. 14F
FIG. 14G

| Term | PValue |
|---|---|
| GO:0034660~ncRNA metabolic process | 5,34E -07 |
| GO:0043039~tRNA aminoacylation | 3,11E -06 |
| GO:0043038~amino acid activation | 3,11E -06 |
| GO:0006418~tRNA aminoacylation for protein translation | 3,11E -06 |
| GO:0006399~tRNA metabolic process | 2,06E -05 |
| GO:0006396~RNA processing | 5,52E -05 |
| GO:0006412~translation | 3,06E -04 |
| GO:0034660~ncRNA metabolic process | 5,34E -07 |
| GO:0034470~ncRNA processing | 0,001201556 |
| GO:0006432~phenylalanyl -tRNA aminoacylation | 0,001489208 |
| GO:0006397~mRNA processing | 0,003053718 |
| GO:0006260~DNA replication | 0,007731845 |
| GO:0016071~mRNA metabolic process | 0,008403937 |
| GO:0043123~positive regulation of I -kappaB kinase/NF -kappaB cascade | 0,00886185 |
| GO:0006259~DNA metabolic process | 0,011189394 |
| GO:0032268~regulation of cellular protein metabolic process | 0,014163531 |
| GO:0006417~regulation of translation | 0,014199449 |
| GO:0006364~rRNA processing | 0,018535588 |
| GO:0007605~sensory perception of sound | 0,019167945 |
| GO:0048663~neuron fate commitment | 0,019850216 |
| GO:0016072~rRNA metabolic process | 0,020331833 |
| GO:0008380~RNA splicing | 0,022282055 |
| GO:0010608~posttranscriptional regulation of gene expression | 0,023399291 |
| GO:0043122~regulation of I -kappaB kinase/NF -kappaB cascade | 0,024794682 |
| GO:0008033~tRNA processing | 0,030900708 |
| GO:0050885~neuromuscular process controlling balance | 0,035221747 |
| GO:0006281~DNA repair | 0,036031873 |
| GO:0050954~sensory perception of mechanical stimulus | 0,036204544 |
| GO:0060548~negative regulation of cell death | 0,036592552 |
| GO:0015031~protein transport | 0,038747958 |
| GO:0008654~phospholipid biosynthetic process | 0,039571922 |

Table S1 (B- GOPB Cell drop out)

FIG. 15A

| | |
|---|---|
| GO:0006338~chromatin remodeling | 0,039968437 |
| GO:0015671~oxygen transport | 0,041644621 |
| GO:0045184~establishment of protein localization | 0,04511632 |
| GO:0043066~negative regulation of apoptosis | 0,045963495 |
| GO:0043069~negative regulation of programmed cell death | 0,056198261 |
| GO:0007179~transforming growth factor beta receptor signaling pathway | 0,059282224 |
| GO:0015669~gas transport | 0,064733689 |
| GO:0042058~regulation of epidermal growth factor receptor signaling pathway | 0,064733689 |
| GO:0051438~regulation of ubiquitin-protein ligase activity | 0,066170603 |
| GO:0032318~regulation of Ras GTPase activity | 0,067036136 |
| GO:0045664~regulation of neuron differentiation | 0,069824626 |
| GO:0043524~negative regulation of neuron apoptosis | 0,071016952 |
| GO:0006084~acetyl-CoA metabolic process | 0,072958657 |
| GO:0006974~response to DNA damage stimulus | 0,074384011 |
| GO:0060284~regulation of cell development | 0,075062878 |
| GO:0008104~protein localization | 0,07671382 |
| GO:0022613~ribonucleoprotein complex biogenesis | 0,077202885 |
| GO:0043087~regulation of GTPase activity | 0,077849976 |
| GO:0009967~positive regulation of signal transduction | 0,080490559 |
| GO:0048741~skeletal muscle fiber development | 0,081496332 |
| GO:0051028~mRNA transport | 0,082284352 |
| GO:0007528~neuromuscular junction development | 0,083608105 |
| GO:0000080~G1 phase of mitotic cell cycle | 0,088232581 |
| GO:0051340~regulation of ligase activity | 0,088232581 |
| GO:0006302~double-strand break repair | 0,09211767 |
| GO:0031123~RNA 3'-end processing | 0,094779917 |
| GO:0010552~positive regulation of specific transcription from RNA polymerase II promoter | 0,094779917 |
| GO:0080135~regulation of cellular response to stress | 0,097167815 |
| GO:0016568~chromatin modification | 0,099227623 |

Table S1 (B- GOPB Cell drop out - continued)

FIG. 15B

| Term | PValue |
|---|---|
| GO:0008380~RNA splicing | 0,01637065 |
| GO:0048593~camera-type eye morphogenesis | 0,02560709 |
| GO:0034728~nucleosome organization | 0,02629497 |
| GO:0006333~chromatin assembly or disassembly | 0,03394217 |
| GO:0019370~leukotriene biosynthetic process | 0,03448161 |
| GO:0016070~RNA metabolic process | 0,04179123 |
| GO:0006334~nucleosome assembly | 0,04609538 |
| GO:0048592~eye morphogenesis | 0,04609538 |
| GO:0060040~retinal bipolar neuron differentiation | 0,04859248 |
| GO:0000082~G1/S transition of mitotic cell cycle | 0,05530344 |
| GO:0044242~cellular lipid catabolic process | 0,05713935 |
| GO:0065004~protein-DNA complex assembly | 0,05800605 |
| GO:0015031~protein transport | 0,05826797 |
| GO:0006397~mRNA processing | 0,05925072 |
| GO:0006396~RNA processing | 0,06029652 |
| GO:0048568~embryonic organ development | 0,06345821 |
| GO:0032940~secretion by cell | 0,06727065 |
| GO:0008645~hexose transport | 0,0709633 |
| GO:0016071~mRNA metabolic process | 0,0721051 |
| GO:0051329~interphase of mitotic cell cycle | 0,0725353 |
| GO:0007423~sensory organ development | 0,07519978 |
| GO:0015749~monosaccharide transport | 0,07961359 |
| GO:0051325~interphase | 0,08608706 |
| GO:0032647~regulation of interferon-alpha production | 0,09230152 |
| GO:0048706~embryonic skeletal system development | 0,09306471 |
| GO:0048562~embryonic organ morphogenesis | 0,09804005 |

Table S1 (B- GOPB early tumor drop out

| Early tumor dropout | | | | | |
|---|---|---|---|---|---|
| Term | Count | % | PValue | Genes | FDR |
| GO:0034660~ncRNA metabolic process | 37 | 2.640970725 | 5.34E-07 | ELAC2, TARS2, NARS, FARS2, UTP6, UTP15, IARS2, FDXACB1, VARS, LIN28B, DMT1, DCAF13, TCP11, CDKN2A, CLP1, TRMT5, RPP30, PIWIL4, NSUN2, EXOSC7, AARS, EXOSC1, LARS2, NOP10, NOP14, TARS, DDX56, RARS, TRMT12, KHSRP, HARS, FARSB, FARSA, PES1, DUS4L, AARS2, DDX51 | 9.47E-04 |
| GO:0043039~tRNA aminoacylation | 15 | 1.070863812 | 3.11E-06 | TARS2, NARS, FARS2, AARS, IARS2, LARS2, FDXACB1, VARS, TARS, RARS, FARSB, HARS, KHSRP, FARSA, AARS2 | 0.005513874 |
| GO:0043038~amino acid activation | 15 | 1.070863812 | 3.11E-06 | TARS2, NARS, FARS2, AARS, IARS2, LARS2, FDXACB1, VARS, TARS, RARS, FARSB, HARS, KHSRP, FARSA, AARS2 | 0.005513874 |
| GO:0006418~tRNA aminoacylation for protein translation | 15 | 1.070863812 | 3.11E-06 | TARS2, NARS, FARS2, AARS, IARS2, LARS2, FDXACB1, VARS, TARS, RARS, FARSB, HARS, KHSRP, FARSA, AARS2 | 0.005513874 |

FIG. 18

| | | | | |
|---|---|---|---|---|
| GO:0006399-tRNA metabolic process | 23 | 1.641084511 | 2.06E-05 | TARS2, ELAC2, NARS, FARS2, AARS, IARS2, LARS2, VARS, FDX1CB1, TARS, TCP11, CLP1, RARS, TRMT12, TRMT5, FARS8, KHSRP, HARS, RPP30, FARSA, DUS4L, NSUN2, AARS2 | 0.030462343 |
| GO:0006396-RNA processing | 55 | 3.997144897 | 5.52E-05 | U2AF2, SNRPD3, LSM7, UTP15, FDX1CB1, YBX1, SMNDC1, DCAF13, APP, CDKN2A, CLP1, TRMT5, RPP30, DBR1, LSM3, ZCCHC8, EXOSC7, AARS, EXOSC1, TTF2, SNRNP48, TRMT12, SNRPB, KHSRP, CPSF6, RBM39, CPSF4, THOC1, XRN2, ELAC2, FARS2, PPIL1, ADAD1, UTP6, LIN28B, DIMT1, TCP11, ZFP36L3, PRPF8, GEMIN8, GEMIN7, NSUN2, CSTF3, SNW1, PRPF18, NOP10, NOP14, DDX56, PAPOLA, SFPQ, PAPOLG, DUS4L, PES1, SNRNP27, CSTF1, DDX51 | 0.097870478 |

FIG. 18 CONTINUED

| | | | | | |
|---|---|---|---|---|---|
| GO:0006412~translation | 42 | 2.997630672 | 3.06E-04 | RPL17, RPL19, EEF1B2, TARS2, NARS, FARS2, HBS1L, EIF5B, RPL35, RPS15A, IARS2, FDXACB1, VARS, MRPL10, EIF3B, MRPL15, RPL7, EIF3H, MRPL36, MRPL53, FLT3L, RPS21, MRPL33 | 0.542295467 |
| | | | | RPS27A, EIF2B5, MRPL2, MRPL4, AARS, MRPS36, DENR, LARS2, RPS8, TARS, MRPL21, RARS, HARS, KHSRP, RPL3L, FARSB, PELO, FARSA, AARS2 | |
| GO:0034470~ncRNA processing | 24 | 1.713062099 | 0.0012013156 | ELAC2, EXOSC7, FARS2, AARS, UTP6, UTP15, EXOSC1, FDXACB1, NOP10, LIN28B, DIMT1, NOP14, DCAF13, DDX36, TCP11, CDKN2A, CLP1, TRMT12, TRMT5, RPP30, PES1, DUS4L, NSUN2, DDX51 | 2.410398683 |
| GO:0006432~phenylalanyl-tRNA aminoacylation | 4 | 0.285510635 | 0.0014392 | FARS2, FARSB, FARSA, FDXACB1 | 2.00935578 |

FIG. 18
CONTINUED

| GO:0006397~mRNA processing | 33 | 2.355468385 | 0.00365372 | PPIL1, SNRPD3, U2AF2, LSM7, YBX1, SMNDC1, ZFP36L3, APP, TCP11, CLP1, PRPF8, DBR1, GEMIN8, LSM3, GEMIN7, ZCCHC8, CSTF3, SNW1, PRPF18, TTF2, PAPOLA, SNRNP48, SFPQ, SNRPB, KHSRP, CPSF6, RBM39, CPSF4, PAPOLG, SNRNP27, CSTF1, THOC3, XRN2 | 5.281374654 |
|---|---|---|---|---|---|
| GO:0006260~DNA replication | 21 | 1.498923336 | 0.0077385 | ING5, UPF1, PDGFB, PHB, GINS4, POLE, LIG4, WRN, RBBP7, TK2, RAD51, RFC5, RFC4, HELB, TOP3A, TEP1, CHAF1B, NFIB, RBMS1 | 12.86445645 |
| GO:0016071~mRNA metabolic | 35 | 2.49821956 | 0.00840394 | PPIL1, SNRPD3, | 13.90561571 |

FIG. 18
CONTINUED

| process | | | | | |
|---|---|---|---|---|---|
| GO:0043123~positive regulation of I-kappaB kinase/NF-kappaB cascade | 8 | 0.5710207 | 0.00886195 | U2AF2, LSM7, MAPKAPK2, YBX1, SMNDC1, ZFP36L3, APP, TCP11, PRPF8, CLP1, DBR1, GEMIN8, LSM3, GEMIN7, ZCCHC8, CSTF3, UPF1, SNW1, PRPF18, TTF2, PAPOLA, SNRNP48, SFPQ, SNRPB, KHSRP, CPSF6, CPSF4, RBM39, PAPOLG, SNRNP27, CSTF1, THOC3, XRN2 UBE2N, MAP3K7, CARD11, LST1, MYD88, NOD1, NUP62, LTB | 14.60824868 |

FIG. 18
CONTINUED

| | | | | |
|---|---|---|---|---|
| GO:0006259--DNA metabolic process | 45 | 3.211991435 | 0.0118939 | ING5, KI F22, HMGB2, APEX2, PDGFB, FAM175A, MRE11A, RNASE H1, BNIP3, SMUG1, TK2, SETX, MUTYH, PI WIL4, CCNO, RBMS1, SGI P1, UPF1, PHB, EME2, MSH4, POLE, GINS4, NEIL1, PAPD7, LIG4, W RN, GTF2H5, RAD52, RBBP7, EEPD1, RAD51, RFC5, UBE2N, XPA, RFC5, HELB, ENDOG, SFPQ, TOP3A, TEP1, RUVBL1, CHAF1B, XRN2, NFIB | 19.09681674 |
| GO:0032268--regulation of cellular protein metabolic process | 32 | 2.284082795 | 0.01416353 | SRP14, ATG10, PDGFB, IMPACT, ADAD1, MKNK2, MKNK1, IGF2BP3, IL1 I, L31RA, PRKAR2B, APP, CDKN2A, HBB-B1, PIWIL4, EIF2B5, | 22.35001433 |
| | | | | FCER1A, UPF1, FBXO2, BARHL2, IREB2, SMAD4, 4931440F15RIK, CDK4, RNF180, UBE2N, CD59B, NGDN, IGFBP3, NCOR1, SRP9, CBS | |

FIG. 18
CONTINUED

| | | | | |
|---|---|---|---|---|
| GO:0006417~regulation of translation | 15 | 1.970063812 | 0.0149945 | SRP14, UPF1, IMPACT, BARHL2, ADAD1, MKNK2, IREB2, MKNK1, IGF2BP3, CDK4, APP, NGDN, PIWIL4, SRP9, EIF2B5 | 22.40917475 |
| GO:0006364~rRNA processing | 12 | 0.856631049 | 0.01863559 | NOP14, DIMT1, DCAF13, DDX56, CDKN2A, EXOSC7, UTP6, UTP15, EXOSC1, PES1, NOP10, DDX51 | 28.24621146 |
| GO:0007605~sensory perception of sound | 13 | 0.927908637 | 0.01916795 | MYO1A, THRB, HEXA, HEXB, SOBP, OTOS, GPR98, ESPN, GJB2, MARVELD2, CLIC5, GTF3C2, AXIN1 | 29.06198548 |
| GO:0048663~neuron fate commitment | 9 | 0.642398287 | 0.0186502 | NOTCH3, DLX1, ISL2, LBX1, HES5, FOXA1, SMAD4, NKX2-1, TLX3 | 29.823631 |
| GO:0016072~rRNA metabolic process | 12 | 0.856631049 | 0.02033183 | NOP14, DIMT1, DCAF13, DDX56, CDKN2A, EXOSC7, UTP6, UTP15, EXOSC1, PES1, NOP10, DDX51 | 30.84066263 |
| GO:0008380~RNA splicing | 24 | 1.713062099 | 0.02228205 | SNRPD3, U2AF2, PPIL1, LSM7, SNW1, PRPF18, YBX1, TTF2, SNRNP40, TCP11, SNRPA, CLP1, PRPF8, SFPQ, SNRPB, KHSRP, DBR1, GEMIN8, LSM3, RBM39, SNRNP27, GEMIN7, THOC3, | 32.95332855 |

FIG. 18
CONTINUED

| GO term | count | | p-value | genes | |
|---|---|---|---|---|---|
| GO:0010608~posttranscriptional regulation of gene expression | 19 | 1.356174161 | 0.02339929 | ZC3H8, SRP14, UPF1, IMPACT, BARHL2, ADAD1, IREB2, MKNK2, MKNK1, IGF2BP3, MAPKAPK2, CDK4, LIN28B, APP, CDKN2A, CLP1, NGDN, PIWIL4, SRP9, EIF2B5 | 34.29963175 |
| GO:0043122~regulation of I-kappaB kinase/NF-kappaB cascade | 8 | 0.5710207 | 0.02479468 | UBE2N, MAP3K7, CARD11, LST1, MYD88, NOD1, NUP62, LTB | 35.94630447 |
| GO:0008033~tRNA processing | 11 | 0.786153462 | 0.03090071 | TCP1, ELAC2, FARS2, CLP1, TRMT2, AARS, TRMT5, RPP30, DUS4L, FDXACB1, NSUN2 | 42.69971538 |
| GO:0050885~neuromuscular process controlling balance | 7 | 0.499643112 | 0.0352175 | APP, TPP1, HEXA, CLIC5, ADCY5, HEXB, AARS | 47.06716372 |
| GO:0006281~DNA repair | 25 | 1.784439686 | 0.0360319 | KIF22, HMGB2, APEX2, FAM175A, MRE11A, SMUG1, SETX, MUTYH, CCNO, UPF1, EME2, POLE, MSH4, NEIL1, GTF2H5, WRN, LIG4, RAD52, EEPD1, RAD51, UBE2N, XPA, SFPQ, CHAF1B, XRN2 | 47.86320284 |

FIG. 18 CONTINUED

| | | | | |
|---|---|---|---|---|
| GO:0050954~sensory perception of mechanical stimulus | 13 | 0.927908637 | 0.03620454 | MYO1A, THRB, HEXA, HEXB, SOBP, OTOS, GPR98, ESPN, GJB2, MARVELD2, CLIC5, GTF3C2, ANN1 | 48.01568968 |
| GO:0060548~negative regulation of cell death | 27 | 1.927194861 | 0.03659255 | STIL, STAT5A, SNCA, BNIP3, SGMS1, BCL2L1, CITED2, MAP3K7, PAK7, G2E3, CHST11, DNAJC5, FAS, PTCRA, SPP1, PIK3CG, AARS, SAP2, LI G4, BCL2L10, NME5, DLX1, CD59B, NUP62, BCL2A1A, AGTR1A, N GF | 48.3857205 |

FIG. 18
CONTINUED

| | | | | |
|---|---|---|---|---|
| GO:0015031~protein transport | 61 | 4.364032834 | 0.00874796 | SRP14, SEC24B, SEC31B, RAB6B, HPS1, VPS52, CCHCR1, COPB2, TIMM9, RANBP2, SAR1B, RAB21, SCAMP1, ZDHHC3, VPS45, VPS41, NUPL2, ATG4C, AGTR1A, RAB17, USO1, TOMM22, SRP9, ARFGAP1, RAB3B, ATG10, SNX1, ARF6, SNX3, TIMM13, RAB42, RAB43, TOMM7, TOMM6, CSE1L, DDX19A, AP3M1, EXOC4, SEC22A, PEX14, PEX13, SNX24, NUP54, TNPO1, TNPO3, ASPSCR1, RAB8B, RABIF, IPO11, TOMM40, NUP155, AP4S1, PREB, ARF1, NUP62, CADPS2, TOMM12, SEC13, HGS, SNX30, ARAP1 | 50.38647209 |
| GO:0008654~phospholipid biosynthetic process | 12 | 0.836531049 | 0.03957192 | PIGK, AGPAT6, SERINC5, PGS1, CDIPT, PIGM, AGPAT5, HEXB, DPM2, PCYT1B, SGMS1, CDS1 | 51.14542295 |
| GO:0006338~chromatin remodeling | 7 | 0.409643112 | 0.03986844 | SATB2, BAZ1B, SMARCB1, BMIP3, INO80, HMG20B, RBBP7 | 51.50202418 |

FIG. 18
CONTINUED

| | | | | |
|---|---|---|---|---|
| GO:0015671~oxygen transport | 4 | 0.28651035 | 0.04164462 | HBB-BH1,HBB-B1, HBA-X, MB | 52.98252166 |
| GO:0045184~establishment of protein localization | 61 | 4.354032834 | 0.04511632 | SRP14, SEC24B, SEC31B, RAB8B, HPS1, VPS52, CCHCR1, COPB2, TIMM9, RANBP2, SAR1B, RAB21, SCAMP1, ZDHHC3, VPS45, VPS41, NUPL2, ATG4C, AGTR1A, RAB17, USO1, TOMM22, SRP9, ARFGAP1, RAB3B, ATG10, SNX1, ARF6, SNX3, TIMM13, RAB42, RAB43, TOMM7, TOMM6, CSE1L, DDX19A, AP3M1, EXOC4, SEC22A, PEX14, PEX13, SNX24, NUP54, TNPO1, TNPO3, ASPSCR1, RAB8B, RABIF, IPO11, TOMM40, NUP155, AP4S1, PREB, ARF1, NUP62, CADPS2, TOM1L2, SEC13, HGS, SNX30, ARAP1 | 55.91436741 |

FIG. 18
CONTINUED

| GO Term | Count | Value | Genes | Score |
|---|---|---|---|---|
| GO:0043066~negative regulation of apoptosis | 26 | 1.858817273 | 0.045962349 | STIL, STAT5A, SNCA, BNIP3, SGMS1, BCL2L1, CITED2, MAP3K7, PAK7, G2E3, CHST11, DNAJC5, FAS, PTCRA, SPP1, PIK3CG, AARS, SKP2, LIG4, BCL2L10, NME5, DLX1, NUP62, BCL2A1A, AGTR1A, NGF | 56.60313774 |
| GO:0043069~negative regulation of programmed cell death | 26 | 1.858817273 | 0.05319826 | STIL, STAT5A, SNCA, BNIP3, SGMS1, BCL2L1, CITED2, MAP3K7, PAK7, G2E3, CHST11, DNAJC5, FAS, PTCRA, SPP1, PIK3CG, AARS, SKP2, LIG4, BCL2L10, NME5, DLX1, NUP62, BCL2A1A, AGTR1A, NGF | 64.16110365 |
| GO:0007179~transforming growth factor beta receptor signaling pathway | 8 | 0.5710207 | 0.05928222 | MAP3K7, PDGFB, LTBP4, SMAD6, USP9X, SMAD4, TAB1, ARAP1 | 66.18286902 |
| GO:0015669~gas transport | 4 | 0.28541035 | 0.06473369 | HBB-BH1, HBB-B1, HBA-X, MB | 69.4959843 |
| GO:0042058~regulation of epidermal growth factor receptor signaling pathway | 4 | 0.28541035 | 0.06473369 | APP, NUP62, SQS1, ZFYVE28 | 69.4959843 |
| GO:0051438~regulation of ubiquitin-protein ligase activity | 3 | 0.21413762 | 0.0661706 | UBE2N, CDKN2A, 4931440F15Rik | 70.31682673 |

FIG. 18
CONTINUED

| GO term | count | | | genes | |
|---|---|---|---|---|---|
| GO:0032318-regulation of Ras GTPase activity | 11 | 0.765153462 | 0.06703614 | ARFGAP1, ALS2, ADAP2, TBC1D12, RALBP1, TBC1D10A, ASAP3, TBC1D20, ARAP1, TBCK, TBC1D9B | 70.80118861 |
| GO:0045664-regulation of neuron differentiation | 13 | 0.927008637 | 0.0698463 | RTN4, LBX1, SOCS2, BARHL2, FOXA1, REST, NOTCH3, ISL2, RNF6, HES5, ROBO2, TLX3, NGF | 72.31131655 |
| GO:0043524-negative regulation of neuron apoptosis | 8 | 0.5710207 | 0.07101695 | DLX1, AGTR1A, SNCA, AARS, DNAJC5, LIG4, BCL2L1, NGF | 72.93427912 |
| GO:0006084-acetyl-CoA metabolic process | 6 | 0.428265525 | 0.07295986 | SDHA, MLYCD, SDHD, IDH2, DLAT, FH1 | 73.92052117 |
| GO:0006974-response to DNA damage stimulus | 29 | 2.069950036 | 0.07438401 | KIF22, HMGB2, APEX2, FAM175A, MRE11A, SMUG1, SETX, MUTYH, CCNO, CDK1, UPF1, EME2, POLE, MSH4, NEIL1, LIG4, GTF2H5, WRN, RAD52, EEPD1, RAD51, UBE2N, MAPK1, XPA, BAZ1B, SFPQ, MAPK3, CHAF1B, XRN2 | 74.62263477 |
| GO:0060284-regulation of cell development | 18 | 1.284796574 | 0.07506288 | RTN4, LBX1, SOCS2, FOXA1, BARHL2, SMAD4, LIG4, REST, NOTCH3, DLX1, ISL2, RNF6, CDKN2A, HES5, ROBO2, TLX3, IGFBP3, NGF | 74.95103753 |

FIG. 18
CONTINUED

| | | | | | |
|---|---|---|---|---|---|
| GO:0008104~protein localization | 67 | 4.792298358 | 0.00761382 | ALS2, SRP14, SEC24B, SEC31B, RAB5B, HPS1, VPS52, CCHCR1, COPB2, TIMM9, RANBP2, SAR1B, RAB21, SCAMP1, ZDHHC3, VPS45, VPS41, NUPL2, AT6C4, AGTR1A, CLIC5, RAB17, USO1, TOMM22, SRP9, ARFGAP1, CAV3, RAB3B, ATG1B, SNX1, ARF6, SNX3, TIMM13, SUFU, RAB42, RAB43, TOMM7, TOMM6, CSE1L, DDX19A, AP3M1, EXOC4, SEC22A, PEX14, PEX13, NUP54, SNX24, TNPO1, TNPO3, ASPSCR1, RAB8B, RABIF, IPO11, TOMM40, NUP155, AP4S1, PREB, SYNE2, ARF1, NUP62, CADPS2, TOM1L2, SEC13, HGS, FAF1, SNX30, ARAP1 | 75.73251455 |
| GO:0022613~ribonucleoprotein complex biogenesis | 16 | 1.142041399 | 0.07720288 | EXOSC7, UTP6, UTP15, EXOSC1, NOP10, SMNDC1, DIMT1, NCP14, DCAF13, MRPL10, DDX56, CDKN2A, CLP1, GEMIN8, PES1, DDX51 | 75.95360013 |

FIG. 18
CONTINUED

| | | | |
|---|---|---|---|
| GO:0043087-regulation of GTPase activity | 12 | 0.856531049 | 0.07764998 | ARFGAP1, ALS2, ADAP2, TBC1D12, RASGRP3, RALBP1, TBC1D10A, ASAP3, TBC1D20, ARAP1, TBCK, TBC1D9B | 76.25368935 |
| GO:0009967-positive regulation of signal transduction | 19 | 1.356174161 | 0.08049835 | FCER1A, LST1, PDGFB, SKP2, SMAD4, IL11, L31PA, CITED2, MAP3K7, UBE2N, CARD11, GPC3, MYD88, CDKN2A, NOD1, NUP62, SOS1, LTB, AXIN1 | 77.43480657 |
| GO:0048741-skeletal muscle fiber development | 6 | 0.422265525 | 0.08148533 | ALS2, APP, ACTA1, TNC, CACNA1S, SNTA1 | 77.86851507 |
| GO:0051028-mRNA transport | 9 | 0.642398287 | 0.08228435 | ENY2, NUP62, DDX19A, KHSRP, NUP54, RANBP2, NUP155, NUPL2, THOC3 | 78.28296721 |
| GO:0007528-neuromuscular junction development | 5 | 0.356897937 | 0.0835081 | ALS2, APP, TNC, CACNA1S, SNTA1 | 78.75408388 |
| GO:0000086-G1 phase of mitotic cell cycle | 3 | 0.214132762 | 0.08822258 | PPP2R3A, CDC123, MTBP | 80.5779625 |
| GO:0051340-regulation of ligase activity | 3 | 0.214132762 | 0.08822258 | UBE2N, CDKN2A, 4931440F15RIK | 80.5779625 |
| GO:0006302-double-strand break repair | 7 | 0.499643112 | 0.09211707 | UBE2N, FAM175A, MRE11A, LIG4, RAD52, SETX, RAD51 | 81.99497006 |
| GO:0031123-RNA 3'-end processing | 5 | 0.356897937 | 0.09477092 | ZFP36L3, APP, PAPOLA, PAPOLG, LIN28B | 82.9090182 |

FIG. 18
CONTINUED

| | | | | |
|---|---|---|---|---|
| GO:0010552-positive regulation of specific transcription from RNA polymerase II promoter | 5 | 0.358687937 | 0.09477992 | HMGB2, HES5, NFKB1, IRF4, CITED2 | 82.90391821 |
| GO:0080135-regulation of cellular response to stress | 10 | 0.713775874 | 0.08716782 | UBE2N, FCER1A, MAP3K7, CDKN2A, MYD88, NOD1, FAM175A, HBB -B1, AXIN1, CBS | 83.69145467 |
| GO:0016568-chromatin modification | 24 | 1.713062099 | 0.08922762 | ENY2, ING5, DPF3, FAM175A, INO80, BNIP3, DMAP1, CHD9, SMARCB1, PET117, ASF1B, SATB2, CSRP2BP, L3MBTL2, HMG20B, PADI4, RBBP7, UBE2N, NPTXR, BAZ1B, SMARCC1, RUVBL1, IRF4, RBM14, NCOR1 | 84.3911046 |

FIG. 18
CONTINUED

Late tumor hits

| Category | Term | Count | % | PValue | Genes | FDR |
|---|---|---|---|---|---|---|
| GOTERM_BP_FAT | GO:0042981~regulation of apoptosis | 30 | 5.464480874 | 0.00136618 | BID, BCLAF1, HTATIP2, FGFR3, SNCB, MGMT, PRKDC, SOX9, PTEN, IKBIP, IRAK3, CDKN2A, LHX3, DEDD2, SPN, PLAGL2, CCAR1, MUC2, NTF3, MUC20, GRIN1, CIDEA, LIG4, PIM2, PEA15A, TAX1BP1, EYA1, GRM2, HIPK1, PTPRV | 2.299894748 |
| GOTERM_BP_FAT | GO:0043067~regulation of programmed cell death | 30 | 5.464480874 | 0.00164957 | BID, BCLAF1, HTATIP2, FGFR3, SNBC, MGMT, PRKDC, SOX9, PTEN, IKBIP, IRAK3, CDKN2A, LHX3, DEDD2, SPN, PLAGL2, CCAR1, MUC2, NTF3, MUC20, GRIN1, CIDEA, LIG4, PIM2, PEA15A | 2.769598617 |
| | | | | | TAX1BP1, EYA1, GRM2, HIPK1, PTPRV | |

FIG. 18
CONTINUED

| | | | | | |
|---|---|---|---|---|---|
| GOTERM_BP_FAT | GO:0010941~regulation of cell death | 30 | 5.464480874 | 0.001783665 | BID, BCL2L1, HTATIP2, FGFR3, SNCB, MGMT, PRKDC, SOX9, PTEN, IKBIP, IRAK3, CDKN2A, LHX3, DEDD2, SPN, PLAGL2, CCAR1, MUC2, NTF3, MUC20, GRIN1, CIDEA, LIG4, PIM2, PEA15A, TAX1BP1, EYA1, GRIN2, HIPK1, PTPRV | 2.991537368 |
| GOTERM_BP_FAT | GO:0043086~negative regulation of catalytic activity | 10 | 1.821493625 | 0.002501466 | IRAK3, CDKN2A, NF2, PKIG, ZFYVE28, GABBR1, IL1B, PPP2R4, NOS3, CASP1D | 4.171462788 |
| GOTERM_BP_FAT | GO:0048585~negative regulation of response to stimulus | 8 | 1.4571949 | 0.002563844 | IRAK3, KLK6, GRIN1, CD276, IL1B, MTOR, GRIN3A, SPN | 4.273362449 |
| GOTERM_BP_FAT | GO:0006816~calcium ion transport | 11 | 2.003642967 | 0.002574947 | ATP2B2, PLN, GRIN1, CACNG6, CACNB3, GRIN3A, CACNA1D, CACNA2D2, CAMK2A, ITPR1, TPCN2 | 4.290656022 |

FIG. 18
CONTINUED

| | | | | |
|---|---|---|---|---|
| GOTERM_BP_FAT | GO:0032102~negative regulation of response to external stimulus | 6 | 1.092896175 | 0.003476997 | KLK8, GRN1, CD276, MTOR, GRIN3A, SPN | 5.763463537 |
| GOTERM_BP_FAT | GO:0051048~negative regulation of transferase activity | 7 | 1.275045537 | 0.004049413 | IRAK3, CDKN2A, NF2, PKIG, ZFYVE28, IL1B, OAS1D | 6.598017324 |
| GOTERM_BP_FAT | GO:0044092~negative regulation of molecular function | 11 | 2.003642867 | 0.004812453 | IRAK3, CDKN2A, THRA, NF2, PKIG, ZFYVE28, GABBR1, IL1B, PPP2R4, NOS3, OAS1D | 7.879272441 |
| GOTERM_BP_FAT | GO:0008285~negative regulation of cell proliferation | 15 | 2.732240437 | 0.005391769 | MUC2, FGFR3, NF2, JARID2, STK11, CD276, CXADR, PTEN, CDKN2A, EIF2AK1, CDKN2B, PTPRV, CDKN2C, NOS3, SPN | 8.787337203 |
| GOTERM_BP_FAT | GO:0044057~regulation of system process | 14 | 2.550091075 | 0.005452298 | EDN3, KLK8, THRA, NTF3, GRIN1, BMPR2, CACNA2D2, ATP2B2, GRM2, P2RX3, PLN, IL1B, NOS3, CAMK2A | 8.881728042 |

FIG. 18
CONTINUED

| | | | | |
|---|---|---|---|---|
| GOTERM_BP_FAT | GO:0043068~positive regulation of programmed cell death | 16 | 2.9143898 | 0.005873626 | BID, MUC2, BCLAF1, HTATIP2, FGFR3, GRIN1, MUC20, PRKDC, PTEN, IKBIP, CDKN2A, HPK1, PTPRV, SPN, CCAR1, PLAGL2 | 9.536243096 |
| GOTERM_BP_FAT | GO:0010942~positive regulation of cell death | 16 | 2.9143898 | 0.006310514 | BID, MUC2, BCLAF1, HTATIP2, FGFR3, GRIN1, MUC20, PRKDC, PTEN, IKBIP, CDKN2A, HPK1, PTPRV, SPN, CCAR1, PLAGL2 | 10.21019358 |
| GOTERM_BP_FAT | GO:0015674~di-, tri-valent inorganic cation transport | 12 | 2.18579235 | 0.008693592 | ATP2B2, PLN, GRIN1, CACNG6, CACNB3, GRIN3A, TCN2, CACNA1D, CACNA2D2, CAMK2A, ITPR1, TPCN2 | 11.10233985 |
| GOTERM_BP_FAT | GO:0046164~alcohol catabolic process | 7 | 1.275045537 | 0.010819172 | GNPDA1, MAOA, PKLR, HK1, ENO4, DLAT, PDHB | 16.88845729 |

FIG. 18
CONTINUED

| | | | | |
|---|---|---|---|---|
| GOTERM_BP_FAT | GO:0043065~positive regulation of apoptosis | 15 | 2.73240437 | 0.012670397 | BID, MUC2, BCLAF1, FGFR3, GRM1, MUC20, PRKDC, PTEN, IKBIP, CDKN2A, HIPK1, PTPRV, SPN, CCAR1, PLAGL2 | 19.50171132 |
| GOTERM_BP_FAT | GO:0050767~regulation of neurogenesis | 10 | 1.821493825 | 0.014040692 | KLK8, EYA1, NTF3, SEMA4F, PLXNB2, SIX1, GRM1, LIG4, NTN1, BMPR1A | 21.38142364 |
| GOTERM_BP_FAT | GO:0033673~negative regulation of kinase activity | 6 | 1.092896175 | 0.015270158 | IRAK3, CDKN2A, NF2, PKIG, ZFYVE28, IL1B | 23.03271618 |
| GOTERM_BP_FAT | GO:0006469~negative regulation of protein kinase activity | 6 | 1.092896175 | 0.015270158 | IRAK3, CDKN2A, NF2, PKIG, ZFYVE28, IL1B | 23.03271618 |
| GOTERM_BP_FAT | GO:0060284~regulation of cell development | 11 | 2.003642987 | 0.016735536 | KLK8, EYA1, CDKN2A, NTF3, SEMA4F, PLXNB2, SIX1, GRM1, LIG4, NTN1, BMPR1A | 24.93324999 |
| GOTERM_BP_FAT | GO:0030334~regulation of cell migration | 8 | 1.4571949 | 0.016735805 | MUC2, EDN3, IRS2, PDPN, RRAS2, UNC5C, PTEN, NTN1 | 24.9381795 |

FIG. 18
CONTINUED

| | | | | | |
|---|---|---|---|---|---|
| GOTERM_BP_FAT | GO:0042110~T cell activation | 9 | 1.638344262 | 0.019793072 | ITGAX, THEMIS, RPL22, PRKDC, LIG4, NCOR1, LCP1, SPN, CD1D2 | 27.89792023 |
| GOTERM_BP_FAT | GO:0046365~monosaccharide catabolic process | 6 | 1.092896175 | 0.019178777 | GNPDA1, PKLR, HK1, ENO4, DLAT, PDHB | 28.08816296 |
| GOTERM_BP_FAT | GO:0006366~transcription from RNA polymerase II promoter | 7 | 1.275045537 | 0.019584752 | SCAF1, TAF13, MED16, THRAP3, MED24, POLR2D, POLR2C | 28.57301645 |
| GOTERM_BP_FAT | GO:0080135~regulation of cellular response to stress | 7 | 1.275045537 | 0.020789861 | KLK8, EYA1, EIF2AK1, CDKN2A, IL1R, MTOR, TLR6 | 30.05206194 |
| GOTERM_BP_FAT | GO:0030217~T cell differentiation | 7 | 1.275045537 | 0.022044262 | THEMIS, RPL22, PRKDC, LIG4, NCOR1, SPN, CD1D2 | 31.56995604 |
| GOTERM_BP_FAT | GO:0007229~integrin - mediated signaling pathway | 7 | 1.275045537 | 0.022044262 | VAV3, ITGAX, ITGB1, ADAMTS13, ADAM23, ITGAE, ITGA4 | 31.56995604 |
| GOTERM_BP_FAT | GO:0031344~regulation of cell projection organization | 6 | 1.092896175 | 0.023692397 | KLK8, SEMA4F, PLXNB2, GRIN1, MTOR, NTN1 | 33.49762317 |
| GOTERM_BP_FAT | GO:0006351~transcription, DNA-dependent | 9 | 1.638344262 | 0.024607005 | SCAF1, TAF13, CDKN2A, MED16, THRAP3, MED24, TCEA2, POLR2D, POLR2C | 34.54890895 |
| GOTERM_BP_FAT | GO:0050770~regulation of axonogenesis | 5 | 0.910746812 | 0.025125899 | KLK8, SEMA4F, PLXNB2, GRIN1, NTN1 | 35.13875611 |

FIG. 18 CONTINUED

| | | | | |
|---|---|---|---|---|
| GOTERM_BP_FAT | GO:0051241~negative regulation of multicellular organismal process | 8 | 1.4571949 | IRAK3, KLK8, GRM2, PLN, BMPR2, NOS3, CXADR, SOX9 | 35.24623903 |
| GOTERM_BP_FAT | GO:0051960~regulation of nervous system development | 10 | 1.821493825 | 0.025220031 | KLK8, EYA1, NTF3, SEMA4F, PLXNB2, SIX1, GRM1, LIG4, NTN1, BMPR1A | 37.57224902 |
| GOTERM_BP_FAT | GO:0007507~heart development | 13 | 2.367841712 | 0.027314722 | MYL2, PRKDC, ITGA4, SOX9, CXADR, PTEN, ECE2, HAND2, PLN, VCAN, MKL2, ENG, BMPR1A | 38.05215168 |
| GOTERM_BP_FAT | GO:0048514~blood vessel morphogenesis | 12 | 2.18579235 | 0.027735837 | SEMA6A, HTATIP2, HAND2, IL1B, NOS3, ADRA2B, ITGA4, MKL2, PTEN, ENG, PNPLA6, CITED1 | 38.31601749 |
| GOTERM_BP_FAT | GO:0044275~cellular carbohydrate catabolic process | 6 | 1.092886175 | 0.027989749 | GNPDA1, PKLR, HK1, ENO4, DLAT, PDHB | 39.21830561 |
| GOTERM_BP_FAT | GO:0051338~regulation of transferase activity | 12 | 2.18579235 | 0.02846129 | IRAK3, CDKN2A, VAV3, NF2, WRAP53, PKIG, ZFYVE28, MUC20, IL1B, MTOR, TLR6, OAS1D | 39.3630447 |

FIG. 18
CONTINUED

| | | | | | |
|---|---|---|---|---|---|
| GOTERM_BP_FAT | GO:0016052~carbohydrate catabolic process | 7 | 1.275045537 | 0.029082116 | GNPDA1, LYG2, PKLR, HK1, ENO4, DLAT, PDHB | 39.47422129 |
| GOTERM_BP_FAT | GO:0032774~RNA biosynthetic process | 9 | 1.639044262 | 0.029117697 | SCAF1, TAF13, CDKN2A, MED16, THRAP3, MED24, TCEA2, POLR2D, POLR2C | 39.51194554 |
| GOTERM_BP_FAT | GO:0030001~metal ion transport | 21 | 3.825196612 | 0.030842264 | SLC9A7, SCN3A, SLC39A10, SLC20A2, CACNG6, GRIN1, CACNB3, GRIN3A, TCN2, KCTD5, CACNA2D2, ITPR1, CNGA2, TPCN2, KCNJ13, ATP2B2, PLN, SLC13A1, CP, CACNA10, CAMK2A | 41.31409014 |
| GOTERM_BP_FAT | GO:0016486~peptide hormone processing | 3 | 0.546448087 | 0.031869318 | PCSK2, EDE2, CHST8 | 42.3850432 |
| GOTERM_BP_FAT | GO:0051270~regulation of cell motion | 8 | 1.4571949 | 0.034736172 | MUC2, EDN3, IRS2, PDPN, RRAS2, UNC5C, | 45.19901867 |

FIG. 18
CONTINUED

| | | | | | |
|---|---|---|---|---|---|
| GOTERM_BP_FAT | GO:0051969~regulation of transmission of nerve impulse | 8 | 1.4571949 | 0.034736172 | PTEN, NTN1, ATP2B2, KLK8, GRM2, NTF3, P2RX3, GRIN1, CACNA2D2, CAMK2A | 45.19991867 |
| GOTERM_BP_FAT | GO:0007155~cell adhesion | 26 | 4.553734062 | 0.034933395 | CLDN17, THRA, CLDN6, ITGAE, ASTN1, SOX9, CXADR, PCDH1, WISP2, ITGAX, ITGB8, KLRA6, ADAM23, PDPN, CPXM2, ITGA4, BTBD9, NCAM2, SIGLEC5, PKP4, CLDN1, DSC3, VCAN, ENG, CDH11 | 45.38919728 |
| GOTERM_BP_FAT | GO:0022610~biological adhesion | 26 | 4.553734062 | 0.035868976 | CLDN17, THRA, CLDN6, ITGAE, ASTN1, SOX9, CXADR, PCDH1, WISP2, ITGAX, ITGB8, KLRA6, ADAM23, PDPN, CPXM2, ITGA4, BTBD9, NCAM2, SIGLEC5, PKP4, CLDN1, DSC3, VCAN, ENG, CDH11 | 46.37763707 |
| GOTERM_BP_FAT | GO:0006096~glycolysis | 5 | 0.910748812 | 0.037114658 | PKLR, HK1, ENO4, DLAT, PDHB | 47.4514436 |

FIG. 18
CONTINUED

| | | | | |
|---|---|---|---|---|
| GOTERM_BP_FAT | GO:0042127~regulation of cell proliferation | 24 | 4.371694899 | 0.038127944 | EDN3, MUC2, IRS2, FGFR3, NF2, STK11, JARID2, CD276, LIG4, FGF21, SOX9, CXADR, PTEN, NTN1, POLD4, CDKN2A, EF2AK1, CDKN2B, HPK1 | 49.38443487 |
| | | | | | PTPRV, CDKN2C, NOS3, SPN, BMPR1A | |
| GOTERM_BP_FAT | GO:0001525~angiogenesis | 9 | 1.639344262 | 0.038326179 | SEMA5A, HTATIP2, HAND2, IL1B, NOS3, ADRA2B, PTEN, ENG, PNPLA6 | 49.56511804 |
| GOTERM_BP_FAT | GO:0040012~regulation of locomotion | 8 | 1.45719494 | 0.039466559 | MUC, EDN3, IRS2, PDPN, RRAS2, UNC5C, PTEN, NTN1 | 49.59463921 |
| GOTERM_BP_FAT | GO:0050680~negative regulation of epithelial cell proliferation | 4 | 0.728969745 | 0.041301972 | CDKN2A, FGFR3, STK11, PTEN | 51.37363407 |
| GOTERM_BP_FAT | GO:0006812~cation transport | 23 | 4.190435537 | 0.042795541 | SLC9A7, SCN3A, SLC9A10, SLC20A2, CACNG6, GRIN1, CACNB3, GRIN3A, TCN2, KCTD5, CACNA2D2, ITPR1, CNGA2, TPCN2, KCNJ13, ATP6V1C1, ATP6B2, PLN, P2RX3, SLC30A1, CP, CACNA1D, CAMK2A | 52.48397615 |

FIG. 18
CONTINUED

| | | | | | |
|---|---|---|---|---|---|
| GOTERM_BP_FAT | GO:0031644~regulation of neurological system process | 8 | 1.4571949 | 0.044578802 | ATP2B2, KLK8, GRM2, NTF3, P2RX3, GRIN1, CACNA2D2, CAMK2A | 53.96708119 |
| GOTERM_BP_FAT | GO:0051094~positive regulation of developmental process | 12 | 2.18579235 | 0.04509441 | LPL, CDKN2A, FGFR3, NTF3, PLXNB2, CD276, IL1B, NOS3, LIG4, MKL2, NTN1, CD1D2 | 54.38854495 |
| GOTERM_BP_FAT | GO:0014031~mesenchymal cell development | 5 | 0.910748812 | 0.045639308 | EDN3, NRTN, HAND2, SOX9, ALX1 | 54.82932021 |
| GOTERM_BP_FAT | GO:0010975~regulation of neuron projection dev elopment | 5 | 0.910748812 | 0.045639308 | KLK8, SEMA4F, PLXNB2, GRIN1, NTN1 | 54.82932021 |
| GOTERM_BP_FAT | GO:0048762~mesenchymal cell differentiation | 5 | 0.910748812 | 0.0518785 | EDN3, NRTN, HAND2, SOX9, ALX1 | 59.59570644 |
| GOTERM_BP_FAT | GO:0002237~response to molecul e of bacteri al origin | 5 | 0.910748812 | 0.0518785 | IRAK3, TAP2, MAPK3, IL1B, 1ID0001/G0RI K | 59.59570644 |
| GOTERM_BP_FAT | GO:0019220~regulation of phosphate metabolic process | 15 | 2.732240437 | 0.052586226 | FGFR3, VAV3, NF2, MUC20, PKIG, BMPR2, TLR6, IRAK3, CDKN2A, EIF2AK1, PPP1R2, ZFYVE28, IL1B, PPP2R4, MTOR | 60.11587427 |

FIG. 18
CONTINUED

| | | | | | |
|---|---|---|---|---|---|
| GOTERM_BP_FAT | GO:0010769~regulation of cell morphogenesis involved in differentiation | 5 | 0.910746812 | 0.055163919 | KLK9, SEMA4F, PLXNB2, GRN1, NTN1 | 61.91548855 |
| GOTERM_BP_FAT | GO:0009894~regulation of catabolic process | 5 | 0.910746812 | 0.055163919 | IRAK3, IL1B, CIDEA, MTOR, PIM2 | 61.91548855 |
| GOTERM_BP_FAT | GO:0060485~mesenchyme development | 5 | 0.910746812 | 0.055163919 | EDN3, NRTN, HAND2, SOX9, ALX1 | 61.91548855 |
| GOTERM_BP_FAT | GO:0019318~hexose metabolic process | 10 | 1.821493625 | 0.055628001 | PTGES3, PPP1R2, GNPDA1, PPP1R1A, PFKFB2, PKLR, HK1, ENO4, DLAT, PDHB | 62.23249293 |
| GOTERM_BP_FAT | GO:0001944~vasculature development | 13 | 2.367941712 | 0.05746593 | HTATIP2, PDPN, ITGA4, PTEN, CITED1, PNPLA6, SEMA5A, HAND2, IL1B, NOS3, ADRA2B, MKL2, ENG | 63.42480542 |
| GOTERM_BP_FAT | GO:0006692~prostanoid metabolic process | 3 | 0.546448087 | 0.069828326 | PTGES3, PTGES2, PDPN | 64.99074558 |
| GOTERM_BP_FAT | GO:0006693~prostaglandin metabolic process | 3 | 0.546448087 | 0.069828326 | PTGES3, PTGES2, PDPN | 64.99074558 |

FIG. 18
CONTINUED

| | | | | | |
|---|---|---|---|---|---|
| GOTERM_BP_FAT | GO:0008219~cell death | 22 | 4.007285974 | 0.002294564 | BID, MUC2, KLK6, HTATIP2, PRKDC, CIDEA, GAN, LIG4, PIM2, PEA15A, PTEN, NTN1, TAX1BP1, IRAK3, TNFRSF11B, CDKN2A, UNC5A, HAND2, UNC5C, PDCD5, DEDD2, CCAR1 | 65.28495056 |
| GOTERM_BP_FAT | GO:0022604~regulation of cell morphogenesis | 7 | 1.275045537 | 0.008751 | KLK6, PDPN, SEMA4F, PLXNB2, EPB4.2, GRIN1, NTN1 | 65.64799803 |
| GOTERM_RM_BP_FAT | GO:0019320~hexose catabolic process | 5 | 0.910746812 | 0.062863417 | PKLR, HK1, ENO4, DLAT, PDHB | 66.38004654 |
| GOTERM_BP_FAT | GO:0006007~glucose catabolic process | 5 | 0.910746812 | 0.062863417 | PKLR, HK1, ENO4, DLAT, PDHB | 66.38004654 |
| GOTERM_BP_FAT | GO:0033077~T cell differentiation in the thymus | 4 | 0.728597745 | 0.063423542 | PRKDC, LIG4, SPN, CD1D2 | 67.19990596 |
| GOTERM_BP_FAT | GO:0006928~cell motion | 17 | 3.096391192 | 0.047708426 | EDN3, NRTN, SMOK2B, VAV3, NTF3, PDPN, ASTN1, PRKDC, ITGA4, PTEN, NTN1, TNP2, SEMA5A, SEMA4F, LHX3, SIX1, IL1B | 67.95709491 |
| GOTERM_BP_FAT | GO:0007389~pattern | 14 | 2.550091075 | 0.066616779 | BMPR2, DLL3 | 69.05139243 |

FIG. 18
CONTINUED

| Category | Term | Count | Value | P-value | Genes | Score |
|---|---|---|---|---|---|---|
| GOTERM_BP_FAT | GO:0007389~pattern specification process | 14 | 2.560091075 | 0.066618779 | BMPR2, DLL3, PRKDC, SEMA5A, CTNNBIP1, EYA1, HOXD8, HIPK1, SFRP1, LHX3, SIX1, ENG, ALX1, BMPR1A | 69.05139243 |
| GOTERM_BP_FAT | GO:0007517~muscle organ development | 10 | 1.821493625 | 0.0681974 | MYL2, PLN, SIX1, MKL2, CXADR, TRIM72, PTEN, CACNA2D2, ENG, TAGLN3 | 69.9310274 |
| GOTERM_BP_FAT | GO:0014033~neural crest cell differentiation | 4 | 0.72869745 | 0.063336868 | EDN3, NRTN, HAND2, SOX9 | 70.00740394 |
| GOTERM_BP_FAT | GO:0014032~neural crest cell development | 4 | 0.72869745 | 0.063336868 | EDN3, NRTN, HAND2, SOX9 | 70.00740394 |
| GOTERM_BP_FAT | GO:0050804~regulation of synaptic transmission | 7 | 1.275045537 | 0.060486872 | ATP2B2, GRM2, NTF3, P2RX3, GRIN1, CACNA2D2, CAMK2A | 70.08965099 |
| GOTERM_BP_FAT | GO:0006690~icosanoid metabolic process | 4 | 0.72869745 | 0.07341703 | PTGES3, GGT5, PTGES2, PDPN | 72.67162064 |
| GOTERM_BP_FAT | GO:0016265~death | 22 | 4.00726974 | 0.073478734 | BID, MUC2, KLK3, HTATIP2, PRKDC, CIDEA, GAN, LIG4, PIM2, PEA15A, PTEN, NTN1, TAX1BP1, IRAK3, TNFRSF11B, CDKN2A, UNC5A, HAND2, UNC5C, PDCD5, DEDD2, CCAR1 | 72.705284 |

FIG. 18 CONTINUED

| | | | | | |
|---|---|---|---|---|---|
| GOTERM_BP_FAT | GO:0045664~regulation of neuron differentiation | 7 | 1.275045537 | KLK3, EYA1, SEMA4F, PLXNB2, SIX1, GR_IN_1, NTN1 | 72.8603048 |
| GOTERM_BP_FAT | GO:0009952~anterior/posterior pattern formation | 9 | 1.639344262 | CTNNBIP1, HOXD8, SFRP1, HPK1, DLL3, BMPR2, PRKDC, BMPR1A, ALX1 | 73.30392897 |
| GOTERM_BP_FAT | GO:0050771~negative regulation of axonogenesis | 3 | 0.546448087 | KLK3, SEMA4F, NTN1 | 73.93968998 |
| GOTERM_BP_FAT | GO:0010627~regulation of protein kinase cascade | 9 | 1.639344262 | FGFR3, NF2, STK11, IL1B, FGF21, PIM2, TLR6, PTEN, NCOR1 | 75.42628631 |
| GOTERM_BP_FAT | GO:0006915~apoptosis | 20 | 3.64298725 | BID, MUC2, HTATIP2, PRKDC, CIDEA, LIG4, PEA15A, PIM2, PTEN, NTN1, TAX1BP1, RAK3, TNFRSF11B, CDKN2A, UNC5A, HAND2, UNC5C, PDCD5, DEDD2, CCAR1 | 76.08527945 |
| GOTERM_BP_FAT | GO:0048738~cardiac muscle tissue development | 5 | 0.910746812 | MYL2, PLN, MKL2, CXADR, PTEN | 76.31936213 |
| GOTERM_BP_FAT | GO:0009617~response to bacterium | 9 | 1.639344262 | MBL1, RAK3, DEFB15, TAP2, MAPK3, IL1B, WFDC15A, 1100001G20RIK, SPN | 77.46532448 |

FIG. 18
CONTINUED

| | | | | | |
|---|---|---|---|---|---|
| GOTERM_BP_FAT | GO:0002568~somatic diversification of T cell receptor genes | 2 | 0.364298725 | 0.083871921 | PRKDC, LIG4 | 77.46933066 |
| GOTERM_BP_FAT | GO:0033153~T cell receptor V(D)J recombination | 2 | 0.364298725 | 0.083871921 | PRKDC, LIG4 | 77.46933066 |
| GOTERM_BP_FAT | GO:0002681~somatic recombination of T cell receptor gene segments | 2 | 0.364298725 | 0.083871921 | PRKDC, LIG4 | 77.46933066 |
| GOTERM_BP_FAT | GO:0033559~unsaturated fatty acid metabolic process | 4 | 0.728598745 | 0.084062516 | PTGES3, GGT5, PTGES2, PDPN | 77.54894247 |
| GOTERM_BP_FAT | GO:0018149~peptide cross-linking | 3 | 0.546448087 | 0.084546704 | SPOCK2, F13A1, EPB42 | 77.74999986 |
| GOTERM_BP_FAT | GO:0051180~vitamin transport | 3 | 0.546448087 | 0.084546704 | PDPN, SLC2A3, TCN2 | 77.74999986 |
| GOTERM_BP_FAT | GO:0010648~negative regulation of cell communication | 10 | 1.821493625 | 0.089019306 | CTNNBIP1, IRAK3, GRM2, NF2, ZFYVE28, IL1B, CIDEA, MTOR, PTEN, NCOR1 | 79.52877711 |
| GOTERM_BP_FAT | GO:0007498~mesoderm development | 5 | 0.910746812 | 0.089562246 | AMH, NF2, DLL3, BMPR2, BMPR1A | 79.73535655 |
| GOTERM_BP_FAT | GO:0012501~programmed cell death | 20 | 3.64298725 | 0.090105793 | BID, MUC2, HTATIP2, PRKDC, CIDEA, LIG4, PEA15A, PIM2, PTEN, NTN1, TAX1BP1, IRAK3, TNFRSF11B, CDKN2A, UNC5C, HAND2, UNC5C, PDCD5, DEDD2, CCAR1 | 79.94020063 |
| GOTERM_BP_FAT | GO:0002709~regulation of T cell mediated immunity | 3 | 0.546448087 | 0.093366037 | TAP2, SPN, CD1D2 | 81.12854892 |

FIG. 18
CONTINUED

| | | | | | |
|---|---|---|---|---|---|
| GOTERM_BP_FAT | GO:0009895~negative regulation of catabolic process | 3 | 0.546448087 | IRAK3, CIDEA, MTOR | 81.12854892 |
| GOTERM_BP_FAT | GO:0001568~blood vessel development | 12 | 2.18579235 | 0.093366037 | 81.28534875 |
| | | | | SEMA5A, HTATIP2, HAND2, IL1B, NOS3, ADRA2B, ITGA4, MKL2, PTEN, ENG, PNPLA6, CITED1 | |
| GOTERM_BP_FAT | GO:0050768~negative regulation of neurogenesis | 4 | 0.72859745 | 0.095323826 | 81.80997544 |
| | | | | KLK8, SEMA4F, NTN1, BMPR1A | |
| GOTERM_BP_FAT | GO:0032496~response to lipopolysaccharide | 4 | 0.72859745 | 0.095323826 | 81.80997544 |
| | | | | IRAK3, MAPK3, IL1B, 1100001G20RIK | |
| GOTERM_BP_FAT | GO:0060537~muscle tissue development | 8 | 1.4571949 | 0.097754734 | 82.62385976 |
| | | | | MYL2, PLN, SIX1, MKL2, CXADR, PTEN, CACNA2D2, ENG | |

FIG. 18
CONTINUED

| Sequence Name | Bases | Sequence |
|---|---|---|
| HK112 | 91 | AATGATACGGCGACCACCGAGATCTACACTCTTTCCCTACACGACGCTCTTCCGATCTTAAGTAGAGTCTTGTGAAAGGACGAAACACCG |
| HK113 | 92 | AATGATACGGCGACCACCGAGATCTACACTCTTTCCCTACACGACGCTCTTCCGATCTGATCTGGCGGTTCTTGTGAAAGGACGAAACACCG |
| HK114 | 93 | AATGATACGGCGACCACCGAGATCTACACTCTTTCCCTACACGACGCTCTTCCGATCTGATCGGGGTTCTTGTGAAAGGACGAAACACCG |
| HK115 | 94 | AATGATACGGCGACCACCGAGATCTACACTCTTTCCCTACACGACGCTCTTCCGATCTCGATCATGATCGTCTTGTGAAAGGACGAAACACCG |
| HK116 | 95 | AATGATACGGCGACCACCGAGATCTACACTCTTTCCCTACACGACGCTCTTCCGATCTTCGATCGTTACCATCTTGTGGAAAGGACGAAACACCG |
| HK117 | 96 | AATGATACGGCGACCACCGAGATCTACACTCTTTCCCTACACGACGCTCTTCCGATCTCGATTATGATTCCTTGGTTCTTGTGAAAGGACGAAACACCG |
| HK118 | 97 | AATGATACGGCGACCACCGAGATCTACACTCTTTCCCTACACGACGCTCTTCCGATCTGATCTGATAACGCATTCTTGTGAAAGGACGAAACACCG |
| HK119 | 98 | AATGATACGGCGACCACCGAGATCTACACTCTTTCCCTACACGACGCTCTTCCGATCTGATCGATACAGGTATTCTTGTGAAAGGACGAAACACCG |
| HK120 | 99 | AATGATACGGCGACCACCGAGATCTACACTCTTTCCCTACACGACGCTCTTCCGATCTACGATCGATAGGTAAGGTCTTGTGAAAGGACGAAACACCG |
| HK121 | 91 | AATGATACGGCGACCACCGAGATCTACACTCTTTCCCTACACGACGCTCTTCCGATCTTAACAATGGTCTTGTGAAAGGACGAAACACCG |
| HK122 | 92 | AATGATACGGCGACCACCGAGATCTACACTCTTTCCCTACACGACGCTCTTCCGATCATACTGTATCCTTGTGAAAGGACGAAACACCG |
| HK123 | 93 | AATGATACGGCGACCACCGAGATCTACACTCTTTCCCTACACGACGCTCTTCCGATCTGCATCTTGTGAAAGGACGAAACACCG |
| HK086 | 92 | CAAGCAGAAGACGGCATACGAGATAAGTAGAGGTGACTGGAGTTCAGACGTGCTCTTCCGATCTTTCTACTATTCTTCCCTGCACTGT |
| HK087 | 93 | CAAGCAGAAGACGGCATACGAGATACGTGACTGGAGTTCAGACGTGTGCTCTTCCGATCATTTCTACTATTCTTCCCTGCACTGT |
| HK088 | 94 | CAAGCAGAAGACGGCATACGAGATCGGCGTGACTGGAGTTCAGACGTGCTCTTCCGATCTGATTCTACTATTCTTTCCCTGCACTGT |
| HK089 | 95 | CAAGCAGAAGACGGCATACGAGATCATGATCGGTGACTGGAGTTCAGACGTGCTCTTCCGATCTGATTCTACTATTCTTTCCCTGCACTGT |

FIG. 18
CONTINUED

| | | |
|---|---|---|
| HK090 | 96 | CAAGCAGAAGACGGCATACGAGATCGAGAGATCGTTACCAGTGACTGGAGTTCAGACGTGTGCTCTTCCGATCCGATCTCTACTATTCTTTCCCTGCACTGT |
| HK091 | 92 | CAAGCAGAAGACGGCATACGAGATTCCTGTGTGACTGGAGTTCAGACGTGTGCTCTTCCGATCTTCTACTATTCTTTCCCTGCACTGT |
| HK112 | 91 | AATGATACGGGCGACCACCGAGATCTACACTCTTTCCCTACACGACGCTCTTCCGATCTTAAGTAGAGTCTTGTGGAAAGGACGAAACACCG |
| HK113 | 92 | AATGATACGGGCGACCACCGAGATCTACACTCTTTCCCTACACGACGCTCTTCCGATCTATACACGATCTGTGGAAAGGACGAAACACCG |
| HK092 | 93 | CAAGCAGAAGACGGCATACGAGATAACGGCATTGTGACTGGAGTTCAGACGTGTGCTCTTCCGATCTATTCTACTATTCTTTCCCTGCACTGT |
| HK093 | 94 | CAAGCAGAAGACGGCATACGAGATCGAGATACAGGTGACTGGAGTTCAGACGTGTGCTCTTCCGATCTGATTCTACTATTCTTTCCCTGCACTGT |
| HK094 | 95 | CAAGCAGAAGACGGCATACGAGATAGGTTAAGGGGTGACTGGAGTTCAGACGTGTGCTCTTCCGATTCGATTCTACTATTCTTTCCCTGCACTGT |
| HK095 | 96 | CAAGCAGAAGACGGCATACGAGATAACAACAATGGGTGACTGGAGTTCAGACGTGTGCTCTTCCGATCGATCTCTACTATTCTTTCCCTGCACTGT |
| HK096 | 92 | CAAGCAGAAGACGGCATACGAGATACTGTATTCGTGACTGGAGTTCAGACGTGTGCTCTTCCGATCTCTACTATTCTTTCCCTGCACTGT |
| HK097 | 93 | CAAGCAGAAGACGGCATACGAGATAGGTCGCAGTGACTGGAGTTCAGACGTGTGCTCTTCCGATCTATTCTACTATTCTTTCCCTGCACTGT |

Single SgRNAs

| Spacer No. | Spacer 20bp | PAM | Target |
|---|---|---|---|
| S001 | GATCCGCACCGTCAATGTCT | NGG | Nf2 |
| S002 | GAAGCTTCATGCGAGAAGCGA | NGG | Nf2 |
| S003 | CTTGCCGTCATAGCTGTCC | NGG | Nf2 |
| S004 | CACTGGGCTTCGGGAAACC | NGG | Nf2 |
| S005 | TGGACTGCAGTATACAATCA | NGG | Nf2 |
| S006 | GTTCGATCATGAGTTTCGA | NGG | Nf2 |
| S007 | ACCGCCAAATTTAACTGCAG | NGG | Pten |

FIG. 18
CONTINUED

| | | | |
|---|---|---|---|
| S008 | GCAGCAATTCACTGTAAAGC | NGG | Pten |
| S009 | TGTCATCTTCACTTAGCCAT | NGG | Pten |
| S010 | ACAATATTGATGATGTAGTA | NGG | Pten |
| S011 | CATACCTCTGCCAGTTAAATT | NGG | Pten |
| S012 | AATCCCATAGCAATAATATT | NGG | Pten |
| S013 | GCTTGACAGCTCCGACGCA | NGG | Trim72 |
| S014 | ATGCTGGGGTTGCCTTGCGT | NGG | Trim72 |
| S015 | ATGTTCCGGGCTCTGATGCC | NGG | Trim72 |
| S016 | GCGCAAGGAGAAGACTGTAG | NGG | Trim72 |
| S017 | CCTGTCAGAGTCACCACCAC | NGG | Trim72 |
| S018 | TTGCTCACCTGCTGGTTACC | NGG | Trim72 |
| S019 | GTCGGATATTTGCGTTCCGC | NGG | Cdkn2a |
| S020 | CCCAAACGCCCCGAACTCTTT | NGG | Cdkn2a |
| S021 | GGGTACGACCGAAAGAGTT | NGG | Cdkn2a |
| S022 | GCCTGGATGTGCGCGATGCC | NGG | Cdkn2a |
| S023 | TCGTCGATCCCGGAGACCC | NGG | Cdkn2a |
| S024 | CCGACCGGAATCCTGGACC | NGG | Cdkn2a |

| | | | |
|---|---|---|---|
| S025 | AGAGGGGCGATTACCCGGGC | NGG | Cryba4 |
| S026 | TGTTAGAACCACCGCGACTCA | NGG | Cryba4 |
| S027 | AAGGAGGTGAGCCCTTCTCCG | NGG | Cryba4 |
| S028 | CTTTACGCCCAGATTGAACA | NGG | Cryba4 |
| S029 | GACAGACTCACGCTCCGCTC | NGG | Cryba4 |
| S030 | AAGAAGGCTTCCAGGGCCGA | NGG | Cryba4 |
| S031 | GTTGATTGACAGAAGCCAAC | NGG | Fga |
| S032 | GTTCATAGACATGAAGCGCC | NGG | Fga |
| S033 | AGTACGTTGGCCAAGAGTTG | NGG | Fga |
| S034 | GGCGCAGAATTGAGATCCTG | NGG | Fga |
| S035 | CACCTGCCTCATCTTGAGCG | NGG | Fga |
| S036 | ACTACAGATACCGAAGATAA | NGG | Fga |
| S037 | GCTACTGGGCCTGAACTTAG | NGG | mmu-mir-345 |
| S038 | CCAGTGCTTGTTGTTGGCTAC | NGG | mmu-mir-345 |
| S039 | GACCCCTTAGTCCAGTGCTTG | NGG | mmu-mir-345 |
| S040 | TGAAGTCCGACACCCAAGTCC | NGG | mmu-mir-345 |
| S041 | AGTCACTGCATTGCACGAACT | NGG | mmu-mir-152 |
| S042 | ATTACACTCCGGACTCGGAAC | NGG | mmu-mir-152 |
| S043 | TTCTGTGATTACATCCGACT | NGG | mmu-mir-152 |
| S044 | CGCGCTTGTCCCCCGGGCCT | NGG | mmu-mir-152 |
| S045 | GGGAGGTATTCGGCTCCCCG | NGG | NonTargetingControlGuideForMouse_0001 |
| S046 | GCTTTTCACGGAGGTTTCACG | NGG | NonTargetingControlGuideForMouse_0002 |
| S047 | ATGTTGCAGTTTGGCTTCGAT | NGG | NonTargetingControlGuideForMouse_0003 |
| S048 | ACGTGTAAGGCGAACCCTTT | NGG | NonTargetingControlGuideForMouse_0004 |

Mouse Valid guide

| long_name | uid | gene | seq | Pool name | spacer num | display |
|---|---|---|---|---|---|---|
| MouseValid_MetsMIR_001_Adra2b | MetsMIR_001 | Adra2b | TACCAGGCGCATTGCCGAAAA | Mouse Valid | _001 | Adra2b_001 |
| MouseValid_MetsMIR_002_Adra2b | MetsMIR_002 | Adra2b | GAACTCCCCGGCGGCCGGA | Mouse Valid | _002 | Adra2b_002 |
| MouseValid_MetsMIR_003_Adra2b | MetsMIR_003 | Adra2b | ACTTCCGCCGTGCCTTTCGA | Mouse Valid | _003 | Adra2b_003 |
| MouseValid_MetsMIR_004_Adra2b | MetsMIR_004 | Adra2b | TGGCAATTACATAGATTCGC | Mouse Valid | _004 | Adra2b_004 |
| MouseValid_MetsMIR_005_Adra2b | MetsMIR_005 | Adra2b | AGAAGAGCACGTCTAGCGCC | Mouse Valid | _005 | Adra2b_005 |
| MouseValid_MetsMIR_006_Adra2b | MetsMIR_006 | Adra2b | CCGGCAAAGGATCCTTCGAA | Mouse Valid | _006 | Adra2b_006 |

FIG. 18 CONTINUED

| | | | | | |
|---|---|---|---|---|---|
| MouseValid_MetsMiR_007_Adra2b | MetsMiR_007 | Adra2b | CCAATAGCCCAGCAGCTCGT | MouseValid_007 | Adra2b_007 |
| MouseValid_MetsMiR_008_Adra2b | MetsMiR_008 | Adra2b | AATGACCACCGCCAGCACAA | MouseValid_008 | Adra2b_008 |
| MouseValid_MetsMiR_009_Adra2b | MetsMiR_009 | Adra2b | GGACATGTCCGGCCCCGCCA | MouseValid_009 | Adra2b_009 |
| MouseValid_MetsMiR_010_Adra2b | MetsMiR_010 | Adra2b | AGCAAAAAAGATCCGATGC | MouseValid_010 | Adra2b_010 |
| MouseValid_MetsMiR_011_Aprt | MetsMiR_011 | Aprt | GTCGATCTTGCCGCTGTGCG | MouseValid_011 | Aprt_011 |
| MouseValid_MetsMiR_012_Aprt | MetsMiR_012 | Aprt | CCGAGCTTCCATCCGCCTCT | MouseValid_012 | Aprt_012 |
| MouseValid_MetsMiR_013_Aprt | MetsMiR_013 | Aprt | CCCTAACAGGTCTAGACTCC | MouseValid_013 | Aprt_013 |
| MouseValid_MetsMiR_014_Aprt | MetsMiR_014 | Aprt | AGCTGACCTCGCTGAAGGGC | MouseValid_014 | Aprt_014 |
| MouseValid_MetsMiR_015_Aprt | MetsMiR_015 | Aprt | CCGGCAGCTTCCCCTGTTTC | MouseValid_015 | Aprt_015 |
| MouseValid_MetsMiR_016_Aprt | MetsMiR_016 | Aprt | CACACTCCACCACTTCAGCC | MouseValid_016 | Aprt_016 |
| MouseValid_MetsMiR_017_Aprt | MetsMiR_017 | Aprt | CGGGCAGAGAGTGGTCATTG | MouseValid_017 | Aprt_017 |
| MouseValid_MetsMiR_018_Aprt | MetsMiR_018 | Aprt | CACAATGACCACTCTCTGCC | MouseValid_018 | Aprt_018 |
| MouseValid_MetsMiR_019_Aprt | MetsMiR_019 | Aprt | CTCGCCCCTCTTGAAAGACC | MouseValid_019 | Aprt_019 |
| MouseValid_MetsMiR_020_Aprt | MetsMiR_020 | Aprt | GCGTGGGCTGTGTGCTCATC | MouseValid_020 | Aprt_020 |
| MouseValid_MetsMiR_021_Atp5s | MetsMiR_021 | Atp5s | GGAGCCAAAGTACGCTACTG | MouseValid_021 | Atp5s_021 |
| MouseValid_MetsMiR_022_Atp5s | MetsMiR_022 | Atp5s | TGCCACCGATTCTTGTATCA | MouseValid_022 | Atp5s_022 |
| MouseValid_MetsMiR_023_Atp5s | MetsMiR_023 | Atp5s | TCATTGCTCTGCGACATTTC | MouseValid_023 | Atp5s_023 |
| MouseValid_MetsMiR_024_Atp5s | MetsMiR_024 | Atp5s | AAATTTACGAAAAAGCCTAT | MouseValid_024 | Atp5s_024 |
| MouseValid_MetsMiR_025_Atp5s | MetsMiR_025 | Atp5s | TCTAGATCAATGATGATGTT | MouseValid_025 | Atp5s_025 |
| MouseValid_MetsMiR_026_Atp5s | MetsMiR_026 | Atp5s | CAACCATTCCCAGAACTATC | MouseValid_026 | Atp5s_026 |
| MouseValid_MetsMiR_027_Atp5s | MetsMiR_027 | Atp5s | CACTTAAGAACAACAAATACTTG | MouseValid_027 | Atp5s_027 |
| MouseValid_MetsMiR_028_Atp5s | MetsMiR_028 | Atp5s | CAGTGCTGTCTTAAAGACTT | MouseValid_028 | Atp5s_028 |

FIG. 18 CONTINUED

| | | | | | |
|---|---|---|---|---|---|
| MouseValid_MetsMiR_029_Atp5s | MetsMiR_029 | Atp5s | GAGTAGATTATGAACGCCTC | MouseValid_029 | Atp5s_029 |
| MouseValid_MetsMiR_030_Atp5s | MetsMiR_030 | Atp5s | TATAGTCGTGTGTAGCCACTTC | MouseValid_030 | Atp5s_030 |
| MouseValid_MetsMiR_031_Babam1 | MetsMiR_031 | Babam1 | TAGTCAATGACGACTCCGCC | MouseValid_031 | Babam1_031 |
| MouseValid_MetsMiR_032_Babam1 | MetsMiR_032 | Babam1 | ACGCCGTCTCCAGGTCATAC | MouseValid_032 | Babam1_032 |
| MouseValid_MetsMiR_033_Babam1 | MetsMiR_033 | Babam1 | CAAGAGCCACGAATTTGCAC | MouseValid_033 | Babam1_033 |
| MouseValid_MetsMiR_034_Babam1 | MetsMiR_034 | Babam1 | TATGTTTCAGATCATCTGTC | MouseValid_034 | Babam1_034 |
| MouseValid_MetsMiR_035_Babam1 | MetsMiR_035 | Babam1 | GCAGAGCTCACGTGGGTCAAG | MouseValid_035 | Babam1_035 |
| MouseValid_MetsMiR_036_Babam1 | MetsMiR_036 | Babam1 | GGAGATGTCTGTGCCAAAGC | MouseValid_036 | Babam1_036 |
| MouseValid_MetsMiR_037_Babam1 | MetsMiR_037 | Babam1 | GCACTCACATGAGGCTGAAG | MouseValid_037 | Babam1_037 |
| MouseValid_MetsMiR_038_Babam1 | MetsMiR_038 | Babam1 | CTACAACCAGTGCAAATTCG | MouseValid_038 | Babam1_038 |
| MouseValid_MetsMiR_039_Babam1 | MetsMiR_039 | Babam1 | CTGCAGCTGCCTGTATGACC | MouseValid_039 | Babam1_039 |
| MouseValid_MetsMiR_040_Babam1 | MetsMiR_040 | Babam1 | CCATTAAAGGACTCCAGCTT | MouseValid_040 | Babam1_040 |
| MouseValid_MetsMiR_041_Bid | MetsMiR_041 | Bid | GGTCCATTCTCATCGCCTATT | MouseValid_041 | Bid_041 |
| MouseValid_MetsMiR_042_Bid | MetsMiR_042 | Bid | GCCAGACATTCGCCCAAAT | MouseValid_042 | Bid_042 |
| MouseValid_MetsMiR_043_Bid | MetsMiR_043 | Bid | CCTTAGGTCAGCAACGGTTC | MouseValid_043 | Bid_043 |
| MouseValid_MetsMiR_044_Bid | MetsMiR_044 | Bid | CTGTGATGTGCTCGGCCCC | MouseValid_044 | Bid_044 |
| MouseValid_MetsMiR_045_Bid | MetsMiR_045 | Bid | TAATAAAGTTGACAGTCGTG | MouseValid_045 | Bid_045 |
| MouseValid_MetsMiR_046_Bid | MetsMiR_046 | Bid | TCTAACCAAGTTCCTCACAT | MouseValid_046 | Bid_046 |
| MouseValid_MetsMiR_047_Bid | MetsMiR_047 | Bid | CTTTCTTAGGAGATGGACTG | MouseValid_047 | Bid_047 |
| MouseValid_MetsMiR_048_Bid | MetsMiR_048 | Bid | CTGTCTGCAGCTCGTCTTCG | MouseValid_048 | Bid_048 |
| MouseValid_MetsMiR_049_Bid | MetsMiR_049 | Bid | CTAGCCGCACAGTTCATGAA | MouseValid_049 | Bid_049 |
| MouseValid_MetsMiR_050_Bid | MetsMiR_050 | Bid | TCATACTTACTTCCTCCGAC | MouseValid_050 | Bid_050 |

| | | | | | |
|---|---|---|---|---|---|
| MouseValid_MetsMR_051_Bmp2 | MetsMR_051 | Bmp2 | ATGCCGGCGGCGAACTTCTTG | MouseValid_051 | Bmp2_051 |
| MouseValid_MetsMR_052_Bmp2 | MetsMR_052 | Bmp2 | ATATGCTAGATCTGTACCGC | MouseValid_052 | Bmp2_052 |
| MouseValid_MetsMR_053_Bmp2 | MetsMR_053 | Bmp2 | GATCAAACTAGAAGCCCGTGG | MouseValid_053 | Bmp2_053 |
| MouseValid_MetsMR_054_Bmp2 | MetsMR_054 | Bmp2 | TTAAATTGAAGAAGAAGCGC | MouseValid_054 | Bmp2_054 |
| MouseValid_MetsMR_055_Bmp2 | MetsMR_055 | Bmp2 | GGGCACCACGAGTCCTTGC | MouseValid_055 | Bmp2_055 |
| MouseValid_MetsMR_056_Bmp2 | MetsMR_056 | Bmp2 | GTCTTCCGAAGGCCGGACA | MouseValid_056 | Bmp2_056 |
| MouseValid_MetsMR_057_Bmp2 | MetsMR_057 | Bmp2 | GCGGTACAGATCTAGACATAT | MouseValid_057 | Bmp2_057 |
| MouseValid_MetsMR_058_Bmp2 | MetsMR_058 | Bmp2 | TGGTCTGGGGCGGGCGCTCC | MouseValid_058 | Bmp2_058 |
| MouseValid_MetsMR_059_Bmp2 | MetsMR_059 | Bmp2 | GTGCGCGAGTTCCATCACGA | MouseValid_059 | Bmp2_059 |
| MouseValid_MetsMR_060_Bmp2 | MetsMR_060 | Bmp2 | TTCGTGATGGAAGCTGCGCA | MouseValid_060 | Bmp2_060 |
| MouseValid_MetsMR_061_Cdkn2a | MetsMR_061 | Cdkn2a | GTGCCGATATTTGCGTTCCGC | MouseValid_061 | Cdkn2a_061 |
| MouseValid_MetsMR_062_Cdkn2a | MetsMR_062 | Cdkn2a | CCCAACGCCCCGAACTCTTT | MouseValid_062 | Cdkn2a_062 |
| MouseValid_MetsMR_063_Cdkn2a | MetsMR_063 | Cdkn2a | GGGGTACCACCGAAAGAGTT | MouseValid_063 | Cdkn2a_063 |
| MouseValid_MetsMR_064_Cdkn2a | MetsMR_064 | Cdkn2a | GGCTGGATGTGCGCGATGCC | MouseValid_064 | Cdkn2a_064 |
| MouseValid_MetsMR_065_Cdkn2a | MetsMR_065 | Cdkn2a | TCGTGCGATCCCGGAGACCC | MouseValid_065 | Cdkn2a_065 |
| MouseValid_MetsMR_066_Cdkn2a | MetsMR_066 | Cdkn2a | CCGCACCGGAATCCTGGACC | MouseValid_066 | Cdkn2a_066 |
| MouseValid_MetsMR_067_Cdkn2a | MetsMR_067 | Cdkn2a | GCCGGATTTAGCTCTGCTCT | MouseValid_067 | Cdkn2a_067 |
| MouseValid_MetsMR_068_Cdkn2a | MetsMR_068 | Cdkn2a | TGCAGGGCCCTGGAACTTCG | MouseValid_068 | Cdkn2a_068 |
| MouseValid_MetsMR_069_Cdkn2a | MetsMR_069 | Cdkn2a | GGGAACGTCGCCCAGACCGA | MouseValid_069 | Cdkn2a_069 |
| MouseValid_MetsMR_070_Cdkn2a | MetsMR_070 | Cdkn2a | AGGGCCCGTGTGCATGACGTG | MouseValid_070 | Cdkn2a_070 |
| MouseValid_MetsMR_071_Cryba4 | MetsMR_071 | Cryba4 | AGAGGGGCGATTACCCGGGC | MouseValid_071 | Cryba4_071 |
| MouseValid_MetsMR_072_Cryba4 | MetsMR_072 | Cryba4 | TGTAGAACCACCGCGACTCA | MouseValid_072 | Cryba4_072 |

| | | | | | |
|---|---|---|---|---|---|
| MouseValid_MetsMiR_073_Cryba4 | MetsMiR_073 | Cryba4 | AAGGAGGTGAGCCTCTCCGC | MouseValid | 073 | Cryba4_073 |
| MouseValid_MetsMiR_074_Cryba4 | MetsMiR_074 | Cryba4 | CTTACGCCCCAGATTGAACA | MouseValid | 074 | Cryba4_074 |
| MouseValid_MetsMiR_075_Cryba4 | MetsMiR_075 | Cryba4 | GACAGACTCACGCTCCGCTC | MouseValid | 075 | Cryba4_075 |
| MouseValid_MetsMiR_076_Cryba4 | MetsMiR_076 | Cryba4 | AAGAAGGCTTCCAGGGCCGA | MouseValid | 076 | Cryba4_076 |
| MouseValid_MetsMiR_077_Cryba4 | MetsMiR_077 | Cryba4 | TTCTGCGCACACTCTGCACC | MouseValid | 077 | Cryba4_077 |
| MouseValid_MetsMiR_078_Cryba4 | MetsMiR_078 | Cryba4 | AGTGCTTGTAGTCACCTGAG | MouseValid | 078 | Cryba4_078 |
| MouseValid_MetsMiR_079_Cryba4 | MetsMiR_079 | Cryba4 | CCAAGGACAGCAATATGTGC | MouseValid | 079 | Cryba4_079 |
| MouseValid_MetsMiR_080_Cryba4 | MetsMiR_080 | Cryba4 | AGATGGTCAGCCTTGAGTCG | MouseValid | 080 | Cryba4_080 |
| MouseValid_MetsMiR_081_Cyp2d12 | MetsMiR_081 | Cyp2d12 | TTGTCTTCTCTGCGCAATTT | MouseValid | 081 | Cyp2d12_081 |
| MouseValid_MetsMiR_082_Cyp2d12 | MetsMiR_082 | Cyp2d12 | CCCACCAGCCTGAGTAGTGA | MouseValid | 082 | Cyp2d12_082 |
| MouseValid_MetsMiR_083_Cyp2d12 | MetsMiR_083 | Cyp2d12 | GTGCCCATCTTTGAGCATCT | MouseValid | 083 | Cyp2d12_083 |
| MouseValid_MetsMiR_084_Cyp2d12 | MetsMiR_084 | Cyp2d12 | GGTTGTGATCAACAGAATGA | MouseValid | 084 | Cyp2d12_084 |
| MouseValid_MetsMiR_085_Cyp2d12 | MetsMiR_085 | Cyp2d12 | ATAACCTGTTGACTGAAAAC | MouseValid | 085 | Cyp2d12_085 |
| MouseValid_MetsMiR_086_Cyp2d12 | MetsMiR_086 | Cyp2d12 | TGAAGGACTTCTGACTTTGC | MouseValid | 086 | Cyp2d12_086 |
| MouseValid_MetsMiR_087_Cyp2d12 | MetsMiR_087 | Cyp2d12 | GATAGTTTGACAGAACTCTC | MouseValid | 087 | Cyp2d12_087 |
| MouseValid_MetsMiR_088_Cyp2d12 | MetsMiR_088 | Cyp2d12 | GTACTTTCAGCATCCATATG | MouseValid | 088 | Cyp2d12_088 |
| MouseValid_MetsMiR_089_Cyp2d12 | MetsMiR_089 | Cyp2d12 | GGTATGATCTTTGCACCCTA | MouseValid | 089 | Cyp2d12_089 |
| MouseValid_MetsMiR_090_Cyp2d12 | MetsMiR_090 | Cyp2d12 | CTGTGATGCCTTCACTACTC | MouseValid | 090 | Cyp2d12_090 |
| MouseValid_MetsMiR_091_Dennd4a | MetsMiR_091 | Dennd4a | GTTAAGTCTCTGGTAGAT | MouseValid | 091 | Dennd4a_091 |
| MouseValid_MetsMiR_092_Dennd4a | MetsMiR_092 | Dennd4a | AATATTGGCAGGTCGTCCAT | MouseValid | 092 | Dennd4a_092 |
| MouseValid_MetsMiR_093_Dennd4a | MetsMiR_093 | Dennd4a | CTGTATCGTTATTCCATCTC | MouseValid | 093 | Dennd4a_093 |
| MouseValid_MetsMiR_094_Dennd4a | MetsMiR_094 | Dennd4a | AAACACGACTCAGAATACGC | MouseValid | 094 | Dennd4a_094 |

FIG. 18 CONTINUED

| | | | | | | | |
|---|---|---|---|---|---|---|---|
| MouseValid_MetsMR_095_Dennd4a | MetsMR_095 | Dennd4a | AACGACTCGTAATCTTCTTG | Mouse Valid | 095 | Dennd4a_095 |
| MouseValid_MetsMR_096_Dennd4a | MetsMR_096 | Dennd4a | CGTACGCACCTTCTCAGCTG | Mouse Valid | 096 | Dennd4a_096 |
| MouseValid_MetsMR_097_Dennd4a | MetsMR_097 | Dennd4a | CTTATGCTATAAAAAGTCAG | Mouse Valid | 097 | Dennd4a_097 |
| MouseValid_MetsMR_098_Dennd4a | MetsMR_098 | Dennd4a | TCTCTCCTAGTGGGGATCTG | Mouse Valid | 098 | Dennd4a_098 |
| MouseValid_MetsMR_099_Dennd4a | MetsMR_099 | Dennd4a | CATTCAATAGTTGCCCCCAT | Mouse Valid | 099 | Dennd4a_099 |
| MouseValid_MetsMR_100_Dennd4a | MetsMR_100 | Dennd4a | AGAGGTATTTGCTATCTGG | Mouse Valid | 100 | Dennd4a_100 |
| MouseValid_MetsMR_101_Dyrk3 | MetsMR_101 | Dyrk3 | ATCGTCGTAGCCACCGTTAT | Mouse Valid | 101 | Dyrk3_101 |
| MouseValid_MetsMR_102_Dyrk3 | MetsMR_102 | Dyrk3 | GGTTGCCACTTCACCGCGCTC | Mouse Valid | 102 | Dyrk3_102 |
| MouseValid_MetsMR_103_Dyrk3 | MetsMR_103 | Dyrk3 | CGCCCGTTACTTCCGCTGCTG | Mouse Valid | 103 | Dyrk3_103 |
| MouseValid_MetsMR_104_Dyrk3 | MetsMR_104 | Dyrk3 | CGTCCTTCCTCCCGGATCG | Mouse Valid | 104 | Dyrk3_104 |
| MouseValid_MetsMR_105_Dyrk3 | MetsMR_105 | Dyrk3 | GTTGCTGAATGTGTCCGAAT | Mouse Valid | 105 | Dyrk3_105 |
| MouseValid_MetsMR_106_Dyrk3 | MetsMR_106 | Dyrk3 | CCTACTTACATTTAGCCTTC | Mouse Valid | 106 | Dyrk3_106 |
| MouseValid_MetsMR_107_Dyrk3 | MetsMR_107 | Dyrk3 | GGGCGAACTTCCGAACCAAC | Mouse Valid | 107 | Dyrk3_107 |
| MouseValid_MetsMR_108_Dyrk3 | MetsMR_108 | Dyrk3 | GCACCACCCTCCGTCCGTC | Mouse Valid | 108 | Dyrk3_108 |
| MouseValid_MetsMR_109_Dyrk3 | MetsMR_109 | Dyrk3 | ACAGCACCCGATCGACATA | Mouse Valid | 109 | Dyrk3_109 |
| MouseValid_MetsMR_110_Dyrk3 | MetsMR_110 | Dyrk3 | TCTCCTCCGGCCGCCTGGCGA | Mouse Valid | 110 | Dyrk3_110 |
| MouseValid_MetsMR_111_Fam110b | MetsMR_111 | Fam110b | CTTCACGTTGCACACCGCTCT | Mouse Valid | 111 | Fam110b_111 |
| MouseValid_MetsMR_112_Fam110b | MetsMR_112 | Fam110b | AGTAGTCGGGTCCTTTGTTC | Mouse Valid | 112 | Fam110b_112 |
| MouseValid_MetsMR_113_Fam110b | MetsMR_113 | Fam110b | CAGGGCCACCGCCGACGTGA | Mouse Valid | 113 | Fam110b_113 |
| MouseValid_MetsMR_114_Fam110b | MetsMR_114 | Fam110b | ACCCGACTACTTCCGCAGGC | Mouse Valid | 114 | Fam110b_114 |
| MouseValid_MetsMR_115_Fam110b | MetsMR_115 | Fam110b | CTTCCTGGCTCTTGACGTATT | Mouse Valid | 115 | Fam110b_115 |
| MouseValid_MetsMR_116_Fam110b | MetsMR_116 | Fam110b | GGCTTTAAGGGGCTTCACAC | Mouse Valid | 116 | Fam110b_116 |

FIG. 18 CONTINUED

| | | | | | |
|---|---|---|---|---|---|
| MouseValid_MetsMR_117_Fam110b | MetsMR_117 | Fam110b | ACAAGCATAGCTCCCGAAAC | Mouse Valid | 117 | Fa_m110b_117 |
| MouseValid_MetsMR_118_Fam110b | MetsMR_118 | Fam110b | CAACTACTGCGGACTTGACC | Mouse Valid | 118 | Fa_m110b_118 |
| MouseValid_MetsMR_119_Fam110b | MetsMR_119 | Fam110b | AGAGCAGCTCCCACGTGAGC | Mouse Valid | 119 | Fa_m110b_119 |
| MouseValid_MetsMR_120_Fam110b | MetsMR_120 | Fam110b | AGCTGATCATGCTTGCGCTG | Mouse Valid | 120 | Fa_m110b_120 |
| MouseValid_MetsMR_121_Fga | MetsMR_121 | Fga | GTTGATTGACGAAGCCAACC | Mouse Valid | 121 | Fga_121 |
| MouseValid_MetsMR_122_Fga | MetsMR_122 | Fga | GTTGATAGACATGAAGCGCC | Mouse Valid | 122 | Fga_122 |
| MouseValid_MetsMR_123_Fga | MetsMR_123 | Fga | AGTACGTGGCCCAAGAGTTG | Mouse Valid | 123 | Fga_123 |
| MouseValid_MetsMR_124_Fga | MetsMR_124 | Fga | GGCGCAGAATTGAGATCCTG | Mouse Valid | 124 | Fga_124 |
| MouseValid_MetsMR_125_Fga | MetsMR_125 | Fga | CACCTGCCTCATCTTGAGCG | Mouse Valid | 125 | Fga_125 |
| MouseValid_MetsMR_126_Fga | MetsMR_126 | Fga | ACTACAGATACCGAAGATAA | Mouse Valid | 126 | Fga_126 |
| MouseValid_MetsMR_127_Fga | MetsMR_127 | Fga | AGCACACATACCAGACTGTGC | Mouse Valid | 127 | Fga_127 |
| MouseValid_MetsMR_128_Fga | MetsMR_128 | Fga | CAAATACTCCATGATATTCC | Mouse Valid | 128 | Fga_128 |
| MouseValid_MetsMR_129_Fga | MetsMR_129 | Fga | CCTTCTGCTCTGATGATGAC | Mouse Valid | 129 | Fga_129 |
| MouseValid_MetsMR_130_Fga | MetsMR_130 | Fga | AGGATTCTAACTCACTGACC | Mouse Valid | 130 | Fga_130 |
| MouseValid_MetsMR_131_Gnal | MetsMR_131 | Gnal | AAATGTCAAAGATGCGATCG | Mouse Valid | 131 | Gnal_131 |
| MouseValid_MetsMR_132_Gnal | MetsMR_132 | Gnal | ATTGTGCACAGTGATCAGC | Mouse Valid | 132 | Gnal_132 |
| MouseValid_MetsMR_133_Gnal | MetsMR_133 | Gnal | GGTTGAAGCCATTGACGTGC | Mouse Valid | 133 | Gnal_133 |
| MouseValid_MetsMR_134_Gnal | MetsMR_134 | Gnal | CTCGTTGGATCTCTCAAAGC | Mouse Valid | 134 | Gnal_134 |
| MouseValid_MetsMR_135_Gnal | MetsMR_135 | Gnal | CCAACCCTGAGAACCAGTTC | Mouse Valid | 135 | Gnal_135 |
| MouseValid_MetsMR_136_Gnal | MetsMR_136 | Gnal | CACTGACTTTGAATATTCCC | Mouse Valid | 136 | Gnal_136 |
| MouseValid_MetsMR_137_Gnal | MetsMR_137 | Gnal | TTCACAGGGGCTGGTGAGTC | Mouse Valid | 137 | Gnal_137 |
| MouseValid_MetsMR_138_Gnal | MetsMR_138 | Gnal | GGAAAAGAAGCAGAAAATTC | Mouse Valid | 138 | Gnal_138 |

FIG. 18 CONTINUED

| | | | | | | |
|---|---|---|---|---|---|---|
| MouseValid_MetsMR_139_Gnal | MetsMR_139 | Gnal | TGCTCTTGATATAATCTGAC | MouseValid | 139 | Gnal_139 |
| MouseValid_MetsMR_140_Gnal | MetsMR_140 | Gnal | GAATATTCAAAGTCAGTGAT | MouseValid | 140 | Gnal_140 |
| MouseValid_MetsMR_141_Gorasp1 | MetsMR_141 | Gorasp1 | CACCAGCCTCGAGTGCCCGA | MouseValid | 141 | Gorasp1_141 |
| MouseValid_MetsMR_142_Gorasp1 | MetsMR_142 | Gorasp1 | CACATGCCACACGTGTTCGC | MouseValid | 142 | Gorasp1_142 |
| MouseValid_MetsMR_143_Gorasp1 | MetsMR_143 | Gorasp1 | CTGGCCGCCCACATGTTGC | MouseValid | 143 | Gorasp1_143 |
| MouseValid_MetsMR_144_Gorasp1 | MetsMR_144 | Gorasp1 | ACAGGTACAAGAGAACTCGC | MouseValid | 144 | Gorasp1_144 |
| MouseValid_MetsMR_145_Gorasp1 | MetsMR_145 | Gorasp1 | TTATACACCATCAGCTTCAG | MouseValid | 145 | Gorasp1_145 |
| MouseValid_MetsMR_146_Gorasp1 | MetsMR_146 | Gorasp1 | CCAACTATGTAGTCTGTGTA | MouseValid | 146 | Gorasp1_146 |
| MouseValid_MetsMR_147_Gorasp1 | MetsMR_147 | Gorasp1 | TACTCTCATTGAGTCCCATG | MouseValid | 147 | Gorasp1_147 |
| MouseValid_MetsMR_148_Gorasp1 | MetsMR_148 | Gorasp1 | CCTTACACAGACTACATAGT | MouseValid | 148 | Gorasp1_148 |
| MouseValid_MetsMR_149_Gorasp1 | MetsMR_149 | Gorasp1 | GAAGCTACAGAAGCGCACGC | MouseValid | 149 | Gorasp1_149 |
| MouseValid_MetsMR_150_Gorasp1 | MetsMR_150 | Gorasp1 | TGCGCTTCTGTAGCTTCCGC | MouseValid | 150 | Gorasp1_150 |
| MouseValid_MetsMR_151_Hdgf | MetsMR_151 | Hdgf | TCTTATCACCGTCACCCTCA | MouseValid | 151 | Hdgf_151 |
| MouseValid_MetsMR_152_Hdgf | MetsMR_152 | Hdgf | CGAGAACAACCCTACAGTCA | MouseValid | 152 | Hdgf_152 |
| MouseValid_MetsMR_153_Hdgf | MetsMR_153 | Hdgf | CTCCTATCCAGGGCATTCCT | MouseValid | 153 | Hdgf_153 |
| MouseValid_MetsMR_154_Hdgf | MetsMR_154 | Hdgf | TGAGAGGCCCCTGCCTGTAG | MouseValid | 154 | Hdgf_154 |
| MouseValid_MetsMR_155_Hdgf | MetsMR_155 | Hdgf | GGTGGAGCCCGAAGCCCATG | MouseValid | 155 | Hdgf_155 |
| MouseValid_MetsMR_156_Hdgf | MetsMR_156 | Hdgf | TCTCATGATCTCTGACGCCC | MouseValid | 156 | Hdgf_156 |
| MouseValid_MetsMR_157_Hdgf | MetsMR_157 | Hdgf | GGGTCCCAAAAAAAAGACT | MouseValid | 157 | Hdgf_157 |
| MouseValid_MetsMR_158_Hdgf | MetsMR_158 | Hdgf | CCAGATTCATGAGATGCCTG | MouseValid | 158 | Hdgf_158 |
| MouseValid_MetsMR_159_Hdgf | MetsMR_159 | Hdgf | CAGCGACGAAGAAGGGAAAC | MouseValid | 159 | Hdgf_159 |
| MouseValid_MetsMR_160_Hdgf | MetsMR_160 | Hdgf | CTGTTTCTTCCACCTCTAC | MouseValid | 160 | Hdgf_160 |

| | | | | |
|---|---|---|---|---|
| MouseValid_MetsMIR_161_Jnk1 | MetsMIR_161 | Jnk1 | CTTAAGTAGTACTCTGGAACCTG | MouseValid_161 | Jnk1_161 |
| MouseValid_MetsMIR_162_Jnk1 | MetsMIR_162 | Jnk1 | TTACGTATTACCAGTCTCTGTC | MouseValid_162 | Jnk1_162 |
| MouseValid_MetsMIR_163_Jnk1 | MetsMIR_163 | Jnk1 | CTGGACCAATTTGTGCCAAA | MouseValid_163 | Jnk1_163 |
| MouseValid_MetsMIR_164_Jnk1 | MetsMIR_164 | Jnk1 | ATGTGTTGCACCAATGCAAC | MouseValid_164 | Jnk1_164 |
| MouseValid_MetsMIR_165_Jnk1 | MetsMIR_165 | Jnk1 | AGGCTCATCCAAGCAATTGG | MouseValid_165 | Jnk1_165 |
| MouseValid_MetsMIR_166_Jnk1 | MetsMIR_166 | Jnk1 | AAAAAGAACTCTGCCCGTT | MouseValid_166 | Jnk1_166 |
| MouseValid_MetsMIR_167_Jnk1 | MetsMIR_167 | Jnk1 | ATGAAAAGAAACTATCGTGC | MouseValid_167 | Jnk1_167 |
| MouseValid_MetsMIR_168_Jnk1 | MetsMIR_168 | Jnk1 | CAAGCTCTGCTAATAGTAAC | MouseValid_168 | Jnk1_168 |
| MouseValid_MetsMIR_169_Jnk1 | MetsMIR_169 | Jnk1 | TTCAATCAGGAGCGAGCCAA | MouseValid_169 | Jnk1_169 |
| MouseValid_MetsMIR_170_Jnk1 | MetsMIR_170 | Jnk1 | CGTGTTAACCAACCAGCAGA | MouseValid_170 | Jnk1_170 |
| MouseValid_MetsMIR_171_Lig4 | MetsMIR_171 | Lig4 | AGCATCGTGCGAGCTCCAC | MouseValid_171 | Lig4_171 |
| MouseValid_MetsMIR_172_Lig4 | MetsMIR_172 | Lig4 | ATGATGTTGTCAAGCCCGAG | MouseValid_172 | Lig4_172 |
| MouseValid_MetsMIR_173_Lig4 | MetsMIR_173 | Lig4 | CCATTTATTCACAATGCGTT | MouseValid_173 | Lig4_173 |
| MouseValid_MetsMIR_174_Lig4 | MetsMIR_174 | Lig4 | ATTAGTCCACTGACGTACTC | MouseValid_174 | Lig4_174 |
| MouseValid_MetsMIR_175_Lig4 | MetsMIR_175 | Lig4 | TACAACTATACCGACCAGTT | MouseValid_175 | Lig4_175 |
| MouseValid_MetsMIR_176_Lig4 | MetsMIR_176 | Lig4 | ACTTAGAATGTCGTTATTCC | MouseValid_176 | Lig4_176 |
| MouseValid_MetsMIR_177_Lig4 | MetsMIR_177 | Lig4 | AGACAAAAACATGCGTGCCG | MouseValid_177 | Lig4_177 |
| MouseValid_MetsMIR_178_Lig4 | MetsMIR_178 | Lig4 | TAATCTCGTGGCTTCAATTC | MouseValid_178 | Lig4_178 |
| MouseValid_MetsMIR_179_Lig4 | MetsMIR_179 | Lig4 | ATTAAACCAGAGTACGTCAG | MouseValid_179 | Lig4_179 |
| MouseValid_MetsMIR_180_Lig4 | MetsMIR_180 | Lig4 | TGAATTAGACGTCCTAATTG | MouseValid_180 | Lig4_180 |
| MouseValid_MetsMIR_181_Mk2 | MetsMIR_181 | Mk2 | TCTTACGTGGCATGATGCCC | MouseValid_181 | Mk2_181 |
| MouseValid_MetsMIR_182_Mk2 | MetsMIR_182 | Mk2 | GCCTCATTGCCACTAGTCT | MouseValid_182 | Mk2_182 |

| | | | | | |
|---|---|---|---|---|---|
| MouseValid_MetsMR_183_Mk2 | MetsMR_183 | Mk2 | CCCAAGAGACTAGTGGCAAATG | Mouse Valid 183 | Mk2_183 |
| MouseValid_MetsMR_184_Mk2 | MetsMR_184 | Mk2 | TTAACAGGAAGTATAGTTCTT | Mouse Valid 184 | Mk2_184 |
| MouseValid_MetsMR_185_Mk2 | MetsMR_185 | Mk2 | TCCTTTGTTGCAGCCTCAGC | Mouse Valid 185 | Mk2_185 |
| MouseValid_MetsMR_186_Mk2 | MetsMR_186 | Mk2 | CCTGTGCTCACAGACTGAAGC | Mouse Valid 186 | Mk2_186 |
| MouseValid_MetsMR_187_Mk2 | MetsMR_187 | Mk2 | GAAGCCTTGTGGCTGCTTCT | Mouse Valid 187 | Mk2_187 |
| MouseValid_MetsMR_188_Mk2 | MetsMR_188 | Mk2 | TCCTCAGCAGTTAAAATTTC | Mouse Valid 188 | Mk2_188 |
| MouseValid_MetsMR_189_Mk2 | MetsMR_189 | Mk2 | GGCTGCATTTAGAACCTGCC | Mouse Valid 189 | Mk2_189 |
| MouseValid_MetsMR_190_Mk2 | MetsMR_190 | Mk2 | AGGTTCAAATGCAGCCTGC | Mouse Valid 190 | Mk2_190 |
| MouseValid_MetsMR_191_Mreg | MetsMR_191 | Mreg | CCTCTCCAGAGTCGCTCCAA | Mouse Valid 191 | Mreg_191 |
| MouseValid_MetsMR_192_Mreg | MetsMR_192 | Mreg | GCTCTCCGAGAGGTACCTCT | Mouse Valid 192 | Mreg_192 |
| MouseValid_MetsMR_193_Mreg | MetsMR_193 | Mreg | CTTCCCTGCGGATCTGCCGC | Mouse Valid 193 | Mreg_193 |
| MouseValid_MetsMR_194_Mreg | MetsMR_194 | Mreg | CCTCTAAGAGATTCGTCTCCAT | Mouse Valid 194 | Mreg_194 |
| MouseValid_MetsMR_195_Mreg | MetsMR_195 | Mreg | AACAATCCGTATTCCTCCTT | Mouse Valid 195 | Mreg_195 |
| MouseValid_MetsMR_196_Mreg | MetsMR_196 | Mreg | CCTCTATCTTCCCGCCAGC | Mouse Valid 196 | Mreg_196 |
| MouseValid_MetsMR_197_Mreg | MetsMR_197 | Mreg | TCCACCAGGCATGGGACCCC | Mouse Valid 197 | Mreg_197 |
| MouseValid_MetsMR_198_Mreg | MetsMR_198 | Mreg | CAAATGTACCCCAAGAAACC | Mouse Valid 198 | Mreg_198 |
| MouseValid_MetsMR_199_Mreg | MetsMR_199 | Mreg | TATCGTCATCCGCCTCTGTG | Mouse Valid 199 | Mreg_199 |
| MouseValid_MetsMR_200_Mreg | MetsMR_200 | Mreg | CCGGGAGATGCTGTTAAAGC | Mouse Valid 200 | Mreg_200 |
| MouseValid_MetsMR_201_Mrch6 | MetsMR_201 | Mrch6 | CTACAGGCCACTCGCGCTCT | Mouse Valid 201 | Mrch6_201 |
| MouseValid_MetsMR_202_Mrch6 | MetsMR_202 | Mrch6 | CATCTCTCCAAGAGCGCGAG | Mouse Valid 202 | Mrch6_202 |
| MouseValid_MetsMR_203_Mrch6 | MetsMR_203 | Mrch6 | GCCCGTTTACTCGCTGATTC | Mouse Valid 203 | Mrch6_203 |
| MouseValid_MetsMR_204_Mrch6 | MetsMR_204 | Mrch6 | CCGGTCCGGGGTAGCGAAC | Mouse Valid 204 | Mrch6_204 |

FIG. 18 CONTINUED

| | | | | | |
|---|---|---|---|---|---|
| MouseValid_MetsMIR_205_Mroh6 | MetsMIR_205 | Mroh6 | TATACAACGCAAGGTCTGCA | Mouse Valid | 205 | Mroh6_205 |
| MouseValid_MetsMIR_206_Mroh6 | MetsMIR_206 | Mroh6 | TGTGGCGGCTCCCGAGTCTG | Mouse Valid | 206 | Mroh6_206 |
| MouseValid_MetsMIR_207_Mroh6 | MetsMIR_207 | Mroh6 | GCAGCCCACGCACCAGACCG | Mouse Valid | 207 | Mroh6_207 |
| MouseValid_MetsMIR_208_Mroh6 | MetsMIR_208 | Mroh6 | GGCTGGCTATGCCGGGACCC | Mouse Valid | 208 | Mroh6_208 |
| MouseValid_MetsMIR_209_Mroh6 | MetsMIR_209 | Mroh6 | TTTGGCAGCCCTTCCCACCGA | Mouse Valid | 209 | Mroh6_209 |
| MouseValid_MetsMIR_210_Mroh6 | MetsMIR_210 | Mroh6 | AGCCGGAATCAGCGAGTAAA | Mouse Valid | 210 | Mroh6_210 |
| MouseValid_MetsMIR_211_Mxra7 | MetsMIR_211 | Mxra7 | CCACGGCGGATGGAGTCGC | Mouse Valid | 211 | Mxra7_211 |
| MouseValid_MetsMIR_212_Mxra7 | MetsMIR_212 | Mxra7 | CCCGTCTGACATCTGCCAA | Mouse Valid | 212 | Mxra7_212 |
| MouseValid_MetsMIR_213_Mxra7 | MetsMIR_213 | Mxra7 | ACTCCGACTCTATGACATGT | Mouse Valid | 213 | Mxra7_213 |
| MouseValid_MetsMIR_214_Mxra7 | MetsMIR_214 | Mxra7 | GCCACGGCTCGGACTGGCT | Mouse Valid | 214 | Mxra7_214 |
| MouseValid_MetsMIR_215_Mxra7 | MetsMIR_215 | Mxra7 | GCCACCACTGAAGAACTG | Mouse Valid | 215 | Mxra7_215 |
| MouseValid_MetsMIR_216_Mxra7 | MetsMIR_216 | Mxra7 | TGCTCACCGTCTTCTTCCTC | Mouse Valid | 216 | Mxra7_216 |
| MouseValid_MetsMIR_217_Mxra7 | MetsMIR_217 | Mxra7 | TGGCTTCCCCTCAGCTGCCC | Mouse Valid | 217 | Mxra7_217 |
| MouseValid_MetsMIR_218_Mxra7 | MetsMIR_218 | Mxra7 | GATGATGACCAAAGAAGAAC | Mouse Valid | 218 | Mxra7_218 |
| MouseValid_MetsMIR_219_Mxra7 | MetsMIR_219 | Mxra7 | CGCCAGCGCCCGTGACCAGCG | Mouse Valid | 219 | Mxra7_219 |
| MouseValid_MetsMIR_220_Mxra7 | MetsMIR_220 | Mxra7 | ACCGGAGCCAGTCCGAGCGG | Mouse Valid | 220 | Mxra7_220 |
| MouseValid_MetsMIR_221_Nf2 | MetsMIR_221 | Nf2 | GATCCGCACCGTGAATGTCT | Mouse Valid | 221 | Nf2_221 |
| MouseValid_MetsMIR_222_Nf2 | MetsMIR_222 | Nf2 | GAAGCTCATGCGAGAAGCGA | Mouse Valid | 222 | Nf2_222 |
| MouseValid_MetsMIR_223_Nf2 | MetsMIR_223 | Nf2 | CTTGGCGTCATATGCTGTCC | Mouse Valid | 223 | Nf2_223 |
| MouseValid_MetsMIR_224_Nf2 | MetsMIR_224 | Nf2 | CACTGGGGCTTCGGGAAACC | Mouse Valid | 224 | Nf2_224 |
| MouseValid_MetsMIR_225_Nf2 | MetsMIR_225 | Nf2 | TGGACTGCAGTATACAATCA | Mouse Valid | 225 | Nf2_225 |
| MouseValid_MetsMIR_226_Nf2 | MetsMIR_226 | Nf2 | GTTGGATCATGATGTTTCGA | Mouse Valid | 226 | Nf2_226 |

FIG. 18 CONTINUED

| | | | | | |
|---|---|---|---|---|---|
| MouseValid_MetsMR_227_Nf2 | MetsMR_227 | Nf2 | AAAGGTCTACTGCCCTCCCG | MouseValid_227 | Nf2_227 |
| MouseValid_MetsMR_228_Nf2 | MetsMR_228 | Nf2 | ACCAGTTACCTTTCACTTCC | MouseValid_228 | Nf2_228 |
| MouseValid_MetsMR_229_Nf2 | MetsMR_229 | Nf2 | CGTCACCATGGACGCCGAGA | MouseValid_229 | Nf2_229 |
| MouseValid_MetsMR_230_Nf2 | MetsMR_230 | Nf2 | AGCCCAAGACATTCACGGTG | MouseValid_230 | Nf2_230 |
| MouseValid_MetsMR_231_Pcdh1 | MetsMR_231 | Pcdh1 | CTGGGCCGTGCTAAGCCGAA | MouseValid_231 | Pcdh1_231 |
| MouseValid_MetsMR_232_Pcdh1 | MetsMR_232 | Pcdh1 | GTTACACCGCCTCGTGGTGA | MouseValid_232 | Pcdh1_232 |
| MouseValid_MetsMR_233_Pcdh1 | MetsMR_233 | Pcdh1 | GTAGGTAGGCCGCTCGAATT | MouseValid_233 | Pcdh1_233 |
| MouseValid_MetsMR_234_Pcdh1 | MetsMR_234 | Pcdh1 | CGGCCATTGGGGCCGGGGTCA | MouseValid_234 | Pcdh1_234 |
| MouseValid_MetsMR_235_Pcdh1 | MetsMR_235 | Pcdh1 | GCCCCGACCATCGAGATCCG | MouseValid_235 | Pcdh1_235 |
| MouseValid_MetsMR_236_Pcdh1 | MetsMR_236 | Pcdh1 | CGTGGCAAGCCCCCTCGCTA | MouseValid_236 | Pcdh1_236 |
| MouseValid_MetsMR_237_Pcdh1 | MetsMR_237 | Pcdh1 | CAGTACTAGTGCTACTGC | MouseValid_237 | Pcdh1_237 |
| MouseValid_MetsMR_238_Pcdh1 | MetsMR_238 | Pcdh1 | CGTGTAGTCAATCTCCGCAT | MouseValid_238 | Pcdh1_238 |
| MouseValid_MetsMR_239_Pcdh1 | MetsMR_239 | Pcdh1 | GCGTGTCCAGGCTATGGACG | MouseValid_239 | Pcdh1_239 |
| MouseValid_MetsMR_240_Pcdh1 | MetsMR_240 | Pcdh1 | CCCCTGGATATTGACATCGC | MouseValid_240 | Pcdh1_240 |
| MouseValid_MetsMR_241_Polr2c | MetsMR_241 | Polr2c | ATCGCAGAGGTGCCCATAAT | MouseValid_241 | Polr2c_241 |
| MouseValid_MetsMR_242_Polr2c | MetsMR_242 | Polr2c | AGACACTAACCGGAATAACC | MouseValid_242 | Polr2c_242 |
| MouseValid_MetsMR_243_Polr2c | MetsMR_243 | Polr2c | GTAGGGTGGCCAATTCCATT | MouseValid_243 | Polr2c_243 |
| MouseValid_MetsMR_244_Polr2c | MetsMR_244 | Polr2c | GCGGATGAATTCATCATGA | MouseValid_244 | Polr2c_244 |
| MouseValid_MetsMR_245_Polr2c | MetsMR_245 | Polr2c | GTCAATCTGAACCCAGTCGA | MouseValid_245 | Polr2c_245 |
| MouseValid_MetsMR_246_Polr2c | MetsMR_246 | Polr2c | CCACAATGTCATCACTAGTG | MouseValid_246 | Polr2c_246 |
| MouseValid_MetsMR_247_Polr2c | MetsMR_247 | Polr2c | CCTCACTAGTGATGACATTG | MouseValid_247 | Polr2c_247 |
| MouseValid_MetsMR_248_Polr2c | MetsMR_248 | Polr2c | GTTCTGCCCCTGAGTGTTCTG | MouseValid_248 | Polr2c_248 |

| | | | | | |
|---|---|---|---|---|---|
| MouseValid_MetsMR_249_Psip2c | MetsMR_249 | Psip2c | TGCGATGAAGACCCTCGAA | MouseValid | 249 | Psip2c_249 |
| MouseValid_MetsMR_250_Psip2c | MetsMR_250 | Psip2c | TCAGATTGACGCCAACTCCT | MouseValid | 250 | Psip2c_250 |
| MouseValid_MetsMR_251_Psip3gi | MetsMR_251 | Psip3gi | CTATTGACAACGCCATCGAT | MouseValid | 251 | Psip3gi_251 |
| MouseValid_MetsMR_252_Psip3gi | MetsMR_252 | Psip3gi | CTTACCAGGGTTCCAATCGA | MouseValid | 252 | Psip3gi_252 |
| MouseValid_MetsMR_253_Psip3gi | MetsMR_253 | Psip3gi | GTGAGCTCAAGATTCGAGTG | MouseValid | 253 | Psip3gi_253 |
| MouseValid_MetsMR_254_Psip3gi | MetsMR_254 | Psip3gi | CCCTAAGAGCCACAGACGATA | MouseValid | 254 | Psip3gi_254 |
| MouseValid_MetsMR_255_Psip3gi | MetsMR_255 | Psip3gi | CACTCGAATCTTGAGCTCAC | MouseValid | 255 | Psip3gi_255 |
| MouseValid_MetsMR_256_Psip3gi | MetsMR_256 | Psip3gi | CCACCATTATCCTTCCCAAG | MouseValid | 256 | Psip3gi_256 |
| MouseValid_MetsMR_257_Psip3gi | MetsMR_257 | Psip3gi | GGCAGCTCCCCTACTTCATC | MouseValid | 257 | Psip3gi_257 |
| MouseValid_MetsMR_258_Psip3gi | MetsMR_258 | Psip3gi | AGAGGAGGGGGAGTATGTCC | MouseValid | 258 | Psip3gi_258 |
| MouseValid_MetsMR_259_Psip3gi | MetsMR_259 | Psip3gi | GGAGACGATACAGAAACTAG | MouseValid | 259 | Psip3gi_259 |
| MouseValid_MetsMR_260_Psip3gi | MetsMR_260 | Psip3gi | TCCTTATCGTCTGTGCTCTT | MouseValid | 260 | Psip3gi_260 |
| MouseValid_MetsMR_261_Ppp2r4 | MetsMR_261 | Ppp2r4 | CACTTCTTGATACGCTGGAT | MouseValid | 261 | Ppp2r4_261 |
| MouseValid_MetsMR_262_Ppp2r4 | MetsMR_262 | Ppp2r4 | TGTGCCATAGTCAATTCGTG | MouseValid | 262 | Ppp2r4_262 |
| MouseValid_MetsMR_263_Ppp2r4 | MetsMR_263 | Ppp2r4 | CTCAGAGACTTTGTAGTCGA | MouseValid | 263 | Ppp2r4_263 |
| MouseValid_MetsMR_264_Ppp2r4 | MetsMR_264 | Ppp2r4 | CGCTTCCATTTGCCCATATC | MouseValid | 264 | Ppp2r4_264 |
| MouseValid_MetsMR_265_Ppp2r4 | MetsMR_265 | Ppp2r4 | GATTGATGAAACCCCGCCAG | MouseValid | 265 | Ppp2r4_265 |
| MouseValid_MetsMR_266_Ppp2r4 | MetsMR_266 | Ppp2r4 | AACTCCACACGAATTGACTA | MouseValid | 266 | Ppp2r4_266 |
| MouseValid_MetsMR_267_Ppp2r4 | MetsMR_267 | Ppp2r4 | TAGGCATATGCTGACTACAT | MouseValid | 267 | Ppp2r4_267 |
| MouseValid_MetsMR_268_Ppp2r4 | MetsMR_268 | Ppp2r4 | ATGATAAAGTTCTGAGTAGT | MouseValid | 268 | Ppp2r4_268 |
| MouseValid_MetsMR_269_Ppp2r4 | MetsMR_269 | Ppp2r4 | TTCACAGGCCATCGAGAAGC | MouseValid | 269 | Ppp2r4_269 |
| MouseValid_MetsMR_270_Ppp2r4 | MetsMR_270 | Ppp2r4 | CAGTCTCACCTGATCAAGTT | MouseValid | 270 | Ppp2r4_270 |

| | | | | | |
|---|---|---|---|---|---|
| MouseValid_MetsMIR_271_Pten | MetsMIR_271 | Pten | ACCGCCAAATTAACTGCAG | Mouse Valid | 271 | Pten_271 |
| MouseValid_MetsMIR_272_Pten | MetsMIR_272 | Pten | GCAGCAATTCACTGTAAAGC | Mouse Valid | 272 | Pten_272 |
| MouseValid_MetsMIR_273_Pten | MetsMIR_273 | Pten | TGTTCATCTTCACTTAGCCAT | Mouse Valid | 273 | Pten_273 |
| MouseValid_MetsMIR_274_Pten | MetsMIR_274 | Pten | ACAATATTGATGATGTAGTA | Mouse Valid | 274 | Pten_274 |
| MouseValid_MetsMIR_275_Pten | MetsMIR_275 | Pten | CATACCTCTGCAGTTAAATT | Mouse Valid | 275 | Pten_275 |
| MouseValid_MetsMIR_276_Pten | MetsMIR_276 | Pten | AATCCCATAGCAATAATATT | Mouse Valid | 276 | Pten_276 |
| MouseValid_MetsMIR_277_Pten | MetsMIR_277 | Pten | ACAGATTGTATATCTTGTAA | Mouse Valid | 277 | Pten_277 |
| MouseValid_MetsMIR_278_Pten | MetsMIR_278 | Pten | GGTTTGATAAGTTCTAGCTG | Mouse Valid | 278 | Pten_278 |
| MouseValid_MetsMIR_279_Pten | MetsMIR_279 | Pten | TCTGTGAAGATCTTGACCAA | Mouse Valid | 279 | Pten_279 |
| MouseValid_MetsMIR_280_Pten | MetsMIR_280 | Pten | TTATCCAAATATTATTGCTA | Mouse Valid | 280 | Pten_280 |
| MouseValid_MetsMIR_281_Ptges2 | MetsMIR_281 | Ptges2 | CGTGTACCGAACACCCGCTG | Mouse Valid | 281 | Ptges2_281 |
| MouseValid_MetsMIR_282_Ptges2 | MetsMIR_282 | Ptges2 | CTTCGACTACATTGTCCGTG | Mouse Valid | 282 | Ptges2_282 |
| MouseValid_MetsMIR_283_Ptges2 | MetsMIR_283 | Ptges2 | CACTTATTACCCACCCATGA | Mouse Valid | 283 | Ptges2_283 |
| MouseValid_MetsMIR_284_Ptges2 | MetsMIR_284 | Ptges2 | TAGTGCCCTCAAGACCTACC | Mouse Valid | 284 | Ptges2_284 |
| MouseValid_MetsMIR_285_Ptges2 | MetsMIR_285 | Ptges2 | AGAAGGGACATGTCTTGTAC | Mouse Valid | 285 | Ptges2_285 |
| MouseValid_MetsMIR_286_Ptges2 | MetsMIR_286 | Ptges2 | CCAGTACTTGTTGCAAAACT | Mouse Valid | 286 | Ptges2_286 |
| MouseValid_MetsMIR_287_Ptges2 | MetsMIR_287 | Ptges2 | GAGTGACTTACCCTGAAACC | Mouse Valid | 287 | Ptges2_287 |
| MouseValid_MetsMIR_288_Ptges2 | MetsMIR_288 | Ptges2 | TGGAGGTGAATCCCGTGAGA | Mouse Valid | 288 | Ptges2_288 |
| MouseValid_MetsMIR_289_Ptges2 | MetsMIR_289 | Ptges2 | AGCGGGTGTTCGGTACACGT | Mouse Valid | 289 | Ptges2_289 |
| MouseValid_MetsMIR_290_Ptges2 | MetsMIR_290 | Ptges2 | GGCAGCCGCGCCCACATACT | Mouse Valid | 290 | Ptges2_290 |
| MouseValid_MetsMIR_291_Rhoh | MetsMIR_291 | Rhoh | ACCCGTATTCTCGTACACCG | Mouse Valid | 291 | Rhoh_291 |
| MouseValid_MetsMIR_292_Rhoh | MetsMIR_292 | Rhoh | ACCCACGGTGTACGAGAATA | Mouse Valid | 292 | Rhoh_292 |

FIG. 18 CONTINUED

| | | | | | |
|---|---|---|---|---|---|
| MouseValid_MetsMiR_293_Rhoh | MetsMiR_293 | Rhoh | CCCTTCTATGGCATTGATGC | MouseValid | 293 | Rhoh_293 |
| MouseValid_MetsMiR_294_Rhoh | MetsMiR_294 | Rhoh | ACGACGCCCTTCAGAAGTATC | MouseValid | 294 | Rhoh_294 |
| MouseValid_MetsMiR_295_Rhoh | MetsMiR_295 | Rhoh | GAGCAACCTACCCTGTACCC | MouseValid | 295 | Rhoh_295 |
| MouseValid_MetsMiR_296_Rhoh | MetsMiR_296 | Rhoh | CAGGGGCCGGATACTTCTGA | MouseValid | 296 | Rhoh_296 |
| MouseValid_MetsMiR_297_Rhoh | MetsMiR_297 | Rhoh | GAGCTCAATCAAGTGCGTGC | MouseValid | 297 | Rhoh_297 |
| MouseValid_MetsMiR_298_Rhoh | MetsMiR_298 | Rhoh | GTCCTACCAGCAGGCAGACG | MouseValid | 298 | Rhoh_298 |
| MouseValid_MetsMiR_299_Rhoh | MetsMiR_299 | Rhoh | TCCTGCATCAATGCCATAGA | MouseValid | 299 | Rhoh_299 |
| MouseValid_MetsMiR_300_Rhoh | MetsMiR_300 | Rhoh | CAAATACCGCTGTACTCCC | MouseValid | 300 | Rhoh_300 |
| MouseValid_MetsMiR_301_Rhox13 | MetsMiR_301 | Rhox13 | CGAGTCGTCATCACTCTCGT | MouseValid | 301 | Rhox13_301 |
| MouseValid_MetsMiR_302_Rhox13 | MetsMiR_302 | Rhox13 | CGACTCGAGCACCAGCGACG | MouseValid | 302 | Rhox13_302 |
| MouseValid_MetsMiR_303_Rhox13 | MetsMiR_303 | Rhox13 | ATGCTGAGAAATATTCCGCC | MouseValid | 303 | Rhox13_303 |
| MouseValid_MetsMiR_304_Rhox13 | MetsMiR_304 | Rhox13 | CCCTCGCTTCGCTCTCCGAT | MouseValid | 304 | Rhox13_304 |
| MouseValid_MetsMiR_305_Rhox13 | MetsMiR_305 | Rhox13 | AAGAACTTTGAATGCCCTG | MouseValid | 305 | Rhox13_305 |
| MouseValid_MetsMiR_306_Rhox13 | MetsMiR_306 | Rhox13 | CTGACCTTCACTTTGACCTC | MouseValid | 306 | Rhox13_306 |
| MouseValid_MetsMiR_307_Rhox13 | MetsMiR_307 | Rhox13 | ATGGCGGTCCAGGGCGACGA | MouseValid | 307 | Rhox13_307 |
| MouseValid_MetsMiR_308_Rhox13 | MetsMiR_308 | Rhox13 | CGACTGCCACTGTGCCAAG | MouseValid | 308 | Rhox13_308 |
| MouseValid_MetsMiR_309_Rhox13 | MetsMiR_309 | Rhox13 | ATCTGAAGTATCCTCGTCGC | MouseValid | 309 | Rhox13_309 |
| MouseValid_MetsMiR_310_Rhox13 | MetsMiR_310 | Rhox13 | CATGTTCGCCGTCGTCGCCG | MouseValid | 310 | Rhox13_310 |
| MouseValid_MetsMiR_311_Sbp | MetsMiR_311 | Sbp | AGCCAATCCCTCGACGCAG | MouseValid | 311 | Sbp_311 |
| MouseValid_MetsMiR_312_Sbp | MetsMiR_312 | Sbp | TGGGAAATATCAATGCTAA | MouseValid | 312 | Sbp_312 |
| MouseValid_MetsMiR_313_Sbp | MetsMiR_313 | Sbp | CTCACTCTGGGCTCCTGCATG | MouseValid | 313 | Sbp_313 |
| MouseValid_MetsMiR_314_Sbp | MetsMiR_314 | Sbp | CATGCTGCTGTTGCTGACTT | MouseValid | 314 | Sbp_314 |

| | | | | | |
|---|---|---|---|---|---|
| MouseValid_MetsMiR_315_Sbp | MetsMiR_315 | Sbp | ACTTGCCAGCAGCATTCCCC | MouseValid | 315 | Sbp_315 |
| MouseValid_MetsMiR_316_Sbp | MetsMiR_316 | Sbp | GATGTCCTGGGGAATGCTGC | MouseValid | 316 | Sbp_316 |
| MouseValid_MetsMiR_317_Sbp | MetsMiR_317 | Sbp | GCACCGGGCCTTCTGCGTCAG | MouseValid | 317 | Sbp_317 |
| MouseValid_MetsMiR_318_Sbp | MetsMiR_318 | Sbp | GGTCGATACTTCAGTGACAC | MouseValid | 318 | Sbp_318 |
| MouseValid_MetsMiR_319_Sbp | MetsMiR_319 | Sbp | TCGACCCCTTCTAACACCAA | MouseValid | 319 | Sbp_319 |
| MouseValid_MetsMiR_320_Sbp | MetsMiR_320 | Sbp | TATCTTCCTTGTTATTATAA | MouseValid | 320 | Sbp_320 |
| MouseValid_MetsMiR_321_Sggb2b3 | MetsMiR_321 | Sgpb2b3 | GTCTATTTGAGCACTGTCTC | MouseValid | 321 | Sgpb2b3_321 |
| MouseValid_MetsMiR_322_Sgpb2b3 | MetsMiR_322 | Sgpb2b3 | TCTTATTTCAACCCTACTGA | MouseValid | 322 | Sgpb2b3_322 |
| MouseValid_MetsMiR_323_Sgpb2b3 | MetsMiR_323 | Sgpb2b3 | AGCCAAGCTCTCCAATCACC | MouseValid | 323 | Sgpb2b3_323 |
| MouseValid_MetsMiR_324_Sgpb2b3 | MetsMiR_324 | Sgpb2b3 | TAAGTGTGATTACCAAGAAA | MouseValid | 324 | Sgpb2b3_324 |
| MouseValid_MetsMiR_325_Sgpb2b3 | MetsMiR_325 | Sgpb2b3 | TAACTTCTACATCCATTTCT | MouseValid | 325 | Sgpb2b3_325 |
| MouseValid_MetsMiR_326_Sgpb2b3 | MetsMiR_326 | Sgpb2b3 | TTCCTGGTGATTGGAGAGCT | MouseValid | 326 | Sgpb2b3_326 |
| MouseValid_MetsMiR_327_Sgpb2b3 | MetsMiR_327 | Sgpb2b3 | AGGACTAAAAGCTAAAAGTC | MouseValid | 327 | Sgpb2b3_327 |
| MouseValid_MetsMiR_328_Sgpb2b3 | MetsMiR_328 | Sgpb2b3 | CTCTTTGTTTCACCATCAGT | MouseValid | 328 | Sgpb2b3_328 |
| MouseValid_MetsMiR_329_Sgpb2b3 | MetsMiR_329 | Sgpb2b3 | GAAGCATGTGCTTCTTTCTT | MouseValid | 329 | Sgpb2b3_329 |
| MouseValid_MetsMiR_330_Sgpb2b3 | MetsMiR_330 | Sgpb2b3 | AAAGAGCTTCAAAAAAATCC | MouseValid | 330 | Sgpb2b3_330 |
| MouseValid_MetsMiR_331_Sik2 | MetsMiR_331 | Sik2 | CTTTAAAACTGGTGAACTGC | MouseValid | 331 | Sik2_331 |
| MouseValid_MetsMiR_332_Sik2 | MetsMiR_332 | Sik2 | ATCCTAATAGATTTCGGCTT | MouseValid | 332 | Sik2_332 |
| MouseValid_MetsMiR_333_Sik2 | MetsMiR_333 | Sik2 | CACAAGGTACAACATACTTT | MouseValid | 333 | Sik2_333 |
| MouseValid_MetsMiR_334_Sik2 | MetsMiR_334 | Sik2 | GGTCTTCTGTGCCACTACCTTC | MouseValid | 334 | Sik2_334 |
| MouseValid_MetsMiR_335_Sik2 | MetsMiR_335 | Sik2 | TCACATCATTAAACTGTATC | MouseValid | 335 | Sik2_335 |
| MouseValid_MetsMiR_336_Sik2 | MetsMiR_336 | Sik2 | TATTCATGTTGTTATCCAGC | MouseValid | 336 | Sik2_336 |

| | | | | | |
|---|---|---|---|---|---|
| MouseValid_MetsMiR_337_Sl k2 | MetsMiR_337 | Slk2 | TGATACAGTTTAATGATGTG | Mouse Valid _337 | Slk2_337 |
| MouseValid_MetsMiR_338_Sl k2 | MetsMiR_338 | Slk2 | GTGACAGAATATGCCAAAAA | Mouse Valid _338 | Slk2_338 |
| MouseValid_MetsMiR_339_Sl k2 | MetsMiR_339 | Slk2 | GCAGTATGAAGGACCACAGC | Mouse Valid _339 | Slk2_339 |
| MouseValid_MetsMiR_340_Sl k2 | MetsMiR_340 | Slk2 | AATACCATATATCCAGCTG | Mouse Valid _340 | Slk2_340 |
| MouseValid_MetsMiR_341_Sl c38a3 | MetsMiR_341 | Slc38a3 | ACGGTAGCCAACTGCTCGT | Mouse Valid _341 | Slc38a3_341 |
| MouseValid_MetsMiR_342_Sl c38a3 | MetsMiR_342 | Slc38a3 | CATCCGTGCCTACGAGCAGT | Mouse Valid _342 | Slc38a3_342 |
| MouseValid_MetsMiR_343_Sl c38a3 | MetsMiR_343 | Slc38a3 | TCTGGGGCTCGCCTACGCCA | Mouse Valid _343 | Slc38a3_343 |
| MouseValid_MetsMiR_344_Sl c38a3 | MetsMiR_344 | Slc38a3 | CCACAATCCCGAAGACTTG | Mouse Valid _344 | Slc38a3_344 |
| MouseValid_MetsMiR_345_Sl c38a3 | MetsMiR_345 | Slc38a3 | GAAAAGGATGATGCCCGTAT | Mouse Valid _345 | Slc38a3_345 |
| MouseValid_MetsMiR_346_Sl c38a3 | MetsMiR_346 | Slc38a3 | CAGCTCACACATCCGTGAACTG | Mouse Valid _346 | Slc38a3_346 |
| MouseValid_MetsMiR_347_Sl c38a3 | MetsMiR_347 | Slc38a3 | GGATGGAATAGCTAGACAAC | Mouse Valid _347 | Slc38a3_347 |
| MouseValid_MetsMiR_348_Sl c38a3 | MetsMiR_348 | Slc38a3 | ACTGAAGACACCCAACACTG | Mouse Valid _348 | Slc38a3_348 |
| MouseValid_MetsMiR_349_Sl c38a3 | MetsMiR_349 | Slc38a3 | TCCAATGTTCTGAAGCGTAA | Mouse Valid _349 | Slc38a3_349 |
| MouseValid_MetsMiR_350_Sl c38a3 | MetsMiR_350 | Slc38a3 | GCCATTACGCTTCAGAACAT | Mouse Valid _350 | Slc38a3_350 |
| MouseValid_MetsMiR_351_Snap47 | MetsMiR_351 | Snap47 | ACATACCCTCCACAGTGACC | Mouse Valid _351 | Snap47_351 |
| MouseValid_MetsMiR_352_Snap47 | MetsMiR_352 | Snap47 | AGCATACCAGCCATCCGCTTCAT | Mouse Valid _352 | Snap47_352 |
| MouseValid_MetsMiR_353_Snap47 | MetsMiR_353 | Snap47 | CCGACCTGCGACTTTGGCTGAC | Mouse Valid _353 | Snap47_353 |
| MouseValid_MetsMiR_354_Snap47 | MetsMiR_354 | Snap47 | ACATCAGCTTTCTCATACGC | Mouse Valid _354 | Snap47_354 |
| MouseValid_MetsMiR_355_Snap47 | MetsMiR_355 | Snap47 | TGTTCCAGCATCCAGACCGA | Mouse Valid _355 | Snap47_355 |
| MouseValid_MetsMiR_356_Snap47 | MetsMiR_356 | Snap47 | CTGGCTTCCAATGAAGCGC | Mouse Valid _356 | Snap47_356 |
| MouseValid_MetsMiR_357_Snap47 | MetsMiR_357 | Snap47 | TGCCATCCAGAGCCGCATCC | Mouse Valid _357 | Snap47_357 |
| MouseValid_MetsMiR_358_Snap47 | MetsMiR_358 | Snap47 | CGGTGTGGAGTGCAGCCCTT | Mouse Valid _358 | Snap47_358 |

| | | | | | | |
|---|---|---|---|---|---|---|
| MouseValid_MetsMR_359_Snap47 | MetsMR_359 | Snap47 | ACTGCAGCCTAGTGTGAAATG | MouseValid | _359 | Snap47_359 |
| MouseValid_MetsMR_360_Snap47 | MetsMR_360 | Snap47 | CTGATATGCGTGTCCACTCC | MouseValid | _360 | Snap47_360 |
| MouseValid_MetsMR_361_Tmem86a | MetsMR_361 | Tmem86a | ATCCTCTACGCCACTCCGATCACC | MouseValid | _361 | Tmem86a_361 |
| MouseValid_MetsMR_362_Tmem86a | MetsMR_362 | Tmem86a | CTGACAGCACTCCGATCACC | MouseValid | _362 | Tmem86a_362 |
| MouseValid_MetsMR_363_Tmem86a | MetsMR_363 | Tmem86a | CTTAAAGAAGGGCACCAGTT | MouseValid | _363 | Tmem86a_363 |
| MouseValid_MetsMR_364_Tmem86a | MetsMR_364 | Tmem86a | AGACAAGTCCACGAAGATG | MouseValid | _364 | Tmem86a_364 |
| MouseValid_MetsMR_365_Tmem86a | MetsMR_365 | Tmem86a | CGGCGCACTCACCAGTGAC | MouseValid | _365 | Tmem86a_365 |
| MouseValid_MetsMR_366_Tmem86a | MetsMR_366 | Tmem86a | CGCCGCCGCCATGGTGTCTC | MouseValid | _366 | Tmem86a_366 |
| MouseValid_MetsMR_367_Tmem86a | MetsMR_367 | Tmem86a | CTGGGCTCTCGACAGCTGAC | MouseValid | _367 | Tmem86a_367 |
| MouseValid_MetsMR_368_Tmem86a | MetsMR_368 | Tmem86a | GCAGAACTTGTTGAGAGCCA | MouseValid | _368 | Tmem86a_368 |
| MouseValid_MetsMR_369_Tmem86a | MetsMR_369 | Tmem86a | AGCCAGTGGCCGCATGCCAA | MouseValid | _369 | Tmem86a_369 |
| MouseValid_MetsMR_370_Tmem86a | MetsMR_370 | Tmem86a | GAAGAGCAGAGCACCACCGC | MouseValid | _370 | Tmem86a_370 |
| MouseValid_MetsMR_371_Trim17 | MetsMR_371 | Trim17 | ACCTACCTGCCACTCAGTTA | MouseValid | _371 | Trim17_371 |
| MouseValid_MetsMR_372_Trim17 | MetsMR_372 | Trim17 | GGACATAAAATATCTACGGG | MouseValid | _372 | Trim17_372 |
| MouseValid_MetsMR_373_Trim17 | MetsMR_373 | Trim17 | GGACCACCAAAGCCGCTCCC | MouseValid | _373 | Trim17_373 |
| MouseValid_MetsMR_374_Trim17 | MetsMR_374 | Trim17 | CTTCAGGTGCACTACCCAG | MouseValid | _374 | Trim17_374 |
| MouseValid_MetsMR_375_Trim17 | MetsMR_375 | Trim17 | GCACAAGGTCTTGATAGCCG | MouseValid | _375 | Trim17_375 |
| MouseValid_MetsMR_376_Trim17 | MetsMR_376 | Trim17 | TCAGGTCCAGGGAGCGGCTT | MouseValid | _376 | Trim17_376 |
| MouseValid_MetsMR_377_Trim17 | MetsMR_377 | Trim17 | ATGTGAAGGACACCTTGAAC | MouseValid | _377 | Trim17_377 |
| MouseValid_MetsMR_378_Trim17 | MetsMR_378 | Trim17 | TTTGAGGACACCTCTATCTGTCC | MouseValid | _378 | Trim17_378 |
| MouseValid_MetsMR_379_Trim17 | MetsMR_379 | Trim17 | GAGGTGCTCAAAAGCTTCCA | MouseValid | _379 | Trim17_379 |
| MouseValid_MetsMR_380_Trim17 | MetsMR_380 | Trim17 | GACGGAGACACTCCAAGCCA | MouseValid | _380 | Trim17_380 |

FIG. 18 CONTINUED

| | | | | | |
|---|---|---|---|---|---|
| MouseValid_MetsMiR_381_Trim72 | MetsMiR_381 | Trim72 | GCTTGACAGCTCCGACGCA | MouseValid_381 | Trim72_381 |
| MouseValid_MetsMiR_382_Trim72 | MetsMiR_382 | Trim72 | ATGTCTGGGGTTGCCTTGCGT | MouseValid_382 | Trim72_382 |
| MouseValid_MetsMiR_383_Trim72 | MetsMiR_383 | Trim72 | ATGTTCCGGGCTCTGATGCC | MouseValid_383 | Trim72_383 |
| MouseValid_MetsMiR_384_Trim72 | MetsMiR_384 | Trim72 | GCGCAAGGAGAAGACTGTAG | MouseValid_384 | Trim72_384 |
| MouseValid_MetsMiR_385_Trim72 | MetsMiR_385 | Trim72 | CCTGTCAGAGTCACCACCAC | MouseValid_385 | Trim72_385 |
| MouseValid_MetsMiR_386_Trim72 | MetsMiR_386 | Trim72 | TTGCTCACCTGCTGGTTACC | MouseValid_386 | Trim72_386 |
| MouseValid_MetsMiR_387_Trim72 | MetsMiR_387 | Trim72 | CTTTTCTCACCAGAAATTCTGCC | MouseValid_387 | Trim72_387 |
| MouseValid_MetsMiR_388_Trim72 | MetsMiR_388 | Trim72 | ACAGACAGAAGATGCAGCTGC | MouseValid_388 | Trim72_388 |
| MouseValid_MetsMiR_389_Trim72 | MetsMiR_389 | Trim72 | AGGAGACAGTGCGCCAGTTC | MouseValid_389 | Trim72_389 |
| MouseValid_MetsMiR_390_Trim72 | MetsMiR_390 | Trim72 | GCTGCTCCCCGACAGCTCCC | MouseValid_390 | Trim72_390 |
| MouseValid_MetsMiR_391_Tlr2 | MetsMiR_391 | Tlr2 | CGTCCGCGATGGCCCGAATA | MouseValid_391 | Tlr2_391 |
| MouseValid_MetsMiR_392_Tlr2 | MetsMiR_392 | Tlr2 | CGAAGCCGCATCGTGTTCGTC | MouseValid_392 | Tlr2_392 |
| MouseValid_MetsMiR_393_Tlr2 | MetsMiR_393 | Tlr2 | CAGACTGTCTAGTTGCCACC | MouseValid_393 | Tlr2_393 |
| MouseValid_MetsMiR_394_Tlr2 | MetsMiR_394 | Tlr2 | AGTTGGTCTCGAAACGTCCCA | MouseValid_394 | Tlr2_394 |
| MouseValid_MetsMiR_395_Tlr2 | MetsMiR_395 | Tlr2 | GCTCGCTCAGGGGCCTCTGC | MouseValid_395 | Tlr2_395 |
| MouseValid_MetsMiR_396_Tlr2 | MetsMiR_396 | Tlr2 | GCAATGCCTACCTGCCCCCA | MouseValid_396 | Tlr2_396 |
| MouseValid_MetsMiR_397_Tlr2 | MetsMiR_397 | Tlr2 | TTCTCACTGTTTATTGCATG | MouseValid_397 | Tlr2_397 |
| MouseValid_MetsMiR_398_Tlr2 | MetsMiR_398 | Tlr2 | TCAGGGTTTGTTTGTTCTACCAC | MouseValid_398 | Tlr2_398 |
| MouseValid_MetsMiR_399_Tlr2 | MetsMiR_399 | Tlr2 | GACGCCGGTCTTTAAGAAGC | MouseValid_399 | Tlr2_399 |
| MouseValid_MetsMiR_400_Tlr2 | MetsMiR_400 | Tlr2 | GAACACATGCGGCTTCGTGC | MouseValid_400 | Tlr2_400 |
| MouseValid_MetsMiR_401_Tubb4a | MetsMiR_401 | Tubb4a | GGAGTTAGTGGAGCCGTCC | MouseValid_401 | Tubb4a_401 |
| MouseValid_MetsMiR_402_Tubb4a | MetsMiR_402 | Tubb4a | TCTGTCTCCGCTCCGCCCTTT | MouseValid_402 | Tubb4a_402 |

FIG. 18 CONTINUED

| | | | | | |
|---|---|---|---|---|---|
| MouseValid_MetsMR_403_Tubb4a | MetsMR_403 | Tubb4a | TCAATGGGTAACCAGATCG | MouseValid | 403 | Tubb4a_403 |
| MouseValid_MetsMR_404_Tubb4a | MetsMR_404 | Tubb4a | GACCCACCTTGGCCCCGATC | MouseValid | 404 | Tubb4a_404 |
| MouseValid_MetsMR_405_Tubb4a | MetsMR_405 | Tubb4a | CAGGTCGACCACGGCTC | MouseValid | 405 | Tubb4a_405 |
| MouseValid_MetsMR_406_Tubb4a | MetsMR_406 | Tubb4a | TCCCAGGTCAATCGGAGC | MouseValid | 406 | Tubb4a_406 |
| MouseValid_MetsMR_407_Tubb4a | MetsMR_407 | Tubb4a | GTCCCATGATAGGTCCAG | MouseValid | 407 | Tubb4a_407 |
| MouseValid_MetsMR_408_Tubb4a | MetsMR_408 | Tubb4a | GACCCACTGGGACCTATCA | MouseValid | 408 | Tubb4a_408 |
| MouseValid_MetsMR_409_Tubb4a | MetsMR_409 | Tubb4a | TACCGCATTGACCGGCTTGC | MouseValid | 409 | Tubb4a_409 |
| MouseValid_MetsMR_410_Tubb4a | MetsMR_410 | Tubb4a | GAACTCGCCCTCTCAGCAG | MouseValid | 410 | Tubb4a_410 |
| MouseValid_MetsMR_411_Ube2g2 | MetsMR_411 | Ub e2g2 | GCTTTCTGTGTGAGCATGC | MouseValid | 411 | Ube2g2_411 |
| MouseValid_MetsMR_412_Ube2g2 | MetsMR_412 | Ub e2g2 | GAGATGCAGACTCTGCCAT | MouseValid | 412 | Ube2g2_412 |
| MouseValid_MetsMR_413_Ube2g2 | MetsMR_413 | Ub e2g2 | TCTCATCTTCGGAGGGCTCA | MouseValid | 413 | Ube2g2_413 |
| MouseValid_MetsMR_414_Ube2g2 | MetsMR_414 | Ub e2g2 | TTACCTGCCACGATTCCTTC | MouseValid | 414 | Ube2g2_414 |
| MouseValid_MetsMR_415_Ube2g2 | MetsMR_415 | Ub e2g2 | GTTGGCATGGAACATCTCCAC | MouseValid | 415 | Ube2g2_415 |
| MouseValid_MetsMR_416_Ube2g2 | MetsMR_416 | Ub e2g2 | TTAACCCTGAATCCTCCAGA | MouseValid | 416 | Ube2g2_416 |
| MouseValid_MetsMR_417_Ube2g2 | MetsMR_417 | Ub e2g2 | AAAAAAATTCTCTTCATTCA | MouseValid | 417 | Ube2g2_417 |
| MouseValid_MetsMR_418_Ube2g2 | MetsMR_418 | Ub e2g2 | ATCTTCTCCACACTCTGCAC | MouseValid | 418 | Ube2g2_418 |
| MouseValid_MetsMR_419_Ube2g2 | MetsMR_419 | Ub e2g2 | GATCATCACCTGGAGCATGC | MouseValid | 419 | Ube2g2_419 |
| MouseValid_MetsMR_420_Ube2g2 | MetsMR_420 | Ub e2g2 | GTTATGAGAGCAGTGCCGAG | MouseValid | 420 | Ube2g2_420 |
| MouseValid_MetsMR_421_Vav3 | MetsMR_421 | Vav 3 | GTTCAACAGTGTCGCCTGCC | MouseValid | 421 | Vav3_421 |
| MouseValid_MetsMR_422_Vav3 | MetsMR_422 | Vav 3 | TCCAGGTTTGCCGAAGATGC | MouseValid | 422 | Vav3_422 |
| MouseValid_MetsMR_423_Vav3 | MetsMR_423 | Vav 3 | TAGGGACGAAACTTAGCTTC | MouseValid | 423 | Vav3_423 |
| MouseValid_MetsMR_424_Vav3 | MetsMR_424 | Vav 3 | ACTTCGGAGAGCTTCCAGAC | MouseValid | 424 | Vav3_424 |

FIG. 18 CONTINUED

| | | | | | |
|---|---|---|---|---|---|
| MouseValid_MetsMR_425_Vav3 | MetsMR_425 | Vav 3 | TTCTTACAGAACGGACCAA | MouseValid | Vav3_425 |
| MouseValid_MetsMR_426_Vav3 | MetsMR_426 | Vav 3 | AGGGCCATTCAAACCACCAG | MouseValid | Vav3_426 |
| MouseValid_MetsMR_427_Vav3 | MetsMR_427 | Vav 3 | TGAGAACTTACACACATGGAGA | MouseValid | Vav3_427 |
| MouseValid_MetsMR_428_Vav3 | MetsMR_428 | Vav 3 | CTTACCTCGTGTGGTTTGAA | MouseValid | Vav3_428 |
| MouseValid_MetsMR_429_Vav3 | MetsMR_429 | Vav 3 | AGGACCACCATTGCATATCC | MouseValid | Vav3_429 |
| MouseValid_MetsMR_430_Vav3 | MetsMR_430 | Vav 3 | CAGACCTGGTCCAACCTGTC | MouseValid | Vav3_430 |
| MouseValid_MetsMR_431_Vmn1r50 | MetsMR_431 | Vmn1r50 | AGCCTTTCTCATCGGACTCA | MouseValid | Vmn1r50_431 |
| MouseValid_MetsMR_432_Vmn1r50 | MetsMR_432 | Vmn1r50 | CAGGAACCATCATCTACTCA | MouseValid | Vmn1r50_432 |
| MouseValid_MetsMR_433_Vmn1r50 | MetsMR_433 | Vmn1r50 | GCTAGCTGGTAGTTCTCCTA | MouseValid | Vmn1r50_433 |
| MouseValid_MetsMR_434_Vmn1r50 | MetsMR_434 | Vmn1r50 | GTTTGGGCTTGTTGTCTCATGA | MouseValid | Vmn1r50_434 |
| MouseValid_MetsMR_435_Vmn1r50 | MetsMR_435 | Vmn1r50 | AAGTTGTCACATCAATGTG | MouseValid | Vmn1r50_435 |
| MouseValid_MetsMR_436_Vmn1r50 | MetsMR_436 | Vmn1r50 | GAAGCCATGAGTAGCATGA | MouseValid | Vmn1r50_436 |
| MouseValid_MetsMR_437_Vmn1r50 | MetsMR_437 | Vmn1r50 | TCCAGAGGTGGACAACAAAA | MouseValid | Vmn1r50_437 |
| MouseValid_MetsMR_438_Vmn1r50 | MetsMR_438 | Vmn1r50 | TAGCAATAATTGATACTAAT | MouseValid | Vmn1r50_438 |
| MouseValid_MetsMR_439_Vmn1r50 | MetsMR_439 | Vmn1r50 | CTTGTTCTAGAGTAACTCAC | MouseValid | Vmn1r50_439 |
| MouseValid_MetsMR_440_Vmn1r50 | MetsMR_440 | Vmn1r50 | TTTCCACAATGATGACCATG | MouseValid | Vmn1r50_440 |
| MouseValid_MetsMR_441_Vwa5b2 | MetsMR_441 | Vwa5b2 | ATCGGCCCGGCTATGCAAC | MouseValid | Vwa5b2_441 |
| MouseValid_MetsMR_442_Vwa5b2 | MetsMR_442 | Vwa5b2 | AGGCGGTTCGTCGTACCCTC | MouseValid | Vwa5b2_442 |
| MouseValid_MetsMR_443_Vwa5b2 | MetsMR_443 | Vwa5b2 | GCCTGAGTAACACGTCGGAG | MouseValid | Vwa5b2_443 |
| MouseValid_MetsMR_444_Vwa5b2 | MetsMR_444 | Vwa5b2 | GAGCGGCAGCGGGGTCCAGC | MouseValid | Vwa5b2_444 |
| MouseValid_MetsMR_445_Vwa5b2 | MetsMR_445 | Vwa5b2 | CGCTCACGACTCCTGCGGTC | MouseValid | Vwa5b2_445 |
| MouseValid_MetsMR_446_Vwa5b2 | MetsMR_446 | Vwa5b2 | CTTCCGGGCTCTGTGACGAC | MouseValid | Vwa5b2_446 |

FIG. 18
CONTINUED

| | | | | | |
|---|---|---|---|---|---|
| MouseValid_MetsMR_447_Vwa5b2 | MetsMR_447 | Vwa5b2 | TCTTTGAGATGTAGTGAC | Mouse Valid | _447 | Vwa5b2_447 |
| MouseValid_MetsMR_448_Vwa5b2 | MetsMR_448 | Vwa5b2 | GCCACACATGCATCACCCCATC | Mouse Valid | _448 | Vwa5b2_448 |
| MouseValid_MetsMR_449_Vwa5b2 | MetsMR_449 | Vwa5b2 | TACACCCGCGCTGCGCAC | Mouse Valid | _449 | Vwa5b2_449 |
| MouseValid_MetsMR_450_Vwa5b2 | MetsMR_450 | Vwa5b2 | GGCGCGCCTGCTGTGGGCTC | Mouse Valid | _450 | Vwa5b2_450 |
| MouseValid_MetsMR_451_Wdfy1 | MetsMR_451 | Wdfy1 | CGGGTGATCACCCGCTAGCG | Mouse Valid | _451 | Wdfy1_451 |
| MouseValid_MetsMR_452_Wdfy1 | MetsMR_452 | Wdfy1 | CAAATATCCGCTCCTGCTCCG | Mouse Valid | _452 | Wdfy1_452 |
| MouseValid_MetsMR_453_Wdfy1 | MetsMR_453 | Wdfy1 | TGGCGGCGGAGATCCACTCC | Mouse Valid | _453 | Wdfy1_453 |
| MouseValid_MetsMR_454_Wdfy1 | MetsMR_454 | Wdfy1 | CATACACACGACAGCACTAGG | Mouse Valid | _454 | Wdfy1_454 |
| MouseValid_MetsMR_455_Wdfy1 | MetsMR_455 | Wdfy1 | TCCACAGAACCATCCCAGTA | Mouse Valid | _455 | Wdfy1_455 |
| MouseValid_MetsMR_456_Wdfy1 | MetsMR_456 | Wdfy1 | AAAGAGACAGGGCCACTAC | Mouse Valid | _456 | Wdfy1_456 |
| MouseValid_MetsMR_457_Wdfy1 | MetsMR_457 | Wdfy1 | ACTCTACTTCGTCCTCCGTAG | Mouse Valid | _457 | Wdfy1_457 |
| MouseValid_MetsMR_458_Wdfy1 | MetsMR_458 | Wdfy1 | GCGCGGCGGGTGAGGGGTCC | Mouse Valid | _458 | Wdfy1_458 |
| MouseValid_MetsMR_459_Wdfy1 | MetsMR_459 | Wdfy1 | CGGCGGCTGCTCATCCCCA | Mouse Valid | _459 | Wdfy1_459 |
| MouseValid_MetsMR_460_Wdfy1 | MetsMR_460 | Wdfy1 | TGATCACGCCGTCCTCCTTG | Mouse Valid | _460 | Wdfy1_460 |
| MouseValid_MetsMR_461_Zfp800 | MetsMR_461 | Zfp800 | TTTTCACTTCAATACCGACGT | Mouse Valid | _461 | Zfp800_461 |
| MouseValid_MetsMR_462_Zfp800 | MetsMR_462 | Zfp800 | TCTGCACTTACGAACCGT | Mouse Valid | _462 | Zfp800_462 |
| MouseValid_MetsMR_463_Zfp800 | MetsMR_463 | Zfp800 | ATAATTGAGTCTTTCCATC | Mouse Valid | _463 | Zfp800_463 |
| MouseValid_MetsMR_464_Zfp800 | MetsMR_464 | Zfp800 | CTTCCATGTAGTTATATCC | Mouse Valid | _464 | Zfp800_464 |
| MouseValid_MetsMR_465_Zfp800 | MetsMR_465 | Zfp800 | TTATGCCTAGTGTCTTTAG | Mouse Valid | _465 | Zfp800_465 |
| MouseValid_MetsMR_466_Zfp800 | MetsMR_466 | Zfp800 | GTAATCCTCTAAAGAGACTA | Mouse Valid | _466 | Zfp800_466 |
| MouseValid_MetsMR_467_Zfp800 | MetsMR_467 | Zfp800 | AAGTATGAAGTAGCCGACGT | Mouse Valid | _467 | Zfp800_467 |
| MouseValid_MetsMR_468_Zfp800 | MetsMR_468 | Zfp800 | CTTGACTCGGTCACTTCAGC | Mouse Valid | _468 | Zfp800_468 |

| | | | | |
|---|---|---|---|---|
| MouseValid_MetsMIR_469_Zfp800 | MetsMIR_469 | Zfp800 | TTATCACATCACGTTTCCGA | MouseValid | 469 | Zfp800_469 |
| MouseValid_MetsMIR_470_Zfp800 | MetsMIR_470 | Zfp800 | AGGCCGAAGTACAAGATCTA | MouseValid | 470 | Zfp800_470 |
| MouseValid_MetsMIR_471_Zfyve28 | MetsMIR_471 | Zfyve28 | ATCCGGCATGACAACTTGGC | MouseValid | 471 | Zfyve28_471 |
| MouseValid_MetsMIR_472_Zfyve28 | MetsMIR_472 | Zfyve28 | GCGATGGGACTCTCCGTGACC | MouseValid | 472 | Zfyve28_472 |
| MouseValid_MetsMIR_473_Zfyve28 | MetsMIR_473 | Zfyve28 | GAGCATGGCCATGCGGCCAC | MouseValid | 473 | Zfyve28_473 |
| MouseValid_MetsMIR_474_Zfyve28 | MetsMIR_474 | Zfyve28 | CAGCCAGTTCCGCTCCTGTC | MouseValid | 474 | Zfyve28_474 |
| MouseValid_MetsMIR_475_Zfyve28 | MetsMIR_475 | Zfyve28 | AACTTGACGCAGAAATCCCG | MouseValid | 475 | Zfyve28_475 |
| MouseValid_MetsMIR_476_Zfyve28 | MetsMIR_476 | Zfyve28 | CAGGGAGTACTATGTGCAGC | MouseValid | 476 | Zfyve28_476 |
| MouseValid_MetsMIR_477_Zfyve28 | MetsMIR_477 | Zfyve28 | GAGGTCAGACCCACAACTGC | MouseValid | 477 | Zfyve28_477 |
| MouseValid_MetsMIR_478_Zfyve28 | MetsMIR_478 | Zfyve28 | CTGCTGCACATAGTACTCCC | MouseValid | 478 | Zfyve28_478 |
| MouseValid_MetsMIR_479_Zfyve28 | MetsMIR_479 | Zfyve28 | TCCCTCAGGACCGTGCCCCT | MouseValid | 479 | Zfyve28_479 |
| MouseValid_MetsMIR_480_Zfyve28 | MetsMIR_480 | Zfyve28 | TTGTCATGCCGGATCTCCTC | MouseValid | 480 | Zfyve28_480 |
| MouseValid_MetsMIR_481_mmu-mir-345 | MetsMIR_481 | mmu-mir-345 | TCAAGCCCGACACCCAAGTCC | MouseValid | 481 | mmu-mir-345_481 |
| MouseValid_MetsMIR_482_mmu-mir-345 | MetsMIR_482 | mmu-mir-345 | GACCCTAGTCCAGTGCTTG | MouseValid | 482 | mmu-mir-345_482 |
| MouseValid_MetsMIR_483_mmu-mir-345 | MetsMIR_483 | mmu-mir-345 | CCAGTGCTTGTGTGGTGCTAC | MouseValid | 483 | mmu-mir-345_483 |
| MouseValid_MetsMIR_484_mmu-mir-345 | MetsMIR_484 | mmu-mir-345 | GCTACTGGGCCCCTGAACTAG | MouseValid | 484 | mmu-mir-345_484 |
| MouseValid_MetsMIR_485_mmu-mir-345 | MetsMIR_485 | mmu-mir-345 | GAACTAGGGGTCTGGAGACC | MouseValid | 485 | mmu-mir-345_485 |
| MouseValid_MetsMIR_486_mmu-mir-345 | MetsMIR_486 | mmu-mir-345 | GACCTGGGTTTGATCTCCAC | MouseValid | 486 | mmu-mir-345_486 |
| MouseValid_MetsMIR_487_mmu-mir-345 | MetsMIR_487 | mmu-mir-345 | CCAGTAGCCACCACAAGCAC | MouseValid | 487 | mmu-mir-345_487 |
| MouseValid_MetsMIR_488_mmu-mir-345 | MetsMIR_488 | mmu-mir-345 | CACCAAGCACTGGACTAG | MouseValid | 488 | mmu-mir-345_488 |
| MouseValid_MetsMIR_489_mmu-mir-345 | MetsMIR_489 | mmu-mir-345 | GGAACTAGGGGTCAGCAGGCC | MouseValid | 489 | mmu-mir-345_489 |
| MouseValid_MetsMIR_490_mmu-mir-345 | MetsMIR_490 | mmu-mir-345 | TGGCCCTGAACTAGGGGTC | MouseValid | 490 | mmu-mir-345_490 |

FIG. 18 CONTINUED

| | | | | | | |
|---|---|---|---|---|---|---|
| MouseValid_MetsMiR_491_mmu-mir-152 | MetsMiR_491 | mmu-mir-152 | CGCGGCTGTTCCCGGGGCT | Mouse Valid | _491 | mmu-mir-152_491 |
| MouseValid_MetsMiR_492_mmu-mir-152 | MetsMiR_492 | mmu-mir-152 | TTCTGTGATACACTCCGACT | Mouse Valid | _492 | mmu-mir-152_492 |
| MouseValid_MetsMiR_493_mmu-mir-152 | MetsMiR_493 | mmu-mir-152 | ATACACTCCGACTCCGGCTC | Mouse Valid | _493 | mmu-mir-152_493 |
| MouseValid_MetsMiR_494_mmu-mir-152 | MetsMiR_494 | mmu-mir-152 | AGTCAGTGCATGACAGAACT | Mouse Valid | _494 | mmu-mir-152_494 |
| MouseValid_MetsMiR_495_mmu-mir-152 | MetsMiR_495 | mmu-mir-152 | TGCATGACAGAACTTGGGGC | Mouse Valid | _495 | mmu-mir-152_495 |
| MouseValid_MetsMiR_496_mmu-mir-152 | MetsMiR_496 | mmu-mir-152 | GACTGCTCCAGAGCCCAGT | Mouse Valid | _496 | mmu-mir-152_496 |
| MouseValid_MetsMiR_497_mmu-mir-152 | MetsMiR_497 | mmu-mir-152 | CGGAGTCTATCACAGAACCT | Mouse Valid | _497 | mmu-mir-152_497 |
| MouseValid_MetsMiR_498_mmu-mir-152 | MetsMiR_498 | mmu-mir-152 | TGTATCACAGAACTAGGGC | Mouse Valid | _498 | mmu-mir-152_498 |
| MouseValid_MetsMiR_499_mmu-mir-152 | MetsMiR_499 | mmu-mir-152 | TCTGTGATACACTCCGACTC | Mouse Valid | _499 | mmu-mir-152_499 |
| MouseValid_MetsMiR_500_mmu-mir-152 | MetsMiR_500 | mmu-mir-152 | GTCAGTGTTAGCAACAGACTT | Mouse Valid | _500 | mmu-mir-152_500 |
| MouseValid_MetsMiR_501_mmu-mir-367 | MetsMiR_501 | mmu-mir-367 | TTGGAATTGCACTTTAGCAA | Mouse Valid | _501 | mmu-mir-367_501 |
| MouseValid_MetsMiR_502_mmu-mir-367 | MetsMiR_502 | mmu-mir-367 | TTGCACTTTAGCAATGGTGA | Mouse Valid | _502 | mmu-mir-367_502 |
| MouseValid_MetsMiR_503_mmu-mir-367 | MetsMiR_503 | mmu-mir-367 | TTGCATGTTAGCAACAGTGA | Mouse Valid | _503 | mmu-mir-367_503 |
| MouseValid_MetsMiR_504_mmu-mir-367 | MetsMiR_504 | mmu-mir-367 | CAACTCTGTTGAATAGAAAT | Mouse Valid | _504 | mmu-mir-367_504 |
| MouseValid_MetsMiR_505_mmu-mir-6537 | MetsMiR_505 | mmu-mir-6537 | TTCTGGTTCTACAGGCAGAG | Mouse Valid | _505 | mmu-mir-6537_505 |
| MouseValid_MetsMiR_506_mmu-mir-6537 | MetsMiR_506 | mmu-mir-6537 | GTTCTACAGGCAGAGCGGT | Mouse Valid | _506 | mmu-mir-6537_506 |
| MouseValid_MetsMiR_507_mmu-mir-6537 | MetsMiR_507 | mmu-mir-6537 | AGTGGGAGAAACTCACCCCT | Mouse Valid | _507 | mmu-mir-6537_507 |
| MouseValid_MetsMiR_508_mmu-mir-6537 | MetsMiR_508 | mmu-mir-6537 | CGCTAGGAAACTCTCTCTA | Mouse Valid | _508 | mmu-mir-6537_508 |
| MouseValid_MetsMiR_509_mmu-mir-6537 | MetsMiR_509 | mmu-mir-6537 | TCTCCCACTGGTGACCAGGA | Mouse Valid | _509 | mmu-mir-6537_509 |
| MouseValid_MetsMiR_510_mmu-mir-6537 | MetsMiR_510 | mmu-mir-6537 | TGACCAGGAAGGTTATCAGG | Mouse Valid | _510 | mmu-mir-6537_510 |
| MouseValid_MetsMiR_511_mmu-mir-6537 | MetsMiR_511 | mmu-mir-6537 | AGTTTCTCCACTGGTGACC | Mouse Valid | _511 | mmu-mir-6537_511 |
| MouseValid_MetsMiR_512_mmu-mir-6537 | MetsMiR_512 | mmu-mir-6537 | TAGCGGGTGAGTTTCTCCCAC | Mouse Valid | _512 | mmu-mir-6537_512 |

FIG. 18 CONTINUED

| | | | | | |
|---|---|---|---|---|---|
| MouseValid_MetsMR_513_mmu-mir-6537 | MetsMR_513 | mmu-mir-6537 | CTTTCCACTTGATAACCTTCC | Mouse Valid | 513 | mmu-mir-6412_513 |
| MouseValid_MetsMR_514_mmu-mir-6537 | MetsMR_514 | mmu-mir-6537 | ATAACCTTCCTGGTCACCAG | Mouse Valid | 514 | mmu-mir-6412_514 |
| MouseValid_MetsMR_515_mmu-mir-6412 | MetsMR_515 | mmu-mir-6412 | ACTGCCTAGTTAGCTTGATG | Mouse Valid | 515 | mmu-mir-6412_515 |
| MouseValid_MetsMR_516_mmu-mir-6412 | MetsMR_516 | mmu-mir-6412 | TACTGCACTCCTATAATCCC | Mouse Valid | 516 | mmu-mir-6412_516 |
| MouseValid_MetsMR_517_mmu-mir-6412 | MetsMR_517 | mmu-mir-6412 | CTCCTATAATCCCAGGGTCT | Mouse Valid | 517 | mmu-mir-6412_517 |
| MouseValid_MetsMR_518_mmu-mir-6412 | MetsMR_518 | mmu-mir-6412 | CTATAATCCCAGGGTCTTGG | Mouse Valid | 518 | mmu-mir-6412_518 |
| MouseValid_MetsMR_519_mmu-mir-6412 | MetsMR_519 | mmu-mir-6412 | TCCCAGGGTCTTGGAGGTCT | Mouse Valid | 519 | mmu-mir-6412_519 |
| MouseValid_MetsMR_520_mmu-mir-6412 | MetsMR_520 | mmu-mir-6412 | AGGGTCTTGGAGGTCTAGGC | Mouse Valid | 520 | mmu-mir-6412_520 |
| MouseValid_MetsMR_521_mmu-mir-6412 | MetsMR_521 | mmu-mir-6412 | GAGGTCTAGGCAGGATGATT | Mouse Valid | 521 | mmu-mir-6412_521 |
| MouseValid_MetsMR_522_mmu-mir-6412 | MetsMR_522 | mmu-mir-6412 | ACTGCACTCCTATAATCCCA | Mouse Valid | 522 | mmu-mir-6412_522 |
| MouseValid_MetsMR_523_mmu-mir-6412 | MetsMR_523 | mmu-mir-6412 | CTCCAAGACCTGGGATTAT | Mouse Valid | 523 | mmu-mir-6412_523 |
| MouseValid_MetsMR_524_mmu-mir-6412 | MetsMR_524 | mmu-mir-6412 | TGCCTAGACCTCCAAGACCC | Mouse Valid | 524 | mmu-mir-6412_524 |
| MouseValid_MetsMR_525_NonTargetingControlGuideForMouse_0001 | MetsMR_525 | NonTargetingControlGuideForMouse_0001 | GCGAGTATTCGGCTCCGCG | Mouse Valid | 525 | NonTargetingControlGuideForMouse_0001_525 |
| MouseValid_MetsMR_525_NonTargetingControlGuideForMouse_0002 | MetsMR_525 | NonTargetingControlGuideForMouse_0002 | GCTTTCACGGAGGTTCGACG | Mouse Valid | 526 | NonTargetingControlGuideForMouse_0002_526 |
| MouseValid_MetsMR_525_NonTargetingControlGuideForMouse_0003 | MetsMR_525 | NonTargetingControlGuideForMouse_0003 | ATGTTCCAGTTCGGCTCGAT | Mouse Valid | 527 | NonTargetingControlGuideForMouse_0003_527 |
| MouseValid_MetsMR_525_NonTargetingControlGuideForMouse_0004 | MetsMR_525 | NonTargetingControlGuideForMouse_0004 | ACGTGTAAGGCGAACGCCTT | Mouse Valid | 528 | NonTargetingControlGuideForMouse_0004_528 |
| MouseValid_MetsMR_525_NonTargetingControlGuideForMouse_0005 | MetsMR_525 | NonTargetingControlGuideForMouse_0005 | GACTCCGGGTACTAAATGTC | Mouse Valid | 529 | NonTargetingControlGuideForMouse_0005_529 |
| MouseValid_MetsMR_525_NonTargetingControlGuideForMouse_0006 | MetsMR_525 | NonTargetingControlGuideForMouse_0006 | CCGGCGTTAGGGAACGAG | Mouse Valid | 530 | NonTargetingControlGuideForMouse_0006_530 |
| MouseValid_MetsMR_525_NonTargetingControlGuideForMouse_0007 | MetsMR_525 | NonTargetingControlGuideForMouse_0007 | ATTTGTTCGACCGTTACGGG | Mouse Valid | 531 | NonTargetingControlGuideForMouse_0007_531 |
| MouseValid_MetsMR_525_NonTargetingControlGuideForMouse_0008 | MetsMR_525 | NonTargetingControlGuideForMouse_0008 | ACCCATCGGGTGCGATATGG | Mouse Valid | 532 | NonTargetingControlGuideForMouse_0008_532 |
| MouseValid_MetsMR_525_NonTargetingControlGuideForMouse_0009 | MetsMR_525 | NonTargetingControlGuideForMouse_0009 | CGGGCGTCACCTGCTAGTAA | Mouse Valid | 533 | NonTargetingControlGuideForMouse_0009_533 |
| MouseValid_MetsMR_525_NonTargetingControlGuideForMouse_0010 | MetsMR_525 | NonTargetingControlGuideForMouse_0010 | GCTTCTACTCGCAACGTATT | Mouse Valid | 534 | NonTargetingControlGuideForMouse_0010_534 |

FIG. 18 CONTINUED

| | | | | | | |
|---|---|---|---|---|---|---|
| MouseValid_MetsMiR_525_NonTargetingControlGuideForMouse_0011 | MetsMiR_535 | NonTargetingControlGuideForMouse_0011 | TACAGTTATACGTCGCGGTG | Mouse Valid | 535 | NonTargetingControlGuideForMouse_0011_535 |
| MouseValid_MetsMiR_525_NonTargetingControlGuideForMouse_0012 | MetsMiR_536 | NonTargetingControlGuideForMouse_0012 | AAGCCACAAGAACGGTCCGCC | Mouse Valid | 536 | NonTargetingControlGuideForMouse_0012_536 |
| MouseValid_MetsMiR_525_NonTargetingControlGuideForMouse_0013 | MetsMiR_537 | NonTargetingControlGuideForMouse_0013 | CAGCCACCGCACCGGCGTAA | Mouse Valid | 537 | NonTargetingControlGuideForMouse_0013_537 |
| MouseValid_MetsMiR_525_NonTargetingControlGuideForMouse_0014 | MetsMiR_538 | NonTargetingControlGuideForMouse_0014 | GTCAAGCCGAACGCTGCCCGG | Mouse Valid | 538 | NonTargetingControlGuideForMouse_0014_538 |
| MouseValid_MetsMiR_525_NonTargetingControlGuideForMouse_0015 | MetsMiR_539 | NonTargetingControlGuideForMouse_0015 | CCTTAGACCCGGGGTGTACCTC | Mouse Valid | 539 | NonTargetingControlGuideForMouse_0015_539 |
| MouseValid_MetsMiR_525_NonTargetingControlGuideForMouse_0016 | MetsMiR_540 | NonTargetingControlGuideForMouse_0016 | AAGTCTATGCGGGGCTCGTA | Mouse Valid | 540 | NonTargetingControlGuideForMouse_0016_540 |
| MouseValid_MetsMiR_525_NonTargetingControlGuideForMouse_0017 | MetsMiR_541 | NonTargetingControlGuideForMouse_0017 | TTGTCAACTTCGGCCAACGC | Mouse Valid | 541 | NonTargetingControlGuideForMouse_0017_541 |
| MouseValid_MetsMiR_525_NonTargetingControlGuideForMouse_0018 | MetsMiR_542 | NonTargetingControlGuideForMouse_0018 | ATAGATGTCTACGCGCCGTT | Mouse Valid | 542 | NonTargetingControlGuideForMouse_0018_542 |
| MouseValid_MetsMiR_525_NonTargetingControlGuideForMouse_0019 | MetsMiR_543 | NonTargetingControlGuideForMouse_0019 | CTCGGGCTATTCAGCGATAG | Mouse Valid | 543 | NonTargetingControlGuideForMouse_0019_543 |
| MouseValid_MetsMiR_525_NonTargetingControlGuideForMouse_0020 | MetsMiR_544 | NonTargetingControlGuideForMouse_0020 | GCGGTTACCGCGGAAAACCAT | Mouse Valid | 544 | NonTargetingControlGuideForMouse_0020_544 |
| MouseValid_MetsMiR_525_NonTargetingControlGuideForMouse_0021 | MetsMiR_545 | NonTargetingControlGuideForMouse_0021 | ACCAACGCTACGATCCCGGA | Mouse Valid | 545 | NonTargetingControlGuideForMouse_0021_545 |
| MouseValid_MetsMiR_525_NonTargetingControlGuideForMouse_0022 | MetsMiR_546 | NonTargetingControlGuideForMouse_0022 | CCCTATATGCGAGATCCATA | Mouse Valid | 546 | NonTargetingControlGuideForMouse_0022_546 |
| MouseValid_MetsMiR_525_NonTargetingControlGuideForMouse_0023 | MetsMiR_547 | NonTargetingControlGuideForMouse_0023 | AGAAAGGCACGTGCGACGTC | Mouse Valid | 547 | NonTargetingControlGuideForMouse_0023_547 |
| MouseValid_MetsMiR_525_NonTargetingControlGuideForMouse_0024 | MetsMiR_548 | NonTargetingControlGuideForMouse_0024 | GACCAACCTTACGGTAACTC | Mouse Valid | 548 | NonTargetingControlGuideForMouse_0024_548 |
| MouseValid_MetsMiR_525_NonTargetingControlGuideForMouse_0025 | MetsMiR_549 | NonTargetingControlGuideForMouse_0025 | ATTATTCCTCCGGATGACGA | Mouse Valid | 549 | NonTargetingControlGuideForMouse_0025_549 |
| MouseValid_MetsMiR_525_NonTargetingControlGuideForMouse_0026 | MetsMiR_550 | NonTargetingControlGuideForMouse_0026 | TCTCAGTTCCTAGCGAACGA | Mouse Valid | 550 | NonTargetingControlGuideForMouse_0026_550 |
| MouseValid_MetsMiR_525_NonTargetingControlGuideForMouse_0027 | MetsMiR_551 | NonTargetingControlGuideForMouse_0027 | TCCCGGGAGGTACGGTGTAC | Mouse Valid | 551 | NonTargetingControlGuideForMouse_0027_551 |
| MouseValid_MetsMiR_525_NonTargetingControlGuideForMouse_0028 | MetsMiR_552 | NonTargetingControlGuideForMouse_0028 | GGGCATGGCCTTACGTCGCG | Mouse Valid | 552 | NonTargetingControlGuideForMouse_0028_552 |
| MouseValid_MetsMiR_525_NonTargetingControlGuideForMouse_0029 | MetsMiR_553 | NonTargetingControlGuideForMouse_0029 | GTATCCTCCTTACGGCCCGT | Mouse Valid | 553 | NonTargetingControlGuideForMouse_0029_553 |
| MouseValid_MetsMiR_525_NonTargetingControlGuideForMouse_0030 | MetsMiR_554 | NonTargetingControlGuideForMouse_0030 | GCTCGGACCTTTAGACGTC | Mouse Valid | 554 | NonTargetingControlGuideForMouse_0030_554 |
| MouseValid_MetsMiR_525_NonTargetingControlGuideForMouse_0031 | MetsMiR_555 | NonTargetingControlGuideForMouse_0031 | GTGGTTACGTTAACGACTAC | Mouse Valid | 555 | NonTargetingControlGuideForMouse_0031_555 |
| MouseValid_MetsMiR_525_NonTargetingControlGuideForMouse_0032 | MetsMiR_556 | NonTargetingControlGuideForMouse_0032 | TGCAACGATGGTTACGGTAC | Mouse Valid | 556 | NonTargetingControlGuideForMouse_0032_556 |

| | | | | | | |
|---|---|---|---|---|---|---|
| MouseValid_MetsMR_525_NonTargetingControlGuideForMouse_0033 | MetsMR_557_NonTargetingControlGuideForMouse_0033 | AACCGGCGCAATACCCTTTT | Mouse Valid | 557 | NonTargetingControlGuideForMouse_0033 | 557 |
| MouseValid_MetsMR_525_NonTargetingControlGuideForMouse_0034 | MetsMR_558_NonTargetingControlGuideForMouse_0034 | TCGTGTCTAGCTATCGAGTG | Mouse Valid | 558 | NonTargetingControlGuideForMouse_0034 | 558 |
| MouseValid_MetsMR_525_NonTargetingControlGuideForMouse_0035 | MetsMR_559_NonTargetingControlGuideForMouse_0035 | GACGTCTAATTCTGGCCGT | Mouse Valid | 559 | NonTargetingControlGuideForMouse_0035 | 559 |
| MouseValid_MetsMR_525_NonTargetingControlGuideForMouse_0036 | MetsMR_560_NonTargetingControlGuideForMouse_0036 | TAGTCCTAGTTAGATTCGCG | Mouse Valid | 560 | NonTargetingControlGuideForMouse_0036 | 560 |
| MouseValid_MetsMR_525_NonTargetingControlGuideForMouse_0037 | MetsMR_561_NonTargetingControlGuideForMouse_0037 | AAGGCCTTAACACGTCGACC | Mouse Valid | 561 | NonTargetingControlGuideForMouse_0037 | 561 |
| MouseValid_MetsMR_525_NonTargetingControlGuideForMouse_0038 | MetsMR_562_NonTargetingControlGuideForMouse_0038 | ATTCGTGCATCGCGGGGTTT | Mouse Valid | 562 | NonTargetingControlGuideForMouse_0038 | 562 |
| MouseValid_MetsMR_525_NonTargetingControlGuideForMouse_0039 | MetsMR_563_NonTargetingControlGuideForMouse_0039 | CAACTCGCGTCATATCACTA | Mouse Valid | 563 | NonTargetingControlGuideForMouse_0039 | 563 |
| MouseValid_MetsMR_525_NonTargetingControlGuideForMouse_0040 | MetsMR_564_NonTargetingControlGuideForMouse_0040 | GACCTCGCAATTGAGCGCTC | Mouse Valid | 564 | NonTargetingControlGuideForMouse_0040 | 564 |
| MouseValid_MetsMR_525_NonTargetingControlGuideForMouse_0041 | MetsMR_565_NonTargetingControlGuideForMouse_0041 | TGTATCCACCGTCGACCCGGT | Mouse Valid | 565 | NonTargetingControlGuideForMouse_0041 | 565 |
| MouseValid_MetsMR_525_NonTargetingControlGuideForMouse_0042 | MetsMR_566_NonTargetingControlGuideForMouse_0042 | GATCTTACCACTCGTCGTAG | Mouse Valid | 566 | NonTargetingControlGuideForMouse_0042 | 566 |
| MouseValid_MetsMR_525_NonTargetingControlGuideForMouse_0043 | MetsMR_567_NonTargetingControlGuideForMouse_0043 | TTCCGCCGGCGACGAAGTCA | Mouse Valid | 567 | NonTargetingControlGuideForMouse_0043 | 567 |
| MouseValid_MetsMR_525_NonTargetingControlGuideForMouse_0044 | MetsMR_568_NonTargetingControlGuideForMouse_0044 | AGCACTAGGATCGCGGCCTT | Mouse Valid | 568 | NonTargetingControlGuideForMouse_0044 | 568 |
| MouseValid_MetsMR_525_NonTargetingControlGuideForMouse_0045 | MetsMR_569_NonTargetingControlGuideForMouse_0045 | CCGTATCTACCCTACCGCCG | Mouse Valid | 569 | NonTargetingControlGuideForMouse_0045 | 569 |
| MouseValid_MetsMR_525_NonTargetingControlGuideForMouse_0046 | MetsMR_570_NonTargetingControlGuideForMouse_0046 | GCGCGAGGGCACCGACAAGT | Mouse Valid | 570 | NonTargetingControlGuideForMouse_0046 | 570 |
| MouseValid_MetsMR_525_NonTargetingControlGuideForMouse_0047 | MetsMR_571_NonTargetingControlGuideForMouse_0047 | CCGCTATATGTCACACGGCA | Mouse Valid | 571 | NonTargetingControlGuideForMouse_0047 | 571 |
| MouseValid_MetsMR_525_NonTargetingControlGuideForMouse_0048 | MetsMR_572_NonTargetingControlGuideForMouse_0048 | TAAAACGATCAGCAGATACGA | Mouse Valid | 572 | NonTargetingControlGuideForMouse_0048 | 572 |
| MouseValid_MetsMR_525_NonTargetingControlGuideForMouse_0049 | MetsMR_573_NonTargetingControlGuideForMouse_0049 | TCCTGCGCGATGACCGTCGG | Mouse Valid | 573 | NonTargetingControlGuideForMouse_0049 | 573 |
| MouseValid_MetsMR_525_NonTargetingControlGuideForMouse_0050 | MetsMR_574_NonTargetingControlGuideForMouse_0050 | TGGCCCACAAGGTCGATAT | Mouse Valid | 574 | NonTargetingControlGuideForMouse_0050 | 574 |
| MouseValid_MetsMR_525_NonTargetingControlGuideForMouse_0051 | MetsMR_575_NonTargetingControlGuideForMouse_0051 | GGGCTAGGCCTAATTACGGA | Mouse Valid | 575 | NonTargetingControlGuideForMouse_0051 | 575 |
| MouseValid_MetsMR_525_NonTargetingControlGuideForMouse_0052 | MetsMR_576_NonTargetingControlGuideForMouse_0052 | CCCTTCGTCTCTCGCAAACA | Mouse Valid | 576 | NonTargetingControlGuideForMouse_0052 | 576 |
| MouseValid_MetsMR_525_NonTargetingControlGuideForMouse_0053 | MetsMR_577_NonTargetingControlGuideForMouse_0053 | TTATGTGCCTCTTCGGCGCAT | Mouse Valid | 577 | NonTargetingControlGuideForMouse_0053 | 577 |
| MouseValid_MetsMR_525_NonTargetingControlGuideForMouse_0054 | MetsMR_578_NonTargetingControlGuideForMouse_0054 | CCGTTCTGACGACGCTAAAG | Mouse Valid | 578 | NonTargetingControlGuideForMouse_0054 | 578 |

| | | | | | |
|---|---|---|---|---|---|
| MouseValid_MetsMIR_579_NonTargetingControlGuideForMouse_0055 | MetsMIR_579_NonTargetingControlGuideForMouse_0055 | MetsMIR_579 | AAACTCCCGTGTCAACCGAT | Mouse Valid | 579 | NonTargetingControlGuideForMouse_0055_579 |
| MouseValid_MetsMIR_580_NonTargetingControlGuideForMouse_0056 | MetsMIR_580_NonTargetingControlGuideForMouse_0056 | MetsMIR_580 | GTTTGCGGAGTCAAAGTACGC | Mouse Valid | 580 | NonTargetingControlGuideForMouse_0056_580 |
| MouseValid_MetsMIR_581_NonTargetingControlGuideForMouse_0057 | MetsMIR_581_NonTargetingControlGuideForMouse_0057 | MetsMIR_581 | GGGTCCACACCCGGGCCTAT | Mouse Valid | 581 | NonTargetingControlGuideForMouse_0057_581 |
| MouseValid_MetsMIR_582_NonTargetingControlGuideForMouse_0058 | MetsMIR_582_NonTargetingControlGuideForMouse_0058 | MetsMIR_582 | CTTTATACCGCGCGTCGGCA | Mouse Valid | 582 | NonTargetingControlGuideForMouse_0058_582 |
| MouseValid_MetsMIR_583_NonTargetingControlGuideForMouse_0059 | MetsMIR_583_NonTargetingControlGuideForMouse_0059 | MetsMIR_583 | TCAAACGCCCGGGCGCCCCA | Mouse Valid | 583 | NonTargetingControlGuideForMouse_0059_583 |
| MouseValid_MetsMIR_584_NonTargetingControlGuideForMouse_0060 | MetsMIR_584_NonTargetingControlGuideForMouse_0060 | MetsMIR_584 | GACCGGTGTGTTTACGCGTG | Mouse Valid | 584 | NonTargetingControlGuideForMouse_0060_584 |
| MouseValid_MetsMIR_585_NonTargetingControlGuideForMouse_0061 | MetsMIR_585_NonTargetingControlGuideForMouse_0061 | MetsMIR_585 | CGGTGAGGATCCCTCTTGCC | Mouse Valid | 585 | NonTargetingControlGuideForMouse_0061_585 |
| MouseValid_MetsMIR_586_NonTargetingControlGuideForMouse_0062 | MetsMIR_586_NonTargetingControlGuideForMouse_0062 | MetsMIR_586 | ACGGTCCCAACGAGCGCGG | Mouse Valid | 586 | NonTargetingControlGuideForMouse_0062_586 |
| MouseValid_MetsMIR_587_NonTargetingControlGuideForMouse_0063 | MetsMIR_587_NonTargetingControlGuideForMouse_0063 | MetsMIR_587 | CGCTTCGTTGCCCGAACGCT | Mouse Valid | 587 | NonTargetingControlGuideForMouse_0063_587 |
| MouseValid_MetsMIR_588_NonTargetingControlGuideForMouse_0064 | MetsMIR_588_NonTargetingControlGuideForMouse_0064 | MetsMIR_588 | TTTATACCGTCACGAGTGCCC | Mouse Valid | 588 | NonTargetingControlGuideForMouse_0064_588 |
| MouseValid_MetsMIR_589_NonTargetingControlGuideForMouse_0065 | MetsMIR_589_NonTargetingControlGuideForMouse_0065 | MetsMIR_589 | TGCACCGGTACGGGCGACTC | Mouse Valid | 589 | NonTargetingControlGuideForMouse_0065_589 |
| MouseValid_MetsMIR_590_NonTargetingControlGuideForMouse_0066 | MetsMIR_590_NonTargetingControlGuideForMouse_0066 | MetsMIR_590 | GAGGCGTACTTCGGCCTCTAA | Mouse Valid | 590 | NonTargetingControlGuideForMouse_0066_590 |
| MouseValid_MetsMIR_591_NonTargetingControlGuideForMouse_0067 | MetsMIR_591_NonTargetingControlGuideForMouse_0067 | MetsMIR_591 | TTTCGAGACGGATACGTCTGC | Mouse Valid | 591 | NonTargetingControlGuideForMouse_0067_591 |
| MouseValid_MetsMIR_592_NonTargetingControlGuideForMouse_0068 | MetsMIR_592_NonTargetingControlGuideForMouse_0068 | MetsMIR_592 | TAGCCCGTCGAGTACTCCCC | Mouse Valid | 592 | NonTargetingControlGuideForMouse_0068_592 |
| MouseValid_MetsMIR_593_NonTargetingControlGuideForMouse_0069 | MetsMIR_593_NonTargetingControlGuideForMouse_0069 | MetsMIR_593 | AGCTTAGATCGTCGTCGTA | Mouse Valid | 593 | NonTargetingControlGuideForMouse_0069_593 |
| MouseValid_MetsMIR_594_NonTargetingControlGuideForMouse_0070 | MetsMIR_594_NonTargetingControlGuideForMouse_0070 | MetsMIR_594 | CGTCCGATGACTGGTGGATA | Mouse Valid | 594 | NonTargetingControlGuideForMouse_0070_594 |
| MouseValid_MetsMIR_595_NonTargetingControlGuideForMouse_0071 | MetsMIR_595_NonTargetingControlGuideForMouse_0071 | MetsMIR_595 | CCGTTTCGCCTATTGGTGCC | Mouse Valid | 595 | NonTargetingControlGuideForMouse_0071_595 |
| MouseValid_MetsMIR_596_NonTargetingControlGuideForMouse_0072 | MetsMIR_596_NonTargetingControlGuideForMouse_0072 | MetsMIR_596 | TTCCACGTGCGGCGTATTGG | Mouse Valid | 596 | NonTargetingControlGuideForMouse_0072_596 |
| MouseValid_MetsMIR_597_NonTargetingControlGuideForMouse_0073 | MetsMIR_597_NonTargetingControlGuideForMouse_0073 | MetsMIR_597 | TTTCAATTGTTCGCCCGAACA | Mouse Valid | 597 | NonTargetingControlGuideForMouse_0073_597 |
| MouseValid_MetsMIR_598_NonTargetingControlGuideForMouse_0074 | MetsMIR_598_NonTargetingControlGuideForMouse_0074 | MetsMIR_598 | GCGGATCTGACGGTTACTTA | Mouse Valid | 598 | NonTargetingControlGuideForMouse_0074_598 |
| MouseValid_MetsMIR_599_NonTargetingControlGuideForMouse_0075 | MetsMIR_599_NonTargetingControlGuideForMouse_0075 | MetsMIR_599 | AATGAAGCACCGATTGCGGA | Mouse Valid | 599 | NonTargetingControlGuideForMouse_0075_599 |
| MouseValid_MetsMIR_600_NonTargetingControlGuideForMouse_0076 | MetsMIR_600_NonTargetingControlGuideForMouse_0076 | MetsMIR_600 | TCCTATAATTGAGCGAACGC | Mouse Valid | 600 | NonTargetingControlGuideForMouse_0076_600 |

FIG. 18 CONTINUED

| | | | | | |
|---|---|---|---|---|---|
| MouseValid_MetsMMR_601_NonTargetingControlGuideForMouse_0077 | MetsMMR_601 | NonTargetingControlGuideForMouse_0077 | GCTACAGATTTGCGTTCGAG | MouseValid_601 | NonTargetingControlGuideForMouse_0077_601 |
| MouseValid_MetsMMR_602_NonTargetingControlGuideForMouse_0078 | MetsMMR_602 | NonTargetingControlGuideForMouse_0078 | GGACTGAAACCGATAGTATC | MouseValid_602 | NonTargetingControlGuideForMouse_0078_602 |
| MouseValid_MetsMMR_603_NonTargetingControlGuideForMouse_0079 | MetsMMR_603 | NonTargetingControlGuideForMouse_0079 | GCAATTCTGCAACGGCACGTC | MouseValid_603 | NonTargetingControlGuideForMouse_0079_603 |
| MouseValid_MetsMMR_604_NonTargetingControlGuideForMouse_0080 | MetsMMR_604 | NonTargetingControlGuideForMouse_0080 | CACCCGACTCGGCCCGTAAAG | MouseValid_604 | NonTargetingControlGuideForMouse_0080_604 |
| MouseValid_MetsMMR_605_NonTargetingControlGuideForMouse_0081 | MetsMMR_605 | NonTargetingControlGuideForMouse_0081 | CAACCGTGCGATGCGCGCTA | MouseValid_605 | NonTargetingControlGuideForMouse_0081_605 |
| MouseValid_MetsMMR_606_NonTargetingControlGuideForMouse_0082 | MetsMMR_606 | NonTargetingControlGuideForMouse_0082 | TGATGGACGCGATACGTTTA | MouseValid_606 | NonTargetingControlGuideForMouse_0082_606 |
| MouseValid_MetsMMR_607_NonTargetingControlGuideForMouse_0083 | MetsMMR_607 | NonTargetingControlGuideForMouse_0083 | TACCCCTTGGAGGGCGCATA | MouseValid_607 | NonTargetingControlGuideForMouse_0083_607 |
| MouseValid_MetsMMR_608_NonTargetingControlGuideForMouse_0084 | MetsMMR_608 | NonTargetingControlGuideForMouse_0084 | CCGTATACGTATCTATGCCG | MouseValid_608 | NonTargetingControlGuideForMouse_0084_608 |
| MouseValid_MetsMMR_609_NonTargetingControlGuideForMouse_0085 | MetsMMR_609 | NonTargetingControlGuideForMouse_0085 | ACAGCGGCCTAATACTTCGC | MouseValid_609 | NonTargetingControlGuideForMouse_0085_609 |
| MouseValid_MetsMMR_610_NonTargetingControlGuideForMouse_0086 | MetsMMR_610 | NonTargetingControlGuideForMouse_0086 | TATCGAACTGCACAGCCAAC | MouseValid_610 | NonTargetingControlGuideForMouse_0086_610 |
| MouseValid_MetsMMR_611_NonTargetingControlGuideForMouse_0087 | MetsMMR_611 | NonTargetingControlGuideForMouse_0087 | TGTCGGACCCATTGTCGAAC | MouseValid_611 | NonTargetingControlGuideForMouse_0087_611 |
| MouseValid_MetsMMR_612_NonTargetingControlGuideForMouse_0088 | MetsMMR_612 | NonTargetingControlGuideForMouse_0088 | AAAACCTAGGTAGATTCGGC | MouseValid_612 | NonTargetingControlGuideForMouse_0088_612 |
| MouseValid_MetsMMR_613_NonTargetingControlGuideForMouse_0089 | MetsMMR_613 | NonTargetingControlGuideForMouse_0089 | TAGATGGTCGCTTCTGTCGG | MouseValid_613 | NonTargetingControlGuideForMouse_0089_613 |
| MouseValid_MetsMMR_614_NonTargetingControlGuideForMouse_0090 | MetsMMR_614 | NonTargetingControlGuideForMouse_0090 | CATCGTAACACACGTACGAG | MouseValid_614 | NonTargetingControlGuideForMouse_0090_614 |
| MouseValid_MetsMMR_615_NonTargetingControlGuideForMouse_0091 | MetsMMR_615 | NonTargetingControlGuideForMouse_0091 | CAACGATCAGGCGGTGTTATC | MouseValid_615 | NonTargetingControlGuideForMouse_0091_615 |
| MouseValid_MetsMMR_616_NonTargetingControlGuideForMouse_0092 | MetsMMR_616 | NonTargetingControlGuideForMouse_0092 | ACAGCAGGGCCCGGAATAA | MouseValid_616 | NonTargetingControlGuideForMouse_0092_616 |
| MouseValid_MetsMMR_617_NonTargetingControlGuideForMouse_0093 | MetsMMR_617 | NonTargetingControlGuideForMouse_0093 | AGCCGGGCTTTCCGTCAAGC | MouseValid_617 | NonTargetingControlGuideForMouse_0093_617 |
| MouseValid_MetsMMR_618_NonTargetingControlGuideForMouse_0094 | MetsMMR_618 | NonTargetingControlGuideForMouse_0094 | ACGGTCCCTCGCGGTCAAT | MouseValid_618 | NonTargetingControlGuideForMouse_0094_618 |
| MouseValid_MetsMMR_619_NonTargetingControlGuideForMouse_0095 | MetsMMR_619 | NonTargetingControlGuideForMouse_0095 | TCAATAGTTCTGCGCGAATT | MouseValid_619 | NonTargetingControlGuideForMouse_0095_619 |
| MouseValid_MetsMMR_620_NonTargetingControlGuideForMouse_0096 | MetsMMR_620 | NonTargetingControlGuideForMouse_0096 | TCGTTACATACCCCGCGGAA | MouseValid_620 | NonTargetingControlGuideForMouse_0096_620 |
| MouseValid_MetsMMR_621_NonTargetingControlGuideForMouse_0097 | MetsMMR_621 | NonTargetingControlGuideForMouse_0097 | CATTCGGTCCGTTCATCTCG | MouseValid_621 | NonTargetingControlGuideForMouse_0097_621 |
| MouseValid_MetsMMR_622_NonTargetingControlGuideForMouse_0098 | MetsMMR_622 | NonTargetingControlGuideForMouse_0098 | TTCGGCTCAATGGCGCGAGC | MouseValid_622 | NonTargetingControlGuideForMouse_0098_622 |

FIG. 18 CONTINUED

| | MouseValid_MetsMIR_623_NonTargetingControlGuideForMouse_0099 | MetsMIR_623 | NonTargetingControlGuideForMouse_0099 | CATTACCCGGCGCCGTGACTCC | MouseValid | _623 | NonTargetingControlGuideForMouse_0099_623 |
|---|---|---|---|---|---|---|---|
| | MouseValid_MetsMIR_624_NonTargetingControlGuideForMouse_0100 | MetsMIR_624 | NonTargetingControlGuideForMouse_0100 | GGACGGATGGGACGACTAGT | MouseValid | _624 | NonTargetingControlGuideForMouse_0100_624 |

Mouse Non-targeting control guides

| long_name | uid | gene | seq | Pool_name |
|---|---|---|---|---|
| MouseDummy_MetsMIR_625_NonTargetingControlGuideForMouse_0001 | MetsMIR_625 | NonTargetingControlGuideForMouse_0001 | GCGAGGTATTCGGGTCCGCG | MouseDummy |
| MouseDummy_MetsMIR_626_NonTargetingControlGuideForMouse_0002 | MetsMIR_626 | NonTargetingControlGuideForMouse_0002 | GCTTTCACGGAGGTTCGACG | MouseDummy |
| MouseDummy_MetsMIR_627_NonTargetingControlGuideForMouse_0003 | MetsMIR_627 | NonTargetingControlGuideForMouse_0003 | ATGTTCCAGTTCGGCTCGAT | MouseDummy |
| MouseDummy_MetsMIR_628_NonTargetingControlGuideForMouse_0004 | MetsMIR_628 | NonTargetingControlGuideForMouse_0004 | ACGTGTAAGGCGAACGCCTTT | MouseDummy |
| MouseDummy_MetsMIR_629_NonTargetingControlGuideForMouse_0005 | MetsMIR_629 | NonTargetingControlGuideForMouse_0005 | GACTCCGGGTACTAAATGTC | MouseDummy |
| MouseDummy_MetsMIR_630_NonTargetingControlGuideForMouse_0006 | MetsMIR_630 | NonTargetingControlGuideForMouse_0006 | CCGCGCCCGTTAGGGAACGAG | MouseDummy |
| MouseDummy_MetsMIR_631_NonTargetingControlGuideForMouse_0007 | MetsMIR_631 | NonTargetingControlGuideForMouse_0007 | ATTGTTCCACCGTCTACGGG | MouseDummy |
| MouseDummy_MetsMIR_632_NonTargetingControlGuideForMouse_0008 | MetsMIR_632 | NonTargetingControlGuideForMouse_0008 | ACCCATCGGGTGCGATATGG | MouseDummy |
| MouseDummy_MetsMIR_633_NonTargetingControlGuideForMouse_0009 | MetsMIR_633 | NonTargetingControlGuideForMouse_0009 | CGGGCGTCACCTCCTAGTAA | MouseDummy |
| MouseDummy_MetsMIR_634_NonTargetingControlGuideForMouse_0010 | MetsMIR_634 | NonTargetingControlGuideForMouse_0010 | GCTTTCTACTCGCAAGTATT | MouseDummy |
| MouseDummy_MetsMIR_635_NonTargetingControlGuideForMouse_0011 | MetsMIR_635 | NonTargetingControlGuideForMouse_0011 | TACAGTTATACGTCGGGGTG | MouseDummy |
| MouseDummy_MetsMIR_636_NonTargetingControlGuideForMouse_0012 | MetsMIR_636 | NonTargetingControlGuideForMouse_0012 | AAGCACAAGAACGGTCCGGC | MouseDummy |
| MouseDummy_MetsMIR_637_NonTargetingControlGuideForMouse_0013 | MetsMIR_637 | NonTargetingControlGuideForMouse_0013 | CAGCCACCGCACCGGCGGTAA | MouseDummy |
| MouseDummy_MetsMIR_638_NonTargetingControlGuideForMouse_0014 | MetsMIR_638 | NonTargetingControlGuideForMouse_0014 | GTCAAGCCGAACGCTGCCGG | MouseDummy |
| MouseDummy_MetsMIR_639_NonTargetingControlGuideForMouse_0015 | MetsMIR_639 | NonTargetingControlGuideForMouse_0015 | CCTTAGACCGGGTGTACCTC | MouseDummy |
| MouseDummy_MetsMIR_640_NonTargetingControlGuideForMouse_0016 | MetsMIR_640 | NonTargetingControlGuideForMouse_0016 | AAGTCTATGCGGGCTCGTA | MouseDummy |
| MouseDummy_MetsMIR_641_NonTargetingControlGuideForMouse_0017 | MetsMIR_641 | NonTargetingControlGuideForMouse_0017 | TTGTCAACTTCGGCCAACGC | MouseDummy |

| | | | | |
|---|---|---|---|---|
| MouseDummy_MetsMiR_642_NonTargetingControlGuideForMouse_0018 | MetsMiR_642 | NonTargetingControlGuideForMouse_0018 | ATAGATGTCTACGCGCGTT | MouseDummy |
| MouseDummy_MetsMiR_643_NonTargetingControlGuideForMouse_0019 | MetsMiR_643 | NonTargetingControlGuideForMouse_0019 | CTTCGGGCTATTCAGCGATAG | MouseDummy |
| MouseDummy_MetsMiR_644_NonTargetingControlGuideForMouse_0020 | MetsMiR_644 | NonTargetingControlGuideForMouse_0020 | GCGGTTACCGGCGAAAACCAT | MouseDummy |
| MouseDummy_MetsMiR_645_NonTargetingControlGuideForMouse_0021 | MetsMiR_645 | NonTargetingControlGuideForMouse_0021 | ACCAACGCTACGATCCCGGA | MouseDummy |
| MouseDummy_MetsMiR_646_NonTargetingControlGuideForMouse_0022 | MetsMiR_646 | NonTargetingControlGuideForMouse_0022 | CCCTATATGCGAGATCCATA | MouseDummy |
| MouseDummy_MetsMiR_647_NonTargetingControlGuideForMouse_0023 | MetsMiR_647 | NonTargetingControlGuideForMouse_0023 | AGAAAGGCACGTGCGACGTC | MouseDummy |
| MouseDummy_MetsMiR_648_NonTargetingControlGuideForMouse_0024 | MetsMiR_648 | NonTargetingControlGuideForMouse_0024 | GACCAACGCTTACGGTAACTC | MouseDummy |
| MouseDummy_MetsMiR_649_NonTargetingControlGuideForMouse_0025 | MetsMiR_649 | NonTargetingControlGuideForMouse_0025 | ATTATTCCTCCGGATGACGA | MouseDummy |
| MouseDummy_MetsMiR_650_NonTargetingControlGuideForMouse_0026 | MetsMiR_650 | NonTargetingControlGuideForMouse_0026 | TCTCAGTTCGTAGCGAACGA | MouseDummy |
| MouseDummy_MetsMiR_651_NonTargetingControlGuideForMouse_0027 | MetsMiR_651 | NonTargetingControlGuideForMouse_0027 | TCCCGGGAGGTACGGTGTAC | MouseDummy |
| MouseDummy_MetsMiR_652_NonTargetingControlGuideForMouse_0028 | MetsMiR_652 | NonTargetingControlGuideForMouse_0028 | GGGGATGGCTTACGGTCGCG | MouseDummy |
| MouseDummy_MetsMiR_653_NonTargetingControlGuideForMouse_0029 | MetsMiR_653 | NonTargetingControlGuideForMouse_0029 | GTATCCTCCTTACGGCCCGT | MouseDummy |
| MouseDummy_MetsMiR_654_NonTargetingControlGuideForMouse_0030 | MetsMiR_654 | NonTargetingControlGuideForMouse_0030 | GCTCGGACCTTTAGAGTC | MouseDummy |
| MouseDummy_MetsMiR_655_NonTargetingControlGuideForMouse_0031 | MetsMiR_655 | NonTargetingControlGuideForMouse_0031 | GTGGTTACGTTAACGACTAC | MouseDummy |
| MouseDummy_MetsMiR_656_NonTargetingControlGuideForMouse_0032 | MetsMiR_656 | NonTargetingControlGuideForMouse_0032 | TGCAACGATGGTTACGGTAC | MouseDummy |
| MouseDummy_MetsMiR_657_NonTargetingControlGuideForMouse_0033 | MetsMiR_657 | NonTargetingControlGuideForMouse_0033 | AACGGGCGCAATACCCTTTT | MouseDummy |
| MouseDummy_MetsMiR_658_NonTargetingControlGuideForMouse_0034 | MetsMiR_658 | NonTargetingControlGuideForMouse_0034 | TCGTGTCTAGCTATCGAGTG | MouseDummy |
| MouseDummy_MetsMiR_659_NonTargetingControlGuideForMouse_0035 | MetsMiR_659 | NonTargetingControlGuideForMouse_0035 | GACGTCTAATTCTGCCGT | MouseDummy |
| MouseDummy_MetsMiR_660_NonTargetingControlGuideForMouse_0036 | MetsMiR_660 | NonTargetingControlGuideForMouse_0036 | TAGTCCTAGTTAGATTCGCG | MouseDummy |
| MouseDummy_MetsMiR_661_NonTargetingControlGuideForMouse_0037 | MetsMiR_661 | NonTargetingControlGuideForMouse_0037 | AAGGCCTTAACACGTCGACC | MouseDummy |
| MouseDummy_MetsMiR_662_NonTargetingControlGuideForMouse_0038 | MetsMiR_662 | NonTargetingControlGuideForMouse_0038 | ATTCGTGCATCGGGGGTTT | MouseDummy |
| MouseDummy_MetsMiR_663_NonTargetingControlGuideForMouse_0039 | MetsMiR_663 | NonTargetingControlGuideForMouse_0039 | CACTTCGCGTCTATCACTA | MouseDummy |

FIG. 18 CONTINUED

| | | | |
|---|---|---|---|
| MouseDummy_MetsMIR_664_NonTargetingControlGuideForMouse_0040 | MetsMIR_664 | NonTargetingControlGuideForMouse_0040 | GACCTTGCCAATTGAGCGCTC | MouseDummy |
| MouseDummy_MetsMIR_665_NonTargetingControlGuideForMouse_0041 | MetsMIR_665 | NonTargetingControlGuideForMouse_0041 | TGTATCCACCGTGACCCGGT | MouseDummy |
| MouseDummy_MetsMIR_666_NonTargetingControlGuideForMouse_0042 | MetsMIR_666 | NonTargetingControlGuideForMouse_0042 | GATCTTACCACTCGTCGTAG | MouseDummy |
| MouseDummy_MetsMIR_667_NonTargetingControlGuideForMouse_0043 | MetsMIR_667 | NonTargetingControlGuideForMouse_0043 | TTCGCCGGCGACAAGTCGA | MouseDummy |
| MouseDummy_MetsMIR_668_NonTargetingControlGuideForMouse_0044 | MetsMIR_668 | NonTargetingControlGuideForMouse_0044 | AGCACTAGGATCGCGGCCTT | MouseDummy |
| MouseDummy_MetsMIR_669_NonTargetingControlGuideForMouse_0045 | MetsMIR_669 | NonTargetingControlGuideForMouse_0045 | GCGTATCTACCCTACCGCG | MouseDummy |
| MouseDummy_MetsMIR_670_NonTargetingControlGuideForMouse_0046 | MetsMIR_670 | NonTargetingControlGuideForMouse_0046 | GCGGAGGCACCGACAAGT | MouseDummy |
| MouseDummy_MetsMIR_671_NonTargetingControlGuideForMouse_0047 | MetsMIR_671 | NonTargetingControlGuideForMouse_0047 | CGGCGTATATGTCACCGGCA | MouseDummy |
| MouseDummy_MetsMIR_672_NonTargetingControlGuideForMouse_0048 | MetsMIR_672 | NonTargetingControlGuideForMouse_0048 | TAAAACCGATCACGATACCA | MouseDummy |
| MouseDummy_MetsMIR_673_NonTargetingControlGuideForMouse_0049 | MetsMIR_673 | NonTargetingControlGuideForMouse_0049 | TCCTCGCGATCACCGTCGG | MouseDummy |
| MouseDummy_MetsMIR_674_NonTargetingControlGuideForMouse_0050 | MetsMIR_674 | NonTargetingControlGuideForMouse_0050 | TGGCCCACAAGGTGCGATAT | MouseDummy |
| MouseDummy_MetsMIR_675_NonTargetingControlGuideForMouse_0051 | MetsMIR_675 | NonTargetingControlGuideForMouse_0051 | GGGGTAGGCCTAATTACGGA | MouseDummy |
| MouseDummy_MetsMIR_676_NonTargetingControlGuideForMouse_0052 | MetsMIR_676 | NonTargetingControlGuideForMouse_0052 | CGGTTCGTCTCTCGCAAACA | MouseDummy |
| MouseDummy_MetsMIR_677_NonTargetingControlGuideForMouse_0053 | MetsMIR_677 | NonTargetingControlGuideForMouse_0053 | TTATGTCCCTCTCGGCGCAT | MouseDummy |
| MouseDummy_MetsMIR_678_NonTargetingControlGuideForMouse_0054 | MetsMIR_678 | NonTargetingControlGuideForMouse_0054 | CCGTTCTGACGACGCTAAAG | MouseDummy |
| MouseDummy_MetsMIR_679_NonTargetingControlGuideForMouse_0055 | MetsMIR_679 | NonTargetingControlGuideForMouse_0055 | AAACTCCGTGTCAACCGAT | MouseDummy |
| MouseDummy_MetsMIR_680_NonTargetingControlGuideForMouse_0056 | MetsMIR_680 | NonTargetingControlGuideForMouse_0056 | GTTTGCGAGTCAAAGTACGC | MouseDummy |
| MouseDummy_MetsMIR_681_NonTargetingControlGuideForMouse_0057 | MetsMIR_681 | NonTargetingControlGuideForMouse_0057 | GGGCTGCACACGCGGCCTAT | MouseDummy |
| MouseDummy_MetsMIR_682_NonTargetingControlGuideForMouse_0058 | MetsMIR_682 | NonTargetingControlGuideForMouse_0058 | CTTTATATACCGCGGGCCCCA | MouseDummy |
| MouseDummy_MetsMIR_683_NonTargetingControlGuideForMouse_0059 | MetsMIR_683 | NonTargetingControlGuideForMouse_0059 | TCAAACGCCCCGGGCCCCCA | MouseDummy |
| MouseDummy_MetsMIR_684_NonTargetingControlGuideForMouse_0060 | MetsMIR_684 | NonTargetingControlGuideForMouse_0060 | GACCGGTGTGTTTACGCGTG | MouseDummy |
| MouseDummy_MetsMIR_685_NonTargetingControlGuideForMouse_0061 | MetsMIR_685 | NonTargetingControlGuideForMouse_0061 | CGGTGAGGATCCCTTGCG | MouseDummy |

FIG. 18 CONTINUED

| | | | |
|---|---|---|---|
| MouseDummy_MetsMiR_686_NonTargetingControlGuideForMouse_0062 | MetsMiR_686 | NonTargetingControlGuideForMouse_0062 | ACGGTCCAACGAGCGGCCGG | MouseDummy |
| MouseDummy_MetsMiR_687_NonTargetingControlGuideForMouse_0063 | MetsMiR_687 | NonTargetingControlGuideForMouse_0063 | CGGTTCATTGCCGAACGCT | MouseDummy |
| MouseDummy_MetsMiR_688_NonTargetingControlGuideForMouse_0064 | MetsMiR_688 | NonTargetingControlGuideForMouse_0064 | TTATACCGTCACGAGTGCC | MouseDummy |
| MouseDummy_MetsMiR_689_NonTargetingControlGuideForMouse_0065 | MetsMiR_689 | NonTargetingControlGuideForMouse_0065 | TGCACCGGTACGGGCGACTC | MouseDummy |
| MouseDummy_MetsMiR_690_NonTargetingControlGuideForMouse_0066 | MetsMiR_690 | NonTargetingControlGuideForMouse_0066 | GAGGCGTACTTCGGCTCTAA | MouseDummy |
| MouseDummy_MetsMiR_691_NonTargetingControlGuideForMouse_0067 | MetsMiR_691 | NonTargetingControlGuideForMouse_0067 | TTCGAGACGGATACGTCTGC | MouseDummy |
| MouseDummy_MetsMiR_692_NonTargetingControlGuideForMouse_0068 | MetsMiR_692 | NonTargetingControlGuideForMouse_0068 | TAGCCGGTGAGTACTCCCC | MouseDummy |
| MouseDummy_MetsMiR_693_NonTargetingControlGuideForMouse_0069 | MetsMiR_693 | NonTargetingControlGuideForMouse_0069 | AGCTTAGATCGTGCGTCGTA | MouseDummy |
| MouseDummy_MetsMiR_694_NonTargetingControlGuideForMouse_0070 | MetsMiR_694 | NonTargetingControlGuideForMouse_0070 | CGGCCGATGACTGGTGGATA | MouseDummy |
| MouseDummy_MetsMiR_695_NonTargetingControlGuideForMouse_0071 | MetsMiR_695 | NonTargetingControlGuideForMouse_0071 | CCGTTTCGCTATTGGTGCG | MouseDummy |
| MouseDummy_MetsMiR_696_NonTargetingControlGuideForMouse_0072 | MetsMiR_696 | NonTargetingControlGuideForMouse_0072 | TTCGACGTGCGGGCGTATTGG | MouseDummy |
| MouseDummy_MetsMiR_697_NonTargetingControlGuideForMouse_0073 | MetsMiR_697 | NonTargetingControlGuideForMouse_0073 | TTCAATTGTTCGCCCGAACA | MouseDummy |
| MouseDummy_MetsMiR_698_NonTargetingControlGuideForMouse_0074 | MetsMiR_698 | NonTargetingControlGuideForMouse_0074 | GCGGATCTGACGGTTACTTA | MouseDummy |
| MouseDummy_MetsMiR_699_NonTargetingControlGuideForMouse_0075 | MetsMiR_699 | NonTargetingControlGuideForMouse_0075 | AATGAAGCACCGATTGCGGA | MouseDummy |
| MouseDummy_MetsMiR_700_NonTargetingControlGuideForMouse_0076 | MetsMiR_700 | NonTargetingControlGuideForMouse_0076 | TCCTATAATTGAGCGAACGG | MouseDummy |
| MouseDummy_MetsMiR_701_NonTargetingControlGuideForMouse_0077 | MetsMiR_701 | NonTargetingControlGuideForMouse_0077 | GCTACAGATTGCGTTCGAG | MouseDummy |
| MouseDummy_MetsMiR_702_NonTargetingControlGuideForMouse_0078 | MetsMiR_702 | NonTargetingControlGuideForMouse_0078 | GGACTGAAACCGATAGTATC | MouseDummy |
| MouseDummy_MetsMiR_703_NonTargetingControlGuideForMouse_0079 | MetsMiR_703 | NonTargetingControlGuideForMouse_0079 | GCAATTCTGCAACGCACGTC | MouseDummy |
| MouseDummy_MetsMiR_704_NonTargetingControlGuideForMouse_0080 | MetsMiR_704 | NonTargetingControlGuideForMouse_0080 | CACCCGACTCGGCCGTAAAG | MouseDummy |
| MouseDummy_MetsMiR_705_NonTargetingControlGuideForMouse_0081 | MetsMiR_705 | NonTargetingControlGuideForMouse_0081 | CAACCGTGCGATGCCGGCTA | MouseDummy |
| MouseDummy_MetsMiR_706_NonTargetingControlGuideForMouse_0082 | MetsMiR_706 | NonTargetingControlGuideForMouse_0082 | TGATGGACGCGATACGTTTA | MouseDummy |
| MouseDummy_MetsMiR_707_NonTargetingControlGuideForMouse_0083 | MetsMiR_707 | NonTargetingControlGuideForMouse_0083 | TACCCCTTGAGGGCGCATA | MouseDummy |

FIG. 18 CONTINUED

| | | | |
|---|---|---|---|
| MouseDummy_MetsMiR_708_NonTargetingControlGuideForMouse_0084 | MetsMiR_708 | NonTargetingControlGuideForMouse_0084 | CCGTATACGTATCTATCCG | MouseDummy |
| MouseDummy_MetsMiR_709_NonTargetingControlGuideForMouse_0085 | MetsMiR_709 | NonTargetingControlGuideForMouse_0085 | ACAGCGGCCTAATACTTCGC | MouseDummy |
| MouseDummy_MetsMiR_710_NonTargetingControlGuideForMouse_0086 | MetsMiR_710 | NonTargetingControlGuideForMouse_0086 | TATCGAACTGCACACGCAAC | MouseDummy |
| MouseDummy_MetsMiR_711_NonTargetingControlGuideForMouse_0087 | MetsMiR_711 | NonTargetingControlGuideForMouse_0087 | TGTCGGACCATTGTGTCGAAC | MouseDummy |
| MouseDummy_MetsMiR_712_NonTargetingControlGuideForMouse_0088 | MetsMiR_712 | NonTargetingControlGuideForMouse_0088 | AAACCTAGCGTAGATTCGGC | MouseDummy |
| MouseDummy_MetsMiR_713_NonTargetingControlGuideForMouse_0089 | MetsMiR_713 | NonTargetingControlGuideForMouse_0089 | TAGATGGTGCTTCTGTCGCG | MouseDummy |
| MouseDummy_MetsMiR_714_NonTargetingControlGuideForMouse_0090 | MetsMiR_714 | NonTargetingControlGuideForMouse_0090 | CATCGTAACACACGTAGGAG | MouseDummy |
| MouseDummy_MetsMiR_715_NonTargetingControlGuideForMouse_0091 | MetsMiR_715 | NonTargetingControlGuideForMouse_0091 | CAACGATCAGGGGTGTTATC | MouseDummy |
| MouseDummy_MetsMiR_716_NonTargetingControlGuideForMouse_0092 | MetsMiR_716 | NonTargetingControlGuideForMouse_0092 | ACACAGCAGGGCCGGAATAA | MouseDummy |
| MouseDummy_MetsMiR_717_NonTargetingControlGuideForMouse_0093 | MetsMiR_717 | NonTargetingControlGuideForMouse_0093 | AGCCCGGCGTTTCCGTCAAGC | MouseDummy |
| MouseDummy_MetsMiR_718_NonTargetingControlGuideForMouse_0094 | MetsMiR_718 | NonTargetingControlGuideForMouse_0094 | ACGGTCCCTCTGGGTCAAT | MouseDummy |
| MouseDummy_MetsMiR_719_NonTargetingControlGuideForMouse_0095 | MetsMiR_719 | NonTargetingControlGuideForMouse_0095 | TCAATAGTTCTGCGCGGAATT | MouseDummy |
| MouseDummy_MetsMiR_720_NonTargetingControlGuideForMouse_0096 | MetsMiR_720 | NonTargetingControlGuideForMouse_0096 | TCGTTACATACCCGCGGGAA | MouseDummy |
| MouseDummy_MetsMiR_721_NonTargetingControlGuideForMouse_0097 | MetsMiR_721 | NonTargetingControlGuideForMouse_0097 | CATTCGGTCCGTCATCTCG | MouseDummy |
| MouseDummy_MetsMiR_722_NonTargetingControlGuideForMouse_0098 | MetsMiR_722 | NonTargetingControlGuideForMouse_0098 | TTCGGCTCAATGGCGGCGAGC | MouseDummy |
| MouseDummy_MetsMiR_723_NonTargetingControlGuideForMouse_0099 | MetsMiR_723 | NonTargetingControlGuideForMouse_0099 | CATACCCGGCCGGTGACTCC | MouseDummy |
| MouseDummy_MetsMiR_724_NonTargetingControlGuideForMouse_0100 | MetsMiR_724 | NonTargetingControlGuideForMouse_0100 | GGACGGATGGGACGACTAGT | MouseDummy |
| MouseDummy_MetsMiR_725_NonTargetingControlGuideForMouse_0101 | MetsMiR_725 | NonTargetingControlGuideForMouse_0101 | GTCCAACGACTGACCCGCGG | MouseDummy |
| MouseDummy_MetsMiR_726_NonTargetingControlGuideForMouse_0102 | MetsMiR_726 | NonTargetingControlGuideForMouse_0102 | CGACACTTGGGCTGACGCGC | MouseDummy |
| MouseDummy_MetsMiR_727_NonTargetingControlGuideForMouse_0103 | MetsMiR_727 | NonTargetingControlGuideForMouse_0103 | TGTGTAATTACGTTTCGCGG | MouseDummy |
| MouseDummy_MetsMiR_728_NonTargetingControlGuideForMouse_0104 | MetsMiR_728 | NonTargetingControlGuideForMouse_0104 | AACCGTACTGCGAGGAGCAT | MouseDummy |
| MouseDummy_MetsMiR_729_NonTargetingControlGuideForMouse_0105 | MetsMiR_729 | NonTargetingControlGuideForMouse_0105 | GATATTTACCCGCCATAAGA | MouseDummy |

| | | | |
|---|---|---|---|
| MouseDummy_MetsMR_730_NonTargetingControlGuideForMouse_0106 | MetsMR_730 | NonTargetingControlGuideForMouse_0106 | GCGAGTGTATCGATCACTC | MouseDummy |
| MouseDummy_MetsMR_731_NonTargetingControlGuideForMouse_0107 | MetsMR_731 | NonTargetingControlGuideForMouse_0107 | TAATGGAAGATCGCGATAC | MouseDummy |
| MouseDummy_MetsMR_732_NonTargetingControlGuideForMouse_0108 | MetsMR_732 | NonTargetingControlGuideForMouse_0108 | TGTCCTACCGAATGAACCGT | MouseDummy |
| MouseDummy_MetsMR_733_NonTargetingControlGuideForMouse_0109 | MetsMR_733 | NonTargetingControlGuideForMouse_0109 | ACGGAAGTGTCGCAGAGTG | MouseDummy |
| MouseDummy_MetsMR_734_NonTargetingControlGuideForMouse_0110 | MetsMR_734 | NonTargetingControlGuideForMouse_0110 | GCAGAGCGCTAATCGGCATCG | MouseDummy |
| MouseDummy_MetsMR_735_NonTargetingControlGuideForMouse_0111 | MetsMR_735 | NonTargetingControlGuideForMouse_0111 | GCCGCGCCATATATCGCCAT | MouseDummy |
| MouseDummy_MetsMR_736_NonTargetingControlGuideForMouse_0112 | MetsMR_736 | NonTargetingControlGuideForMouse_0112 | CGAATGCGCCGGAGAATATT | MouseDummy |
| MouseDummy_MetsMR_737_NonTargetingControlGuideForMouse_0113 | MetsMR_737 | NonTargetingControlGuideForMouse_0113 | CCCGCCTGGCGATTCACGGG | MouseDummy |
| MouseDummy_MetsMR_738_NonTargetingControlGuideForMouse_0114 | MetsMR_738 | NonTargetingControlGuideForMouse_0114 | AGCCTAGTCGCGCTAATATT | MouseDummy |
| MouseDummy_MetsMR_739_NonTargetingControlGuideForMouse_0115 | MetsMR_739 | NonTargetingControlGuideForMouse_0115 | GTGTGCCCTCGCAGAGCGTAAG | MouseDummy |
| MouseDummy_MetsMR_740_NonTargetingControlGuideForMouse_0116 | MetsMR_740 | NonTargetingControlGuideForMouse_0116 | TCATGGCCTCGTAATACCT | MouseDummy |
| MouseDummy_MetsMR_741_NonTargetingControlGuideForMouse_0117 | MetsMR_741 | NonTargetingControlGuideForMouse_0117 | TGTGCCACGCCGCTGCAACG | MouseDummy |
| MouseDummy_MetsMR_742_NonTargetingControlGuideForMouse_0118 | MetsMR_742 | NonTargetingControlGuideForMouse_0118 | GCAAATAGGTCGGAGCGTGT | MouseDummy |
| MouseDummy_MetsMR_743_NonTargetingControlGuideForMouse_0119 | MetsMR_743 | NonTargetingControlGuideForMouse_0119 | GGATAGCCCGGTTGGTGCGT | MouseDummy |
| MouseDummy_MetsMR_744_NonTargetingControlGuideForMouse_0120 | MetsMR_744 | NonTargetingControlGuideForMouse_0120 | TCGCAAAATGCGGATTCCGT | MouseDummy |
| MouseDummy_MetsMR_745_NonTargetingControlGuideForMouse_0121 | MetsMR_745 | NonTargetingControlGuideForMouse_0121 | GGTGCAGTCCGTTTAGTCGG | MouseDummy |
| MouseDummy_MetsMR_746_NonTargetingControlGuideForMouse_0122 | MetsMR_746 | NonTargetingControlGuideForMouse_0122 | TGGGTTCCGGCCCCATGTAC | MouseDummy |
| MouseDummy_MetsMR_747_NonTargetingControlGuideForMouse_0123 | MetsMR_747 | NonTargetingControlGuideForMouse_0123 | CCTTCGGATTCGTAGGCTGG | MouseDummy |
| MouseDummy_MetsMR_748_NonTargetingControlGuideForMouse_0124 | MetsMR_748 | NonTargetingControlGuideForMouse_0124 | TCCCCGTACGTGTATGTCG | MouseDummy |
| MouseDummy_MetsMR_749_NonTargetingControlGuideForMouse_0125 | MetsMR_749 | NonTargetingControlGuideForMouse_0125 | AGGTCGGTGTCAACGGTAG | MouseDummy |
| MouseDummy_MetsMR_750_NonTargetingControlGuideForMouse_0126 | MetsMR_750 | NonTargetingControlGuideForMouse_0126 | AAAAGTCCGCGATTACGTC | MouseDummy |
| MouseDummy_MetsMR_751_NonTargetingControlGuideForMouse_0127 | MetsMR_751 | NonTargetingControlGuideForMouse_0127 | TTATCGCACAACCCGAAAG | MouseDummy |

| MouseDummy_MetsMR_752_NonTargetingControlGuideForMouse_0128 | MetsMR_752 | NonTargetingControlGuideForMouse_0128 | CACCCCGTAGCAACGATAAA | MouseDummy |
|---|---|---|---|---|
| MouseDummy_MetsMR_753_NonTargetingControlGuideForMouse_0129 | MetsMR_753 | NonTargetingControlGuideForMouse_0129 | TAACAGCTTCCGCGTAATAT | MouseDummy |
| MouseDummy_MetsMR_754_NonTargetingControlGuideForMouse_0130 | MetsMR_754 | NonTargetingControlGuideForMouse_0130 | GCCATAGCCAATCGCTAGTT | MouseDummy |
| MouseDummy_MetsMR_755_NonTargetingControlGuideForMouse_0131 | MetsMR_755 | NonTargetingControlGuideForMouse_0131 | CATTCTATGAGACGTGCGTAC | MouseDummy |
| MouseDummy_MetsMR_756_NonTargetingControlGuideForMouse_0132 | MetsMR_756 | NonTargetingControlGuideForMouse_0132 | TTGATAAACCGCGGCCCGAAA | MouseDummy |
| MouseDummy_MetsMR_757_NonTargetingControlGuideForMouse_0133 | MetsMR_757 | NonTargetingControlGuideForMouse_0133 | GTATCCTCGCAATCGTTAGG | MouseDummy |
| MouseDummy_MetsMR_758_NonTargetingControlGuideForMouse_0134 | MetsMR_758 | NonTargetingControlGuideForMouse_0134 | TGGCGCTCCTGCGCACACGA | MouseDummy |
| MouseDummy_MetsMR_759_NonTargetingControlGuideForMouse_0135 | MetsMR_759 | NonTargetingControlGuideForMouse_0135 | TTCGAAGTCTAACCGGCGGG | MouseDummy |
| MouseDummy_MetsMR_760_NonTargetingControlGuideForMouse_0136 | MetsMR_760 | NonTargetingControlGuideForMouse_0136 | GTTTCCCGGACTGTCGCGT | MouseDummy |
| MouseDummy_MetsMR_761_NonTargetingControlGuideForMouse_0137 | MetsMR_761 | NonTargetingControlGuideForMouse_0137 | AACGCCCCGGATTTCGTTGA | MouseDummy |
| MouseDummy_MetsMR_762_NonTargetingControlGuideForMouse_0138 | MetsMR_762 | NonTargetingControlGuideForMouse_0138 | ACAACACGGCGACAAGTCTA | MouseDummy |
| MouseDummy_MetsMR_763_NonTargetingControlGuideForMouse_0139 | MetsMR_763 | NonTargetingControlGuideForMouse_0139 | TAAGCGGCGTCATCTCCCC | MouseDummy |
| MouseDummy_MetsMR_764_NonTargetingControlGuideForMouse_0140 | MetsMR_764 | NonTargetingControlGuideForMouse_0140 | CCGCCCCTGCGAACTGCGTT | MouseDummy |
| MouseDummy_MetsMR_765_NonTargetingControlGuideForMouse_0141 | MetsMR_765 | NonTargetingControlGuideForMouse_0141 | TATCTAATCGGGAGTCGTA | MouseDummy |
| MouseDummy_MetsMR_766_NonTargetingControlGuideForMouse_0142 | MetsMR_766 | NonTargetingControlGuideForMouse_0142 | ACGCTATAGTGTACGCTCTAA | MouseDummy |
| MouseDummy_MetsMR_767_NonTargetingControlGuideForMouse_0143 | MetsMR_767 | NonTargetingControlGuideForMouse_0143 | GTAGACATATTGCGTAATCG | MouseDummy |
| MouseDummy_MetsMR_768_NonTargetingControlGuideForMouse_0144 | MetsMR_768 | NonTargetingControlGuideForMouse_0144 | CGTAAACCATAACGTTGGTC | MouseDummy |
| MouseDummy_MetsMR_769_NonTargetingControlGuideForMouse_0145 | MetsMR_769 | NonTargetingControlGuideForMouse_0145 | GGACGTAGATTAGGCGTAA | MouseDummy |
| MouseDummy_MetsMR_770_NonTargetingControlGuideForMouse_0146 | MetsMR_770 | NonTargetingControlGuideForMouse_0146 | CGGGCAATATGATCGTAGGC | MouseDummy |
| MouseDummy_MetsMR_771_NonTargetingControlGuideForMouse_0147 | MetsMR_771 | NonTargetingControlGuideForMouse_0147 | GGACCAATGTTACGTAGT | MouseDummy |
| MouseDummy_MetsMR_772_NonTargetingControlGuideForMouse_0148 | MetsMR_772 | NonTargetingControlGuideForMouse_0148 | CAGGGACGTAGCCGCGTTA | MouseDummy |
| MouseDummy_MetsMR_773_NonTargetingControlGuideForMouse_0149 | MetsMR_773 | NonTargetingControlGuideForMouse_0149 | AACCCCCGGCTGTCATCGCCG | MouseDummy |

| | | | |
|---|---|---|---|
| MouseDummy_MetsMR_795_NonTargetingControlGuideForMouse_0171 | MetsMR_774 | NonTargetingControlGuideForMouse_0150 | GATTCATTATGGCATAGG | MouseDummy |
| MouseDummy_MetsMR_775_NonTargetingControlGuideForMouse_0151 | MetsMR_775 | NonTargetingControlGuideForMouse_0151 | AGTCATCCTCTATGCCGTA | MouseDummy |
| MouseDummy_MetsMR_776_NonTargetingControlGuideForMouse_0152 | MetsMR_776 | NonTargetingControlGuideForMouse_0152 | CGTACGGCGGCGCCGTCCAT | MouseDummy |
| MouseDummy_MetsMR_777_NonTargetingControlGuideForMouse_0153 | MetsMR_777 | NonTargetingControlGuideForMouse_0153 | TTGCGTGTGCGTTGTTAACG | MouseDummy |
| MouseDummy_MetsMR_778_NonTargetingControlGuideForMouse_0154 | MetsMR_778 | NonTargetingControlGuideForMouse_0154 | GACCATACGCCTCGTATGCC | MouseDummy |
| MouseDummy_MetsMR_779_NonTargetingControlGuideForMouse_0155 | MetsMR_779 | NonTargetingControlGuideForMouse_0155 | CGGCAATGTGTGGCGACCGG | MouseDummy |
| MouseDummy_MetsMR_780_NonTargetingControlGuideForMouse_0156 | MetsMR_780 | NonTargetingControlGuideForMouse_0156 | TCGTAAGCCGGGTAATACT | MouseDummy |
| MouseDummy_MetsMR_781_NonTargetingControlGuideForMouse_0157 | MetsMR_781 | NonTargetingControlGuideForMouse_0157 | TTTCTAATTACCCGATAGT | MouseDummy |
| MouseDummy_MetsMR_782_NonTargetingControlGuideForMouse_0158 | MetsMR_782 | NonTargetingControlGuideForMouse_0158 | ACCAGGACTGCCCGTGAGG | MouseDummy |
| MouseDummy_MetsMR_783_NonTargetingControlGuideForMouse_0159 | MetsMR_783 | NonTargetingControlGuideForMouse_0159 | GCGCGTACATATAAATAGGT | MouseDummy |
| MouseDummy_MetsMR_784_NonTargetingControlGuideForMouse_0160 | MetsMR_784 | NonTargetingControlGuideForMouse_0160 | CTTATCCATAATAGGCGGGG | MouseDummy |
| MouseDummy_MetsMR_785_NonTargetingControlGuideForMouse_0161 | MetsMR_785 | NonTargetingControlGuideForMouse_0161 | GTTATTGCGCCTTGCCCGTA | MouseDummy |
| MouseDummy_MetsMR_786_NonTargetingControlGuideForMouse_0162 | MetsMR_786 | NonTargetingControlGuideForMouse_0162 | TAAAGTGGTGCCTCGTCGT | MouseDummy |
| MouseDummy_MetsMR_787_NonTargetingControlGuideForMouse_0163 | MetsMR_787 | NonTargetingControlGuideForMouse_0163 | CTCGTGAAACAAGATCCGAC | MouseDummy |
| MouseDummy_MetsMR_788_NonTargetingControlGuideForMouse_0164 | MetsMR_788 | NonTargetingControlGuideForMouse_0164 | TAAACGATTCACCGATAACA | MouseDummy |
| MouseDummy_MetsMR_789_NonTargetingControlGuideForMouse_0165 | MetsMR_789 | NonTargetingControlGuideForMouse_0165 | CGGCCGTAGTGACGAATGGA | MouseDummy |
| MouseDummy_MetsMR_790_NonTargetingControlGuideForMouse_0166 | MetsMR_790 | NonTargetingControlGuideForMouse_0166 | ACCGGTCGAAGTCTGGATT | MouseDummy |
| MouseDummy_MetsMR_791_NonTargetingControlGuideForMouse_0167 | MetsMR_791 | NonTargetingControlGuideForMouse_0167 | TCCGTACATCGACTATTAC | MouseDummy |
| MouseDummy_MetsMR_792_NonTargetingControlGuideForMouse_0168 | MetsMR_792 | NonTargetingControlGuideForMouse_0168 | CGACACGATGGTCATACTAC | MouseDummy |
| MouseDummy_MetsMR_793_NonTargetingControlGuideForMouse_0169 | MetsMR_793 | NonTargetingControlGuideForMouse_0169 | ACTCGGACCTAACGTCGATGT | MouseDummy |
| MouseDummy_MetsMR_794_NonTargetingControlGuideForMouse_0170 | MetsMR_794 | NonTargetingControlGuideForMouse_0170 | TGCAGAATCGCGAAGCGACTA | MouseDummy |
| MouseDummy_MetsMR_795_NonTargetingControlGuideForMouse_0171 | MetsMR_795 | NonTargetingControlGuideForMouse_0171 | TCTAGGATACTCTTAACGGG | MouseDummy |

| | | | |
|---|---|---|---|
| MouseDummy_MetsMR_796_NonTargetingControlGuideForMouse_0172 | MetsMR_796 | NonTargetingControlGuideForMouse_0172 | GGTCTGTCGTTGCGACCAC | MouseDummy |
| MouseDummy_MetsMR_797_NonTargetingControlGuideForMouse_0173 | MetsMR_797 | NonTargetingControlGuideForMouse_0173 | ACCGGATGCCGATATGCCGT | MouseDummy |
| MouseDummy_MetsMR_798_NonTargetingControlGuideForMouse_0174 | MetsMR_798 | NonTargetingControlGuideForMouse_0174 | CTCGTATAGTATTGCGTGGT | MouseDummy |
| MouseDummy_MetsMR_799_NonTargetingControlGuideForMouse_0175 | MetsMR_799 | NonTargetingControlGuideForMouse_0175 | CTTTAGTCACGATATACGTC | MouseDummy |
| MouseDummy_MetsMR_800_NonTargetingControlGuideForMouse_0176 | MetsMR_800 | NonTargetingControlGuideForMouse_0176 | GCGGCCCGTCACCGTTCAAT | MouseDummy |
| MouseDummy_MetsMR_801_NonTargetingControlGuideForMouse_0177 | MetsMR_801 | NonTargetingControlGuideForMouse_0177 | CCGGTTTATAAATTACGTGG | MouseDummy |
| MouseDummy_MetsMR_802_NonTargetingControlGuideForMouse_0178 | MetsMR_802 | NonTargetingControlGuideForMouse_0178 | CAGCTCACCCTGCGTACGGT | MouseDummy |
| MouseDummy_MetsMR_803_NonTargetingControlGuideForMouse_0179 | MetsMR_803 | NonTargetingControlGuideForMouse_0179 | CTCGGCTTTACGATCGATCA | MouseDummy |
| MouseDummy_MetsMR_804_NonTargetingControlGuideForMouse_0180 | MetsMR_804 | NonTargetingControlGuideForMouse_0180 | TCTGCACGGACTAGCTT | MouseDummy |
| MouseDummy_MetsMR_805_NonTargetingControlGuideForMouse_0181 | MetsMR_805 | NonTargetingControlGuideForMouse_0181 | GGCTTATAGACGAGACTCGA | MouseDummy |
| MouseDummy_MetsMR_806_NonTargetingControlGuideForMouse_0182 | MetsMR_806 | NonTargetingControlGuideForMouse_0182 | ACCGGATGTGGCGCCTCTC | MouseDummy |
| MouseDummy_MetsMR_807_NonTargetingControlGuideForMouse_0183 | MetsMR_807 | NonTargetingControlGuideForMouse_0183 | CATTACGTGTCGAGCTCGG | MouseDummy |
| MouseDummy_MetsMR_808_NonTargetingControlGuideForMouse_0184 | MetsMR_808 | NonTargetingControlGuideForMouse_0184 | GATGCGGTGGAAAACGTTA | MouseDummy |
| MouseDummy_MetsMR_809_NonTargetingControlGuideForMouse_0185 | MetsMR_809 | NonTargetingControlGuideForMouse_0185 | GCAAAAGCGCACACGCGAC | MouseDummy |
| MouseDummy_MetsMR_810_NonTargetingControlGuideForMouse_0186 | MetsMR_810 | NonTargetingControlGuideForMouse_0186 | CGAGGATGTACATACGTAAA | MouseDummy |
| MouseDummy_MetsMR_811_NonTargetingControlGuideForMouse_0187 | MetsMR_811 | NonTargetingControlGuideForMouse_0187 | ACACGTCTTCGGCTATACGC | MouseDummy |
| MouseDummy_MetsMR_812_NonTargetingControlGuideForMouse_0188 | MetsMR_812 | NonTargetingControlGuideForMouse_0188 | TCGTGCCTAGCTCGGTTGAG | MouseDummy |
| MouseDummy_MetsMR_813_NonTargetingControlGuideForMouse_0189 | MetsMR_813 | NonTargetingControlGuideForMouse_0189 | TCACACGGGATCTCGCCGGT | MouseDummy |
| MouseDummy_MetsMR_814_NonTargetingControlGuideForMouse_0190 | MetsMR_814 | NonTargetingControlGuideForMouse_0190 | CGTGCGTTCGTAATAAACGG | MouseDummy |
| MouseDummy_MetsMR_815_NonTargetingControlGuideForMouse_0191 | MetsMR_815 | NonTargetingControlGuideForMouse_0191 | CCCCTTCGATATCCGCCGGT | MouseDummy |
| MouseDummy_MetsMR_816_NonTargetingControlGuideForMouse_0192 | MetsMR_816 | NonTargetingControlGuideForMouse_0192 | CGTGATTCCTAAGCGCCCGC | MouseDummy |
| MouseDummy_MetsMR_817_NonTargetingControlGuideForMouse_0193 | MetsMR_817 | NonTargetingControlGuideForMouse_0193 | GCGTGCCATGGCAGGCGGTT | MouseDummy |

FIG. 18 CONTINUED

| | | | |
|---|---|---|---|
| MouseDummy_MetsMR_818_NonTargetingControlGuideForMouse_0194 | MetsMR_818 | NonTargetingControlGuideForMouse_0194 | GGCTTTAAGTAAGGAGCGTA | MouseDummy |
| MouseDummy_MetsMR_819_NonTargetingControlGuideForMouse_0195 | MetsMR_819 | NonTargetingControlGuideForMouse_0195 | ACCCTAGCTCATCGCGACC | MouseDummy |
| MouseDummy_MetsMR_820_NonTargetingControlGuideForMouse_0196 | MetsMR_820 | NonTargetingControlGuideForMouse_0196 | GCTGATTACACCCGGCGTAA | MouseDummy |
| MouseDummy_MetsMR_821_NonTargetingControlGuideForMouse_0197 | MetsMR_821 | NonTargetingControlGuideForMouse_0197 | GTTACCCTTTGGCGGAAG | MouseDummy |
| MouseDummy_MetsMR_822_NonTargetingControlGuideForMouse_0198 | MetsMR_822 | NonTargetingControlGuideForMouse_0198 | TAACGTTATGTCAAACGTC | MouseDummy |
| MouseDummy_MetsMR_823_NonTargetingControlGuideForMouse_0199 | MetsMR_823 | NonTargetingControlGuideForMouse_0199 | GGATCGATCCAGGAACGTG | MouseDummy |
| MouseDummy_MetsMR_824_NonTargetingControlGuideForMouse_0200 | MetsMR_824 | NonTargetingControlGuideForMouse_0200 | CTGCACGGCACGACATCCAA | MouseDummy |
| MouseDummy_MetsMR_825_NonTargetingControlGuideForMouse_0201 | MetsMR_825 | NonTargetingControlGuideForMouse_0201 | GGTCAAAGCGATGTTAGCCG | MouseDummy |
| MouseDummy_MetsMR_826_NonTargetingControlGuideForMouse_0202 | MetsMR_826 | NonTargetingControlGuideForMouse_0202 | GCTTGTAATCTAAAGACGCG | MouseDummy |
| MouseDummy_MetsMR_827_NonTargetingControlGuideForMouse_0203 | MetsMR_827 | NonTargetingControlGuideForMouse_0203 | GAGATTAAATTAACCCGGGC | MouseDummy |
| MouseDummy_MetsMR_828_NonTargetingControlGuideForMouse_0204 | MetsMR_828 | NonTargetingControlGuideForMouse_0204 | CGAATCGGAAGGCGGGTGT | MouseDummy |
| MouseDummy_MetsMR_829_NonTargetingControlGuideForMouse_0205 | MetsMR_829 | NonTargetingControlGuideForMouse_0205 | GGGAGCGTCATCCAGTGACG | MouseDummy |
| MouseDummy_MetsMR_830_NonTargetingControlGuideForMouse_0206 | MetsMR_830 | NonTargetingControlGuideForMouse_0206 | AGCGGGTAAGGCGTAGTTAC | MouseDummy |
| MouseDummy_MetsMR_831_NonTargetingControlGuideForMouse_0207 | MetsMR_831 | NonTargetingControlGuideForMouse_0207 | GTTTCAGGCCGAGTTGCGCG | MouseDummy |
| MouseDummy_MetsMR_832_NonTargetingControlGuideForMouse_0208 | MetsMR_832 | NonTargetingControlGuideForMouse_0208 | TCCTGCGTTCCACTCGTACT | MouseDummy |
| MouseDummy_MetsMR_833_NonTargetingControlGuideForMouse_0209 | MetsMR_833 | NonTargetingControlGuideForMouse_0209 | GTTATTGTCTGTGCGAAACG | MouseDummy |
| MouseDummy_MetsMR_834_NonTargetingControlGuideForMouse_0210 | MetsMR_834 | NonTargetingControlGuideForMouse_0210 | AATAAGCCTACCGGCGAGA | MouseDummy |
| MouseDummy_MetsMR_835_NonTargetingControlGuideForMouse_0211 | MetsMR_835 | NonTargetingControlGuideForMouse_0211 | GTACATGCGCCAAGTCGACT | MouseDummy |
| MouseDummy_MetsMR_836_NonTargetingControlGuideForMouse_0212 | MetsMR_836 | NonTargetingControlGuideForMouse_0212 | AGCAGTTCGGTAACGCCCA | MouseDummy |
| MouseDummy_MetsMR_837_NonTargetingControlGuideForMouse_0213 | MetsMR_837 | NonTargetingControlGuideForMouse_0213 | TGTACTCGCATAAGCGGGGC | MouseDummy |
| MouseDummy_MetsMR_838_NonTargetingControlGuideForMouse_0214 | MetsMR_838 | NonTargetingControlGuideForMouse_0214 | AACTCGGTGGGAGTCCGG | MouseDummy |
| MouseDummy_MetsMR_839_NonTargetingControlGuideForMouse_0215 | MetsMR_839 | NonTargetingControlGuideForMouse_0215 | CCTTGTGGCTGCCAAACGA | MouseDummy |

| | | | |
|---|---|---|---|
| MouseDummy_MetsMR_840_NonTargetingControlGuideForMouse_0216 | MetsMR_840 | NonTargetingControlGuideForMouse_0216 | TGCGGACGGACGCAGCGTA | MouseDummy |
| MouseDummy_MetsMR_841_NonTargetingControlGuideForMouse_0217 | MetsMR_841 | NonTargetingControlGuideForMouse_0217 | TGCGGCAATGTTAACCCTTA | MouseDummy |
| MouseDummy_MetsMR_842_NonTargetingControlGuideForMouse_0218 | MetsMR_842 | NonTargetingControlGuideForMouse_0218 | TGTATAGTCATCCCGTAAT | MouseDummy |
| MouseDummy_MetsMR_843_NonTargetingControlGuideForMouse_0219 | MetsMR_843 | NonTargetingControlGuideForMouse_0219 | TAGGCGGACGGTTACATATA | MouseDummy |
| MouseDummy_MetsMR_844_NonTargetingControlGuideForMouse_0220 | MetsMR_844 | NonTargetingControlGuideForMouse_0220 | GATAAGACTCGCGAGCTTC | MouseDummy |
| MouseDummy_MetsMR_845_NonTargetingControlGuideForMouse_0221 | MetsMR_845 | NonTargetingControlGuideForMouse_0221 | TCCTGCCGAATAACCACTA | MouseDummy |
| MouseDummy_MetsMR_846_NonTargetingControlGuideForMouse_0222 | MetsMR_846 | NonTargetingControlGuideForMouse_0222 | CGAGTAATTATTTGCGGTCG | MouseDummy |
| MouseDummy_MetsMR_847_NonTargetingControlGuideForMouse_0223 | MetsMR_847 | NonTargetingControlGuideForMouse_0223 | TACTTACGGACCGACAAACG | MouseDummy |
| MouseDummy_MetsMR_848_NonTargetingControlGuideForMouse_0224 | MetsMR_848 | NonTargetingControlGuideForMouse_0224 | ATGGTGGCTGTACTCGTAAC | MouseDummy |
| MouseDummy_MetsMR_849_NonTargetingControlGuideForMouse_0225 | MetsMR_849 | NonTargetingControlGuideForMouse_0225 | TCGTAAGTTCCTATATGCC | MouseDummy |
| MouseDummy_MetsMR_850_NonTargetingControlGuideForMouse_0226 | MetsMR_850 | NonTargetingControlGuideForMouse_0226 | CCGGCTTGAATACCGTGCGG | MouseDummy |
| MouseDummy_MetsMR_851_NonTargetingControlGuideForMouse_0227 | MetsMR_851 | NonTargetingControlGuideForMouse_0227 | GGCCAACGAAACTAGCGTG | MouseDummy |
| MouseDummy_MetsMR_852_NonTargetingControlGuideForMouse_0228 | MetsMR_852 | NonTargetingControlGuideForMouse_0228 | AGCGCGGCCCCAAAGCTTTT | MouseDummy |
| MouseDummy_MetsMR_853_NonTargetingControlGuideForMouse_0229 | MetsMR_853 | NonTargetingControlGuideForMouse_0229 | ACACGACCGACCGGTGGAAT | MouseDummy |
| MouseDummy_MetsMR_854_NonTargetingControlGuideForMouse_0230 | MetsMR_854 | NonTargetingControlGuideForMouse_0230 | AAACTCATACGTACGGAATC | MouseDummy |
| MouseDummy_MetsMR_855_NonTargetingControlGuideForMouse_0231 | MetsMR_855 | NonTargetingControlGuideForMouse_0231 | CGATTGACGTTGGCCTCTCA | MouseDummy |
| MouseDummy_MetsMR_856_NonTargetingControlGuideForMouse_0232 | MetsMR_856 | NonTargetingControlGuideForMouse_0232 | AACCAGCATTTCACGGCGCT | MouseDummy |
| MouseDummy_MetsMR_857_NonTargetingControlGuideForMouse_0233 | MetsMR_857 | NonTargetingControlGuideForMouse_0233 | ACGTCGGTCTAGAGTTAAGT | MouseDummy |
| MouseDummy_MetsMR_858_NonTargetingControlGuideForMouse_0234 | MetsMR_858 | NonTargetingControlGuideForMouse_0234 | CTTCCGGACGTGCATCCGAGA | MouseDummy |
| MouseDummy_MetsMR_859_NonTargetingControlGuideForMouse_0235 | MetsMR_859 | NonTargetingControlGuideForMouse_0235 | ATAAGTCCAGGTGCGCGC | MouseDummy |
| MouseDummy_MetsMR_860_NonTargetingControlGuideForMouse_0236 | MetsMR_860 | NonTargetingControlGuideForMouse_0236 | GCCGCTCTTGATAACGACGC | MouseDummy |
| MouseDummy_MetsMR_861_NonTargetingControlGuideForMouse_0237 | MetsMR_861 | NonTargetingControlGuideForMouse_0237 | CGAAACCATACTCCTTCGA | MouseDummy |

| | | | |
|---|---|---|---|
| MouseDummy_NetsMR_862_NonTargetingControlGuideFor_Mouse_0238 | NetsMR_862 | NonTargetingControlGuideForMouse_0238 | CGGCGCTTACCCTTTTACCGC | MouseDummy |
| MouseDummy_NetsMR_863_NonTargetingControlGuideFor_Mouse_0239 | NetsMR_863 | NonTargetingControlGuideForMouse_0239 | TACCCCTCTGCGATGCCGGT | MouseDummy |
| MouseDummy_NetsMR_864_NonTargetingControlGuideFor_Mouse_0240 | NetsMR_864 | NonTargetingControlGuideForMouse_0240 | ATATGTCCATACGATCGG | MouseDummy |
| MouseDummy_NetsMR_865_NonTargetingControlGuideFor_Mouse_0241 | NetsMR_865 | NonTargetingControlGuideForMouse_0241 | GGATTGACGAGACGATATCG | MouseDummy |
| MouseDummy_NetsMR_866_NonTargetingControlGuideFor_Mouse_0242 | NetsMR_866 | NonTargetingControlGuideForMouse_0242 | CACGTAAGACGCTCCACTTA | MouseDummy |
| MouseDummy_NetsMR_867_NonTargetingControlGuideFor_Mouse_0243 | NetsMR_867 | NonTargetingControlGuideForMouse_0243 | GGAGTCTTCACGCAATTAGCG | MouseDummy |
| MouseDummy_NetsMR_868_NonTargetingControlGuideFor_Mouse_0244 | NetsMR_868 | NonTargetingControlGuideForMouse_0244 | ATCGCAGTCTACGCAGAGT | MouseDummy |
| MouseDummy_NetsMR_869_NonTargetingControlGuideFor_Mouse_0245 | NetsMR_869 | NonTargetingControlGuideForMouse_0245 | CGGTCGTGACAGACCTGGTG | MouseDummy |
| MouseDummy_NetsMR_870_NonTargetingControlGuideFor_Mouse_0246 | NetsMR_870 | NonTargetingControlGuideForMouse_0246 | GCCACTCCGTCGTCTTCTAGA | MouseDummy |
| MouseDummy_NetsMR_871_NonTargetingControlGuideFor_Mouse_0247 | NetsMR_871 | NonTargetingControlGuideForMouse_0247 | CCGTCGAGCAATCCCGCCAA | MouseDummy |
| MouseDummy_NetsMR_872_NonTargetingControlGuideFor_Mouse_0248 | NetsMR_872 | NonTargetingControlGuideForMouse_0248 | GAGTCGAGTTAATAACGCTC | MouseDummy |
| MouseDummy_NetsMR_873_NonTargetingControlGuideFor_Mouse_0249 | NetsMR_873 | NonTargetingControlGuideForMouse_0249 | CAATATCTAAGCGCTAACGA | MouseDummy |
| MouseDummy_NetsMR_874_NonTargetingControlGuideFor_Mouse_0250 | NetsMR_874 | NonTargetingControlGuideForMouse_0250 | ACCCATCCCGCGTCCGAGA | MouseDummy |
| MouseDummy_NetsMR_875_NonTargetingControlGuideFor_Mouse_0251 | NetsMR_875 | NonTargetingControlGuideForMouse_0251 | TAATGAGTAACGCTCATCGG | MouseDummy |
| MouseDummy_NetsMR_876_NonTargetingControlGuideFor_Mouse_0252 | NetsMR_876 | NonTargetingControlGuideForMouse_0252 | AACGGTTAGCGTACCCGTAA | MouseDummy |
| MouseDummy_NetsMR_877_NonTargetingControlGuideFor_Mouse_0253 | NetsMR_877 | NonTargetingControlGuideForMouse_0253 | CATCGAGGGTAAACGCCATT | MouseDum |
| MouseDummy_NetsMR_878_NonTargetingControlGuideFor_Mouse_0254 | NetsMR_878 | NonTargetingControlGuideForMouse_0254 | CGTCACCGGTAGTAATGATG | MouseDummy |
| MouseDummy_NetsMR_879_NonTargetingControlGuideFor_Mouse_0255 | NetsMR_879 | NonTargetingControlGuideForMouse_0255 | AATCACCGACAACGTAAGAC | MouseDummy |
| MouseDummy_NetsMR_880_NonTargetingControlGuideFor_Mouse_0256 | NetsMR_880 | NonTargetingControlGuideForMouse_0256 | CACTCAGCGGTTGGACGCCC | MouseDummy |
| MouseDummy_NetsMR_881_NonTargetingControlGuideFor_Mouse_0257 | NetsMR_881 | NonTargetingControlGuideForMouse_0257 | TCCGTAGGACGTATATATTC | MouseDummy |
| MouseDummy_NetsMR_882_NonTargetingControlGuideFor_Mouse_0258 | NetsMR_882 | NonTargetingControlGuideForMouse_0258 | AAAACGTAATTATACCGAGC | MouseDummy |
| MouseDummy_NetsMR_883_NonTargetingControlGuideFor_Mouse_0259 | NetsMR_883 | NonTargetingControlGuideForMouse_0259 | TAGCCGCTCAGGCCGCACT | MouseDummy |

| | | | |
|---|---|---|---|
| MouseDummy_MetsMR_884_NonTargetingControlGuideFor Mouse_0260 | MetsMR_884 | NonTargetingControlGuideForMouse_0260 | CCCACTTAATAACGCCGCTT | MouseDummy |
| MouseDummy_MetsMR_885_NonTargetingControlGuideFor Mouse_0261 | MetsMR_885 | NonTargetingControlGuideForMouse_0261 | ACCATACGGGGTCTGTCGA | MouseDummy |
| MouseDummy_MetsMR_886_NonTargetingControlGuideFor Mouse_0262 | MetsMR_886 | NonTargetingControlGuideForMouse_0262 | ACGGAACCCGATCGGAACGG | MouseDummy |
| MouseDummy_MetsMR_887_NonTargetingControlGuideFor Mouse_0263 | MetsMR_887 | NonTargetingControlGuideForMouse_0263 | GTTGCGTCCATTCCGTCGCC | MouseDummy |
| MouseDummy_MetsMR_888_NonTargetingControlGuideFor Mouse_0264 | MetsMR_888 | NonTargetingControlGuideForMouse_0264 | ATTCCGTTTGCAGCGAGACC | MouseDummy |
| MouseDummy_MetsMR_889_NonTargetingControlGuideFor Mouse_0265 | MetsMR_889 | NonTargetingControlGuideForMouse_0265 | CCATCGGTTCGACTTACCGC | MouseDummy |
| MouseDummy_MetsMR_890_NonTargetingControlGuideFor Mouse_0266 | MetsMR_890 | NonTargetingControlGuideForMouse_0266 | CATCGGCTATGTCGGGACA | MouseDummy |
| MouseDummy_MetsMR_891_NonTargetingControlGuideFor Mouse_0267 | MetsMR_891 | NonTargetingControlGuideForMouse_0267 | AATGAGCGTCTCTCGATCGC | MouseDummy |
| MouseDummy_MetsMR_892_NonTargetingControlGuideFor Mouse_0268 | MetsMR_892 | NonTargetingControlGuideForMouse_0268 | TTACTGATCAGTCGGACGCA | MouseDummy |
| MouseDummy_MetsMR_893_NonTargetingControlGuideFor Mouse_0269 | MetsMR_893 | NonTargetingControlGuideForMouse_0269 | GATTGAGAAGCCGCGGTATC | MouseDummy |
| MouseDummy_MetsMR_894_NonTargetingControlGuideFor Mouse_0270 | MetsMR_894 | NonTargetingControlGuideForMouse_0270 | GTGATGGCCACGTCCGAACC | MouseDummy |
| MouseDummy_MetsMR_895_NonTargetingControlGuideFor Mouse_0271 | MetsMR_895 | NonTargetingControlGuideForMouse_0271 | TTTGGACGTACACTTTCGTTC | MouseDummy |
| MouseDummy_MetsMR_896_NonTargetingControlGuideFor Mouse_0272 | MetsMR_896 | NonTargetingControlGuideForMouse_0272 | ACTGCGGGTATAGGACGCAA | MouseDummy |
| MouseDummy_MetsMR_897_NonTargetingControlGuideFor Mouse_0273 | MetsMR_897 | NonTargetingControlGuideForMouse_0273 | TAGCCTGTTTACGCCGACCTG | MouseDummy |
| MouseDummy_MetsMR_898_NonTargetingControlGuideFor Mouse_0274 | MetsMR_898 | NonTargetingControlGuideForMouse_0274 | CATGCCCCGTCTGCCCGCAT | MouseDummy |
| MouseDummy_MetsMR_899_NonTargetingControlGuideFor Mouse_0275 | MetsMR_899 | NonTargetingControlGuideForMouse_0275 | TCAACTATGAACCGCCGTGC | MouseDummy |
| MouseDummy_MetsMR_900_NonTargetingControlGuideFor Mouse_0276 | MetsMR_900 | NonTargetingControlGuideForMouse_0276 | CGTTACGTTTCTTGCCAGGA | MouseDummy |
| MouseDummy_MetsMR_901_NonTargetingControlGuideFor Mouse_0277 | MetsMR_901 | NonTargetingControlGuideForMouse_0277 | TCTATATCTAGTCTCGGCGC | MouseDummy |
| MouseDummy_MetsMR_902_NonTargetingControlGuideFor Mouse_0278 | MetsMR_902 | NonTargetingControlGuideForMouse_0278 | CTCCTCGAGGCTGGCTACGT | MouseDummy |
| MouseDummy_MetsMR_903_NonTargetingControlGuideFor Mouse_0279 | MetsMR_903 | NonTargetingControlGuideForMouse_0279 | TCGTACGCAGTGTAAGCC | MouseDummy |
| MouseDummy_MetsMR_904_NonTargetingControlGuideFor Mouse_0280 | MetsMR_904 | NonTargetingControlGuideForMouse_0280 | CGGGCACTAACCCGATACAC | MouseDummy |
| MouseDummy_MetsMR_905_NonTargetingControlGuideFor Mouse_0281 | MetsMR_905 | NonTargetingControlGuideForMouse_0281 | GAACGTAACGGCATGCATCA | MouseDummy |

FIG. 18 CONTINUED

| | | | |
|---|---|---|---|
| MouseDummy_MetsMR_0286_NonTargetingControlGuideForMouse_0282 | MetsMR_0286 | NonTargetingControlGuideForMouse_0282 | GCCCGATAGAATTACCCATT | MouseDummy |
| MouseDummy_MetsMR_0287_NonTargetingControlGuideForMouse_0283 | MetsMR_0287 | NonTargetingControlGuideForMouse_0283 | GCCCTCGAGCTCACGATCAG | MouseDummy |
| MouseDummy_MetsMR_0288_NonTargetingControlGuideForMouse_0284 | MetsMR_0288 | NonTargetingControlGuideForMouse_0284 | TTAGGACGTGCTTCCGAGGG | MouseDummy |
| MouseDummy_MetsMR_0289_NonTargetingControlGuideForMouse_0285 | MetsMR_0289 | NonTargetingControlGuideForMouse_0285 | TAGTTAACCGTAAAGTGGGC | MouseDummy |
| MouseDummy_MetsMR_0290_NonTargetingControlGuideForMouse_0286 | MetsMR_0290 | NonTargetingControlGuideForMouse_0286 | GTGGCTGACCGTTCTCGAC | MouseDummy |
| MouseDummy_MetsMR_0291_NonTargetingControlGuideForMouse_0287 | MetsMR_0291 | NonTargetingControlGuideForMouse_0287 | CAAGAGTTAACCTCGACCGG | MouseDummy |
| MouseDummy_MetsMR_0292_NonTargetingControlGuideForMouse_0288 | MetsMR_0292 | NonTargetingControlGuideForMouse_0288 | TATGACTGCACGACTCGCTA | MouseDummy |
| MouseDummy_MetsMR_0293_NonTargetingControlGuideForMouse_0289 | MetsMR_0293 | NonTargetingControlGuideForMouse_0289 | GAACCGGGCGTGCGTTAGCGG | MouseDummy |
| MouseDummy_MetsMR_0294_NonTargetingControlGuideForMouse_0290 | MetsMR_0294 | NonTargetingControlGuideForMouse_0290 | TTCGATATAGGGACGGCCGG | MouseDummy |
| MouseDummy_MetsMR_0295_NonTargetingControlGuideForMouse_0291 | MetsMR_0295 | NonTargetingControlGuideForMouse_0291 | GCCGTAAGCGGGCCGGTTGA | MouseDummy |
| MouseDummy_MetsMR_0296_NonTargetingControlGuideForMouse_0292 | MetsMR_0296 | NonTargetingControlGuideForMouse_0292 | CGTAACCGGAGATAATATTA | MouseDummy |
| MouseDummy_MetsMR_0297_NonTargetingControlGuideForMouse_0293 | MetsMR_0297 | NonTargetingControlGuideForMouse_0293 | CGGCGATAACAGCGACATCG | MouseDummy |
| MouseDummy_MetsMR_0298_NonTargetingControlGuideForMouse_0294 | MetsMR_0298 | NonTargetingControlGuideForMouse_0294 | TCACTTCGGGCATTACGAGC | MouseDummy |
| MouseDummy_MetsMR_0299_NonTargetingControlGuideForMouse_0295 | MetsMR_0299 | NonTargetingControlGuideForMouse_0295 | TAATAAACTATGTCCCGCCG | MouseDummy |
| MouseDummy_MetsMR_0300_NonTargetingControlGuideForMouse_0296 | MetsMR_0300 | NonTargetingControlGuideForMouse_0296 | TGGCACGGAGTTGCATACGC | MouseDummy |
| MouseDummy_MetsMR_0301_NonTargetingControlGuideForMouse_0297 | MetsMR_0301 | NonTargetingControlGuideForMouse_0297 | GCTAGTTCCTCCCGGGCAAA | MouseDummy |
| MouseDummy_MetsMR_0302_NonTargetingControlGuideForMouse_0298 | MetsMR_0302 | NonTargetingControlGuideForMouse_0298 | GTTCCGGTTGCSGCTTACACG | MouseDummy |
| MouseDummy_MetsMR_0303_NonTargetingControlGuideForMouse_0299 | MetsMR_0303 | NonTargetingControlGuideForMouse_0299 | GCACCTCTAGCGCGCTCGGC | MouseDummy |
| MouseDummy_MetsMR_0304_NonTargetingControlGuideForMouse_0300 | MetsMR_0304 | NonTargetingControlGuideForMouse_0300 | CATTGTAGACTCGTACGGAT | MouseDummy |
| MouseDummy_MetsMR_0305_NonTargetingControlGuideForMouse_0301 | MetsMR_0305 | NonTargetingControlGuideForMouse_0301 | TCGGAATTCCCAGGCCGAG | MouseDummy |
| MouseDummy_MetsMR_0306_NonTargetingControlGuideForMouse_0302 | MetsMR_0306 | NonTargetingControlGuideForMouse_0302 | GATTACGGGGTTCCGTAACT | MouseDummy |
| MouseDummy_MetsMR_0307_NonTargetingControlGuideForMouse_0303 | MetsMR_0307 | NonTargetingControlGuideForMouse_0303 | GCCTATGTGAATCGGAATT | MouseDummy |

FIG. 18 CONTINUED

| | | | |
|---|---|---|---|
| MouseDummy_MetsMR_928_NonTargetingControlGuideForMouse_0304 | MetsMR_928 | NonTargetingControlGuideForMouse_0304 | CTCGGACGGCATAGACACAAT | MouseDummy |
| MouseDummy_MetsMR_929_NonTargetingControlGuideForMouse_0305 | MetsMR_929 | NonTargetingControlGuideForMouse_0305 | CATATGCTCGACGGTATAAA | MouseDummy |
| MouseDummy_MetsMR_930_NonTargetingControlGuideForMouse_0306 | MetsMR_930 | NonTargetingControlGuideForMouse_0306 | CTTCATGTACGCCTTCGCTAC | MouseDummy |
| MouseDummy_MetsMR_931_NonTargetingControlGuideForMouse_0307 | MetsMR_931 | NonTargetingControlGuideForMouse_0307 | TTACAGTTCATACCGTCGCC | MouseDummy |
| MouseDummy_MetsMR_932_NonTargetingControlGuideForMouse_0308 | MetsMR_932 | NonTargetingControlGuideForMouse_0308 | GATGGCCAGTAACGCGGTCA | MouseDummy |
| MouseDummy_MetsMR_933_NonTargetingControlGuideForMouse_0309 | MetsMR_933 | NonTargetingControlGuideForMouse_0309 | ATTTGAATGCTCCCGTCGAC | MouseDummy |
| MouseDummy_MetsMR_934_NonTargetingControlGuideForMouse_0310 | MetsMR_934 | NonTargetingControlGuideForMouse_0310 | CAACGGTCACGCTAGAATAA | MouseDummy |
| MouseDummy_MetsMR_935_NonTargetingControlGuideForMouse_0311 | MetsMR_935 | NonTargetingControlGuideForMouse_0311 | CTTAAGTTCCGGACGGAATG | MouseDummy |
| MouseDummy_MetsMR_936_NonTargetingControlGuideForMouse_0312 | MetsMR_936 | NonTargetingControlGuideForMouse_0312 | TACTTAGGTCCGGTAAAGC | MouseDummy |
| MouseDummy_MetsMR_937_NonTargetingControlGuideForMouse_0313 | MetsMR_937 | NonTargetingControlGuideForMouse_0313 | GGTTAAAAATTAAGCGGTCC | MouseDummy |
| MouseDummy_MetsMR_938_NonTargetingControlGuideForMouse_0314 | MetsMR_938 | NonTargetingControlGuideForMouse_0314 | AAAACGGCTCGATCGTGAT | MouseDummy |
| MouseDummy_MetsMR_939_NonTargetingControlGuideForMouse_0315 | MetsMR_939 | NonTargetingControlGuideForMouse_0315 | ATGTTACGTACGTGATCTCC | MouseDummy |
| MouseDummy_MetsMR_940_NonTargetingControlGuideForMouse_0316 | MetsMR_940 | NonTargetingControlGuideForMouse_0316 | AGTAGACGCTATGTTCGCGC | MouseDummy |
| MouseDummy_MetsMR_941_NonTargetingControlGuideForMouse_0317 | MetsMR_941 | NonTargetingControlGuideForMouse_0317 | TACTGCGTACCGCAGTAAGC | MouseDummy |
| MouseDummy_MetsMR_942_NonTargetingControlGuideForMouse_0318 | MetsMR_942 | NonTargetingControlGuideForMouse_0318 | CCCATCATTCGGCTGACGT | MouseDummy |
| MouseDummy_MetsMR_943_NonTargetingControlGuideForMouse_0319 | MetsMR_943 | NonTargetingControlGuideForMouse_0319 | CGACTATTGCCGTCCATCTC | MouseDummy |
| MouseDummy_MetsMR_944_NonTargetingControlGuideForMouse_0320 | MetsMR_944 | NonTargetingControlGuideForMouse_0320 | ATCCGTACCAAACACGCTAC | MouseDummy |
| MouseDummy_MetsMR_945_NonTargetingControlGuideForMouse_0321 | MetsMR_945 | NonTargetingControlGuideForMouse_0321 | TGCGTAAAACTTGCGCTCGA | MouseDummy |
| MouseDummy_MetsMR_946_NonTargetingControlGuideForMouse_0322 | MetsMR_946 | NonTargetingControlGuideForMouse_0322 | CATATGCCTATAACCGGCGG | MouseDummy |
| MouseDummy_MetsMR_947_NonTargetingControlGuideForMouse_0323 | MetsMR_947 | NonTargetingControlGuideForMouse_0323 | GTTCCGGATATATACGGTTA | MouseDummy |
| MouseDummy_MetsMR_948_NonTargetingControlGuideForMouse_0324 | MetsMR_948 | NonTargetingControlGuideForMouse_0324 | CTTAATACACCCGGACGGTAC | MouseDummy |
| MouseDummy_MetsMR_949_NonTargetingControlGuideForMouse_0325 | MetsMR_949 | NonTargetingControlGuideForMouse_0325 | GGGCGGGACGTAATATTATG | MouseDummy |

| | | | |
|---|---|---|---|
| MouseDummy_MetsMR_950_NonTargetingControlGuideFor_Mouse_0326 | MetsMR_950 | NonTargetingControlGuideForMouse_0326 | ACTTTACATCATGTGTCTGT | MouseDummy |
| MouseDummy_MetsMR_951_NonTargetingControlGuideFor_Mouse_0327 | MetsMR_951 | NonTargetingControlGuideForMouse_0327 | CTGATCGGTGCATATCTCGG | MouseDummy |
| MouseDummy_MetsMR_952_NonTargetingControlGuideFor_Mouse_0328 | MetsMR_952 | NonTargetingControlGuideForMouse_0328 | GAGCCCCAACGCGCGAAGCA | MouseDummy |
| MouseDummy_MetsMR_953_NonTargetingControlGuideFor_Mouse_0329 | MetsMR_953 | NonTargetingControlGuideForMouse_0329 | GCTAAGATTCATCCGAACAC | MouseDummy |
| MouseDummy_MetsMR_954_NonTargetingControlGuideFor_Mouse_0330 | MetsMR_954 | NonTargetingControlGuideForMouse_0330 | GTTACCGTGACGATAAGAAT | MouseDummy |
| MouseDummy_MetsMR_955_NonTargetingControlGuideFor_Mouse_0331 | MetsMR_955 | NonTargetingControlGuideForMouse_0331 | GCTAAACGTATTTTACGGGC | MouseDummy |
| MouseDummy_MetsMR_956_NonTargetingControlGuideFor_Mouse_0332 | MetsMR_956 | NonTargetingControlGuideForMouse_0332 | CCGAGCCGAATTGGGCGTGT | MouseDummy |
| MouseDummy_MetsMR_957_NonTargetingControlGuideFor_Mouse_0333 | MetsMR_957 | NonTargetingControlGuideForMouse_0333 | GTTGCGTGTGTCCGTACAAA | MouseDummy |
| MouseDummy_MetsMR_958_NonTargetingControlGuideFor_Mouse_0334 | MetsMR_958 | NonTargetingControlGuideForMouse_0334 | CTTTATTCCGTTGCATGTCG | MouseDummy |
| MouseDummy_MetsMR_959_NonTargetingControlGuideFor_Mouse_0335 | MetsMR_959 | NonTargetingControlGuideForMouse_0335 | AAGCGTACCCACTCGTTAA | MouseDummy |
| MouseDummy_MetsMR_960_NonTargetingControlGuideFor_Mouse_0336 | MetsMR_960 | NonTargetingControlGuideForMouse_0336 | ATCCGAGATCTGCGAATTAT | MouseDummy |
| MouseDummy_MetsMR_961_NonTargetingControlGuideFor_Mouse_0337 | MetsMR_961 | NonTargetingControlGuideForMouse_0337 | TCTTGACTCCGACTTCGGGC | MouseDummy |
| MouseDummy_MetsMR_962_NonTargetingControlGuideFor_Mouse_0338 | MetsMR_962 | NonTargetingControlGuideForMouse_0338 | ACCATGATGTCACCGCCGCA | MouseDummy |
| MouseDummy_MetsMR_963_NonTargetingControlGuideFor_Mouse_0339 | MetsMR_963 | NonTargetingControlGuideForMouse_0339 | TCAACTTAACCTCGAGTCCG | MouseDummy |
| MouseDummy_MetsMR_964_NonTargetingControlGuideFor_Mouse_0340 | MetsMR_964 | NonTargetingControlGuideForMouse_0340 | CTACGAGGCCGCCGAGCGGT | MouseDummy |
| MouseDummy_MetsMR_965_NonTargetingControlGuideFor_Mouse_0341 | MetsMR_965 | NonTargetingControlGuideForMouse_0341 | ATGTCTCATAGCGGCGTAGG | MouseDummy |
| MouseDummy_MetsMR_966_NonTargetingControlGuideFor_Mouse_0342 | MetsMR_966 | NonTargetingControlGuideForMouse_0342 | TGTAACGATCGGGCGGTCT | MouseDummy |
| MouseDummy_MetsMR_967_NonTargetingControlGuideFor_Mouse_0343 | MetsMR_967 | NonTargetingControlGuideForMouse_0343 | CCGATCGGCTACGCCTACGG | MouseDummy |
| MouseDummy_MetsMR_968_NonTargetingControlGuideFor_Mouse_0344 | MetsMR_968 | NonTargetingControlGuideForMouse_0344 | CAATATTCGACCTACGCTCC | MouseDummy |
| MouseDummy_MetsMR_969_NonTargetingControlGuideFor_Mouse_0345 | MetsMR_969 | NonTargetingControlGuideForMouse_0345 | TGATAAACGATGCGAACTCG | MouseDummy |
| MouseDummy_MetsMR_970_NonTargetingControlGuideFor_Mouse_0346 | MetsMR_970 | NonTargetingControlGuideForMouse_0346 | TGATTGGGGTGTTCGGCCA | MouseDummy |
| MouseDummy_MetsMR_971_NonTargetingControlGuideFor_Mouse_0347 | MetsMR_971 | NonTargetingControlGuideForMouse_0347 | TAGTCAGTCGGCCCTCCGTGC | MouseDummy |

FIG. 18 CONTINUED

| | | | |
|---|---|---|---|
| MouseDummy_MeisMR_972_NonTargetingControlGuideFor_Mouse_0948 | MeisMR_972 | NonTargetingControlGuideForMouse_0948 | AACCGGCTGGCGGTTGCAA | MouseDummy |
| MouseDummy_MeisMR_973_NonTargetingControlGuideFor_Mouse_0949 | MeisMR_973 | NonTargetingControlGuideForMouse_0949 | GTGCCTGATAGTGTGAAGCG | MouseDummy |
| MouseDummy_MeisMR_974_NonTargetingControlGuideFor_Mouse_0950 | MeisMR_974 | NonTargetingControlGuideForMouse_0950 | CGACGACCCATTTCGGTTAT | MouseDummy |
| MouseDummy_MeisMR_975_NonTargetingControlGuideFor_Mouse_0951 | MeisMR_975 | NonTargetingControlGuideForMouse_0951 | GGGGGTCTAATACCGATTG | MouseDummy |
| MouseDummy_MeisMR_976_NonTargetingControlGuideFor_Mouse_0952 | MeisMR_976 | NonTargetingControlGuideForMouse_0952 | TTTTTAGACCTAATTCGCGC | MouseDummy |
| MouseDummy_MeisMR_977_NonTargetingControlGuideFor_Mouse_0953 | MeisMR_977 | NonTargetingControlGuideForMouse_0953 | TCTACACGCGCGTTCAACCG | MouseDummy |
| MouseDummy_MeisMR_978_NonTargetingControlGuideFor_Mouse_0954 | MeisMR_978 | NonTargetingControlGuideForMouse_0954 | CGGGGGTACATGTGTGCC | MouseDummy |
| MouseDummy_MeisMR_979_NonTargetingControlGuideFor_Mouse_0955 | MeisMR_979 | NonTargetingControlGuideForMouse_0955 | CGACTCGCTTAACCGTGCAG | MouseDummy |
| MouseDummy_MeisMR_980_NonTargetingControlGuideFor_Mouse_0956 | MeisMR_980 | NonTargetingControlGuideForMouse_0956 | GCGTACCTATCGATAAACCA | MouseDummy |
| MouseDummy_MeisMR_981_NonTargetingControlGuideFor_Mouse_0957 | MeisMR_981 | NonTargetingControlGuideForMouse_0957 | ATATGAGCCCGACTCTCGA | MouseDummy |
| MouseDummy_MeisMR_982_NonTargetingControlGuideFor_Mouse_0958 | MeisMR_982 | NonTargetingControlGuideForMouse_0958 | CGCGCCGAGGGCTCGTTAC | MouseDummy |
| MouseDummy_MeisMR_983_NonTargetingControlGuideFor_Mouse_0959 | MeisMR_983 | NonTargetingControlGuideForMouse_0959 | CTCCGACGACTACGCAAGGA | MouseDummy |
| MouseDummy_MeisMR_984_NonTargetingControlGuideFor_Mouse_0960 | MeisMR_984 | NonTargetingControlGuideForMouse_0960 | TATCTCTGGATGCGTCGGT | MouseDummy |
| MouseDummy_MeisMR_985_NonTargetingControlGuideFor_Mouse_0961 | MeisMR_985 | NonTargetingControlGuideForMouse_0961 | TTTTCAGTTGTCGCGGACTC | MouseDummy |
| MouseDummy_MeisMR_986_NonTargetingControlGuideFor_Mouse_0962 | MeisMR_986 | NonTargetingControlGuideForMouse_0962 | AGTTTAGCGTCCGATGTC | MouseDummy |
| MouseDummy_MeisMR_987_NonTargetingControlGuideFor_Mouse_0963 | MeisMR_987 | NonTargetingControlGuideForMouse_0963 | GCGTGACGCGATCAAACGGT | MouseDummy |
| MouseDummy_MeisMR_988_NonTargetingControlGuideFor_Mouse_0964 | MeisMR_988 | NonTargetingControlGuideForMouse_0964 | ACTAGCTCCATAACGTGTAC | MouseDummy |
| MouseDummy_MeisMR_989_NonTargetingControlGuideFor_Mouse_0965 | MeisMR_989 | NonTargetingControlGuideForMouse_0965 | CGCATAGTGTACCGTTGCGC | MouseDummy |
| MouseDummy_MeisMR_990_NonTargetingControlGuideFor_Mouse_0966 | MeisMR_990 | NonTargetingControlGuideForMouse_0966 | CCGGCTTGGCGGCTATTAATT | MouseDummy |
| MouseDummy_MeisMR_991_NonTargetingControlGuideFor_Mouse_0967 | MeisMR_991 | NonTargetingControlGuideForMouse_0967 | GCTTCATTATTAACGGCGT | MouseDummy |
| MouseDummy_MeisMR_992_NonTargetingControlGuideFor_Mouse_0968 | MeisMR_992 | NonTargetingControlGuideForMouse_0968 | TATACTCGCCTGTCACACCG | MouseDummy |
| MouseDummy_MeisMR_993_NonTargetingControlGuideFor_Mouse_0969 | MeisMR_993 | NonTargetingControlGuideForMouse_0969 | ACGCTGTTCGTAACCGGGG | MouseDummy |

FIG. 18
CONTINUED

| | | | |
|---|---|---|---|
| MouseDummy_MetsMR_994_NonTargetingControlGuideFor_Mouse_0370 | MetsMR_994 | NonTargetingControlGuideForMouse_0370 | AGACGTTGATTATACGGCCA | MouseDummy |
| MouseDummy_MetsMR_995_NonTargetingControlGuideFor_Mouse_0371 | MetsMR_995 | NonTargetingControlGuideForMouse_0371 | AACGGTCAAATCCGTGAGGG | MouseDummy |
| MouseDummy_MetsMR_996_NonTargetingControlGuideFor_Mouse_0372 | MetsMR_996 | NonTargetingControlGuideForMouse_0372 | CATAGCAACGCCCAAACTCG | MouseDummy |
| MouseDummy_MetsMR_997_NonTargetingControlGuideFor_Mouse_0373 | MetsMR_997 | NonTargetingControlGuideForMouse_0373 | CGTCAATGTCTCCGGACGGT | MouseDummy |
| MouseDummy_MetsMR_998_NonTargetingControlGuideFor_Mouse_0374 | MetsMR_998 | NonTargetingControlGuideForMouse_0374 | ACTGTCCATTGTACGACGG | MouseDummy |
| MouseDummy_MetsMR_999_NonTargetingControlGuideFor_Mouse_0375 | MetsMR_999 | NonTargetingControlGuideForMouse_0375 | CTATCGGCCCGCAGTCATGG | MouseDummy |
| MouseDummy_MetsMR_1000_NonTargetingControlGuideForMouse_0376 | MetsMR_1000 | NonTargetingControlGuideForMouse_0376 | GATCGAGTGACACCCAACCG | MouseDummy |
| MouseDummy_MetsMR_1001_NonTargetingControlGuideForMouse_0377 | MetsMR_1001 | NonTargetingControlGuideForMouse_0377 | TCCGCGGCAAGTTGGGTC | MouseDummy |
| MouseDummy_MetsMR_1002_NonTargetingControlGuideForMouse_0378 | MetsMR_1002 | NonTargetingControlGuideForMouse_0378 | ACTTGTATACGACGGCTAGA | MouseDummy |
| MouseDummy_MetsMR_1003_NonTargetingControlGuideForMouse_0379 | MetsMR_1003 | NonTargetingControlGuideForMouse_0379 | TTCGACTGCGCACGCCATGA | MouseDummy |
| MouseDummy_MetsMR_1004_NonTargetingControlGuideForMouse_0380 | MetsMR_1004 | NonTargetingControlGuideForMouse_0380 | AGCATGGAGTCAACGTCCGC | MouseDummy |
| MouseDummy_MetsMR_1005_NonTargetingControlGuideForMouse_0381 | MetsMR_1005 | NonTargetingControlGuideForMouse_0381 | TGACTTGACACGTTCGATAT | MouseDummy |
| MouseDummy_MetsMR_1006_NonTargetingControlGuideForMouse_0382 | MetsMR_1006 | NonTargetingControlGuideForMouse_0382 | CCGGACTTGTTATACTTGAT | MouseDummy |
| MouseDummy_MetsMR_1007_NonTargetingControlGuideForMouse_0383 | MetsMR_1007 | NonTargetingControlGuideForMouse_0383 | GTACCATGATAACGTACTA | MouseDummy |
| MouseDummy_MetsMR_1008_NonTargetingControlGuideForMouse_0384 | MetsMR_1008 | NonTargetingControlGuideForMouse_0384 | CACCGCTGCCCTAGTACCGG | MouseDummy |
| MouseDummy_MetsMR_1009_NonTargetingControlGuideForMouse_0385 | MetsMR_1009 | NonTargetingControlGuideForMouse_0385 | GGATATTCGGCGGGTCTTCA | MouseDummy |
| MouseDummy_MetsMR_1010_NonTargetingControlGuideForMouse_0386 | MetsMR_1010 | NonTargetingControlGuideForMouse_0386 | AGGCAGCCCGCGTTAGAGAT | MouseDummy |
| MouseDummy_MetsMR_1011_NonTargetingControlGuideForMouse_0387 | MetsMR_1011 | NonTargetingControlGuideForMouse_0387 | TTCTCCATACGTAACTCG | MouseDummy |
| MouseDummy_MetsMR_1012_NonTargetingControlGuideForMouse_0388 | MetsMR_1012 | NonTargetingControlGuideForMouse_0388 | ACCCGGCATATGCGCCTAAG | MouseDummy |
| MouseDummy_MetsMR_1013_NonTargetingControlGuideForMouse_0389 | MetsMR_1013 | NonTargetingControlGuideForMouse_0389 | CGAAGTACGGTTCTCTCG | MouseDummy |
| MouseDummy_MetsMR_1014_NonTargetingControlGuideForMouse_0390 | MetsMR_1014 | NonTargetingControlGuideForMouse_0390 | CACCAATACGGGCAGAGGTC | MouseDummy |
| MouseDummy_MetsMR_1015_NonTargetingControlGuideForMouse_0391 | MetsMR_1015 | NonTargetingControlGuideForMouse_0391 | TGAGACCAATGCCGGGAAT | MouseDummy |

FIG. 18
CONTINUED

| | | | |
|---|---|---|---|
| MouseDummy_MetsMR_1016_NonTargetingControlGuideForMouse_0392 | MetsMR_1016 | NonTargetingControlGuideForMouse_0392 | CTTCGGACCCAGTAGTAGACGG | MouseDummy |
| MouseDummy_MetsMR_1017_NonTargetingControlGuideForMouse_0393 | MetsMR_1017 | NonTargetingControlGuideForMouse_0393 | CGTACCGACAGTAGTCCAAG | MouseDummy |
| MouseDummy_MetsMR_1018_NonTargetingControlGuideForMouse_0394 | MetsMR_1018 | NonTargetingControlGuideForMouse_0394 | AATTGTCTGATCCGCCATA | MouseDummy |
| MouseDummy_MetsMR_1019_NonTargetingControlGuideForMouse_0395 | MetsMR_1019 | NonTargetingControlGuideForMouse_0395 | TTTAGTCAGAGAGCCGGAT | MouseDummy |
| MouseDummy_MetsMR_1020_NonTargetingControlGuideForMouse_0396 | MetsMR_1020 | NonTargetingControlGuideForMouse_0396 | TGCGGCTCCTGTTATGACCG | MouseDummy |
| MouseDummy_MetsMR_1021_NonTargetingControlGuideForMouse_0397 | MetsMR_1021 | NonTargetingControlGuideForMouse_0397 | CTTATCGATTTGGGTTCAAC | MouseDummy |
| MouseDummy_MetsMR_1022_NonTargetingControlGuideForMouse_0398 | MetsMR_1022 | NonTargetingControlGuideForMouse_0398 | AACATGTTAAGTCGGTTAT | MouseDummy |
| MouseDummy_MetsMR_1023_NonTargetingControlGuideForMouse_0399 | MetsMR_1023 | NonTargetingControlGuideForMouse_0399 | TACGACATGGCATGGTAAG | MouseDummy |
| MouseDummy_MetsMR_1024_NonTargetingControlGuideForMouse_0400 | MetsMR_1024 | NonTargetingControlGuideForMouse_0400 | CAGCTGACCGTTAATCGATA | MouseDummy |
| MouseDummy_MetsMR_1025_NonTargetingControlGuideForMouse_0401 | MetsMR_1025 | NonTargetingControlGuideForMouse_0401 | TACACGCCCTAAGCTAGTAA | MouseDummy |
| MouseDummy_MetsMR_1026_NonTargetingControlGuideForMouse_0402 | MetsMR_1026 | NonTargetingControlGuideForMouse_0402 | CCGACTGCCGAGCTAGGCGT | MouseDummy |
| MouseDummy_MetsMR_1027_NonTargetingControlGuideForMouse_0403 | MetsMR_1027 | NonTargetingControlGuideForMouse_0403 | GTTGCGGCGACCTAGATATC | MouseDummy |
| MouseDummy_MetsMR_1028_NonTargetingControlGuideForMouse_0404 | MetsMR_1028 | NonTargetingControlGuideForMouse_0404 | TAGACGTCCACCGACTCTGA | MouseDummy |
| MouseDummy_MetsMR_1029_NonTargetingControlGuideForMouse_0405 | MetsMR_1029 | NonTargetingControlGuideForMouse_0405 | TCAACGACGACTAAGGGAAT | MouseDummy |
| MouseDummy_MetsMR_1030_NonTargetingControlGuideForMouse_0406 | MetsMR_1030 | NonTargetingControlGuideForMouse_0406 | GCTTATCGTTCCGCTACGAT | MouseDummy |
| MouseDummy_MetsMR_1031_NonTargetingControlGuideForMouse_0407 | MetsMR_1031 | NonTargetingControlGuideForMouse_0407 | ACCGGTTCAGCCGCCGGAAC | MouseDummy |
| MouseDummy_MetsMR_1032_NonTargetingControlGuideForMouse_0408 | MetsMR_1032 | NonTargetingControlGuideForMouse_0408 | CTACCGTCTATTACGATCT | MouseDummy |
| MouseDummy_MetsMR_1033_NonTargetingControlGuideForMouse_0409 | MetsMR_1033 | NonTargetingControlGuideForMouse_0409 | TGTCGCCGATGGTCAGTCGC | MouseDummy |
| MouseDummy_MetsMR_1034_NonTargetingControlGuideForMouse_0410 | MetsMR_1034 | NonTargetingControlGuideForMouse_0410 | CGGGCGGTAAGAGCTCTACG | MouseDummy |
| MouseDummy_MetsMR_1035_NonTargetingControlGuideForMouse_0411 | MetsMR_1035 | NonTargetingControlGuideForMouse_0411 | GGCACCGTTCGGAAACCGAC | MouseDummy |
| MouseDummy_MetsMR_1036_NonTargetingControlGuideForMouse_0412 | MetsMR_1036 | NonTargetingControlGuideForMouse_0412 | TCTCGAATAAATTTCTCGC | MouseDummy |
| MouseDummy_MetsMR_1037_NonTargetingControlGuideForMouse_0413 | MetsMR_1037 | NonTargetingControlGuideForMouse_0413 | GCATTCTTGAGCTCCGGCC | MouseDummy |

FIG. 18 CONTINUED

| | | | | |
|---|---|---|---|---|
| MouseDummy_MeisMR_1038_NonTargetingControlGuideForMouse_0414 | MeisMR_1038 | NonTargetingControlGuideForMouse_0414 | ATTCGGACCGTTATCTCCACC | MouseDummy |
| MouseDummy_MeisMR_1039_NonTargetingControlGuideForMouse_0415 | MeisMR_1039 | NonTargetingControlGuideForMouse_0415 | GTTCTTCAAAGACGGGCGGC | MouseDummy |
| MouseDummy_MeisMR_1040_NonTargetingControlGuideForMouse_0416 | MeisMR_1040 | NonTargetingControlGuideForMouse_0416 | TTCCCCGCCCGTGCGGTCAT | MouseDummy |
| MouseDummy_MeisMR_1041_NonTargetingControlGuideForMouse_0417 | MeisMR_1041 | NonTargetingControlGuideForMouse_0417 | TAGTAGGTTGATCGGTCGC | MouseDummy |
| MouseDummy_MeisMR_1042_NonTargetingControlGuideForMouse_0418 | MeisMR_1042 | NonTargetingControlGuideForMouse_0418 | CGGTCGGTGACGTATACACG | MouseDummy |
| MouseDummy_MeisMR_1043_NonTargetingControlGuideForMouse_0419 | MeisMR_1043 | NonTargetingControlGuideForMouse_0419 | ATTATAGCCAGCCCCCGAAT | MouseDummy |
| MouseDummy_MeisMR_1044_NonTargetingControlGuideForMouse_0420 | MeisMR_1044 | NonTargetingControlGuideForMouse_0420 | CGGTCAGTGGTCTTCCGGA | MouseDummy |
| MouseDummy_MeisMR_1045_NonTargetingControlGuideForMouse_0421 | MeisMR_1045 | NonTargetingControlGuideForMouse_0421 | TGGATCGCTTCGCACGGCG | MouseDummy |
| MouseDummy_MeisMR_1046_NonTargetingControlGuideForMouse_0422 | MeisMR_1046 | NonTargetingControlGuideForMouse_0422 | AAACCCCGCCCGAGCGTC | MouseDummy |
| MouseDummy_MeisMR_1047_NonTargetingControlGuideForMouse_0423 | MeisMR_1047 | NonTargetingControlGuideForMouse_0423 | CATAGATCCGCGATTGTACG | MouseDummy |
| MouseDummy_MeisMR_1048_NonTargetingControlGuideForMouse_0424 | MeisMR_1048 | NonTargetingControlGuideForMouse_0424 | GTTTCAGGAAGACGGGCGAG | MouseDummy |
| MouseDummy_MeisMR_1049_NonTargetingControlGuideForMouse_0425 | MeisMR_1049 | NonTargetingControlGuideForMouse_0425 | ACCGTCTCTATTATACGGCA | MouseDummy |
| MouseDummy_MeisMR_1050_NonTargetingControlGuideForMouse_0426 | MeisMR_1050 | NonTargetingControlGuideForMouse_0426 | TGTTCGCCCTCTCACGATTG | MouseDummy |
| MouseDummy_MeisMR_1051_NonTargetingControlGuideForMouse_0427 | MeisMR_1051 | NonTargetingControlGuideForMouse_0427 | AACTAACTCACTACGCACGA | MouseDummy |
| MouseDummy_MeisMR_1052_NonTargetingControlGuideForMouse_0428 | MeisMR_1052 | NonTargetingControlGuideForMouse_0428 | TCGCTCCGGCTAGTAGTGGGT | MouseDummy |
| MouseDummy_MeisMR_1053_NonTargetingControlGuideForMouse_0429 | MeisMR_1053 | NonTargetingControlGuideForMouse_0429 | TCGGGGCAGCCTAATGTATA | MouseDummy |
| MouseDummy_MeisMR_1054_NonTargetingControlGuideForMouse_0430 | MeisMR_1054 | NonTargetingControlGuideForMouse_0430 | CAACCTGCCTAGCACCCGC | MouseDummy |
| MouseDummy_MeisMR_1055_NonTargetingControlGuideForMouse_0431 | MeisMR_1055 | NonTargetingControlGuideForMouse_0431 | GTCGGCTCATCGGAAAATAT | MouseDummy |
| MouseDummy_MeisMR_1056_NonTargetingControlGuideForMouse_0432 | MeisMR_1056 | NonTargetingControlGuideForMouse_0432 | GACAGTTGACGCGACGGAGA | MouseDummy |
| MouseDummy_MeisMR_1057_NonTargetingControlGuideForMouse_0433 | MeisMR_1057 | NonTargetingControlGuideForMouse_0433 | CCCTGATGTCTATACGCGC | MouseDummy |
| MouseDummy_MeisMR_1058_NonTargetingControlGuideForMouse_0434 | MeisMR_1058 | NonTargetingControlGuideForMouse_0434 | TAACCCTTGATCAACCATA | MouseDummy |
| MouseDummy_MeisMR_1059_NonTargetingControlGuideForMouse_0435 | MeisMR_1059 | NonTargetingControlGuideForMouse_0435 | CTATTGGGAGCGGGCTCTCG | MouseDummy |

FIG. 18 CONTINUED

| | | | |
|---|---|---|---|
| MouseDummy_MetsMR_1060_NonTargetingControlGuideForMouse_0436 | MetsMR_1060 | NonTargetingControlGuideForMouse_0436 | GCTTATCGTCATGTGGGTGA | MouseDummy |
| MouseDummy_MetsMR_1061_NonTargetingControlGuideForMouse_0437 | MetsMR_1061 | NonTargetingControlGuideForMouse_0437 | TGATGCCTGGTACCCGTAACT | MouseDummy |
| MouseDummy_MetsMR_1062_NonTargetingControlGuideForMouse_0438 | MetsMR_1062 | NonTargetingControlGuideForMouse_0438 | GGGCGTACTGTAATGACGGT | MouseDummy |
| MouseDummy_MetsMR_1063_NonTargetingControlGuideForMouse_0439 | MetsMR_1063 | NonTargetingControlGuideForMouse_0439 | ACGGATTGCTGAGCTATCA | MouseDummy |
| MouseDummy_MetsMR_1064_NonTargetingControlGuideForMouse_0440 | MetsMR_1064 | NonTargetingControlGuideForMouse_0440 | TAATGCGAATGCGACCTCTC | MouseDummy |
| MouseDummy_MetsMR_1065_NonTargetingControlGuideForMouse_0441 | MetsMR_1065 | NonTargetingControlGuideForMouse_0441 | TTTAACTGGGGGACCGGACG | MouseDummy |
| MouseDummy_MetsMR_1066_NonTargetingControlGuideForMouse_0442 | MetsMR_1066 | NonTargetingControlGuideForMouse_0442 | CGCAGAGTTCAAATCCGGC | MouseDummy |
| MouseDummy_MetsMR_1067_NonTargetingControlGuideForMouse_0443 | MetsMR_1067 | NonTargetingControlGuideForMouse_0443 | TGTTTATGGGAACTTCGCC | MouseDummy |
| MouseDummy_MetsMR_1068_NonTargetingControlGuideForMouse_0444 | MetsMR_1068 | NonTargetingControlGuideForMouse_0444 | ACAGACCGAATAACCGGAGA | MouseDummy |
| MouseDummy_MetsMR_1069_NonTargetingControlGuideForMouse_0445 | MetsMR_1069 | NonTargetingControlGuideForMouse_0445 | TGACGCTAAGGCCCGCTAAC | MouseDummy |
| MouseDummy_MetsMR_1070_NonTargetingControlGuideForMouse_0446 | MetsMR_1070 | NonTargetingControlGuideForMouse_0446 | ACTCGCGAAACGTACATGA | MouseDummy |
| MouseDummy_MetsMR_1071_NonTargetingControlGuideForMouse_0447 | MetsMR_1071 | NonTargetingControlGuideForMouse_0447 | ATAGGGCCACGGGCTACTCC | MouseDummy |
| MouseDummy_MetsMR_1072_NonTargetingControlGuideForMouse_0448 | MetsMR_1072 | NonTargetingControlGuideForMouse_0448 | AGATTCTCGCGTAACCAGAG | MouseDummy |
| MouseDummy_MetsMR_1073_NonTargetingControlGuideForMouse_0449 | MetsMR_1073 | NonTargetingControlGuideForMouse_0449 | ACAATTCGGTTTATGCGCGT | MouseDummy |
| MouseDummy_MetsMR_1074_NonTargetingControlGuideForMouse_0450 | MetsMR_1074 | NonTargetingControlGuideForMouse_0450 | CGGGTCCTTATAGATAGTGTCG | MouseDummy |
| MouseDummy_MetsMR_1075_NonTargetingControlGuideForMouse_0451 | MetsMR_1075 | NonTargetingControlGuideForMouse_0451 | AGGGTTAGGCTGACCGGCGA | MouseDummy |
| MouseDummy_MetsMR_1076_NonTargetingControlGuideForMouse_0452 | MetsMR_1076 | NonTargetingControlGuideForMouse_0452 | AGCTATCCCACGTTCCGCGG | MouseDummy |
| MouseDummy_MetsMR_1077_NonTargetingControlGuideForMouse_0453 | MetsMR_1077 | NonTargetingControlGuideForMouse_0453 | ATCATGCCTTCGCATTAACC | MouseDummy |
| MouseDummy_MetsMR_1078_NonTargetingControlGuideForMouse_0454 | MetsMR_1078 | NonTargetingControlGuideForMouse_0454 | TGGGTCCTAAACGCGGTTCA | MouseDummy |
| MouseDummy_MetsMR_1079_NonTargetingControlGuideForMouse_0455 | MetsMR_1079 | NonTargetingControlGuideForMouse_0455 | CATTACTGTTATCGACCGGCA | MouseDummy |
| MouseDummy_MetsMR_1080_NonTargetingControlGuideForMouse_0456 | MetsMR_1080 | NonTargetingControlGuideForMouse_0456 | TGAGCGCTTTCCGATCCGG | MouseDummy |
| MouseDummy_MetsMR_1081_NonTargetingControlGuideForMouse_0457 | MetsMR_1081 | NonTargetingControlGuideForMouse_0457 | GCCTTCCTCGCAGACCCGAC | MouseDummy |

| | | | | |
|---|---|---|---|---|
| MouseDummy_MetsMiR_1082_NonTargetingControlGuideForMouse_0458 | MetsMiR_1082 | NonTargetingControlGuideForMouse_0458 | CCCTTAAAGTGACGGACGAA | MouseDummy |
| MouseDummy_MetsMiR_1083_NonTargetingControlGuideForMouse_0459 | MetsMiR_1083 | NonTargetingControlGuideForMouse_0459 | TGGTTCGACCAACATGGTTC | MouseDummy |
| MouseDummy_MetsMiR_1084_NonTargetingControlGuideForMouse_0460 | MetsMiR_1084 | NonTargetingControlGuideForMouse_0460 | TGGGCCATAGTGGGCGTGA | MouseDummy |
| MouseDummy_MetsMiR_1085_NonTargetingControlGuideForMouse_0461 | MetsMiR_1085 | NonTargetingControlGuideForMouse_0461 | TCATATTAGACAATCTCCGC | MouseDummy |
| MouseDummy_MetsMiR_1086_NonTargetingControlGuideForMouse_0462 | MetsMiR_1086 | NonTargetingControlGuideForMouse_0462 | TAGCCGAGTTCACGCCAGTA | MouseDummy |
| MouseDummy_MetsMiR_1087_NonTargetingControlGuideForMouse_0463 | MetsMiR_1087 | NonTargetingControlGuideForMouse_0463 | ACCAGGCGCGGCACCGCACAT | MouseDummy |
| MouseDummy_MetsMiR_1088_NonTargetingControlGuideForMouse_0464 | MetsMiR_1088 | NonTargetingControlGuideForMouse_0464 | GCGCGAGTGCCAAACGAGTC | MouseDummy |
| MouseDummy_MetsMiR_1089_NonTargetingControlGuideForMouse_0465 | MetsMiR_1089 | NonTargetingControlGuideForMouse_0465 | AAGGGCTGGCGCCGGGCAA | MouseDummy |
| MouseDummy_MetsMiR_1090_NonTargetingControlGuideForMouse_0466 | MetsMiR_1090 | NonTargetingControlGuideForMouse_0466 | ACGGTTCGAGCACGGTTATGA | MouseDummy |
| MouseDummy_MetsMiR_1091_NonTargetingControlGuideForMouse_0467 | MetsMiR_1091 | NonTargetingControlGuideForMouse_0467 | TCATGTTCGGTCGTCCGTTA | MouseDummy |
| MouseDummy_MetsMiR_1092_NonTargetingControlGuideForMouse_0468 | MetsMiR_1092 | NonTargetingControlGuideForMouse_0468 | CGGTCCGTATCCTCTCATAA | MouseDummy |
| MouseDummy_MetsMiR_1093_NonTargetingControlGuideForMouse_0469 | MetsMiR_1093 | NonTargetingControlGuideForMouse_0469 | AAACGAGGCTGTTCGTACAC | MouseDummy |
| MouseDummy_MetsMiR_1094_NonTargetingControlGuideForMouse_0470 | MetsMiR_1094 | NonTargetingControlGuideForMouse_0470 | CACGGTATAGCGGGCGGG | MouseDummy |
| MouseDummy_MetsMiR_1095_NonTargetingControlGuideForMouse_0471 | MetsMiR_1095 | NonTargetingControlGuideForMouse_0471 | ATCGAGCACCGAGTTGTGAT | MouseDummy |
| MouseDummy_MetsMiR_1096_NonTargetingControlGuideForMouse_0472 | MetsMiR_1096 | NonTargetingControlGuideForMouse_0472 | TCACTTTAAGCACCCCGCGC | MouseDummy |
| MouseDummy_MetsMiR_1097_NonTargetingControlGuideForMouse_0473 | MetsMiR_1097 | NonTargetingControlGuideForMouse_0473 | CTACTTGTGACGACTCGGCG | MouseDummy |
| MouseDummy_MetsMiR_1098_NonTargetingControlGuideForMouse_0474 | MetsMiR_1098 | NonTargetingControlGuideForMouse_0474 | CTACGCGATAGGCGGGGTGA | MouseDummy |
| MouseDummy_MetsMiR_1099_NonTargetingControlGuideForMouse_0475 | MetsMiR_1099 | NonTargetingControlGuideForMouse_0475 | GCTTACCTACTCCGCCCCGC | MouseDummy |
| MouseDummy_MetsMiR_1100_NonTargetingControlGuideForMouse_0476 | MetsMiR_1100 | NonTargetingControlGuideForMouse_0476 | TAACACGCACTCACGTCCGG | MouseDummy |
| MouseDummy_MetsMiR_1101_NonTargetingControlGuideForMouse_0477 | MetsMiR_1101 | NonTargetingControlGuideForMouse_0477 | ACTCACCGTGCACGATGTA | MouseDummy |
| MouseDummy_MetsMiR_1102_NonTargetingControlGuideForMouse_0478 | MetsMiR_1102 | NonTargetingControlGuideForMouse_0478 | ACACCCGTGTATGCACCGGG | MouseDummy |
| MouseDummy_MetsMiR_1103_NonTargetingControlGuideForMouse_0479 | MetsMiR_1103 | NonTargetingControlGuideForMouse_0479 | GCATAACGCCGAGCACCAC | MouseDummy |

FIG. 18 CONTINUED

| | | | |
|---|---|---|---|
| MouseDummy_MetsMR_1104_NonTargetingControlGuideForMouse_0480 | MetsMR_1104 | NonTargetingControlGuideForMouse_0480 | CCAGCGGACGGCGAACTCCA | MouseDummy |
| MouseDummy_MetsMR_1105_NonTargetingControlGuideForMouse_0481 | MetsMR_1105 | NonTargetingControlGuideForMouse_0481 | TGACCCTCTTAATCTCCGGT | MouseDummy |
| MouseDummy_MetsMR_1106_NonTargetingControlGuideForMouse_0482 | MetsMR_1106 | NonTargetingControlGuideForMouse_0482 | CCCTAACCATAGTTTCGCC | MouseDummy |
| MouseDummy_MetsMR_1107_NonTargetingControlGuideForMouse_0483 | MetsMR_1107 | NonTargetingControlGuideForMouse_0483 | CCCTAGCTCGGTTAGAGAAT | MouseDummy |
| MouseDummy_MetsMR_1108_NonTargetingControlGuideForMouse_0484 | MetsMR_1108 | NonTargetingControlGuideForMouse_0484 | GAATTGAGCGCCAACTCGGC | MouseDummy |
| MouseDummy_MetsMR_1109_NonTargetingControlGuideForMouse_0485 | MetsMR_1109 | NonTargetingControlGuideForMouse_0485 | TGCTTAGGGCCCTTCGGCGG | MouseDummy |
| MouseDummy_MetsMR_1110_NonTargetingControlGuideForMouse_0486 | MetsMR_1110 | NonTargetingControlGuideForMouse_0486 | TCTCCGGGGCCGTGTTAGACC | MouseDummy |
| MouseDummy_MetsMR_1111_NonTargetingControlGuideForMouse_0487 | MetsMR_1111 | NonTargetingControlGuideForMouse_0487 | ATTCACAGTTAAACGGGGG | MouseDummy |
| MouseDummy_MetsMR_1112_NonTargetingControlGuideForMouse_0488 | MetsMR_1112 | NonTargetingControlGuideForMouse_0488 | GATCCCCTAGCTTCAACCT | MouseDummy |
| MouseDummy_MetsMR_1113_NonTargetingControlGuideForMouse_0489 | MetsMR_1113 | NonTargetingControlGuideForMouse_0489 | TTATTACGGCTGAACTTG | MouseDummy |
| MouseDummy_MetsMR_1114_NonTargetingControlGuideForMouse_0490 | MetsMR_1114 | NonTargetingControlGuideForMouse_0490 | ACGTTGTTCCGTCGAAAC | MouseDummy |
| MouseDummy_MetsMR_1115_NonTargetingControlGuideForMouse_0491 | MetsMR_1115 | NonTargetingControlGuideForMouse_0491 | CGAGACGAATCCATCATGCG | MouseDummy |
| MouseDummy_MetsMR_1116_NonTargetingControlGuideForMouse_0492 | MetsMR_1116 | NonTargetingControlGuideForMouse_0492 | ATATGCTCGACCCAATGTCC | MouseDummy |
| MouseDummy_MetsMR_1117_NonTargetingControlGuideForMouse_0493 | MetsMR_1117 | NonTargetingControlGuideForMouse_0493 | AACCTTGGTCTCATGTACGAA | MouseDummy |
| MouseDummy_MetsMR_1118_NonTargetingControlGuideForMouse_0494 | MetsMR_1118 | NonTargetingControlGuideForMouse_0494 | AATTTTTCGGAATCTAGCG | MouseDummy |
| MouseDummy_MetsMR_1119_NonTargetingControlGuideForMouse_0495 | MetsMR_1119 | NonTargetingControlGuideForMouse_0495 | AGGGAGTGTCCGTGACGTTC | MouseDummy |
| MouseDummy_MetsMR_1120_NonTargetingControlGuideForMouse_0496 | MetsMR_1120 | NonTargetingControlGuideForMouse_0496 | AACGTTACCAACCTCGATCC | MouseDummy |
| MouseDummy_MetsMR_1121_NonTargetingControlGuideForMouse_0497 | MetsMR_1121 | NonTargetingControlGuideForMouse_0497 | GTCCTAGATCCTATCGGGAG | MouseDummy |
| MouseDummy_MetsMR_1122_NonTargetingControlGuideForMouse_0498 | MetsMR_1122 | NonTargetingControlGuideForMouse_0498 | CATATACTTGGCTAGAC | MouseDummy |
| MouseDummy_MetsMR_1123_NonTargetingControlGuideForMouse_0499 | MetsMR_1123 | NonTargetingControlGuideForMouse_0499 | ACGTCGATGCTTATCCGTCT | MouseDummy |
| MouseDummy_MetsMR_1124_NonTargetingControlGuideForMouse_0500 | MetsMR_1124 | NonTargetingControlGuideForMouse_0500 | CCGCGCATTAACGATCAGTA | MouseDummy |
| MouseDummy_MetsMR_1125_NonTargetingControlGuideForMouse_0501 | MetsMR_1125 | NonTargetingControlGuideForMouse_0501 | CCTATTAGTAGTCCGGTTAGTC | MouseDummy |

| | | | |
|---|---|---|---|
| MouseDummy_MetsMR_1126_NonTargetingControlGuideForMouse_0502 | MetsMR_1126 | ACCTCGTGCAAATCGGTGGC | MouseDummy |
| MouseDummy_MetsMR_1127_NonTargetingControlGuideForMouse_0503 | MetsMR_1127 | CACGCAGGAGCGGCGGACACT | MouseDummy |
| MouseDummy_MetsMR_1128_NonTargetingControlGuideForMouse_0504 | MetsMR_1128 | GTCCGGCCGCCTTAACCTTTC | MouseDummy |
| MouseDummy_MetsMR_1129_NonTargetingControlGuideForMouse_0505 | MetsMR_1129 | TGATCAACGTCGTGGACGG | MouseDummy |
| MouseDummy_MetsMR_1130_NonTargetingControlGuideForMouse_0506 | MetsMR_1130 | GAACCACGAGGAGGGTATA | MouseDummy |
| MouseDummy_MetsMR_1131_NonTargetingControlGuideForMouse_0507 | MetsMR_1131 | GAACCCGGGAAACACGTCCG | MouseDummy |
| MouseDummy_MetsMR_1132_NonTargetingControlGuideForMouse_0508 | MetsMR_1132 | GGAAACGTTACATTCCGACGC | MouseDummy |
| MouseDummy_MetsMR_1133_NonTargetingControlGuideForMouse_0509 | MetsMR_1133 | AATAGGAACTCCGACCCGGA | MouseDummy |
| MouseDummy_MetsMR_1134_NonTargetingControlGuideForMouse_0510 | MetsMR_1134 | GTAGTGCGTGTGATGTCGGG | MouseDummy |
| MouseDummy_MetsMR_1135_NonTargetingControlGuideForMouse_0511 | MetsMR_1135 | TTTGACATTTCGTCTCTCGCG | MouseDummy |
| MouseDummy_MetsMR_1136_NonTargetingControlGuideForMouse_0512 | MetsMR_1136 | AGTCCGCTGGCGCAATGGG | MouseDummy |
| MouseDummy_MetsMR_1137_NonTargetingControlGuideForMouse_0513 | MetsMR_1137 | CCGCCCGGGTGTCAGTTGAG | MouseDummy |
| MouseDummy_MetsMR_1138_NonTargetingControlGuideForMouse_0514 | MetsMR_1138 | GCCGAGGGCGTAAGCGCGA | MouseDummy |
| MouseDummy_MetsMR_1139_NonTargetingControlGuideForMouse_0515 | MetsMR_1139 | TAATTCGCAACTCGGATCAT | MouseDummy |
| MouseDummy_MetsMR_1140_NonTargetingControlGuideForMouse_0516 | MetsMR_1140 | TTAAGACTGGGTCGTCCCGGT | MouseDummy |
| MouseDummy_MetsMR_1141_NonTargetingControlGuideForMouse_0517 | MetsMR_1141 | TTACGCCAAGCTCAGTTGAG | MouseDummy |
| MouseDummy_MetsMR_1142_NonTargetingControlGuideForMouse_0518 | MetsMR_1142 | GGACACTGGCCGACCCCACT | MouseDummy |
| MouseDummy_MetsMR_1143_NonTargetingControlGuideForMouse_0519 | MetsMR_1143 | TACGTCGGGCAAATAGAAT | MouseDummy |
| MouseDummy_MetsMR_1144_NonTargetingControlGuideForMouse_0520 | MetsMR_1144 | ATACGCGTCATCGACCTTATG | MouseDummy |
| MouseDummy_MetsMR_1145_NonTargetingControlGuideForMouse_0521 | MetsMR_1145 | CGGCGACTGCAGTCGGACAT | MouseDummy |
| MouseDummy_MetsMR_1146_NonTargetingControlGuideForMouse_0522 | MetsMR_1146 | ACTTCCCGGTTCCGTTGA | MouseDummy |
| MouseDummy_MetsMR_1147_NonTargetingControlGuideForMouse_0523 | MetsMR_1147 | TTATGACCTCCATGCGACAT | MouseDummy |

FIG. 18 CONTINUED

| | | | | |
|---|---|---|---|---|
| MouseDummy_MetsMR_1148_NonTargetingControlGuideForMouse_0624 | MetsMR_1148 | NonTargetingControlGuideForMouse_0624 | TGAGGGCCTCGGACCAACC | MouseDummy |
| MouseDummy_MetsMR_1149_NonTargetingControlGuideForMouse_0625 | MetsMR_1149 | NonTargetingControlGuideForMouse_0625 | TATCCGATCCGGAAACTAG | MouseDummy |
| MouseDummy_MetsMR_1150_NonTargetingControlGuideForMouse_0626 | MetsMR_1150 | NonTargetingControlGuideForMouse_0626 | AGTACACTATCGACTTCG | MouseDummy |
| MouseDummy_MetsMR_1151_NonTargetingControlGuideForMouse_0627 | MetsMR_1151 | NonTargetingControlGuideForMouse_0627 | TTCCAGTATACCGAATTCGC | MouseDummy |
| MouseDummy_MetsMR_1152_NonTargetingControlGuideForMouse_0628 | MetsMR_1152 | NonTargetingControlGuideForMouse_0628 | CCCGGCAGACTAACTAGCGG | MouseDummy |
| MouseDummy_MetsMR_1153_NonTargetingControlGuideForMouse_0629 | MetsMR_1153 | NonTargetingControlGuideForMouse_0629 | GCAACGGACAGTCATCGAAC | MouseDummy |
| MouseDummy_MetsMR_1154_NonTargetingControlGuideForMouse_0630 | MetsMR_1154 | NonTargetingControlGuideForMouse_0630 | GCTAGCGTTCAGCCCGATGT | MouseDummy |
| MouseDummy_MetsMR_1155_NonTargetingControlGuideForMouse_0631 | MetsMR_1155 | NonTargetingControlGuideForMouse_0631 | TATGAACTAGGGTAAACGG | MouseDummy |
| MouseDummy_MetsMR_1156_NonTargetingControlGuideForMouse_0632 | MetsMR_1156 | NonTargetingControlGuideForMouse_0632 | CGGCGGGATTATTAAACTTC | MouseDummy |
| MouseDummy_MetsMR_1157_NonTargetingControlGuideForMouse_0633 | MetsMR_1157 | NonTargetingControlGuideForMouse_0633 | AAGCAGGACTACTCGACGC | MouseDummy |
| MouseDummy_MetsMR_1158_NonTargetingControlGuideForMouse_0634 | MetsMR_1158 | NonTargetingControlGuideForMouse_0634 | CCCCTATAGGCGCGCTAAGG | MouseDummy |
| MouseDummy_MetsMR_1159_NonTargetingControlGuideForMouse_0635 | MetsMR_1159 | NonTargetingControlGuideForMouse_0635 | CCGAGATGGCTCGGATAGAC | MouseDummy |
| MouseDummy_MetsMR_1160_NonTargetingControlGuideForMouse_0636 | MetsMR_1160 | NonTargetingControlGuideForMouse_0636 | AGCACCGGCACAAGAGCCGC | MouseDummy |
| MouseDummy_MetsMR_1161_NonTargetingControlGuideForMouse_0637 | MetsMR_1161 | NonTargetingControlGuideForMouse_0637 | TCGTAAAGTCGCAGCGACGT | MouseDummy |
| MouseDummy_MetsMR_1162_NonTargetingControlGuideForMouse_0638 | MetsMR_1162 | NonTargetingControlGuideForMouse_0638 | GTCTAACATCGGCGCACGTG | MouseDummy |
| MouseDummy_MetsMR_1163_NonTargetingControlGuideForMouse_0639 | MetsMR_1163 | NonTargetingControlGuideForMouse_0639 | TTCAACGACGAAGACGCGC | MouseDummy |
| MouseDummy_MetsMR_1164_NonTargetingControlGuideForMouse_0640 | MetsMR_1164 | NonTargetingControlGuideForMouse_0640 | CGTTCGGTAAGGTCGATTGG | MouseDummy |
| MouseDummy_MetsMR_1165_NonTargetingControlGuideForMouse_0641 | MetsMR_1165 | NonTargetingControlGuideForMouse_0641 | TAGGGTGGCGATTAGACTA | MouseDummy |
| MouseDummy_MetsMR_1166_NonTargetingControlGuideForMouse_0642 | MetsMR_1166 | NonTargetingControlGuideForMouse_0642 | GCCCGACTCCACGTAAATC | MouseDummy |
| MouseDummy_MetsMR_1167_NonTargetingControlGuideForMouse_0643 | MetsMR_1167 | NonTargetingControlGuideForMouse_0643 | TATGAAACATCGGCGACG | MouseDummy |
| MouseDummy_MetsMR_1168_NonTargetingControlGuideForMouse_0644 | MetsMR_1168 | NonTargetingControlGuideForMouse_0644 | CTGCTTGAACGCCTAGACGC | MouseDummy |
| MouseDummy_MetsMR_1169_NonTargetingControlGuideForMouse_0645 | MetsMR_1169 | NonTargetingControlGuideForMouse_0645 | GGGCCCGGCACTCTGTCGGAC | MouseDummy |

FIG. 18 CONTINUED

| | | | |
|---|---|---|---|
| MouseDummy_MetsMR_1170_NonTargetingControlGuideForMouse_0546 | MetsMR_1170 | NonTargetingControlGuideForMouse_0546 | GCCGACCACGGATGACCACG | MouseDummy |
| MouseDummy_MetsMR_1171_NonTargetingControlGuideForMouse_0547 | MetsMR_1171 | NonTargetingControlGuideForMouse_0547 | ATCGGCGGCGTGCTGAGGCTT | MouseDummy |
| MouseDummy_MetsMR_1172_NonTargetingControlGuideForMouse_0548 | MetsMR_1172 | NonTargetingControlGuideForMouse_0548 | CGACGGTGTGCTGAGGCTT | MouseDummy |
| MouseDummy_MetsMR_1173_NonTargetingControlGuideForMouse_0549 | MetsMR_1173 | NonTargetingControlGuideForMouse_0549 | CGGATCCTCCCGTACTATCC | MouseDummy |
| MouseDummy_MetsMR_1174_NonTargetingControlGuideForMouse_0550 | MetsMR_1174 | NonTargetingControlGuideForMouse_0550 | CCATTAGTACGAACATTGCG | MouseDummy |
| MouseDummy_MetsMR_1175_NonTargetingControlGuideForMouse_0551 | MetsMR_1175 | NonTargetingControlGuideForMouse_0551 | GTTCATACTGATGAACGTCC | MouseDummy |
| MouseDummy_MetsMR_1176_NonTargetingControlGuideForMouse_0552 | MetsMR_1176 | NonTargetingControlGuideForMouse_0552 | GCCGAATGCGTTATTCCAA | MouseDummy |
| MouseDummy_MetsMR_1177_NonTargetingControlGuideForMouse_0553 | MetsMR_1177 | NonTargetingControlGuideForMouse_0553 | CAAGGATCGTCGCGTGATTT | MouseDummy |
| MouseDummy_MetsMR_1178_NonTargetingControlGuideForMouse_0554 | MetsMR_1178 | NonTargetingControlGuideForMouse_0554 | GTTAATATTGTGCCCGCCAC | MouseDummy |
| MouseDummy_MetsMR_1179_NonTargetingControlGuideForMouse_0555 | MetsMR_1179 | NonTargetingControlGuideForMouse_0555 | CCAACCCGGCATCGTCCGCT | MouseDummy |
| MouseDummy_MetsMR_1180_NonTargetingControlGuideForMouse_0556 | MetsMR_1180 | NonTargetingControlGuideForMouse_0556 | GCGAGGCGTATCCCGGTGGA | MouseDummy |
| MouseDummy_MetsMR_1181_NonTargetingControlGuideForMouse_0557 | MetsMR_1181 | NonTargetingControlGuideForMouse_0557 | GTGATGACGAGAAGCGAAG | MouseDummy |
| MouseDummy_MetsMR_1182_NonTargetingControlGuideForMouse_0558 | MetsMR_1182 | NonTargetingControlGuideForMouse_0558 | GGTGTGGACCGCTTTTACGC | MouseDummy |
| MouseDummy_MetsMR_1183_NonTargetingControlGuideForMouse_0559 | MetsMR_1183 | NonTargetingControlGuideForMouse_0559 | GTTATACCACTACTATGAC | MouseDummy |
| MouseDummy_MetsMR_1184_NonTargetingControlGuideForMouse_0560 | MetsMR_1184 | NonTargetingControlGuideForMouse_0560 | GATACGTGAGGTTGCCGGTG | MouseDummy |
| MouseDummy_MetsMR_1185_NonTargetingControlGuideForMouse_0561 | MetsMR_1185 | NonTargetingControlGuideForMouse_0561 | TATGCCATATGCCCGTTTTT | MouseDummy |
| MouseDummy_MetsMR_1186_NonTargetingControlGuideForMouse_0562 | MetsMR_1186 | NonTargetingControlGuideForMouse_0562 | TCATCTACGGTATCGAAAGG | MouseDummy |
| MouseDummy_MetsMR_1187_NonTargetingControlGuideForMouse_0563 | MetsMR_1187 | NonTargetingControlGuideForMouse_0563 | ACTGTGCACGGCAAAGTCGAC | MouseDummy |
| MouseDummy_MetsMR_1188_NonTargetingControlGuideForMouse_0564 | MetsMR_1188 | NonTargetingControlGuideForMouse_0564 | CAATGGGTCTGCCGTTCAG | MouseDummy |
| MouseDummy_MetsMR_1189_NonTargetingControlGuideForMouse_0565 | MetsMR_1189 | NonTargetingControlGuideForMouse_0565 | GCTCCTGATGTGTAATCCG | MouseDummy |
| MouseDummy_MetsMR_1190_NonTargetingControlGuideForMouse_0566 | MetsMR_1190 | NonTargetingControlGuideForMouse_0566 | GGATACATGGCGCGCTAGT | MouseDummy |
| MouseDummy_MetsMR_1191_NonTargetingControlGuideForMouse_0567 | MetsMR_1191 | NonTargetingControlGuideForMouse_0567 | CACCACCGCGTCGTGCCGG | MouseDummy |

FIG. 18 CONTINUED

| | | | | |
|---|---|---|---|---|
| MouseDummy_MetsMiR_1192_NonTargetingControlGuideForMouse_0568 | MetsMiR_1192 | NonTargetingControlGuideForMouse_0568 | CGATGTCGAAAGTCGGTCAA | MouseDummy |
| MouseDummy_MetsMiR_1193_NonTargetingControlGuideForMouse_0569 | MetsMiR_1193 | NonTargetingControlGuideForMouse_0569 | CGATAGGCTATAGAGAATAGTC | MouseDummy |
| MouseDummy_MetsMiR_1194_NonTargetingControlGuideForMouse_0570 | MetsMiR_1194 | NonTargetingControlGuideForMouse_0570 | GGCTGGGAGTTCGTCGCTCTT | MouseDummy |
| MouseDummy_MetsMiR_1195_NonTargetingControlGuideForMouse_0571 | MetsMiR_1195 | NonTargetingControlGuideForMouse_0571 | CACAACGCCTACCAGCGGAC | MouseDummy |
| MouseDummy_MetsMiR_1196_NonTargetingControlGuideForMouse_0572 | MetsMiR_1196 | NonTargetingControlGuideForMouse_0572 | ATTTGCCCGTCCATACGCGG | MouseDummy |
| MouseDummy_MetsMiR_1197_NonTargetingControlGuideForMouse_0573 | MetsMiR_1197 | NonTargetingControlGuideForMouse_0573 | CGGTAAGATGGTTATACGT | MouseDummy |
| MouseDummy_MetsMiR_1198_NonTargetingControlGuideForMouse_0574 | MetsMiR_1198 | NonTargetingControlGuideForMouse_0574 | GTTCGCGGGGCCTTCTATCA | MouseDummy |
| MouseDummy_MetsMiR_1199_NonTargetingControlGuideForMouse_0575 | MetsMiR_1199 | NonTargetingControlGuideForMouse_0575 | GGCACCGGTTTATTGCACT | MouseDummy |
| MouseDummy_MetsMiR_1200_NonTargetingControlGuideForMouse_0576 | MetsMiR_1200 | NonTargetingControlGuideForMouse_0576 | TGACAACCGGGTACCTCTA | MouseDummy |
| MouseDummy_MetsMiR_1201_NonTargetingControlGuideForMouse_0577 | MetsMiR_1201 | NonTargetingControlGuideForMouse_0577 | GGTCGCTCGGATTTCATTTAA | MouseDummy |
| MouseDummy_MetsMiR_1202_NonTargetingControlGuideForMouse_0578 | MetsMiR_1202 | NonTargetingControlGuideForMouse_0578 | GACGAAAGTCCTACGAAGT | MouseDummy |
| MouseDummy_MetsMiR_1203_NonTargetingControlGuideForMouse_0579 | MetsMiR_1203 | NonTargetingControlGuideForMouse_0579 | GTACCACTTATCGACCTTGC | MouseDummy |
| MouseDummy_MetsMiR_1204_NonTargetingControlGuideForMouse_0580 | MetsMiR_1204 | NonTargetingControlGuideForMouse_0580 | TTTCAAGTCGTTATCGACGCGG | MouseDummy |
| MouseDummy_MetsMiR_1205_NonTargetingControlGuideForMouse_0581 | MetsMiR_1205 | NonTargetingControlGuideForMouse_0581 | TGAGAGCAAGGCGCATACGG | MouseDummy |
| MouseDummy_MetsMiR_1206_NonTargetingControlGuideForMouse_0582 | MetsMiR_1206 | NonTargetingControlGuideForMouse_0582 | CATTCTCTGACGAATGCGCC | MouseDummy |
| MouseDummy_MetsMiR_1207_NonTargetingControlGuideForMouse_0583 | MetsMiR_1207 | NonTargetingControlGuideForMouse_0583 | ATCCCCCGACTTAGGGATT | MouseDummy |
| MouseDummy_MetsMiR_1208_NonTargetingControlGuideForMouse_0584 | MetsMiR_1208 | NonTargetingControlGuideForMouse_0584 | CAGTGCCGGTAGCGGCACGG | MouseDummy |
| MouseDummy_MetsMiR_1209_NonTargetingControlGuideForMouse_0585 | MetsMiR_1209 | NonTargetingControlGuideForMouse_0585 | ACGACTTCCGGCCTGTGTGTAT | MouseDummy |
| MouseDummy_MetsMiR_1210_NonTargetingControlGuideForMouse_0586 | MetsMiR_1210 | NonTargetingControlGuideForMouse_0586 | GCGCTTCGAACAAACATGGTC | MouseDummy |
| MouseDummy_MetsMiR_1211_NonTargetingControlGuideForMouse_0587 | MetsMiR_1211 | NonTargetingControlGuideForMouse_0587 | GGCAACGCACGCTGGGTTGT | MouseDummy |
| MouseDummy_MetsMiR_1212_NonTargetingControlGuideForMouse_0588 | MetsMiR_1212 | NonTargetingControlGuideForMouse_0588 | GCTATTCCGCTCGTCAATTT | MouseDummy |
| MouseDummy_MetsMiR_1213_NonTargetingControlGuideForMouse_0589 | MetsMiR_1213 | NonTargetingControlGuideForMouse_0589 | TTCATCGCCAGATCGATTTCG | MouseDummy |

FIG. 18 CONTINUED

| | | | |
|---|---|---|---|
| MouseDummy_MetsMR_1214_NonTargetingControlGuideForMouse_0590 | MetsMR_1214 | NonTargetingControlGuideForMouse_0590 | TTCATCCTTCGTAGCGGAAGC | MouseDummy |
| MouseDummy_MetsMR_1215_NonTargetingControlGuideForMouse_0591 | MetsMR_1215 | NonTargetingControlGuideForMouse_0591 | TGGTTCACCACTCGAGATCG | MouseDummy |
| MouseDummy_MetsMR_1216_NonTargetingControlGuideForMouse_0592 | MetsMR_1216 | NonTargetingControlGuideForMouse_0592 | TTGAGCGGACCCCGTACAA | MouseDummy |
| MouseDummy_MetsMR_1217_NonTargetingControlGuideForMouse_0593 | MetsMR_1217 | NonTargetingControlGuideForMouse_0593 | ATGTGTATGAAGCCGGTCAT | MouseDummy |
| MouseDummy_MetsMR_1218_NonTargetingControlGuideForMouse_0594 | MetsMR_1218 | NonTargetingControlGuideForMouse_0594 | TAGGTGGCGCCCAATCGGAC | MouseDummy |
| MouseDummy_MetsMR_1219_NonTargetingControlGuideForMouse_0595 | MetsMR_1219 | NonTargetingControlGuideForMouse_0595 | CTCGTGTCACTCCTCGGTTC | MouseDummy |
| MouseDummy_MetsMR_1220_NonTargetingControlGuideForMouse_0596 | MetsMR_1220 | NonTargetingControlGuideForMouse_0596 | ATGCCAATGCGGTTGTTAGC | MouseDummy |
| MouseDummy_MetsMR_1221_NonTargetingControlGuideForMouse_0597 | MetsMR_1221 | NonTargetingControlGuideForMouse_0597 | CCTTACGGGAGAAGGAGT | MouseDummy |
| MouseDummy_MetsMR_1222_NonTargetingControlGuideForMouse_0598 | MetsMR_1222 | NonTargetingControlGuideForMouse_0598 | CGCCCGGATCTTCCGTACAA | MouseDummy |
| MouseDummy_MetsMR_1223_NonTargetingControlGuideForMouse_0599 | MetsMR_1223 | NonTargetingControlGuideForMouse_0599 | CGGCAAGCGCATTCCTATGG | MouseDummy |
| MouseDummy_MetsMR_1224_NonTargetingControlGuideForMouse_0600 | MetsMR_1224 | NonTargetingControlGuideForMouse_0600 | TATGATCGTATGCCCTTCC | MouseDummy |
| MouseDummy_MetsMR_1225_NonTargetingControlGuideForMouse_0601 | MetsMR_1225 | NonTargetingControlGuideForMouse_0601 | ATCGCCTAGCCCAAGCGACG | MouseDummy |
| MouseDummy_MetsMR_1226_NonTargetingControlGuideForMouse_0602 | MetsMR_1226 | NonTargetingControlGuideForMouse_0602 | GCGATCGCCGGTATAGCTTT | MouseDummy |
| MouseDummy_MetsMR_1227_NonTargetingControlGuideForMouse_0603 | MetsMR_1227 | NonTargetingControlGuideForMouse_0603 | CCGTTCAATTATGCTGGCGT | MouseDummy |
| MouseDummy_MetsMR_1228_NonTargetingControlGuideForMouse_0604 | MetsMR_1228 | NonTargetingControlGuideForMouse_0604 | CCAGCTAACGTTTAGTACG | MouseDummy |
| MouseDummy_MetsMR_1229_NonTargetingControlGuideForMouse_0605 | MetsMR_1229 | NonTargetingControlGuideForMouse_0605 | TCCCCTTCGTCGGCGCAGG | MouseDummy |
| MouseDummy_MetsMR_1230_NonTargetingControlGuideForMouse_0606 | MetsMR_1230 | NonTargetingControlGuideForMouse_0606 | TTCTGATTAGATACGTACGA | MouseDummy |
| MouseDummy_MetsMR_1231_NonTargetingControlGuideForMouse_0607 | MetsMR_1231 | NonTargetingControlGuideForMouse_0607 | TTTTCGTCGACTAAGTCAAG | MouseDummy |
| MouseDummy_MetsMR_1232_NonTargetingControlGuideForMouse_0608 | MetsMR_1232 | NonTargetingControlGuideForMouse_0608 | TCAATTAGTGCCGCCAAGC | MouseDummy |
| MouseDummy_MetsMR_1233_NonTargetingControlGuideForMouse_0609 | MetsMR_1233 | NonTargetingControlGuideForMouse_0609 | TCAGCTACGATCGGACCAA | MouseDummy |
| MouseDummy_MetsMR_1234_NonTargetingControlGuideForMouse_0610 | MetsMR_1234 | NonTargetingControlGuideForMouse_0610 | GCACGAACCGGTTCGTATGG | MouseDummy |
| MouseDummy_MetsMR_1235_NonTargetingControlGuideForMouse_0611 | MetsMR_1235 | NonTargetingControlGuideForMouse_0611 | CAATATGCACGTAGCCTTCGT | MouseDummy |

FIG. 18 CONTINUED

| | | | |
|---|---|---|---|
| MouseDummy_MetsMIR_1236_NonTargetingControlGuideForMouse_0612 | MetsMIR_1236 | NonTargetingControlGuideForMouse_0611 | GACCGACGAGGGTATACCCTACT | MouseDummy |
| MouseDummy_MetsMIR_1236_NonTargetingControlGuideForMouse_0613 | MetsMIR_1237 | NonTargetingControlGuideForMouse_0612 | TTGAAGTAGGGTCGGATTGA | MouseDummy |
| MouseDummy_MetsMIR_1236_NonTargetingControlGuideForMouse_0614 | MetsMIR_1238 | NonTargetingControlGuideForMouse_0613 | AAGGGTAAACGAGTACACG | MouseDummy |
| MouseDummy_MetsMIR_1236_NonTargetingControlGuideForMouse_0615 | MetsMIR_1239 | NonTargetingControlGuideForMouse_0614 | AATGACCTTCCAGTTCGTCT | MouseDummy |
| MouseDummy_MetsMIR_1236_NonTargetingControlGuideForMouse_0616 | MetsMIR_1240 | NonTargetingControlGuideForMouse_0615 | ACGTGTTCTCGTACTTAGCT | MouseDummy |
| MouseDummy_MetsMIR_1236_NonTargetingControlGuideForMouse_0617 | MetsMIR_1241 | NonTargetingControlGuideForMouse_0616 | TTAGCCTTGCCCCGTCATAC | MouseDummy |
| MouseDummy_MetsMIR_1236_NonTargetingControlGuideForMouse_0618 | MetsMIR_1242 | NonTargetingControlGuideForMouse_0617 | GCCTTTTCCGCCCGTTCAAG | MouseDummy |
| MouseDummy_MetsMIR_1236_NonTargetingControlGuideForMouse_0619 | MetsMIR_1243 | NonTargetingControlGuideForMouse_0618 | CAGAAACTCTTACCGAGCGC | MouseDummy |
| MouseDummy_MetsMIR_1236_NonTargetingControlGuideForMouse_0620 | MetsMIR_1244 | NonTargetingControlGuideForMouse_0619 | CTTGAAAAAGGGCGGACTAT | MouseDummy |
| MouseDummy_MetsMIR_1236_NonTargetingControlGuideForMouse_0621 | MetsMIR_1245 | NonTargetingControlGuideForMouse_0620 | CCTACTAACGACGAGTCAAA | MouseDummy |
| MouseDummy_MetsMIR_1236_NonTargetingControlGuideForMouse_0622 | MetsMIR_1246 | NonTargetingControlGuideForMouse_0621 | CATTTCCGGGGTCCGATGCA | MouseDummy |
| MouseDummy_MetsMIR_1236_NonTargetingControlGuideForMouse_0623 | MetsMIR_1247 | NonTargetingControlGuideForMouse_0622 | CCGGGCGCCGTATCCCTAC | MouseDummy |
| MouseDummy_MetsMIR_1236_NonTargetingControlGuideForMouse_0624 | MetsMIR_1248 | NonTargetingControlGuideForMouse_0623 | GAGACCCATTATGATCCTAG | MouseDummy |

FIG. 18
CONTINUED

SEQUENCE LISTING

```
<160> NUMBER OF SEQ ID NOS: 1367

<210> SEQ ID NO 1
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 1
nnnnnnnnnn nnnnnnnnnn ngg                                            23

<210> SEQ ID NO 2
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other

<400> SEQUENCE: 2
nnnnnnnnnn nnngg                                                          15

<210> SEQ ID NO 3
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 3
nnnnnnnnnn nnnnnnnnnn ngg                                                 23

<210> SEQ ID NO 4
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other

<400> SEQUENCE: 4
nnnnnnnnnn nngg                                                           14

<210> SEQ ID NO 5
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 5
nnnnnnnnnn nnnnnnnnnn nnagaaw                                             27
```

```
<210> SEQ ID NO 6
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 6
nnnnnnnnnn nnnnagaaw                                                    19

<210> SEQ ID NO 7
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 7
nnnnnnnnnn nnnnnnnnnn nnagaaw                                           27

<210> SEQ ID NO 8
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 8
nnnnnnnnnn nnnagaaw                                                     18

<210> SEQ ID NO 9
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
```

```
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 9
nnnnnnnnnn nnnnnnnnnn nggng                               25

<210> SEQ ID NO 10
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 10
nnnnnnnnnn nnnggng                                        17

<210> SEQ ID NO 11
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 11
nnnnnnnnnn nnnnnnnnnn nggng                               25

<210> SEQ ID NO 12
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
```

```
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 12
nnnnnnnnnn nnggng                                                          16

<210> SEQ ID NO 13
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 13
nnnnnnnnnn nnnnnnnnnn gttttgtac tctcaagatt tagaaataaa tcttgcagaa           60
gctacaaaga taaggcttca tgccgaaatc aacaccctgt cattttatgg cagggtgttt          120
tcgttattta attttt                                                         137

<210> SEQ ID NO 14
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 14
nnnnnnnnnn nnnnnnnnnn gttttgtac tctcagaaat gcagaagcta caaagataag           60
gcttcatgcc gaaatcaaca ccctgtcatt ttatggcagg gtgttttcgt tatttaattt         120
ttt                                                                      123

<210> SEQ ID NO 15
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 15
nnnnnnnnnn nnnnnnnnnn gttttgtac tctcagaaat gcagaagcta caaagataag           60
gcttcatgcc gaaatcaaca ccctgtcatt ttatggcagg gtgttttttt                    110

<210> SEQ ID NO 16
<211> LENGTH: 102
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 16
nnnnnnnnnn nnnnnnnnnn gttttagagc tagaaatagc aagttaaaat aaggctagtc      60
cgttatcaac ttgaaaaagt ggcaccgagt cggtgctttt tt                        102

<210> SEQ ID NO 17
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 17
nnnnnnnnnn nnnnnnnnnn gttttagagc tagaaatagc aagttaaaat aaggctagtc      60
cgttatcaac ttgaaaaagt gttttttt                                         88

<210> SEQ ID NO 18
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 18
nnnnnnnnnn nnnnnnnnnn gttttagagc tagaaatagc aagttaaaat aaggctagtc      60
cgttatcatt tttttt                                                      76

<210> SEQ ID NO 19
<211> LENGTH: 20
<212> TYPE: DNA
<213> ORGANISM: Homo sapiens

<400> SEQUENCE: 19
gagtccgagc agaagaagaa                                                  20

<210> SEQ ID NO 20
<211> LENGTH: 20
<212> TYPE: DNA
<213> ORGANISM: Homo sapiens

<400> SEQUENCE: 20
gagtcctagc aggagaagaa                                                  20

<210> SEQ ID NO 21
```

-continued

```
<211> LENGTH: 20
<212> TYPE: DNA
<213> ORGANISM: Homo sapiens

<400> SEQUENCE: 21
gagtctaagc agaagaagaa                                                  20

<210> SEQ ID NO 22
<211> LENGTH: 7
<212> TYPE: PRT
<213> ORGANISM: Simian virus 40

<400> SEQUENCE: 22

Pro Lys Lys Lys Arg Lys Val
1               5

<210> SEQ ID NO 23
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 23

Lys Arg Pro Ala Ala Thr Lys Lys Ala Gly Gln Ala Lys Lys Lys Lys
1               5                   10                  15

<210> SEQ ID NO 24
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 24

Pro Ala Ala Lys Arg Val Lys Leu Asp
1               5

<210> SEQ ID NO 25
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 25

Arg Gln Arg Arg Asn Glu Leu Lys Arg Ser Pro
1               5                   10

<210> SEQ ID NO 26
<211> LENGTH: 38
<212> TYPE: PRT
<213> ORGANISM: Homo sapiens

<400> SEQUENCE: 26

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
```

```
<210> SEQ ID NO 27
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 27

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40

<210> SEQ ID NO 28
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 28

Val Ser Arg Lys Arg Pro Arg Pro
1               5

<210> SEQ ID NO 29
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 29

Pro Pro Lys Lys Ala Arg Glu Asp
1               5

<210> SEQ ID NO 30
<211> LENGTH: 8
<212> TYPE: PRT
<213> ORGANISM: Homo sapiens

<400> SEQUENCE: 30

Pro Gln Pro Lys Lys Lys Pro Leu
1               5

<210> SEQ ID NO 31
<211> LENGTH: 12
<212> TYPE: PRT
<213> ORGANISM: Mus musculus

<400> SEQUENCE: 31

Ser Ala Leu Ile Lys Lys Lys Lys Lys Met Ala Pro
1               5                   10

<210> SEQ ID NO 32
<211> LENGTH: 5
<212> TYPE: PRT
```

```
<213> ORGANISM: Influenza virus

<400> SEQUENCE: 32

Asp Arg Leu Arg Arg
1               5

<210> SEQ ID NO 33
<211> LENGTH: 7
<212> TYPE: PRT
<213> ORGANISM: Influenza virus

<400> SEQUENCE: 33

Pro Lys Gln Lys Lys Arg Lys
1               5

<210> SEQ ID NO 34
<211> LENGTH: 10
<212> TYPE: PRT
<213> ORGANISM: Hepatitis delta virus

<400> SEQUENCE: 34

Arg Lys Leu Lys Lys Lys Ile Lys Lys Leu
1               5                   10

<210> SEQ ID NO 35
<211> LENGTH: 10
<212> TYPE: PRT
<213> ORGANISM: Mus musculus

<400> SEQUENCE: 35

Arg Glu Lys Lys Lys Phe Leu Lys Arg Arg
1               5                   10

<210> SEQ ID NO 36
<211> LENGTH: 20
<212> TYPE: PRT
<213> ORGANISM: Homo sapiens

<400> SEQUENCE: 36

Lys Arg Lys Gly Asp Glu Val Asp Gly Val Asp Glu Val Ala Lys Lys
1               5                   10                  15

Lys Ser Lys Lys
            20

<210> SEQ ID NO 37
<211> LENGTH: 17
<212> TYPE: PRT
<213> ORGANISM: Homo sapiens

<400> SEQUENCE: 37

Arg Lys Cys Leu Gln Ala Gly Met Asn Leu Glu Ala Arg Lys Thr Lys
1               5                   10                  15

Lys

<210> SEQ ID NO 38
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
```
guuuuagagc ua                                                                     12

<210> SEQ ID NO 39
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gly Gly Gly Ser
1

<210> SEQ ID NO 40
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gly Gly Gly Ser Gly Gly Gly Ser Gly Gly Gly Ser
1               5                   10

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ala Glu Ala Ala Ala Lys Ala
1               5

<210> SEQ ID NO 42
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
aatgatacgg cgaccaccga gatctacact ctttccctac acgacgctct tccgatctta      60
agtagagtct tgtggaaagg acgaaacacc g                                    91

<210> SEQ ID NO 43
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
caagcagaag acggcatacg agataagtag aggtgactgg agttcagacg tgtgctcttc      60
cgatctttct actattcttt cccctcactg t                                    91

<210> SEQ ID NO 44
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
cccgagggga cccagagag                                              19

<210> SEQ ID NO 45
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
gcgcaccgtg ggcttgtac                                              19

<210> SEQ ID NO 46
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
aatgatacgg cgaccaccga gatctacact ctttccctac acgacgctct tccgatctta      60
agtagagtct tgtggaaagg acgaaacacc g                                    91

<210> SEQ ID NO 47
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
aatgatacgg cgaccaccga gatctacact ctttccctac acgacgctct tccgatctat      60
acacgatctc ttgtggaaag gacgaaacac cg                                   92

<210> SEQ ID NO 48
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
aatgatacgg cgaccaccga gatctacact ctttccctac acgacgctct tccgatctga      60
tcgcgcggtt cttgtggaaa ggacgaaaca ccg                                  93

<210> SEQ ID NO 49
<211> LENGTH: 94

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
aatgatacgg cgaccaccga gatctacact cttccctac acgacgctct tccgatctcg   60
atcatgatcg tcttgtggaa aggacgaaac accg                              94

<210> SEQ ID NO 50
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
aatgatacgg cgaccaccga gatctacact ctttccctac acgacgctct tccgatcttc   60
gatcgttacc atcttgtgga aaggacgaaa caccg                             95

<210> SEQ ID NO 51
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
aatgatacgg cgaccaccga gatctacact ctttccctac acgacgctct tccgatctat   60
cgattccttg gttcttgtgg aaaggacgaa acaccg                            96

<210> SEQ ID NO 52
<211> LENGTH: 97
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
aatgatacgg cgaccaccga gatctacact ctttccctac acgacgctct tccgatctga   60
tcgataacgc atttcttgtg gaaaggacga acaccg                            97

<210> SEQ ID NO 53
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
aatgatacgg cgaccaccga gatctacact ctttccctac acgacgctct tccgatctcg   60
atcgatacag gtattcttgt ggaaaggacg aaacaccg                          98

<210> SEQ ID NO 54
```

```
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
aatgatacgg cgaccaccga gatctacact ctttccctac acgacgctct tccgatctac    60
gatcgatagg taaggtcttg tggaaaggac gaaacaccg                           99

<210> SEQ ID NO 55
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
aatgatacgg cgaccaccga gatctacact ctttccctac acgacgctct tccgatctta    60
acaatggtct tgtggaaagg acgaaacacc g                                   91

<210> SEQ ID NO 56
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
aatgatacgg cgaccaccga gatctacact ctttccctac acgacgctct tccgatctat    60
actgtatctc ttgtggaaag gacgaaacac cg                                  92

<210> SEQ ID NO 57
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
aatgatacgg cgaccaccga gatctacact ctttccctac acgacgctct tccgatctga    60
taggtcgcat cttgtggaaa ggacgaaaca ccg                                 93

<210> SEQ ID NO 58
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
caagcagaag acggcatacg agataagtag aggtgactgg agttcagacg tgtgctcttc    60
cgatctttct actattcttt cccctgcact gt                                  92
```

```
<210> SEQ ID NO 59
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59
caagcagaag acggcatacg agatacacga tcgtgactgg agttcagacg tgtgctcttc    60
cgatctattc tactattctt tccccctgcac tgt                                93

<210> SEQ ID NO 60
<211> LENGTH: 94
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
caagcagaag acggcatacg agatcgcgcg gtgtgactgg agttcagacg tgtgctcttc    60
cgatctgatt ctactattct ttccccctgca ctgt                               94

<210> SEQ ID NO 61
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
caagcagaag acggcatacg agatcatgat cggtgactgg agttcagacg tgtgctcttc    60
cgatctcgat tctactattc tttccccctgc actgt                              95

<210> SEQ ID NO 62
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
caagcagaag acggcatacg agatcgttac cagtgactgg agttcagacg tgtgctcttc    60
cgatctcgat ctctactatt ctttccccctg cactgt                             96

<210> SEQ ID NO 63
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
caagcagaag acggcatacg agattccttg gtgtgactgg agttcagacg tgtgctcttc    60
cgatctttct actattcttt ccccctgcact gt                                 92
```

```
<210> SEQ ID NO 64
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
aatgatacgg cgaccaccga gatctacact ctttccctac acgacgctct tccgatctta      60
agtagagtct tgtggaaagg acgaaacacc g                                    91

<210> SEQ ID NO 65
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
aatgatacgg cgaccaccga gatctacact ctttccctac acgacgctct tccgatctat      60
acacgatctc ttgtggaaag gacgaaacac cg                                   92

<210> SEQ ID NO 66
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
caagcagaag acggcatacg agataacgca ttgtgactgg agttcagacg tgtgctcttc      60
cgatctattc tactattctt tccctgcac tgt                                   93

<210> SEQ ID NO 67
<211> LENGTH: 94
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
caagcagaag acggcatacg agatacaggt atgtgactgg agttcagacg tgtgctcttc      60
cgatctgatt ctactattct ttcccctgca ctgt                                 94

<210> SEQ ID NO 68
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
caagcagaag acggcatacg agataggtaa gggtgactgg agttcagacg tgtgctcttc      60
cgatctcgat tctactattc ttttcccctgc actgt                                95
```

```
<210> SEQ ID NO 69
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
caagcagaag acggcatacg agataacaat gggtgactgg agttcagacg tgtgctcttc    60
cgatctcgat ctctactatt ctttcccctg cactgt                              96

<210> SEQ ID NO 70
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
caagcagaag acggcatacg agatactgta tcgtgactgg agttcagacg tgtgctcttc    60
cgatctttct actattcttt ccctgcact gt                                   92

<210> SEQ ID NO 71
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
caagcagaag acggcatacg agataggtcg cagtgactgg agttcagacg tgtgctcttc    60
cgatctattc tactattctt tcccctgcac tgt                                 93

<210> SEQ ID NO 72
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 72
gatccgcacc gtgaatgtct ngg                                            23

<210> SEQ ID NO 73
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
```

```
<223> OTHER INFORMATION: a, c, t, g, unknown or other

<400> SEQUENCE: 73
gaagctcatg cgagaagcga ngg                                          23

<210> SEQ ID NO 74
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 74
cttggcgtca tatgctgtcc ngg                                          23

<210> SEQ ID NO 75
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 75
cactggggct tcgggaaacc ngg                                          23

<210> SEQ ID NO 76
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 76
tggactgcag tatacaatca ngg                                          23

<210> SEQ ID NO 77
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 77
gttggatcat gatgtttcga ngg                                          23
```

-continued

```
<210> SEQ ID NO 78
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 78
accgccaaat ttaactgcag ngg                                           23

<210> SEQ ID NO 79
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 79
gcagcaattc actgtaaagc ngg                                           23

<210> SEQ ID NO 80
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 80
tgtcatcttc acttagccat ngg                                           23

<210> SEQ ID NO 81
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 81
acaatattga tgatgtagta ngg                                           23

<210> SEQ ID NO 82
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 82
catacctctg cagttaaatt ngg                                            23

<210> SEQ ID NO 83
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 83
aatcccatag caataatatt ngg                                            23

<210> SEQ ID NO 84
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 84
gcttgacagc tcccgacgca ngg                                            23

<210> SEQ ID NO 85
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 85
atgctggggt tgccttgcgt ngg                                            23

<210> SEQ ID NO 86
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 86
```
atgttccggg ctctgatgcc ngg                                              23

<210> SEQ ID NO 87
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 87
gcgcaaggag aagactgtag ngg                                              23

<210> SEQ ID NO 88
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 88
cctgtcagag tcaccaccac ngg                                              23

<210> SEQ ID NO 89
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 89
ttgctcacct gctggttacc ngg                                              23

<210> SEQ ID NO 90
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 90
gtgcgatatt tgcgttccgc ngg                                              23

<210> SEQ ID NO 91
<211> LENGTH: 23
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 91
cccaacgccc cgaactcttt ngg                                          23

<210> SEQ ID NO 92
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 92
ggggtacgac cgaaagagtt ngg                                          23

<210> SEQ ID NO 93
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 93
ggctggatgt gcgcgatgcc ngg                                          23

<210> SEQ ID NO 94
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 94
tcgtgcgatc ccggagaccc ngg                                          23

<210> SEQ ID NO 95
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
```

<222> LOCATION: (21)..(21)
<223> OTHER INFORMATION: a, c, t, g, unknown or other

<400> SEQUENCE: 95
ccgcaccgga atcctggacc ngg                                                23

<210> SEQ ID NO 96
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 96
agaggggcga ttacccgggc ngg                                                23

<210> SEQ ID NO 97
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 97
tgtagaacca ccgcgactca ngg                                                23

<210> SEQ ID NO 98
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 98
aaggaggtga gcctctccgc ngg                                                23

<210> SEQ ID NO 99
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 99
cttacgcccc agattgaaca ngg                                                23

<210> SEQ ID NO 100
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 100
gacagactca cgctccgctc ngg                                              23

<210> SEQ ID NO 101
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 101
aagaaggctt ccagggccga ngg                                              23

<210> SEQ ID NO 102
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 102
gttgattgac gaagccaacc ngg                                              23

<210> SEQ ID NO 103
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 103
gttgatagac atgaagcgcc ngg                                              23

<210> SEQ ID NO 104
<211> LENGTH: 23
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 104
agtacgtggc ccaagagttg ngg                                              23

<210> SEQ ID NO 105
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 105
ggcgcagaat tgagatcctg ngg                                              23

<210> SEQ ID NO 106
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 106
cacctgcctc atcttgagcg ngg                                              23

<210> SEQ ID NO 107
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 107
actacagata ccgaagataa ngg                                              23

<210> SEQ ID NO 108
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other
```

-continued

```
<400> SEQUENCE: 108
gctactgggc cctgaactag ngg                                          23

<210> SEQ ID NO 109
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 109
ccagtgcttg tggtggctac ngg                                          23

<210> SEQ ID NO 110
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 110
gacccctagt ccagtgcttg ngg                                          23

<210> SEQ ID NO 111
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 111
tgaagccgac acccaagtcc ngg                                          23

<210> SEQ ID NO 112
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 112
agtcagtgca tgacagaact ngg                                          23

<210> SEQ ID NO 113
<211> LENGTH: 23
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 113
atacactccg actcgggctc ngg                                           23

<210> SEQ ID NO 114
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 114
ttctgtgata cactccgact ngg                                           23

<210> SEQ ID NO 115
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 115
cgccgctgtt ccccgggcct ngg                                           23

<210> SEQ ID NO 116
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 116
gcgaggtatt cggctccgcg ngg                                           23

<210> SEQ ID NO 117
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: modified_base
<222> LOCATION: (21)..(21)
<223> OTHER INFORMATION: a, c, t, g, unknown or other

<400> SEQUENCE: 117
gctttcacgg aggttcgacg ngg                                              23

<210> SEQ ID NO 118
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 118
atgttgcagt tcggctcgat ngg                                              23

<210> SEQ ID NO 119
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: a, c, t, g, unknown or other

<400> SEQUENCE: 119
acgtgtaagg cgaacgcctt ngg                                              23

<210> SEQ ID NO 120
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
taccagcgca ttgccgaaaa                                                  20

<210> SEQ ID NO 121
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
gaactccccc ggcggccgga                                                  20

<210> SEQ ID NO 122
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 122
acttccgccg tgcctttcga                                                20

<210> SEQ ID NO 123
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
tggcaattac atagattcgc                                                20

<210> SEQ ID NO 124
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
agaagagcac gtctagcgcc                                                20

<210> SEQ ID NO 125
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
ccggcaaagg atccttcgaa                                                20

<210> SEQ ID NO 126
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
ccaatagccc agcagctcgt                                                20

<210> SEQ ID NO 127
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
aatgaccacc gccagcacaa                                                20

<210> SEQ ID NO 128
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
ggacatgtcc ggccccgcca                                              20

<210> SEQ ID NO 129
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
agcaaaaaaa gatccgatgc                                              20

<210> SEQ ID NO 130
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
gtcgatcttg ccgctgtgcg                                              20

<210> SEQ ID NO 131
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
ccgagcttcc atccgcctct                                              20

<210> SEQ ID NO 132
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
ccctaacagg tctagactcc                                              20

<210> SEQ ID NO 133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
```

```
agctgacctc gctgaagggc                                               20

<210> SEQ ID NO 134
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
ccggcagctt cccctgtttc                                               20

<210> SEQ ID NO 135
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
cacactccac cacttcagcc                                               20

<210> SEQ ID NO 136
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
cgggcagaga gtggtcattg                                               20

<210> SEQ ID NO 137
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
cacaatgacc actctctgcc                                               20

<210> SEQ ID NO 138
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
ctcgcccctc ttgaaagacc                                               20

<210> SEQ ID NO 139
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 139
gcgtgggctg tgtgctcatc                                               20

<210> SEQ ID NO 140
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
ggagccaaag tacgctactg                                               20

<210> SEQ ID NO 141
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
tgccaccgat tcttgtatca                                               20

<210> SEQ ID NO 142
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
tcattgctct gcgacatttc                                               20

<210> SEQ ID NO 143
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
aaatttacga aaaagcctat                                               20

<210> SEQ ID NO 144
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
tctagatcaa tgatgatgtt                                               20
```

```
<210> SEQ ID NO 145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
caaccattcc cagaagtatc                                                  20

<210> SEQ ID NO 146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
cacttaagaa caaatacttg                                                  20

<210> SEQ ID NO 147
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
cagtgctgtc ttaaagactt                                                  20

<210> SEQ ID NO 148
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
gagtagatta tgaacgcctc                                                  20

<210> SEQ ID NO 149
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
tatagtcgtg tagccacttc                                                  20

<210> SEQ ID NO 150
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 150
tagtgaatga cgactccgcc                                              20

<210> SEQ ID NO 151
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
acgccgtctc caggtcatac                                              20

<210> SEQ ID NO 152
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
caagagccac gaatttgcac                                              20

<210> SEQ ID NO 153
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
tatgtttcag atcatctgtc                                              20

<210> SEQ ID NO 154
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
gcagagctca cgtgggtcag                                              20

<210> SEQ ID NO 155
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
ggagatgtct gtgccaaagc                                              20

<210> SEQ ID NO 156
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 156
gcactcacat gaggctgaag                                               20

<210> SEQ ID NO 157
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
ctacaaccag tgcaaattcg                                               20

<210> SEQ ID NO 158
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
ctgcagctgc ctgtatgacc                                               20

<210> SEQ ID NO 159
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
ccattaaagg actccagctt                                               20

<210> SEQ ID NO 160
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
ggtccatctc atcgcctatt                                               20

<210> SEQ ID NO 161
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
gccagacatc tcgcccaaat                                               20
```

<210> SEQ ID NO 162
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
ccttaggtca gcaacggttc                                           20

<210> SEQ ID NO 163
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
ctgtgatgtg ctcggccccc                                           20

<210> SEQ ID NO 164
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
taataaagtt gacagtcgtg                                           20

<210> SEQ ID NO 165
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
tctaaccaag ttcctcacat                                           20

<210> SEQ ID NO 166
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
ctttcttagg agatggactg                                           20

<210> SEQ ID NO 167
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 167
ctgtctgcag ctcgtcttcg                                          20

<210> SEQ ID NO 168
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
ctagccgcac agttcatgaa                                          20

<210> SEQ ID NO 169
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
tcatacttac ttcctccgac                                          20

<210> SEQ ID NO 170
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
atgccgcggc gaacttcttg                                          20

<210> SEQ ID NO 171
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
atatgctaga tctgtaccgc                                          20

<210> SEQ ID NO 172
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
gatcaaacta gaagccgtgg                                          20

<210> SEQ ID NO 173
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
ttaaattgaa gaagaagcgc                                               20

<210> SEQ ID NO 174
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
gggcaccacg acgtccttgc                                               20

<210> SEQ ID NO 175
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
gtcttccgaa ggccgggaca                                               20

<210> SEQ ID NO 176
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
gcggtacaga tctagcatat                                               20

<210> SEQ ID NO 177
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
tggtctgggg cgggcgctcc                                               20

<210> SEQ ID NO 178
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gtgcgcagct tccatcacga                                               20
```

```
<210> SEQ ID NO 179
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
ttcgtgatgg aagctgcgca                                               20

<210> SEQ ID NO 180
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
gtgcgatatt tgcgttccgc                                               20

<210> SEQ ID NO 181
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
cccaacgccc cgaactcttt                                               20

<210> SEQ ID NO 182
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
ggggtacgac cgaaagagtt                                               20

<210> SEQ ID NO 183
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
ggctggatgt gcgcgatgcc                                               20

<210> SEQ ID NO 184
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 184
tcgtgcgatc ccggagaccc                                               20

<210> SEQ ID NO 185
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
ccgcaccgga atcctggacc                                               20

<210> SEQ ID NO 186
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
gccggattta gctctgctct                                               20

<210> SEQ ID NO 187
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
tgcagggccc tggaacttcg                                               20

<210> SEQ ID NO 188
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
gggaacgtcg cccagaccga                                               20

<210> SEQ ID NO 189
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
agggccgtgt gcatgacgtg                                               20

<210> SEQ ID NO 190
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
agaggggcga ttacccgggc                                               20

<210> SEQ ID NO 191
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
tgtagaacca ccgcgactca                                               20

<210> SEQ ID NO 192
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
aaggaggtga gcctctccgc                                               20

<210> SEQ ID NO 193
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
cttacgcccc agattgaaca                                               20

<210> SEQ ID NO 194
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
gacagactca cgctccgctc                                               20

<210> SEQ ID NO 195
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
```
aagaaggctt ccagggccga                                            20

<210> SEQ ID NO 196
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
ttctgcgcac actctgcacc                                            20

<210> SEQ ID NO 197
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
agtgcttgta gtcacctgag                                            20

<210> SEQ ID NO 198
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
ccaaggacag caatatgtgc                                            20

<210> SEQ ID NO 199
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
agatggtcag ccttgagtcg                                            20

<210> SEQ ID NO 200
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
ttgtcttctc tgcgcaattt                                            20

<210> SEQ ID NO 201
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 201
cccaccagcc tgagtagtga                                              20

<210> SEQ ID NO 202
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
gtgcccatct ttgagcatct                                              20

<210> SEQ ID NO 203
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
ggttgtgatc aacagaatga                                              20

<210> SEQ ID NO 204
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
ataacctgtt gactgaaaac                                              20

<210> SEQ ID NO 205
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
tgaaggactt ctgactttgc                                              20

<210> SEQ ID NO 206
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
gatagtttga cagaactctc                                              20

<210> SEQ ID NO 207
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
gtactttcag catcctgatg                                               20

<210> SEQ ID NO 208
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
ggtatgatct ttgcaccta                                                20

<210> SEQ ID NO 209
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
ctgtgatgcc ttcactactc                                               20

<210> SEQ ID NO 210
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
gtttaacgtc tctggtagat                                               20

<210> SEQ ID NO 211
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
aatattggca ggtcgtccat                                               20

<210> SEQ ID NO 212
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
```
ctgtatcgtt attccatctc                                         20

<210> SEQ ID NO 213
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
aaacacgact cagaatacgc                                         20

<210> SEQ ID NO 214
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
aacgactcgt aatcttcttg                                         20

<210> SEQ ID NO 215
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
cgtacgcacc ttctcagctg                                         20

<210> SEQ ID NO 216
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
cttatgctat aaaaagtcag                                         20

<210> SEQ ID NO 217
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
tctctcctag tggggatctg                                         20

<210> SEQ ID NO 218
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 218
cattcaatag ttgcccccat                                                     20

<210> SEQ ID NO 219
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
agagggtatt tgctatctgg                                                     20

<210> SEQ ID NO 220
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
atcgtcgtag ccaccgttat                                                     20

<210> SEQ ID NO 221
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
ggttgcactt caccgcgctc                                                     20

<210> SEQ ID NO 222
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
cgccgttacc tccgctgctg                                                     20

<210> SEQ ID NO 223
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
cgtccttcct cccgcgatcg                                                     20
```

```
<210> SEQ ID NO 224
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
gttgctgaat gtgtccgaat                                           20

<210> SEQ ID NO 225
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
cctacttaca tttagccttc                                           20

<210> SEQ ID NO 226
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
gggcgaactt ccgaaccaac                                           20

<210> SEQ ID NO 227
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
gcaccaccct cccgtccgtc                                           20

<210> SEQ ID NO 228
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
acagcacccc gatcgacata                                           20

<210> SEQ ID NO 229
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 229
tctcctcggc cgcctggcga                                              20

<210> SEQ ID NO 230
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
ctcacgttgc acaccgctct                                              20

<210> SEQ ID NO 231
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
agtagtcggg tcctttgttc                                              20

<210> SEQ ID NO 232
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
caggggcacc gccgacgtga                                              20

<210> SEQ ID NO 233
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
acccgactac ttccgcaggc                                              20

<210> SEQ ID NO 234
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
ctcctggctc ttgacgtatt                                              20

<210> SEQ ID NO 235
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 235
ggctttaagg ggcttcacac                                             20

<210> SEQ ID NO 236
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
acaagcatag ctcccgaaac                                             20

<210> SEQ ID NO 237
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
caactactgc ggacttgacc                                             20

<210> SEQ ID NO 238
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
agagcagctc ccacgtgagc                                             20

<210> SEQ ID NO 239
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
agctgatcat gcttgcgctg                                             20

<210> SEQ ID NO 240
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
gttgattgac gaagccaacc                                             20
```

<210> SEQ ID NO 241
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
gttgatagac atgaagcgcc                                          20

<210> SEQ ID NO 242
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
agtacgtggc ccaagagttg                                          20

<210> SEQ ID NO 243
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
ggcgcagaat tgagatcctg                                          20

<210> SEQ ID NO 244
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
cacctgcctc atcttgagcg                                          20

<210> SEQ ID NO 245
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
actacagata ccgaagataa                                          20

<210> SEQ ID NO 246
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
agcacatacc cagactgtgc                                               20

<210> SEQ ID NO 247
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
caaatactcc atgatattcc                                               20

<210> SEQ ID NO 248
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
ccttctgctc tgatgatgac                                               20

<210> SEQ ID NO 249
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
aggattctaa ctcactgacc                                               20

<210> SEQ ID NO 250
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
aaatgtcaaa gatgcgatcg                                               20

<210> SEQ ID NO 251
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
attgtgcaca gtcgatcagc                                               20

<210> SEQ ID NO 252
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
ggttgaagcc attgacgtgc                                                 20

<210> SEQ ID NO 253
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
ctcgttggat ctctcaaagc                                                 20

<210> SEQ ID NO 254
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
ccaaccctga gaaccagttc                                                 20

<210> SEQ ID NO 255
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
cactgacttt gaatattccc                                                 20

<210> SEQ ID NO 256
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
ttcacagggg ctggtgagtc                                                 20

<210> SEQ ID NO 257
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
ggaaaagaag cagaaaattc                                                 20
```

<210> SEQ ID NO 258
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 258
tgctcttgat ataatctgac                                               20

<210> SEQ ID NO 259
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 259
gaatattcaa agtcagtgat                                               20

<210> SEQ ID NO 260
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 260
caccagcctc gagtgcccga                                               20

<210> SEQ ID NO 261
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 261
cacatgccac acgtgttcgc                                               20

<210> SEQ ID NO 262
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 262
ctggccgccc cacatgttgc                                               20

<210> SEQ ID NO 263
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 263
acaggtacaa gagaactcgc                                       20

<210> SEQ ID NO 264
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
ttatacacca tcagcttcag                                       20

<210> SEQ ID NO 265
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
ccaactatgt agtctgtgta                                       20

<210> SEQ ID NO 266
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
tactctcatt gagtcccatg                                       20

<210> SEQ ID NO 267
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
ccttacacag actacatagt                                       20

<210> SEQ ID NO 268
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
gaagctacag aagcgcacgc                                       20

<210> SEQ ID NO 269
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
tgcgcttctg tagcttccgc                                              20

<210> SEQ ID NO 270
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
tcttatcacc gtcaccctca                                              20

<210> SEQ ID NO 271
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
cgagaacaac cctacagtca                                              20

<210> SEQ ID NO 272
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
ctcctatcca gggcattcct                                              20

<210> SEQ ID NO 273
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
tgagaggccc ctgcctgtag                                              20

<210> SEQ ID NO 274
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
```

```
ggtggagccc gaagcccatg                                           20

<210> SEQ ID NO 275
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
tctcatgatc tctgacgccc                                           20

<210> SEQ ID NO 276
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
gggtcccaaa aaaaaagact                                           20

<210> SEQ ID NO 277
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
ccagattgat gagatgcctg                                           20

<210> SEQ ID NO 278
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
cagcgacgaa gaagggaaac                                           20

<210> SEQ ID NO 279
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
ctgttcttct ccacctctac                                           20

<210> SEQ ID NO 280
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 280
cttaagtact ctcgaacctg                                               20

<210> SEQ ID NO 281
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
ttacgtatta ccagtctgtc                                               20

<210> SEQ ID NO 282
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
ctggaccaat tgtgccaaa                                                20

<210> SEQ ID NO 283
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
atgtgttgca ccaatgcaac                                               20

<210> SEQ ID NO 284
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
aggctcatcc aagcaattgg                                               20

<210> SEQ ID NO 285
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
aaaaaagaac tctgcccgtt                                               20

<210> SEQ ID NO 286
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
atgaaaagaa actatcgtgc                                                      20

<210> SEQ ID NO 287
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
caagctctgc taatagtaac                                                      20

<210> SEQ ID NO 288
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
ttcaatcagc agcgagcgaa                                                      20

<210> SEQ ID NO 289
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
cgtgttaacc aaccagcaga                                                      20

<210> SEQ ID NO 290
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
agcatccgtg cgagctccac                                                      20

<210> SEQ ID NO 291
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
```
atgatgttgt caagcccgag                                               20

<210> SEQ ID NO 292
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
ccatttattc acaatgcgtt                                               20

<210> SEQ ID NO 293
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
attagtccac tgacgtactc                                               20

<210> SEQ ID NO 294
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
tacaactata ccgaccagtt                                               20

<210> SEQ ID NO 295
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
acttagaatg tcgttattcc                                               20

<210> SEQ ID NO 296
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
agacaaaaac atgcgtgccg                                               20

<210> SEQ ID NO 297
<211> LENGTH: 20
<212> TYPE: DNA
<213> ORGANISM: Artificial Sequence
<220> FEATURE:

```
-continued

<221> NAME/KEY: source
<223> OTHER INFORMATION: /note="Description of Artificial Sequence:
      Synthetic oligonucleotide"

<400> SEQUENCE: 297
taatctcgtg gcttcaattc                                               20

<210> SEQ ID NO 298
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
attaaaccag agtacgtcag                                               20

<210> SEQ ID NO 299
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
tgaattagac gtcctaattg                                               20

<210> SEQ ID NO 300
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
tcttacgtgg catgatgccc                                               20

<210> SEQ ID NO 301
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
gcctcatttg ccactagtct                                               20

<210> SEQ ID NO 302
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
cccaagacta gtggcaaatg                                               20
```

```
<210> SEQ ID NO 303
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
ttaacaggaa gtatagtctt                                              20

<210> SEQ ID NO 304
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
tcctttgttg cagcctcagc                                              20

<210> SEQ ID NO 305
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
cctgtgctca cagactgagc                                              20

<210> SEQ ID NO 306
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
gaagccttgt ggctgcttct                                              20

<210> SEQ ID NO 307
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
tcctcagcag ttaaaatttc                                              20

<210> SEQ ID NO 308
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 308
ggctgcattt agaacctgcc                                               20

<210> SEQ ID NO 309
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
aggttctaaa tgcagcctgc                                               20

<210> SEQ ID NO 310
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
cctctccaga gtcgctccaa                                               20

<210> SEQ ID NO 311
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
gctctccgag aggtacctct                                               20

<210> SEQ ID NO 312
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
cttccctgcg gatctgccgc                                               20

<210> SEQ ID NO 313
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
cctctaagat tcgtctccat                                               20

<210> SEQ ID NO 314
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 314
aacaatccgt attcctcctt                                               20

<210> SEQ ID NO 315
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
cctctatctt ccccgccagc                                               20

<210> SEQ ID NO 316
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
tccaccaggc atgggacccc                                               20

<210> SEQ ID NO 317
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
caaatgtacc ccaagaaacc                                               20

<210> SEQ ID NO 318
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
tatcgtcatc cgcctctgtg                                               20

<210> SEQ ID NO 319
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
ccgggagatg ctgttaaagc                                               20
```

```
<210> SEQ ID NO 320
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
ctacaggcca ctcgcgctct                                              20

<210> SEQ ID NO 321
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
catctctcca agagcgcgag                                              20

<210> SEQ ID NO 322
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
gcccgtttac tcgctgattc                                              20

<210> SEQ ID NO 323
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
ccggtccggg ggtagcgaac                                              20

<210> SEQ ID NO 324
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
tatacaacgc aaggtctgca                                              20

<210> SEQ ID NO 325
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 325
tgtggcggct cccgagtctg                                               20

<210> SEQ ID NO 326
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
gcagcccacg caccagaccg                                               20

<210> SEQ ID NO 327
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
ggctggctat gccgggaccc                                               20

<210> SEQ ID NO 328
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
tttgggagcc ttcccaccga                                               20

<210> SEQ ID NO 329
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
agccggaatc agcgagtaaa                                               20

<210> SEQ ID NO 330
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
ccacggcgcg atggagtcgc                                               20

<210> SEQ ID NO 331
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
cccgtctgac atctcgccaa                                          20

<210> SEQ ID NO 332
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
actccgactc tatgacatgt                                          20

<210> SEQ ID NO 333
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
gccacgcgct cggactggct                                          20

<210> SEQ ID NO 334
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
gccacccact gaagaacctg                                          20

<210> SEQ ID NO 335
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
tgctcaccgt cttcttcctc                                          20

<210> SEQ ID NO 336
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
tggcttcccc tcagctgccc                                          20
```

```
<210> SEQ ID NO 337
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
gatgatgacc aaagaagaac                                                  20

<210> SEQ ID NO 338
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
cgccagcgcc gtgaccagcg                                                  20

<210> SEQ ID NO 339
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
accgagccag tccgagcgcg                                                  20

<210> SEQ ID NO 340
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
gatccgcacc gtgaatgtct                                                  20

<210> SEQ ID NO 341
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
gaagctcatg cgagaagcga                                                  20

<210> SEQ ID NO 342
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 342
cttggcgtca tatgctgtcc                                        20

<210> SEQ ID NO 343
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
cactggggct tcgggaaacc                                        20

<210> SEQ ID NO 344
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
tggactgcag tatacaatca                                        20

<210> SEQ ID NO 345
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
gttggatcat gatgtttcga                                        20

<210> SEQ ID NO 346
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
aaaggtctac tgccctcccg                                        20

<210> SEQ ID NO 347
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
accagttacc tttcacttcc                                        20

<210> SEQ ID NO 348
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
cgtcaccatg gacgccgaga                                           20

<210> SEQ ID NO 349
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
agcccaagac attcacggtg                                           20

<210> SEQ ID NO 350
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
ctggggcgtg ctaagccgaa                                           20

<210> SEQ ID NO 351
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
gttacaccgc ctcgtggtga                                           20

<210> SEQ ID NO 352
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
gtaggtaggc cgctcgaatt                                           20

<210> SEQ ID NO 353
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
```
cgccattggg gccggcgtca                                              20

<210> SEQ ID NO 354
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
gccccgacca tcgagatccg                                              20

<210> SEQ ID NO 355
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
cgtggcaagc ccctcgcta                                               20

<210> SEQ ID NO 356
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
cagtactagt gcgctactgc                                              20

<210> SEQ ID NO 357
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
cgtgtagtca atctccgcat                                              20

<210> SEQ ID NO 358
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
gcgtgtccag gctatggacg                                              20

<210> SEQ ID NO 359
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 359
cccctggata ttgacatcgc                                              20

<210> SEQ ID NO 360
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
atcgcagagg tgcccataat                                              20

<210> SEQ ID NO 361
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
agacactaac cggaataacc                                              20

<210> SEQ ID NO 362
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
gtagggtggc caattccatt                                              20

<210> SEQ ID NO 363
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
gcgcgatgaa ttcatcatga                                              20

<210> SEQ ID NO 364
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
gtcaatctga acccagtcga                                              20

<210> SEQ ID NO 365
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
ccacaatgtc atcactagtg                                              20

<210> SEQ ID NO 366
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
cctcactagt gatgacattg                                              20

<210> SEQ ID NO 367
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
gttctgccct gagtgttctg                                              20

<210> SEQ ID NO 368
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
tgcgatgaag accctccgaa                                              20

<210> SEQ ID NO 369
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
tcagattgac gccaactcct                                              20

<210> SEQ ID NO 370
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
```

```
ctattgacaa cgccatcgat                                              20

<210> SEQ ID NO 371
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
cttaccaggg ttccaatcga                                              20

<210> SEQ ID NO 372
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
gtgagctcaa gattcgagtg                                              20

<210> SEQ ID NO 373
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
ccctaagagc acagacgata                                              20

<210> SEQ ID NO 374
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
cactcgaatc ttgagctcac                                              20

<210> SEQ ID NO 375
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
ccaccattat ccttcccaag                                              20

<210> SEQ ID NO 376
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 376
ggcagctccc ctacttcatc                                              20

<210> SEQ ID NO 377
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
agaggagggg gagtatgtcc                                              20

<210> SEQ ID NO 378
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
ggagacgata cagaaactag                                              20

<210> SEQ ID NO 379
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
tccttatcgt ctgtgctctt                                              20

<210> SEQ ID NO 380
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
cacttcttga tacgctggat                                              20

<210> SEQ ID NO 381
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
tgtgccatag tcaattcgtg                                              20
```

```
<210> SEQ ID NO 382
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
ctcagagact ttgtagtcga                                            20

<210> SEQ ID NO 383
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
cgcttccatt tgcccatatc                                            20

<210> SEQ ID NO 384
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
gattgatgaa accccgccag                                            20

<210> SEQ ID NO 385
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
aactccacac gaattgacta                                            20

<210> SEQ ID NO 386
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
taggcatatg ctgactacat                                            20

<210> SEQ ID NO 387
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 387
atgataaagt tctgagtagt                                                20

<210> SEQ ID NO 388
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
ttcacaggcc atcgagaagc                                                20

<210> SEQ ID NO 389
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
cagtctcacc tgatcaagtt                                                20

<210> SEQ ID NO 390
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
accgccaaat ttaactgcag                                                20

<210> SEQ ID NO 391
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
gcagcaattc actgtaaagc                                                20

<210> SEQ ID NO 392
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
tgtcatcttc acttagccat                                                20

<210> SEQ ID NO 393
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 393
acaatattga tgatgtagta                                              20

<210> SEQ ID NO 394
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
catacctctg cagttaaatt                                              20

<210> SEQ ID NO 395
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
aatcccatag caataatatt                                              20

<210> SEQ ID NO 396
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
acagattgta tatcttgtaa                                              20

<210> SEQ ID NO 397
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
ggtttgataa gttctagctg                                              20

<210> SEQ ID NO 398
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
tctgtgaaga tcttgaccaa                                              20
```

```
<210> SEQ ID NO 399
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
ttatccaaat attattgcta                                               20

<210> SEQ ID NO 400
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
cgtgtaccga acacccgctg                                               20

<210> SEQ ID NO 401
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
cttcgactac attgtccgtg                                               20

<210> SEQ ID NO 402
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
cacttattac ccacccatga                                               20

<210> SEQ ID NO 403
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
tagtgccctc aagacctacc                                               20

<210> SEQ ID NO 404
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 404
agaagggaca tgtcttgtac                                              20

<210> SEQ ID NO 405
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
ccagtacttg ttgcaaaact                                              20

<210> SEQ ID NO 406
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
gagtgactta ccctgaaacc                                              20

<210> SEQ ID NO 407
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
tggaggtgaa tcccgtgaga                                              20

<210> SEQ ID NO 408
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
agcgggtgtt cggtacacgt                                              20

<210> SEQ ID NO 409
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
ggcagccgcg cccacatact                                              20

<210> SEQ ID NO 410
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
acccgtattc tcgtacaccg                                              20

<210> SEQ ID NO 411
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
acccacggtg tacgagaata                                              20

<210> SEQ ID NO 412
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
cccttctatg gcattgatgc                                              20

<210> SEQ ID NO 413
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
acgacgcctt cagaagtatc                                              20

<210> SEQ ID NO 414
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
gagcaaccta ccctgtaccc                                              20

<210> SEQ ID NO 415
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415 cagggggccgg atacttctga                                             20
```

```
<210> SEQ ID NO 416
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
gagctcaatc aagtgcgtgc                                              20

<210> SEQ ID NO 417
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
gtcctaccag caggcagacg                                              20

<210> SEQ ID NO 418
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
tcctgcatca atgccataga                                              20

<210> SEQ ID NO 419
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
caaatacctg ctgtactccc                                              20

<210> SEQ ID NO 420
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
cgagtcgtca tcactctcgt                                              20

<210> SEQ ID NO 421
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 421
cgactcgagc accagcgacg                                               20

<210> SEQ ID NO 422
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
atgctgagaa atattccgcc                                               20

<210> SEQ ID NO 423
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
cctctgcttc gctctccgat                                               20

<210> SEQ ID NO 424
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
aagaactttg aatgtgcctg                                               20

<210> SEQ ID NO 425
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
ctgaccttca ctttgacctc                                               20

<210> SEQ ID NO 426
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
atggcggtcc acggcgacga                                               20

<210> SEQ ID NO 427
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
cgacctgcca ctgtgcgaag                                               20

<210> SEQ ID NO 428
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
atctgaagta tcctcgtcgc                                               20

<210> SEQ ID NO 429
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
catgttcgcc gtcgtcgccg                                               20

<210> SEQ ID NO 430
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
agccaatccc tctgacgcag                                               20

<210> SEQ ID NO 431
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
tggggaaata tcaatgctaa                                               20

<210> SEQ ID NO 432
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
```
ctcactctgg gctctgcatg                                              20

<210> SEQ ID NO 433
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
catgctgctg ttgctgactt                                              20

<210> SEQ ID NO 434
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
acttgccagc agcattcccc                                              20

<210> SEQ ID NO 435
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
gatgtcctgg ggaatgctgc                                              20

<210> SEQ ID NO 436
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
gcaccgggcc tctgcgtcag                                              20

<210> SEQ ID NO 437
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
ggtcgatact tcagtgacac                                              20

<210> SEQ ID NO 438
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 438 tcgaccccttctaacaccaa                                                      20

<210> SEQ ID NO 439
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439 tatcttccttgttattataa                                                      20

<210> SEQ ID NO 440
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440 gtctatttgagcactgtctc                                                      20

<210> SEQ ID NO 441
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441 tcttatttcaaccctactga                                                      20

<210> SEQ ID NO 442
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442 agccaagctctccaatcacc                                                      20

<210> SEQ ID NO 443
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443 taagtgtgattaccaagaaa                                                      20

<210> SEQ ID NO 444
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
taacttctac atccatttct                                              20

<210> SEQ ID NO 445
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
ttcctggtga ttggagagct                                              20

<210> SEQ ID NO 446
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
aggactaaaa gctaaaagtc                                              20

<210> SEQ ID NO 447
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
ctctttgttt caccatcagt                                              20

<210> SEQ ID NO 448
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
gaagcatgtg cttctttctt                                              20

<210> SEQ ID NO 449
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
```
aaagagcttc aaaaaaatcc                                          20

<210> SEQ ID NO 450
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
ctttaaaact ggtgaactgc                                          20

<210> SEQ ID NO 451
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
atcctaatag atttcggctt                                          20

<210> SEQ ID NO 452
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
cacaaggtac aacatacttt                                          20

<210> SEQ ID NO 453
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
ggtctctgtg cactaccttc                                          20

<210> SEQ ID NO 454
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
tcacatcatt aaactgtatc                                          20

<210> SEQ ID NO 455
<211> LENGTH: 20
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 455
tattcatgtt gttatccagc                                              20

<210> SEQ ID NO 456
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
tgatacagtt taatgatgtg                                              20

<210> SEQ ID NO 457
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
gtgacagaat atgccaaaaa                                              20

<210> SEQ ID NO 458
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
gcagtatgaa ggaccacagc                                              20

<210> SEQ ID NO 459
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
aatacccata tatccagctg                                              20

<210> SEQ ID NO 460
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
acggtagccc aactgctcgt                                              20

```
<210> SEQ ID NO 461
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
catccgtgcc tacgagcagt                                                20

<210> SEQ ID NO 462
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
tctggggctc gcctacgcca                                                20

<210> SEQ ID NO 463
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
ccacaatccc cgaagacttg                                                20

<210> SEQ ID NO 464
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
gaaaaggatg atgcccgtat                                                20

<210> SEQ ID NO 465
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
cagctcacat cggtgaagtg                                                20

<210> SEQ ID NO 466
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 466
ggatggaata gctagacaac                                              20

<210> SEQ ID NO 467
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
actgaagaca cccaacactg                                              20

<210> SEQ ID NO 468
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
tccaatgttc tgaagcgtaa                                              20

<210> SEQ ID NO 469
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
gccattacgc ttcagaacat                                              20

<210> SEQ ID NO 470
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
acataccctc ccacgtgacc                                              20

<210> SEQ ID NO 471
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
agcatacgcc agcgcttcat                                              20

<210> SEQ ID NO 472
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 472
ccgacctgga cgtggctgac                                                    20

<210> SEQ ID NO 473
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
acatcagctt tctcatacgc                                                    20

<210> SEQ ID NO 474
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
tgttccagca tccagaccga                                                    20

<210> SEQ ID NO 475
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
ctggcttccc aatgaagcgc                                                    20

<210> SEQ ID NO 476
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
tgccatccag agccgcatcc                                                    20

<210> SEQ ID NO 477
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
cggtgtggag tgcagcccTT                                                    20
```

```
<210> SEQ ID NO 478
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
actgcagcct agtcgaaatg                                                    20

<210> SEQ ID NO 479
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
ctgatatgcg tgtccactcc                                                    20

<210> SEQ ID NO 480
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
atcctctacg ccgcggcctt                                                    20

<210> SEQ ID NO 481
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
ctgacagcac tccgatcacc                                                    20

<210> SEQ ID NO 482
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
cttaaagaag ggcaccagtt                                                    20

<210> SEQ ID NO 483
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 483
agacaagtcc cacgaagatg                                            20

<210> SEQ ID NO 484
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
cgcgcactca ccacagtgac                                            20

<210> SEQ ID NO 485
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
cgccgccgcc atggtgtctc                                            20

<210> SEQ ID NO 486
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
ctcggctctc gacagctgac                                            20

<210> SEQ ID NO 487
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
gcagaacttg ttgagagcga                                            20

<210> SEQ ID NO 488
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
agccagtggc cgcatgccaa                                            20

<210> SEQ ID NO 489
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
gaagagcaga gcaccaccgc                                              20

<210> SEQ ID NO 490
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
acctacctgc cactcagtta                                              20

<210> SEQ ID NO 491
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
ggacataaaa tatctacggg                                              20

<210> SEQ ID NO 492
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
ggaccaccaa agccgctccc                                              20

<210> SEQ ID NO 493
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
cttcagcgtg cagtacccag                                              20

<210> SEQ ID NO 494
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
gcacaaggtc ttgatagccg                                              20
```

<210> SEQ ID NO 495
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
tcaggtccag ggagcggctt                                          20

<210> SEQ ID NO 496
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
atgtgaagga caccttgaac                                          20

<210> SEQ ID NO 497
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
ttgagcacct ctatctgtcc                                          20

<210> SEQ ID NO 498
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
gaggtgctca aaagcttcca                                          20

<210> SEQ ID NO 499
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
gacggagaca ctgcaagcca                                          20

<210> SEQ ID NO 500
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 500
gcttgacagc tcccgacgca                                               20

<210> SEQ ID NO 501
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
atgctggggt tgccttgcgt                                               20

<210> SEQ ID NO 502
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
atgttccggg ctctgatgcc                                               20

<210> SEQ ID NO 503
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
gcgcaaggag aagactgtag                                               20

<210> SEQ ID NO 504
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
cctgtcagag tcaccaccac                                               20

<210> SEQ ID NO 505
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
ttgctcacct gctggttacc                                               20

<210> SEQ ID NO 506
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
ctttctccag aaattctgcc                                              20

<210> SEQ ID NO 507
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
acagcagaag atgcagctgc                                              20

<210> SEQ ID NO 508
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
aggagacagt gcgccagttc                                              20

<210> SEQ ID NO 509
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
gctgctcccc gacagctccc                                              20

<210> SEQ ID NO 510
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
cgtccgcgat ggcccgaata                                              20

<210> SEQ ID NO 511
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
```
cgaagccgca tgtgttcgtc                                           20

<210> SEQ ID NO 512
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
cagactgtct agttgccacc                                           20

<210> SEQ ID NO 513
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
agtggtgtgg aaacgtccca                                           20

<210> SEQ ID NO 514
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
gctcgctcag gggcctctcc                                           20

<210> SEQ ID NO 515
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
gcaatgccta cctgccgcca                                           20

<210> SEQ ID NO 516
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
ttctcactgt ttattgcatg                                           20

<210> SEQ ID NO 517
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 517
tcagggtttg tttctaccac                                                    20

<210> SEQ ID NO 518
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
gacgccggtc tttaagaagc                                                    20

<210> SEQ ID NO 519
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
gaacacatgc ggcttcgtgc                                                    20

<210> SEQ ID NO 520
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
ggagttagtg gatgccgtcc                                                    20

<210> SEQ ID NO 521
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
tctgtccgct ccggcccttt                                                    20

<210> SEQ ID NO 522
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 522
tcaatgcggt aaccagatcg                                                    20

<210> SEQ ID NO 523
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
gacgcacctt ggccccgatc                                              20

<210> SEQ ID NO 524
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
caggtcgacc agcacggctc                                              20

<210> SEQ ID NO 525
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
tccccaggtc aatccggagc                                              20

<210> SEQ ID NO 526
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
gtccccatga taggtcccag                                              20

<210> SEQ ID NO 527
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
gaccccactg ggacctatca                                              20

<210> SEQ ID NO 528
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
```

```
taccgcattg accggcttgc                                            20

<210> SEQ ID NO 529
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
gaactcgccc tcttcagcag                                            20

<210> SEQ ID NO 530
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
gctttctgtt gtgagcatgc                                            20

<210> SEQ ID NO 531
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
gagatgcaga ctctgccatc                                            20

<210> SEQ ID NO 532
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
tctcatcttc ggagggctca                                            20

<210> SEQ ID NO 533
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
ttacctgcca cgattccttc                                            20

<210> SEQ ID NO 534
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 534
gttgggatgg aacatctcac                                              20

<210> SEQ ID NO 535
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
ttaaccctga atcctccaga                                              20

<210> SEQ ID NO 536
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
aaaaaaattc tcttcattca                                              20

<210> SEQ ID NO 537
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
atcttctcca cactctgcac                                              20

<210> SEQ ID NO 538
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
gatcatcacc tggagcatgc                                              20

<210> SEQ ID NO 539
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
gttatgagag cagtgccgag                                              20
```

```
<210> SEQ ID NO 540
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
gttcaacagt gtcgcctgcc                                          20

<210> SEQ ID NO 541
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
tccaggtttg ccgaagatgc                                          20

<210> SEQ ID NO 542
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
tagggacgaa acttagcttc                                          20

<210> SEQ ID NO 543
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
acttcggaga gcttccagac                                          20

<210> SEQ ID NO 544
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
ttcttacaga aacggaccaa                                          20

<210> SEQ ID NO 545
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 545
agggccattc aaaccaccag                                              20

<210> SEQ ID NO 546
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
tgagaactta cacatggaga                                              20

<210> SEQ ID NO 547
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
cttacctctg gtggtttgaa                                              20

<210> SEQ ID NO 548
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
aggaccacca ttgcatatcc                                              20

<210> SEQ ID NO 549
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
cagacctggg tccacctgtc                                              20

<210> SEQ ID NO 550
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
agcctttctc atcggactca                                              20

<210> SEQ ID NO 551
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 551
cagtaccatc atgctactca                                                   20

<210> SEQ ID NO 552
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
ggtacgtggt agttctccta                                                   20

<210> SEQ ID NO 553
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
gtttgggctt gttctcatga                                                   20

<210> SEQ ID NO 554
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
aagtttgtca catcaatgtg                                                   20

<210> SEQ ID NO 555
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
gaagcccatg agtagcatga                                                   20

<210> SEQ ID NO 556
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
tgcagaggtg gacaacaaaa                                                   20
```

<210> SEQ ID NO 557
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
tagcaataat tgatactaat                                              20

<210> SEQ ID NO 558
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
cttgttctag agtaactcac                                              20

<210> SEQ ID NO 559
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
tttccacaat gatgaccatg                                              20

<210> SEQ ID NO 560
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
atcggcgccg gctatgcaac                                              20

<210> SEQ ID NO 561
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
aggcgtgttc gtgtaccctc                                              20

<210> SEQ ID NO 562
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 562
gcctgagaac acgtccggag                                              20

<210> SEQ ID NO 563
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
gagcggcagc ggcgtccagc                                              20

<210> SEQ ID NO 564
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
cgctcaccga ctcctgcgtc                                              20

<210> SEQ ID NO 565
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
ctccggggct ctgtgacgac                                              20

<210> SEQ ID NO 566
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
tctttcgaga tgctagtgac                                              20

<210> SEQ ID NO 567
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
gccacatgca tcaccccatc                                              20

<210> SEQ ID NO 568
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
tacaccccgc cgctgcgcac                                                    20

<210> SEQ ID NO 569
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
ggccgcctgc tgtcgcgctc                                                    20

<210> SEQ ID NO 570
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
cggcgtgatc accgctagcg                                                    20

<210> SEQ ID NO 571
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
caaatatccg cctgctgtcg                                                    20

<210> SEQ ID NO 572
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
tggcggcgga gatccactcc                                                    20

<210> SEQ ID NO 573
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
cataccacca cgacagcagg                                                    20
```

```
<210> SEQ ID NO 574
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
tccacagaac catccgagta                                              20

<210> SEQ ID NO 575
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
aaagagacag cggccagtac                                              20

<210> SEQ ID NO 576
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
actctacctg tcctcgctag                                              20

<210> SEQ ID NO 577
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
gcgcggcggt gacggcgtcc                                              20

<210> SEQ ID NO 578
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
cgccgcgctg ctcatcccca                                              20

<210> SEQ ID NO 579
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 579
tgatcacgcc gtcctccttg                      20

<210> SEQ ID NO 580
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
tttcacttca ataccgacgt                      20

<210> SEQ ID NO 581
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
tctgcactta cgaaacccgt                      20

<210> SEQ ID NO 582
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
ataattgagt gctttcgatc                      20

<210> SEQ ID NO 583
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
cttccatgta gtttatatcc                      20

<210> SEQ ID NO 584
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
ttatgccgta gtctctttag                      20

<210> SEQ ID NO 585
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
gtaatcctct aaagagacta                                                   20

<210> SEQ ID NO 586
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
aagtatgaag tagccgacgt                                                   20

<210> SEQ ID NO 587
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
cttgactcgg tcacttcagc                                                   20

<210> SEQ ID NO 588
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
ttatcacatc acgtttccga                                                   20

<210> SEQ ID NO 589
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
aggccgaagt acaagatcta                                                   20

<210> SEQ ID NO 590
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
```
atccggcatg acaacttggc        20

<210> SEQ ID NO 591
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
gcggggcact ctccgtgacc        20

<210> SEQ ID NO 592
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
gagcatggcc atgcggccac        20

<210> SEQ ID NO 593
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
cagccagttc cgctcctgtc        20

<210> SEQ ID NO 594
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
aacttgacgc agaaatcccg        20

<210> SEQ ID NO 595
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
cagggagtac tatgtgcagc        20

<210> SEQ ID NO 596
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 596
gaggtcagac ccacaactgc                                                   20

<210> SEQ ID NO 597
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
ctgctgcaca tagtactccc                                                   20

<210> SEQ ID NO 598
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
tccctcagga ccgtgcccct                                                   20

<210> SEQ ID NO 599
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
ttgtcatgcc ggatctcctc                                                   20

<210> SEQ ID NO 600
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
tgaagccgac acccaagtcc                                                   20

<210> SEQ ID NO 601
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
gacccctagt ccagtgcttg                                                   20

<210> SEQ ID NO 602
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
ccagtgcttg tggtggctac                                                  20

<210> SEQ ID NO 603
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
gctactgggc cctgaactag                                                  20

<210> SEQ ID NO 604
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
gaactagggg tctggagacc                                                  20

<210> SEQ ID NO 605
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
gacctgggtt tgatctccac                                                  20

<210> SEQ ID NO 606
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
ccagtagcca ccacaagcac                                                  20

<210> SEQ ID NO 607
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
```
caccacaagc actggactag                                              20

<210> SEQ ID NO 608
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
ggactagggg tcagcaggcc                                              20

<210> SEQ ID NO 609
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
tgggccctga actagggtc                                               20

<210> SEQ ID NO 610
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
cgccgctgtt ccccgggcct                                              20

<210> SEQ ID NO 611
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
ttctgtgata cactccgact                                              20

<210> SEQ ID NO 612
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
atacactccg actcgggctc                                              20

<210> SEQ ID NO 613
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 613
agtcagtgca tgacagaact                                              20

<210> SEQ ID NO 614
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
tgcatgacag aacttgggcc                                              20

<210> SEQ ID NO 615
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
gactgctcca gagcccgagt                                              20

<210> SEQ ID NO 616
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
cggagtgtat cacagaacct                                              20

<210> SEQ ID NO 617
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
tgtatcacag aacctaggcc                                              20

<210> SEQ ID NO 618
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
tctgtgatac actccgactc                                              20
```

```
<210> SEQ ID NO 619
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
gtcagtgcat gacagaactt                                              20

<210> SEQ ID NO 620
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
ttggaattgc actttagcaa                                              20

<210> SEQ ID NO 621
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
ttgcacttta gcaatggtga                                              20

<210> SEQ ID NO 622
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
ttgcatgtta gcaacagtga                                              20

<210> SEQ ID NO 623
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
caactctgtt gaatagaaat                                              20

<210> SEQ ID NO 624
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 624
ttctggttct acaggcagag                                         20

<210> SEQ ID NO 625
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
gttctacagg cagagagggt                                         20

<210> SEQ ID NO 626
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
agtgggagaa actcaccgct                                         20

<210> SEQ ID NO 627
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
cgctaggaaa ctcttctcta                                         20

<210> SEQ ID NO 628
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
tctcccactg gtgaccagga                                         20

<210> SEQ ID NO 629
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
tgaccaggaa ggttatcagg                                         20

<210> SEQ ID NO 630
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 630
agtttctccc actggtgacc                                                 20

<210> SEQ ID NO 631
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
tagcggtgag tttctcccac                                                 20

<210> SEQ ID NO 632
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
cttccacctg ataaccttcc                                                 20

<210> SEQ ID NO 633
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
ataaccttcc tggtcaccag                                                 20

<210> SEQ ID NO 634
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
actgcctagt tagcttgatg                                                 20

<210> SEQ ID NO 635
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
tactgcactc ctataatccc                                                 20
```

<210> SEQ ID NO 636
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 636
ctcctataat cccagggtct                                         20

<210> SEQ ID NO 637
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 637
ctataatccc agggtcttgg                                         20

<210> SEQ ID NO 638
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 638
tcccagggtc ttggaggtct                                         20

<210> SEQ ID NO 639
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 639
agggtcttgg aggtctaggc                                         20

<210> SEQ ID NO 640
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 640
gaggtctagg caggatgatt                                         20

<210> SEQ ID NO 641
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 641
actgcactcc tataatccca                                                  20

<210> SEQ ID NO 642
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
ctccaagacc ctgggattat                                                  20

<210> SEQ ID NO 643
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
tgcctagacc tccaagaccc                                                  20

<210> SEQ ID NO 644
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
gcgaggtatt cggctccgcg                                                  20

<210> SEQ ID NO 645
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
gctttcacgg aggttcgacg                                                  20

<210> SEQ ID NO 646
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 646
atgttgcagt tcggctcgat                                                  20

<210> SEQ ID NO 647
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
acgtgtaagg cgaacgcctt                                              20

<210> SEQ ID NO 648
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
gactccgggt actaaatgtc                                              20

<210> SEQ ID NO 649
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
ccgcgccgtt agggaacgag                                              20

<210> SEQ ID NO 650
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
attgttcgac cgtctacggg                                              20

<210> SEQ ID NO 651
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
acccatcggg tgcgatatgg                                              20

<210> SEQ ID NO 652
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
cgggcgtcac ctgctagtaa                                              20
```

<210> SEQ ID NO 653
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
gcttctactc gcaacgtatt                                          20

<210> SEQ ID NO 654
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
tacagttata cgtcgcggtg                                          20

<210> SEQ ID NO 655
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
aagcacaaga acggtccgcc                                          20

<210> SEQ ID NO 656
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
cagccaccgc accggcgtaa                                          20

<210> SEQ ID NO 657
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
gtcaagccga acgctgccgg                                          20

<210> SEQ ID NO 658
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

```
      Synthetic oligonucleotide"

<400> SEQUENCE: 658
ccttagaccg ggtgtacctc                                              20

<210> SEQ ID NO 659
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
aagtctatgc ggggctcgta                                              20

<210> SEQ ID NO 660
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
ttgtcaactt cggccaacgc                                              20

<210> SEQ ID NO 661
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
atagatgtct acgcgccgtt                                              20

<210> SEQ ID NO 662
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
ctcgggctat tcagcgatag                                              20

<210> SEQ ID NO 663
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
gcggttaccg cgaaaaccat                                              20

<210> SEQ ID NO 664
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
accaacgcta cgatcccgga                                                  20

<210> SEQ ID NO 665
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
ccctatatgc gagatccata                                                  20

<210> SEQ ID NO 666
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 666
agaaaggcac gtgcgacgtc                                                  20

<210> SEQ ID NO 667
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
gaccaacctt acggtaactc                                                  20

<210> SEQ ID NO 668
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
attattcctc cggatgacga                                                  20

<210> SEQ ID NO 669
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
```

```
tctcagttcg tagcgaacga                                              20

<210> SEQ ID NO 670
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
tcccgggagg tacggtgtac                                              20

<210> SEQ ID NO 671
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
ggggatggcc ttacgtcgcg                                              20

<210> SEQ ID NO 672
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 672
gtatcctcct tacggcccgt                                              20

<210> SEQ ID NO 673
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 673
gctcggacct tttagacgtc                                              20

<210> SEQ ID NO 674
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674
gtggttacgt taacgactac                                              20

<210> SEQ ID NO 675
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 675
tgcaacgatg gttacggtac                                                    20

<210> SEQ ID NO 676
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
aacgggcgca atacccttt                                                     20

<210> SEQ ID NO 677
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
tcgtgtctag ctatcgagtg                                                    20

<210> SEQ ID NO 678
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 678
gacgtctaat ttctggccgt                                                    20

<210> SEQ ID NO 679
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 679
tagtcctagt tagattcgcg                                                    20

<210> SEQ ID NO 680
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680
aaggccttaa cacgtcgacc                                                    20

<210> SEQ ID NO 681
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 681
attcgtgcat cgcggggttt                                             20

<210> SEQ ID NO 682
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
cacctcgcgt catatcacta                                             20

<210> SEQ ID NO 683
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
gacctcgcaa ttgagcgctc                                             20

<210> SEQ ID NO 684
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 684
tgtatccacc gtgacccggt                                             20

<210> SEQ ID NO 685
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
gatcttacca ctcgtcgtag                                             20

<210> SEQ ID NO 686
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
```
ttcgccggcg acgaagtgca                                          20

<210> SEQ ID NO 687
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 687
agcactagga tcgcggcctt                                          20

<210> SEQ ID NO 688
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
gcgtatctac cctaccgccg                                          20

<210> SEQ ID NO 689
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 689
gcgcgagggc accgacaagt                                          20

<210> SEQ ID NO 690
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 690
cgcgtatatg tcacacggca                                          20

<210> SEQ ID NO 691
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691
taaaaccgat cacgatacga                                          20

<210> SEQ ID NO 692
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 692
tcctgcgcga tgaccgtcgg                                              20

<210> SEQ ID NO 693
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 693
tggcccacaa ggtgcgatat                                              20

<210> SEQ ID NO 694
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 694
ggggtaggcc taattacgga                                              20

<210> SEQ ID NO 695
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
cgcttcgtct ctcgcaaaca                                              20

<210> SEQ ID NO 696
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696
ttatgtgcct ctcggcgcat                                              20

<210> SEQ ID NO 697
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 697
ccgttctgac gacgctaaag                                              20
```

```
<210> SEQ ID NO 698
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698
aaactcccgt gtcaaccgat                                                 20

<210> SEQ ID NO 699
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699
gtttgcgagt caaagtacgc                                                 20

<210> SEQ ID NO 700
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 700
gggtgcacac gccggcctat                                                 20

<210> SEQ ID NO 701
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 701
ctttataccg cgcgtcggca                                                 20

<210> SEQ ID NO 702
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
tcaaacgccc gggcgcccca                                                 20

<210> SEQ ID NO 703
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 703
gaccggtgtg tttacgcgtg                                              20

<210> SEQ ID NO 704
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
cggtgaggat ccctcttgcg                                              20

<210> SEQ ID NO 705
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
acggtcccaa cgagcgccgg                                              20

<210> SEQ ID NO 706
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
cgcttcattg cccgaacgct                                              20

<210> SEQ ID NO 707
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
ttataccgtc acgagtgccc                                              20

<210> SEQ ID NO 708
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
tgcaccggta cgggcgactc                                              20

<210> SEQ ID NO 709
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 709
gaggcgtact tcggctctaa                                                   20

<210> SEQ ID NO 710
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710
ttcgagacgg atacgtctgc                                                   20

<210> SEQ ID NO 711
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
tagcccgtcg agtactcccc                                                   20

<210> SEQ ID NO 712
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
agcttagatc gtgcgtcgta                                                   20

<210> SEQ ID NO 713
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713
cgccggatga ctggtggata                                                   20

<210> SEQ ID NO 714
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 714
ccgtttcgcc tattggtgcg                                                   20
```

```
<210> SEQ ID NO 715
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 715
ttcgacgtgc ggcgtattgg                                              20

<210> SEQ ID NO 716
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 716
ttcaattgtt cgcccgaaca                                              20

<210> SEQ ID NO 717
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 717
gcggatctga cggttactta                                              20

<210> SEQ ID NO 718
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 718
aatgaagcac cgattgcgga                                              20

<210> SEQ ID NO 719
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 719
tcctataatt gagcgaacgg                                              20

<210> SEQ ID NO 720
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 720
gctacagatt tgcgttcgag                                           20

<210> SEQ ID NO 721
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 721
ggactgaaac cgatagtatc                                           20

<210> SEQ ID NO 722
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 722
gcaattctgc aacgcacgtc                                           20

<210> SEQ ID NO 723
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 723
cacccgactc ggccgtaaag                                           20

<210> SEQ ID NO 724
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 724
caaccgtgcg atgcgcgcta                                           20

<210> SEQ ID NO 725
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 725
tgatggacgc gatacgttta                                           20

<210> SEQ ID NO 726
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
taccccttga ggggcgcata                                                    20

<210> SEQ ID NO 727
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 727
ccgtatacgt atctatgccg                                                    20

<210> SEQ ID NO 728
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
acagcggcct aatacttcgc                                                    20

<210> SEQ ID NO 729
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
tatcgaactg cacacgcaac                                                    20

<210> SEQ ID NO 730
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
tgtcggaccc attgtcgaac                                                    20

<210> SEQ ID NO 731
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 731
aaacctagcg tagattcggc                                                    20
```

<210> SEQ ID NO 732
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 732
tagatggtgc ttctgtcgcg                                               20

<210> SEQ ID NO 733
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 733
catcgtaaca cacgtacgag                                               20

<210> SEQ ID NO 734
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 734
caacgatcag gcgtgttatc                                               20

<210> SEQ ID NO 735
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 735
acagcagggg ccgcgaataa                                               20

<210> SEQ ID NO 736
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 736
agccgggctt tccgtcaagc                                               20

<210> SEQ ID NO 737
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 737
acggtccctc tcgggtcaat                                               20

<210> SEQ ID NO 738
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
tcaatagttc tgcgcgaatt                                               20

<210> SEQ ID NO 739
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739
tcgttacata ccccgcggaa                                               20

<210> SEQ ID NO 740
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 740
cattcggtcc gttcatctcg                                               20

<210> SEQ ID NO 741
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741
ttcggctcaa tggcgcgagc                                               20

<210> SEQ ID NO 742
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 742
catacccgcg ccgtgactcc                                               20

<210> SEQ ID NO 743
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
ggacggatgg gacgactagt                                                   20

<210> SEQ ID NO 744
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 744
gcgaggtatt cggctccgcg                                                   20

<210> SEQ ID NO 745
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 745
gctttcacgg aggttcgacg                                                   20

<210> SEQ ID NO 746
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 746
atgttgcagt tcggctcgat                                                   20

<210> SEQ ID NO 747
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
acgtgtaagg cgaacgcctt                                                   20

<210> SEQ ID NO 748
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
```

```
gactccgggt actaaatgtc                                               20

<210> SEQ ID NO 749
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
ccgcgccgtt agggaacgag                                               20

<210> SEQ ID NO 750
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 750
attgttcgac cgtctacggg                                               20

<210> SEQ ID NO 751
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 751
acccatcggg tgcgatatgg                                               20

<210> SEQ ID NO 752
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 752
cgggcgtcac ctgctagtaa                                               20

<210> SEQ ID NO 753
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 753
gcttctactc gcaacgtatt                                               20

<210> SEQ ID NO 754
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 754
tacagttata cgtcgcggtg                                                  20

<210> SEQ ID NO 755
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 755
aagcacaaga acggtccgcc                                                  20

<210> SEQ ID NO 756
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 756
cagccaccgc accggcgtaa                                                  20

<210> SEQ ID NO 757
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 757
gtcaagccga acgctgccgg                                                  20

<210> SEQ ID NO 758
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 758
ccttagaccg ggtgtacctc                                                  20

<210> SEQ ID NO 759
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 759
aagtctatgc ggggctcgta                                                  20

<210> SEQ ID NO 760
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
ttgtcaactt cggccaacgc                                                 20

<210> SEQ ID NO 761
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761
atagatgtct acgcgccgtt                                                 20

<210> SEQ ID NO 762
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
ctcgggctat tcagcgatag                                                 20

<210> SEQ ID NO 763
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 763
gcggttaccg cgaaaaccat                                                 20

<210> SEQ ID NO 764
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
accaacgcta cgatcccgga                                                 20

<210> SEQ ID NO 765
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 765
``` cccktatatgc gagatccata                                              20

<210> SEQ ID NO 766
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 766
agaaaggcac gtgcgacgtc                                               20

<210> SEQ ID NO 767
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 767
gaccaacctt acggtaactc                                               20

<210> SEQ ID NO 768
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
attattcctc cggatgacga                                               20

<210> SEQ ID NO 769
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 769
tctcagttcg tagcgaacga                                               20

<210> SEQ ID NO 770
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 770
tcccgggagg tacggtgtac                                               20

<210> SEQ ID NO 771
<211> LENGTH: 20
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 771
ggggatggcc ttacgtcgcg                                               20

<210> SEQ ID NO 772
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 772
gtatcctcct tacggcccgt                                               20

<210> SEQ ID NO 773
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 773
gctcggacct tttagacgtc                                               20

<210> SEQ ID NO 774
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 774
gtggttacgt taacgactac                                               20

<210> SEQ ID NO 775
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 775
tgcaacgatg gttacggtac                                               20

<210> SEQ ID NO 776
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 776
aacgggcgca ataccctttt                                               20

```
<210> SEQ ID NO 777
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 777
tcgtgtctag ctatcgagtg                                                   20

<210> SEQ ID NO 778
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 778
gacgtctaat ttctggccgt                                                   20

<210> SEQ ID NO 779
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 779
tagtcctagt tagattcgcg                                                   20

<210> SEQ ID NO 780
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 780
aaggccttaa cacgtcgacc                                                   20

<210> SEQ ID NO 781
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 781
attcgtgcat cgcggggttt                                                   20

<210> SEQ ID NO 782
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 782
cacctcgcgt catatcacta                                              20

<210> SEQ ID NO 783
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 783
gacctcgcaa ttgagcgctc                                              20

<210> SEQ ID NO 784
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 784
tgtatccacc gtgacccggt                                              20

<210> SEQ ID NO 785
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 785
gatcttacca ctcgtcgtag                                              20

<210> SEQ ID NO 786
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 786
ttcgccggcg acgaagtgca                                              20

<210> SEQ ID NO 787
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 787
agcactagga tcgcggcctt                                              20

<210> SEQ ID NO 788
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 788
gcgtatctac cctaccgccg                                              20

<210> SEQ ID NO 789
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 789
gcgcgagggc accgacaagt                                              20

<210> SEQ ID NO 790
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 790
cgcgtatatg tcacacggca                                              20

<210> SEQ ID NO 791
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 791
taaaaccgat cacgatacga                                              20

<210> SEQ ID NO 792
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 792
tcctgcgcga tgaccgtcgg                                              20

<210> SEQ ID NO 793
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 793
tggcccacaa ggtgcgatat                                              20
```

<210> SEQ ID NO 794
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 794
ggggtaggcc taattacgga                                               20

<210> SEQ ID NO 795
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 795
cgcttcgtct ctcgcaaaca                                               20

<210> SEQ ID NO 796
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 796
ttatgtgcct ctcggcgcat                                               20

<210> SEQ ID NO 797
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 797
ccgttctgac gacgctaaag                                               20

<210> SEQ ID NO 798
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 798
aaactcccgt gtcaaccgat                                               20

<210> SEQ ID NO 799
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 799
gtttgcgagt caaagtacgc					20

<210> SEQ ID NO 800
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 800
gggtgcacac gccggcctat					20

<210> SEQ ID NO 801
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 801
ctttataccg cgcgtcggca					20

<210> SEQ ID NO 802
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 802
tcaaacgccc gggcgcccca					20

<210> SEQ ID NO 803
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 803
gaccggtgtg tttacgcgtg					20

<210> SEQ ID NO 804
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 804
cggtgaggat ccctcttgcg					20

<210> SEQ ID NO 805
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 805
acggtcccaa cgagcgccgg                                                   20

<210> SEQ ID NO 806
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 806
cgcttcattg cccgaacgct                                                   20

<210> SEQ ID NO 807
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 807
ttataccgtc acgagtgccc                                                   20

<210> SEQ ID NO 808
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 808
tgcaccggta cgggcgactc                                                   20

<210> SEQ ID NO 809
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 809
gaggcgtact tcggctctaa                                                   20

<210> SEQ ID NO 810
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 810
ttcgagacgg atacgtctgc                                                   20
```

```
<210> SEQ ID NO 811
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 811
tagcccgtcg agtactcccc                                                    20

<210> SEQ ID NO 812
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 812
agcttagatc gtgcgtcgta                                                    20

<210> SEQ ID NO 813
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 813
cgccggatga ctggtggata                                                    20

<210> SEQ ID NO 814
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 814
ccgtttcgcc tattggtgcg                                                    20

<210> SEQ ID NO 815
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 815
ttcgacgtgc ggcgtattgg                                                    20

<210> SEQ ID NO 816
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 816
ttcaattgtt cgcccgaaca                                          20

<210> SEQ ID NO 817
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 817
gcggatctga cggttactta                                          20

<210> SEQ ID NO 818
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 818
aatgaagcac cgattgcgga                                          20

<210> SEQ ID NO 819
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 819
tcctataatt gagcgaacgg                                          20

<210> SEQ ID NO 820
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 820
gctacagatt tgcgttcgag                                          20

<210> SEQ ID NO 821
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 821
ggactgaaac cgatagtatc                                          20

<210> SEQ ID NO 822
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 822
gcaattctgc aacgcacgtc                                              20

<210> SEQ ID NO 823
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 823
cacccgactc ggccgtaaag                                              20

<210> SEQ ID NO 824
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 824
caaccgtgcg atgcgcgcta                                              20

<210> SEQ ID NO 825
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 825
tgatggacgc gatacgttta                                              20

<210> SEQ ID NO 826
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 826
taccccttga ggggcgcata                                              20

<210> SEQ ID NO 827
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 827
```
ccgtatacgt atctatgccg                                          20

<210> SEQ ID NO 828
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 828
acagcggcct aatacttcgc                                          20

<210> SEQ ID NO 829
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829
tatcgaactg cacacgcaac                                          20

<210> SEQ ID NO 830
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 830
tgtcggaccc attgtcgaac                                          20

<210> SEQ ID NO 831
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 831
aaacctagcg tagattcggc                                          20

<210> SEQ ID NO 832
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 832
tagatggtgc ttctgtcgcg                                          20

<210> SEQ ID NO 833
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 833
catcgtaaca cacgtacgag                                              20

<210> SEQ ID NO 834
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 834
caacgatcag gcgtgttatc                                              20

<210> SEQ ID NO 835
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 835
acagcagggg ccgcgaataa                                              20

<210> SEQ ID NO 836
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 836
agccgggctt tccgtcaagc                                              20

<210> SEQ ID NO 837
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 837
acggtccctc tcgggtcaat                                              20

<210> SEQ ID NO 838
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 838
tcaatagttc tgcgcgaatt                                              20

<210> SEQ ID NO 839

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 839
tcgttacata ccccgcggaa                                              20

<210> SEQ ID NO 840
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 840
cattcggtcc gttcatctcg                                              20

<210> SEQ ID NO 841
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 841
ttcggctcaa tggcgcgagc                                              20

<210> SEQ ID NO 842
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 842
catacccgcg ccgtgactcc                                              20

<210> SEQ ID NO 843
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843
ggacggatgg gacgactagt                                              20

<210> SEQ ID NO 844
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 844
```
gtgcaacgac tgacccgcgg                                              20

<210> SEQ ID NO 845
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845
cgacacttgg gctgacgcgc                                              20

<210> SEQ ID NO 846
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 846
tgtgtaatta cgtttcgcgg                                              20

<210> SEQ ID NO 847
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 847
aaccgtactg cgaggagcat                                              20

<210> SEQ ID NO 848
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 848
gatatttacc ggcgataaga                                              20

<210> SEQ ID NO 849
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 849
gcgacgtgta tcgatcactc                                              20

<210> SEQ ID NO 850
<211> LENGTH: 20
<212> TYPE: DNA
<213> ORGANISM: Artificial Sequence
<220> FEATURE:

<210> SEQ ID NO 850
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 850
taatggaaga tgcgcgatac                                            20

<210> SEQ ID NO 851
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 851
tgtcctaccg aatgaaccgt                                            20

<210> SEQ ID NO 852
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 852
acgcgaagtg tcgcagagtg                                            20

<210> SEQ ID NO 853
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 853
gcagagcgta atcggcatcg                                            20

<210> SEQ ID NO 854
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 854
gccgcgccat aatatgccat                                            20

<210> SEQ ID NO 855
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 855
cgaatgcgcc ggagaatatt                                            20

```
<210> SEQ ID NO 856
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 856
cccgcctggc gattcacggg                                                    20

<210> SEQ ID NO 857
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 857
agcctagtcg cgctaatatt                                                    20

<210> SEQ ID NO 858
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 858
gtgtgcctcg acagcgtaag                                                    20

<210> SEQ ID NO 859
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 859
tcatgcgcct cgtaatacct                                                    20

<210> SEQ ID NO 860
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 860
tgtgccacgc cgctgcaacg                                                    20

<210> SEQ ID NO 861
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 861
gcaaataggt cggagcgtgt                                               20

<210> SEQ ID NO 862
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 862
ggatagcccg gttggtgcgt                                               20

<210> SEQ ID NO 863
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 863
tcgcaaaatg cggattccgt                                               20

<210> SEQ ID NO 864
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 864
ggtgcagtcc gtttagtcgg                                               20

<210> SEQ ID NO 865
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 865
tgggttccgg ccccatgtac                                               20

<210> SEQ ID NO 866
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 866
ccttcggatt cgtaggctgg                                               20

<210> SEQ ID NO 867
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 867
tcccccgtac gtgtatgtcg                                             20

<210> SEQ ID NO 868
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 868
aggtgcgtgt caaccggtag                                             20

<210> SEQ ID NO 869
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 869
aaaaagtccg cgattacgtc                                             20

<210> SEQ ID NO 870
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 870
ttatcgcaca accccgaaag                                             20

<210> SEQ ID NO 871
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 871
caccccgtag caacgataaa                                             20

<210> SEQ ID NO 872
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 872
taacagcttc cgcgtaatat                                             20
```

<210> SEQ ID NO 873
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 873
gccatagcca atcgctagtt                                              20

<210> SEQ ID NO 874
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 874
catctatgag acgtgcgtac                                              20

<210> SEQ ID NO 875
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 875
ttgataaacc gcggccgaaa                                              20

<210> SEQ ID NO 876
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 876
gtatcctcgc aatcgttagg                                              20

<210> SEQ ID NO 877
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 877
tggcgctcct gcgcacacga                                              20

<210> SEQ ID NO 878
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 878
ttcgaagtct aacccgcggg                                              20

<210> SEQ ID NO 879
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 879
gtttcccggg actgtcgcgt                                              20

<210> SEQ ID NO 880
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 880
aacgccccgg atttcgttga                                              20

<210> SEQ ID NO 881
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 881
acaacacgcc gacacgtcta                                              20

<210> SEQ ID NO 882
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882
taagcggcgt catgtcgccc                                              20

<210> SEQ ID NO 883
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 883
ccgcccctgc gaactgcgtt                                              20

<210> SEQ ID NO 884
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 884
tatctaatcg cggagtcgta                                                    20

<210> SEQ ID NO 885
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 885
acgctatagt gtacgtctaa                                                    20

<210> SEQ ID NO 886
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 886
gtagacatat tgcgtaatcg                                                    20

<210> SEQ ID NO 887
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 887
cgtaaaccat aacgttggtc                                                    20

<210> SEQ ID NO 888
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 888
ggacgtagat tagggcgtaa                                                    20

<210> SEQ ID NO 889
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 889
cgggcaatat gatcgtaggc                                                    20
```

```
<210> SEQ ID NO 890
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 890
ggaccaatgt taccgtaggt                                               20

<210> SEQ ID NO 891
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 891
cagggacgta gccgccgtta                                               20

<210> SEQ ID NO 892
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 892
aaccccggct gtcatcgccg                                               20

<210> SEQ ID NO 893
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 893
gattcattat cggcatacgg                                               20

<210> SEQ ID NO 894
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 894
agtcatcctc tatgcgcgta                                               20

<210> SEQ ID NO 895
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 895
cgtacgggcg cgccgtccat                                           20

<210> SEQ ID NO 896
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 896
ttgcgtgtgc gttgttaacg                                           20

<210> SEQ ID NO 897
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 897
gaccatacgc ctcgtatgcc                                           20

<210> SEQ ID NO 898
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 898
cggcaatgtg tggcgaccgc                                           20

<210> SEQ ID NO 899
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 899
tcgctaagcc gggtaatact                                           20

<210> SEQ ID NO 900
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 900
tttctaatta cccgatacgt                                           20

<210> SEQ ID NO 901
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 901
accaggactg ccgcgtgagg                                               20

<210> SEQ ID NO 902
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 902
gcgcgtacat ataaataggt                                               20

<210> SEQ ID NO 903
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 903
cttatccata ataggcggcg                                               20

<210> SEQ ID NO 904
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 904
gttattgcgc cttggccgta                                               20

<210> SEQ ID NO 905
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 905
taaaagtggt gcgtcgtcgt                                               20

<210> SEQ ID NO 906
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 906
```
ctcgtgaaac aagatccgac                                               20

<210> SEQ ID NO 907
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 907
taaacgattc accgataaca                                               20

<210> SEQ ID NO 908
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 908
cggccgtagt gacgaatgga                                               20

<210> SEQ ID NO 909
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 909
accggtcgaa gtctgggatt                                               20

<210> SEQ ID NO 910
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 910
tccgtacatc gacctattac                                               20

<210> SEQ ID NO 911
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 911
cgacacgatg gtcatactac                                               20

<210> SEQ ID NO 912
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 912
actcgaccta acgtcgatgt                                              20

<210> SEQ ID NO 913
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 913
tgcagatcgc gaagcgacta                                              20

<210> SEQ ID NO 914
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 914
tctaggatac tcttaacggg                                              20

<210> SEQ ID NO 915
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 915
ggtctgtccg ttgcgaccac                                              20

<210> SEQ ID NO 916
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 916
accggactgc gatatgccgt                                              20

<210> SEQ ID NO 917
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 917
ctcgtatagt attgcgtggt                                              20

<210> SEQ ID NO 918
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 918
ctttagtcac gatatacgtc                                            20

<210> SEQ ID NO 919
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 919
gcggcccgtg accgttcaat                                            20

<210> SEQ ID NO 920
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 920
ccggtttata aattacgtgg                                            20

<210> SEQ ID NO 921
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 921
cagctcaccc tgcgtacggt                                            20

<210> SEQ ID NO 922
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 922
ctcggcttta cgatcgatca                                            20

<210> SEQ ID NO 923
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 923
```
tctgcaccgc gacttagctt                                              20

<210> SEQ ID NO 924
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 924
ggcttataga cgagactcga                                              20

<210> SEQ ID NO 925
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 925
accggatgtg ggcgcctctc                                              20

<210> SEQ ID NO 926
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 926
cattacgtgt cgagctccgg                                              20

<210> SEQ ID NO 927
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 927
gatgcgggtg gaaaacgtta                                              20

<210> SEQ ID NO 928
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 928
gcaaaaagcg gacacgcgac                                              20

<210> SEQ ID NO 929
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 929
cgaggatgta catacgtaaa                                              20

<210> SEQ ID NO 930
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 930
acacgtcttc ggctatacgc                                              20

<210> SEQ ID NO 931
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 931
tcgtgcctag ctcggttgag                                              20

<210> SEQ ID NO 932
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 932
tcacacggga tctcgccggt                                              20

<210> SEQ ID NO 933
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 933
cgtgcgttcg taataaaagg                                              20

<210> SEQ ID NO 934
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 934
ccccttcgat atccgatgac                                              20
```

```
<210> SEQ ID NO 935
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 935
cgtgattcct aagcccccgc                                                    20

<210> SEQ ID NO 936
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 936
gcgtgccatg ggaggccgtt                                                    20

<210> SEQ ID NO 937
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 937
ggctttacgt aaggagcgta                                                    20

<210> SEQ ID NO 938
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 938
accctagcct catcgcgacc                                                    20

<210> SEQ ID NO 939
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 939
gctgattaga cccggcgtaa                                                    20

<210> SEQ ID NO 940
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 940
gttacccctt tggccggaag                                              20

<210> SEQ ID NO 941
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 941
taacgttatg tcaaacgctc                                              20

<210> SEQ ID NO 942
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 942
ggatcgatcc gaggaacgtg                                              20

<210> SEQ ID NO 943
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 943
ctgcacggca cgacatccaa                                              20

<210> SEQ ID NO 944
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 944
ggtcaaagcg atgttagccg                                              20

<210> SEQ ID NO 945
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 945
gcttgtaatc taaagacgcg                                              20

<210> SEQ ID NO 946
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 946
gagattaaat taacgccggc                                                    20

<210> SEQ ID NO 947
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 947
cgaatcggga aggcgcgtgt                                                    20

<210> SEQ ID NO 948
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 948
gggacgctca tcgagtgacg                                                    20

<210> SEQ ID NO 949
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 949
agcgcgtaag gcgtagttac                                                    20

<210> SEQ ID NO 950
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 950
gtttcagcgc gagttgcgcg                                                    20

<210> SEQ ID NO 951
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 951
tcctgcgttc cactcgtact                                                    20
```

<210> SEQ ID NO 952
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 952
gttatttgtc tgtcgaaacg                                                 20

<210> SEQ ID NO 953
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 953
aataagccta cccggcgaga                                                 20

<210> SEQ ID NO 954
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 954
gtacatgcgg caagtcgact                                                 20

<210> SEQ ID NO 955
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 955
agcagttcgg gtaacgccca                                                 20

<210> SEQ ID NO 956
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 956
tgtactcgca tagcgggggc                                                 20

<210> SEQ ID NO 957
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 957
aactcgcgtg ggaagtccgg                                              20

<210> SEQ ID NO 958
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 958
ccttgtggcg tgccaaacga                                              20

<210> SEQ ID NO 959
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 959
tgccgacgcg acgcagcgta                                              20

<210> SEQ ID NO 960
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 960
tgcggcaatg ttaaccctta                                              20

<210> SEQ ID NO 961
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 961
tgtatagtca tcgccgtaat                                              20

<210> SEQ ID NO 962
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 962
taggcggacg gttacatata                                              20

<210> SEQ ID NO 963
<211> LENGTH: 20
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 963
gataagactc cgcgagcttc                                                    20

<210> SEQ ID NO 964
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 964
tcgtgccgga ataaccacta                                                    20

<210> SEQ ID NO 965
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 965
cgagtaatta tttgcggtcg                                                    20

<210> SEQ ID NO 966
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 966
tacttaccga ccgacaaacg                                                    20

<210> SEQ ID NO 967
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 967
atggtggctg tactcgtaac                                                    20

<210> SEQ ID NO 968
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 968
tcgtaagttc gctatatgcc                                                    20

```
<210> SEQ ID NO 969
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 969
ccggcttgaa taccgtgcgg                                                   20

<210> SEQ ID NO 970
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 970
ggcccaacga aactagcgtg                                                   20

<210> SEQ ID NO 971
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 971
agccgcgccg caaagctttt                                                   20

<210> SEQ ID NO 972
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 972
acacgaccga ccggtggaat                                                   20

<210> SEQ ID NO 973
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 973
aaactcatac gtagcgaatc                                                   20

<210> SEQ ID NO 974
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"

<400> SEQUENCE: 974
cgattgacgt tgggctctca                                           20

<210> SEQ ID NO 975
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 975
aaccagcatt tgaccgcgct                                           20

<210> SEQ ID NO 976
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 976
acgtcggtct agagttaagt                                           20

<210> SEQ ID NO 977
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 977
ctccggacgt gcatccgaga                                           20

<210> SEQ ID NO 978
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 978
ataaagtccc aggtgcgcgc                                           20

<210> SEQ ID NO 979
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 979
gccgctcttg ataacgacgc                                           20

<210> SEQ ID NO 980
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 980
cgaaaccata cctccttcga                                              20

<210> SEQ ID NO 981
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 981
cgcgcctacc cttttaccgc                                              20

<210> SEQ ID NO 982
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 982
tacccctctg cgatgccggt                                              20

<210> SEQ ID NO 983
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 983
atattgtccc atacgatcgg                                              20

<210> SEQ ID NO 984
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 984
ggattgacga gacgatatcg                                              20

<210> SEQ ID NO 985
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 985
```
cacgtaagac gctccactta                                               20

<210> SEQ ID NO 986
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 986
ggagtctcac gcaattagcg                                               20

<210> SEQ ID NO 987
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 987
atcgcaggtc tacgcagagt                                               20

<210> SEQ ID NO 988
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 988
cggtcgtgac agacctggtg                                               20

<210> SEQ ID NO 989
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 989
gccactccgc tcgttctaga                                               20

<210> SEQ ID NO 990
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 990
ccgtcgagca atcccgccaa                                               20

<210> SEQ ID NO 991
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 991
gagtcgagtt aataacgctc                                                  20

<210> SEQ ID NO 992
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 992
caatatctaa gcgctaacga                                                  20

<210> SEQ ID NO 993
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 993
acccatcccc gcgtccgaga                                                  20

<210> SEQ ID NO 994
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 994
taatgagtaa cgctcatcgg                                                  20

<210> SEQ ID NO 995
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 995
aacggtagcg tacccgtgaa                                                  20

<210> SEQ ID NO 996
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 996
catcgagggt aaacgccatt                                                  20

<210> SEQ ID NO 997
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 997
cgtcaccgct agtaatgatg                                                   20

<210> SEQ ID NO 998
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 998
aatcaccgac aacgtaagac                                                   20

<210> SEQ ID NO 999
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 999
cactcagcgg ttggacgccc                                                   20

<210> SEQ ID NO 1000
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1000
tccgtaggac gtatatattc                                                   20

<210> SEQ ID NO 1001
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1001
aaaacgtaat tataccgagc                                                   20

<210> SEQ ID NO 1002
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1002
```
taggccgctc aggccgcact                                                   20

<210> SEQ ID NO 1003
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1003
cccacttaat aacgccgctt                                                   20

<210> SEQ ID NO 1004
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1004
accatacggg gtcttgtcga                                                   20

<210> SEQ ID NO 1005
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1005
acggaacccg atcggaacgg                                                   20

<210> SEQ ID NO 1006
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1006
gttgcgtcca ttccgtcgcc                                                   20

<210> SEQ ID NO 1007
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1007
attccgtttg cagcgagacc                                                   20

<210> SEQ ID NO 1008
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 1008
ccatcggttc gacttaccgc                                               20

<210> SEQ ID NO 1009
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1009
catcggctat gtcggggaca                                               20

<210> SEQ ID NO 1010
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1010
aatgagcgtc tctcgatcgc                                               20

<210> SEQ ID NO 1011
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1011
ttactgatca gtcggacgca                                               20

<210> SEQ ID NO 1012
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1012
gattgagaag ccgcggtatc                                               20

<210> SEQ ID NO 1013
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1013
gtgatggcca cgtccgaacc                                               20
```

```
<210> SEQ ID NO 1014
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1014
ttggacgtac actttcgttc                                                   20

<210> SEQ ID NO 1015
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1015
actgcgcgta taggacgcaa                                                   20

<210> SEQ ID NO 1016
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1016
tagctgttta cgccgacctg                                                   20

<210> SEQ ID NO 1017
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1017
catgcccgtc tgcgccgcat                                                   20

<210> SEQ ID NO 1018
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1018
tcaactatga accgccgtgc                                                   20

<210> SEQ ID NO 1019
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 1019
cgttacgttt cttgccagga                                               20

<210> SEQ ID NO 1020
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1020
tctatatcta gtctcggcgc                                               20

<210> SEQ ID NO 1021
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1021
ctcctcgagg ctggctacgt                                               20

<210> SEQ ID NO 1022
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1022
tcgtaccgca cgtgtaagcc                                               20

<210> SEQ ID NO 1023
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1023
cgggcactaa cccgatacac                                               20

<210> SEQ ID NO 1024
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1024
gaacgtaacg gcatgcatca                                               20

<210> SEQ ID NO 1025
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 1025
gcccgataga attacccatt                                              20

<210> SEQ ID NO 1026
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1026
gccctcgagc tcacgatgag                                              20

<210> SEQ ID NO 1027
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1027
ttaggacgtg cttccgaggg                                              20

<210> SEQ ID NO 1028
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1028
tagttaaccg taaagtgggc                                              20

<210> SEQ ID NO 1029
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1029
gtgggctgac cgttctcgac                                              20

<210> SEQ ID NO 1030
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1030
caagagttaa cctcgaccgg                                              20
```

<210> SEQ ID NO 1031
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1031
tatgactgca cgactcgcta                                                    20

<210> SEQ ID NO 1032
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1032
gaaccggcgt gcgttagcgg                                                    20

<210> SEQ ID NO 1033
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1033
ttcgatatag gggacggcgg                                                    20

<210> SEQ ID NO 1034
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1034
gccgtaagcg ggccggttga                                                    20

<210> SEQ ID NO 1035
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1035
cgtaaccgga gataatatta                                                    20

<210> SEQ ID NO 1036
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 1036
cggcgataac agcgacatcg                                             20

<210> SEQ ID NO 1037
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1037
tcacttcggg cattacgagc                                             20

<210> SEQ ID NO 1038
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1038
taataaacta tgtcccgccg                                             20

<210> SEQ ID NO 1039
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1039
tggcacggag ttgcatacgc                                             20

<210> SEQ ID NO 1040
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1040
gctagttctc ccgggcgaaa                                             20

<210> SEQ ID NO 1041
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1041
gttcggttgc agcttacacg                                             20

<210> SEQ ID NO 1042
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1042
gcacctctag cgcgctcggc                                                 20

<210> SEQ ID NO 1043
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1043
cattgtagac tcgtacggat                                                 20

<210> SEQ ID NO 1044
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1044
tcggaattcc gcaggccgag                                                 20

<210> SEQ ID NO 1045
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1045
gattacgggg ttccgtaact                                                 20

<210> SEQ ID NO 1046
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1046
gcctatgtga atcgcgaatt                                                 20

<210> SEQ ID NO 1047
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1047
ctcggacggc atacgacaat                                                 20
```

<210> SEQ ID NO 1048
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1048
catatgctcg acggtataaa          20

<210> SEQ ID NO 1049
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1049
ctcatgtacg ccttcgctac          20

<210> SEQ ID NO 1050
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1050
ttacagttca taccgtcgcc          20

<210> SEQ ID NO 1051
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1051
gatggccagt aacggcgtca          20

<210> SEQ ID NO 1052
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1052
atttgaatgc tcccgtcgac          20

<210> SEQ ID NO 1053
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 1053
caacggtcac gctagaataa                                                    20

<210> SEQ ID NO 1054
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1054
cttaagttcg cgacggaatg                                                    20

<210> SEQ ID NO 1055
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1055
tacttaggtc cgcgtaaagc                                                    20

<210> SEQ ID NO 1056
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1056
ggttaaaaat taagcggtcc                                                    20

<210> SEQ ID NO 1057
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1057
aaaacggctc gatcggtgat                                                    20

<210> SEQ ID NO 1058
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1058
atgttacgta cgtgatctcc                                                    20

<210> SEQ ID NO 1059
<211> LENGTH: 20

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1059
agtagacgct atgttcgcgc                                               20

<210> SEQ ID NO 1060
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1060
tactgcgtac cgcagtaagc                                               20

<210> SEQ ID NO 1061
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1061
cccatcattc gcgctgacgt                                               20

<210> SEQ ID NO 1062
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1062
cgactattgc cgtccatctc                                               20

<210> SEQ ID NO 1063
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1063
atccgtacca aacacgctac                                               20

<210> SEQ ID NO 1064
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1064
```
tgcgtaaaac ttgcgctcga                                               20

<210> SEQ ID NO 1065
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1065
catatgccta taaccggcgg                                               20

<210> SEQ ID NO 1066
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1066
gttccggata tatcggtta                                                20

<210> SEQ ID NO 1067
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1067
ctaatacacc cggacggtac                                               20

<210> SEQ ID NO 1068
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1068
gggcgggacg taatattatg                                               20

<210> SEQ ID NO 1069
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1069
actttacatc atgtcgtcgt                                               20

<210> SEQ ID NO 1070
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 1070
ctgatcggtg catatctcgg                                              20

<210> SEQ ID NO 1071
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1071
gagccccaac gcgcgaagca                                              20

<210> SEQ ID NO 1072
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1072
gctaagattc atccgaacac                                              20

<210> SEQ ID NO 1073
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1073
gttaccgtga cgataagaat                                              20

<210> SEQ ID NO 1074
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1074
gctaaacgta ttttacgggc                                              20

<210> SEQ ID NO 1075
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1075
ccgagccgaa ttgggcgtgt                                              20

<210> SEQ ID NO 1076
```

-continued

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1076
gttgcgtgtg tccgtacaaa                                                 20

<210> SEQ ID NO 1077
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1077
ctttattccg ttgcatgtcg                                                 20

<210> SEQ ID NO 1078
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1078
aagcgtaccc cactcgttaa                                                 20

<210> SEQ ID NO 1079
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1079
atccgagatc tgcgaattat                                                 20

<210> SEQ ID NO 1080
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1080
tcttgactcc gacttcgggc                                                 20

<210> SEQ ID NO 1081
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1081
```

-continued accatgatgt caccgccgca                                               20

<210> SEQ ID NO 1082
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1082
tcaacttaac ctcgagtccg                                               20

<210> SEQ ID NO 1083
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1083
ctacgagggc cgcgagcggt                                               20

<210> SEQ ID NO 1084
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1084
atgtgtcata gcggcgtagg                                               20

<210> SEQ ID NO 1085
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1085
tgtaacgatc tgggcggtct                                               20

<210> SEQ ID NO 1086
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1086
ccggatcggc tacgctacgg                                               20

<210> SEQ ID NO 1087
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 1087
caatattcga cctacgctcc                                                 20

<210> SEQ ID NO 1088
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1088
tgataaacga tgcgaactcg                                                 20

<210> SEQ ID NO 1089
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1089
tgattggggg tcgttcgcca                                                 20

<210> SEQ ID NO 1090
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1090
tagtcagtcg gcctccgtgc                                                 20

<210> SEQ ID NO 1091
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1091
aaccggctgc gcgtttgcaa                                                 20

<210> SEQ ID NO 1092
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1092
gtgcctgata gtgtgaagcg                                                 20
```

```
<210> SEQ ID NO 1093
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1093
cgacgaccca tttcggttat                                                    20

<210> SEQ ID NO 1094
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1094 gggggggtcta ataccgattg                                                   20

<210> SEQ ID NO 1095
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1095
tttttagacc taattcgcgc                                                    20

<210> SEQ ID NO 1096
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1096
tctacacgcg cgttcaaccg                                                    20

<210> SEQ ID NO 1097
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1097
cggggcgtac atgtgtggcc                                                    20

<210> SEQ ID NO 1098
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 1098
cgactcgctt aaccgtgcag                                              20

<210> SEQ ID NO 1099
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1099
gcgtacctat cgataaacca                                              20

<210> SEQ ID NO 1100
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1100
atatgagccc gacctctcga                                              20

<210> SEQ ID NO 1101
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1101
cgcgccgagg gcctcgttac                                              20

<210> SEQ ID NO 1102
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1102
ctccgacgac tacgcaagga                                              20

<210> SEQ ID NO 1103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1103
tatctctgga tgccgtcggt                                              20

<210> SEQ ID NO 1104
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 1104
tttcagttgt cgcgcgactc                                                 20

<210> SEQ ID NO 1105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1105
agtttacgtg gtccgatgtc                                                 20

<210> SEQ ID NO 1106
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1106
gcgtgacgcg atcaaacggt                                                 20

<210> SEQ ID NO 1107
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1107
actagctcca taacgtgtac                                                 20

<210> SEQ ID NO 1108
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1108
cgcatagtgt accgttgcgc                                                 20

<210> SEQ ID NO 1109
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1109
ccgcttgggc gctattaatt                                                 20
```

```
<210> SEQ ID NO 1110
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1110
gcttcattat taaccggcgt                                                20

<210> SEQ ID NO 1111
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1111
tatactcgcc tgtcacagcg                                                20

<210> SEQ ID NO 1112
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1112
acgctgttcg taaccgcggg                                                20

<210> SEQ ID NO 1113
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1113
agacgttgat ttaccggcca                                                20

<210> SEQ ID NO 1114
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1114
aacggtcaaa tccgtgaggg                                                20

<210> SEQ ID NO 1115
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1115
catagcaacg cccaaactcg                                              20

<210> SEQ ID NO 1116
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1116
cgtcaatgtg tccggacggt                                              20

<210> SEQ ID NO 1117
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1117
actgtcccat tgtacgacgg                                              20

<210> SEQ ID NO 1118
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1118
ctatcggccc gcagtgatgg                                              20

<210> SEQ ID NO 1119
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1119
gatcgagtga cacccacccg                                              20

<210> SEQ ID NO 1120
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1120
tccgcggcaa cgtttgggtc                                              20

<210> SEQ ID NO 1121
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1121
acttgtatac gacggctaga                                              20

<210> SEQ ID NO 1122
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1122
ttcgactgcg cacgccatga                                              20

<210> SEQ ID NO 1123
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1123
agcatggagt caacgtccgc                                              20

<210> SEQ ID NO 1124
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1124
tgacttgaca cgttcgatat                                              20

<210> SEQ ID NO 1125
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1125
ccggacttgt tatacttgat                                              20

<210> SEQ ID NO 1126
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1126
gtaccatgat aaccgtacta                                              20
```

<210> SEQ ID NO 1127
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1127
caccgctgcc ctagtaccgg                                              20

<210> SEQ ID NO 1128
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1128
ggatattcgc gcggtcttca                                              20

<210> SEQ ID NO 1129
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1129
aggcagcccg cgttagagat                                              20

<210> SEQ ID NO 1130
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1130
ttctccatac cgtaactccg                                              20

<210> SEQ ID NO 1131
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1131
acccgcatat gccgcctaag                                              20

<210> SEQ ID NO 1132
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 1132
cgaagtacac ggttctctcg                                           20

<210> SEQ ID NO 1133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1133
cacaatacgc ggcagaggtc                                           20

<210> SEQ ID NO 1134
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1134
tgagaccaat gccgcggaat                                           20

<210> SEQ ID NO 1135
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1135
ctcgacccag tagtagacgg                                           20

<210> SEQ ID NO 1136
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1136
cgtaccgaca gtagtccaag                                           20

<210> SEQ ID NO 1137
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1137
aattgtctga tcgcgccata                                           20

<210> SEQ ID NO 1138
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1138
tttagtcaga cgagccggat                                             20

<210> SEQ ID NO 1139
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1139
tgcgcgtcct gttatgaccg                                             20

<210> SEQ ID NO 1140
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1140
cttatcgatt tgggttcaac                                             20

<210> SEQ ID NO 1141
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1141
aacatgttaa gtcgcgttat                                             20

<210> SEQ ID NO 1142
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1142
tacgacatcg catggtaacg                                             20

<210> SEQ ID NO 1143
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1143
```
cagctgaccg ttaatcgata                                              20

<210> SEQ ID NO 1144
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1144
tacacgccct aagctagtaa                                              20

<210> SEQ ID NO 1145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1145
ccgactgccg agctaggcgt                                              20

<210> SEQ ID NO 1146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1146
gttgcggcga cctagatatc                                              20

<210> SEQ ID NO 1147
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1147
tagacgtcca ccgactctga                                              20

<210> SEQ ID NO 1148
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1148
tcacgcacga ctaagggaat                                              20

<210> SEQ ID NO 1149
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 1149
gcttatcgtt ccgctacgat                                               20

<210> SEQ ID NO 1150
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1150
accggttcag ccgccggaac                                               20

<210> SEQ ID NO 1151
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1151
ctacccgtct attacgatct                                               20

<210> SEQ ID NO 1152
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1152
tgtcgccgat ggtcagtcgc                                               20

<210> SEQ ID NO 1153
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1153
cgggcggtaa gagctctacg                                               20

<210> SEQ ID NO 1154
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1154
ggcaccgttc ggaaaccgac                                               20

<210> SEQ ID NO 1155
```

-continued

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1155
tctcgaataa attttctcgc                                           20

<210> SEQ ID NO 1156
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1156
gcattcttga gctccgcgcc                                           20

<210> SEQ ID NO 1157
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1157
attcggaccg ttatctcacc                                           20

<210> SEQ ID NO 1158
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1158
gttcttcaaa gacgggcggc                                           20

<210> SEQ ID NO 1159
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1159
ttccccgccc gtgcggtcat                                           20

<210> SEQ ID NO 1160
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1160
```
tagtaggttg atcgcgtcgc                                                20

<210> SEQ ID NO 1161
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1161
cgctcggtga cgtatacacg                                                20

<210> SEQ ID NO 1162
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1162
attatagcag cccccccgaat                                               20

<210> SEQ ID NO 1163
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1163
cggtcagtcg tcttcccgga                                                20

<210> SEQ ID NO 1164
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1164
tggatccgct tcgcacggcg                                                20

<210> SEQ ID NO 1165
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1165 aaaccccgc gcggagcgtc                                                 20

<210> SEQ ID NO 1166
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 1166
catagatccg cgattgtacg                                                   20

<210> SEQ ID NO 1167
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1167
gtttcaggaa cgacggcgag                                                   20

<210> SEQ ID NO 1168
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1168
accgtctcta ttatacggca                                                   20

<210> SEQ ID NO 1169
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1169
tgttcgccct ctcacgattg                                                   20

<210> SEQ ID NO 1170
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1170
aactaactca ctacgcacga                                                   20

<210> SEQ ID NO 1171
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1171
tcgctccgct agtagtgggt                                                   20
```

<210> SEQ ID NO 1172
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1172
tcggcgcagc ctaatgtata                                             20

<210> SEQ ID NO 1173
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1173
caacctgcct agcgacccgc                                             20

<210> SEQ ID NO 1174
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1174
gtcggctcat cggaaaatat                                             20

<210> SEQ ID NO 1175
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1175
gacagttgac gcgacggaga                                             20

<210> SEQ ID NO 1176
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1176
ccctgatgtg ctatacgcgc                                             20

<210> SEQ ID NO 1177
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 1177
taacccttga tcaaccgata                                              20

<210> SEQ ID NO 1178
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1178
ctattgggag cggcctctcg                                              20

<210> SEQ ID NO 1179
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1179
gcttatcgtc atgcgggtga                                              20

<210> SEQ ID NO 1180
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1180
tgatgccggt acccgtaact                                              20

<210> SEQ ID NO 1181
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1181
ggcgctactg taatgacggt                                              20

<210> SEQ ID NO 1182
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1182
acggattgct gacgctatca                                              20

<210> SEQ ID NO 1183
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 1183
taatgcgaat gcgacctctc                                                     20

<210> SEQ ID NO 1184
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1184
ttaactgggg ggaccggacg                                                     20

<210> SEQ ID NO 1185
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1185
cgcagagttc aaatccgcgc                                                     20

<210> SEQ ID NO 1186
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1186
tgtttatgcg gaacttccgc                                                     20

<210> SEQ ID NO 1187
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1187
acagaccgaa taaccgacga                                                     20

<210> SEQ ID NO 1188
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1188
tgacgctaag gcccgctaac                                                     20
```

```
<210> SEQ ID NO 1189
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1189
actcgcgaaa ccgtacatga                                                20

<210> SEQ ID NO 1190
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1190
ataggcgcac gggctactcc                                                20

<210> SEQ ID NO 1191
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1191
agattctcgc gtaaccagag                                                20

<210> SEQ ID NO 1192
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1192
acaattcggt ttatgcgcgt                                                20

<210> SEQ ID NO 1193
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1193
cgggttatag atagtcgtcg                                                20

<210> SEQ ID NO 1194
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 1194
agggttaggc tgacccgcga                                                   20

<210> SEQ ID NO 1195
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1195
agctatcccc acgttcgcgg                                                   20

<210> SEQ ID NO 1196
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1196
atcatgcctt cgcattaacc                                                   20

<210> SEQ ID NO 1197
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1197
tgggtcctaa acgcggttca                                                   20

<210> SEQ ID NO 1198
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1198
catactgtta tcgacccgca                                                   20

<210> SEQ ID NO 1199
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1199
tgagcgcttt cccgatccgg                                                   20

<210> SEQ ID NO 1200
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1200
gccttcctcg cagacccgac                                            20

<210> SEQ ID NO 1201
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1201
cccttaaagt gacggacgaa                                            20

<210> SEQ ID NO 1202
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1202
tggttcgacc aacatggttc                                            20

<210> SEQ ID NO 1203
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1203
tgggccatag tggcgcgtga                                            20

<210> SEQ ID NO 1204
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1204
tcatattaga caatctccgc                                            20

<210> SEQ ID NO 1205
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1205
tagccgagtt cacgccagta                                            20
```

```
<210> SEQ ID NO 1206
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1206
accaggcgcg gaccgcacat                                                      20

<210> SEQ ID NO 1207
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1207
gcgcgagtgc caaacgagtg                                                      20

<210> SEQ ID NO 1208
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1208
aacggctgcg cccgcggcaa                                                      20

<210> SEQ ID NO 1209
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1209
acggtcgagc acggttatga                                                      20

<210> SEQ ID NO 1210
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1210
tcatgttgcg tcgtccgtta                                                      20

<210> SEQ ID NO 1211
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 1211
cgctccgtat cctctcataa                                          20

<210> SEQ ID NO 1212
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1212
aaacgaggct gttcgtacac                                          20

<210> SEQ ID NO 1213
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1213
cacgtatact taggtcagcg                                          20

<210> SEQ ID NO 1214
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1214
atcgagcacc gagttgtgat                                          20

<210> SEQ ID NO 1215
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1215
tcactttaag caccccgcgc                                          20

<210> SEQ ID NO 1216
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1216
ctacttgtga cgacctcgcg                                          20

<210> SEQ ID NO 1217
<211> LENGTH: 20

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1217
ctacggatag gcgcgggtga                                              20

<210> SEQ ID NO 1218
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1218
gcttacctac tccgccccgc                                              20

<210> SEQ ID NO 1219
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1219
taacacgcac tcacgtccgg                                              20

<210> SEQ ID NO 1220
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1220
actcacctcg cacgatcgta                                              20

<210> SEQ ID NO 1221
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1221
acacccgtgt atgcaccggg                                              20

<210> SEQ ID NO 1222
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1222
```

```
gcataacggc cgagcaccac                                               20
```

<210> SEQ ID NO 1223
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1223

```
ccagcggacg gcgaactcca                                               20
```

<210> SEQ ID NO 1224
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1224

```
tgaccctctt aatctccggt                                               20
```

<210> SEQ ID NO 1225
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1225

```
ccctaaacca tagtttcgcc                                               20
```

<210> SEQ ID NO 1226
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1226

```
ccctagctcg gttagagaat                                               20
```

<210> SEQ ID NO 1227
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1227

```
gaattgagcc gcaactcggc                                               20
```

<210> SEQ ID NO 1228
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 1228
tgcttagggc ccttcggcgg                                               20

<210> SEQ ID NO 1229
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1229
tctccgggcc gtgttagacc                                               20

<210> SEQ ID NO 1230
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1230
atcacacgtt aaacggggcg                                               20

<210> SEQ ID NO 1231
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1231
gatcccctac gcttcaacct                                               20

<210> SEQ ID NO 1232
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1232
ttatttacgc gctgaacttg                                               20

<210> SEQ ID NO 1233
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1233
accgttgttt ccgtcgaaac                                               20

<210> SEQ ID NO 1234
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1234
cgagacgaat ccatcatgcg                                               20

<210> SEQ ID NO 1235
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1235
atatgctcga cccatcgtcc                                               20

<210> SEQ ID NO 1236
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1236
aacctcgtct catgtacgaa                                               20

<210> SEQ ID NO 1237
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1237
aattttttcg gaatctagcg                                               20

<210> SEQ ID NO 1238
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1238
agcgagtgtc cgtgacgttc                                               20

<210> SEQ ID NO 1239
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1239
```
aacgtcacca acctcgatcc                                                    20

<210> SEQ ID NO 1240
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1240
gtcctagatc ctatcgggag                                                    20

<210> SEQ ID NO 1241
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1241
catatactct tgcgctagac                                                    20

<210> SEQ ID NO 1242
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1242
acgtcgatgc ttatccgtct                                                    20

<210> SEQ ID NO 1243
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1243
ccgcgcatta acgatcagta                                                    20

<210> SEQ ID NO 1244
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1244
cctattagtc cggtttagtc                                                    20

<210> SEQ ID NO 1245
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 1245
acctcgtgca aatcggtggc                                                     20

<210> SEQ ID NO 1246
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1246
cacgcaggag cggcgacact                                                     20

<210> SEQ ID NO 1247
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1247
gtcggccgct taacccttc                                                      20

<210> SEQ ID NO 1248
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1248
tgatcaacgt cggtggacgg                                                     20

<210> SEQ ID NO 1249
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1249
gaaccacgag cgagcgtata                                                     20

<210> SEQ ID NO 1250
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1250
gaacccggga aacacgtccg                                                     20
```

```
<210> SEQ ID NO 1251
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1251
ggaaacgtta cattcgacgc                                                20

<210> SEQ ID NO 1252
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1252
aataggaact ccgcacccga                                                20

<210> SEQ ID NO 1253
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1253
gtagtgcgtg tgatgtcggg                                                20

<210> SEQ ID NO 1254
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1254
tttgacattt tcgtctcgcg                                                20

<210> SEQ ID NO 1255
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1255
aggtccgctg gcgcaatggg                                                20

<210> SEQ ID NO 1256
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 1256
ccgcccgggt gtgagttgag                                        20

<210> SEQ ID NO 1257
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1257
gccgagaggc gtaagcgcga                                        20

<210> SEQ ID NO 1258
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1258
taattcgcaa ctcggatcat                                        20

<210> SEQ ID NO 1259
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1259
taagactggg tgtcccgcgt                                        20

<210> SEQ ID NO 1260
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1260
ttacgcaaag ctgcgatgag                                        20

<210> SEQ ID NO 1261
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1261
ggacactcgc cgaccccact                                        20

<210> SEQ ID NO 1262
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 1262
tacgtctgcg caaatagaat                                              20

<210> SEQ ID NO 1263
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1263
atacgcgtga tgaccttatg                                              20

<210> SEQ ID NO 1264
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1264
cgcgcgactg cagctaatct                                              20

<210> SEQ ID NO 1265
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1265
acttcccgcg gttccgttga                                              20

<210> SEQ ID NO 1266
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1266
ttatgacctc gatgcgacat                                              20

<210> SEQ ID NO 1267
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1267
tgacgcgcct cggaccaacc                                              20
```

<210> SEQ ID NO 1268
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1268
tatcccgatc cggaaactag                                               20

<210> SEQ ID NO 1269
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1269
agtacactac atcgacttcg                                               20

<210> SEQ ID NO 1270
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1270
ttccagtata ccgaattcgc                                               20

<210> SEQ ID NO 1271
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1271
cccggcagac taactagcgc                                               20

<210> SEQ ID NO 1272
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1272
gcaacggaca gtcatcgaac                                               20

<210> SEQ ID NO 1273
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1273
gctagcgttc agcccgatgt                                               20

<210> SEQ ID NO 1274
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1274
tatgaactag gcgtaaacgg                                               20

<210> SEQ ID NO 1275
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1275
cgcgcggata tttaaacttc                                               20

<210> SEQ ID NO 1276
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1276
aagcagcgac tactcgacgc                                               20

<210> SEQ ID NO 1277
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1277
cccctatagg cgcgctaagg                                               20

<210> SEQ ID NO 1278
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1278
ccgagatggc tcggatagac                                               20

<210> SEQ ID NO 1279
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1279
agcacgcgca caagagccgc                                                     20

<210> SEQ ID NO 1280
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1280
tcgtaaagtc gcagcgacgt                                                     20

<210> SEQ ID NO 1281
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1281
gtctaacatc ggcgcacgtg                                                     20

<210> SEQ ID NO 1282
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1282
ttcaacgacg gaagacgcgc                                                     20

<210> SEQ ID NO 1283
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1283
cgctcggtaa ggtcgattgg                                                     20

<210> SEQ ID NO 1284
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1284 tagggtgcg cattagacta                                                      20
```

<210> SEQ ID NO 1285
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1285
gcccgacctc cacgtaaatc                                              20

<210> SEQ ID NO 1286
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1286
tatgaaacat ctcggcgacg                                              20

<210> SEQ ID NO 1287
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1287
ctgcttgaac gcctagacgg                                              20

<210> SEQ ID NO 1288
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1288
gggccggcac tctgtcggac                                              20

<210> SEQ ID NO 1289
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1289
gccgaccaac gatgaccacg                                              20

<210> SEQ ID NO 1290
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

```
                Synthetic oligonucleotide"

<400> SEQUENCE: 1290
atcgcggcgc gttaaggcag                                                    20

<210> SEQ ID NO 1291
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1291
cgacggttgt gctgaggctt                                                    20

<210> SEQ ID NO 1292
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1292
cggatcctcc cgtactatcc                                                    20

<210> SEQ ID NO 1293
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1293
ccattagtac gaacattgcg                                                    20

<210> SEQ ID NO 1294
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1294
gctcatactg atgaacgtcc                                                    20

<210> SEQ ID NO 1295
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1295
gccgaatcgc gttattccaa                                                    20

<210> SEQ ID NO 1296
<211> LENGTH: 20
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1296
caaggatcgt gccgtgattt                                               20

<210> SEQ ID NO 1297
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1297
gttaatattg tggcccgcac                                               20

<210> SEQ ID NO 1298
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1298
ccaacccggc atcgtccgct                                               20

<210> SEQ ID NO 1299
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1299
gcgagcgcta tcccggtgga                                               20

<210> SEQ ID NO 1300
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1300
gtgtatgacg agaagcgaag                                               20

<210> SEQ ID NO 1301
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1301
```
ggtgtggacc gcttttacgc                                              20

<210> SEQ ID NO 1302
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1302
gttataccac ctactatgac                                              20

<210> SEQ ID NO 1303
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1303
gatacgtgag gttgccggtg                                              20

<210> SEQ ID NO 1304
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1304
tatgccatat gcccgttttt                                              20

<210> SEQ ID NO 1305
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1305
tcatctacgg tatcgaaagg                                              20

<210> SEQ ID NO 1306
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1306
agtgtcacgg caaagtcgag                                              20

<210> SEQ ID NO 1307
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1307
caatggcgtc tgccgttcag                                                    20

<210> SEQ ID NO 1308
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1308
gctcgctgat gtgtaatccg                                                    20

<210> SEQ ID NO 1309
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1309
ggatacatcg gcgcgctagt                                                    20

<210> SEQ ID NO 1310
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1310
cagcaccacg cgtcgtgcgg                                                    20

<210> SEQ ID NO 1311
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1311
cgatgtcgaa agtcggtcaa                                                    20

<210> SEQ ID NO 1312
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1312
cgatacgcta tagaatagtc                                                    20

<210> SEQ ID NO 1313

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1313
gcgtggagtt cgtcgctctt                                                    20

<210> SEQ ID NO 1314
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1314
cacaacgcct accagcggac                                                    20

<210> SEQ ID NO 1315
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1315
atttgcccgt ccatacgcgg                                                    20

<210> SEQ ID NO 1316
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1316
cggtaagatg gttataccgt                                                    20

<210> SEQ ID NO 1317
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1317
gttcgcgggg gcttctatca                                                    20

<210> SEQ ID NO 1318
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1318
```
ggcaccgcgt ttattgcact                                           20

<210> SEQ ID NO 1319
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1319
tgacaaccgc ggtacctcta                                           20

<210> SEQ ID NO 1320
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1320
ggtcgctcga tttcatttaa                                           20

<210> SEQ ID NO 1321
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1321
gacgaaaggt cctacgaagt                                           20

<210> SEQ ID NO 1322
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1322
gtaccactta tcgaccttgc                                           20

<210> SEQ ID NO 1323
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1323
ttcaagtgtt atggacgcgc                                           20

<210> SEQ ID NO 1324
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 1324
tgagagcaag gcgcatacgc                                                    20

<210> SEQ ID NO 1325
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1325
cattctctga cgaatgcgcc                                                    20

<210> SEQ ID NO 1326
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1326 atcccccga cttagggatt                                                     20

<210> SEQ ID NO 1327
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1327
cagtgccggt agcggcacgg                                                    20

<210> SEQ ID NO 1328
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1328
acgacgtccg ctgtgtgtat                                                    20

<210> SEQ ID NO 1329
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1329
gcgctcgaac aaacatggtc                                                    20
```

```
<210> SEQ ID NO 1330
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1330
ggcaacgcac gctgggttgt                                                    20

<210> SEQ ID NO 1331
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1331
gctattccgc tcgtcaattt                                                    20

<210> SEQ ID NO 1332
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1332
ttcatcgcag atcgatttcg                                                    20

<210> SEQ ID NO 1333
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1333
ttcatccttc gtagcgcagc                                                    20

<210> SEQ ID NO 1334
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1334
tggttcacca ctcgagatcg                                                    20

<210> SEQ ID NO 1335
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1335
ttgagcggac cccctacaa                                                  20

<210> SEQ ID NO 1336
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1336
atgtgtatga agcccgtcat                                                 20

<210> SEQ ID NO 1337
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1337
taggtggcgc ccaatcggac                                                 20

<210> SEQ ID NO 1338
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1338
ctcgtgtcac tcctcggttc                                                 20

<210> SEQ ID NO 1339
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1339
atgccaatgc cgttgttagc                                                 20

<210> SEQ ID NO 1340
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1340
ccttacggcg gagaacgagt                                                 20

<210> SEQ ID NO 1341
<211> LENGTH: 20
<212> TYPE: DNA
<213> ORGANISM: Artificial Sequence
```

```
-continued

<220> FEATURE:
<221> NAME/KEY: source
<223> OTHER INFORMATION: /note="Description of Artificial Sequence:
      Synthetic oligonucleotide"

<400> SEQUENCE: 1341
cgcgcggatc ttccgtacaa                                               20

<210> SEQ ID NO 1342
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1342
cggcaagcgc attcctatgg                                               20

<210> SEQ ID NO 1343
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1343
tatgatcgta tggcccttcc                                               20

<210> SEQ ID NO 1344
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1344
atcgcctagc ccaagcgacg                                               20

<210> SEQ ID NO 1345
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1345
gcgatcgccg gtatagcttt                                               20

<210> SEQ ID NO 1346
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1346
ccgttcaatt atgctggcgt                                               20
```

-continued

```
<210> SEQ ID NO 1347
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1347
ccagctaacg ttttagtacg                                              20

<210> SEQ ID NO 1348
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1348
tccccttcgt cggcgccagg                                              20

<210> SEQ ID NO 1349
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1349
ttctgattag atacgtacga                                              20

<210> SEQ ID NO 1350
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1350
ttttcgtcga ctaagtcaag                                              20

<210> SEQ ID NO 1351
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1351
tcaattagtg gccgccaagc                                              20

<210> SEQ ID NO 1352
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 1352
tcagctacga tcggacccaa                                          20

<210> SEQ ID NO 1353
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1353
gcacgaaccc gttcgtatgg                                          20

<210> SEQ ID NO 1354
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1354
caatatgcac gtagcctcgt                                          20

<210> SEQ ID NO 1355
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1355
gaccgacggt atccctact                                           20

<210> SEQ ID NO 1356
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1356
ttgaagtagg gtcggattga                                          20

<210> SEQ ID NO 1357
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1357
aaggcgtaaa cgagtacacg                                          20

<210> SEQ ID NO 1358
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1358
aatgagcttc gagttcgtct                                              20

<210> SEQ ID NO 1359
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1359
acgtgttctc gtacttagct                                              20

<210> SEQ ID NO 1360
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1360
ttagccttgc cccgtcatac                                              20

<210> SEQ ID NO 1361
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1361
gccttttccg cccgttcaag                                              20

<210> SEQ ID NO 1362
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1362
cagaaactct taccgagcgc                                              20

<210> SEQ ID NO 1363
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1363
cttgaaaaag gggcgactat                                              20
```

<210> SEQ ID NO 1364
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1364
cctactaacg acgagtcaaa                                          20

<210> SEQ ID NO 1365
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1365
catttccggg gtccgatgca                                          20

<210> SEQ ID NO 1366
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1366
ccgggcgccg tatcccctac                                          20

<210> SEQ ID NO 1367
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1367
gagacccatt atgatcctag                                          20

CRISPR MEDIATED IN VIVO MODELING AND GENETIC SCREENING OF TUMOR GROWTH AND METASTASIS

RELATED APPLICATIONS AND/OR INCORPORATION BY REFERENCE

This application is a continuation-in-part of International patent application Serial No. PCT/US2015/00194 filed Dec. 23, 2015 and published as PCT Publication No. WO2016/108926 on Jul. 7, 2016 and which claims benefit of and priority to U.S. provisional application Ser. No. 62/098,285, filed Dec. 30, 2014.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT OF FEDERALLY SPONSORED RESEARCH

This invention was made with government support under grant numbers MH100706, CA133404, CA151884, CA14051 and HG008171 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 22, 2016, is named 47627_99_2092_SL.txt and is 363,391 bytes in size.

FIELD OF THE INVENTION

The present invention relates to modeling of tumorigenesis and metastasis. The present invention provides hereto in vivo systems for identifying genes involved in tumorigenesis and metastasis, as well as associated methodology and kits.

BACKGROUND OF THE INVENTION

Cancer genomes have complex landscape of mutations and diverse types of aberrations (Lawrence et al., 2013; Weinberg, 2007). A major challenge in understanding the cancer genome is to disentangle alterations that are driving the processes of tumor evolution (Garraway and Lander, 2013). Genetic screens are powerful tools for identifying causal genes in various hallmarks of cancer progression (Hanahan and Weinberg, 2011). Loss-of-function genetic screens have been applied in identifying tumor suppressors in liver cancer and skin cancer models (Schramek et al., 2014; Shao et al., 2014; Zender et al., 2008). Current genetic screens in cancer primarily utilize either RNA interference (RNAi) reagents, which act through knock-down of the mRNAs of the target genes, or overexpression of open reading frames.

Metastasis is a major lethal factor of cancer (Valastyan and Weinberg, 2011). Clinical observation suggested that the probability of detecting metastases in a patient positively correlates with the size of a primary tumor (Weinberg, 2007). Metastasis of cancer cells involves intravasation, survival and traveling in circulation, extravasation and clonal growth at a distant site (Valastyan and Weinberg, 2011). This is a multi-step process regulated by many genes in complex pathways. Many studies using various approaches had been carried out to search for, and to characterize, genes regulating metastases (Kang et al., 2003; Nguyen et al., 2009; Valiente et al., 2014; Winslow et al., 2011).

CRISPR (Clustered Regularly Interspaced Short Palindromic Repeats) Cas9-mediated gene disruption has been widely used in generating loss-of-function mutations in diverse organisms including mammals (Cong et al., 2013; Mali et al., 2013) (reviewed in (Hsu et al., 2014)). Cas9-based knockout screens have been applied in identifying essential genes and genes involved in drug resistance in various cell lines (Koike-Yusa et al., 2014; Shalem et al., 2014; Wang et al., 2014). However, in vivo studies using pooled libraries have been challenging, due to the complexity of the library and the representation requirement in a successful screen, as well as the complex dynamics of cellular behavior in animals.

Citation or identification of any document in this application is not an admission that such document is available as prior art to the present invention.

SUMMARY OF THE INVENTION

There exists a pressing need for alternative and robust systems and techniques for experimental in vivo modeling of cancer mutations, especially cancer mutations affecting not only tumorigenesis, but also tumor progression and tumor evolution, in particular tumor metastasis.

Aspects of this invention may address this need and provide related advantages. Aspects of the present invention may address herein discussed challenges and need in the art by advantageously providing methods, systems, compositions and models for ex vivo and in vivo modeling of multiple genetic, e.g., cancer or tissue-specific mutations. Aspects of the invention provide methods for enabling rapid and direct in vivo and ex vivo modeling of the dynamics of multiple genetic, e.g., cancer or tissue-specific mutations. Aspects of the present invention involve sequence targeting, such as genome perturbation or induction of multiple mutations using the Clustered Regularly Interspaced Short Palindromic Repeats (CRISPR) system or components thereof. The invention provides systematic reverse engineering of causal genetic variations, including through selective perturbation of individual, and moreover, multiple genetic elements. For instance, in non-human eukaryote, e.g., animal, such as fish, e.g., zebra fish, mammal, e.g., primate, e.g., ape, chimpanzee, macaque, rodent, e.g., mouse, rabbit, rat, canine or dog, livestock (cow/bovine, sheep/ovine, goat or pig), fowl or poultry, e.g., chicken, insect, arthropod or plant, e.g., dicot (e.g., nightshade such as tobacco, tuber such as potato) or monocot (e.g., corn) models that constitutively or through induction or through administration or delivery, have cells that contain Cas9. The invention provides tools for studying genetic interaction between multiple individual genetic elements by allowing selective perturbation of e.g., one or more cancer-associated or correlated gene(s)/genetic element(s). In an aspect, the invention provides methods for using one or more elements/components of a CRISPR-Cas system via a vector and/or particle and/or nanoparticle delivery formulation or system as a means to modify a target polynucleotide. In preferred embodiments, the delivery is via a viral vector (e.g., AAV, adenovirus, lentivirus). The CRISPR complex of the invention provides an effective means for modifying a target polynucleotide. The CRISPR complex of the invention has a wide variety of utilities including modifying (e.g., deleting, inserting, translocating, inactivating, activating) a target polynucleotide in a multiplicity of cell types in various tissues and organs, e.g., endothelial cells, skin, heart, muscle or lung. As such the CRISPR complex of the invention has a broad spectrum of applications in modeling of multiple genetic, e.g., cancer or tissue-specific mutations, and hence gene therapy, drug discovery, drug screening, disease diagnosis, and prognosis.

The present invention generally relates to methods for modeling tumor formation and/or tumor evolution. In certain aspects, the invention relates to methods for identifying genes which are involved in tumor formation and tumor evolution. More particularly methods are provided to identify genes whose loss-of function confers a proliferative or metastatic phenotype. The methods according to the invention foresee hereto the introduction of manipulated eukaryotic cells in a non-human eukaryote. The cells are in particular manipulated by the CRISPR/Cas system. Manipulation of the cells therefore entails the introduction or delivery of the components of the CRISPR/Cas system in the eukaryotic cells. Through the introduction or expression of Cas in combination with specific RNAs which are capable of guiding Cas to a genomic target locus, specific alterations of that target locus are accomplished, such as in particular gene inactivating mutations, but also epigenetic modifications or alterations of gene transcription. Cells so manipulated are subsequently introduced in a non-human eukaryote, after which in vivo tumor formation and/or evolution can be monitored, analyzed, or otherwise modeled.

Advantageously, the methods according to the present invention not only allow the identification of genes involved in primary tumor formation and evolution, but also the identification of genes involved in secondary tumor formation and evolution, i.e. metastases. In particular, the methods according to the invention allow for the identification of tumor suppressor genes and/or metastasis suppressor genes.

In a particularly preferred embodiment of the invention, the methods as described herein comprise administering a plurality of eukaryotic cells treated with the CRISPR/Cas system as described above, wherein each of the cells comprises or expresses a different RNA capable of guiding Cas to a genetic target locus of said eukaryote. Advantageously, a library of such RNAs may be used to this effect. The plurality of cells may be transplanted in a non-human eukaryote and allows genetic screening for genes involved in tumor formation and/or evolution. Specifically targeted genes which are involved in tumor formation and/or evolution become enriched over time. Moreover, analysis of the targeted genes in metastases allows identification of genes specifically involved in the development and/or progression of metastasis.

In related aspects, the invention provides for kits comprising one or more of the components for practicing the methods as described above. Such kits may thus comprise eukaryotic cells; Cas polypeptide, mRNA, or a polynucleotide such as an expression and/or delivery vector encoding Cas; and/or one or more RNA(s) capable of guiding Cas to a genomic target locus in the eukaryotic cell, or expression and/or delivery vector(s) encoding RNA(s) capable of guiding Cas to (a) genomic target locus/loci in the eukaryotic cell. Such kits may also include a non-human eukaryote into which the cells manipulated with the CRISPR/Cas system are to be introduced.

It will be appreciated that in the present methods, where the non-human transgenic Cas9 organism is multicellular, e.g., an animal or plant, the modification may occur ex vivo or in vitro, for instance in a cell culture and in some instances not in vivo. In other embodiments, it may occur in vivo. In an aspect, the invention provides a method of modifying an organism or a non-human organism by manipulation of a target sequence in a genomic locus of interest comprising: Delivering, e.g., via particle(s) or nanoparticle(s) or vector(s) (e.g., viral vector, e.g., AAV, adenovirus, lentivirus) a non-naturally occurring or engineered composition. The composition can comprise: A) I. RNA(s) having polynucleotide sequence(s), e.g., a CRISPR-Cas system chimeric RNA (chiRNA) having polynucleotide a sequence, wherein the polynucleotide sequence comprises: (a) a guide sequence capable of hybridizing to a target sequence in a eukaryotic cell, (b) a tracr mate sequence, and (c) a tracr sequence; wherein (a), (b) and (c) are arranged in a 5' to 3' orientation. The composition can also comprise A) II. a polynucleotide sequence encoding a CRISPR enzyme advantageously comprising at least one or more or two or more nuclear localization sequences. When transcribed, the tracr mate sequence hybridizes to the tracr sequence and the guide sequence directs sequence-specific binding of a CRISPR complex to the target sequence, wherein the CRISPR complex comprises the CRISPR enzyme complexed with (1) the guide sequence that is hybridizable to the target sequence, and (2) the tracr mate sequence that is hybridizable to the tracr sequence. The polynucleotide sequence encoding a CRISPR enzyme is DNA or RNA. When the Cas9 is already present in the cell, e.g., through the cell having already been provided (A) II. or through the cell expressing Cas9, e.g., through the cell having been transformed to express Cas9, e.g., Cas9 is expressed constitutively or conditionally or inducibly—for instance when the cell is part of or from a non-human transgenic eukaryote, e.g., animal, mammal, primate, rodent, etc as herein discussed—then (A) I. is provided as the CRISPR complex is formed in situ or in vivo. In an aspect, the invention provides a method of modifying an organism or a non-human organism by manipulation of a target sequence in a genomic locus of interest comprising: Delivering, e.g., via particle(s) or nanoparticle(s) or vector(s) (e.g., viral vector, e.g., AAV, adenovirus, lentivirus) a non-naturally occurring or engineered composition. The composition can comprise (B) I. polynucleotides comprising: (a) a guide sequence capable of hybridizing to a target sequence in a eukaryotic cell, and (b) at least one or more tracr mate sequences. The composition can also comprise (B) II. a polynucleotide sequence comprising a tracr sequence. The composition can also comprise (B) III. a polynucleotide sequence encoding a CRISPR enzyme advantageously comprising at least one or more or two or more nuclear localization sequences. When transcribed, the tracr mate sequence hybridizes to the tracr sequence and the guide sequence directs sequence-specific binding of a CRISPR complex to the target sequence. The CRISPR complex comprises the CRISPR enzyme complexed with (1) the guide sequence that is hybridizable to the target sequence, and (2) the tracr mate sequence that is hybridizable to the tracr sequence, and the polynucleotide sequence encoding a CRISPR enzyme is DNA or RNA. When the Cas9 is already present in the cell, e.g., through the cell having already been provided (B) III. or through the cell expressing Cas9, e.g., through the cell having been transformed to express Cas9, e.g., Cas9 is expressed constitutively or conditionally or inducibly—for instance when the cell is part of or from a non-human transgenic eukaryote, e.g., animal, mammal, primate, rodent, etc as herein discussed—then (B) I. and (B) II. are provided as the CRISPR complex is formed in situ or in vivo. Accordingly, components I and II or I, II and III or the foregoing embodiments can be delivered separately; for instance, in embodiments involving components I, II and III, components I and II can be delivered together, while component II can be delivered separately, e.g., prior to components I and II., so that the cell or eukaryote expresses Cas9. It will be further appreciated that heretofore it could not be expected that multiple, specific mutations, especially in the numbers herein discussed, e.g., 3-50 or more, or 3, 16, 32, 48 or 50 or more, could be able to be achieved. In undertaking embodiments of the invention, the Applicants have indeed divined that such multiple mutations are present in significant numbers of cells of the non-human eukaryote. For instance, it was surprising and unexpected that cells and tumors of the non-human transgenic organisms of the invention could have multiple mutations of the delivered RNA(s) (sgRNAs); indeed, all of the multiple mutations.

In some embodiments the invention comprehends delivering a CRISPR enzyme comprising delivering to a cell mRNA encoding the CRISPR enzyme, e.g., via nanoparticle complex(es). In some of these methods the CRISPR enzyme is a Cas9. In certain preferred embodiments the Cas9 enzyme is constitutively present, e.g., through knock-in. Thus, in a preferred embodiment of the invention, the Cas9 enzyme is constitutively present in vivo (e.g, a non-human transgenic eukaryote, animal, mammal, primate, rodent, etc) or ex vivo (cells comprising a vector containing nucleic acid molecule(s) for in vivo expression of the Cas9). The CRISPR enzyme is a type I or III CRISPR enzyme, preferably a type II CRISPR enzyme. This type II CRISPR enzyme may be any Cas enzyme. A preferred Cas enzyme may be identified as Cas9 as this can refer to the general class of enzymes that share homology to the biggest nuclease with multiple nuclease domains from the type II CRISPR system. Most preferably, the Cas9 enzyme is from, or is derived from, SpCas9 or SaCas9. It will be appreciated that SpCas9 or SaCas9 are those from or derived from *S. pyogenes* or *S. aureus* Cas9. By derived, Applicants mean that the derived enzyme is largely based, in the sense of having a high degree of sequence homology with, a wildtype enzyme, but that it has been mutated (modified) in some way as described herein It will be appreciated that the terms Cas and CRISPR enzyme are generally used herein interchangeably, unless otherwise apparent. The Cas enzyme can be for instance any naturally-occurring bacterial Cas9 as well as any chimaeras, mutants, homologs or orthologs. Many of the residue numberings used herein refer to the Cas9 enzyme from the type II CRISPR locus in *Streptococcus pyogenes* (annotated alternatively as SpCas9 or spCas9). However, it will be appreciated that this invention includes many more Cas9s from other species of microbes, e.g., orthologs of SpCas9, or Cas9s derived from microbes in addition to *S. pyogenes*, e.g., SaCas9 derived from *S. aureus*, St1Cas9 derived from *S. thermophilus* and so forth. The skilled person will be able to determine appropriate corresponding residues in Cas9 enzymes other than SpCas9 by comparison of the relevant amino acid sequences. Thus, where a specific amino acid replacement is referred to using the SpCas9 numbering, then, unless the context makes it apparent this is not intended to refer to other Cas9 enzymes, the disclosure is intended to encompass corresponding modifications in other Cas9 enzymes. Cas9 orthologs typically share the general organization of 3-4 RuvC domains and a HNH domain. The 5' most RuvC domain cleaves the non-complementary strand, and the HNH domain cleaves the complementary strand. All notations are in reference to the guide sequence. The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Francisella novicida* type II CRISPR locus), and the conserved Asp residue (D10) is mutated to alanine to convert Cas9 into a complementary-strand nicking enzyme. Similarly, the conserved His and Asn residues in the HNH domains are mutated to Alanine to convert Cas9 into a non-complementary-strand nicking enzyme. In some embodiments, both sets of mutations may be made, to convert Cas9 into a non-cutting enzyme. Thus, the Cas9 may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (e.g., D10 and H840) in the RuvC and HNH catalytic domains respectively; or the CRISPR enzyme can comprise one or more mutations selected from the group consisting of D10A, E762A, H840A, N854A, N863A or D986A and/or one or more mutations in a RuvC1 or HNH domain of the CRISPR enzyme or has a mutation as otherwise as discussed herein. In one aspect of the invention, the Cas9 enzyme may be fused to a protein, e.g., a TAG, and/or an inducible/controllable domain such as a chemically inducible/controllable domain. The Cas9 in the invention may be a chimeric Cas9 proteins; e.g., a Cas9 having enhanced function by being a chimera. Chimeric Cas9 proteins may be new Cas9 containing fragments from more than one naturally occurring Cas9. These may comprise fusions of N-terminal fragment(s) of one Cas9 homolog with C-terminal fragment(s) of another Cas9 homolog. The Cas9 can be delivered into the cell in the form of mRNA. The expression of Cas9 can be under the control of an inducible promoter.

The tracrRNA and direct repeat sequences can be mutant sequences or the invention can encompass RNA of the CRISPR-Cas system that includes mutant chimeric guide sequences that allow for enhancing performance of these RNAs in cells. A suitable promoter, such as the Pol III promoter, such as a U6 promoter, can be added onto the guide RNA that is advantageously delivered via AAV or particle or nanoparticle. Aspects of the invention also relate to the guide RNA being transcribed in vitro or ordered from a synthesis company and directly transfected. Expression of RNA(s), e.g., guide RNAs or sgRNA under the control of the T7 promoter driven by the expression of T7 polymerase in the cell is also envisioned. In an advantageous embodiment, the cell is a eukaryotic cell. In a preferred embodiment the eukaryotic cell is a human cell. In a more preferred embodiment the cell is a patient-specific cell, e.g., a cell in which 3-50 or more mutations associated or correlated with a patient's genetic disease, e.g., cancer, are expressed in the cell, e.g., via Cas9 being present in the cell and RNA(s) for such mutations delivered to the cell (e.g., any whole number between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector), whereby the CRISPR-Cas complexes result in the cells having the mutations and the cells and the eukaryote, e.g., animal, containing the cells being a model for the patient's genetic disease. In an advantageous embodiment, AAV may package U6 tandem sgRNA targeting up to about 50 genes.

A codon optimized sequence can be a sequence optimized for a eukaryote, or for specific organs such as the lung. It will be appreciated that where reference is made to a polynucleotide, where that polynucleotide is RNA and is said to 'comprise' a feature such as a tracr mate sequence, the RNA sequence includes the feature. Where the polynucleotide is DNA and is said to comprise a feature such as a tracr mate sequence, the DNA sequence is or can be transcribed into the RNA that comprises the feature at issue. Where the feature is a protein, such as the CRISPR enzyme, the DNA or RNA sequence referred to is, or can be, translated (and in the case of DNA transcribed first). Furthermore, in cases where an RNA encoding the CRISPR enzyme is provided to a cell, it is understood that the RNA is capable of being translated by the cell into which it is delivered. By manipulation of a target sequence, Applicants mean the alteration of the target sequence, which may include the epigenetic manipulation of a target sequence. This epigenetic manipulation may be of the chromatin state of a target sequence, such as by modification of the methylation state of the target sequence (i.e. addition or removal of methylation or methylation patterns or CpG islands), histone modification, increasing or reducing accessibility to the target sequence, or by promoting 3D folding. It will be appreciated that where reference is made to a method of modifying an organism or mammal including human or a non-human mammal or organism by manipulation of a target sequence in a genomic locus of interest, this may apply to the organism (or mammal) as a whole or just a single cell or population of cells from that organism (if the organism is multicellular). Applicants envisage, inter alia, a single cell or a population of cells and these may preferably be modified ex vivo and then re-introduced, e.g., transplanted to make transgenic organisms that express Cas9 in certain cells. The invention in some embodiments comprehends a method of modifying a eukaryote, such as a Cas9 transgenic eukaryote comprising delivering, e.g., via vector(s) and/or particle(s) and/or nanoparticles a non-naturally occurring or engineered composition. The composition comprises: I. a first regulatory element operably linked to (a) a first guide sequence capable of hybridizing to a first target sequence, and (b) at least one or more tracr mate sequences, II. a second regulatory element operably linked to (a) a second guide sequence capable of hybridizing to a second target sequence, and (b) at least one or more tracr mate sequences, III. a third regulatory element operably linked to (a) a third guide sequence capable of hybridizing to a third target sequence, and (b) at least one or more tracr mate sequences, and IV. a fourth regulatory element operably linked to a tracr sequence. There can be additional regulatory element(s) operably linked to additional guide sequence(s). Optionally, the composition can involve V. a fifth regulatory element operably linked to an enzyme-coding sequence encoding a CRISPR enzyme (e.g., for establishing the Cas9 transgenic eukaryote). Components I, II, III and IV (as well as any other regulatory element(s) linked to additional guide sequence(s)) are located on the same or different vectors and/or particles and/or nanoparticles of the system. When transcribed, the tracr mate sequence hybridizes to the tracr sequence and the first, second and the third guide sequences direct sequence-specific binding of a first, second and a third CRISPR complexes to the first, second and third target sequences respectively, wherein the first CRISPR complex comprises the CRISPR enzyme complexed with (1) the first guide sequence that is hybridizable to the first target sequence, and (2) the tracr mate sequence that is hybridizable to the tracr sequence, wherein the second CRISPR complex comprises the CRISPR enzyme complexed with (1) the second guide sequence that is hybridizable to the second target sequence, and (2) the tracr mate sequence that is hybridizable to the tracr sequence, and wherein the third CRISPR complex comprises the CRISPR enzyme complexed with (1) the third guide sequence that is hybridizable to the third target sequence, and (2) the tracr mate sequence that is hybridizable to the tracr sequence, whereby in a Cas9 transgenic eukaryote or cell thereof, at least three (3) mutations may be induced, and advantageously the mutations are correlated or associated with a genetic disease condition, whereby the eukaryote or cell becomes a model of the disease, e.g., cancer. The invention also provides a vector system as described herein. The system may comprise one, two, three or four different vectors; and the system may comprise one, two, three or four different nanoparticle complex(es) delivering the component(s) of the system. Components I, II, III and IV may thus be located on one, two, three or four different vectors, and may be delivered by one, two, three or four different particle or nanoparticle complex(es) or AAVs or components I, II, III and IV can be located on same or different vector(s)/particle(s)/nanoparticle(s), with all combinations of locations envisaged. And complexes that target lung or lung tissue or cells are advantageous.

In some methods of the invention any or all of the polynucleotide sequence encoding the CRISPR enzyme, the first and the second guide sequence, the first and the second tracr mate sequence or the first and the second tracr sequence, is/are RNA; and advantageously delivered via nanoparticle complex(es). Embodiments of the invention also comprehend the guide RNAs comprising a guide sequence fused to a tracr mate sequence and a tracr sequence. In an aspect of the invention the Cas protein is codon optimized for expression in a eukaryotic cell, preferably a mammalian cell or a human cell. The invention also comprehends an engineered, non-naturally occurring vector system. The system comprises one or more vectors comprising: (a) a first regulatory element operably linked to each of two or more e.g., three, CRISPR-Cas system guide RNAs that target a first target sequence, a second target sequence and a third target sequence respectively of a double stranded DNA molecule, wherein either strand of the double stranded DNA molecule may be targeted by each CRISPR-Cas system guide RNA. The system can also comprise (b) a second regulatory element operably linked to a Cas protein. Components (a) and (b) are located on same or different vectors of the system, but advantageously separate vectors as it is preferred that cells receiving (a) contain Cas9, e.g., via the cells being those of a transgenic Cas9 eukaryote (whereby (b) may have been administered to cells that gave rise to the eukaryote). The guide RNAs target DNA and at least three mutations are induced in the cells, e.g., mutations correlated to or associated with a genetic disorder such as cancer.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence; and advantageously the complex or a component thereof has been delivered via nanoparticle complex(es). In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. The mutation can be a mutation correlated to or associated with a genetic disease condition, such as cancer. In some embodiments, said mutation results in one or more amino acid changes in a protein expressed from a gene comprising the target sequence. In some embodiments, vectors are delivered to the eukaryotic cell in a transgenic Cas9 eukaryote. In some embodiments, said modifying takes place in said eukaryotic cell in a cell culture. In one aspect, the invention provides a method of generating a model eukaryotic cell or a model Cas9 transgenic eukaryote comprising mutated disease gene(s), e.g., having 3-50 mutations correlated to or associated with a genetic disease such as cancer (e.g., any whole number between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector). In some embodiments, a disease gene is any gene associated with an increase in the risk of having or developing a disease.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In certain embodiments, the target sequence is flanked or followed, at its 3' end, by a PAM suitable for the CRISPR enzyme, typically a Cas and in particular a Cas9. For example, a suitable PAM is 5'-NRG or 5'-NNGRR for SpCas9 or SaCas9 enzymes (or derived enzymes), respectively.

Delivery can be in the form of a vector which may be a plasmid or other nucleic acid molecule form, especially when the delivery is via a nanoparticle complex; and the vector also can be viral vector, such as a herpes, e.g., herpes simplex virus, lenti- or baculo- or adeno-viral or adeno-associated viral vectors, but other means of delivery are known (such as yeast systems, microvesicles, gene guns/means of attaching vectors to gold nanoparticles) and are provided, especially as to those aspects of the complex not delivered via a nanoparticle complex. A vector may mean not only a viral or yeast system (for instance, where the nucleic acids of interest may be operably linked to and under the control of (in terms of expression, such as to ultimately provide a processed RNA) a promoter), but also direct delivery of nucleic acids into a host cell; and advantageously the complex or a component thereof is delivered via nanoparticle complex(es). Also envisaged is a method of delivering the present CRISPR enzyme comprising delivering to a cell mRNA encoding the CRISPR enzyme; and advantageously the complex or a component thereof has been delivered via nanoparticle complex(es). It will be appreciated that in certain embodiments the CRISPR enzyme is truncated, and/or comprised of less than one thousand amino acids or less than four thousand amino acids, and/or is a nuclease or nickase, and/or is codon-optimized, and/or comprises one or more mutations, and/or comprises a chimeric CRISPR enzyme, and/or the other options as herein discussed. When not delivering via a nanoparticle complex, AAV is a preferred vector. In certain embodiments, multiple RNA(s) or guide RNAs or sgRNAs formulated in one or more delivery vehicles (e.g., where some guide RNAs are provided in a vector and others are formulated in nanoparticles); and these may be provided alone (e.g., when Cas9 is already in a cell) or with a Cas9 delivery system. In certain embodiments, the Cas9 is also delivered in a nanoparticle formulation. In certain instances the RNA(s) or guide RNA or sgRNA-vector and/or particle and/or nanoparticle formulation(s) and the Cas9 vector and/or particle and/or nanoparticle formulation(s) may be delivered separately or may be delivered substantially contemporaneously (i.e., co-delivery). Sequential delivery could be done at separate points in time, separated by days, weeks or even months. And as Cas9 is advantageously present in a transgenic organism in the practice of the invention, e.g., through being constitutively or conditionally or inducibly present, sequential delivery can include initially administering or delivering the Cas9 vector and/or particle and/or nanoparticle formulation(s) to cells that give rise to the non-human Cas9 transgenic eukaryote, and thereafter, at a suitable time in the life of the transgenic eukaryote, administering the RNA(s) or guide RNA or sgRNA-vector and/or particle and/or nanoparticle formulation(s), e.g., so as to give rise to one or more, advantageously 3-50 mutations in the transgenic eukaryote (e.g., any whole number between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector), and advantageously the mutations are associated or correlated with a genetic disease, whereby the transgenic eukaryote is a model of the genetic disease, e.g., cancer. Multiple mutations may thus be introduced using any number of sgRNAs, e.g. the vector may comprise at least 3 sgRNAs, at least 8 sgRNAs, at least 16 sgRNAs, at least 32 sgRNAs, at least 48 sgRNAs, or at least 50 sgRNAs. Alternatively, the vector may comprise 1-2 sgRNAs, 1-3 sgRNAs, 1-4 sgRNAs, 1-5 sgRNAs, 3-6 sgRNAs, 3-7 sgRNAs, 3-8 sgRNAs, 3-9 sgRNAs, 3-10 sgRNAs, 3-16 sgRNAs, 3-30 sgRNAs, 3-32 sgRNAs, 3-48 sgRNAs or 3-50 sgRNAs. In certain embodiments, vector (e.g., AAV, adenovirus, lentivirus) and/or particle and/or nanoparticle formulations comprising one or more RNA(s) e.g. guide RNAs or sgRNA are adapted for delivery in vitro, ex vivo or in vivo in the context of the CRISPR-Cas system, e.g., so as to form CRISPR-Cas complexes in vitro, ex vivo or in vivo, to different target genes, different target cells or different target different tissues/organs, with different target genes and/or cells of the lung. Multiplexed gene targeting using nanoparticle formulations comprising one or more guide RNAs are also envisioned. In an embodiment, a nanoparticle formulation comprising one or more components of the CRISPR-Cas system is provided. In an embodiment, a RNA(s) or gRNA or sgRNA-nanoparticle formulation comprising one or more guide RNAs or sgRNA is provided. In certain embodiments, a composition comprising a nanoparticle formulation comprising one or more components of the CRISPR-Cas system is provided. In certain embodiments, a composition, e.g., a pharmaceutical or veterinary composition, comprising a vector (e.g., AAV, adenovirus, lentivirus) and/or particle and/or nanoparticle formulation comprising one or more components of the CRISPR-Cas system and/or nucleic acid molecule(s) coding therefor, advantageously with such nucleic acid molecule(s) operably linked to promoter(s) is provided. Accordingly, in certain embodiments, it may be useful to deliver the RNA(s) or guide RNA or sgRNA, e.g., vector and/or particle and/or nanoparticle formulations separately from the Cas9 or nucleic acid molecule(s) coding therefor. A dual-delivery system is envisaged such that the Cas 9 may be delivered via a vector and the RNA(s), e.g., guide RNAs or sgRNA are/is provided in a particle or nanoparticle formulation, for example, first Cas9 vector is delivered via a vector system followed by delivery of sgRNA-nanoparticle formulation. Vectors may be considered in the broadest light as simply any means of delivery, rather than specifically viral vectors.

In one aspect, the present invention provides a Cas9 transgenic eukaryote, e.g., mouse. In certain preferred embodiments, the Cas 9 transgenic eukaryote, e.g., mouse comprises a Cas9 transgene knocked into the Rosa26 locus. In one aspect, the present invention provides a Cas9 transgenic eukaryote, e.g., mouse wherein Cas9 transgene is driven by the ubiquitous CAG promoter thereby providing for constitutive expression of Cas9 in all tissues/cells/cell types of the mouse. In one aspect, the present invention provides a Cas9 transgenic eukaryote, e.g., mouse wherein the Cas9 transgene driven by the ubiquitous CAG promoter further comprises a Lox-Stop-polyA-Lox (LSL) cassette (Rosa26-LSL-Cas9 mouse) thereby rendering Cas9 expression inducible by the Cre recombinase. In one aspect, the present invention provides a constitutive Cas9 expressing eukaryote, e.g., mouse line obtained by crossing of the Rosa26-LSL-Cas9 mouse with a beta-actin-Cre eukaryote, e.g., mouse line. In certain embodiments, progeny (or progenies) derived from said Cas9 expressing eukaryote, e.g., mouse line, may be successfully bred over at least five generations without exhibiting increased levels of genome instability or cellular toxicity. In one aspect, the present invention provides a modular viral vector construct comprising a plurality of sgRNAs driven by a single RNA polymerase III promoter (e.g., U6), wherein the sgRNAs are in tandem, or where each of the sgRNAs is driven by one RNA polymerase III promoter. In one aspect, the present invention provides a modular viral vector construct comprising one or more cassettes expressing Cre recombinase, a plurality of sgRNAs to guide Cas9 cutting, and optionally including a Homology Directed Repair (HDR) template to model the dynamics of a complex pathological disease or disorder involving two or more genetic elements simultaneously using a single vector construct (in embodiments where the HDR template is not involved, the cutting creates the mutation to model the dynamics of a complex pathological disease or disorder (e.g., loss of function or gain of function). In certain non-limiting embodiments, the complex pathological disease or disorder is cancer. It can be appreciated that any kind of cancer of any tissue type are within the scope of the present invention. In a preferred embodiment, the present invention provides for modeling of lung cancer. In one aspect, the present invention provides a modular viral vector construct to model the dynamics of multiple cancer lesions simultaneously using a single vector.

In certain embodiments, the modular viral vector construct comprises one or more cassettes expressing Cre recombinase, a plurality of sgRNAs to guide Cas9 cutting, and optionally one or more Homology Directed Repair (HDR) template(s) to introduce specific gain-of-function mutations or precise sequence substitution in target loci. In one aspect, the present invention provides a method for simultaneously introducing multiple mutations ex vivo in a tissue, organ or a cell line, or in vivo in the same animal comprising delivering a single viral vector construct, wherein the viral vector construct comprises one or more cassettes expressing Cre recombinase, a plurality of sgRNAs to guide Cas9 cutting, and optionally HDR template(s) for achieving targeted insertion or precise sequence substitution at specific target loci of interest. In one aspect, the present invention provides a method for generating loss-of-function mutations in two or more tumor suppressor genes and gain-of-function mutations in one or more proto-oncogenes using a modular viral vector construct which comprises one or more cassettes expressing Cre recombinase, a plurality of sgRNAs to guide Cas9 cutting, and optionally inhibiting one or more HDR template(s). In certain non-limiting embodiments, tumor suppressor genes may include p53 and Lkb1 (serine/threonine kinase 11). In certain non-limiting embodiments, the proto-oncogene may include Kras. Heretofore, it had not been expected that multiple mutations wherein some mutations are loss of function (knock out) and some mutations are gain of function (knock in) could be achieved; and it had not been expected to achieve mutations in p53, Lkb1 and Kras and nor had there heretofore been any direction to select these particular genes for being mutated together. It can be readily appreciated that mutations in any cancer-associated gene is within the scope of the present invention. In one aspect, the present invention provides a method for delivering ex vivo or in vivo of any of the modular viral constructs disclosed herein using an AAV. Selection of the AAV serotype is based on its suitability and specificity for a tissue type. In certain preferred embodiments, AAV9 is used for delivery to lung tissue. In one aspect, the present invention provides a method for ex vivo and/or in vivo genome editing comprising delivering any of the above modular viral vector constructs, which comprise one or more cassettes expressing Cre recombinase, a plurality of sgRNAs to guide Cas9 cutting, and optionally one or more HDR template(s), into a Cas9 transgenic eukaryote (e.g., Rosa26-LSL-Cas9). In certain embodiments, the viral vector is AAV9. In one aspect, the present invention provides a Cas9 transgenic non-human eukaryote, e.g., animal model for lung cancer said model having loss-of-function mutations in p53 and/or Lkb1 and gain-of-function mutation in Kras. It can be appreciated that using the novel CRISPR-Cas9 tools disclosed herein, Cas9 transgenic non-human eukaryote, e.g., animal model with multiple mutations in any number of loci can be envisioned and are within the scope of the present invention. It will be appreciated that such a transgenic non-human eukaryote, e.g., animal model provides a valuable tool for research purposes, e.g., to delineate specific roles/contribution of individual mutations to cancer progression, to recapitulate specific combinations of mutations in a given cancer type, and opens the door for developing and testing new therapeutic interventions for cancers involving mutations at multiple loci. Such uses are within the scope of the present invention. In one aspect, the present invention provides a method of treating or inhibiting the development of a genetic disease in a subject in need thereof, comprising providing individualized or personalized treatment (or an individualized or personalized model or patient specific-modeling)

comprising: delivering RNA(s), e.g., sgRNA, that targets a genetic locus correlated or associated with the genetic disease, e.g., cancer, to a Cas9 non-human transgenic eukaryote (e.g., animal, mammal, primate, rodent, fish etc as herein discussed), e.g., via vector such as AAV, adenovirus, lentivirus, or particle(s) or nanoparticle(s), whereby mutation(s), advantageously a plurality, e.g., 3-50 mutations (e.g., any whole number between 3 and 50 of mutations, with it noted that in some embodiments there can be up to 16 different RNA(s), e.g., sgRNAs each having its own a promoter, in a vector, such as AAV, and that when each sgRNA does not have its own promoter, there can be twice to thrice that amount of different RNA(s), e.g., sgRNAs, e.g., 32 or even 48 different guides delivered by one vector), are induced in the eukaryote and the eukaryote is a model for the disease; and obtaining and/or extrapolating data from the Cas9 non-human transgenic eukaryote to humans to provide individualized or personalized treatment. The obtaining and/or extrapolating data can be subjecting the eukaryote to putative treatment(s) and/or therapy(ies), e.g., gene therapy, ascertaining whether such putative treatment(s) and/or therapy(ies) give rise to remission or treatment or alleviation or mitigation or stasis of the disease, and if so, then administering in dosing scaled to a 70 kg individual or subject, the putative treatment(s) and/or therapy(ies). The invention thus allows for one to ascertain whether a particular treatment and/or therapy may be effective as to a particular individual's disease.

In certain aspects the invention provides vector(s), particle(s) or nanoparticle(s) containing nucleic acid molecule(s), whereby in vivo in a eukaryotic cell containing or conditionally or inducibly expressing Cas9: the vector(s) express(es) a plurality of RNAs to guide the Cas9 and optionally delivers donor templates (e.g., HDR templates, and in certain embodiments advantageously includes and delivers such donor templates), and optionally in the event Cas9 is conditionally or inducibly expressed in the cell that which induces Cas9, e.g., Cre recombinase; whereby a plurality of specific mutations or precise sequence substitutions in a plurality of target loci are introduced. The vector(s) can be a viral vector such as lentivirus, adenovirus, or adeno-associated virus (AAV), e.g., AAV6 or AAV9. The Cas9 can be from S. thermophiles, S. aureus, or S. pyogenes. The eukaryotic cell can comprise a Cas9 transgene is functionally linked to a constitutive promoter, or a tissue specific promoter, or an inducible promoter; and, the eukaryotic cell can be part of a non-human transgenic eukaryote, e.g., a non-human mammal, primate, rodent, mouse, rat, rabbit, canine, dog, cow, bovine, sheep, ovine, goat, pig, fowl, poultry, chicken, fish, insect or arthropod; advantageously a mouse. The isolated eukaryotic cell or the non-human transgenic eukaryote can express an additional protein or enzyme, such as Cre; and, the expression of Cre can be driven by coding therefor functionally or operatively linked to a constitutive promoter, or a tissue specific promoter, or an inducible promoter.

The RNAs to guide Cas9 can comprise CRISPR RNA and transactivating (tracr) RNA. The tracr mate and the tracr sequence can be connected to form a transactivating (tracer) sequence. The tracr mate and the tracr sequence can optionally be designed to form a single guide RNA (sgRNA). Indeed, it is advantageous that the RNAs to guide Cas9 can comprise chimeric single guide RNA (sgRNA). The tracr sequence and tracr mate sequence along the length of the shorter of the two when optimally aligned can be about or more than about 25%, 30%, 40%, 50%, 60%, 70%, 80%, 90%, 95%, 97.5%, 99%, or higher. The tracr sequence can be about or more than about 5, 6, 7, 8, 9, 10, 11, 12, 13, 14, 15, 16, 17, 18, 19, 20, 25, 30, 40, 50, or more nucleotides in length. The degree of complementarity between a guide sequence and its corresponding target sequence can be about or more than about 50%, 60%, 75%, 80%, 85%, 90%, 95%, 97.5%, 99%, or 100%. A guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. A guide or RNA or sgRNA can be less than about 75, 50, 45, 40, 35, 30, 25, 20, 15, 12, or fewer nucleotides in length.

The vector(s) can include the regulatory element(s), e.g., promoter(s). The vector(s) can comprise at least 3 or 8 or 16 or 32 or 48 or 50 RNA(s) (e.g., sgRNAs), such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNA(s) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short, www.nature.com/mt/journal/v16/n9/abs/mt2008144a.html). In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters-especially as to the numbers of RNAs or guides or sgRNAs discussed herein, without any undue experimentation.

The RNA(s), e.g., sgRNA(s), can be functionally or operatively linked to regulatory element(s) and hence the regulatory element(s) drive expression. The promoter(s) can be constitutive promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the 0-actin promoter, the phosphoglycerol kinase (PGK) promoter, and the EF1α promoter. An advantageous promoter is the promoter is U6.

Advantageously, each RNA (e.g., sgRNA) is specific to a different target sequence. Each different target sequence can be associated with or correlated to a form of cancer. Each RNA or sgRNA can be specific to a different target sequence but these RNA(s) or sgRNA(s) target specific gene sequences associated with or correlated to cancer, advantageously a particular type or form of cancer; for instance each RNA or sgRNA can be specific to a different target sequence but the target sequences of the RNA(s) or sgRNA(s) are associated with or correlated to the same type or form of cancer. The cancer selected from the group consisting of Lung cancer, Lung adenocarcinoma, Lung squamous cell carcinoma, Acute myeloid leukemia, Basal cell carcinoma (skin), Bladder cancer, Breast cancer, Carcinoid, Chronic lymphocytic leukemia, Colorectal cancer, Diffuse large B-cell lymphoma, Endometrial, Esophageal cancer, Esophageal adenocarcinoma, Glioblastoma multiforme, Glioma, Head and neck cancer, Kidney clear cell cancer, Medulloblastoma, Melanoma, Multiple myeloma, Nasopharyngeal, Neuroblastoma, Ovarian cancer, Prostate cancer, Rhabdoid tumor, Testicular germ cell tumor, Thyroid cancer, and Urinary bladder cancer.

Advantageously, each sgRNA can be driven by an independent U6 promoter. The vector can be an AAV, e.g., an AAV9. Each of the sgRNAs can target a different genetic locus associated with a multigenic disease or disorder, e.g., a cancer, such as lung cancer. The sgRNAs can target one or more tumor suppressor genes so as to introduce loss-of-function mutations. The tumor suppressor genes can be, without limitation, p53 and/or Lkb1. The sgRNAs can target one or more proto-oncogenes or oncogenes so as to introduce a loss-of-function mutation. The proto-oncogenes or oncogenes can be Kras. The sgRNAs can target one or more of p53, Lkb1, or Kras loci. From 3 to 50 specific mutations or precise sequence substitutions in from 3 to 50 target loci can be introduced. More generally, the sgRNAs can target one or more, e.g., 3 to 50 loci specific to a cancer.

In an aspect, the invention provides a method for modeling tumor formation and/or tumor evolution. In an embodiment of the invention, the method comprises the steps of providing an isolated Cas transgenic eukaryotic cell expressing Cas or capable of inducibly and/or conditionally expressing Cas, introducing into said Cas transgenic eukaryotic cell one or more RNA capable of guiding Cas to one or more genetic target locus of a eukaryote, or introducing into said Cas transgenic eukaryotic cell one or more polynucleotide encoding one or more RNA capable of guiding Cas to one or more genetic target locus of a eukaryote, introducing said Cas transgenic eukaryotic cell into a non-human eukaryote, and analyzing tumor formation and/or tumor evolution in said non-human eukaryote.

In one embodiment, the method comprises introducing a plurality of Cas transgenic eukaryotic cells in a non-human eukaryote, each cell of said plurality of Cas transgenic eukaryotic cells comprising a different RNA capable of guiding Cas to a genetic target locus of said eukaryote; or each cell of said plurality of Cas transgenic eukaryotic cells comprising a different polynucleotide encoding an RNA capable of guiding Cas to a genetic target locus of said eukaryote.

In an embodiment of the invention, the method comprises identifying one or more genes which are involved in tumor formation and/or evolution. In certain embodiments, the method comprises analyzing tumor metastasis. In certain embodiments, the method comprises analyzing gene expression. In certain embodiments, the method comprises analyzing gene expression in the tumor. In certain such embodiments, the method comprises identifying one or more of said RNAs introduced into the transgenic cell.

In an aspect, the invention provides a method for identifying genes which are involved in tumor formation and/or tumor metastasis. The method comprises the steps of providing an isolated Cas transgenic eukaryotic cell expressing Cas or capable of inducibly and/or conditionally expressing Cas, introducing into the Cas transgenic eukaryotic cell one or more RNA capable of guiding Cas to one or more genetic target locus of a eukaryote, or introducing into said Cas transgenic eukaryotic cell one or more polynucleotide encoding one or more RNA capable of guiding Cas to one or more genetic target locus of a eukaryote, introducing a plurality of said Cas transgenic eukaryotic cells into a non-human eukaryote, each cell of said plurality of Cas transgenic eukaryotic cells comprising a different RNA capable of guiding Cas to a genetic target locus, or each cell of said plurality of Cas transgenic eukaryotic cells comprising a different polynucleotide encoding an RNA capable of guiding Cas to a genetic target locus, and identifying genes which are involved in tumor formation and/or tumor metastasis in said non-human eukaryote based on the identification in said tumor or tumor metastasis of one or more of said RNA capable of guiding Cas to one or more genetic target locus.

In certain embodiments, the genes involved in tumor formation, tumor evolution, and/or tumor metastasis are tumor suppressor genes and/or metastasis suppressor genes. In certain embodiments, the method comprises introducing one or more genomic mutations into said Cas transgenic eukaryotic cell.

In an embodiment of the invention, the RNA capable of guiding Cas comprises CRISPR RNA and transactivating (tracr) RNA. In an embodiment of the invention, the RNA capable of guiding Cas comprises a single guide (sg) RNA.

In an embodiment of the invention, the RNA capable of guiding Cas is introduced into said Cas transgenic eukaryotic cell by means of transduction. In an embodiment of the invention, the RNA capable of guiding Cas is introduced in said Cas transgenic eukaryotic cell by means of lentiviral transduction.

In certain embodiments, the one or more polynucleotide encoding one or more RNA capable of guiding Cas is capable of constitutively expressing said RNA or alternatively inducibly and/or conditionally expressing said RNA.

In an embodiment of the invention, the Cas transgenic eukaryotic cell is a tumor cell. In an embodiment of the invention, the Cas transgenic eukaryotic cell is a non-metastasizing tumor cell.

In an embodiment of the invention, the Cas transgenic eukaryotic cell is characterized by oncogenic expression of Kras (KrasG12D), homozygous p53 loss (p53−/−), and/or heterozygous Dicer1 loss (Dicer+/−), preferably all.

In an embodiment of the invention, the Cas is a type II Cas. In certain embodiments, the Cas is Cas9. In certain embodiments, the Cas is a Cas originating from *Streptococcus pyogenes*, *Streptococcus* thermophiles, or *Staphylococcus aureus*.

In an embodiment of the invention, the Cas is a mutated Cas having an altered catalytic activity. In one such embodiment, the Cas is a catalytically inactive Cas. In another embodiment, the Cas is fused to an enzyme which modifies genomic DNA or genomic DNA architecture. In another embodiment, the Cas is fused to a polypeptide which alters gene transcription.

In an embodiment, the Cas transgenic eukaryotic cell is a cell from an animal. In certain such embodiments, the Cas transgenic eukaryotic cell is a cell from a eukaryote selected from the group consisting of mammal, primate, rodent, mouse, rat, rabbit, canine, dog, cow, bovine, sheep, ovine, goat, pig, fowl, poultry, chicken, fish, insect, and arthropod. In certain such embodiments, the Cas transgenic eukaryotic cell is a mammalian cell, preferably a mouse cell. In certain embodiments, the eukaryote into which is inserted a Cas transgenic eukaryotic cell is an animal, preferably a mammal. In certain embodiments, the eukaryote is an immunocompromised animal, preferably an immunocompromised mammal. In certain embodiments, the eukaryote is selected from mammal, primate, rodent, mouse, rat, rabbit, canine, dog, cow, bovine, sheep, ovine, goat, pig, fowl, poultry, chicken, fish, insect, and arthropod. In an embodiment of the invention the eukaryote is a mouse.

In an embodiment of the invention, the method comprises introducing Cas transgenic eukaryotic cells subcutaneously.

In an embodiment of the invention, the selected tumor comprises, without limitation, lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdoid tumor, thyroid cancer, or urinary bladder cancer.

In an aspect, the invention provides a tumor sample or a tumor metastasis sample isolated from a non-human eukaryote after introduction of a Cas transgenic eukaryotic cell. In an non-limiting embodiment of the invention, the tumor is selected from lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdoid tumor, thyroid cancer, and urinary bladder cancer.

In an aspect, the invention provides a cell from the tumor sample or the tumor metastasis sample from a non-human eukaryote after introduction of a Cas transgenic eukaryotic cell. In an aspect, the invention provides a cell line obtained or obtainable from the tumor sample or the tumor metastasis sample.

In an aspect, the invention provides a method for generating a non-human eukaryote model for tumor formation and/or tumor evolution, comprising the steps of providing an isolated Cas transgenic eukaryotic cell expressing Cas or capable of inducibly and/or conditionally expressing Cas, introducing in said Cas transgenic eukaryotic cell one or more RNA capable of guiding Cas to one or more genetic target locus of a eukaryote, or introducing in said Cas transgenic eukaryotic cell one or more polynucleotide encoding one or more RNA capable of guiding Cas to one or more genetic target locus of a eukaryote, introducing a plurality of the Cas transgenic eukaryotic cell after step (b) in a non-human eukaryote, each cell of said plurality of Cas transgenic eukaryotic cells comprising a different RNA capable of guiding Cas to a genetic target locus, or each cell of said plurality of Cas transgenic eukaryotic cells comprising a different polynucleotide encoding an RNA capable of guiding Cas to a genetic target locus.

In an aspect, the invention provides a method for generating a non-human eukaryote model for identifying genes involved in formation and/or tumor evolution, comprising the steps of providing an isolated Cas transgenic eukaryotic cell expressing Cas or capable of inducibly and/or conditionally expressing Cas, introducing in said Cas transgenic eukaryotic cell one or more RNA capable of guiding Cas to one or more genetic target locus of a eukaryote or introducing in said Cas transgenic eukaryotic cell one or more polynucleotide encoding one or more RNA capable of guiding Cas to one or more genetic target locus of a eukaryote, introducing a plurality of the Cas transgenic eukaryotic cells in a non-human eukaryote, each cell of said plurality of Cas transgenic eukaryotic cells comprising a different RNA capable of guiding Cas to a genetic target locus, or each cell of said plurality of Cas transgenic eukaryotic cells comprising a different polynucleotide encoding an RNA capable of guiding Cas to a genetic target locus. In an aspect, the invention provides a non-human eukaryote obtained by In an aspect, the invention provides a non-human eukaryote obtained or obtainable from the eukaryotic model. In an embodiment the animal is a mammal. In another embodiment, the eukaryote is an immunocompromised animal or mammal. In another embodiment, the eukaryote is selected from a mammal, primate, rodent, mouse, rat, rabbit, canine, dog, cow, bovine, sheep, ovine, goat, pig, fowl, poultry, chicken, fish, insect, or arthropod. In yet another embodiment, the eukaryote is a mouse.

In an aspect, the invention provides a method for determining whether a compound is capable of suppressing tumor formation and/or tumor evolution comprising providing a non-human eukaryote model of tumor formation and/or tumor evolution, administering the compound to the animal model, and determining whether or not the compound is capable of suppressing tumor formation and/or tumor evolution in said animal model.

In an aspect, the invention provides a kit comprising an isolated Cas transgenic eukaryotic cell expressing Cas or capable of inducibly and/or conditionally expressing Cas, one or more RNA capable of guiding Cas to one or more genetic target locus, or one or more polynucleotide encoding one or more RNA capable of guiding Cas to one or more genetic target locus. In an embodiment the kit comprises a non-human eukaryote. In an embodiment, the kit comprises instructions for performing a method for modeling tumor formation and/or tumor evolution, a method for identifying genes which are involved in tumor formation and/or tumor metastasis, or a method for generating a non-human eukaryote model for identifying genes involved in tumor formation and/or tumor evolution, or a method for determining whether a compound is capable of suppressing tumor formation. In an embodiment, the kit comprises one or more RNA capable of guiding Cas to one or more genetic target locus, or one or more polynucleotide encoding one or more RNA capable of guiding Cas to one or more genetic target locus are comprised in a vector, preferably a lentiviral vector. In an embodiment, the kit comprises a plurality of RNAs capable of guiding Cas to a genetic target locus; or a plurality of polynucleotides encoding an RNA capable of guiding Cas to a genetic target locus. In an embodiment, the kit comprises an RNA capable of guiding Cas comprises CRISPR RNA and transactivating (tracr) RNA. In an embodiment, the kit comprises an RNA capable of guiding Cas comprises a single guide (sg) RNA. In another embodiment, the kit comprises a polynucleotide encoding one or more RNA capable of guiding Cas is capable of constitutively expressing said RNA or alternatively inducibly and/or conditionally expressing said RNA. In an embodiment, the Cas transgenic eukaryotic cell is a tumor cell.

In an embodiment, the Cas transgenic eukaryotic cell of the kit is a non-metastasizing tumor cell. In an embodiment, the Cas is a type II Cas. 61. In an embodiment, the Cas is Cas9. In an embodiment, the Cas9 originated from *Streptococcus pyogenes, Streptococcus thermophiles,* or *Staphylococcus aureus*. In another embodiment, the Cas is a mutated Cas having an altered catalytic activity. In one such embodiment, the Cas is a catalytically inactive Cas. In another embodiment, the Cas is fused to an enzyme which modifies genomic DNA or genomic DNA architecture. In an embodiment, the Cas is fused to a polypeptide which alters gene transcription. In an embodiment, the Cas transgenic eukaryotic cell is a cell from an animal. In certain embodiments, the Cas transgenic cell is selected from mammal, primate, rodent, mouse, rat, rabbit, canine, dog, cow, bovine, sheep, ovine, goat, pig, fowl, poultry, chicken, fish, insect, or arthropod. In an embodiment, the kit comprises a mouse cell.

In certain aspects, the invention provides a method for diagnosing tumorigenesis and/or tumor metastasis, a method for prognosing tumorigenesis and/or tumor metastasis, and a method of determining the likelihood of developing tumor metastasis.

In certain embodiments of the invention, analyzing expression of one or more genes comprises comparing expression level with a predetermined expression level. In certain embodiments of the invention, the gene comprises Nf2, Pten, Trim72, Cdkn2a, miR-152, or miR-345. In an embodiment, the tumor metastasis is lung metastasis. In an embodiment, the tumor or tumor metastasis is selected from lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdoid tumor, thyroid cancer, or urinary bladder cancer.

The invention also relates to a non-human eukaryote to which the methods as described above have been applied, i.e. a non-human eukaryote having transplanted eukaryotic cells which have been subjected to the CRISPR/Cas system as described herein.

The invention further relates to tumors, tumor samples, and cells derived therefrom, or cell lines derived from such tumors, tumor samples, or cells derived therefrom, which tumors originate from a non-human eukaryote to which the methods as described above have been applied. Such tumors, tumor samples, and cells derived therefrom, or cell lines derived from such tumors, tumor samples, or cells derived therefrom comprise one or more genetic modification, epigenetic modification, or gene transcription alteration. Such tumors, tumor samples, and cells derived therefrom, or cell lines derived from such tumors, tumor samples, or cells derived therefrom may also be provided in a kit.

The invention further relates to tumor metastases, tumor metastase samples, and cells derived therefrom, or cell lines derived from such tumor metastases, tumor metastase samples, or cells derived therefrom, which tumor metastases originate from a non-human eukaryote to which the methods as described above have been applied. Such tumor metastases, tumor metastase samples, and cells derived therefrom, or cell lines derived from such tumor metastases, tumor metastase samples, or cells derived therefrom comprise one or more genetic modification, epigenetic modification, or gene transcription alteration. Such tumor metastases, tumor metastase samples, and cells derived therefrom, or cell lines derived from such tumor metastases, tumor metastase samples, or cells derived therefrom may also be provided in a kit.

In further aspects, the invention relates to methods for diagnosing and/or prognosing cancer, being it the formation and/or evolution of primary tumors or the formation and/or evolution of secondary tumors, i.e. metastases. Such methods include analysis of one or more of the genes which are identified in the methods according to the invention as described herein. Genetic analysis and/or expression analysis of such genes may provide diagnostic and/or prognostic information of tumor and/or metastasis development and/or evolution, as well as disease progression and/or outcome. Genetic or epigenetic as well as transcriptional alterations may be correlated with disease type, progression, evolution, prognosis, etc.

In related aspects, the invention also foresees in methods for treating cancer, being it a primary tumor or secondary tumor, i.e. metastasis. The non-human eukaryote to which the methods as described herein are applied may be used as a test model for therapeutic applications. Therapeutic applications obtained as such may then be applied to a subject in need thereof.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. It may be advantageous in the practice of the invention to be in compliance with Art. 53(c) EPC and Rule 28(b) and (c) EPC. Nothing herein is intended as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is intended as a promise.

These and other embodiments are disclosed or are obvious from and encompassed by, the following Detailed Description.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The patent or application file contains at least one drawing executed in color. Copies of this patent or patent application publication with color drawing(s) will be provided by the Office upon request and payment of the necessary fee.

FIG. 4A-4H: (A) Pie charts of the most abundant sgRNAs in three individual lobes of the lungs of two representative animals transplanted with Cas9+mGeCKOa infected cells. The area for each sgRNA corresponds to the fraction of total reads from the lobe for the sgRNA. All sgRNAs with ≥2% of total reads are plotted individually. (B) Pie charts of the most abundant sgRNAs in the lung (averaged across three individual lobes) for the two animals shown in (A). All sgRNAs with ≥2% of average reads are plotted individually. (C) Left: Percentage of late tumor reads for the significantly enriched (FDR<0.2%) mGeCKOa sgRNAs found in the lung metastases (averaged across three dissected lobes). Right: In purple, the percentage of late tumor reads for the significantly enriched (FDR<0.2%) mGeCKOa sgRNAs found in the lung metastases (average across all mice, n=9 mice). In grey, the percentage of late tumor reads for random, size-matched samples of sgRNAs present in the late tumor (n=100 samples). (D) Inset: All sgRNAs found in individual lung lobes ordered by the percent of lobes in which a particular sgRNA was amongst the significantly enriched (FDR<0.2%) sgRNAs for that lobe. Main panel: Enlargement and gene labels for sgRNAs at the top of the list from the inset (boxed region). (E) Inset: All sgRNAs found in individual mouse (averaged across three dissected lobes) ordered by the percent of mice in which a particular sgRNA was amongst the significantly enriched (FDR<0.2%) sgRNAs for that mouse. Main panel: Enlargement and gene labels for sgRNAs at the top of the list from the inset (boxed region). (F) Bottom: Metastasis Primary Ratio (MPR) for the sgRNAs in mGeCKOa with enrichment in metastases over late tumor (MPR>1) observed in at least 3 mice. The sgRNAs are sorted by the number of mice in which the MPR for the sgRNA is greater than 1. Bottom: Number of mice in which the MPR for this sgRNA is greater than 1. In both panels, individual sgRNAs are labeled by gene target. (G) Number of genes with 0, 1, 2 or 3 significantly enriched (FDR<0.2% for at least one mouse) mGeCKOa sgRNAs in the lung metastases. For genes with 2 enriched sgRNAs, gene names are indicated in the colored bubble adjacent to the bar. (H) Number of mice and percentage of mice in which each sgRNA was enriched in the lung metastases for all genes with multiple enriched sgRNAs.

FIG. 5A-5F: (A) Schematic representation of lentiviral transduction of Cas9-EGFP KPD cells with single sgRNAs designed to target one gene or miRNA. After puromycin selection, the cell population is transplanted into Nu/Nu mice and also deep sequenced to examine the distribution of indels at the target site. After 6 weeks, the primary tumor and lungs are examined. (B) Histograms of indel sizes at the genomic locus targeted by a representative sgRNA for each gene/miRNA after 3 days of puromycin selection. (C) Representative H&E staining of lung lobes from uninjected animals (n=3 animals), animals transplanted with cells transduced with Cas9 only (n=5), and animals transplanted with cells containing Cas9 and a single sgRNA (n=6). Single sgRNAs are either control/non-targeting sgRNAs (n=6 mice for control sgRNAs, 3 distinct control sgRNAs with 2 mice each) or targeting sgRNAs (n=6 mice for each gene/miRNA target, 3 sgRNAs per target with 2 mice each). Blue arrows indicate lung metastases. Scale bar: 10 μm. (D) Percent of lung lobes with metastases after 6 weeks for the mice in (C). (E) Primary tumor growth curve of Nu/Nu mice transplanted with NSCLC cells transduced with Cas9 only (n=5) or single sgRNAs (n=6 mice per gene/miRNA target, 3 sgRNAs per target with 2 mice each; n=6 mice for control sgRNAs, 3 control sgRNAs with 2 mice each). (F) Correlation between primary tumor volume and percent of lobes with metastases for each gene in (D) and (E). Error bars indicate s.e.m.

FIG. 6A-6E: (A) Schematic representation of the loss-of-function metastasis minipool screen 624 sgRNAs. Briefly, Cas9-EGFP KPD cells were transduced with either validation or control (non-targeting) pools of 624 sgRNAs. After puromycin selection, the cell pools are transplanted into Nu/Nu mice. After 6 weeks, minipool sgRNAs are sequenced from primary tumor and lung samples. (B) Primary tumor growth curve of Nu/Nu mice transplanted with Cas9 vector+validation pool cells (n=5 mice) or Cas9+ control pool cells (n=5 mice). (C) Percent of lung lobes with metastases after 6 weeks for the mice in (B). C=control pool. V=validation pool. (D) Boxplot of the sgRNA normalized read counts for the plasmid library, cells before transplantation, primary tumor and lung metastases using the validation minipool. (E) Cumulative probability distribution of library sgRNAs in the validation plasmid pool, cells before transplantation, early tumor and lung metastases. Tumor and metastases distributions are averaged across mice.

FIG. 7A-7E: (A) Pie charts of the most abundant sgRNAs in the primary tumor and the whole lung of two representative mice transplanted with Cas9+validation pool cells. The area for each sgRNA corresponds to the fraction of total reads from the tissue (primary tumor or lung metastases) for the sgRNA. All sgRNAs with ≥2% of total reads are plotted individually. (B) Scatterplot of normalized sgRNA read counts in primary tumor and lung metastases for all sgRNAs in the validation minipool for each mouse (different color dots indicate different mice). (C) Base-2 logarithm of the ratio of sgRNA abundance in the lung metastases over the primary tumor (Metastasis-Primary Ratio, or MPR) plotted against the abundance in the lung metastases (n=5 mice per sgRNA). Green dots are the 100 control sgRNAs. Dots with black outlines are non-control sgRNAs that target genes or miRNAs. Red dots indicate non-control sgRNAs for which more than one sgRNA targeting the same gene/miRNA is enriched in the lung metastases over the primary tumor (i.e. log 2(MPR)>0) and are labeled with the gene/miRNA targeted. The lung-primary ratio is calculated for individual mice and these quantities are averaged across mice. (D) Number of genes with 0 to 10 significantly enriched (FDR<0.2% in at least one mouse) validation minipool sgRNAs in the lung metastases. For genes/miRNAs with 2 or more enriched sgRNAs, genes/miRNAs are categorized by how many sgRNAs targeting that gene/miRNAs are enriched as indicated in the colored bubbles adjacent to each bar. (E) Schematic illustration of tumor growth and metastasis in the library-transduced NSCLC transplant model. The initially diverse set of loss-of-function mutations in the subcutaneously transplanted pool is selected over time for mutations that promote growth of the primary tumor. These mutants are also found in higher numbers in the blood and, subsequently, in lung metastases where a subset of mutations from the primary tumor are able to proliferate.

FIG. 8A-8D: (A) Brightfield image of the parental KrasG12D/+; p53−/−; Dicer1+/− NSCLC cell line and EGFP fluorescence images of clonally derived lines after transduction with a NLS-3×FLAG-Cas9-EGFP lentivirus. (B) Western blot analysis of Cas9 expression in clonally derived lines from (A) using anti-FLAG and anti-Cas9 antibodies. Both antibodies detect an ~190 kDa band. (C) Micro-CT snapshots of the lungs of representative mice transplanted with control (Cas9 only) and mGeCKOa-transduced (Cas9+mGeCKOa) cell pools. Yellow arrows indicate lung metastases. (D) Dissecting scope snapshots of the lungs of representative mice transplanted with control (Cas9 only) and mGeCKOa-transduced (Cas9+mGeCKOa) cell pools. Yellow arrows indicate lung metastases.

FIG. 13A-13G: (A) Western blot protein analysis of individual sgRNAs targeting Nf2 and Pten. For subsequent in vivo experiments, Nf2 sgRNAs 1, 2 and 4 and Pten sgRNAs 1, 3 and 4 were used. (B) Distribution of cell size (diameter) of the Cas9-GFP transduced mouse $Kras^{G12D/+}$; $p53^{-/-}$; $Dicer1^{+/-}$ NSCLC cell line using Cellometer Auto T4. (C) (upper) Schematics of CTC capturing device. (lower) Brightfield and EGFP images of NLS-3×FLAG-Cas9-EGFP transduced $Kras^{G12D/+}$; $p53^{-/-}$; $Dicer1^{+/-}$ NSCLC cells trapped in PDMS cell capture device. Scale bar: 50 µm. (D) Quantification of circulating tumor cells (CTCs) from the blood of mice injected with sg-Nf2, sg-Pten, sg-Cdkn2a, sg-Trim72 or control (pooled Cas9-only and non-targeting sgRNAs) cells at ~5 weeks after transplantation. CTCs from n=2~4 mice were captured for each condition. Sg-miR152 has only one replicate thus is not plotted in this panel. (E) Correlation between primary tumor size and CTC concentration for genes in (D). (F) Correlation between CTC concentration and lung metastasis rate for genes in (D).

FIG. 14A-14I: (A) Pearson correlation of sgRNA normalized read counts between two technical replicates of the Validation minipool transduced cells before transplantation (~7 days post-transduction). Technical replicates have separate PCR readout and Illumina sequencing. (B) Pearson correlation of sgRNA normalized read counts between the Validation minipool plasmid and the transduced cell pool before transplantation (~7 days post-transduction). (C) Number of unique sgRNAs from the mGeCKOa library detected in the plasmid pool, cells before transplantation, primary tumors, and lung metastases. Different mice are denoted by m1-m5. (D) Pearson correlation of normalized sgRNA read counts and dendrogram based on complete linkage (farthest neighbor) clustering for all samples in validation minipool screen. TR, technical replicate. (E) Venn diagram of sgRNAs from the mGeCKOa library detected in primary tumors of 5 different mice at ~6 weeks after transplantation of the validation minipool transduced cell pool from a single infection replicate. (F) Venn diagram of sgRNAs from the mGeCKOa library detected in lung metastases of 5 different mice at ~6 weeks after transplantation of the validation minipool transduced cell pool from a single infection replicate. (G) All sgRNAs from the Validation minipool found in the lungs of individual mice ordered by the percent of mice where this sgRNA was amongst the top 10 most enriched sgRNAs for that lobe. In cases where more than 1 sgRNA for the gene was enriched, distinct sgRNAs are labeled. NTCs denote non-targeting, control sgRNAs from the validation minipool. (H) Pie charts of the top 10 most abundant sgRNAs in the primary tumors of 5 mice transplanted with Cas9+Validation minipool infected cells. The area for each sgRNA corresponds to the fraction of total reads from the tumor for the sgRNA. The 10 most abundant sgRNAs are plotted individually. (I) Pie charts of the top 10 most abundant sgRNAs in the lung metastases of 5 mice transplanted with Cas9+Validation minipool infected cells. The area for each sgRNA corresponds to the fraction of total reads from the tumor for the sgRNA. The 10 most abundant sgRNAs are plotted individually.

FIG. 15A-15C: Comparison of the overall distributions of sgRNAs from early primary tumors with those in the cell populations. Identification of the sgRNAs which are depleted in cells and in early tumors.

FIG. 18: Supplemental tables disclose SEQ ID NOS 46-1,367, respectively, in order of appearance.

DETAILED DESCRIPTION OF THE INVENTION

Figure 1A:
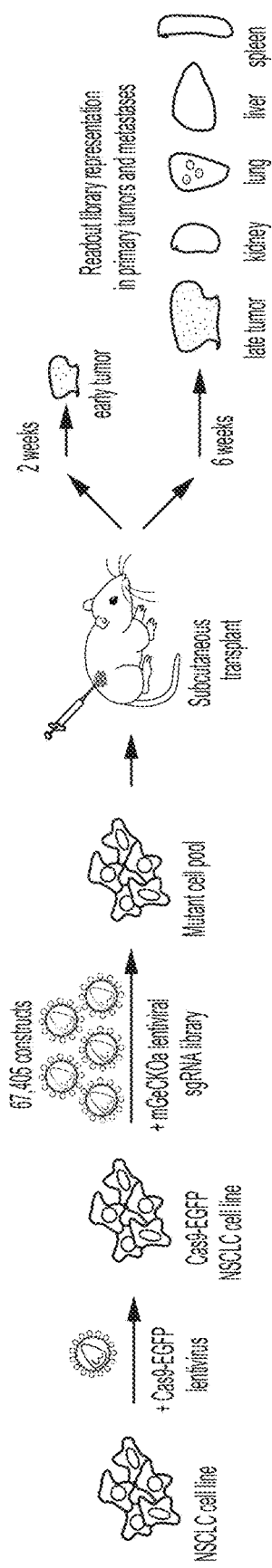
FIG. 1A-1F: Schematic representation of the loss-of-function metastasis screen using the mouse genome-scale CRISPR/Cas9 knock-out (mGeCKOa) library. (B) Representative hematoxylin and eosin (H&E) stains of primary tumor and various organs of Nu/Nu mice subcutaneously transplanted with a KrasG12D/+; p53−/−; Dicer1+/− NSCLC cell line, which was transduced with lentivirus carrying a Cas9 vector (Cas9 only), or a Cas9 vector plus the mGeCKOa library (Cas9+mGeCKOa). (C) Primary tumor growth curve of Nu/Nu mice transplanted with Cas9 vector cells (n=3 mice) or Cas9+mGeCKOa cells (n=9 mice). (D) Representative EGFP fluorescence images of lung lobes of animals transplanted with Cas9 vector or Cas9+mGeCKOa cells. Yellow arrows indicate lung metastases. (E) Number of lobes with metastases visible after dissection of Nu/Nu mice transplanted with Cas9 vector cells (n=3 mice) or Cas9+mGeCKOa cells with three independent infection replicate experiments (R1, R2 and R3, n=3 mice per replicate). (F) Representative H&E stains from various organs of Nu/Nu mice subcutaneously transplanted with Cas9 only or Cas9+mGeCKOa cells.

Before the present methods of the invention are described, it is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) ("Ausubel et al. 1992"); the series Methods in Enzymology (Academic Press, Inc.); Innis et al., PCR Protocols: A Guide to Methods and Applications, Academic Press: San Diego, 1990; PCR 2: A Practical Approach (M. J. MacPherson, B. D. Hames and G. R. Taylor eds. (1995); Harlow and Lane, eds. (1988) Antibodies, a Laboratory Manual; and Animal Cell Culture (R. I. Freshney, ed. (1987). General principles of microbiology are set forth, for example, in Davis, B. D. et al., Microbiology, 3rd edition, Harper & Row, publishers, Philadelphia, Pa. (1980).

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the following detailed description of the invention, reference is made to the accompanying drawings that form a part hereof, and in which are shown by way of illustration only of specific embodiments in which the invention may be practiced. It is to be understood that other embodiments may be utilised and structural or logical changes may be made without departing from the scope of the present invention. The following detailed description, therefore, is not to be taken in a limiting sense, and the scope of the present invention is defined by the appended claims.

It is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

Preferred statements (features) and embodiments of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the below numbered statements and embodiments 1 to 75, with any other statement and/or embodiments.

1. A method for modeling tumor formation and/or tumor evolution comprising the steps of:
   (a) providing an isolated Cas (transient or stable) transgenic eukaryotic cell expressing Cas or capable of inducibly and/or conditionally expressing Cas;
   (b) introducing in said Cas transgenic eukaryotic cell one or more RNA capable of guiding Cas to one or more genetic target locus of a eukaryote; or
   introducing in said Cas transgenic eukaryotic cell one or more polynucleotide encoding one or more RNA capable of guiding Cas to one or more genetic target locus of a eukaryote;
   (c) introducing said Cas transgenic eukaryotic cell after step (b) in a non-human eukaryote;
   (d) analyzing tumor formation and/or tumor evolution in said non-human eukaryote.
2. The method according to statement 1, 78, or 79, wherein step (c) comprises introducing a plurality of eukaryotic cells in a non-human eukaryote, each cell of said plurality of eukaryotic cells comprising a different RNA capable of guiding Cas to a genetic target locus of said eukaryote; or
   each cell of said plurality of eukaryotic cells comprising a different polynucleotide encoding an RNA capable of guiding Cas to a genetic target locus of said eukaryote.
3. The method according to any of statements 1 to 2 or 78 to 79, wherein step (d) comprises identifying one or more genes which are involved in tumor formation and/or evolution.
4. The method according to any of statements 1 to 3 or 78 to 79, wherein step (d) comprises analyzing tumor metastasis.
5. The method according to any of statements 1 to 4 or 78 to 79, wherein step (d) comprises analyzing gene expression.
6. The method according to any of statements 1 to 5 or 78 to 79, wherein step (d) comprises analyzing gene expression in said tumor.
7. The method according to any of statements 1 to 5 or 78 to 79, wherein step (d) comprises identifying one or more of said RNA of step (b) in said tumor.
8. The method according to any of statements 4 to 5 or 78 to 79, wherein step (d) comprises analyzing gene expression in said tumor metastasis.
9. The method according to any of statements 4 to 5 or 78 to 79, wherein step (d) comprises identifying one or more of said RNA of step (b) in said tumor metastasis.
10. A method for identifying genes which are involved in tumor formation and/or tumor metastasis, comprising the steps of:
    (a) providing an isolated Cas transgenic eukaryotic cell expressing Cas or capable of inducibly and/or conditionally expressing Cas;
    (b) introducing in said Cas transgenic eukaryotic cell one or more RNA capable of guiding Cas to one or more genetic target locus of a eukaryote; or
    introducing in said Cas transgenic eukaryotic cell one or more polynucleotide encoding one or more RNA capable of guiding Cas to one or more genetic target locus of a eukaryote;
    (c) introducing a plurality of said Cas transgenic eukaryotic cell after step (b) in a non-human eukaryote, each cell of said plurality of Cas transgenic eukaryotic cells comprising a different RNA capable of guiding Cas to a genetic target locus, or each cell of said plurality of Cas transgenic eukaryotic cells comprising a different polynucleotide encoding an RNA capable of guiding Cas to a genetic target locus;
    (d) identifying genes which are involved in tumor formation and/or tumor metastasis in said non-human eukaryote based on the identification in said tumor or tumor metastasis of one or more of said RNA capable of guiding Cas to one or more genetic target locus.
11. The method according to any of statements 3 to 10, 42-43, 47 or 78 to 81, wherein said genes involved in tumor formation, tumor evolution, and/or tumor metastasis are tumor suppressor genes and/or metastasis suppressor genes.
12. The method according to any of statements 1 to 11, 42-43, 47 or 78 to 81, wherein said method after step (b) comprises introducing one or more genomic mutations in said eukaryotic cell.
13. The method according to any of statements 1 to 12, 42-43, 47 or 78 to 81, wherein said RNA capable of guiding Cas comprises CRISPR RNA and transactivating (tracr) RNA.
14. The method according to any of statements 1 to 13, 42-43, 47 or 78 to 81, wherein said RNA capable of guiding Cas comprises a single guide (sg) RNA.
15. The method according to any of statements 1 to 14, 42-43, 47 or 78 to 81, wherein said RNA capable of guiding Cas is introduced in said eukaryotic cell by means of transduction.
16. The method according to any of statements 1 to 15, 42-43, 47 or 78 to 81, wherein said RNA capable of guiding Cas is introduced in said eukaryotic cell by means of lentiviral transduction.
17. The method according to any of statements 1 to 16, 42-43, 47 or 78 to 81, wherein said polynucleotide encoding one or more RNA capable of guiding Cas is capable of constitutively expressing said RNA or alternatively inducibly and/or conditionally expressing said RNA.
18. The method according to any of statements 1 to 17, 42-43, 47 or 78 to 81, wherein said eukaryotic cell of step (a) is a tumor cell.
19. The method according to any of statements 1 to 18, 42-43, 47 or 78 to 81, wherein said eukaryotic cell of step (a) is a non-metastasizing tumor cell.
20. The method according to any of statements 1 to 18, 42-43, 47 or 78 to 81, wherein said eukaryotic cell of step (a) is characterized by oncogenic expression of Kras (KrasG12D), homozygous p53 loss (p53−/−), and/or heterozygous Dicer1 loss (Dicer+/−), preferably all.
21. The method according to any of statements 1 to 20, 42-43, 47 or 78 to 81, wherein said Cas is a type II Cas.
22. The method according to any of statements 1 to 21, 42-43, 47 or 78 to 81, wherein said Cas is Cas9.
23. The method according to any of statements 1 to 22, 42-43, 47 or 78 to 81, wherein said Cas is a Cas originating from *Streptococcus pyogenes, Streptococcus thermophiles*, or *Staphylococcus aureus*.
24. The method according to any of statements 1 to 23, 42-43, 47 or 78 to 81, wherein said Cas is a mutated Cas having an altered catalytic activity.
25. The method according to any of statements 1 to 24, 42-43, 47 or 78 to 81, wherein said Cas is a catalytically inactive Cas.
26. The method according to any of statements 1 to 25, 42-43, 47 or 78 to 81, wherein said Cas is fused to an enzyme which modifies genomic DNA or genomic DNA architecture.

27. The method according to any of statements 1 to 26, 42-43, 47 or 78 to 81, wherein said Cas is fused to a polypeptide which alters gene transcription.
28. The method according to any of statements 1 to 27, 42-43, 47 or 78 to 81, wherein said eukaryotic cell is a cell from an animal.
29. The method according to any of statements 1 to 28, 42-43, 47 or 78 to 81, wherein said eukaryotic cell is a cell from a eukaryote selected from the group consisting of mammal, primate, rodent, mouse, rat, rabbit, canine, dog, cow, bovine, sheep, ovine, goat, pig, fowl, poultry, chicken, fish, insect, and arthropod.
30. The method according to any of statements 1 to 29, 42-43, 47 or 78 to 81, wherein said eukaryotic cell is a mammalian cell, preferably a mouse cell.
31. The method according to any of statements 1 to 30, 42-43, 47 or 78 to 81, wherein said eukaryote in step (c) is an animal, preferably a mammal.
32. The method according to any of statements 1 to 31, 42-43, 47 or 78 to 81, wherein said eukaryote in step (c) is an immunocompromised animal, preferably an immunocompromised mammal.
33. The method according to any of statements 1 to 32, 42-43, 47 or 78 to 81, wherein said eukaryote in step (c) is selected from the group consisting of mammal, primate, rodent, mouse, rat, rabbit, canine, dog, cow, bovine, sheep, ovine, goat, pig, fowl, poultry, chicken, fish, insect, and arthropod.
34. The method according to any of statements 1 to 33, 42-43, 47 or 78 to 81, wherein said eukaryote in step (c) is a mouse.
35. The method according to any of statements 1 to 34, 42-43, 47 or 78 to 81, wherein step (c) comprises introducing said cells subcutaneously.
36. The method according to any of statements 1 to 35, 42-43, 47 or 78 to 81, wherein said tumor is selected from the group consisting of lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdoid tumor, thyroid cancer, and urinary bladder cancer.
37. A tumor sample or a tumor metastasis sample isolated from said non-human eukaryote after introduction of said Cas transgenic eukaryotic cell of step (c) in statement 1.
38. The tumor sample or the tumor metastasis sample according to statement 37, wherein said tumor is selected from the group consisting of lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdoid tumor, thyroid cancer, and urinary bladder cancer.
39. A cell isolated from said tumor sample or said tumor metastasis sample according to any of statements 37 to 38.
40. A cell line obtained or obtainable from said tumor sample or said tumor metastasis sample according to any of statements 37 to 38.
41. A cell line obtained or obtainable from said cell of statement 39.
42. A method for generating an non-human eukaryote model for tumor formation and/or tumor evolution, comprising the steps of:
(a) providing an isolated Cas transgenic eukaryotic cell expressing Cas or capable of inducibly and/or conditionally expressing Cas;
(b) introducing in said Cas transgenic eukaryotic cell one or more RNA capable of guiding Cas to one or more genetic target locus of a eukaryote; or introducing in said Cas transgenic eukaryotic cell one or more polynucleotide encoding one or more RNA capable of guiding Cas to one or more genetic target locus of a eukaryote;
(c) introducing a plurality of said Cas transgenic eukaryotic cell after step (b) in a non-human eukaryote, each cell of said plurality of Cas transgenic eukaryotic cells comprising a different RNA capable of guiding Cas to a genetic target locus, or each cell of said plurality of Cas transgenic eukaryotic cells comprising a different polynucleotide encoding an RNA capable of guiding Cas to a genetic target locus;
43. A method for generating a non-human eukaryote model for identifying genes involved in formation and/or tumor evolution, comprising the steps of:
(a) providing an isolated Cas transgenic eukaryotic cell expressing Cas or capable of inducibly and/or conditionally expressing Cas;
(b) introducing in said Cas transgenic eukaryotic cell one or more RNA capable of guiding Cas to one or more genetic target locus of a eukaryote; or introducing in said Cas transgenic eukaryotic cell one or more polynucleotide encoding one or more RNA capable of guiding Cas to one or more genetic target locus of a eukaryote;
(c) introducing a plurality of said Cas transgenic eukaryotic cell after step (b) in a non-human eukaryote, each cell of said plurality of Cas transgenic eukaryotic cells comprising a different RNA capable of guiding Cas to a genetic target locus, or each cell of said plurality of Cas transgenic eukaryotic cells comprising a different polynucleotide encoding an RNA capable of guiding Cas to a genetic target locus;
44. A non-human eukaryote obtained or obtainable by statement 42 or 43.
45. The non-human eukaryote according to statement 44, wherein said eukaryote is an animal, preferably a mammal.
46. The non-human eukaryote according to any of statements 44 to 45, wherein said eukaryote is an immunocompromised animal, preferably an immunocompromised mammal.
47. The non-human eukaryote according to any of statements 44 to 46, wherein said eukaryote is selected from the group consisting of mammal, primate, rodent, mouse, rat, rabbit, canine, dog, cow, bovine, sheep, ovine, goat, pig, fowl, poultry, chicken, fish, insect, and arthropod.
48. The non-human eukaryote according to any of statements 44 to 47, wherein said eukaryote is a mouse.

49. A method for determining whether a compound is capable of suppressing tumor formation and/or tumor evolution comprising the steps of:
    (a) providing an animal model according to the method of statement 42,
    (b) administering said compound to said animal model,
    (c) determining the whether or not said compound is capable of suppressing tumor formation and/or tumor evolution in said animal model.
50. A kit comprising:
    an isolated Cas transgenic eukaryotic cell expressing Cas or capable of inducibly and/or conditionally expressing Cas;
    one or more RNA capable of guiding Cas to one or more genetic target locus, or one or more polynucleotide encoding one or more RNA capable of guiding Cas to one or more genetic target locus.
51. The kit according to statement 50, further comprising a non-human eukaryote.
52. The kit according to any of statements 50 to 51, further comprising instructions for performing the method according to any of statements 1 to 36.
53. The kit according to any of statements 50 to 52, wherein said one or more RNA capable of guiding Cas to one or more genetic target locus, or one or more polynucleotide encoding one or more RNA capable of guiding Cas to one or more genetic target locus are comprised in a vector, preferably a lentiviral vector.
54. The kit according to any of statements 50 to 53, comprising a plurality of RNAs capable of guiding Cas to a genetic target locus; or a plurality of polynucleotides encoding an RNA capable of guiding Cas to a genetic target locus.
55. The kit according to any of statements 50 to 54, wherein said RNA capable of guiding Cas comprises CRISPR RNA and transactivating (tracr) RNA.
56. The kit according to any of statements 50 to 55, wherein said RNA capable of guiding Cas comprises a single guide (sg) RNA.
57. The kit according to any of statements 50 to 56, wherein said polynucleotide encoding one or more RNA capable of guiding Cas is capable of constitutively expressing said RNA or alternatively inducibly and/or conditionally expressing said RNA.
58. The kit according to any of statements 50 to 57, wherein said Cas transgenic eukaryotic cell is a tumor cell.
59. The kit according to any of statements 50 to 58, wherein said Cas transgenic eukaryotic cell is a non-metastasizing tumor cell.
60. The kit according to any of statements 50 to 59, wherein said Cas is a type II Cas.
61. The kit according to any of statements 50 to 60, wherein said Cas is Cas9.
62. The kit according to any of statements 50 to 61, wherein said Cas is a Cas originating from *Streptococcus pyogenes, Streptococcus* thermophiles, or *Staphylococcus aureus*.
63. The kit according to any of statements 50 to 62, wherein said Cas is a mutated Cas having an altered catalytic activity.
64. The kit according to any of statements 50 to 63, wherein said Cas is a catalytically inactive Cas.
65. The kit according to any of statements 50 to 64, wherein said Cas is fused to an enzyme which modifies genomic DNA or genomic DNA architecture.
66. The kit according to any of statements 50 to 65, wherein said Cas is fused to a polypeptide which alters gene transcription.
67. The kit according to any of statements 50 to 66, wherein said Cas transgenic eukaryotic cell is a cell from an animal.
68. The kit according to any of statements 50 to 67, wherein said Cas transgenic eukaryotic cell is a cell from a eukaryote selected from the group consisting of mammal, primate, rodent, mouse, rat, rabbit, canine, dog, cow, bovine, sheep, ovine, goat, pig, fowl, poultry, chicken, fish, insect, and arthropod.
69. The kit according to any of statements 50 to 68, wherein said Cas transgenic eukaryotic cell is a mammalian cell, preferably a mouse cell.
70. The kit according to any of statements 51 to 69, wherein said eukaryote is an animal, preferably a mammal.
71. The kit according to any of statements 51 to 70, wherein said eukaryote is an immunocompromised animal, preferably an immunocompromised mammal.
72. The kit according to any of statements 51 to 71, wherein said eukaryote is selected from the group consisting of mammal, primate, rodent, mouse, rat, rabbit, canine, dog, cow, bovine, sheep, ovine, goat, pig, fowl, poultry, chicken, fish, insect, and arthropod.
73. The kit according to any of statements 52 to 72, wherein said eukaryote is a mouse.
74. A method for diagnosing tumorigenesis and/or tumor metastasis, comprising the step of genetically analyzing or analyzing expression of one or more genes identified according to the method according to any of statements 10 to 36 or 83 to 84.
75. A method for prognosing tumorigenesis and/or tumor metastasis, comprising the step of genetically analyzing or analyzing expression of one or more genes identified according to the method according to any of statements 10 to 36 or 83 to 84.
76. A method for determining the likelihood of developing tumor metastasis, comprising the step of genetically analyzing or analyzing expression of one or more genes identified according to the method according to any of statements 10 to 36 or 83 to 84.
77. The method according to any of statements 74 to 76, wherein analyzing expression of said one or more genes comprises comparing expression level with a predetermined expression level.
78. The method according to any of statements 74 to 77, wherein said one or more gene is selected from the group consisting of Nf2, Pten, Trim72, and Ube2g2.
79. The method according to statement 78, wherein said tumor metastasis is lung metastasis.
80. The method according to any of statements 74 to 79, wherein said tumor or tumor metastasis is selected from the group consisting of lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdoid tumor, thyroid cancer, and urinary bladder cancer.

81. A method for modeling tumor formation and/or tumor evolution comprising the steps of:
(a) introducing in a eukaryotic cell a Cas polypeptide; or stably or transiently introducing in a eukaryotic cell a polynucleotide encoding a Cas polypeptide, said polynucleotide being capable of constitutively expressing said Cas or alternatively inducibly and/or conditionally expressing said Cas;
(b) introducing in said eukaryotic cell one or more RNA capable of guiding Cas to one or more genetic target locus of a eukaryote; or introducing in said eukaryotic cell stably or transiently one or more polynucleotide encoding one or more RNA capable of guiding Cas to one or more genetic target locus of a eukaryote, said polynucleotide being capable of constitutively expressing said RNA or alternatively inducibly and/or conditionally expressing said RNA;
wherein steps (a) and (b) are performed simultaneously or subsequently, in either order;
(c) subsequently introducing said eukaryotic cell in a non-human eukaryote;
(d) analyzing tumor formation and/or tumor evolution in said non-human eukaryote.

82. A method for modeling tumor formation and/or tumor evolution comprising the steps of:
(a) providing an isolated eukaryotic cell,
said cell comprising a Cas polypeptide, or stably or transiently expressing Cas or capable of inducibly and/or conditionally expressing Cas; and
said cell comprising one or more RNA capable of guiding Cas to one or more genetic target locus of a eukaryote, or stably or transiently expressing one or more RNA capable of guiding Cas to one or more genetic target locus of a eukaryote or capable of inducibly and/or conditionally expressing one or more RNA capable of guiding Cas to one or more genetic target locus of a eukaryote;
(b) subsequently introducing said eukaryotic cell in a non-human eukaryote;
(c) analyzing tumor formation and/or tumor evolution in said non-human eukaryote.

83. A method for identifying genes which are involved in tumor formation and/or tumor metastasis, comprising the steps of:
(a) introducing in a eukaryotic cell a Cas polypeptide; or stably or transiently introducing in a eukaryotic cell a polynucleotide encoding a Cas polypeptide, said polynucleotide being capable of constitutively expressing said Cas or alternatively inducibly and/or conditionally expressing said Cas;
(b) introducing in said eukaryotic cell one or more RNA capable of guiding Cas to one or more genetic target locus of a eukaryote; or
introducing in said eukaryotic cell stably or transiently one or more polynucleotide encoding one or more RNA capable of guiding Cas to one or more genetic target locus of a eukaryote, said polynucleotide being capable of constitutively expressing said RNA or alternatively inducibly and/or conditionally expressing said RNA;
wherein steps (a) and (b) are performed simultaneously or subsequently, in either order;
(c) subsequently introducing a plurality of said eukaryotic cells in a non-human eukaryote, each cell of said plurality of eukaryotic cells comprising a different RNA capable of guiding Cas to a genetic target locus, or each cell of said plurality of eukaryotic cells comprising a different polynucleotide encoding an RNA capable of guiding Cas to a genetic target locus;
(d) identifying genes which are involved in tumor formation and/or tumor metastasis in said non-human eukaryote based on the identification in said tumor or tumor metastasis of one or more of said RNA capable of guiding Cas to one or more genetic target locus.

84. A method for identifying genes which are involved in tumor formation and/or tumor metastasis, comprising the steps of:
(a) providing an isolated eukaryotic cell
said cell comprising a Cas polypeptide, or stably or transiently expressing Cas or capable of inducibly and/or conditionally expressing Cas; and
said cell comprising one or more RNA capable of guiding Cas to one or more genetic target locus of a eukaryote, or stably or transiently expressing one or more RNA capable of guiding Cas to one or more genetic target locus of a eukaryote or capable of inducibly and/or conditionally expressing one or more RNA capable of guiding Cas to one or more genetic target locus of a eukaryote;
(b) subsequently introducing a plurality of said eukaryotic cells in a non-human eukaryote, each cell of said plurality of eukaryotic cells comprising a different RNA capable of guiding Cas to a genetic target locus, or each cell of said plurality of eukaryotic cells comprising a different polynucleotide encoding an RNA capable of guiding Cas to a genetic target locus;
(c) identifying genes which are involved in tumor formation and/or tumor metastasis in said non-human eukaryote based on the identification in said tumor or tumor metastasis of one or more of said RNA capable of guiding Cas to one or more genetic target locus.

As used herein, the term "modeling tumor formation and/or tumor evolution" and "modeling tumor metastasis formation and/or tumor evolution" generally encompasses the analysis of tumor (metastasis) formation and/or tumor (metastasis) evolution. Such analyses may encompass structural and functional analyses, as is known in the art. Also spatio-temporal analyses of tumor (metastasis) formation and/or evolution are envisaged. Non-limiting examples of such analyses include, but are not limited to (epi)genetic and/or morphological characterization of the tumor (metastases), analysis of the type or stage and growth characteristics of the tumor (metastases), including changes over time. Also transcriptome and/or proteome analyses are included, as well as analyses of individual genes and/or expression products.

As used herein, the term "gene(s) which is (are) involved in tumor formation and/or evolution" refers to genes—any type of gene, i.e. including for instance microRNA genes—the mutation of which, or the altered expression of which is causally correlated with tumor formation and/or evolution. In certain embodiments, the method according to the invention allow identification of tumor suppressor genes and/or metastasis suppressor genes. Tumor suppressor genes are those genes which prevent tumor formation and/or development. Metastasis suppressors are those genes which prevent metastasis formation and/or development. A metastasizing tumor cell is a cell capable of leading to tumor metastasis, i.e. a cell capable of undergoing the typical hallmarks of metastasis, i.e. local invasion into the surrounding tissue, intravasation into the blood stream from the primary tumor site, circulation in the blood stream, and extravasation from the blood stream into a secondary site, followed by settling/colonization and metastasis growth and development. In this context, a non-metastasising tumor cell is thus a cell which does not undergo, or is not capable of undergoing the above cascade of events.

As used herein, the term "genetic target locus" refers to a specific physical site in the genome of the eukaryotic cell which is targeted by the CRISPR/Cas system as referred to herein elsewhere. Such genetic target locus is preferably but need not be a specific sequence of a gene, including intron, exon, promoter, and other regulatory sequences including terminators, translational regulatory sequences such as ribosome binding sites and internal ribosome entry sites, enhancers, silencers, insulators, boundary elements, replication origins, matrix attachment sites and locus control regions, in as far as targeting the locus results in genomic alteration and/or altered gene expression.

An altered expression of one or more genome sequences can be determined by assaying for a difference in the mRNA levels of the corresponding genes between the test model cell and a control cell. Alternatively, the differential expression of sequences is determined by detecting a difference in the level of the encoded polypeptide or gene product.

As used herein, the term "eukaryotic cell" may refer to a cell or a plurality of cells derived from a eukaryotic organism. In preferred embodiments, such eukaryotic cells are derived from an animal, such as mammal, primate, rodent, mouse, rat, rabbit, canine, dog, cow, bovine, sheep, ovine, goat, pig, fowl, poultry, chicken, fish, insect, or arthropod, preferably a mammal, such as a rodent, in particular a mouse. In certain embodiments, such eukaryotic cells are non-human eukaryotic cells. The cell type and cell origin are not particularly limiting according to embodiments of the invention. Eukaryotic cells may be primary cells or cell lines. Eukaryotic cells may be dividing cells (e.g. stem cells) or partially or terminally differentiated cells. Eukaryotic cells may in certain embodiments be tumor cells, which may or may not be capable of metastasis or which may or may not be derived from a metastatic tumor. Eukaryotic cells may also be in vitro transformed eukaryotic cells, e.g. in order to render them tumorigenic, whether or not with metastatic potential. Exemplary eukaryotic cell lines include, but are not limited to C8161, CCRF-CEM, MOLT, mI CD-3, NHDF, HeLa-S3, Huh 1, Huh4, Huh7, HUVEC, HASMC, HEKn, HEKa, MiaPaCell, Panel, PC-3, TFI, CTLL-2, CiR, Rat6, CV1, RPTE, A10, T24, 0.182, A375, ARH-77, Calul, SW480, SW620, S OV3, SK-UT, CaCo2, P388D1, SEM-K2, WEHI-231, HB56, TIB55, Jurkat, J45.0L LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780eis, A172, A20, A253, A431, A-549, ALC, B16, B35, BCP-1 cells, BEAS-2B, bEnd.3, ! !-2 1. BR 293, BxPC3, C3H-10T1/2, C6/36, Cal-27, CHO, CHO-7, CeO-IR, CHO-K1, CHO-K2, CHQ-T, CHO Dhfr –/–, COR-L23, COR-L23/CPR, COR-L23/ 5010, CGR-L23/R23, COS-7, COV-434, CM L Tl, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Flepa1 c1 c7, HL-60, HMEC, HT-29, Jurkat, JY cells, 562 cells, Ku812, KCL22, KG1, KA'O1, LNCap, Ma-Mel 1-48, MC-38, MCF-7, MCF-IOA, MDA-MB-231, MDA-MB-468, MDA-MB-435, MDCK II, MDCK II, MOR/0.2R, MONO-MAC 6, MTD-1A, My End, NCI-H69/CPR, NCI-H69/LX10, NCI-H69/LX20, NCI-H69/LX4, \H i-3T3. N ALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, TI-IPl cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR/Cas system as described herein (such as by transient transfection of one or more vectors, or transfection with RNA), and modified through the activity of a CRISPR complex, is used to establish a new cell line comprising cells containing the modification but lacking any other exogenous sequence.

As used herein, the term "non-human eukaryote" refers to a eukaryotic organism different than Homo sapiens. In preferred embodiments, such eukaryote is a non-human animal, such as non-human mammal, non-human primate, rodent, mouse, rat, rabbit, canine, dog, cow, bovine, sheep, ovine, goat, pig, fowl, poultry, chicken, fish, insect, or arthropod, preferably a mammal, such as a rodent, in particular a mouse. The skilled person will appreciate that the eukaryotic cells which are transplanted or introduced in a non-human eukaryote according to the methods as referred to herein are preferably derived from or originate from the same species as the eukaryote to which they are transplanted. For example, a mouse cell is transplanted in a mouse in certain embodiment according to the methods of the invention as described herein. In certain embodiments, the eukaryote is an immunocompromised eukaryote, i.e. a eukaryote in which the immune system is partially or completely shut down. For instance, immunocompromised mice may be used in the methods according to the invention as described herein. Examples of immunocompromised mice include, but are not limited to Nude mice, RAG –/–mice, SCID (severe compromised immunodeficiency) mice, SCID-Beige mice, NOD (non-obese diabetic)-SCID mice, NOG or NSG mice, etc.

As used herein "introducing a eukaryotic cell in a non-human eukaryote" generally refers to transplanting or grafting eukaryotic cells in a non-human eukaryote. In particular embodiments, the eukaryotic cell is introduced into a non-human eukaryote of a different species, such as, but not limited to a human cell into a rodent.

Typically, cells in a suitable carrier or medium are injected in the animal at a desired site, such as without limitation subdermal, intradermal, transdermal, intracavernous, intravitreal, intra-articular, transscleral, intracerebral, intrathecal, epidural, intramuscular, intravenous, intracardiac, intraosseous, intraperitoneal, etc. the amount and concentration of cells to be injected may vary, but typically the amount of injected cells will be between $10^2$ to $10^{10}$ or between $10^2$ to $10^9$, or between $10^1$ to $10^{10}$ or between $10^1$ to $10^9$, or between $10^4$ to $10^{10}$ or between $10^4$ to $10^9$, such as between $10^4$ and $10^8$, or between $10^1$ and $10^7$, e.g., about $1\times10^5$, about $5\times10^5$, about $1\times10^6$, about $5\times10^6$, about $1\times10^7$, about $5\times10^7$, about $1\times10^8$, about $5\times10^8$, about $1\times10^9$, about $2\times10^9$, about $3\times10^9$, about $4\times10^9$, about $5\times10^9$, about $6\times10^9$, about $7\times10^9$, about $8\times10^9$, about $9\times10^9$ or about $1\times10^{10}$ cells per injection site. For example, such number of cells may particularly refer to the total number of cells to be administered to a non-human eukaryote, which administration may be suitably distributed over one or more doses (e.g., distributed over 2, 3, 4, 5, 6, 7, 8 9 or 10 or more doses) administered over one or more days (e.g., over 1, 2, 3, 4 or 5 or more days). Suitably, in a composition to be administered, cells may be present at a concentration between about $10^4$/ml to about $10^8$/ml, preferably between about $10^5$/ml and about $10^7$/ml, yet more preferably between about $1\times10^6$/ml and about $1\times10^7$/ml, such as, e.g., about $5\times10^6$/ml.

In certain preferred embodiments, one RNA capable of guiding Cas to a genomic target locus may be used in the methods according to the invention. Introduction of a single RNA into a pool of cells will result in a variety of different genetic modifications at the same locus.

In certain preferred embodiments, a plurality of RNAs capable of guiding Cas to a genomic target locus may be used in the methods according to the invention. Advantageously, a genome-wide library, such as a knock-out library, may be used, such as for instance provided in Sanjana et al. (2014); Shalem et al. (2014); and as described in WO 2014/093701, which is incorporated herein by reference in its entirety. A genome wide library may comprise a plurality of CRISPR-Cas system guide RNAs that may comprise guide sequences that are capable of targeting a plurality of target sequences in a plurality of genomic loci, wherein said targeting preferably results in a knockout of gene function. This library may potentially comprise guide RNAs that target each and every gene in the genome of an organism. In some embodiments of the invention the organism or subject is a eukaryote (including mammal including human) or a non-human eukaryote or a non-human animal or a non-human mammal. In some embodiments, the organism or subject is a non-human animal, and may be an arthropod, for example, an insect, or may be a nematode. In some methods of the invention the organism or subject is a plant. In some methods of the invention the organism or subject is a mammal or a non-human mammal. A non-human mammal may be for example a rodent (preferably a mouse or a rat), an ungulate, or a primate. In some methods of the invention the organism or subject is algae, including microalgae, or is a fungus. A eukaryotic cell population can thus be established in which each cell has a different RNA of the library, such that the entire library or substantially the entire library is represented in the cell population. A gene knock-out cell library may thus be generated, in which each cell has a single gene knocked out. The skilled person will understand that the cell population may represent the library multiple times.

As uses herein, "hybridization" or "hybridizing" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PGR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic ceil. As used herein "expression" of a gene or nucleic acid encompasses not only cellular gene expression, but also the transcription and translation of nucleic acid(s) in cloning systems and in any other context.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or I, optical isomers, and amino acid analogs and peptidomimetics.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

As used herein, "diagnosis" or "diagnosing" in the context of tumor (metastasis) formation refers to the determination as to whether a subject has a tumor or a tumor metastasis. As used herein, "prognosis" or "prognosing" in the context of tumor (metastasis) refers to establishing or predicting the progression of a tumor or tumor metastasis or clinical outcome of a subject having a tumor or tumor metastasis. As used herein, "determining the likeliness of developing tumor metastasis" refers to establishing the chance or risk that a tumor will evolve to produce metastasis. These methods generally involve the determination of a genetic event identified as being involved in tumor (metastasis) formation and/or evolution according to the in vivo methods according to the invention as described herein. In certain embodiments, the invention relates to such diagnostic and/or prognostic and/or predictive methods wherein the genetic status or expression status of Nf2 (neurofibromin 2), Pten (phosphatase and tensin homolog), Trim72 (tripartite motif-containing protein 72), and/or Ube2g2 (ubiquitin-conjugating enzyme E2 G2) is determined. These genes have been identified with the in vivo methods according to the invention as described herein as being involved in tumor metastasis, i.e. these genes are knocked out in tumor metastasis, in particular in lung metastasis.

As used herein, the terms "chimeric RNA", "chimeric guide RNA", "guide RNA", "single guide RNA" and "synthetic guide RNA" are used interchangeably and refer to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)".

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publication US 2015-0031134 (U.S. application Ser. No. 14/497,627), which is allowed; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), PCT/US2015/051691, PCT/US2015/051830. Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/835,973, 61/836,080, 61/836,101, and 61/836,127, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT/US2014/62558 filed Oct. 28, 2014, and U.S. Provisional Patent Applications Ser. Nos. 61/915,148, 61/915,150, 61/915,153, 61/915,203, 61/915,251, 61/915,301, 61/915,267, 61/915,260, and 61/915,397, each filed Dec. 12, 2013; 61/757,972 and 61/768,959, filed on Jan. 29, 2013 and Feb. 25, 2013; 62/010,888 and 62/010,879, both filed Jun. 11, 2014; 62/010,329, 62/010,439 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/055,484, 62/055,460 and 62/055,487, each filed Sep. 25, 2014; and 62/069,243, filed Oct. 27, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to PCT application designating, inter alia, the United States, application No. PCT/US14/41806, filed Jun. 10, 2014.

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, and 62/285,349, filed 22 Oct. 2015, NOVEL CRISPR ENZYMES AND SYSTEMS, U.S. application 62/232,067, 24 Sep. 2015, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

*Multiplex genome engineering using CRISPR/Cas systems.* Cong, L., Ran, F. A., Cox, D., Lin, S., Barretto, R., Habib, N., Hsu, P. D., Wu, X., Jiang, W., Marraffini, L. A., & Zhang, F. *Science* February 15; 339(6121):819-23 (2013);

*RNA-guided editing of bacterial genomes using CRISPR-Cas systems.* Jiang W., Bikard D., Cox D., Zhang F, Marraffini L A. Nat Biotechnol March; 31(3):233-9 (2013);

*One-Step Generation of Mice Carrying Mutations in Multiple Genes by CRISPR/Cas-Mediated Genome Engineering.* Wang H., Yang H., Shivalila C S., Dawlaty M M., Cheng A W., Zhang F., Jaenisch R. Cell May 9; 153(4): 910-8 (2013);

*Optical control of mammalian endogenous transcription and epigenetic states.* Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature12466. Epub 2013 Aug. 23;

*Double Nicking by RNA-Guided CRISPR Cas9 for Enhanced Genome Editing Spec ficity.* Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5. (2013);

*DNA targeting specificity of RNA-guided Cas9nucleases.* Hsu, P., Scott, D., Weinstein, J., Ran, FA., Konermann, S., Agarwala, V., Li, Y., Fine, E., Wu, X., Shalem, O., Cradick, TJ., Marraffini, LA., Bao, G., & Zhang, F. Nat Biotechnol doi:10.1038/nbt.2647 (2013);

*Genome engineering using the CRISPR-Cas9 system.* Ran, FA., Hsu, PD., Wright, J., Agarwala, V., Scott, DA., Zhang, F. Nature Protocols November; 8(11):2281-308. (2013);

*Genome-Scale CRISPR-Cas9 Knockout Screening in Human Cells.* Shalem, O., Sanjana, NE., Hartenian, E., Shi, X., Scott, DA., Mikkelson, T., Heckl, D., Ebert, BL., Root, DE., Doench, JG., Zhang, F. *Science* December 12. (2013). [Epub ahead of print];

*Crystal structure of cas9 in complex with guide RNA and target DNA.* Nishimasu, H., Ran, FA., Hsu, PD., Konermann, S., Shehata, SI., Dohmae, N., Ishitani, R., Zhang, F., Nureki, O. *Cell* February 27. (2014). 156(5):935-49;

*Genome-wide binding of the CRISPR endonuclease Cas9 in mammalian cells*. Wu X., Scott D A., Kriz A J., Chiu A C., Hsu P D., Dadon D B., Cheng A W., Trevino A E., Konermann S., Chen S., Jaenisch R., Zhang F., Sharp P A. *Nat Biotechnol.* (2014) Apr. 20. doi: 10.1038/nbt.2889,

*CRISPR-Cas9 Knockin Mice for Genome Editing and Cancer Modeling*, Platt et al., Cell 159(2): 440-455 (2014) DOI: 10.1016/j.cell.2014.09.014,

*Development and Applications of CRISPR-Cas9 for Genome Engineering*, Hsu et al, Cell 157, 1262-1278 (Jun. 5, 2014) (Hsu 2014),

*Genetic screens in human cells using the CRISPR/Cas9 system*, Wang et al., Science. 2014 Jan. 3; 343(6166): 80-84. doi:10.1126/science.1246981,

*Rational design of highly active sgRNAs for CRISPR-Cas9-mediated gene inactivation*, Doench et al., Nature Biotechnology published online 3 Sep. 2014; doi:10.1038/nbt.3026, and

*In vivo interrogation of gene function in the mammalian brain using CRISPR-Cas9*, Swiech et al, Nature Biotechnology; published online 19 Oct. 2014; doi:10.1038/nbt.3055.

*Genome-scale transcriptional activation by an engineered CRISPR-Cas9 complex*, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

*A split-Cas9 architecture for inducible genome editing and transcription modulation*, Zetsche B, Volz S E, Zhang F., (published online 2 Feb. 2015) Nat Biotechnol. February; 33(2):139-42 (2015);

*Genome-wide CRISPR Screen in a Mouse Model of Tumor Growth and Metastasis*, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and

*In vivo genome editing using Staphylococcus aureus Cas9*, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

*High-throughput functional genomics using CRISPR-Cas9*, Shalem et al., Nature Reviews Genetics 16, 299-311 (May 2015).

*Sequence determinants of improved CRISPR sgRNA design*, Xu et al., Genome Research 25, 1147-1157 (August 2015).

*A Genome-wide CRISPR Screen in Primary Immune Cells to Dissect Regulatory Networks*, Parnas et al., Cell 162, 675-686 (Jul. 30, 2015).

*CRISPR/Cas9 cleavage of viral DNA efficiently suppresses hepatitis B virus*, Ramanan et al., Scientific Reports 5:10833. doi: 10.1038/srep10$^{833}$ (Jun. 2, 2015).

*Crystal Structure of Staphylococcus aureus Cas9*, Nishimasu et al., Cell 162, 1113-1126 (Aug. 27, 2015).

BCL11A enhancer dissection by Cas9-mediated in situ saturating mutagenesis, Canver et al., Nature 527(7577): 192-7 (Nov. 12, 2015) doi: 10.1038/nature15521. Epub 2015 Sep. 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molcel.2015.10.008 Epub Oct. 22, 2015.

*Rationally engineered Cas9 nucleases with improved specificity*, Slaymaker et al., Science 2015 Dec. 1. pii: aad5227. [Epub ahead of print]

each of which is incorporated herein by reference, and discussed briefly below:

Cong et al. engineered type II CRISPR/Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR/Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MFD12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 Å resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lenti-viral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2015) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Mention is also made of Tsai et al, "Dimeric CRISPR RNA-guided FokI nucleases for highly specific genome editing," Nature Biotechnology 32(6): 569-77 (2014) which is not believed to be prior art to the instant invention or application, but which may be considered in the practice of the instant invention. Mention is also made of Konermann et al., "Genome-scale transcription activation by an engineered CRISPR-Cas9 complex," doi:10.1038/nature14136, incorporated herein by reference.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") enzyme, including sequences encoding or delivering a Cas enzyme, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.source-forge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence, i.e. an RNA capable of guiding Cas to a genomic target locus, may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNNXGG (SEQ ID NO: 1) where NNNNNNNNNNNNXGG (SEQ ID NO: 2) (N is A, G, T, or C; and X can be anything) has a single occurrence in the genome. A unique target sequence in a genome may include an S. pyogenes Cas9 target site of the form MMMMMMMMMNNNNNNNNNNNXGG (SEQ ID NO: 3) where NNNNNNNNNNNXGG (SEQ ID NO: 4) (N is A, G, T, or C; and X can be anything) has a single occurrence in the genome. For the S. thermophilus CRISPR1 Cas9, a unique target sequence in a genome may include a Cas9 target site of the form MMMMMMMMNNNNNNNNNNNNXXAGAAW (SEQ ID NO: 5) where NNNNNNNNNNNNXXAGAAW (SEQ ID NO: 6) (N is A, G, T, or C; X can be anything; and W is A or T) has a single occurrence in the genome. A unique target sequence in a genome may include an S. thermophilus CRISPR1 Cas9 target site of the form MMMMMMMMMNNNNNNNNNNNXXAGAAW (SEQ ID NO: 7) where NNNNNNNNNNNXXAGAAW (SEQ ID NO: 8) (N is A, G, T, or C; and W is A or T) has a single occurrence in the genome. For the S. pyogenes Cas9, a unique target sequence in a genome may include a Cas9 target site of the form MMMMMMMMMNNNNNNNNNNNXGGXG (SEQ ID NO: 9) where NNNNNNNNNNNXGGXG (SEQ ID NO: 10) (N is A, G, T, or C; and X can be anything) has a single occurrence in the genome. A unique target sequence in a genome may include an S. pyogenes Cas9 target site of the form MMMMMMMMMMNNNNNNNNNNXGGXG (SEQ ID NO: 11) where NNNNNNNNNNNXGGXG (SEQ ID NO: 12) (N is A, G, T, or C; and X can be anything) has a single occurrence in the genome. In each of these sequences "M" may be A, G, T, or C, and need not be considered in identifying a sequence as unique. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactctcaagatt-taGAAAtaaatcttgcagaagctacaaagataaggctt catgccgaaat-caacaccctgtcattttatggcagggtgttttcgtatataaTTTTTT (SEQ ID NO: 13); (2) NNNNNNNNNNNNNNNNNNNNgttttgtactctca GAAAtgcagaagctacaaagataaggcttcatgccgaaatca acaccctgt-cattttatggcagggtgttttcgttatttaaTTTTTT; (SEQ ID NO: 14) (3) NNNNNNNNNNNNNNNNNNNNgttttgtactctca GAAAtgcagaagctacaaagataaggcttcatgccgaaatca acaccctgt-cattttatggcagggtgtTTTTTT; (SEQ ID NO: 15) (4) NNNNNNNNNNNNNNNNNNNNgttt-tagagctaGAAAtagcaagttaaaataaggetagtecgttatcaacttgaaaa agtggcaccgagtcggtgcTTTTTT; (SEQ ID NO: 16) (5) NNNNNNNNNNNNNNNNNNNNgttt-tagagctaGAAATAGcaagttaaaataaggctagtccgttatcaacttgaa aaagtgTTTTTTT; and (SEQ ID NO: 17) (6) NNNNNNNNNNNNNNNNNNNNgttt-tagagctagAAATAGcaagttaaaataaggctagtccgttatcaTTTTT TTT (SEQ ID NO: 18). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

The RNAs to guide Cas, such as Cas9, can comprise CRISPR RNA and transactivating (tracr) RNA. The tracr mate and the tracr sequence can be connected to form a transactivating (tracer) sequence. The tracr mate and the tracr sequence can optionally be designed to form a single guide RNA (sgRNA). Indeed, it is advantageous that the RNAs to guide Cas can comprise chimeric single guide RNA (sgRNA). The tracr sequence and tracr mate sequence along the length of the shorter of the two when optimally aligned can be about or more than about 25%, 30%, 40%, 50%, 60%, 70%, 80%, 90%, 95%, 97.5%, 99%, or higher. The tracr sequence can be about or more than about 5, 6, 7, 8, 9, 10, 11, 12, 13, 14, 15, 16, 17, 18, 19, 20, 25, 30, 40, 50, or more nucleotides in length. The degree of complementarity between a guide sequence and its corresponding target sequence can be about or more than about 50%, 60%, 75%, 80%, 85%, 90%, 95%, 97.5%, 99%, or 100%. A guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. A guide or RNA or sgRNA can be less than about 75, 50, 45, 40, 35, 30, 25, 20, 15, 12, or fewer nucleotides in length.

In particularly preferred embodiments according to the invention, the RNA capable of guiding Cas to a genomic target locus may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) or RNA(s) or sgRNA(s) resulting in loss-of-function and/or gain of function of the target(s). The mutations can include the introduction, deletion, or substitution of 1-75 nucleotides at each target sequence of said cell(s) via the guide(s) or RNA(s) sgRNA(s) resulting in loss-of-function or gain of function of the target(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) or RNA(s) or sgRNA(s) resulting in loss-of-function or gain of function of the target(s). The mutations can include the introduction, deletion, or substitution of 40, 45, 50, 75, 100, 200, 300, 400 or 500 nucleotides at each target sequence of said cell(s) via the guide(s) or RNA(s) or sgRNA(s) resulting in loss-of-function or gain of function of the target. The method or mutation(s) thereof, when cell treated as such are implanted in a eukaryote can induce a cancer which may or may not metastasize, e.g., Lung cancer, Lung adenocarcinoma, Lung squamous cell carcinoma, Acute myeloid leukemia, Basal cell carcinoma (skin), Bladder cancer, Breast cancer, Carcinoid, Chronic lymphocytic leukemia, Colorectal cancer, Diffuse large B-cell lymphoma, Endometrial, Esophageal cancer, Esophageal adenocarcinoma, Glioblastoma multiforme, Glioma, Head and neck cancer, Kidney clear cell cancer, Medulloblastoma, Melanoma, Multiple myeloma, Nasopharyngeal, Neuroblastoma, Ovarian cancer, Prostate cancer, Rhabdoid tumor, Testicular germ cell tumor, Thyroid cancer, or Urinary bladder cancer. The methods as described herein, may thus also be used to identify genes or allow identification of genes which are involved in cancer and/or metastasis.

In certain embodiments, each RNA (e.g., sgRNA) used in the methods as described herein is specific to a different target sequence. Each different target sequence can be associated with or correlated to a form of cancer. Each RNA or sgRNA can be specific to a different target sequence but these RNA(s) or sgRNA(s) target specific gene sequences associated with or correlated to cancer, advantageously a particular type or form of cancer; for instance each RNA or sgRNA can be specific to a different target sequence but the target sequences of the RNA(s) or sgRNA(s) are associated with or correlated to the same type or form of cancer. The cancer selected from the group consisting of Lung cancer, Lung adenocarcinoma, Lung squamous cell carcinoma, Acute myeloid leukemia, Basal cell carcinoma (skin), Bladder cancer, Breast cancer, Carcinoid, Chronic lymphocytic leukemia, Colorectal cancer, Diffuse large B-cell lymphoma, Endometrial, Esophageal cancer, Esophageal adenocarcinoma, Glioblastoma multiforme, Glioma, Head and neck cancer, Kidney clear cell cancer, Medulloblastoma, Melanoma, Multiple myeloma, Nasopharyngeal, Neuroblastoma, Ovarian cancer, Prostate cancer, Rhabdoid tumor, Testicular germ cell tumor, Thyroid cancer, and Urinary bladder cancer.

For minimization of toxicity and off-target effect, it will be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 19) in the EMX1 gene of the human genome, deep sequencing can be used to assess the level of modification at the following two off-target loci, 1: 5'-GAGTCCTAGCAG-GAGAAGAA-3' (SEQ ID NO: 20) and 2: 5'-GAGTCTAAGCAGAAGAAGAA-3'(SEQ ID NO: 21). The concentration that gives the highest level of on-target modification while minimizing the level of off-target modification should be chosen for in vivo delivery. Alternatively, to minimize the level of toxicity and off-target effect, Cas nickase mRNA (for example *S. pyogenes* Cas9 with the D10A mutation) can be delivered with a pair of guide RNAs targeting a site of interest. The two guide RNAs need to be spaced as follows. Guide sequences and strategies to minimize toxicity and off-target effects can be as in WO 2014/093622 (PCT/US2013/074667).

In some embodiments, the CRISPR system is derived advantageously from a type II CRISPR system. In some embodiments, one or more elements of a CRISPR system is derived from a particular organism comprising an endogenous CRISPR system, such as *Streptococcus pyogenes*. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. A preferred Cas enzyme may be identified as Cas9 as this can refer to the general class of enzymes that share homology to the biggest nuclease with multiple nuclease domains from the type II CRISPR system. Most preferably, the Cas9 enzyme is from, or is derived from, SpCas9 or SaCas9. It will be appreciated that SpCas9 or SaCas9 are those from or derived from *S. pyogenes* or *S. aureus* Cas9. By derived, Applicants mean that the derived enzyme is largely based, in the sense of having a high degree of sequence homology with, a wildtype enzyme, but that it has been mutated (modified) in some way as described herein It will be appreciated that the terms Cas and CRISPR enzyme are generally used herein interchangeably, unless otherwise apparent. The Cas enzyme can be for instance any naturally-occurring bacterial Cas9 as well as any chimaeras, mutants, homologs or orthologs. Many of the residue numberings used herein refer to the Cas9 enzyme from the type II CRISPR locus in *Streptococcus pyogenes* (annotated alternatively as SpCas9 or spCas9). However, it will be appreciated that this invention includes many more Cas9s from other species of microbes, e.g., orthologs of SpCas9, or Cas9s derived from microbes in addition to *S. pyogenes*, e.g., SaCas9 derived from *S. aureus*, St1Cas9 derived from *S. thermophilus* and so forth. The skilled person will be able to determine appropriate corresponding residues in Cas9 enzymes other than SpCas9 by comparison of the relevant amino acid sequences. Thus, where a specific amino acid replacement is referred to using the SpCas9 numbering, then, unless the context makes it apparent this is not intended to refer to other Cas9 enzymes, the disclosure is intended to encompass corresponding modifications in other Cas9 enzymes.

In some embodiments, the unmodified Cas has DNA cleavage activity, such as Cas9. In some embodiments, the Cas directs cleavage of one or both strands at the location of a target sequence, such as within the target sequence and/or within the complement of the target sequence. In some embodiments, the Cas directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a Cas that is mutated to with respect to a corresponding wild-type enzyme such that the mutated Cas lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a Cas is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Thus, the Cas may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (e.g., D10 and H840) in the RuvC and HNH catalytic domains respectively; or the CRISPR enzyme can comprise one or more mutations selected from the group consisting of D10A, E762A, H840A, N854A, N863A or D986A and/or one or more mutations in a RuvC1 or HNH domain of the Cas or has a mutation as otherwise as discussed herein. In one aspect of the invention, the Cas enzyme may be fused to a protein, e.g., a TAG, and/or an inducible/controllable domain such as a chemically inducible/controllable domain. The Cas in the invention may be a chimeric Cas proteins; e.g., a Cas having enhanced function by being a chimera. Chimeric Cas proteins may be new Cas containing fragments from more than one naturally occurring Cas. These may comprise fusions of N-terminal fragment(s) of one Cas9 homolog with C-terminal fragment(s) of another Cas homolog. The Cas can be delivered into the cell in the form of mRNA. The expression of Cas can be under the control of an inducible promoter.

Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (*S. pyogenes* Cas9) or saCas9 (*S. aureus* Cas9). StCas9" refers to wild type Cas9 from *S. thermophilus*, the protein sequence of which is given in the SwissProt database under accession number G3ECR1. Similarly, *S pyogenes* Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defence in bacteria and archaea, Mole Cell 2010, January 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic DNA binding protein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

In some embodiments, the Cas as referred to herein is a codon optimized Cas. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

As used herein, the term "Cas transgenic eukaryotic cell" refers to a eukaryotic cell in which a Cas gene has been genomically integrated. The nature, type, or origin of the eukaryotic cell are not particularly limiting according to the present invention. Also the way how the Cas transgene is introduced in the eukaryotic cell is may vary and can be any method as is known in the art. In certain embodiments, the Cas transgenic eukaryotic cell is obtained by introducing the Cas transgene in an isolated eukaryotic cell. In certain other embodiments, the Cas transgenic eukaryotic cell is obtained by isolating cells from a Cas transgenic eukaryote. By means of example, and without limitation, the Cas transgenic eukaryotic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic eukaryotic cell may be obtained by introducing the Cas transgene in an isolated eukaryotic cell. Delivery systems for transgenes are well known in the art. By means of example, the Cas transgene may be delivered in the eukaryotic cell by means of vector (e.g., AAV, adenovirus, lentivirus) and/or particle and/or nanoparticle delivery, as also described herein elsewhere.

It will be understood by the skilled person that the eukaryotic cell, such as the Cas transgenic eukaryotic cell, as referred to herein may comprise further genomic alterations besides having an integrated Cas gene or the mutations arising from the sequence specific action of Cas when complexed with RNA capable of guiding Cas to a genomic target locus, such as for instance one or more oncogenic mutations, as for instance and without limitation described in Platt et al. (2014), Chen et al., (2014) or Kumar et al. (2009). In certain embodiments, the eukaryotic cell as used herein has a homozygous inactivation of p53 and/or a heterozygous inactivation of Dicer 1 and/or an oncogenic mutation in Kras G12D.

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 22); the NLS from nucleoplasmin (e.g. the nucleoplasmin bipartite NLS with the sequence KRPAATKKAGQAKKKK) (SEQ ID NO: 23); the c-myc NLS having the amino acid sequence PAAKRVKLD (SEQ ID NO: 24) or RQRRNELKRSP (SEQ ID NO: 25); the hRNPAI M9 NLS having the sequence NQSSNFGPMKGG-NFGGRSSGPYGGGGQYFAKPRNQGGY(SEQ ID NO: 26); the sequence RMRIZFKNKGKDTAELRRRRVEVS-VELRKAKKDEQILKRRNV (SEQ ID NO: 27) of the IBB domain from importin-alpha; the sequences VSRKRPRP (SEQ ID NO: 28) and PPKKARED (SEQ ID NO: 29) of the myoma T protein; the sequence PQPKKKPL (SEQ ID NO: 30) of human p53; the sequence SALIKKKKKMAP (SEQ ID NO: 31) of mouse c-abl IV; the sequences DRLRR (SEQ ID NO: 32) and PKQKKRK (SEQ ID NO: 33) of the influenza virus NS1; the sequence RKLKKKIKKL (SEQ ID NO: 34) of the Hepatitis virus delta antigen; the sequence REKKKFLKRR (SEQ ID NO: 35) of the mouse Mx1 protein; the sequence KRKGDEVDGVDEVAKKKSKK (SEQ ID NO: 36) of the human poly(ADP-ribose) polymerase; and the sequence RKCLQAGMNLEARKTKK (SEQ ID NO: 37) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

In certain aspects the invention involves vectors, e.g. for delivering or introducing in a eukaryotic cell Cas and/or RNA capable of guiding Cas to a genomic target locus, but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas, and/or a single, but possibly also can comprise at least 3 or 8 or 16 or 32 or 48 or 50 RNA(s) (e.g., sgRNAs), such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s)(e.g., sgRNA(s) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short, www.nature.com/mt/journal/v16/n9/abs/mt2008144a.html). In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters—especially as to the numbers of RNAs or guides or sgRNAs discussed herein, without any undue experimentation.

The RNA(s), e.g., sgRNA(s), can be functionally or operatively linked to regulatory element(s) and hence the regulatory element(s) drive expression. The promoter(s) can be constitutive promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Aspects of the invention also relate to bicistronic vectors for chimeric RNA and Cas. Bicistronic expression vectors for chimeric RNA and Cas are preferred. In general and particularly in this embodiment Cas is preferably driven by the CBh promoter. The chimeric RNA may preferably be driven by a Pol III promoter, such as a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 38). This may be followed by the loop sequence GAAA. Both of these are preferred examples. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or nonfusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerivisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucknow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Haloarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azoarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*. In some embodiments, one or more vectors driving expression of one or more elements of a CRISPR system (such as the Cas and/or the RNA guiding the Cas to a genomic target locus in a eukaryotic cell as referred to herein elsewhere) are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a Cas and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the Cas, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622(PCT/US2013/074667). In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a Cas protein. Cas protein or Cas mRNA or CRISPR guide RNA or RNA(s) can be delivered separately; and advantageously at least one of these is delivered via a particle complex. Cas mRNA can be delivered prior to the guide RNA to give time for Cas to be expressed. Cas mRNA might be administered 1-12 hours (preferably around 2-6 hours) prior to the administration of guide RNA. Alternatively, Cas mRNA and guide RNA can be administered together. Advantageously, a second booster dose of guide RNA can be administered 1-12 hours (preferably around 2-6 hours) after the initial administration of Cas mRNA+guide RNA. Additional administrations of Cas mRNA and/or guide RNA might be useful to achieve the most efficient levels of genome modification.

In certain embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control, such as oncogenes or tumor suppressor genes or metastasis suppressor genes. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the Cas used, but PAMs are typically 2-5 base pair sequences adjacent the protospacer (that is, the target sequence. In some embodiments, the method comprises allowing a CRISPR complex to bind to the target polynucleotide to effect cleavage of said target polynucleotide thereby modifying the target polynucleotide, wherein the CRISPR complex comprises a Cas complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a Cas complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention. In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

In certain embodiments, a Cas and/or an RNA capable of guiding the Cas to a target locus as described herein elsewhere is delivered to or introduced in a eukaryotic cell. Conventional viral and non-viral based gene transfer methods can be used to introduce nucleic acids in cells. Non-viral vector delivery systems include DNA plasmids, RNA (e.g. a transcript of a vector described herein), naked nucleic acid, and nucleic acid complexed with a delivery vehicle, such as a liposome. Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). Viral vector delivery systems include DNA and RNA viruses, which have either episomal or integrated genomes after delivery to the cell. Viral vectors can be used to treat cells in vitro, and the modified cells can then be administered to a eukaryote, such as a non-human eukaryote. Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues. The tropism of a retrovirus can be altered by incorporating foreign envelope proteins, expanding the potential target population of target cells. Lentiviral vectors are retroviral vectors (and hence both lentiviral and retroviral vectors may be used in the practice of the invention). Moreover, lentiviral vectors are preferred as they are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors that may be used in the practice of the invention include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). Zou et al. administered about 10 µl of a recombinant lentivirus having a titer of 1×109 transducing units (TU)/ml by an intrathecal catheter. These sorts of dosages can be adapted or extrapolated to use of a retroviral or lentiviral vector in the present invention.

If a Cas transgenic eukaryotic cell provided for herein is used, then only delivery of guide(s) is necessary, i.e. RNA capable of guiding Cas to a genomic target locus. In some embodiments, one or more vectors described herein are used to produce a non-human transgenic Cas9 eukaryote, e.g., animal, mammal, primate, rodent, mouse, rat, rabbit. In some embodiments, the transgenic animal is a mammal, such as a mouse, rat, or rabbit. Guides or RNA(s) can be delivered via the same vector types as Cas9. When both guides or RNA(s) and Cas9 are being delivered a dual-vector system where the Cas9 is delivered via in vivo expression from an AAV vector and the guide(s) are delivered by a separate AAV vector. This can be done substantially contemporaneously (i.e., co-delivery), but it could also be done at separate points in time, separated even by weeks or months. Of course, the ultimate separation is where the transgenic Cas9 eukaryote is generated and thereafter the guide(s) or RNA(s) are delivered. Alternatively a first round of CRISPR-Cas9 systems can be delivered, and subsequently further guides or RNA(s) are delivered as the original Cas9 is still functional in the target cells may be re-used. If the Cas9 is under the control of an inducible promoter, then induction of transcription of new CAs9 in the target cells is preferred.

Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors is described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producer a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Accordingly, AAV is considered an ideal candidate for use as a transducing vector. Such AAV transducing vectors can comprise sufficient cis-acting functions to replicate in the presence of adenovirus or herpesvirus or poxvirus (e.g., vaccinia virus) helper functions provided in trans. Recombinant AAV (rAAV) can be used to carry exogenous genes into cells of a variety of lineages. In these vectors, the AAV cap and/or rep genes are deleted from the viral genome and replaced with a DNA segment of choice. Current AAV vectors may accommodate up to 4300 bases of inserted DNA. There are a number of ways to produce rAAV, and the invention provides rAAV and methods for preparing rAAV. For example, plasmid(s) containing or consisting essentially of the desired viral construct are transfected into AAV-infected cells. In addition, a second or additional helper plasmid is cotransfected into these cells to provide the AAV rep and/or cap genes which are obligatory for replication and packaging of the recombinant viral construct. Under these conditions, the rep and/or cap proteins of AAV act in trans to stimulate replication and packaging of the rAAV construct. Two to Three days after transfection, rAAV is harvested. Traditionally rAAV is harvested from the cells along with adenovirus. The contaminating adenovirus is then inactivated by heat treatment. In the instant invention, rAAV is advantageously harvested not from the cells themselves, but from cell supernatant. Accordingly, in an initial aspect the invention provides for preparing rAAV, and in addition to the foregoing, rAAV can be prepared by a method that comprises or consists essentially of: infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus) provides the cap and/or rev function that the rAAV lacks); or infecting susceptible cells with a rAAV containing exogenous DNA including DNA for expression, wherein the recombinant lacks functioning cap and/or rep, and transfecting said cells with a plasmid supplying cap and/or rep function that the rAAV lacks; or infecting susceptible cells with a rAAV containing exogenous DNA including DNA for expression, wherein the recombinant lacks functioning cap and/or rep, wherein said cells supply cap and/or rep function that the recombinant lacks; or transfecting the susceptible cells with an AAV lacking functioning cap and/or rep and plasmids for inserting exogenous DNA into the recombinant so that the exogenous DNA is expressed by the recombinant and for supplying rep and/or cap functions whereby transfection results in an rAAV containing the exogenous DNA including DNA for expression that lacks functioning cap and/or rep. The rAAV can be from an AAV as herein described, and advantageously can be an rAAV1, rAAV2, AAV5 or rAAV having hybrid or capsid which may comprise AAV1, AAV2, AAV5 or any combination thereof. One can select the AAV of the rAAV with regard to the cells to be targeted by the rAAV. In addition to 293 cells, other cells that can be used in the practice of the invention and the relative infectivity of certain AAV serotypes in vitro as to these cells; see Grimm, D. et al, J. Virol. 82: 5887-5911 (2008) The invention provides rAAV that contains or consists essentially of an exogenous nucleic acid molecule encoding a CRISPR (Clustered Regularly Interspaced Short Palindromic Repeats) system or component(s) or coding therefor, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cas9 and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn).

AAV has a packaging limit of 4.5 or 4.75 Kb. This means that Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

| Species | Cas9 Size |
|---|---|
| *Corynebacter diphtheriae* | 3252 |
| *Eubacterium ventriosum* | 3321 |
| *Streptococcus pasteurianus* | 3390 |
| *Lactobacillus farciminis* | 3378 |
| *Sphaerochaeta globus* | 3537 |
| *Azospirillum* B510 | 3504 |
| *Gluconacetobacter diazotrophicus* | 3150 |
| *Neisseria cinerea* | 3246 |
| *Roseburia intestinalis* | 3420 |
| *Parvibaculum lavamentivorans* | 3111 |
| *Staphylococcus aureus* | 3159 |
| *Nitratifractor salsuginis* DSM 16511 | 3396 |
| *Campylobacter lari* CF89-12 | 3009 |
| *Streptococcus thermophilus* LMD-9 | 3396 |

The invention also can be practiced with an adenovirus vector, e.g., an E1-, partial E3-, E4-deleted adenoviral vector may be used in the practice of the invention. Such vectors are safe as twenty-eight patients with advanced neovascular age-related macular degeneration (AMD) were given a single intravitreous injection of an E1-, partial E3-, E4-deleted adenoviral vector expressing human pigment epithelium-derived factor (AdPEDF.ll) (see, e.g., Campochiaro et al., Human Gene Therapy 17:167-176 (February 2006)); and previous adenovirus doses ranging from 106 to 109.5 particle units (PU) can be adapted or employed in the practice of the instant invention (see, e.g., Campochiaro et al., Human Gene Therapy 17:167-176 (February 2006)). Adenoviral vector-mediated RNA transfer appears to be a viable approach for delivery of RNA(S). For adenoviral vector injections into a rat, 2×109 infectious particles were injected in 3 ml of normal saline solution (NSS). This can be adapted to or extrapolated from in the practice of the present invention. For siRNA, a rat was injected into the great saphenous vein with 12.5 μg of a siRNA and a primate was injected into the great saphenous vein with 750 μg of a siRNA. This can be adapted to or extrapolated from in the practice of the present invention.

In certain embodiments the Cas and/or RNA capable of guiding Cas to a genomic target locus may be delivered by lentiviral delivery systems. Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4 C. They were then aliquoted and immediately frozen at −80° C.

Also useful in the practice of the invention is a minimal non-primate lentiviral vector, such as a lentiviral vector based on the equine infectious anemia virus (EIAV)(see, e.g., Balagaan, J Gene Med 2006; 8: 275 285, Published online 21 Nov. 2005 in Wiley InterScience (www.interscience.wiley.com). DOI: 10.1002/jgm.845). The vectors may have cytomegalovirus (CMV) promoter driving expression of the target gene. Intracameral, subretinal, intraocular and intravitreal injections are all within the ambit of the instant invention (see, e.g., Balagaan, J Gene Med 2006; 8: 275 285, Published online 21 Nov. 2005 in Wiley InterScience (www.interscience.wiley.com). DOI: 10.1002/jgm.845). In this regard, mention is made of RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)). Such a vector may be modified for practice of the present invention. Dosing of RetinoStat® (e.g., 1.1×105 transducing units per eye (TU/eye) in a total volume of 100 μl) can be applied or extrapolated from in practicing the present invention with a lentivirus.

In certain embodiments, use is made of self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used and/or adapted to the CRISPR-Cas system of the present invention. A minimum of 2.5×106 CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (CellGenix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin, Takara Bio Inc.).

Accordingly, the invention contemplates amongst vector(s) useful in the practice of the invention: viral vectors, including retroviral vectors, lentiviral vectors, adenovirus vectors, or AAV vectors.

The Cas, for instance a Cas9, and/or any of the present RNAs, for instance a guide RNA, can also be delivered in the form of RNA. Cas mRNA can be generated using in vitro transcription. For example, Cas mRNA can be synthesized using a PCR cassette containing the following elements: T7_promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

Several types of particle and nanoparticle delivery systems and/or formulations are known to be useful in a diverse spectrum of biomedical applications; and particle and nanoparticle delivery systems in the practice of the instant invention can be as in WO 2014/093622 (PCT/US13/74667). In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm. As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter)

of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm. Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., Cas enzyme or mRNA or guide RNA, or any combination thereof, and may include additional carriers and/or excipients) to provide particles of an optimal size for delivery according to certain embodiments of the present invention. In certain preferred embodiments, particle dimension (e.g., diameter) characterization is based on measurements using dynamic laser scattering (DLS). Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

In general, a "nanoparticle" refers to any particle having a diameter of less than 1000 nm. In certain preferred embodiments, nanoparticles have a greatest dimension (e.g., diameter) of 500 nm or less. In other preferred embodiments, nanoparticles have a greatest dimension ranging between 25 nm and 200 nm. In other preferred embodiments, nanoparticles have a greatest dimension of 100 nm or less. In other preferred embodiments, nanoparticles have a greatest dimension ranging between 35 nm and 60 nm. Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

With regard to particles that can deliver RNA, see, e.g., Alabi et al., Proc Natl Acad Sci USA. 2013 Aug. 6; 110 (32):12881-6; Zhang et al., Adv Mater. 2013 Sep. 6; 25(33): 4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

Lipid particles, Spherical Nucleic Acid ($SNA^T M$) constructs, nanoplexes and other particles (particularly gold particles) are also contemplate as a means for delivery of CRISPR/Cas system or component(s) thereof or vector(s) to intended targets. Particles, nanoparticles, and the like and vectors are advantageous for delivering the RNA(s) of the CRISPR-Cas system and particles and nanoparticles and the like may be advantageous for delivery of vector containing nucleic acid(s) encoding or comprising RNA(s) of the invention. In certain instances, e.g., where Cas is constitutively or inducibly or conditionally expressed by an organism or cells thereof, it is useful to deliver the RNA(s) (also herein sometimes termed "guides") of the CRISPR-Cas system separately from the Cas9. It is considered as advantageous that the Cas may be delivered via a viral vector or be constitutively or inducibly or conditionally expressed and that guides specific to genomic targets are delivered separately. A recent publication, entitled "In vivo endothelial siRNA delivery using polymeric nanoparticles with low molecular weight" by James E. Dahlman and Carmen Barnes et al. Nature Nanotechnology (2014) published online 11 May 2014, doi:10.1038/nnano.2014.84, incorporated herein in its entirety, showed that polymeric particles made of low-molecular-weight polyamines and lipids can deliver siRNA to endothelial cells with high efficiency, thereby facilitating the simultaneous silencing of multiple endothelial genes in vivo. The authors reported that unlike lipid or lipid-like particles, the particle formulation they used (termed 7C1), differed from traditional lipid-based particle formulations because it can deliver siRNA to lung endothelial cells at low doses without substantially reducing gene expression in pulmonary immune cells, hepatocytes or peritoneal immune cells. The study further demonstrated that 7C1-mediated endothelial gene silencing affects function in vivo, by using the nanoformulation to modify mouse models of vascular permeability, emphysema, lung tumor growth and lung metastasis.

In some embodiments, the Cas is part of a fusion protein (i.e. chimeric protein) comprising one or more heterologous protein domains (e.g. about or more than about 1, 2, 3, 4, 5, 6, 7, 8, 9, 10, or more domains in addition to the Cas). A Cas fusion protein may comprise any additional protein sequence, and optionally a linker sequence between any two domains. Examples of protein domains that may be fused to a Cas include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. In such embodiments, it is preferred that Cas itself is catalytically inactive, or partially catalytically inactive. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A Cas may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a Cas are described in US20110059502, incorporated herein by reference. In some embodiments, a tagged Cas is used to identify the location of a target sequence. In certain embodiments, Cas is fused to a heterologous protein capable of manipulating a target sequence. By manipulation of a target sequence, Applicants mean the alteration of the target sequence, which may include the epigenetic manipulation of a target sequence. This epigenetic manipulation may be of the chromatin state of a target sequence, such as by modification of the methylation state of the target sequence (i.e. addition or removal of methylation or methylation patterns or CpG islands), histone modification, increasing or reducing accessibility to the target sequence, or by promoting 3D folding.

In some embodiments, a Cas f ensequence and/or RNA capable of guiding Cas to a genomic target locus may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the Cas sequence and/or RNA capable of guiding Cas to a genomic target locus may be a part of a Light Inducible Transcriptional Effector (LITE) to direct changes in transcriptional activity in a sequence-specific manner. The components of a LITE may include a Cas sequence and/or RNA capable of guiding Cas to a genomic target locus, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

In certain embodiments, one or more of the components of the CRISPR-Cas system may be conditionally (e.g. tissue or cell type specific) and/or inducibly (e.g. chemically inducible) expressed in the cell. Inducible and conditional expression systems are described herein elsewhere. In particular embodiments, one or more of the guide RNA(s) may be conditionally and/or inducibly expressed in the cell. In particular preferred embodiments, the Cas may be conditionally and/or inducibly expressed in the cell.

In an aspect the invention also features a non-naturally occurring or engineered inducible Cas9 CRISPR-Cas system, comprising: a first Cas9 fusion construct attached to a first half of an inducible dimer and a second Cas9 fusion construct attached to a second half of the inducible dimer, wherein the first Cas9 fusion construct is operably linked to one or more nuclear localization signals, wherein the second Cas9 fusion construct is operably linked to one or more nuclear export signals, wherein contact with an inducer energy source brings the first and second halves of the inducible dimer together, wherein bringing the first and second halves of the inducible dimer together allows the first and second Cas9 fusion constructs to constitute a functional Cas9 CRISPR-Cas system, wherein the Cas9 CRISPR-Cas system comprises a guide RNA (gRNA) comprising a guide sequence capable of hybridizing to a target sequence in a genomic locus of interest in a cell, and wherein the functional Cas9 CRISPR-Cas system binds to the target sequence and, optionally, edits the genomic locus to alter gene expression.

In an aspect of the invention in the inducible Cas9 CRISPR-Cas system, the inducible dimer is or comprises or consists essentially of or consists of an inducible heterodimer. In an aspect, in inducible Cas9 CRISPR-Cas system, the first half or a first portion or a first fragment of the inducible heterodimer is or comprises or consists of or consists essentially of an FKBP, optionally FKBP12. In an aspect of the invention, in the inducible Cas9 CRISPR-Cas system, the second half or a second portion or a second fragment of the inducible heterodimer is or comprises or consists of or consists essentially of FRB. In an aspect of the invention, in the inducible Cas9 CRISPR-Cas system, the arrangement of the first Cas9 fusion construct is or comprises or consists of or consists essentially of N' terminal Cas9 part-FRB-NES. In an aspect of the invention, in the inducible Cas9 CRISPR-Cas system, the arrangement of the first Cas9 fusion construct is or comprises or consists of or consists essentially of NES-N' terminal Cas9 part-FRB-NES. In an aspect of the invention, in the inducible Cas9 CRISPR-Cas system, the arrangement of the second Cas9 fusion construct is or comprises or consists essentially of or consists of C' terminal Cas9 part-FKBP-NLS. In an aspect the invention provides in the inducible Cas9 CRISPR-Cas system, the arrangement of the second Cas9 fusion construct is or comprises or consists of or consists essentially of NLS-C' terminal Cas9 part-FKBP-NLS. In an aspect, in inducible Cas9 CRISPR-Cas system there can be a linker that separates the Cas9 part from the half or portion or fragment of the inducible dimer. In an aspect, in the inducible Cas9 CRISPR-Cas system, the inducer energy source is or comprises or consists essentially of or consists of rapamycin. In an aspect, in inducible Cas9 CRISPR-Cas system, the inducible dimer is an inducible homodimer. In an aspect, in inducible Cas9 CRISPR-Cas system, the Cas9 is FnCas9. In an aspect, in the inducible Cas9 CRISPR-Cas system, one or more functional domains are associated with one or both parts of the Cas9, e.g., the functional domains optionally including a transcriptional activator, a transcriptional or a nuclease such as a Fok1 nuclease. In an aspect, in the inducible Cas9 CRISPR-Cas system, the functional Cas9 CRISPR-Cas system binds to the target sequence and the enzyme is a dead-Cas9, optionally having a diminished nuclease activity of at least 97%, or 100% (or no more than 3% and advantageously 0% nuclease activity) as compared with the Cas9 not having the at least one mutation. The invention further comprehends and an aspect of the invention provides, a polynucleotide encoding the inducible Cas9 CRISPR-Cas system as herein discussed.

In an aspect, the invention provides a vector for delivery of the first Cas9 fusion construct, attached to a first half or portion or fragment of an inducible dimer and operably linked to one or more nuclear localization signals, according as herein discussed. In an aspect, the invention provides a vector for delivery of the second Cas9 fusion construct, attached to a second half or portion or fragment of an inducible dimer and operably linked to one or more nuclear export signals.

In an aspect, the invention provides a vector for delivery of both: the first Cas9 fusion construct, attached to a first half or portion or fragment of an inducible dimer and operably linked to one or more nuclear localization signals, as herein discussed; and the second Cas9 fusion construct, attached to a second half or portion or fragment of an inducible dimer and operably linked to one or more nuclear export signals, as herein discussed.

In an aspect, the vector can be single plasmid or expression cassette.

The invention, in an aspect, provides a eukaryotic host cell or cell line transformed with any of the vectors herein discussed or expressing the inducible Cas9 CRISPR-Cas system as herein discussed.

The invention, in an aspect provides, a transgenic organism transformed with any of the vectors herein discussed or expressing the inducible Cas9 CRISPR-Cas system herein discussed, or the progeny thereof. In an aspect, the invention provides a model organism which constitutively expresses the inducible Cas9 CRISPR-Cas system as herein discussed.

In an aspect, the invention provides non-naturally occurring or engineered inducible Cas9 CRISPR-Cas system, comprising: a first Cas9 fusion construct attached to a first half of an inducible heterodimer and a second Cas9 fusion construct attached to a second half of the inducible heterodimer, wherein the first Cas9 fusion construct is operably linked to one or more nuclear localization signals, wherein the second Cas9 fusion construct is operably linked to a nuclear export signal, wherein contact with an inducer energy source brings the first and second halves of the inducible heterodimer together, wherein bringing the first and second halves of the inducible heterodimer together allows the first and second Cas9 fusion constructs to constitute a functional Cas9 CRISPR-Cas system, wherein the Cas9 CRISPR-Cas system comprises a guide RNA (gRNA) comprising a guide sequence capable of hybridizing to a target sequence in a genomic locus of interest in a cell, and wherein the functional Cas9 CRISPR-Cas system edits the genomic locus to alter gene expression.

In an aspect, the invention provides a method of treating a subject in need thereof, comprising inducing gene editing by transforming the subject with the polynucleotide as herein discussed or any of the vectors herein discussed and administering an inducer energy source to the subject. The invention comprehends uses of such a polynucleotide or vector in the manufacture of a medicament, e.g., such a medicament for treating a subject or for such a method of treating a subject. The invention comprehends the polynucleotide as herein discussed or any of the vectors herein discussed for use in a method of treating a subject in need thereof comprising inducing gene editing, wherein the method further comprises administering an inducer energy source to the subject. In an aspect, in the method, a repair template is also provided, for example delivered by a vector comprising said repair template.

The invention also provides a method of treating a subject in need thereof, comprising inducing transcriptional activation or repression by transforming the subject with the polynucleotide herein discussed or any of the vectors herein discussed, wherein said polynucleotide or vector encodes or comprises the catalytically inactive Cas9 and one or more associated functional domains as herein discussed; the method further comprising administering an inducer energy source to the subject. The invention also provides the polynucleotide herein discussed or any of the vectors herein discussed for use in a method of treating a subject in need thereof comprising inducing transcriptional activation or repression, wherein the method further comprises administering an inducer energy source to the subject.

Accordingly, the invention comprehends inter alia homodimers as well as heterodimers, dead-Cas9 or Cas9 having essentially no nuclease activity, e.g., through mutation, systems or complexes wherein there is one or more NLS and/or one or more NES; functional domain(s) linked to split Cas9; methods, including methods of treatment, and uses.

It will be appreciated that where reference is made herein to Cas9, Cas9 protein or Cas9 enzyme, this includes the present split Cas9. In one aspect, the invention provides a method for altering or modifying expression of a gene product. The said method may comprise introducing into a cell containing and expressing a DNA molecule encoding the gene product an engineered, non-naturally occurring Cas9 CRISPR-Cas system comprising a Cas9 protein and guide RNA that targets the DNA molecule, whereby the guide RNA targets the DNA molecule encoding the gene product and the Cas9 protein cleaves the DNA molecule encoding the gene product, whereby expression of the gene product is altered; and, wherein the Cas9 protein and the guide RNA do not naturally occur together. The invention comprehends the guide RNA comprising a guide sequence linked to a direct repeat (DR) sequence. The invention further comprehends the Cas9 protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In one aspect, the invention provides an engineered, non-naturally occurring Cas9 CRISPR-Cas system comprising a Cas9 protein and a guide RNA that targets a DNA molecule encoding a gene product in a cell, whereby the guide RNA targets the DNA molecule encoding the gene product and the Cas9 protein cleaves the DNA molecule encoding the gene product, whereby expression of the gene product is altered; and, wherein the Cas9 protein and the guide RNA do not naturally occur together; this including the present split Cas9. The invention comprehends the guide RNA comprising a guide sequence linked to a DR sequence. The invention further comprehends the Cas9 protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to a Cas9 CRISPR-Cas system guide RNA that targets a DNA molecule encoding a gene product and a second regulatory element operably linked to a Cas9 protein; this includes the present split Cas9. Components (a) and (b) may be located on same or different vectors of the system. The guide RNA targets the DNA molecule encoding the gene product in a cell and the Cas9 protein cleaves the DNA molecule encoding the gene product, whereby expression of the gene product is altered; and, wherein the Cas9 protein and the guide RNA do not naturally occur together. The invention comprehends the guide RNA comprising a guide sequence linked to a DR sequence. The invention further comprehends the Cas9 protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In one aspect, the invention provides a vector system comprising one or more vectors. In some embodiments, the system comprises: (a) a first regulatory element operably linked to a DR sequence and one or more insertion sites for inserting one or more guide sequences downstream of the DR sequence, wherein when expressed, the guide sequence directs sequence-specific binding of a Cas9 CRISPR-Cas complex to a target sequence in a eukaryotic cell, wherein the Cas9 CRISPR-Cas complex comprises Cas9 complexed with (1) the guide sequence that is hybridized to the target sequence, and (2) the DR sequence; and (b) a second regulatory element operably linked to an enzyme-coding sequence encoding said Cas9 enzyme comprising a nuclear localization sequence; wherein components (a) and (b) are located on the same or different vectors of the system; this includes the present split Cas9. In some embodiments, component (a) further comprises two or more guide sequences operably linked to the first regulatory element, wherein when expressed, each of the two or more guide sequences direct sequence specific binding of a Cas9 CRISPR-Cas complex to a different target sequence in a eukaryotic cell.

In some embodiments, the Cas9 CRISPR-Cas complex comprises one or more nuclear localization sequences of sufficient strength to drive accumulation of said Cas9 CRISPR-Cas complex in a detectable amount in the nucleus of a eukaryotic cell. Without wishing to be bound by theory, it is believed that a nuclear localization sequence is not necessary for Cas9 CRISPR-Cas complex activity in eukaryotes, but that including such sequences enhances activity of the system, especially as to targeting nucleic acid molecules in the nucleus.

In some embodiments, the Cas9 enzyme is Cas9 of a bacterial species selected from the group consisting of *Francisella tularensis* 1, *Francisella tularensis* subsp. *novicida*, *Prevotella albensis*, Lachnospiraceae *bacterium* MC2017 1, *Butyrivibrio proteoclasticus*, Peregrinibacteria *bacterium* GW2011_GWA2_33_10, Parcubacteria *bacterium* GW2011_GWC2_44_17, *Smithella* sp. SCADC, *Acidaminococcus* sp. BV3L6, Lachnospiraceae *bacterium* MA2020, *Candidatus* Methanoplasma *termitum*, *Eubacterium eligens*, *Moraxella bovoculi* 237, *Leptospira inadai*, Lachnospiraceae *bacterium* ND2006, *Porphyromonas crevioricanis* 3, *Prevotella disiens*, and *Porphyromonas macacae*, and may include mutated Cas9 derived from these organisms. The enzyme may be a Cas9 homolog or ortholog. In some embodiments, the Cas9 is codon-optimized for expression in a eukaryotic cell. In some embodiments, the Cas9 directs cleavage of one or two strands at the location of the target sequence. In a preferred embodiment, the strand break is a staggered cut with a 5' overhang. In some embodiments, the first regulatory element is a polymerase III promoter. In some embodiments, the second regulatory element is a polymerase II promoter. In some embodiments, the direct repeat has a minimum length of 16 nts and a single stem loop. In further embodiments the direct repeat has a length longer than 16 nts, preferably more than 17 nts, and has more than one stem loop or optimized secondary structures.

In one aspect, the invention provides a eukaryotic host cell comprising (a) a first regulatory element operably linked to a direct repeat sequence and one or more insertion sites for inserting one or more guide sequences downstream of the DR sequence, wherein when expressed, the guide sequence directs sequence-specific binding of a Cas9 CRISPR-Cas complex to a target sequence in a eukaryotic cell, wherein the Cas9 CRISPR-Cas complex comprises Cas9 complexed with (1) the guide sequence that is hybridized to the target sequence, and (2) the DR sequence; and/or (b) a second regulatory element operably linked to an enzyme-coding sequence encoding said Cas9 enzyme comprising a nuclear localization sequence. In some embodiments, the host cell comprises components (a) and (b); this includes the present split Cas9. In some embodiments, component (a), component (b), or components (a) and (b) are stably integrated into a genome of the host eukaryotic cell. In some embodiments, component (a) further comprises two or more guide sequences operably linked to the first regulatory element, wherein when expressed, each of the two or more guide sequences direct sequence specific binding of a Cas9 CRISPR-Cas complex to a different target sequence in a eukaryotic cell. In some embodiments, the Cas9 is codon-optimized for expression in a eukaryotic cell. In some embodiments, the Cas9 directs cleavage of one or two strands at the location of the target sequence. In a preferred embodiment, the strand break is a staggered cut with a 5' overhang. In some embodiments, the Cas9 lacks DNA strand cleavage activity. In some embodiments, the first regulatory element is a polymerase III promoter. In some embodiments, the direct repeat has a minimum length of 16 nts and a single stem loop. In further embodiments the direct repeat has a length longer than 16 nts, preferably more than 17 nts, and has more than one stem loop or optimized secondary structures. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus.

In one aspect, the invention provides a kit comprising one or more of the components described herein. In some embodiments, the kit comprises a vector system and instructions for using the kit. In some embodiments, the vector system comprises (a) a first regulatory element operably linked to a direct repeat sequence and one or more insertion sites for inserting one or more guide sequences downstream of the DR sequence, wherein when expressed, the guide sequence directs sequence-specific binding of a Cas9 CRISPR-Cas complex to a target sequence in a eukaryotic cell, wherein the Cas9 CRISPR-Cas complex comprises Cas9 complexed with (1) the guide sequence that is hybridized to the target sequence, and (2) the DR sequence; and/or (b) a second regulatory element operably linked to an enzyme-coding sequence encoding said Cas9 enzyme comprising a nuclear localization sequence and advantageously this includes the present split Cas9. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a Cas9 CRISPR-Cas complex to a different target sequence in a eukaryotic cell. In some embodiments, the Cas9 comprises one or more nuclear localization sequences of sufficient strength to drive accumulation of said Cas9 in a detectable amount in the nucleus of a eukaryotic cell. In some embodiments, the Cas9 enzyme is Cas9 of a bacterial species selected from the group consisting of *Francisella tularensis* 1, *Francisella tularensis* subsp. *novicida*, *Prevotella albensis*, Lachnospiraceae *bacterium* MC2017 1, *Butyrivibrio*

*proteoclasticus*, Peregrinibacteria *bacterium* GW2011_GWA2_33_10, Parcubacteria *bacterium* GW2011_GWC2_44_17, *Smithella* sp. SCADC, *Acidaminococcus* sp. BV3L6, Lachnospiraceae *bacterium* MA2020, *Candidatus* Methanoplasma *termitum, Eubacterium eligens, Moraxella bovoculi* 237, *Leptospira inadai*, Lachnospiraceae *bacterium* ND2006, *Porphyromonas crevioricanis* 3, *Prevotella disiens*, and *Porphyromonas macacae*, and may include mutated Cas9 derived from these organisms. The enzyme may be a Cas9 homolog or ortholog. In some embodiments, the Cas9 is codon-optimized for expression in a eukaryotic cell. In some embodiments, the Cas9 directs cleavage of one or two strands at the location of the target sequence. In a preferred embodiment, the strand break is a staggered cut with a 5' overhang. In some embodiments, the CRISPR enzyme lacks DNA strand cleavage activity. In some embodiments, the direct repeat has a minimum length of 16 nts and a single stem loop. In further embodiments the direct repeat has a length longer than 16 nts, preferably more than 17 nts, and has more than one stem loop or optimized secondary structures.

In one aspect, the invention provides a method of modifying a target polynucleotide in a eukaryotic cell. In some embodiments, the method comprises allowing a Cas9 CRISPR-Cas complex to bind to the target polynucleotide to effect cleavage of said target polynucleotide thereby modifying the target polynucleotide, wherein the Cas9 CRISPR-Cas complex comprises Cas9 complexed with a guide sequence hybridized to a target sequence within said target polynucleotide, wherein said guide sequence is linked to a direct repeat sequence. In some embodiments, said cleavage comprises cleaving one or two strands at the location of the target sequence by said Cas9; this includes the present split Cas9. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the Cas9, and the guide sequence linked to the DR sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a Cas9 CRISPR-Cas complex to bind to the polynucleotide such that said binding results in increased or decreased expression of said polynucleotide; wherein the Cas9 CRISPR-Cas complex comprises Cas9 complexed with a guide sequence hybridized to a target sequence within said polynucleotide, wherein said guide sequence is linked to a direct repeat sequence; this includes the present split Cas9. In some embodiments, the method further comprises delivering one or more vectors to said eukaryotic cells, wherein the one or more vectors drive expression of one or more of: the Cas9, and the guide sequence linked to the DR sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: Cas9, and a guide sequence linked to a direct repeat sequence; and (b) allowing a Cas9 CRISPR-Cas complex to bind to a target polynucleotide to effect cleavage of the target polynucleotide within said disease gene, wherein the Cas9 CRISPR-Cas complex comprises the Cas9 complexed with (1) the guide sequence that is hybridized to the target sequence within the target polynucleotide, and (2) the DR sequence, thereby generating a model eukaryotic cell comprising a mutated disease gene; this includes the present split Cas9. In some embodiments, said cleavage comprises cleaving one or two strands at the location of the target sequence by said Cas9. In a preferred embodiment, the strand break is a staggered cut with a 5' overhang. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence downstream of a direct repeat sequence, wherein the guide sequence when expressed directs sequence-specific binding of a Cas9 CRISPR-Cas complex to a corresponding target sequence present in a eukaryotic cell. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell (s), the method comprising: introducing one or more vectors into the cell (s), wherein the one or more vectors drive expression of one or more of: Cas9, a guide sequence linked to a direct repeat sequence, and an editing template; wherein the editing template comprises the one or more mutations that abolish Cas9 cleavage; allowing homologous recombination of the editing template with the target polynucleotide in the cell(s) to be selected; allowing a Cas9 CRISPR-Cas complex to bind to a target polynucleotide to effect cleavage of the target polynucleotide within said gene, wherein the Cas9 CRISPR- Cas complex comprises the Cas9 complexed with (1) the guide sequence that is hybridized to the target sequence within the target polynucleotide, and (2) the direct repeat sequence, wherein binding of the Cas9 CRISPR-Cas complex to the target polynucleotide induces cell death, thereby allowing one or more cell(s) in which one or more mutations have been introduced to be selected; this includes the present split Cas9. In another preferred embodiment of the invention the cell to be selected may be a eukaryotic cell. Aspects of the invention allow for selection of specific cells without requiring a selection marker or a two-step process that may include a counter-selection system.

Herein there is the phrase "this includes the present split Cas9" or similar text; and, this is to indicate that Cas9 in embodiments herein can be a split Cas9 as herein discussed.

In an aspect the invention involves a non-naturally occurring or engineered inducible Cas9 CRISPR-Cas system, comprising a first Cas9 fusion construct attached to a first half of an inducible heterodimer and a second Cas9 fusion construct attached to a second half of the inducible heterodimer, wherein the first Cas9 fusion construct is operably linked to one or more nuclear localization signals, wherein the second Cas9 fusion construct is operably linked to a nuclear export signal, wherein contact with an inducer energy source brings the first and second halves of the inducible heterodimer together, wherein bringing the first and second halves of the inducible heterodimer together allows the first and second Cas9 fusion constructs to constitute a functional Cas9 CRISPR-Cas system, wherein the Cas9 CRISPR-Cas system comprises a guide RNA (gRNA) comprising a guide sequence capable of hybridizing to a target sequence in a genomic locus of interest in a cell, and wherein the functional Cas9 CRISPR-Cas system edits the genomic locus to alter gene expression. In an embodiment of the invention the first half of the inducible heterodimer is FKBP12 and the second half of the inducible heterodimer is FRB. In another embodiment of the invention the inducer energy source is rapamycin.

An inducer energy source may be considered to be simply an inducer or a dimerizing agent. The term 'inducer energy source' is used herein throughout for consistency. The inducer energy source (or inducer) acts to reconstitute the Cas9. In some embodiments, the inducer energy source brings the two parts of the Cas9 together through the action of the two halves of the inducible dimer. The two halves of the inducible dimer therefore are brought tougher in the presence of the inducer energy source. The two halves of the dimer will not form into the dimer (dimerize) without the inducer energy source.

Thus, the two halves of the inducible dimer cooperate with the inducer energy source to dimerize the dimer. This in turn reconstitutes the Cas9 by bringing the first and second parts of the Cas9 together.

The CRISPR enzyme fusion constructs each comprise one part of the split Cas9. These are fused, preferably via a linker such as a GlySer linker described herein, to one of the two halves of the dimer. The two halves of the dimer may be substantially the same two monomers that together that form the homodimer, or they may be different monomers that together form the heterodimer. As such, the two monomers can be thought of as one half of the full dimer.

The Cas9 is split in the sense that the two parts of the Cas9 enzyme substantially comprise a functioning Cas9. That Cas9 may function as a genome editing enzyme (when forming a complex with the target DNA and the guide), such as a nickase or a nuclease (cleaving both strands of the DNA), or it may be a dead-Cas9 which is essentially a DNA-binding protein with very little or no catalytic activity, due to typically mutation(s) in its catalytic domains.

The two parts of the split Cas9 can be thought of as the N' terminal part and the C' terminal part of the split Cas9. The fusion is typically at the split point of the Cas9. In other words, the C' terminal of the N' terminal part of the split Cas9 is fused to one of the dimer halves, whilst the N' terminal of the C' terminal part is fused to the other dimer half.

The Cas9 does not have to be split in the sense that the break is newly created. The split point is typically designed in silico and cloned into the constructs. Together, the two parts of the split Cas9, the N' terminal and C' terminal parts, form a full Cas9, comprising preferably at least 70% or more of the wildtype amino acids (or nucleotides encoding them), preferably at least 80% or more, preferably at least 90% or more, preferably at least 95% or more, and most preferably at least 99% or more of the wildtype amino acids (or nucleotides encoding them). Some trimming may be possible, and mutants are envisaged. Non-functional domains may be removed entirely. What is important is that the two parts may be brought together and that the desired Cas9 function is restored or reconstituted.

The dimer may be a homodimer or a heterodimer.

One or more, preferably two, NLSs may be used in operable linkage to the first Cas9 construct. One or more, preferably two, NESs may be used in operable linkage to the first Cas9 construct. The NLSs and/or the NESs preferably flank the split Cas9-dimer (i.e., half dimer) fusion, i.e., one NLS may be positioned at the N' terminal of the first Cas9 construct and one NLS may be at the C' terminal of the first Cas9 construct. Similarly, one NES may be positioned at the N' terminal of the second Cas9 construct and one NES may be at the C' terminal of the second Cas9 construct. Where reference is made to N' or C' terminals, it will be appreciated that these correspond to 5' ad 3' ends in the corresponding nucleotide sequence.

A preferred arrangement is that the first Cas9 construct is arranged 5'-NLS-(N' terminal Cas9 part)-linker-(first half of the dimer)-NLS-3'. A preferred arrangement is that the second Cas9 construct is arranged 5'-NES-(second half of the dimer)-linker-(C' terminal Cas9 part)-NES-3'. A suitable promoter is preferably upstream of each of these constructs. The two constructs may be delivered separately or together.

In some embodiments, one or all of the NES(s) in operable linkage to the second Cas9 construct may be swapped out for an NLS. However, this may be typically not preferred and, in other embodiments, the localization signal in operable linkage to the second Cas9 construct is one or more NES(s).

It will also be appreciated that the NES may be operably linked to the N' terminal fragment of the split Cas9 and that the NLS may be operably linked to the C' terminal fragment of the split Cas9. However, the arrangement where the NLS is operably linked to the N' terminal fragment of the split Cas9 and that the NES is operably linked to the C' terminal fragment of the split Cas9 may be preferred.

The NES functions to localize the second Cas9 fusion construct outside of the nucleus, at least until the inducer energy source is provided (e.g., at least until an energy source is provided to the inducer to perform its function). The presence of the inducer stimulates dimerization of the two Cas9 fusions within the cytoplasm and makes it thermodynamically worthwhile for the dimerized, first and second, Cas9 fusions to localize to the nucleus. Without being bound by theory, Applicants believe that the NES sequesters the second Cas9 fusion to the cytoplasm (i.e., outside of the nucleus). The NLS on the first Cas9 fusion localizes it to the nucleus. In both cases, Applicants use the NES or NLS to shift an equilibrium (the equilibrium of nuclear transport) to a desired direction. The dimerization typically occurs outside of the nucleus (a very small fraction might happen in the nucleus) and the NLSs on the dimerized complex shift the equilibrium of nuclear transport to nuclear localization, so the dimerized and hence reconstituted Cas9 enters the nucleus.

Beneficially, Applicants are able to reconstitute function in the split Cas9. Transient transfection is used to prove the concept and dimerization occurs in the background in the presence of the inducer energy source. No activity is seen with separate fragments of the Cas9. Stable expression through lentiviral delivery is then used to develop this and show that a split Cas9 approach can be used.

This present split Cas9 approach is beneficial as it allows the Cas9 activity to be inducible, thus allowing for temporal control. Furthermore, different localization sequences may be used (i.e., the NES and NLS as preferred) to reduce background activity from auto-assembled complexes. Tissue specific promoters, for example one for each of the first and second Cas9 fusion constructs, may also be used for tissue-specific targeting, thus providing spatial control. Two different tissue specific promoters may be used to exert a finer degree of control if required. The same approach may be used in respect of stage-specific promoters or there may a mixture of stage and tissue specific promoters, where one of the first and second Cas9 fusion constructs is under the control of (i.e. operably linked to or comprises) a tissue-specific promoter, whilst the other of the first and second Cas9 fusion constructs is under the control of (i.e. operably linked to or comprises) a stage-specific promoter.

The inducible Cas9 CRISPR-Cas system comprises one or more nuclear localization sequences (NLSs), as described herein, for example as operably linked to the first Cas9 fusion construct. These nuclear localization sequences are ideally of sufficient strength to drive accumulation of said first Cas9 fusion construct in a detectable amount in the nucleus of a eukaryotic cell. Without wishing to be bound by theory, it is believed that a nuclear localization sequence is not necessary for Cas9 CRISPR-Cas complex activity in eukaryotes, but that including such sequences enhances activity of the system, especially as to targeting nucleic acid molecules in the nucleus, and assists with the operation of the present 2-part system.

Equally, the second Cas9 fusion construct is operably linked to a nuclear export sequence (NES). Indeed, it may be linked to one or more nuclear export sequences. In other words, the number of export sequences used with the second Cas9 fusion construct is preferably 1 or 2 or 3. Typically 2 is preferred, but 1 is enough and so is preferred in some embodiments. Suitable examples of NLS and NES are known in the art. For example, a preferred nuclear export signal (NES) is human protein tyrosin kinase 2. Preferred signals will be species specific.

Where the FRB and FKBP system are used, the FKBP is preferably flanked by nuclear localization sequences (NLSs). Where the FRB and FKBP system are used, the preferred arrangement is N' terminal Cas9-FRB-NES: C' terminal Cas9-FKBP-NLS. Thus, the first Cas9 fusion construct would comprise the C' terminal Cas9 part and the second Cas9 fusion construct would comprise the N' terminal Cas9 part.

Another beneficial aspect to the present invention is that it may be turned on quickly, i.e. that is has a rapid response. It is believed, without being bound by theory, that Cas9 activity can be induced through dimerization of existing (already present) fusion constructs (through contact with the inducer energy source) more rapidly than through the expression (especially translation) of new fusion constructs. As such, the first and second Cas9 fusion constructs may be expressed in the target cell ahead of time, i.e. before Cas9 activity is required. Cas9 activity can then be temporally controlled and then quickly constituted through addition of the inducer energy source, which ideally acts more quickly (to dimerize the heterodimer and thereby provide Cas9 activity) than through expression (including induction of transcription) of Cas9 delivered by a vector, for example.

The terms Cas9 or Cas9 enzyme and CRISPR enzyme are used interchangeably herein unless otherwise apparent.

Applicants demonstrate that Cas9 can be split into two components, which reconstitute a functional nuclease when brought back together. Employing rapamycin sensitive dimerization domains, Applicants generate a chemically inducible Cas9 for temporal control of Cas9-mediated genome editing and transcription modulation. Put another way, Applicants demonstrate that Cas9 can be rendered chemically inducible by being split into two fragments and that rapamycin-sensitive dimerization domains may be used for controlled reassembly of the Cas9. Applicants show that the re-assembled Cas9 may be used to mediate genome editing (through nuclease/nickase activity) as well as transcription modulation (as a DNA-binding domain, the so-called "dead Cas9").

As such, the use of rapamycin-sensitive dimerization domains is preferred. Reassembly of the Cas9 is preferred. Reassembly can be determined by restoration of binding activity. Where the Cas9 is a nickase or induces a double-strand break, suitable comparison percentages compared to a wildtype are described herein.

Rapamycin treatments can last 12 days. The dose can be 200 nM. This temporal and/or molar dosage is an example of an appropriate dose for Human embryonic kidney 293FT (HEK293FT) cell lines and this may also be used in other cell lines. This figure can be extrapolated out for therapeutic use in vivo into, for example, mg/kg. However, it is also envisaged that the standard dosage for administering rapamycin to a subject is used here as well. By the "standard dosage", it is meant the dosage under rapamycin's normal therapeutic use or primary indication (i.e. the dose used when rapamycin is administered for use to prevent organ rejection).

It is noteworthy that the preferred arrangement of Cas9-FRB/FKBP pieces are separate and inactive until rapamycin-induced dimerization of FRB and FKBP results in reassembly of a functional full-length Cas9 nuclease. Thus, it is preferred that first Cas9 fusion construct attached to a first half of an inducible heterodimer is delivered separately and/or is localized separately from the second Cas9 fusion construct attached to a first half of an inducible heterodimer.

To sequester the Cas9(N)-FRB fragment in the cytoplasm, where it is less likely to dimerize with the nuclear-localized Cas9(C)-FKBP fragment, it is preferable to use on Cas9(N)-FRB a single nuclear export sequence (NES) from the human protein tyrosin kinase 2 (Cas9(N)-FRB-NES). In the presence of rapamycin, Cas9(N)—FRB-NES dimerizes with Cas9(C)-FKBP-2×NLS to reconstitute a complete Cas9 protein, which shifts the balance of nuclear trafficking toward nuclear import and allows DNA targeting.

High dosage of Cas9 can exacerbate indel frequencies at off-target (OT) sequences which exhibit few mismatches to the guide strand. Such sequences are especially susceptible, if mismatches are non-consecutive and/or outside of the seed region of the guide. Accordingly, temporal control of Cas9 activity could be used to reduce dosage in long-term expression experiments and therefore result in reduced off-target indels compared to constitutively active Cas9.

Viral delivery is preferred. In particular, a lentiviral or AAV delivery vector is envisaged. Applicants generate a split-Cas9 lentivirus construct, similar to the lentiCRISPR plasmid. The split pieces should be small enough to fit the ~4.7 kb size limitation of AAV.

Applicants demonstrate that stable, low copy expression of split Cas9 can be used to induce substantial indels at a targeted locus without significant mutation at off-target sites. Applicants clone Cas9 fragments (2 parts based on split 5, described herein).

A dead Cas9 may also be used, comprising a VP64 transactivation domain, for example added to Cas9(C)-FKBP-2×NLS (dead-Cas9(C)-FKBP-2×NLS-VP64). These fragments reconstitute a catalytically inactive Cas9-VP64 fusion (dead-Cas9-VP64). Transcriptional activation is induced by VP64 in the presence of rapamycin to induce the dimerization of the Cas9(C)-FKBP fusion and the Cas9(N)-FRB fusion. In other words, Applicants test the inducibility of split dead-Cas9-VP64 and show that transcriptional activation is induced by split dead-Cas9-VP64 in the presence of rapamycin. As such, the present inducible Cas9 may be associated with one or more functional domain, such as a transcriptional activator or repressor or a nuclease (such as Fok1). A functional domain may be bound to or fused with one part of the split Cas9.

A preferred arrangement is that the first Cas9 construct is arranged 5'-First Localization Signal-(N' terminal Cas9 part)-linker-(first half of the dimer)-First Localization Signal-3' and the second Cas9 construct is arranged 5'-Second Localization Signal-(second half of the dimer)-linker-(C' terminal Cas9 part)-Second Localization Signal-Functional Domain-3'. Here, a functional domain is placed at the 3' end of the second Cas9 construct. Alternatively, a functional domain may be placed at the 5' end of the first Cas9 construct. One or more functional domains may be used at the 3' end or the 5' end or at both ends. A suitable promoter is preferably upstream of each of these constructs. The two constructs may be delivered separately or together. The Localization Signals may be an NLS or an NES, so long as they are not inter-mixed on each construct.

In an aspect the invention provides an inducible Cas9 CRISPR-Cas system wherein the Cas9 has a diminished nuclease activity of at least 97%, or 100% as compared with the Cas9 enzyme not having the at least one mutation.

Accordingly, it is also preferred that the Cas9 is a dead-Cas9. Ideally, the split should always be so that the catalytic domain(s) are unaffected. For the dead-Cas9 the intention is that DNA binding occurs, but not cleavage or nickase activity is shown.

In an aspect the invention provides an inducible Cas9 CRISPR-Cas system as herein discussed wherein one or more functional domains is associated with the Cas9. This functional domain may be associated with (i.e. bound to or fused with) one part of the split Cas9 or both. There may be one associated with each of the two parts of the split Cas9. These may therefore be typically provided as part of the first and/or second Cas9 fusion constructs, as fusions within that construct. The functional domains are typically fused via a linker, such as GlySer linker, as discussed herein. The one or more functional domains may be transcriptional activation domain or a repressor domain. Although they may be different domains it is preferred that all the functional domains are either activator or repressor and that a mixture of the two is not used.

The transcriptional activation domain may comprise VP64, p65, MyoD1, HSF1, RTA or SET7/9.

In an aspect, the invention provides an inducible Cas9 CRISPR-Cas system as herein discussed wherein the one or more functional domains associated with the Cas9 is a transcriptional repressor domain.

In an aspect, the invention provides an inducible Cas9 CRISPR-Cas system as herein discussed wherein the transcriptional repressor domain is a KRAB domain.

In an aspect, the invention provides an inducible Cas9 CRISPR-Cas system as herein discussed wherein the transcriptional repressor domain is a NuE domain, NcoR domain, SID domain or a SID4X domain.

In an aspect the invention provides an inducible Cas9 CRISPR-Cas system as herein discussed wherein the one or more functional domains associated with the adaptor protein have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

Histone modifying domains are also preferred in some embodiments. Exemplary histone modifying domains are discussed below. Transposase domains, HR (Homologous Recombination) machinery domains, recombinase domains, and/or integrase domains are also preferred as the present functional domains. In some embodiments, DNA integration activity includes HR machinery domains, integrase domains, recombinase domains and/or transposase domains.

In an aspect the invention provides an inducible Cas9 CRISPR-Cas system as herein discussed wherein the DNA cleavage activity is due to a nuclease.

In an aspect the invention provides an inducible Cas9 CRISPR-Cas system as herein discussed wherein the nuclease comprises a Fok1 nuclease.

The use of such functional domains, which are preferred with the present split Cas9 system, is also discussed in detail in Konermann et al. ("Genome-scale transcriptional activation with an engineered CRISPR-Cas9 complex" Nature published 11 Dec. 2014).

The present system may be used with any guide.

Modified guides may be used in certain embodiments. Particularly preferred are guides embodying the teachings of Konermann Nature 11 Dec. 2014 paper mentioned above. These guides are modified so that protein-binding RNA portions (such as aptamers) are added. Such portion(s) may replace a portion of the guide. Corresponding RNA-binding protein domains can be used to then recognise the RNA and recruit functional domains, such as those described herein, to the guide. This is primarily for use with dead-Cas9 leading to transcriptional activation or repression or DNA cleavage through nucleases such as Fok1. The use of such guides in combination with dead-Cas9 is powerful, and it is especially powerful if the Cas9 itself is also associated with its own functional domain, as discussed herein. When a dead-Cas9 (with or without its own associated functional domain) is induced to reconstitute in accordance with the present invention, i.e. is a split Cas9, then the tool is especially useful.

A guide RNA (gRNA), also preferred for use in the present invention, can comprise a guide sequence capable of hybridizing to a target sequence in a genomic locus of interest in a cell, wherein the gRNA is modified by the insertion of distinct RNA sequence(s) that bind to one or more adaptor proteins, and wherein the adaptor protein is associated with one or more functional domains. The Cas9 may comprise at least one mutation, such that the Cas9 enzyme has no more than 5% of the nuclease activity of the Cas9 enzyme not having the at least one mutation; and/or at least one or more nuclear localization sequences. Also provided is a non-naturally occurring or engineered composition comprising: one or more guide RNA (gRNA) comprising a guide sequence capable of hybridizing to a target sequence in a genomic locus of interest in a cell, a Cas9 enzyme comprising at least one or more nuclear localization sequences, wherein the Cas9 enzyme comprises at least one mutation, such that the Cas9 enzyme has no more than 5% of the nuclease activity of the Cas9 enzyme not having the at least one mutation, wherein the at least one gRNA is modified by the insertion of distinct RNA sequence(s) that bind to one or more adaptor proteins, and wherein the adaptor protein is associated with one or more functional domains.

The gRNA that is preferably modified by the insertion of distinct RNA sequence(s) that bind to one or more adaptor proteins. The insertion of distinct RNA sequence(s) that bind to one or more adaptor proteins is preferably an aptamer sequence or two or more aptamer sequences specific to the same or different adaptor protein(s). The adaptor protein preferably comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. Cell lines stably expressing inter alia split dead-Cas9 can be useful.

Applicants demonstrate that Cas9 can be split into two distinct fragments, which reconstitute a functional full-length Cas9 nuclease when brought back together using chemical induction. The split Cas9 architecture will be useful for a variety of applications. For example, split Cas9 may enable genetic strategies for restricting Cas9 activity to intersectional cell populations by putting each fragment under a different tissue specific promoter. Additionally, different chemically inducible dimerization domains such as APA and gibberellin may also be employed.

The inducer energy source is preferably chemical induction.

The split position or location is the point at which the first part of the Cas9 enzyme is separated from the second part. In some embodiments, the first part will comprise or encode amino acids 1 to X, whilst the second part will comprise or encode amino acids X+1 to the end. In this example, the numbering is contiguous, but this may not always be necessary as amino acids (or the nucleotides encoding them) could be trimmed from the end of either of the split ends, provided that sufficient DNA binding activity and, if required, DNA nickase or cleavage activity is retained, for example at least 40%, 50%, 60%, 70%, 80%, 90% or 95% activity compared to wildtype Cas9.

The exemplary numbering provided herein may be in reference to the wildtype protein, preferably the wildtype FnCas9. However, it is envisaged that mutants of the wildtype Cas9 such as of FnCas9 protein can be used. The numbering may also not follow exactly the FnCas9 numbering as, for instance, some N' or C' terminal truncations or deletions may be used, but this can be addressed using standard sequence alignment tools. Orthologs are also preferred as a sequence alignment tool.

Thus, the split position may be selected using ordinary skill in the art, for instance based on crystal data and/or computational structure predictions.

Figure 2A:
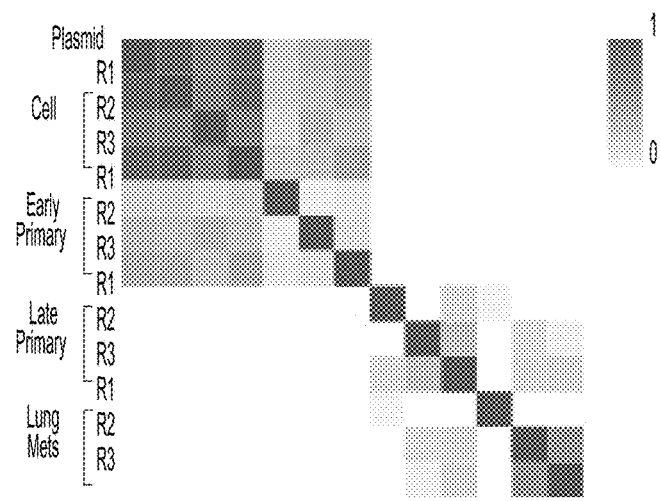
FIG. 2A-2D: (A) Pearson correlation coefficient of the normalized sgRNA read counts from the mGeCKOa plasmid pool, cells before transplantation (day 7 after spinfection), early tumors (~2 weeks after transplantation), and lungs (~6 weeks after transplantation). For each biological sample type, 3 independent infection replicates (R1, R2 and R3) are shown. n=1 mouse per infection replicate for early primary tumors and n=3 mice per infection replicate for late primary tumors and lung samples. (B) Number of unique sgRNAs in the plasmid, cells before transplantation, early and late primary tumors and lung metastases as in (A); (C) Boxplot of the sgRNA normalized read counts for the mGeCKOa plasmid pool, cells before transplantation, early and late primary tumors and lung metastases as in (A). Gray dots overlayed on each boxplot indicate read counts for the 1,000 control (non-targeting) sgRNAs in the mGeCKOa library. (D) Cumulative probability distribution of library sgRNAs in the plasmid, cells before transplantation, early and late primary tumors and lung metastases as in (A). Distributions for each sample type are averaged across individual mice and infection replications.
Figure 2B:
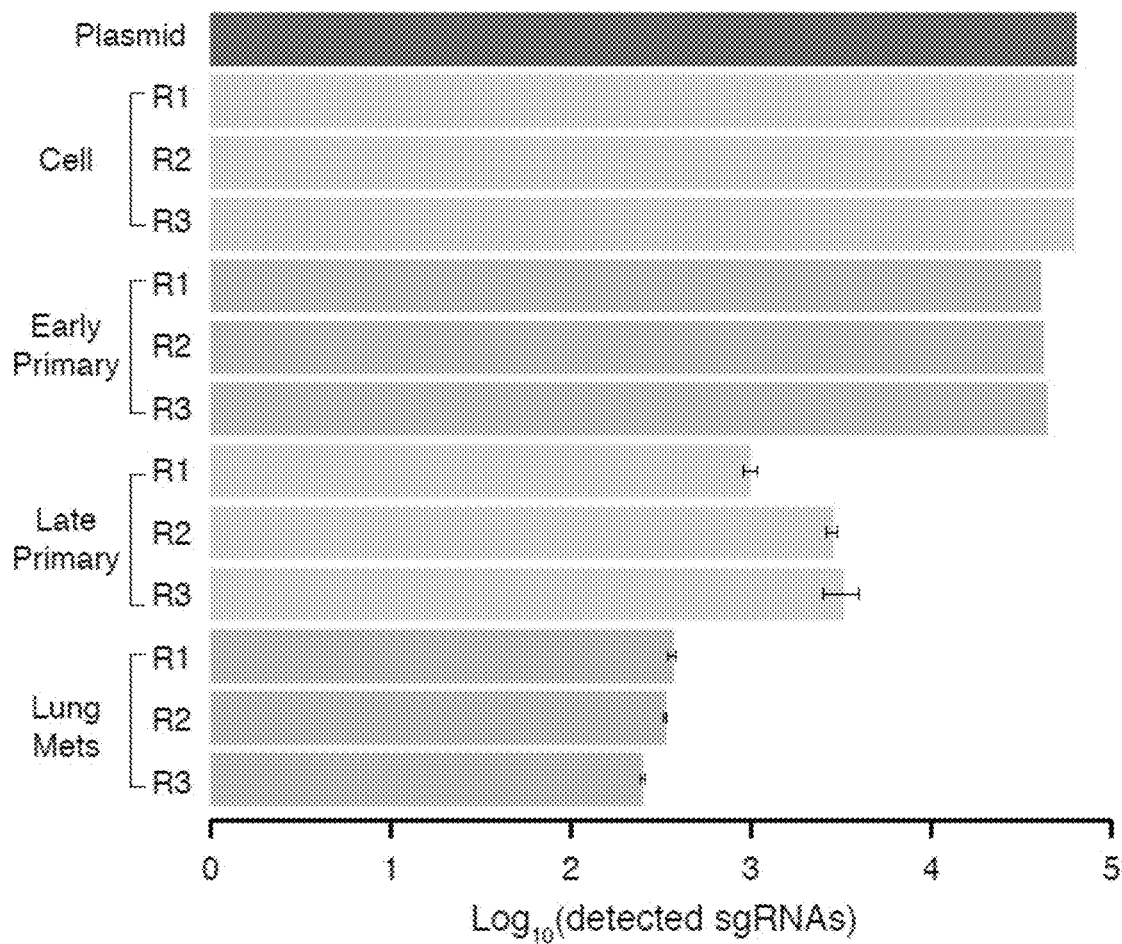
Figure 2C:
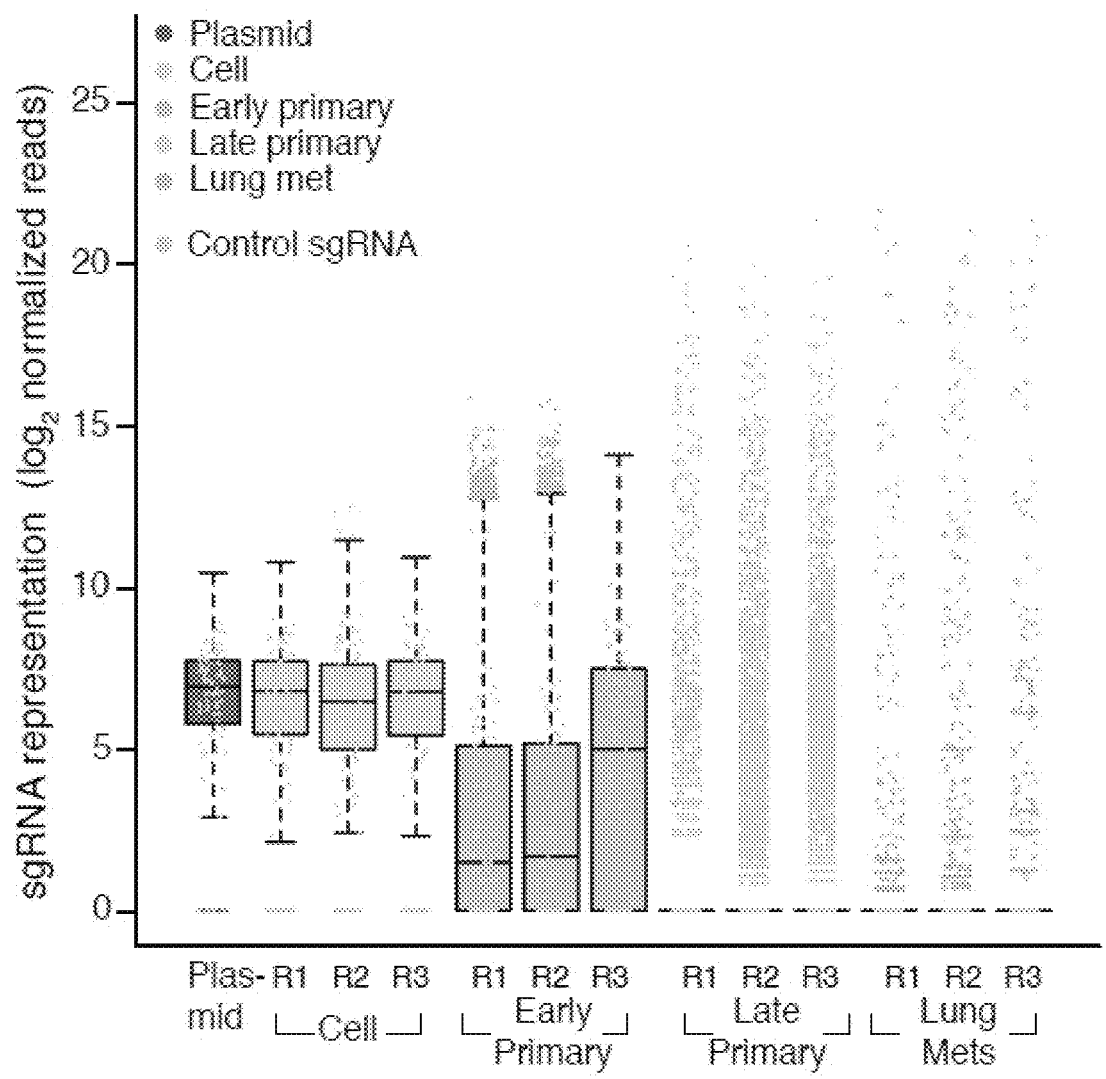
Figure 2D:
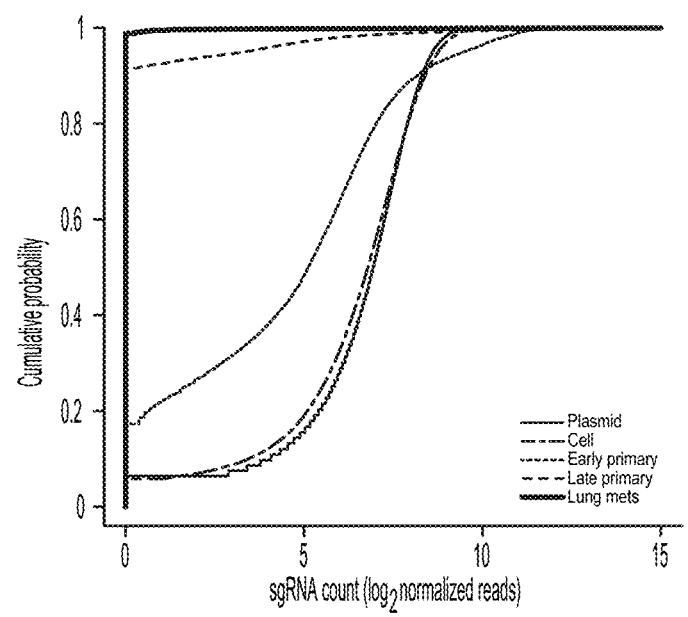
Figure 3A:
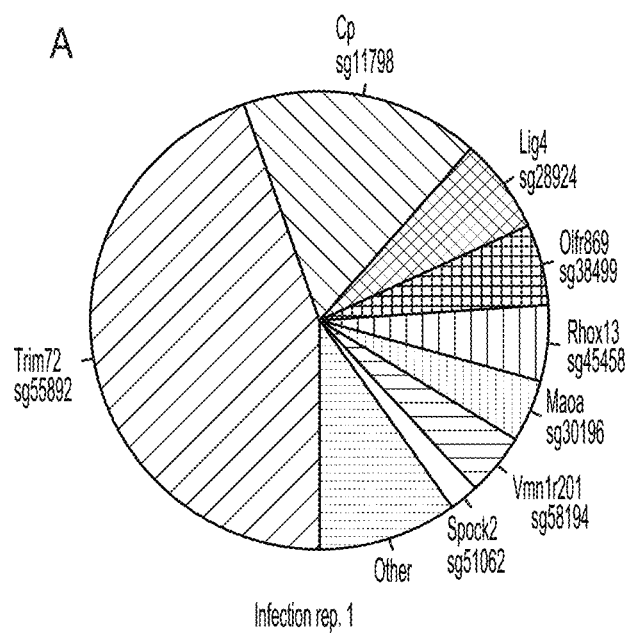
FIG. 3A-3C: (A) Pie charts of the most abundant sgRNAs in the primary tumors (at ~6 weeks post-transplantation) of three representative mice (one from each replicate mGeCKOa infection). The area for each sgRNA corresponds to the fraction of total reads from the lobe for the sgRNA. All sgRNAs with ≥2% of total reads are plotted individually. (B) Number of genes with 0, 1, 2 or 3 significantly enriched (FDR<0.2% for at least one mouse) mGeCKOa sgRNAs targeting that gene. For genes/miRNAs with 2 or more enriched sgRNAs, genes/miRNAs are categorized by how many sgRNAs targeting that gene/miRNAs are enriched as indicated in the colored bubbles adjacent to each bar. (C) Inset: Waterfall plot of sgRNAs where multiple sgRNAs targeting the same gene are significantly enriched in primary tumors. Each sgRNA is ranked by the number of mice in which it is enriched. Only sgRNAs enriched in 2 or more mice are shown. Main panel: Enlargement and gene labels for sgRNAs at the top of the list from the inset (boxed region).
Figure 3B:
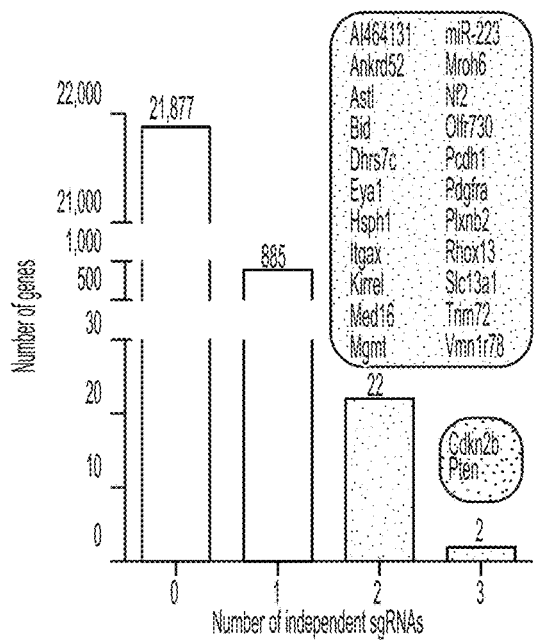
Figure 3C:
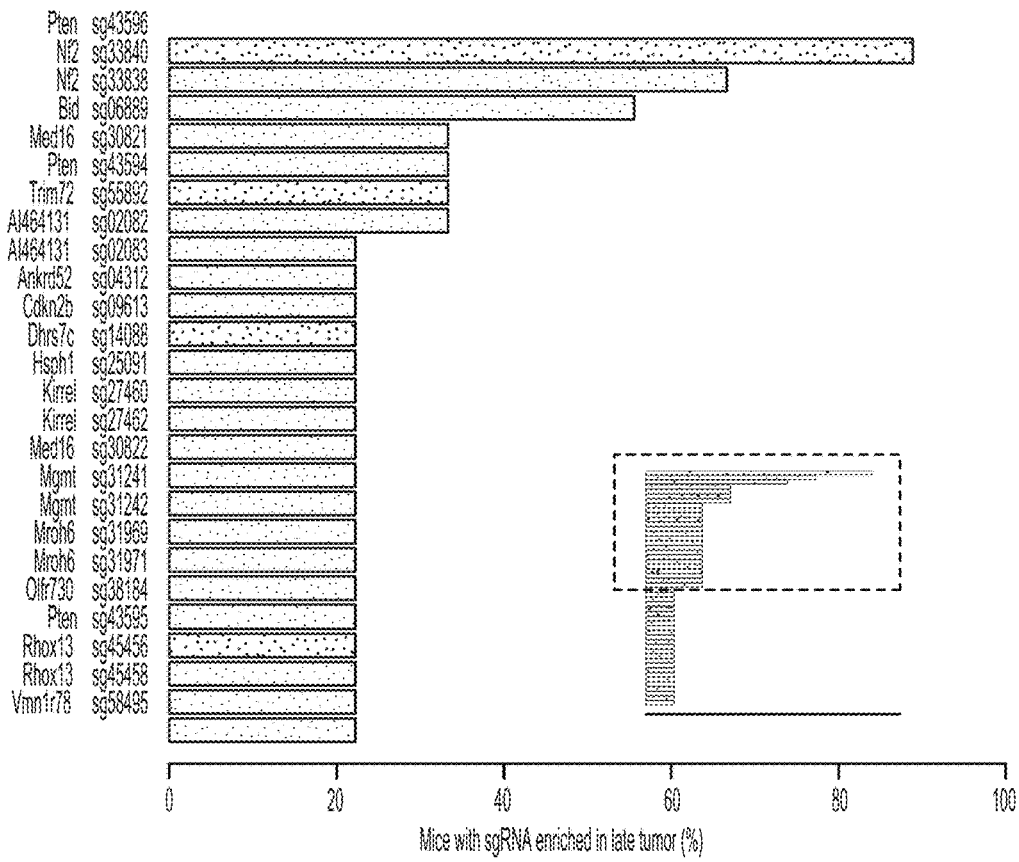

For example, computational analysis of the primary structure of Cas9 nucleases reveals three distinct regions (FIG. 1). First a C-terminal RuvC like domain, which is the only functional characterized domain. Second a N-terminal alpha-helical region and thirst a mixed alpha and beta region, located between the RuvC like domain and the alpha-helical region. Several small stretches of unstructured regions are predicted within the Cas9 primary structure. Unstructured regions, which are exposed to the solvent and not conserved within different Cas9 orthologs, may represent preferred sides for splits (FIG. 2 and FIG. 3).

The following table presents non-limiting potential split regions within As and LbCas9. A split site within such a region may be opportune.

| Split region | AsCas9 | LbCas9 |
|---|---|---|
| 1 | 575-588 | 566-571 |
| 2 | 631-645 | 754-757 |
| 3 | 653-664 | — |
| 4 | 818-844 | — |

For Fn, As and Lb Cas9 mutants, it should be readily apparent what the corresponding position for a potential split site is, for example, based on a sequence alignment. For non-Fn, As and Lb enzymes one can use the crystal structure of an ortholog if a relatively high degree of homology exists between the ortholog and the intended Cas9, or one can use computational prediction.

Ideally, the split position should be located within a region or loop. Preferably, the split position occurs where an interruption of the amino acid sequence does not result in the partial or full destruction of a structural feature (e.g. alpha-helixes or beta-sheets). Unstructured regions (regions that do not show up in the crystal structure because these regions are not structured enough to be "frozen" in a crystal) are often preferred options. Applicants can for example make splits in unstructured regions that are exposed on the surface of Cas9.

In one aspect the invention involves a method for generating an non-human eukaryote model for tumor formation and/or tumor evolution by introducing into a non-human animal a plurality of eukaryotic Cas transgenic cells, each cell comprising one or more RNA capable of guiding Cas to one or more genetic target locus of a eukaryote. The Applicants have found that a when the plurality of cells originates from an immortal (cancer) cell line which does not have the capacity to metastasize upon injection into a non-human eukaryote (or at least not until the primary tumor is too large), upon introduction into such cells of one or more RNA capable of guiding Cas to one or more genetic target locus of a eukaryote, will cause the cells to form macroscopic metastases in the non-human eukaryotic animal. The applicants have moreover found that the model can be used to analyse human tumors in a non-human animal. In principle virtually any cell lines can be used as xenografts, including human cell lines.

In particular embodiments, the methods comprise the steps of: (a) providing an isolated Cas transgenic eukaryotic cell expressing Cas or capable of inducibly and/or conditionally expressing Cas; (b) introducing in said Cas transgenic eukaryotic cell one or more RNA capable of guiding Cas to one or more genetic target locus of a eukaryote; or introducing in said Cas transgenic eukaryotic cell one or more polynucleotide encoding one or more RNA capable of guiding Cas to one or more genetic target locus of a eukaryote; (c) introducing a plurality of said Cas transgenic eukaryotic cell after step (b) in a non-human eukaryote, each cell of said plurality of Cas transgenic eukaryotic cells comprising a different RNA capable of guiding Cas to a genetic target locus, or each cell of said plurality of Cas transgenic eukaryotic cells comprising a different polynucleotide encoding an RNA capable of guiding Cas to a genetic target locus. In particular embodiments, the one or more RNA capable of guiding Cas to one or more genetic target locus of a eukaryote is a CRISPR library with multiple sgRNAs targeting each gene that is likely to generate loss of function mutation. In further particular embodiments, a customized library is used, whereby genes are selected based on genomic analysis, pathways, clinical relevance, literature or customized informatics for focused libraries for screens. Indeed, this allows the possibility to reduce the size of the library. In particular embodiments, a targeted sub-pool is used to confirm a primary screen. This can optionally including libraries comprising multiple RNAs guiding to the same target genes.

It will be understood that even where only one CAS guiding RNA is used (i.e. to one target DNA sequence), introduction thereof into a plurality of eukaryotic cells may nevertheless result in a variety of phenotypes resulting from the different possibilities that the repair mechanism will address the DNA cleavage. However, in particular embodiments, more than one CAS guiding RNA is used.

Accordingly, also provided herein is a concept of multiple levels of screening which allows further validation of the identified targets. More particularly, a first level may include the introduction of a genome-wide library targeting each gene that is likely to generate loss of function mutation. In a further level the library may aim to target a sub-pool of genes which have been identified in a first level screen to affect tumor formation and evolution. The identification of the sub-pool of genes which most strongly affect tumor formation and evolution may be performed based either on relative abundance of the sgRNAs, i.e. by taking sgRNAs above certain threshold, based on rank, i.e. by taking top ranked sgRNAs in each mouse, or based on false discovery rate (FDR), i.e. by taking sgRNAs enriched compared to the distribution of the 1,000 non-targeting sgRNAs at 0.2% FDR. In particular embodiments, the genes identified in two out of three or in all three methods are selected as a sub-pool. In particular embodiments, the targeting of the subpool may comprise using multiple RNAs, such as 10 RNAs per gene. Typically, the methods will also comprise a validation the individual genes. In particular embodiments this is ensured by cloning multiple sgRNAs targeting one gene into the same lentiviral vector, transducing them into a cell line, introducing them into a non-human eukaryote and considering the tumor formation and evolution of said cell line. Additionally or alternatively, the methods may also take into account the different bottlenecks that can affect CAS guiding RNA representation in the library. In one level, the method may involve introducing individual RNAs into cells and cultivating cells prior to mixing them and introducing them into the non-human eukaryote animal. For instance the method can comprise maintaining separate populations of cells comprising different RNAs for guiding Cas, whereby these are combined only upon injection into the non-human animal. Representation of each of the RNAs within the RNA population can be investigated at the plasmid, cell pool, primary tumor and metastasis level. This targeted subpool strategy provides a higher-throughput method for validating the top candidates and assaying competing mutants in parallel. This strategy is of interest for any type of genome-scale screens and more particularly loss-of-function screens such as the one described herein or RNAi-based screens.

In an aspect, the invention involves a non-human eukaryote, such as an animal, preferably a mammal, primate, rodent, mouse, rat, rabbit, canine, dog, cow, bovine, sheep, ovine, goat, pig, fowl, poultry, chicken, fish, insect, or arthropod, etc or cell thereof or tissue thereof that may be used as a disease model for cancer, such as a tumor isolated therefrom, in particular a primary tumor or a metastasis, or a cell isolated from such tumor or metastasis, or a cell line derived therefrom.

For example, a method of the invention may be used to create a non-human eukaryote, e.g., an animal, mammal, primate, rodent or cell that comprises a cell or a plurality of cells having one or more modification, e.g., 1-50 modifications, such as in one or more nucleic acid sequences associated or correlated with cancer. It is to be understood that such modifications result from the methods as described herein. Such a mutated nucleic acid sequence be associated or correlated with cancer (including metastasis) and may encode a cancer or metastasis associated protein sequence or may be a cancer or metastasis associated or correlated control sequence. The cell may be in vivo or ex vivo in the cases of multicellular organisms. In the instance where the cell is in culture (i.e. in vitro), a cell line may be established if appropriate culturing conditions are met and preferably if the cell is suitably adapted for this purpose (for instance a stem cell). Hence, cell lines are also envisaged. In some methods, the disease model can be used to study the effects of mutations on the animal or cell and development and/or progression of cancer and/or metastasis using measures commonly used in the study of cancer. Alternatively, such a cancer model is useful for studying the effect of a putatively pharmaceutically active compound or gene therapy on the cancer or metastasis. A cancer- or metastasis-associated gene or polynucleotide can be modified to give rise to cancer or metastasis in the model, and then putatively pharmaceutically active compound and/or gene therapy can be administered so as to observe whether cancer or metastasis development and/or progression is inhibited or reduced. In particular, the method comprises modifying so as to produce, one or more, such as a plurality cancer or metastasis-associated or correlated gene(s) or polynucleotide(s). the plurality of cancer or metastasis associated or correlated gene(s) or polynucleotide(s) may in certain embodiments also be targeted by introduction in a plurality of cells of a library of RNAs capable of guiding Cas to a genomic target locus, preferably in such way that in each cell a different genomic locus is targeted (or different regions of a genomic locus). Accordingly, in some methods, a genetically modified animal may be compared with an animal predisposed to development of the disease, such that administering putative gene therapy, or pharmaceutically acceptable compound(s), or any combination thereof can be performed to assess how such putative therapy(ies) or treatment(s) may perform in a human. The invention can involve administering to a eukaryote obtained by a method as described herein a test compound or contacting a test compound with a tumor or metastasis tissue, cell or cell line derived therefrom, wherein the tissue, or cell comprises—or wherein the eukaryote comprises a cancerous or metastatic tissue or cell that comprises—one or more, e.g., 1-50 or more mutations from the CRISPR-Cas system, e.g., in an animal comprising cells expressing Cas and to which RNA(s) generating the mutations has/have been administered; and detecting a reduction or an augmentation of a cell signaling event associated with the mutation(s) or lack thereof. Screening of such putative pharmaceutically active compound(s) and/or gene therapy(ies) can be by cellular function change and/or intracellular signaling or extracellular signaling change. Such screening can involve evaluating for dosages or dose curves, as well as combinations of potential drugs and/or therapies. An altered expression of one or more genome sequences associated with a signaling biochemical pathway can be determined by assaying for a difference in the mRNA levels of the corresponding genes between the disease model eukaryote or animal or cell or tissue thereof and a normal eukaryote, animal, tissue or cell, and to ascertain whether when the disease model is administered or contacted with a candidate chemical agent or gene therapy it reverts to or towards normal. An assay can be for mutation(s)-induced alteration in the level of mRNA transcripts or corresponding polynucleotides in comparison with such level(s) in a normal eukaryote or animal and whether such level(s) are placed towards or to normal when a therapy or treatment or agent is employed.

In an aspect the invention involves cells, e.g., non-human eukaryotic, e.g., animal, such as mammal, e.g., primate, rodent, mouse, rat, rabbit, etc. as described herein elsewhere, or even human cells, containing Cas polypeptide or transformed to constitutively express or alternatively inducibly and/or conditionally express Cas, e.g., such cells as to which a vector that contains nucleic acid molecule(s) encoding a Cas, e.g., with nucleic acid(s) encoding a promoter and preferably at least one NLS, advantageously two or more NLSs, or such cells that have had their genome altered, e.g., through the vector being an integrating virus or through such cells being stem cells or cells that give rise to a cell line or a living organism (but wherein such an organism is advantageously non-human), that contains and expresses nucleic acid molecule(s) encoding Cas. To these cells is then administered (simultaneously or subsequently) RNA(s) or vector(s), e.g., AAV, adenovirus, lentivirus containing or providing RNA(s) that guide Cas to a genomic target locus, e.g., under the control of a promoter such as a U6 promoter and/or particle(s) and/or nanoparticle(s) containing the RNA(s) and/or vector(s), whereby the RNA(s) direct the Cas in the cells to provide a mutation, or a plurality of mutation(s) such as from 3 to 50 mutations, advantageously mutation(s) associated or correlated with cancer. Such cells are then transplanted into or onto a eukaryote, such as an animal suitable for being a cancer model, e.g., a rodent such as a mouse (see, e.g., literature on mouse transplantation cancer models, generally discussed at the NIH website; see emice.nci.nih.gov/aam/mouse/transplantation-mouse-models-1), chickens or chicken embryo or chicken embryo membrane (Kuzminien et al, "Evaluation of the Chicken Embryo chorioallantoic membrane Model for Laryngeal Tumor Transplantation," Papers on Anthropology XX, 2011, pp. 229-240), zebra fish (see, e.g., Haldi et al, "Human melanoma cells transplanted into zebrafish proliferate, migrate, produce melanin, form masses and stimulate angiogenesis in zebrafish," Angiogenesis. 2006; 9(3):139-51. Epub 2006 Oct. 19)). The cells proliferate on or in the non-human eukaryote, e.g., animal model and tumor formation and/or evolution can be studied.

The non-human eukaryote, e.g., animal model can then be used for testing, e.g., as to potential therapy and/or putative treatment via a possibly pharmaceutically active compound. The administering of such compound can be at or to or for body delivery to the proliferated heterologous transplanted cells, e.g., direct injection at or near such proliferated heterologous transplanted cells, or injection or other administration in such a way that the compound is delivered into the heterologous transplanted cells, e.g., injection into the bloodstream whereby bodily functions transport to the proliferated heterologous transplanted cells. In an aspect of the invention, barcoding techniques of WO/2013/138585 A1 can be adapted or integrated into the practice of the invention.

The invention also comprehends a method for the identification of a treatment, e.g., chemical or gene therapy treatment, for cancer comprising applying, administering or delivering one or more treatments to the non-human transgenic eukaryote obtained by the methods as herein discussed and identifying whether the cancer has improved; and, the cancer can be Lung cancer, Lung adenocarcinoma, Lung squamous cell carcinoma, Acute myeloid leukemia, Basal cell carcinoma (skin), Bladder cancer, Breast cancer, Carcinoid, Chronic lymphocytic leukemia, Colorectal cancer, Diffuse large B-cell lymphoma, Endometrial, Esophageal cancer, Esophageal adenocarcinoma, Glioblastoma multiforme, Glioma, Head and neck cancer, Kidney clear cell cancer, Medulloblastoma, Melanoma, Multiple myeloma, Nasopharyngeal, Neuroblastoma, Ovarian cancer, Prostate cancer, Rhabdoid tumor, Testicular germ cell tumor, Thyroid cancer, or Urinary bladder cancer. The method can comprise applying, administering or delivering different doses of the treatment and/or employing different routes of administration and/or different carriers or excipients and/or applying, administering or delivering at different time intervals, e.g., applying, administering or delivering different does at different time intervals.

The invention thus also envisions an individualized or personalized treatment of cancer, being it a primary tumor or metastasis, in a subject in need of such treatment comprising: (a) performing any of the methods as described herein; (b) testing treatment(s) for the developed or developing cancer and/or metastasis; and (c) treating the subject based on results from the testing of treatment(s) of step (b).

In an aspect, the invention provides kits containing any one or more of the elements discussed herein. Elements may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises Cas (or a vector encoding Cas, or a Cas transgenic eukaryotic cell) and/or one or more, such as a library, oligonucleotides corresponding to a guide sequence for insertion into a vector (or vectors having already inserted such oligonucleotides) so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allow the provision of all elements of the systems of the invention. Kits can involve vector(s) and/or particle(s) and/or nanoparticle(s) containing or encoding RNA(s) to be administered to a eukaryotic cell, e.g., animal, mammal, primate, rodent, etc., with such a kit including instructions for administering to such a cell; and such a kit can optionally include a non-human eukaryote.

The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

It will be appreciated that where reference is made to a polynucleotide, where that polynucleotide is RNA and is said to 'comprise' a feature such as a tracr mate sequence, the RNA sequence includes the feature. Where the polynucleotide is DNA and is said to comprise a feature such as a tracr mate sequence, the DNA sequence is or can be transcribed into the RNA that comprises the feature at issue. Where the feature is a protein, such as the CRISPR enzyme, the DNA or RNA sequence referred to is, or can be, translated (and in the case of DNA transcribed first). Furthermore, in cases where an RNA encoding the CRISPR enzyme is provided to a cell, it is understood that the RNA is capable of being translated by the cell into which it is delivered.

As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point (Tm). The Tm is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the Tm. In order to require at least about 70% nucleotide complementarity of hybridized sequences, moderately-stringent washing conditions are selected to be about 15 to 30° C. lower than the Tm. Highly permissive (very low stringency) washing conditions may be as low as 50° C. below the Tm, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p 387). Examples of other software than may perform sequence comparisons include, but are not limited to, the BLAST package (see Ausubel et al., 1999 Short Protocols in Molecular Biology, 4th Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

TABLE 3

| Set | Sub-set | | |
|---|---|---|---|
| Hydrophobic | FWYHKMTLVAGC | Aromatic | FWYH |
| | | Aliphatic | ILV |
| Polar | WYHKREDCSTNQ | Charged | HKRED |
| | | Positively charged | HKR |
| | | Negatively charged | ED |
| Small | VCAGSPTND | Tiny | AGS |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridyl-alanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR.

Crystallization of CRISPR-Cas9 and Characterization of Crystal Structure

The crystals of the Cas9 can be obtained by techniques of protein crystallography, including batch, liquid bridge, dialysis, vapor diffusion and hanging drop methods. Generally, the crystals of the invention are grown by dissolving substantially pure CRISPR-Cas9 and a nucleic acid molecule to which it binds in an aqueous buffer containing a precipitant at a concentration just below that necessary to precipitate. Water is removed by controlled evaporation to produce precipitating conditions, which are maintained until crystal growth ceases. The crystal structure information is described in U.S. provisional applications 61/915,251 filed Dec. 12, 2013, 61/930,214 filed on Jan. 22, 2014, 61/980, 012 filed Apr. 15, 2014; and Nishimasu et al, "Crystal Structure of Cas9 in Complex with Guide RNA and Target DNA," Cell 156(5):935-949, DOI: dx.doi.org/10.1016/j.cel.2014.02.001 (2014), and PCT/US14/70175; each and all of which are incorporated herein by reference, and together are "herein cited materials" concerning the Cas9 crystal structure. Uses of the Crystals, Crystal Structure and Atomic Structure Co-Ordinates of the herein cited materials: The crystals of the Cas9, and particularly the atomic structure co-ordinates obtained therefrom, have a wide variety of uses. The crystals and structure co-ordinates are particularly useful for identifying compounds (nucleic acid molecules) that bind to CRISPR-Cas9, and CRISPR-Cas9s that can bind to particular compounds (nucleic acid molecules). Thus, the structure co-ordinates described herein can be used as phasing models in determining the crystal structures of additional synthetic or mutated CRISPR-Cas9s, Cas9s, nickases, binding domains. The provision of the crystal structure of CRISPR-Cas9 complexed with a nucleic acid molecule as applied in conjunction with the herein teachings provides the skilled artisan with a detailed insight into the mechanisms of action of CRISPR-Cas9. This insight provides a means to design modified CRISPR-Cas9s, such as by attaching thereto a functional group, such as a repressor or activator. While one can attach a functional group such as a repressor or activator to the N or C terminal of CRISPR-Cas9, the crystal structure demonstrates that the N terminal seems obscured or hidden, whereas the C terminal is more available for a functional group such as repressor or activator. Moreover, the crystal structure demonstrates that there is a flexible loop between approximately CRISPR-Cas9 (*S. pyogenes*) residues 534-676 which is suitable for attachment of a functional group such as an activator or repressor. Attachment can be via a linker, e.g., a flexible glycine-serine (GlyGlyGlySer) (SEQ ID NO: 39) or (GGGS)$_3$ (SEQ ID NO: 40) or a rigid alpha-helical linker such as (Ala(GluAlaAlaAlaLys)Ala) (SEQ ID NO: 41). In addition to the flexible loop there is also a nuclease or H3 region, an H2 region and a helical region. By "helix" or "helical", is meant a helix as known in the art, including, but not limited to an alpha-helix. Additionally, the term helix or helical may also be used to indicate a c-terminal helical element with an N-terminal turn. The provision of the crystal structure of CRISPR-Cas9 complexed with a nucleic acid molecule allows a novel approach for drug or compound discovery, identification, and design for compounds that can bind to CRISPR-Cas9 and thus the invention provides tools useful in diagnosis, treatment, or prevention of conditions or diseases of multicellular organisms, e.g., algae, plants, invertebrates, fish, amphibians, reptiles, avians, mammals; for example domesticated plants, animals (e.g., production animals such as swine, bovine, chicken; companion animal such as felines, canines, rodents (rabbit, gerbil, hamster); laboratory animals such as mouse, rat), and humans. The invention further involves, in place of or in addition to "in silico" methods, other "wet" methods, including high throughput screening of a binder (e.g., target nucleic acid molecule) and a candidate CRISPR-Cas9 system (e.g., *S. pyogenes* Cas9), or a candidate binder (e.g., target nucleic acid molecule) and a CRISPR-Cas9 system (e.g., *S. pyogenes* Cas9), or a candidate binder (e.g., target nucleic acid molecule) and a candidate CRISPR-Cas9 system (e.g., *S. pyogenes* Cas9) (the foregoing CRISPR-Cas9 system(s) with or without one or more functional group(s)), to select compounds with binding activity. Those pairs of binder and CRISPR-Cas9 system which show binding activity may be selected and further crystallized with the CRISPR-Cas9 crystal having a structure herein, e.g., by co-crystallization or by soaking, for X-ray analysis. The resulting X-ray structure may be compared with that of the Cas9 Crystal Structure for a variety of purposes, e.g., for areas of overlap. Having designed, identified, or selected possible pairs of binder and CRISPR-Cas9 system by determining those which have favorable fitting properties, e.g., predicted strong attraction based on the pairs of binder and CRISPR-Cas9 crystal structure data herein, these possible pairs can then be screened by "wet" methods for activity. Consequently, in an aspect the invention can involve: obtaining or synthesizing the possible pairs; and contacting a binder (e.g., target nucleic acid molecule) and a candidate CRISPR-Cas9 system (e.g., *S. pyogenes* Cas9), or a candidate binder (e.g., target nucleic acid molecule) and a CRISPR-Cas9 system (e.g., *S. pyogenes* Cas9), or a candidate binder (e.g., target nucleic acid molecule) and a candidate CRISPR-Cas9 system (e.g., *S. pyogenes* Cas9) (the foregoing CRISPR-Cas9 system(s) with or without one or more functional group(s)) to determine ability to bind. In the latter step, the contacting is advantageously under conditions to determine function. Instead of, or in addition to, performing such an assay, the invention may comprise: obtaining or synthesizing complex(es) from said contacting and analyzing the complex(es), e.g., by X-ray diffraction or NMR or other means, to determine the ability to bind or interact. Detailed structural information can then be obtained about the binding, and in light of this information, adjustments can be made to the structure or functionality of a candidate CRISPR-Cas9 system or components thereof. These steps may be repeated and re-repeated as necessary. Alternatively or additionally, potential CRISPR-Cas9 systems from or in the foregoing methods can be with nucleic acid molecules in vivo, including without limitation by way of administration to an organism (including non-human animal and human) to ascertain or confirm function, including whether a desired outcome (e.g., reduction of symptoms, treatment) results therefrom. If X-ray crystallographic or NMR spectroscopic data are provided for a CRISPR-cas system or complex of unknown crystal structure, the structure of a CRISPR-Cas9 complex as defined of the herein cited materials may be used to interpret that data to provide a likely structure for the unknown system or complex by such techniques as by phase modeling in the case of X-ray crystallography. Thus, from this disclosure and the knowledge in the art one can perform a method comprising: aligning a representation of the CRISPR-cas system or complex having an unknown crystal structure with an analogous representation of the CRISPR-cas(9) system and complex of the crystal structure herein to match homologous or analogous regions (e.g., homologous or analogous sequences); modeling the structure of the matched homologous or analogous regions (e.g., sequences) of the CRISPR-cas system or complex of unknown crystal structure based on the structure of the Cas9 Crystal Structure of the corresponding regions (e.g., sequences); and, determining a conformation (e.g. taking into consideration favorable interactions should be formed so that a low energy conformation is formed) for the unknown crystal structure which substantially preserves the structure of said matched homologous regions. "Homologous regions" describes, for example as to amino acids, amino acid residues in two sequences that are identical or have similar, e.g., aliphatic, aromatic, polar, negatively charged, or positively charged, side-chain chemical groups. Homologous regions as to nucleic acid molecules can include at least 85% or 86% or 87% or 88% or 89% or 90% or 91% or 92% or 93% or 94% or 95% or 96% or 97% or 98% or 99% homology or identity. Identical and similar regions are sometimes described as being respectively "invariant" and "conserved" by those skilled in the art. Homology modeling is a technique that is well known to those skilled in the art (see, e.g., Greer, Science vol. 228 (1985) 1055, and Blundell et al. Eur J Biochem vol 172 (1988), 513). The computer representation of the conserved regions of the CRISPR-Cas9 crystal structure and those of a CRISPR-cas system of unknown crystal structure aid in the prediction and determination of the crystal structure of the CRISPR-cas system of unknown crystal structure. The CRISPR-Cas9 crystal structure in silico may be equally applied to new CRISPR-cas crystal structures divined by using the teachings herein and the herein cited materials concerning the CRISPR-Cas9 crystal structure. In this fashion, a library of CRISPR-Cas crystal structures can be obtained. Rational CRISPR-Cas system design is thus provided by the instant invention. For instance, having obtained a CRISPR-Cas system or complex using teachings herein and determining a conformation or crystal structure of a CRISPR-Cas system or complex, such a conformation may be used in a computer-based methods herein for determining the conformation or crystal structure of other CRISPR-Cas systems or complexes whose crystal structures are yet unknown. Data from all of these crystal structures can be in a database, and the herein methods can be more robust by having herein comparisons involving the herein crystal structure or portions thereof be with respect to one or more crystal structures in the library. Thus, there is the provision of systems, such as computer systems, intended to generate structures and/or perform rational design of a CRISPR-Cas system or complex. The system can contain: atomic co-ordinate data according to the herein cited materials concerning the Cas9 Crystal Structure or be derived therefrom e.g., by modeling, said data defining the three-dimensional structure of a CRISPR-Cas system or complex or at least one domain or sub-domain thereof, or structure factor data therefor, said structure factor data being derivable from the atomic co-ordinate data of the herein-referenced Crystal Structure. The invention also involves computer readable media with: atomic co-ordinate data according to the teachings herein e.g., by or from homology modeling, said data defining the three-dimensional structure of a CRISPR-Cas system or complex or at least one domain or sub-domain thereof, or structure factor data therefor, said structure factor data being derivable from the atomic co-ordinate data of the herein-referenced Crystal Structure. "Computer readable media" refers to any media which can be read and accessed directly by a computer, and includes, but is not limited to: magnetic storage media; optical storage media; electrical storage media; cloud storage and hybrids of these categories. By providing such computer readable media, the atomic co-ordinate data can be routinely accessed for modeling or other "in silico" methods. The invention further comprehends methods of doing business by providing access to such computer readable media, for instance on a subscription basis, via the Internet or a global communication/computer network; or, the computer system can be available to a user, on a subscription basis. A "computer system" refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a display or monitor is provided to visualize structure data. The invention further comprehends methods of transmitting information obtained in any method or step thereof described herein or any information described herein, e.g., via telecommunications, telephone, mass communications, mass media, presentations, internet, email, etc. The crystal structures of the invention can be analyzed to generate Fourier electron density map(s) of CRISPR-Cas systems or complexes; advantageously, the three-dimensional structure being as defined by the atomic co-ordinate data according to the herein-referenced Crystal Structure. Fourier electron density maps can be calculated based on X-ray diffraction patterns. These maps can then be used to determine aspects of binding or other interactions. Electron density maps can be calculated using known programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., Acta Crystallography A47 (1991), 110-119) can be used.

The herein cited materials concerning the Crystal Structure gives atomic co-ordinate data for a CRISPR-Cas9 (*S. pyogenes*), and lists each atom by a unique number; the chemical element and its position for each amino acid residue (as determined by electron density maps and antibody sequence comparisons), the amino acid residue in which the element is located, the chain identifier, the number of the residue, co-ordinates (e.g., X, Y, Z) which define with respect to the crystallographic axes the atomic position (in angstroms) of the respective atom, the occupancy of the atom in the respective position, "B", isotropic displacement parameter (in angstroms$^2$) which accounts for movement of the atom around its atomic center, and atomic number. The conformational variations in the crystal structures of the CRISPR-Cas9 system or of components of the CRISPR-Cas9 may provide important and critical information about the flexibility or movement of protein structure regions relative to nucleotide (RNA or DNA) structure regions that may be important for CRISPR-Cas system function. The structural information provided for Cas9 (e.g. *S. pyogenes* Cas9) as the CRISPR enzyme in the present application may be used to further engineer and optimize the CRISPR-Cas system and this may be extrapolated to interrogate structure-function relationships in other CRISPR enzyme systems as well. The herein cited materials relate to the crystal structure of *S. pyogenes* Cas9 in complex with sgRNA and its target DNA at 2.4 Å resolution. The structure revealed a bilobed architecture composed of target recognition and nuclease lobes, accommodating a sgRNA:DNA duplex in a positively-charged groove at their interface. The recognition lobe is essential for sgRNA and DNA binding and the nuclease lobe contains the HNH and RuvC nuclease domains, which are properly positioned for the cleavage of complementary and non-complementary strands of the target DNA, respectively. This high-resolution structure and the functional analyses provided herein elucidate the molecular mechanism of RNA-guided DNA targeting by Cas9, and provides an abundance of information for generating optimized CRISPR-Cas systems and components thereof. The crystal structure in conjunction with herein teachings may provide steps towards understanding the molecular mechanism of RNA-guided DNA targeting by Cas9. The structural and functional analyses of herein teachings and herein cited materials provide a useful scaffold for rational engineering of Cas9-based genome modulating technologies and may provide guidance as to Cas9-mediated recognition of PAM sequences on the target DNA or mismatch tolerance between the sgRNA:DNA duplex. Aspects of the invention may also relate to truncation mutants, e.g. an *S. pyogenes* Cas9 truncation mutant may facilitate packaging of Cas9 into size-constrained viral vectors for in vivo and therapeutic applications. Similarly, engineering of the PAM Interacting (PI) domain may allow programing of PAM specificity, improve target site recognition fidelity, and increase the versatility of the Cas9 genome engineering platform.

The invention comprehends optimized functional CRISPR-Cas enzyme systems. In particular the CRISPR enzyme comprises one or more mutations that converts it to a DNA binding protein to which ligase domains may be recruited or appended or inserted or attached. In certain embodiments, the CRISPR enzyme comprises one or more mutations which include but are not limited to D10A, E762A, H840A, N854A, N863A or D986A (based on the amino acid position numbering of a *S. pyogenes* Cas9) and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence.

The teachings herein and structural information of herein cited materials provided herein allows for interrogation of sgRNA (or chimeric RNA) interaction with the target DNA and the CRISPR enzyme (e.g. Cas9) permitting engineering or alteration of sgRNA structure to optimize functionality of the entire CRISPR-Cas system. For example, loops of the sgRNA may be extended, without colliding with the Cas9 protein by the insertion of distinct RNA loop(s) or distinct sequence(s) that may recruit adaptor proteins that can bind to the distinct RNA loop(s) or distinct sequence(s). The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7 s and PRR1. These adaptor proteins or orthogonal RNA binding proteins can further recruit effector proteins or fusions which comprise one or more ligase domains.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Genome-Wide CRISPR Screen in a Mouse Model of Tumor Growth and Metastasis Materials and Methods Generation of Cas9-GFP Expression Vector and Transduction of Mouse NSCLC Cell Lines A lentiviral vector, lenti-NLS-FLAG-Cas9-GFP, was generated by subcloning Cas9 from pX330 vector into a lentiviral vector (Cong et al., 2013). The plasmid was co-transfected into HEK293FT cells (Invitrogen R700-07) with lentiviral packaging plasmids psPAX2 and pMD2.G (Addgene 12260 and 12259). HEK293FT cells were cultured in D10 media and seeded in a 15 cm culture dish the day before transfection such that they would be 80-90% confluent at the time of transfection. Two hours before transfection, the media was replaced with 15 ml of prewarmed OptiMEM (Invitrogen 51985-091). The transfection mix was aspirated after 12 hours and replaced with fresh prewarmed DMEM+10% FBS. Viral particles were harvested 48 hours after this media change and frozen at −80 C.

Cas9-GFP Expressing Mouse NSCLC Cell Lines

A mouse NSCLC cell line with genotype KrasG12D/+; p53−/−; Dicer1+/− (KPD cell line) was derived from a mouse model (Kumar et al., 2009) and described in (Chen et al., 2014) and cultured in high-glucose DMEM (Invitrogen 10566-024)+10% FBS (Hyclone). This cell line was transduced with a lentiviral vector encoding NLS-Cas9-GFP (lentiCas9-EGFP) at low MOI (<0.01). GFP-positive cells were sorted as single cells into 96-well plates and cultured as clonal cell lines. Multiple clonal lines were established and genotyped by PCR. Lines with 100% cell GFP-positive were kept and those with segregating GFP expression were discarded. FLAG-Cas9 expression was confirmed by antibodies against FLAG (Sigma) or Cas9 (Diagenode).

Pooled Guide-Only Library Cloning and Viral Production

A genome-wide mouse CRISPR knockout guide-only library (Sanjana et al., 2014) containing 67,405 sgRNAs (mGeCKOa, Addgene 1000000053) was used for the transduction of the clonal lentiCas9-EGFP-expressing NSCLC cells. Briefly, the library of sgRNA oligos was cloned into an sgRNA-expressing vector that also expresses puromycin resistance (lentiGuide-Puro) using Gibson assembly, transformed into E coli electrocompetent cells (Lucigen), and spread onto ten 245 mm×245 mm plates (Corning) agar plates containing 100 µg/ml carbenicillin. The number of colonies was estimated to be >2.5×10$^6$ (>35× coverage). All colonies were scraped off and pooled for plasmid purification using EndoFree Maxi Kit (Qiagen) with 0.5 g per maxi reaction.

After plasmid purification, Applicants amplified the libraries using the following primers in to ensure adequate representation: Library Amp F: AATGATACGGCGAC-CACCGAGATCTACACTCTTTCCCTA-CACGACGCTCTTCCGATC TtAAGTAGAGtcttgtg-gaaaggacgaaacaccg (SEQ ID NO: 42); Library Amp R: CAAGCAGAAGACGGCATACGAGA-TAAGTAGAGGTGACTGGAGTTCAGACGTGTGCT CTTCCGATCTtTCTACTATTCTTTCCCCTCACTGT (SEQ ID NO: 43). With ~15M reads, Applicants identified 94% of the designed sgRNAs and there was a <10-fold difference in representation between the 10th and 90th percentile of sgRNA read counts. Two technical replicates of the PCR amplification and sequencing readout of the plasmid library (15M reads per replicate) were well correlated ($r^2$=0.98).

To produce virus, the mGeCKOa pooled plasmid was co-transfected into HEK293FT cells (Invitrogen R700-07) with lentiviral packaging plasmids psPAX2 and pMD2.G (Addgene 12260 and 12259). HEK293FT cells were cultured in DMEM (Invitrogen 10566-024)+10% FBS (Hyclone) and seeded in T-225 flasks the day before transfection such that they would be 80-90% confluent at the time of transfection. Two hours before transfection, the media was replaced with 13 ml of prewarmed OptiMEM (Invitrogen 51985-091). For transfection of each T-225 flask, 200 ul of Plus reagent (Invitrogen 11514-015) was diluted into 4 mL of OptiMEM and then the following DNA was added: 20 ug mGeCKOa, 15 ug psPAX2, 10 ug pMD2.G. Separately, 100 ul of Lipofectamine 2000 was diluted into 4 mL of OptiMEM, briefly vortexed, and incubated at room temperature for 5 minutes. After incubation, the Plus+DNA and Lipofectamine 2000 (Invitrogen 11668019) mixtures were combined, briefly vortexed, and incubated at room temperature for 20 minutes. The mixture was then very gently added to the T-225 flask with 13 ml OptiMEM. All media was aspirated after 6 hours and replaced with fresh prewarmed DMEM+10% FBS. Viral particles were harvested 48 hours after this media change and frozen at −80° C.

Pooled Library Transduction into Mouse NSCLC Cell Line

The virus was titred by spinfection of 3×10$^6$ mouse NSCLC cells per well in a 12-well plate with different dilutions of the virus (and no virus control) in each well. After adding virus, cells were spun at 2000 rpm for 2 hours at 37° C. and then placed into the incubator overnight. The next day 1.5×10$^5$ cells from each viral concentration were plated into two replicate wells of a 6-well plate. At 24 hours post-transduction, 2 µg/ml puromycin (Sigma) was added to one of the replicate wells. Cells not transduced with the library (no virus control) did not survive past 24 hours with puromycin at 2 µg/ml. After 72 hours, cells were counted in all wells to determine the viral volume that resulted in 20-40% of cells surviving in puromycin. Assuming infection events occur independently, this corresponds to a multiplicity of infection (MOI) of 0.2-0.5 and a single-infection percentage (SIP) of 77% (at 40% puromycin survival) to 89% (at 20% puromycin survival).

The SIP is calculated directly from the puromycin survival ($p_{survival}$), as shown below. The probability of a cell being infected by n viral particles if the MOI is m is given by the Poisson distribution, $$P(n) = \frac{m^n \cdot e^{-m}}{n!}$$

and the observed percent of cells surviving puromycin selection is $$p_{survival} = P(n>0) = 1 - P(n=0) = 1 - e^{-m}$$

Solving for the SIP as a function of $p_{survival}$, we get:

$$SIP = \frac{P(n=1)}{P(n \geq 1)} = \frac{P(n=1)}{P(n>0)} = -\frac{(1-p_{survival})\ln(1-p_{survival})}{p_{survival}}$$

For each experimental replicate of the pooled screen, a total of $1.2 \times 10^8$ cells were infected at MOI~0.4, and selected with puromycin at 2 ug/ml for 7 days. MOI was calculated with an in-line control using a similar procedure as given in the previous paragraph. Infected cells were expanded under puromycin selection for 7 days and split every 2-3 days. After 7 days, $3 \times 10^7$ cells were spun down and frozen for genomic DNA extraction. At the same time, $1.7 \times 10^8$ cells were washed twice in sterile PBS and resuspended at $5 \times 10^7$ cells/ml in PBS for tumor transplantation.

Animal Work Statement

All animal work were performed under the guidelines of Division of Comparative Medicine (DCM), with protocols (0411-040-14, 0414-024-17, 0911-098-11, 0911-098-14 and 0914-091-17) approved by Massachusetts Institute of Technology Committee for Animal Care (CAC), and were consistent with the Guide for Care and Use of Laboratory Animals, National Research Council, 1996 (institutional animal welfare assurance no. A-3125-01).

Mice, Tumor Transplant and Metastasis Analysis

NSCLC cells infected with NLS-Cas9-GFP vector only or NLS-Cas9-GFP and mGeCKOa library were injected subcutaneously into the right side flank of Nu/Nu mice at $3 \times 10^7$ cells per mouse. Transplanted primary tumor sizes were measured by caliper. At 6 weeks post transplantation, mice were sacrificed and several organs (liver, lung, kidney and spleen) were dissected for examination of metastases under a fluorescent stereoscope.

Mouse Tissue Collection

Primary tumors and other organs were dissected manually. For molecular biology, tissues were flash frozen with liquid nitrogen, ground in 24 Well Polyethylene Vials with metal beads in a GenoGrinder machine (OPS diagnostics). Homogenized tissues were used for DNA/RNA/protein extractions using standard molecular biology protocols. Tissues for histology were then fixed in 4% formaldehyde or 10% formalin overnight, embedded in paraffin, and sectioned at 6 μm with a microtome as described previously (Chen et al., 2014). Slices were subjected to hematoxylin and eosin (H&E) staining as described previously (Chen et al., 2014).

MicroCT

MicroCT (μCT) were performed as described previously (Platt et al., 2014). Briefly, μCT imaging was performed using standard imaging protocol with a μCT machine (GE Healthcare). Briefly, animals were anesthetized using isoflurane, and setup in the imaging bed with a nosecone providing constant isoflurane. A total of 720 views were acquired for each mouse using a soft-tissue-fast-scan setting. Raw image stacks were processed for lung reconstruction using the standard ROI tool (MicroView). Rendering and quantification were performed using render volume tool and measurement tool in MicroView.

Genomic DNA Extraction from Cells and Mouse Tissues

Genomic DNA from cells and tissues (primary tumors and lungs) was extracted using a homemade modified salting out precipitation method similar to the Puregene (Qiagen/Gentra) procedure. After a hands-on comparison of several commercial DNA extractions kits, such as the QIAamp Blood Midi/Max (Qiagen), the Quick-gDNA MidiPrep (Zymo) and Puregene (Qiagen), Applicants found that Applicants' homemade version provided consistent, high-quality yields with a low-cost, simple protocol.

For gDNA extraction from either 100-200 mg of frozen ground tissue or $3 \times 10^7$-$5 \times 10^7$ frozen cells, the same procedure was used. For different amounts of tissue or cells, the quantities below can be scaled as needed. In a 15 ml conical tube, Applicants added 6 ml of NK Lysis Buffer (50 mM Tris, 50 mM EDTA, 1% SDS, pH 8) and 30 μl of 20 mg/ml Proteinase K (Qiagen 19131) to the tissue/cell sample and incubated at 55° C. overnight. The next day, Applicants added 30 μl of 10 mg/ml RNAse A (Qiagen 19101, diluted in NK Lysis Buffer to 10 mg/ml) to the lysed sample, inverted 25 times and incubated at 37° C. for 30 minutes. Samples were cooled on ice before addition of 2 ml of pre-chilled 7.5M ammonium acetate (Sigma A1542) to precipitate proteins. Stock solutions of 7.5M ammonium acetate should be made in sterile $H_2O$ and kept at 4° C. until use. After adding ammonium acetate, the samples were vortexed at high speed for 20 seconds and then centrifuged at ≥4,000×g for 10 minutes. After the spin, a tight pellet was visible and the supernatant was carefully decanted into a new 15 ml conical tube. Applicants then added 6 ml 100% isopropanol to the tube, invert 50 times and centrifuged at ≥4,000×g for 10 minutes. Genomic DNA were visible as a small white pellet. Applicants discarded the supernatant and add 6 ml of freshly prepared 70% ethanol, inverted the tube 10 times, and centrifuged at ≥4,000×g for 1 minute. Applicants then discarded the supernatant by pouring, briefly spun again, and used a P200 pipette to remove any remaining ethanol. After air drying for 10-30 minutes, the DNA changed appearance from a milky white pellet to slightly translucent. At this stage, Applicants added 500 μl of 1×TE buffer (Sigma T9285) and incubated at 65° C. for 1 hour and at room temperature overnight to fully resuspend the DNA. The next day, Applicants vortexed the samples briefly and then used a Nanodrop (Thermo Scientific) to measure the DNA concentration.

SgRNA Library Readout by Deep Sequencing

The sgRNA library for each sample (plasmid, genomic DNA from cells and tissues) was amplified and prepared for Illumina sequencing using a two-step PCR procedure. For PCR #1, we amplified using primers specific to the sgRNA-expression vector (lentiGuide-PCR1-F (pHKO25-F3), and lentiGuide-PCR1-R (pHKO25-R1)):

pHKO25-F3
(SEQ ID NO: 44)
CCCGAGGGGACCCAGAGAG.

pHKO25-R1
(SEQ ID NO: 45)
GCGCACCGTGGGCTTGTAC.

All PCR was performed using Phusion Flash High Fidelity Master Mix (Thermo). For PCR #1, the thermocycling parameters were: 98° C. for 30 s, 18-24 cycles of (98° C. for 1 s, 62° C. for 5 s, 72° C. for 35 s), and 72° C. for 1 minute. In each PCR #1 reaction, Applicants used 3 µg of gDNA. For each sample, the appropriate number of PCR #1 reactions was used to capture the full representation of the screen. For example, at ~400× coverage of Applicants' 67,405 mGeCKOa sgRNA library, Applicants used gDNA from $3 \times 10^7$ cells. Assuming 6.6 µg of gDNA per cell, Applicants would use ~200 µg of gDNA per sample. Since Applicants used 3 µg of gDNA per 100 µl PCR #1 reaction, each biological sample required 67 PCR #1 reactions.

PCR #1 products for each biological sample were pooled and then amplified with barcoded second PCR primers (FIG. 18—Supplemental Tables). For each sample, Applicants performed at least 7 PCR #2 reactions (One 100 ul reaction per $10^4$ constructs in the library) using 10 µl of the pooled PCR #1 product per PCR #2 reaction.

Second PCR products were pooled and then normalized for each biological sample before combining uniquely barcoded separate biological samples. The pooled product was then gel purified from a 2% E-gel EX (Life Technologies) using the QiaQuick kit (Qiagen). The purified pooled library was then quantified with dsDNA High-Sensitivity Qubit (Life Technologies) and/or a gel-based method using the Low-Range Quantitative Ladder Life Technologies). Diluted libraries with 5-20% PhiX were sequenced with MiSeq or HiSeq 2500 (Illumina).

sgRNA Deep Sequencing Data Processing

Deep sequencing data were processed for sgRNA representation using custom scripts. Briefly, sequencing reads were demultiplexed using the 8-basepair barcodes in the reverse primer, and then demultiplexed using the 8-basepair barcodes in the forward primer. Demultiplexed reads were trimmed using cutadapt (Martin, 2011), leaving only the 20 bp spacer (guide) sequences. The spacer sequences were then mapped to the spacers of designed sgRNA library using bowtie (Langmead et al., 2009). For mapping, a maximum of one mismatch was allowed in the 20 bp spacer sequence. Mapped sgRNA spacers were then quantified by counting the total number of reads. In each biological sample, any sgRNA spacer with only a single read was filtered out. The total numbers of reads for all sgRNAs in each sample were normalized Figures were generated using the normalized read counts in R and RStudio (R project, Revolution Analytics), Matlab (Mathworks), and the Gene Set Enrichment Analysis tool (Broad Institute).

Validation and Control Minipool Synthesis, Viral Transduction and In Vivo Transplantation Validation and control minipools were synthesized in a single oligonucleotide pool using a semiconductor-based electrochemical detritylation synthesis (CustomArray) and SAFC Proligo reagents (Sigma). Each minipool was separately PCR amplified from the pooled synthesis, gel purified and cloned into the lentiGuide-Puro vector using Gibson assembly, as previously described (Sanjana et al., 2014; Shalem et al., 2014). Cloned minipool libraries were deep-sequenced to verify representation (Illumina) and lentivirus was produced in the same manner as for the mGeCKOa library. As before, validation and control minipool library viruses were titred by spinfection of $3 \times 10^6$ mouse Cas9-EGFP NSCLC cells per well in a 12-well plate with different dilutions of the virus (and no virus control) in each well to find what viral volume was need to yield a 20-40% survival after treatment for 48 hours with 2 ug/ml puromycin (Sigma).

Using these viral volumes, the same clonal Cas9-EGFP NSCLC mouse cell line as used for the mGeCKOa screen was transduced via spinfection with either control or validation minipool virus. Representation for both screens (validation and control minipool) was ~1,000 fold. Cells were maintained in D10 media with 2 ug/ml puromycin and split 1:4 every 2-3 days.

After 7 days in culture, Cas8-EGFP NSCLC cells infected with validation minipool or control minipool were injected subcutaneously into the right side flank of Nu/Nu mice at $3 \times 10^7$ cells per mouse. For each minipool, cells were transplanted into 5 mice. After five weeks, mice were sacrificed and primary tumors and lungs were dissected. Histology samples and genomic DNA were collected in a similar manner as described above for the mGeCKOa screen.

Single sgRNA Design, Lentiviral Transduction and In Vivo Transplantation

Six sgRNAs per protein coding gene and four per microRNA gene were chosen for single agent validation. For protein coding genes, we cloned both the 3 sgRNAs from the mGeCKOa library and 3 additional sgRNAs to target each gene. For miRNAs, we used all 4 sgRNAs from the mGeCKOa library. SgRNAs targeting individual genes/miRNAs were cloned into the lentiGuide-Puro vector (Addgene). Single sgRNA viruses were generated by transfection of HEK293FT using the same procedure as described for the mGeCKOa library virus. After harvest, viruses were functionally tittered (percent puromycin survival) and used to transduce Cas9-EGFP NSCLC cells at a MOI <<1 for all transductions. Cells were maintained in D10 media (with 2 ug/ml puromycin added at 24 hours post-transduction) and split 1:4 every 2-3 days.

After 3 days in culture, a portion of the cells infected with each single sgRNA virus was collected in QuickExtract buffer (Epicentre) and subjected to amplicon-sequencing (Illumina) for indels, as described previously (Hsu et al., 2013). After 7 days in culture, another portion of the cells was collected in RIPA buffer for western blot of protein levels using antibodies against Nf2 or Pten (CST). SgRNAs that were efficient in generating indels or in reducing protein levels were chosen for in vivo experiments. After 7 days in culture, cells were injected subcutaneously into the right side flank of Nu/Nu mice at $5 \times 10^6$ cells per mouse. Each gene or microRNA was targeted with three independent sgRNAs that went into validation experiments, with two mice injected per sgRNA. A total of 6 mice were used to validate each gene or miRNA. After five weeks, mice were sacrificed and primary tumors and lungs were dissected. Histology samples were collected and analyzed in a similar manner as described above for the mGeCKOa screen.

CTC Chip Design and Capture

Applicants designed a microfluidic device for CTC capture similar to one previously described (Chung et al., 2013). This device has two functions: magnetic depletion of leukocytes, and capture CTCs based on their size criteria (5~30 µm). The microfluidic system were fabricated with standard soft lithography and boned with glass substrate. Each CTC chip contains a large number of capturing sites (>10,000). Peripheral blood was collected from mice after injected with cells for five weeks, using terminal cardiac puncture method. The blood samples were depleted of red blood cells using red blood cell lysis buffer (BD and/or Miltenyi), fixed with 2% formaldehyde and subject to CTC capture. For each sample, 250~500 μl of the fixed cells was run through the chip at flow rate of 2-5 mL/hour. The chips with captured cells were imaged under a fluorescence microscope with 15~17 images tiling the whole chip for each sample. GFP-positive cells were counted across all images for each chip using custom Matlab scripts.

Standard Molecular Biology

Routine DNA cloning, nucleic acid purification western blot were performed using standard molecular biology protocols with commercially available kits.

Results

CRISPR/Cas9 Library-Mediated Mutagenesis Accelerates Metastasis

The Applicants derived and cloned a cancer cell line (Chen et al., 2014) from a mouse non-small cell lung cancer (NSCLC) (Kumar et al., 2009). This cell line possesses an oncogenic Kras in conjunction with homozygous p53 loss and heterozygous Dicer1 loss ($Kras^{G12D}$/+; p53−/−; Dicer1+/−, or KPD), and is capable of inducing tumors when transplanted into immunocompromised mice (Chen et al., 2014; Kumar et al., 2009). This KPD cell line was transduced with a lentivirus carrying a Cas9 transgene fused to a nuclear localization sequence (NLS), a triple FLAG epitope (3×FLAG), and a green fluorescent protein (GFP). The transduction was performed at low multiplicity of infection (MOI<0.01) to ensure that most cells receive only one lentiviral transgene. Clonal cell lines expressing Cas9-GFP were established (termed Cas9-GFP KPD cell lines thereafter), as shown by fluorescence imaging and western blot using antibodies against Cas9 or FLAG (FIG. 8 A-B). A clonal Cas9-GFP KPD cell line was selected to provide cellular homogeneity for the subsequent screen.

For the knockout screens, the Applicants utilized a pooled genome-wide mouse sgRNA library cloned into lentiGuide-Puro, a bicistronic lentiviral vector that expresses both the sgRNA and a puromycin resistance gene (Sanjana et al., 2014). This library (termed mouse Genome-scale CRISPR knockout library A, or mGeCKOa thereafter) has 67,405 sgRNAs targeting 20,611 annotated protein-coding and 1,175 microRNA precursor genes in the mouse genome. The library also contains 1,000 control sgRNAs (termed non-targeting sgRNAs) designed to have minimal homology to sequences in the mouse genome (Sanjana et al., 2014; Shalem et al., 2014). The Applicants transduced the Cas9-GFP KPD cell line with the mGeCKOa lentiviral library with three independent infection replicates with greater than 400× coverage for each replicate (FIG. 1A). In these three infection replicates, the MOI was on average 0.4+/−0.02, which ensures that over 80% of the cells surviving puromycin selection received only one sgRNA-expressing lentiviral integrant.

After culture in vitro for a week, the Applicants subcutaneously transplanted $3×10^7$ cells into the flanks of immunocompromised Nu/Nu mice (FIG. 1A). With the cells from each infection replicate, Applicants transplanted 4 mice, using one mouse for early tumor sequencing and three for later stage (see below and FIG. 1A). Both mGeCKOa transduced and untransduced Cas9-GFP KPD cells form tumors at the injection site (FIG. 1B). Like most subcutaneously transplanted tumors, these tumors were poorly differentiated. The primary tumors induced by mGeCKOa transduced cells grew slightly faster than tumors from the untransduced cells at an early stage (FIG. 1C) (two weeks post-transplantation) (paired two-tailed t-test, p=0.05), but at late stages all tumors were similar in size (paired two-tailed 1-test, p=0.18 for four weeks, and p=0.6 for six week) (FIG. 1C).

Figure 1D:
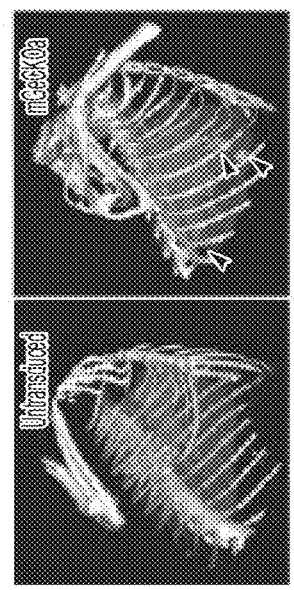
Figure 1C:
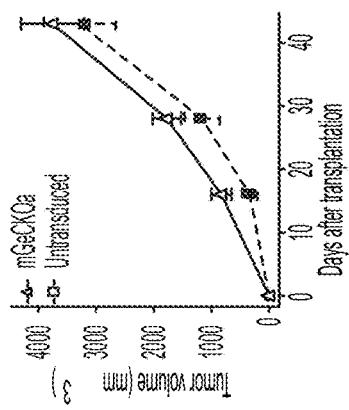
Figure 1B:
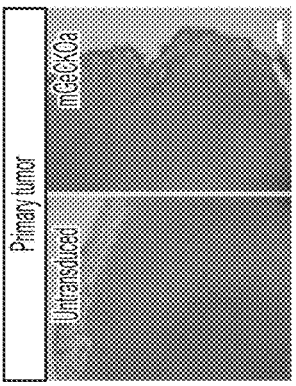
Figure 1E:
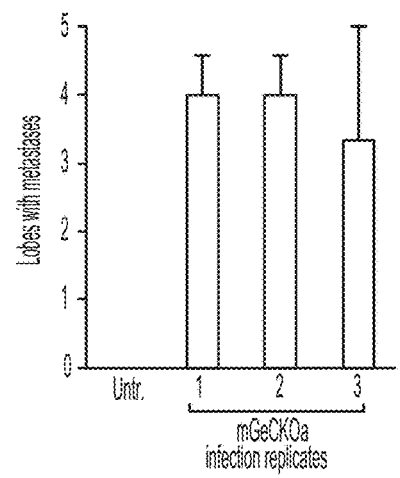
Figure 1F:
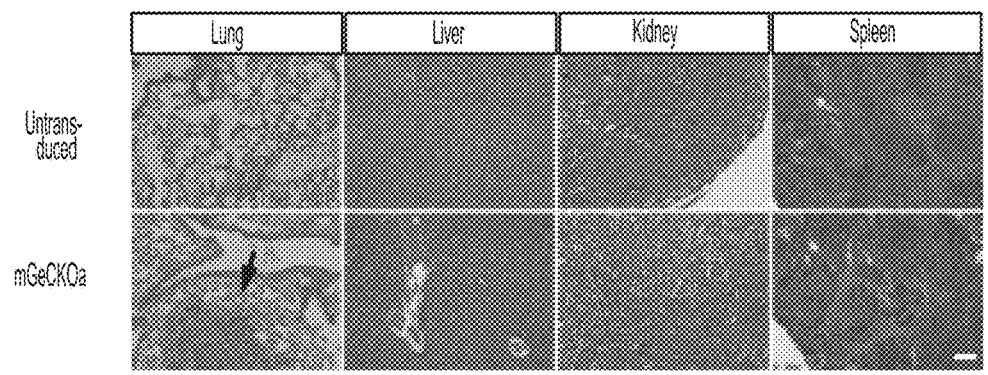
Figure 8C:
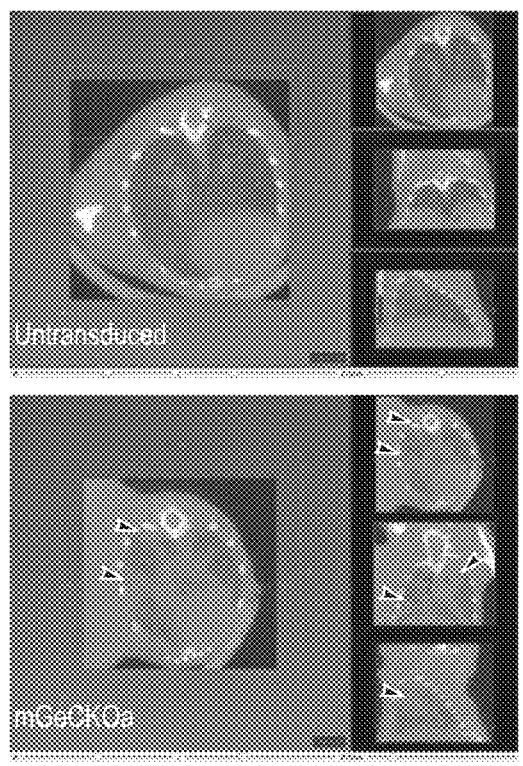
Figure 8D:
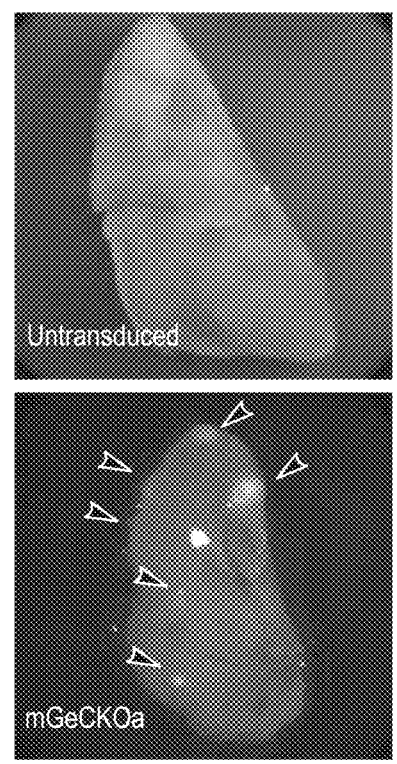

At 6 weeks post-transplantation, Applicants imaged the mice using micro-computed tomography (μCT), and found tumors in the lungs of the mice transplanted with mGeCKOa transduced Cas9-GFP KPD cells (mGeCKOa mice), but not in the mice transplanted with untransduced Cas9-GFP KPD cells (control mice) (FIG. 1D, FIG. 8C). Mice were sacrificed and examined for metastases in various organs. Under a fluorescent stereoscope at 6× magnification, metastases were visually detected in the lung in 90% (8/9) of the mGeCKOa mice (FIG. 8D). In three independent experiments, mGeCKOa mice on average had 80% of their lobes positive for metastases (FIG. 1E). In contrast, none (0/3) of the Cas9-only control animals developed detectable metastases (FIG. 1E). At this time, metastases were not detected in the liver, kidney or spleen in either group (FIG. 1F). These data suggested that mGeCKOa library transduction accelerate the ability of the Cas9-GFP KPD cells to form metastases in the lung.

Figures 9A, 9B, 9C, 9D:
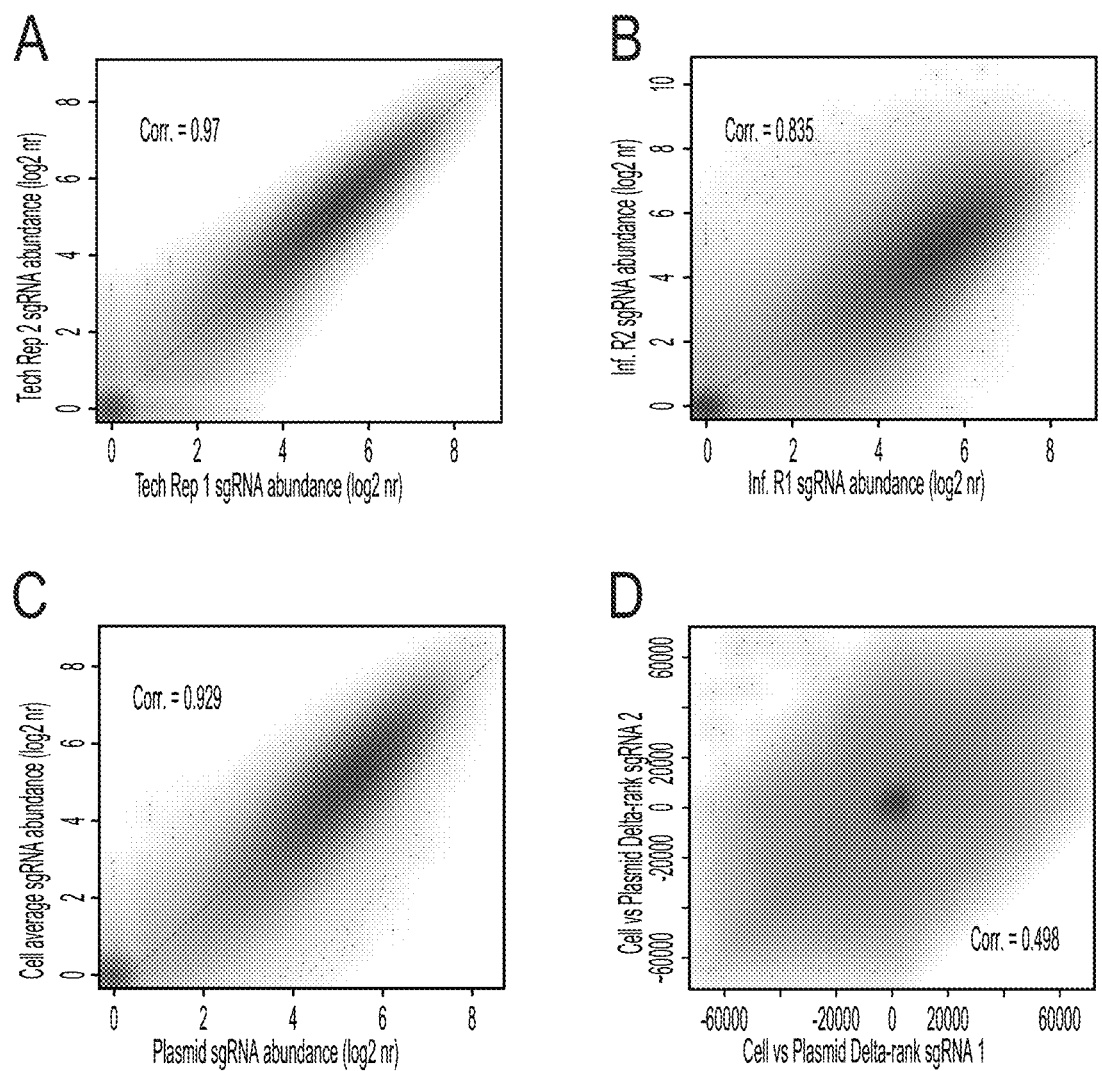
FIG. 9A-9F: (A) Pearson correlation of sgRNA normalized read counts between two technical replicates of the mGeCKOa-transduced cell pool from infection replicate 1 (R1) before transplantation. Technical replicates have separate PCR readout and Illumina sequencing. (B) Pearson correlation of sgRNA normalized read counts between two infection replicates (R1 and R2) of the transduced cell pool before transplantation. (C) Pearson correlation of sgRNA normalized read counts between the mGeCKOa plasmid and the transduced cell pools (average of all 3 infection replicates). (D) Pearson correlation of change in rank between mGeCKOa plasmid and transduced cell pools (average of all 3 infection replicates) for all pairs of sgRNAs targeting the same gene. (E) Pearson correlation of normalized sgRNA read counts and dendrogram based on complete linkage (farthest neighbor) clustering for all samples in mGeCKOa initial screen. Plasmid denotes the mGeCKOa plasmid before lentivirus production. Cell denotes the mGeCKOa-transduced cell pool at 7 days post-transduction. Early tumor denotes samples harvested from the primary tumor at ~2 weeks after transplantation of the transduced cell pool. Late tumor and lobe denote samples harvested from the primary tumor and lungs, respectively, at ~6 weeks after transplantation of the transduced cell pool. Rn denotes independent infection replicates and mn denotes different mice for that infection replicate. (F) Gene Set Enrichment Analysis (GSEA) of the 10 most depleted gene sets in the cells before transplantation compared to the plasmid pool (FDR q<10-3). Gray lines indicate the rank position of a single gene from the gene set indicated. The green bar indicates the cross-over between enriched and depleted genes. The red line indicates the position of the median gene rank for the genes in the set. Numbers next to the gene set name are the Normalized Enrichment Score.
Figure 9E:
Figure 9E:
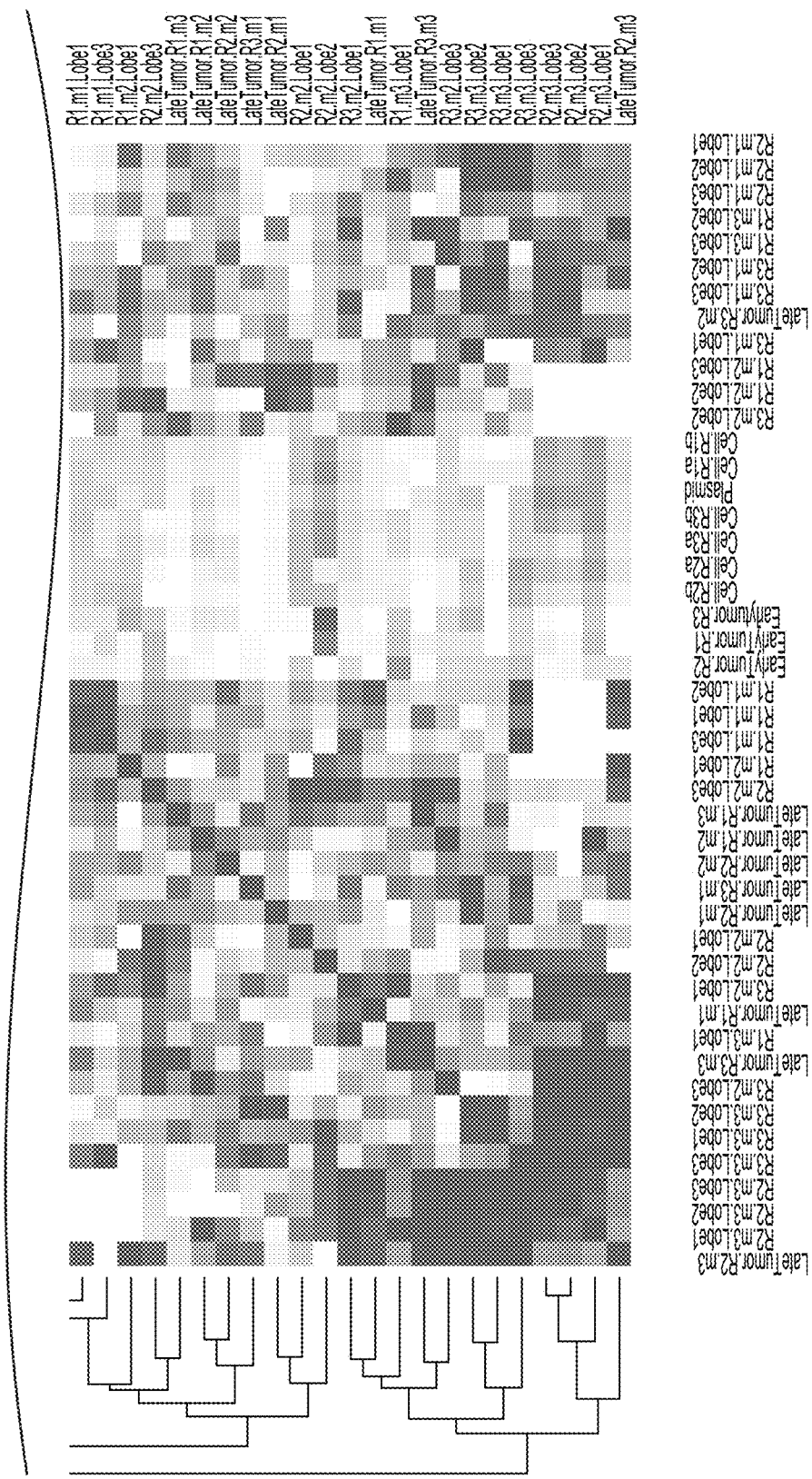
Figure 9F:
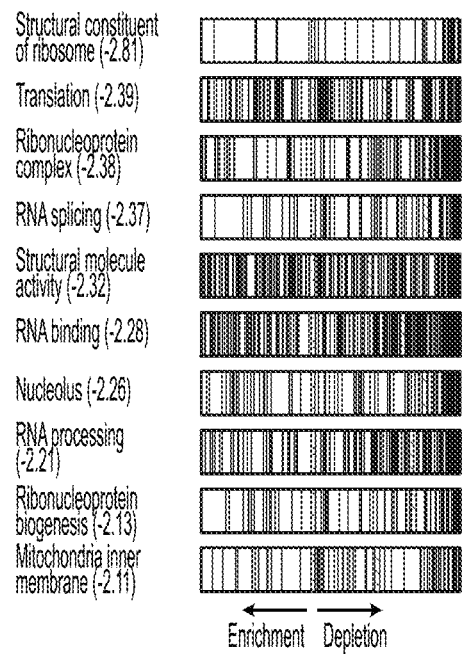

Dynamic Evolution of sgRNA Library Representation During Tumor Growth and Metastasis To investigate the sgRNA representation through different stages of tumor evolution and to infer genes whose loss-of function confers a proliferative or metastatic phenotype, Applicants used deep sequencing to read out the sgRNa representation. At six-week post transplantation, Applicants harvested and sequences the late stage primary tumor and three random lobes from the lung of each of the nine mGeCKOa mice (FIG. 1A). In parallel, Applicants also sequenced the mGeCKOa plasmid library, the pre-transplantation mGeCKOa transduced Cas9-GFP KPD cells, as well as early stage primary tumors (two-week post transplantation, one animal from each replicate experiment). In the cell samples, the sgRNA representations showed high concordance between technical replicates (correlation, $\rho=0.95$ on average) and biological infection replicates (correlation, $\rho=0.84$ on average) (FIG. 2A, FIG. 9A, B, F). Cell pools on average highly correlate with the plasmid representation (correlation, $\rho=0.93$) (FIG. 2A, FIG. 9C, F). Furthermore, different sgRNAs that target the same gene are correlated in terms of rank change (correlation $\rho=0.49$ on average) (FIG. 9D). The sgRNAs with significantly decreased abundance in cells compared to plasmid are enriched for multiple categories of essential genes, such as ribosomal proteins, translation factors, RNA splicing factors and RNA processing factors, indicating selection against the loss of these genes after one-week in culture (FIG. 9F).

Figure 10A:
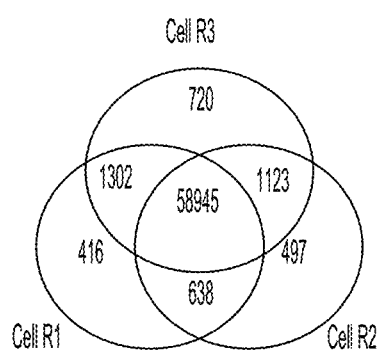
FIG. 10A-10G: (A) Venn diagram of sgRNAs from the mGeCKOa library detected in the 3 infection replicates of the mGeCKOa-transduced cell pool at 7 days post-transduction. (B) Venn diagram of sgRNAs from the mGeCKOa library detected in the 3 infection replicates of the primary tumor at ~2 weeks after transplantation of the transduced cell pool. (C) Number of unique sgRNAs from the mGeCKOa library detected in the plasmid pool, cells before transplantation, early and late primary tumors, and lung metastases. Plasmid denotes the mGeCKOa plasmid before lentivirus production. Cell denotes the mGeCKOa-transduced cell pool at 7 days post-transduction. Early tumor denotes samples harvested from the primary tumor at ~2 weeks after transplantation of the transduced cell pool. Late tumor and lobe denote samples harvested from the primary tumor and lungs, respectively, at ~6 weeks after transplantation of the transduced cell pool. Rn denotes independent infection replicates and mn denotes different mice for that infection replicate. Technical replicates of PCR readout and sequencing for Cell are denoted by a or b after the infection replicate (R1, R2, R3). (D) Boxplot of the sgRNA normalized read counts for the mGeCKOa plasmid pool, cells before transplantation, early and late primary tumors, and lung metastases at lobe level with labels as given in FIG. 11. Green dots indicate 1,000 control (non-targeting) sgRNAs in the mGeCKOa library. (E) Venn diagram of sgRNAs from the mGeCKOa library detected in lung metastases and primary tumors across all 3 infection replicates (n=3 mice per replicate, 9 mice total) at ~6 weeks after transplantation of the transduced cell pool. (F) Scatterplot of the number of sgRNAs detected in the primary tumor and the lung metastases for each individual mouse transplanted with mGeCKOa cells, showing correlation of sgRNA diversity between lung and late primary tumors for each mouse (n=9). (G) Pearson correlation of mGeCKOa sgRNA abundance in late primary tumor and lung metastases in the same mouse (taken from one representative mouse with a median correlation among the 9 mice).
Figure 10B:
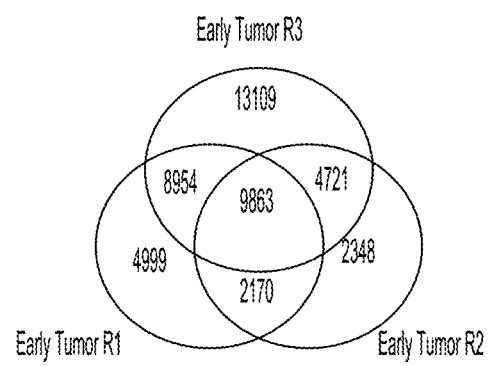
Figure 10C:
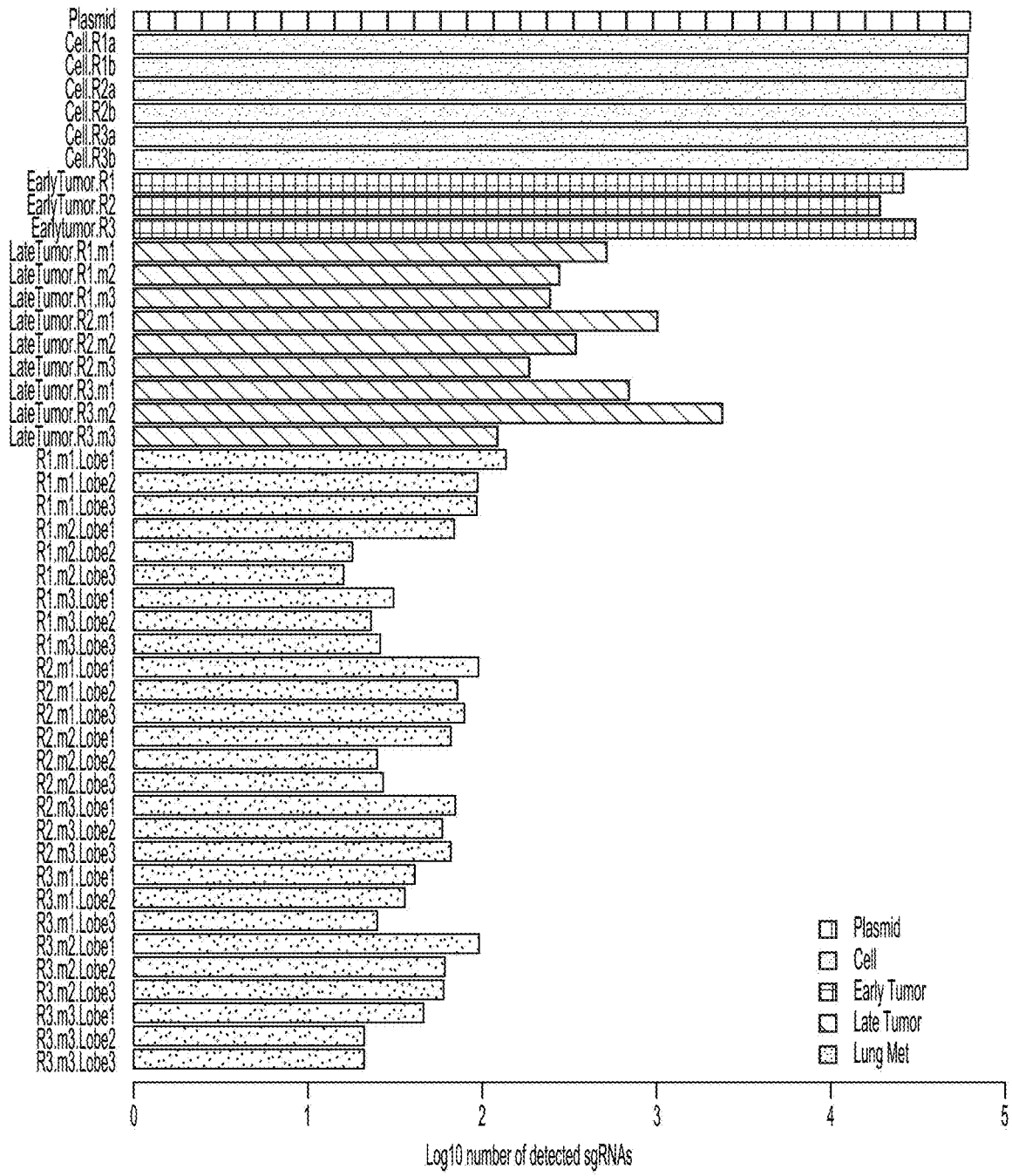

To investigate the sgRNA library dynamics in different sample types (plasmid, cell, early primary tumor, late primary tumor and lung metastases), Applicants compared the overall distributions of sgRNAs from all samples sequenced. Cell samples tightly clustered with each other and the plasmid, forming a cell-plasmid clade in the overall clustering dendrogram (FIG. 2A, FIG. 9E). Early primary tumor samples also clustered with each other and then with the cell-plasmid clade, whereas late tumors and lung metastases clustered with each other as a clade (FIG. 2A, FIG. 9E). The detected sgRNAs in different replicates of infected cell populations overlap by more than 95% with each other (FIG. 10 A). The detected sgRNAs in the three biological replicates of early tumor overlap 63~76% with each other (FIG. 10B). Early primary tumors retained less than half (31.5~49.4%) of the sgRNAs as compared to the cell populations (FIG. 2B-C, FIG. 10C-D). Compared to the cell pool, sgRNAs whose targets are essential genes are further depleted in early tumors (FIG. 15).

Interestingly, only a small fraction of sgRNAs (less than 4% of all sgRNAs, or less than 8% of the sgRNAs in early primary tumor of corresponding replicate) was detected in the late stage primary tumor samples (FIG. 2B-C, FIG. 10C-D). The sgRNA diversity (i.e. number of different sgRNAs detected) further decreases in samples from lung metastases (FIG. 2B-C, FIG. 10C-D). The lung samples retained at most 0.4% of all sgRNAs, or at most 1.1% of the sgRNAs in early primary tumor of corresponding replicate were found in the lung samples, with a subset of highly enriched ones (FIG. 2B-C, FIG. 10C-D). The global patterns of sgRNA distributions in different sample types are distinct, as is evident in the strong shifts in respective cumulative distribution functions (Kolmogorov-Smirnov (KS) test, $p<10^{-15}$ for all pairwise comparisons) (FIG. 2D), reflective of cancer evolution at different stages.

Enriched sgRNAs in Primary Tumors

Figure 11A:
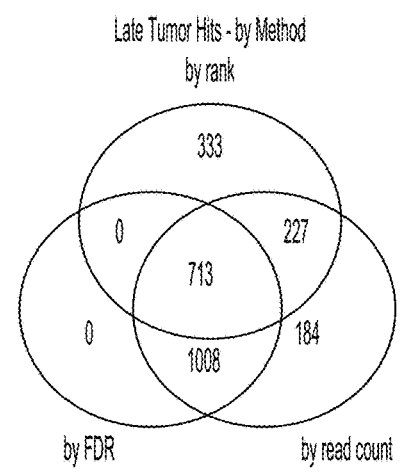
FIG. 11A-11F: (A) Venn diagram of enriched sgRNAs in late primary tumor, using three different methods, by rank, by read count cutoff, or by FDR. (B) Histogram of all 713 sgRNAs with a Metastasis-Primary Ratio (MPR: ratio of normalized reads in metastases [averaged over lobes] to normalized reads in late tumor) greater than 1 in at least one mouse. sgRNAs are binned by how many mice for which the MPR>1. Red-filled bars indicate the sgRNAs plotted in FIG. 4F (MPR>1 in 3 or more mice). Inset: Distribution of MPRs for all sgRNAs in the mGeCKOa library detected in either late tumor or metastases. Values are averaged over all mice (n=9 mice). (C) Venn diagram of enriched sgRNAs in lung metastases, using three different methods, by rank, by read count cutoff, or by FDR. (D) Venn diagram of sgRNAs from the mGeCKOa library enriched in 3 lobes of the lung from a single mouse at ~6 weeks after transplantation of the transduced cell pool. (E) Venn diagram of sgRNAs from the mGeCKOa library enriched in 3 different mice at ~6 weeks after transplantation of the transduced cell pool from a single infection replicate. The union of the sgRNAs from 3 lung lobes is used for each mouse. (F) Venn diagram of sgRNAs from the mGeCKOa library enriched in lung metastases across all mice from 3 independent infection replicates (n=3 mice per replicate) at ~6 weeks after transplantation of the transduced cell pool.

Late primary tumors retain few sgRNAs (on average 813+/−264 sgRNAs, n=9 mice), with even fewer at high frequencies (4+/−1sg RNAs with less than 5% of total reads) in each mouse (FIG. 2B-C, FIG. 9C-D, FIG. 3A). Applicants used three methods to identify enriched sgRNAs in late primary tumor. The first method was based on relative abundance, i.e. by taking sgRNAs above certain threshold; the second method was based on ranks, i.e. by taking top ranked sgRNAs in each mouse; the third method was based on false discovery rate (FDR), i.e. by taking sgRNAs enriched compared to the distribution of the 1,000 non-targeting sgRNAs at 0.2% FDR. All three methods generated similar results (FIG. 11A). Taking the results from the FDR method as an example, a total of 935 sgRNAs (targeting 909 genes) are enriched over the non-targeting controls (FDR cut-off=0.2%) in the late primary tumor of one or more mice (FIG. 3 B-C). These sgRNAs target genes that are highly enriched in apoptosis pathway (FIG. 18—Supplemental tables), with many of them being pro-apoptotic, such as BH3 interacting-domain death agonist (Bid), Phosphatase and Tensin Homolog (Pten), Cyclin-dependent kinase inhibitor 2a (Cdkn2a), and O-6-Methylguanine-DNA Methyltransferase (Mgmt), suggesting strong selection for mutations inactivating apoptosis in primary tumor cells.

Figure 12A:
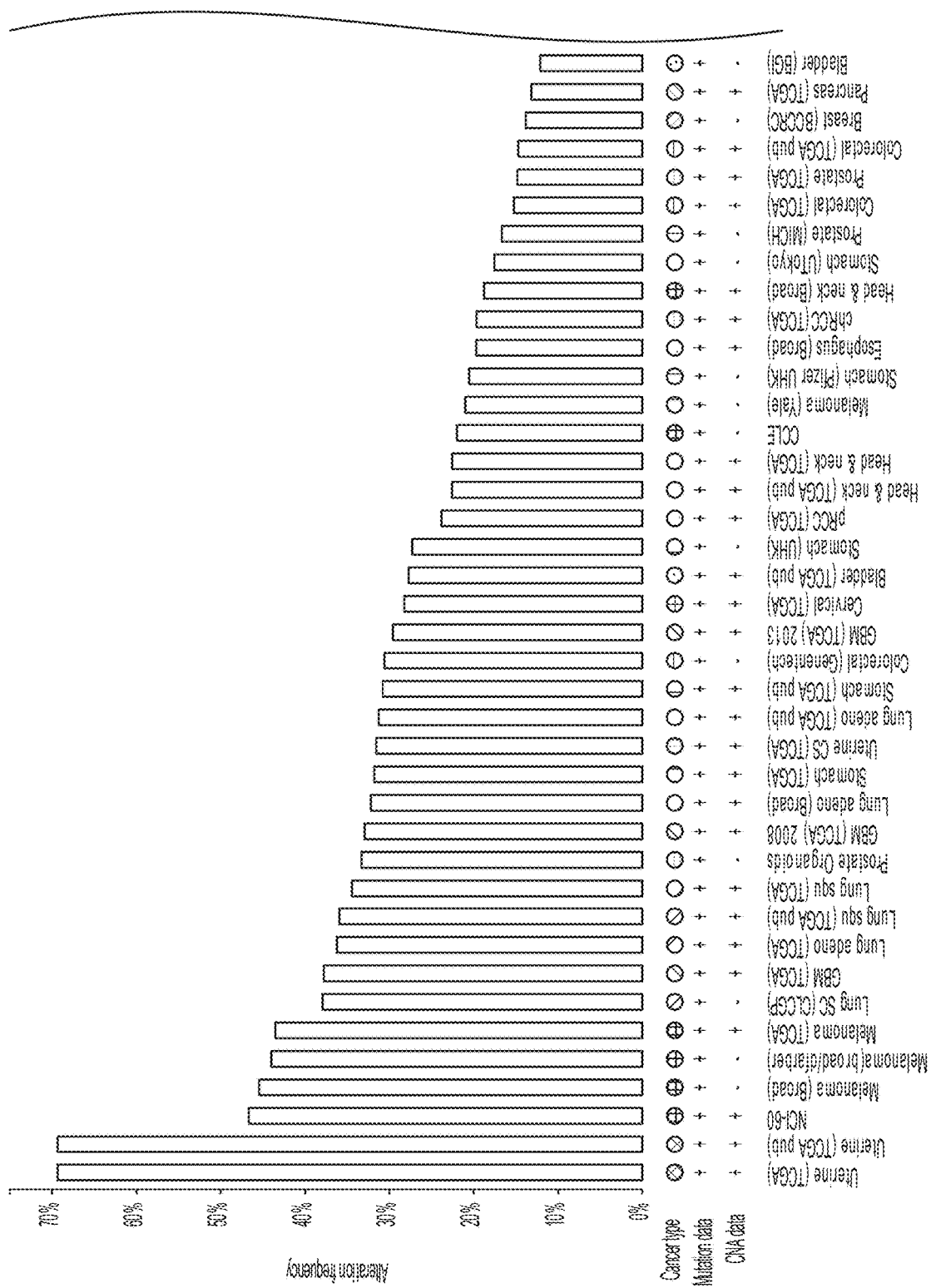
FIG. 12A-12C: (A) Barplot of mutation frequency of the late primary multi-hit gene set (24 multiple enriched sgRNA—targeting genes in late primary tumor) in human cancer sequencing datasets. (B) Co-mutation plot of the late primary multi-hit gene set in TCGA LUAD patients. (C) Co-mutation plot of the late primary multi-hit gene set in TCGA LUSC patients.
Figure 12A:
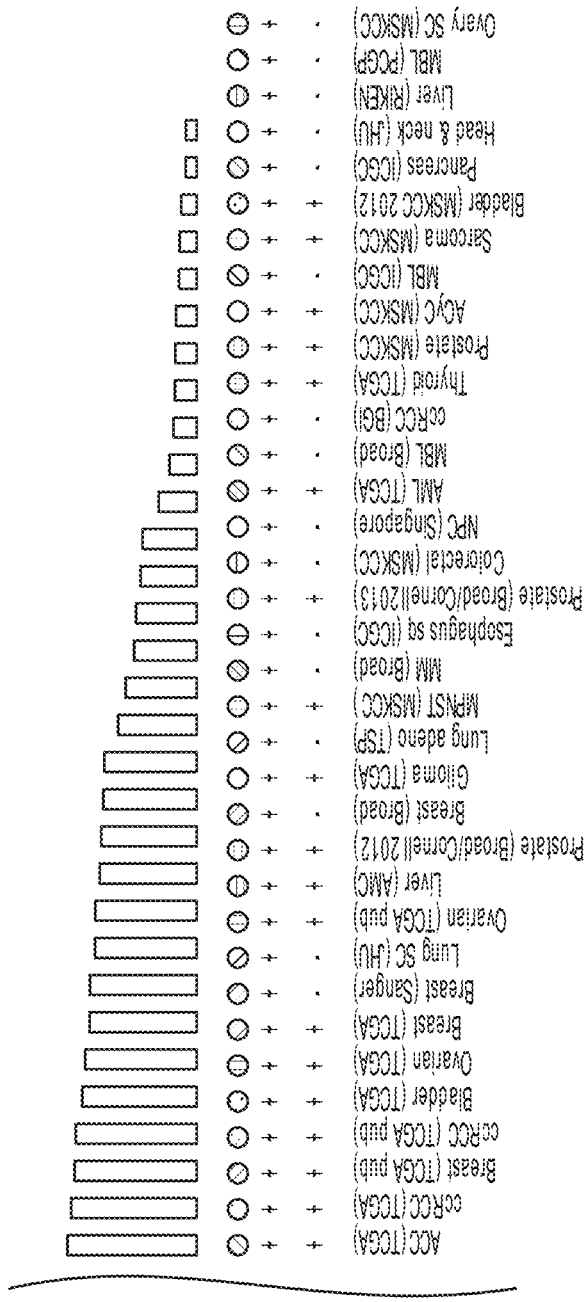
Figure 12B:
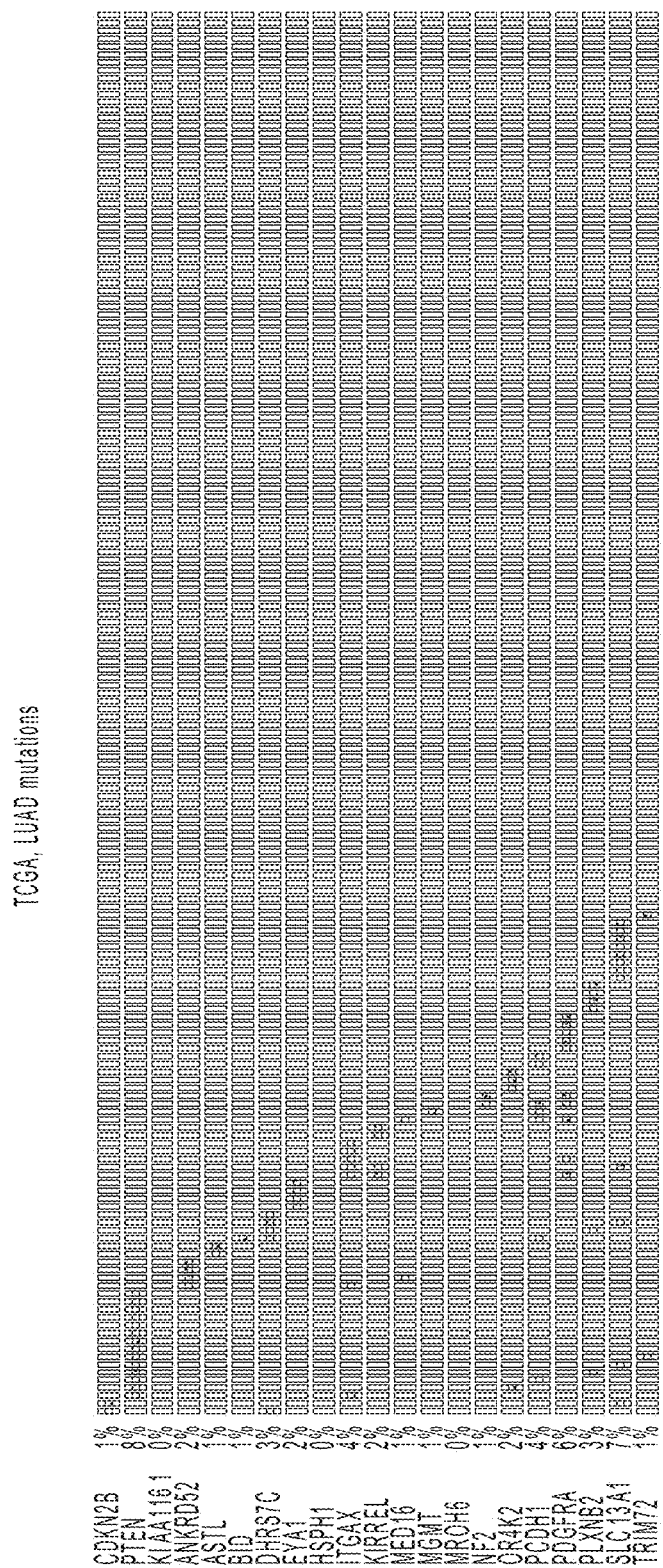
Figure 12C:
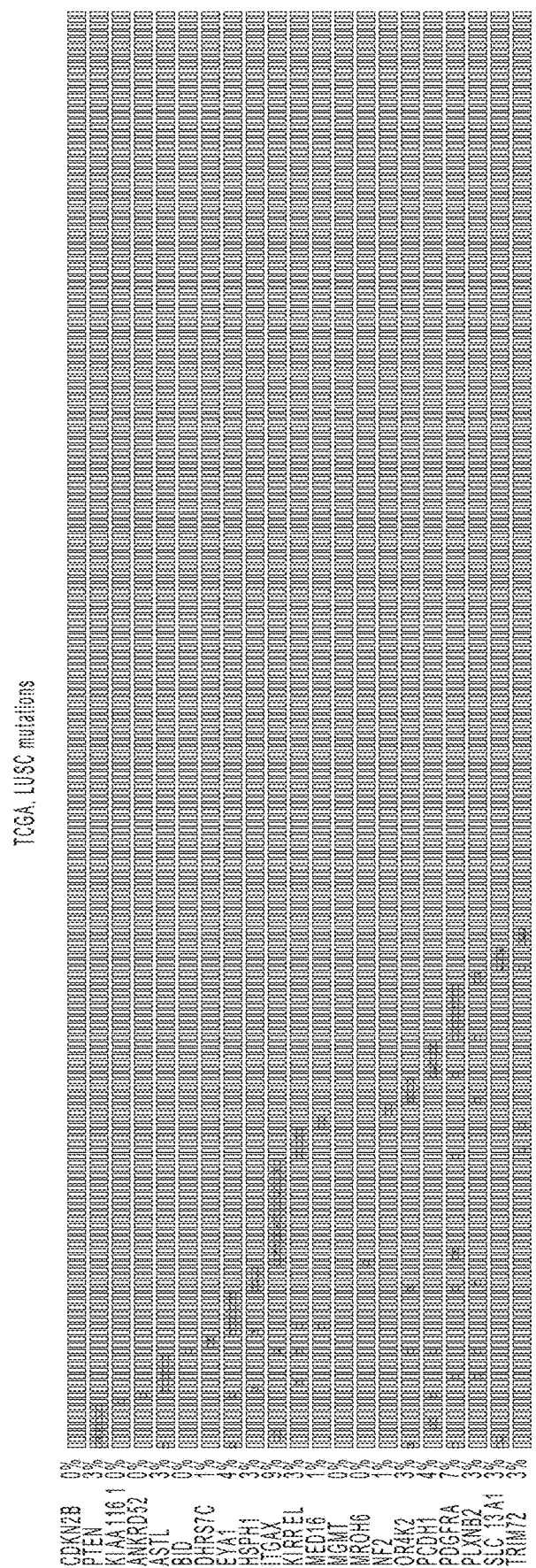

There are 24 genes targeted by two or more independent sgRNAs enriched in late primary tumors (FIG. 3 B-C). These genes were found to be mutated in patients in many previously reported cancer sequencing studies curated by cBioPortal (Cerami et al. 2013; Gao et al. 2013). For example, in somatic mutations identified by The Cancer Genome Atlas (TCGA) for non-small cell lung cancer (NSCLC), including adenocarcinoma (LUAD) (TCGA-Network, 2014b) and lung squamous cell carcinoma (LUSC) (TCGA-Network, 2012), 36% (107/407) of the patients have one or more of these 24 genes mutated (FIG. 12B-C). Several of them are well-known tumor suppressors, such as Pten, Cyclin-dependent kinase inhibitor 2b (Cdkn2b), Neurofibromin 2 (Nf2, Merlin), Alpha-type platelet-derived growth factor receptor (Pdgfra), and Integrin alpha X (Itgax). Several of these genes are associated with cancer, but their functions in tumor growth are poorly understood. For example, Mgmt, a gene with two enriched sgRNAs, is required for DNA repair and thus crucial for genome stability (Kaina et al., 2007; Tano et al., 1990; Teo et al., 2001). Mutation, silencing or promoter methylation of MGMT is associated with primary glioblastomas (Hegi et al., 2005; Jesien-Lewandowicz et al., 2009; Molenaar et al., 2014). Med16 encodes the $16^{th}$ subunit of the mediator complex of transcription regulation (Herbig et al., 2010), which has been recently implicated in cancer (Huang et al., 2012; Schiano et al., 2014).

Enriched sgRNAs in Metastases

Figure 10D:
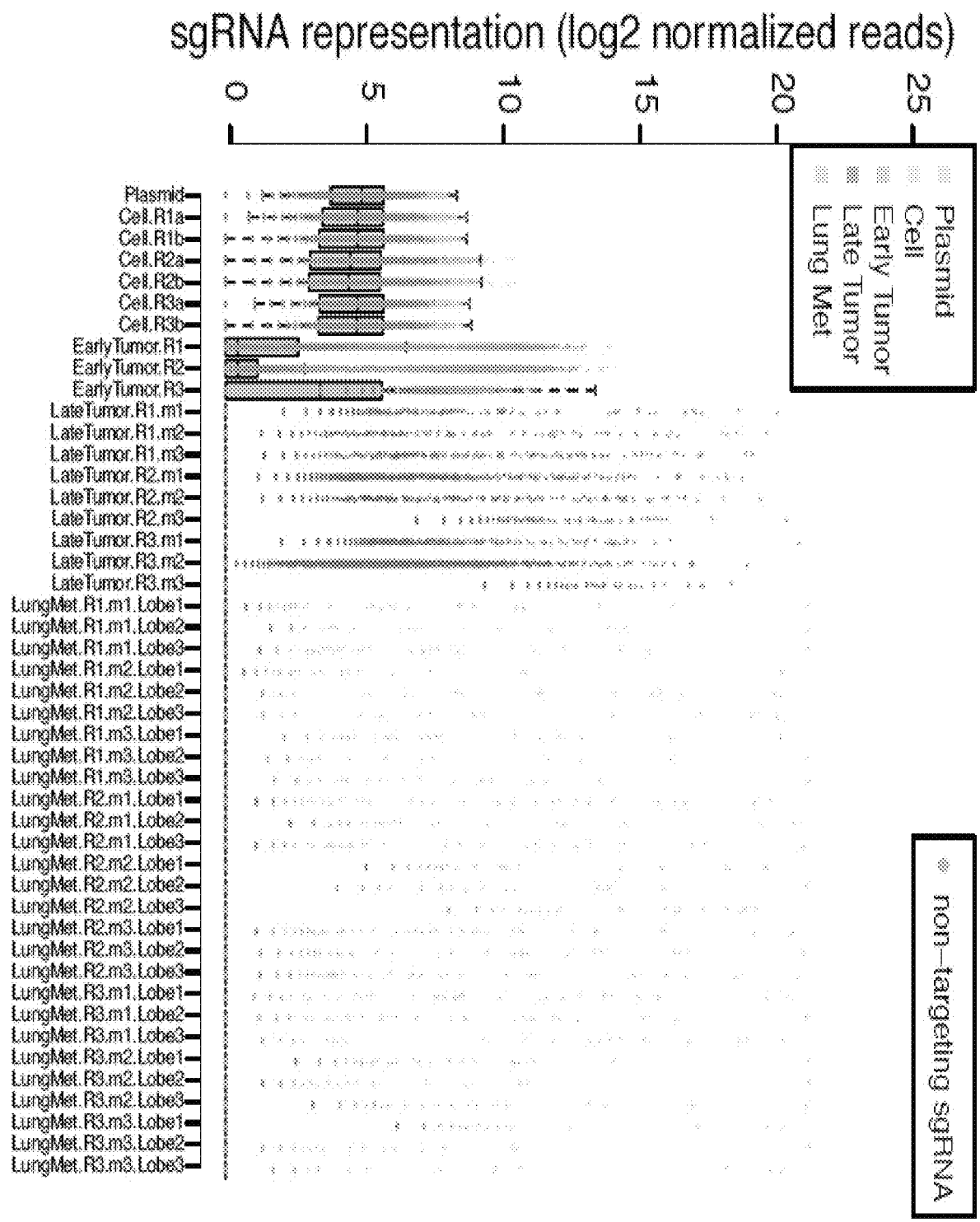

Applicants also sequenced the sgRNA distributions from three lung lobes for each mouse transplanted with mGeCKOa-transduced Cas9-GFP KPD cell. In each lobe the sgRNA representation is dominated by one or a few sgRNAs (FIG. 4A, FIG. 10D). In each mouse, the lung sgRNA representation (average of normalized sgRNA representations from three lobes) is also dominated by a small number of sgRNAs (on average 3.4+/−0.4 sgRNAs with >5% of total reads)(FIG. 4B), suggesting those select sgRNAs-integrated cells seeded metastases and grew to dominance over this time scale. Non-targeting sgRNAs were occasionally detected in the metastases, but never observed at high frequency (every Non-targeting sgRNA occupies <0.1% of total reads in any lobe) (FIG. 2C, FIG. 4A-4B). These observations are consistent with the fact that untransduced tumors are not metastatic (FIG. 1E), suggesting specific sgRNA-mediated mutations led to metastasis.

Figure 10E:
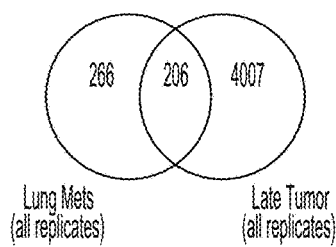
Figure 10F:
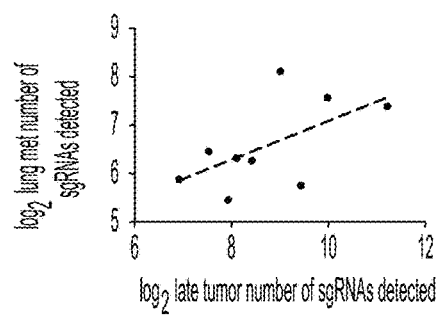
Figure 10G:
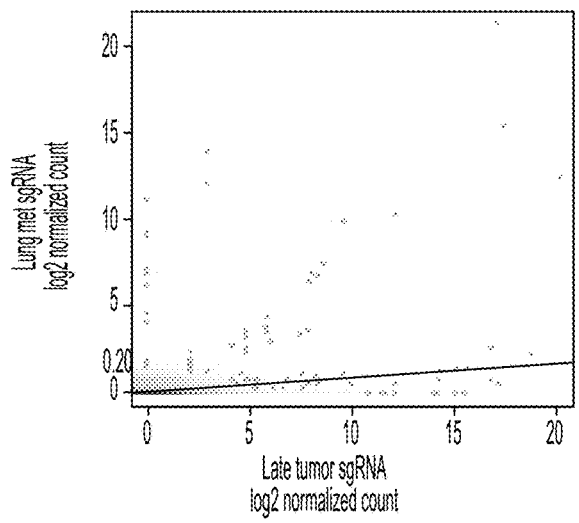

The sgRNA representations in the lung metastases are similar to those in the late stage primary tumors in several ways. First, the detected sgRNAs in lung samples significantly overlap with those in late tumor samples (Chi-square test, $p<10^{-15}$) (FIG. 10E). Second, the number of sgRNA detected in lung samples correlates, albeit weakly, with the number of sgRNAs detected in late primary tumor samples (correlation, $\rho=0.42$, F-test, $\rho=0.097$) (FIG. 10F). Third, as a genome-wide measurement, the abundance of sgRNAs in the lung positively correlates with that in the late primary tumors of the same animal (correlation, $\rho=0.18$ on average, F-test, $\rho<0.001$, n=9) (FIG. 10G). Fourth, in most mice (8/9), the lung metastasis enriched sgRNAs occupy a large fraction of reads in the late primary tumor of the same animal (FIG. 4 E, left panel), significantly larger than random samplings of the same numbers of sgRNAs (FIG. 4 E, right panel). These data indicate that mutants with preferential ability to proliferate in late primary tumors are more likely to dominate the metastases.

Figure 4D:
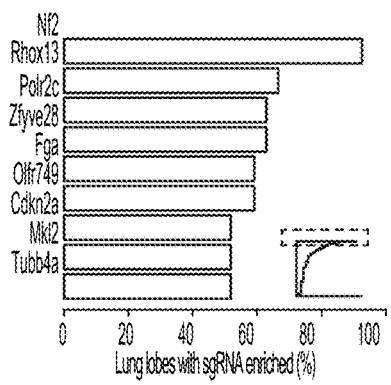
Figure 4E:
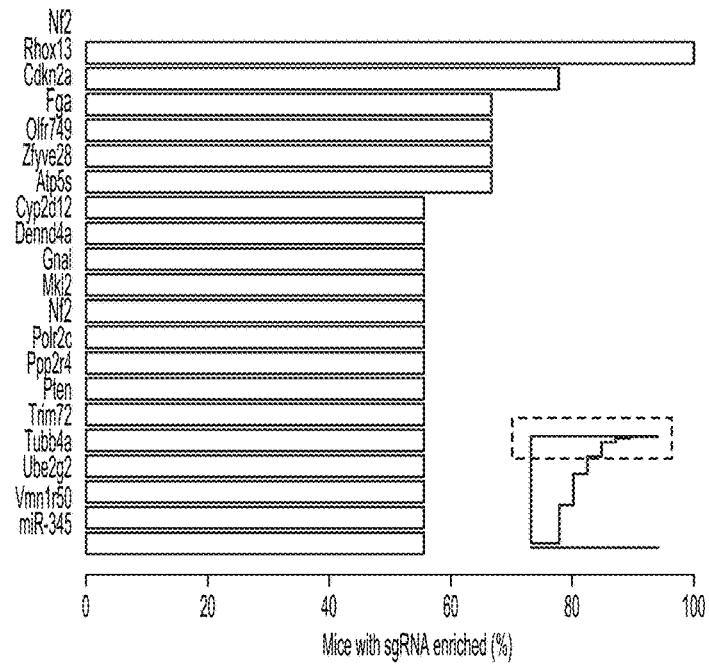
Figure 4F:
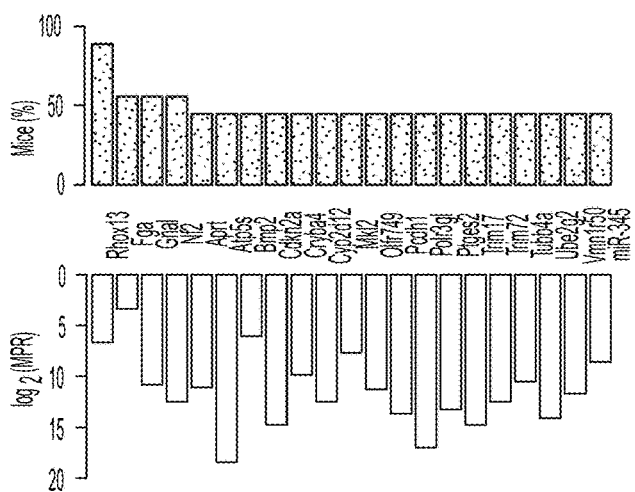
Figure 11B:
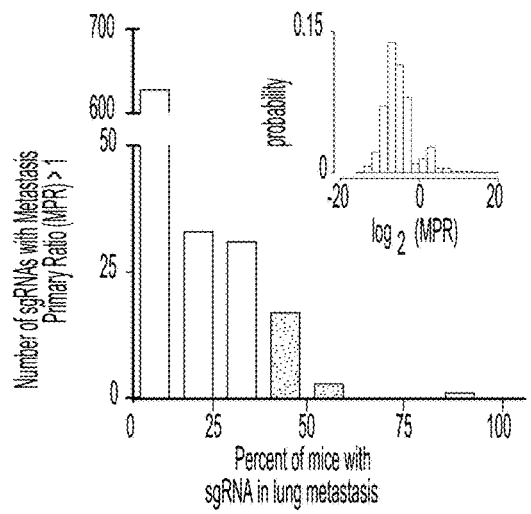
Figure 11C:
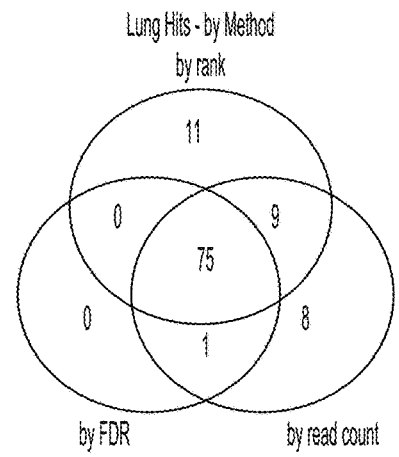
Figure 11D:
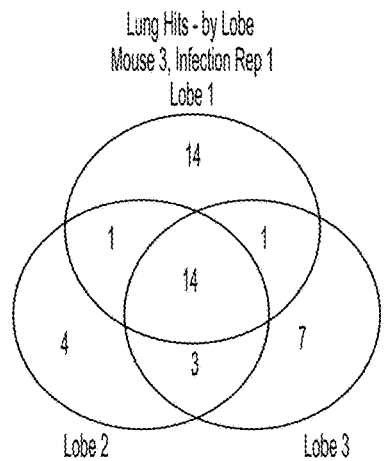
Figure 11E:
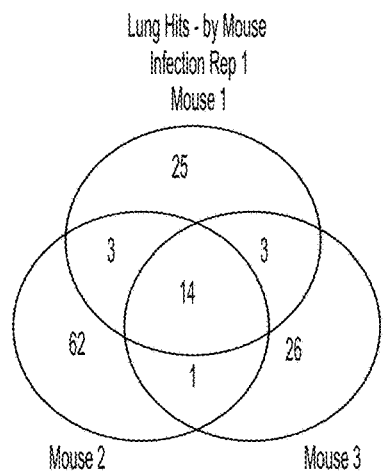

The three methods (by threshold, by rank, or by FDR) of finding enriched sgRNAs in the lung metastases yield similar results, overlapping with each other by 87~99% in pairwise comparison (FIG. 11B). Taking the analysis by FDR for example, the detected sgRNAs in different lobes of the same animal overlap with each other by more than 40% (FIG. 11C), while different animals show substantial variability (overlap by 10~20%) (FIG. 11D). The detected sgRNAs in different biological/infection replicate experiments, with a union set of all animals pooled from each replicate, overlap with each other by more than 55% (FIG. 11E), suggesting pooling animals in the same experiment facilitate capturing the identification of shared strong hits. Overall, a small fraction of sgRNAs was found enriched multiple times (in one or more lobes, or in one or more animals) (FIG. 4C-4D). These include sgRNAs targeting Nf2, Pten, Tripartite motif-containing protein 72 (Trim72), Bid, Cyclin-dependent kinase inhibitor 2a (Cdkn2a), Zinc Finger, FYVE Domain Containing 28 (Zfyve28), Reproductive homeobox 13 (Rhox13), BRISC and BRCA1 A complex member 1 (Babam1), as well as microRNA genes miR-152 and miR-345. Intriguingly, a few sgRNAs targeting the Pol II subunits and olfactory receptor are also enriched in the lung, likely due to unknown or off-target effects. In four genes, Nf2, Pten, Trim72, and Zfyve28, two independent sgRNAs targeting different regions of the same gene were observed as enriched (FIG. 4H). One of the Zfyve28 sgRNA, however, is enriched in only one animal; wherewa Nf2, Pten or Trim72 all have two sgRNAs enriched in multiple animals. These three genes, several representative genes with one sgRNA with high enrichment in more than one sample (Cdkn2a, Fga, Cryba4), and the top two scoring microRNAs (miR-152 and miR-345) were chosen to assay individually for primary tumor and metastases formation. The most frequently enriched sgRNA is an sgRNA targeting Nf2, appearing in 90% of the lobes (FIG. 4D), or 100% of the animals (FIG. 4E), suggesting Nf2 loss-of-function mutants are the best competitors in the library for metastases in this setting.

Figure 11F:
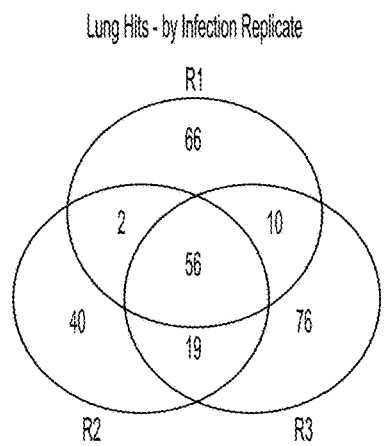

For most sgRNAs detected in metastases, the relative abundance in metastasis is lower than in primary tumor of the same mouse, with a metastasis-primary ratio (MPR) less than 1 (FIG. 11F), likely due to more skewed distributions of sgRNAs in the metastasis compared to those in the late primary tumors. A small subset of sgRNAs, however, are more abundant in metastasis than in primary tumor (MPR>1) in multiple mice, such as sgRNAs targeting Nf2, Trim72, Prostaglandin E Synthase 2 (Ptgse2) or Ubiquitin-conjugating enzyme E2G 2 (Ube2g2) (FIG. 4F, FIG. 11F). The strongest hits (i.e. genes targeted by the most abundant sgRNAs, by multiple enriched sgRNAs, and/or by occurrence in multiple animals) in late primary tumor also partly overlap with those in the lung metastases (described later in text) (Compare FIGS. 3 and 4).

Figure 4G:
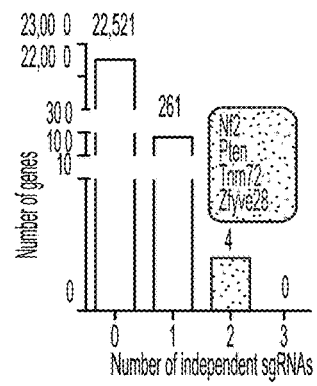
Figure 4H:
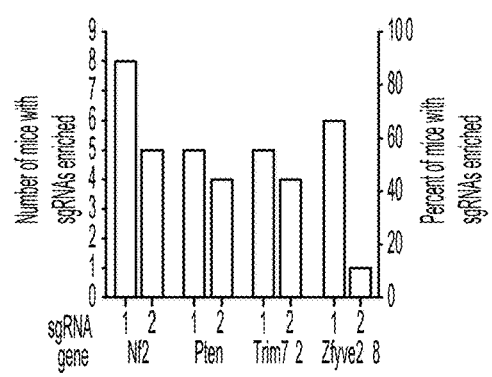

In four genes, Nf2, Pten, Trim72, and Zfyve28, two independent sgRNAs targeting different regions of the same gene were enriched in lung metastases (FIG. 4G). One of the Zfyve28-targeting sgRNAs, however, is enriched in only one animal; whereas Nf2, Pten or Trim72 all have two sgRNAs enriched in multiple animals (FIG. 4H). These three genes, several representative genes with one sgRNA having high enrichment in more than one mice (Cdkn2a, Fga, Cryba4), and the top two scoring microRNAs (miR-152 and miR-345) were chosen to assay individually for primary tumor growth and metastases formation.

Validation of Genes Using Single sgRNAs

Figure 5B:
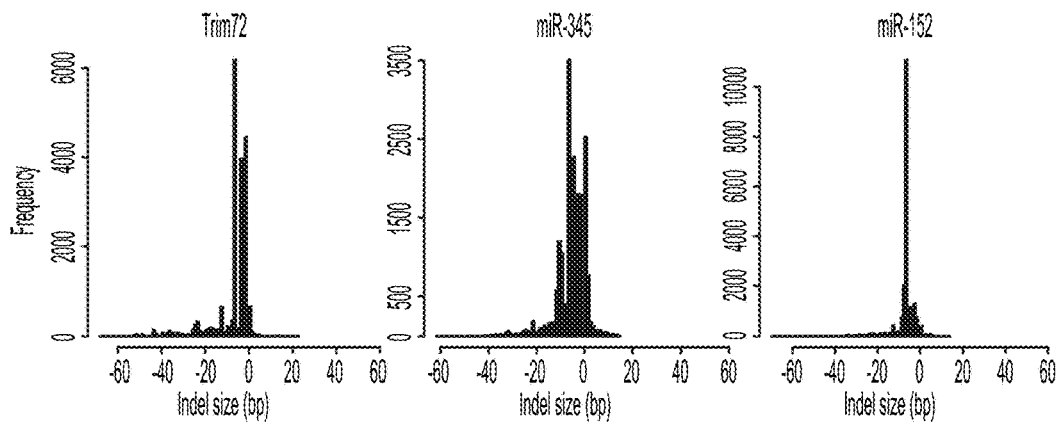
Figure 13A:
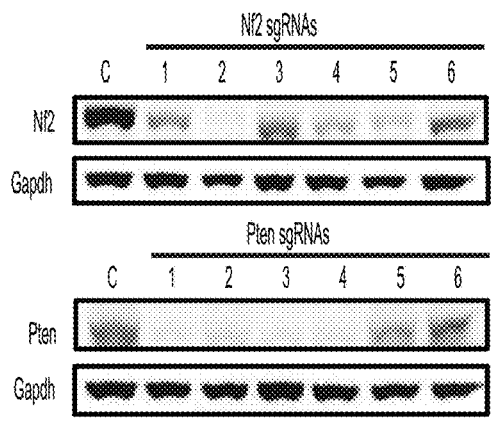

For these targets (Nf2, Pten, Trim72, Cdkn2a, Fga, Cryba4, miR-152 and miR-345), Applicants cloned multiple sgRNAs targeting each of them into the same lentiviral vector (lentiGuid-Puro), and transduced them into the Cas9-GFP KPD cell line (FIG. 5A). As expected, these sgRNAs generated a broad distribution of NHEJ-mediated indels at the target site when examined three days post-transduction, with a bias toward deletions (FIG. 5B). For protein coding genes, the majority (>80%) of indels are out-of-frame, which potentially disrupt the protein functions. SgRNAs targeting either the loop or mature 5p- or 3p-microRNAs for miR-152 and miR-345 generated deletions (average size=~7 bp), overlapping with the loop or mature micro-RNA sequences in the hairpins, which are structures required for the maturation of microRNAs. For protein-coding genes where specific antibodies are available (Nf2 and Pten), the majority of the protein products were significantly reduced one week after lentiviral sgRNA infection (FIG. 13A).

Figure 5C:
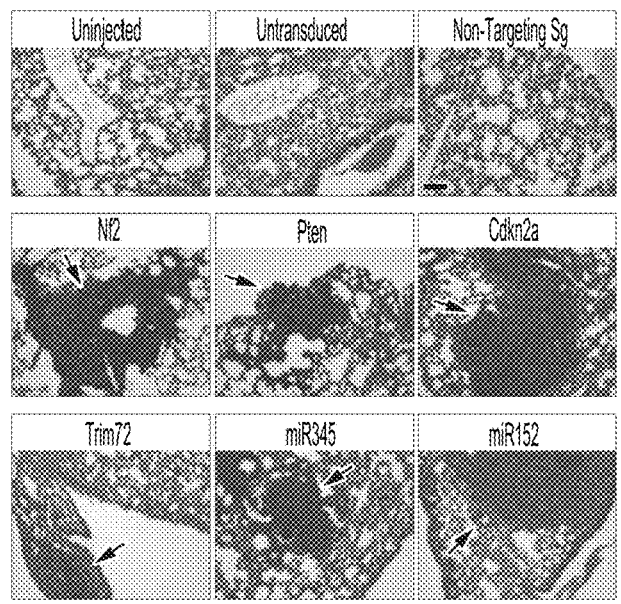
Figure 5D:
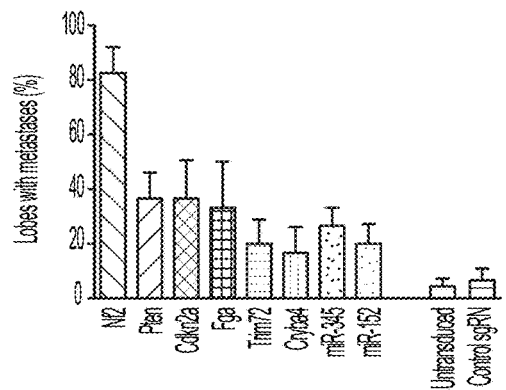

When these single-sgRNA-transduced cells were transplanted into the flanks of immunocompromised mice, they all formed tumors in situ. With two animals injected per sgRNA and three sgRNAs per gene, all genes tested showed increased lung metastases formation compared to controls (untransduced and non-targeting sgRNAs), with the most significant ones being Nf2, Pten and Cdkn2a (One tailed t test, $p<0.05$) (FIG. 5C-5D). Trim72 and Fga also have effects but were marginally significant (One tailed t test, $p=0.056$). Cryba4 is not statistically different from controls ($p=0.11$). Both of the microRNAs targeted significantly increased metastasis ($p<0.05$). These data suggest that loss-of-function mutations in any of Nf2, Pten, Cdkn2a, Trim72, Fga, miR345 or miR-152 alone are sufficient to accelerate the rate of metastasis formation in this genetic background. Among these genes Nf2, has the strongest effect, with metastases detected in all mice and in over 80% of the lobes examined.

Figure 13B:
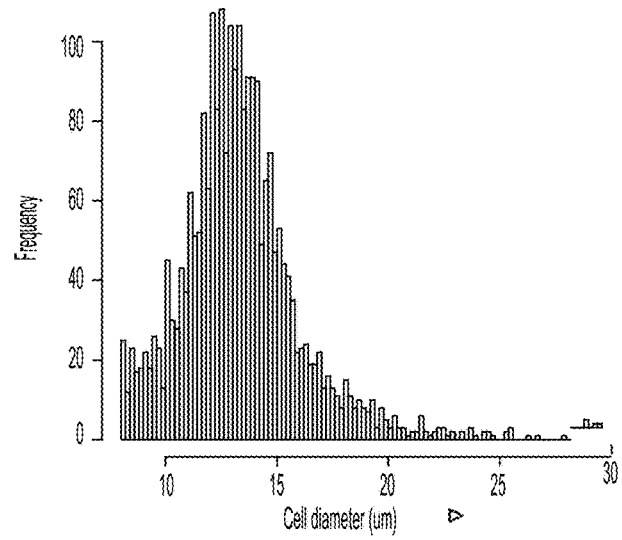
Figure 13C:
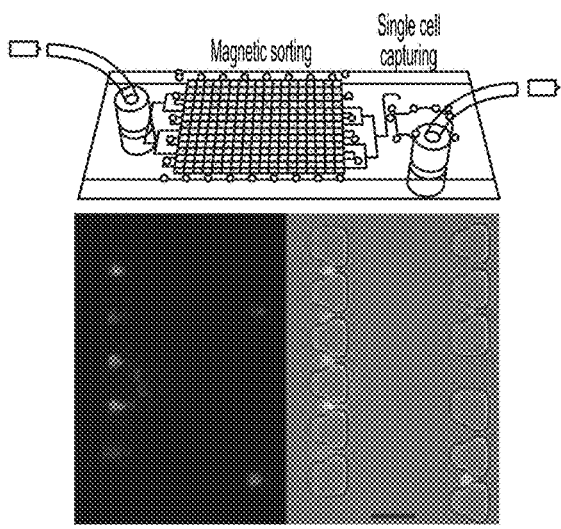
Figure 13D:
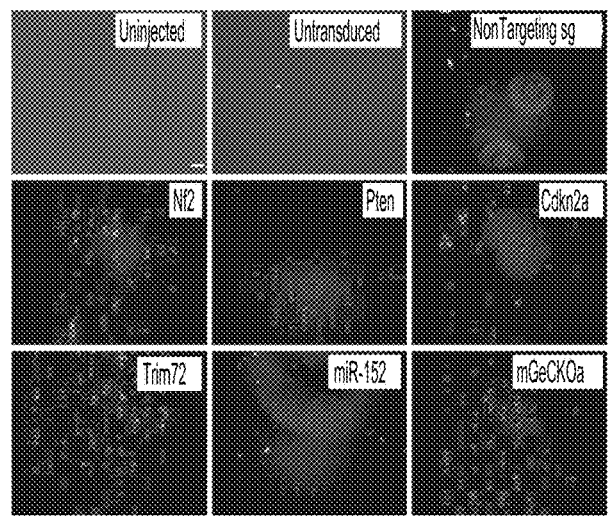
Figure 13E:
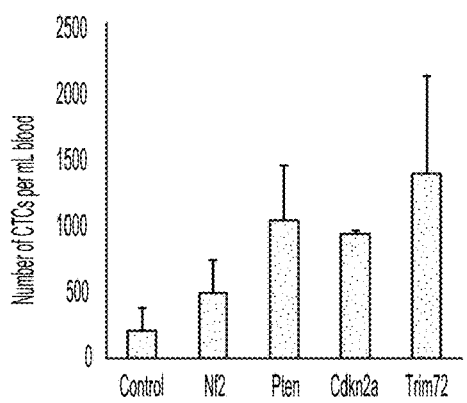
Figure 13F:
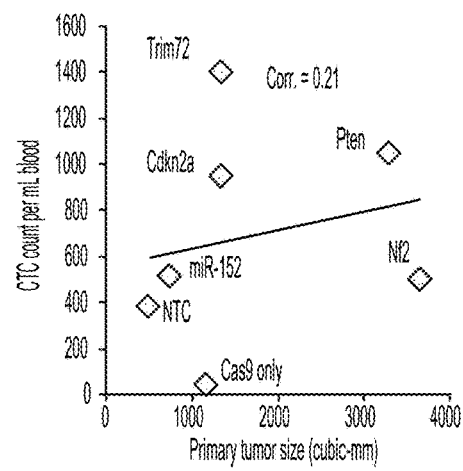

To examine if primary tumor shedding could explain which gene targets were more likely to form lung metastases, Applicants analyzed blood samples for the presence of circulating tumor cells (CTCs). A microfluidic device was generated based on the physical size of the Cas9-GFP KPD cells to capture CTCs (FIG. 13B-C). CTC capture was performed with terminal peripheral blood samples from animals injected with sg-Nf2, sg-Pten, sg-Trim72, sg-Cdkn2a, sg-miR-152 and control cells (FIG. 13C). Animals transplanted with either sg-Nf2, sg-Pten, sg-Trim72, sg-Cdkn2a or sg-miR-152 cells had a higher concentration of CTCs as compared to controls (FIG. 13D), consistent with the higher rate of lung metastasis formation. The absolute number of CTCs captured by this device, however, is only weakly correlated with either primary tumor size or metastasis formation rate in a gene-by-gene analysis (FIG. 13E-F), suggesting CTC count alone can not explain all of the variation in metastasis under this setting, as metastasis is also influenced by multiple other factors, such as extravasation or clonal growth at destination site. This is not surprising since metastasis is also influenced by multiple other factors such as extravasation or clonal growth at destination site.

Figure 5E:
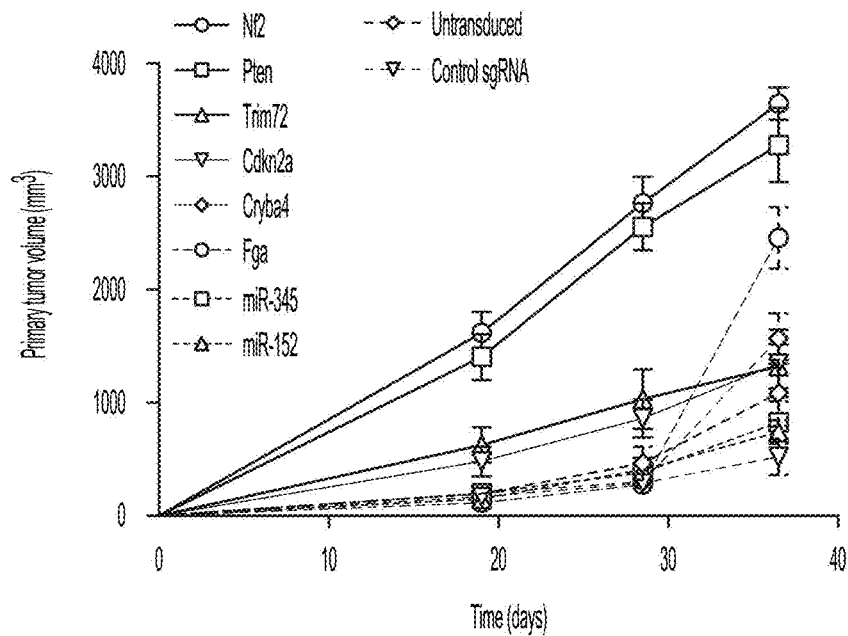
Figure 5F:
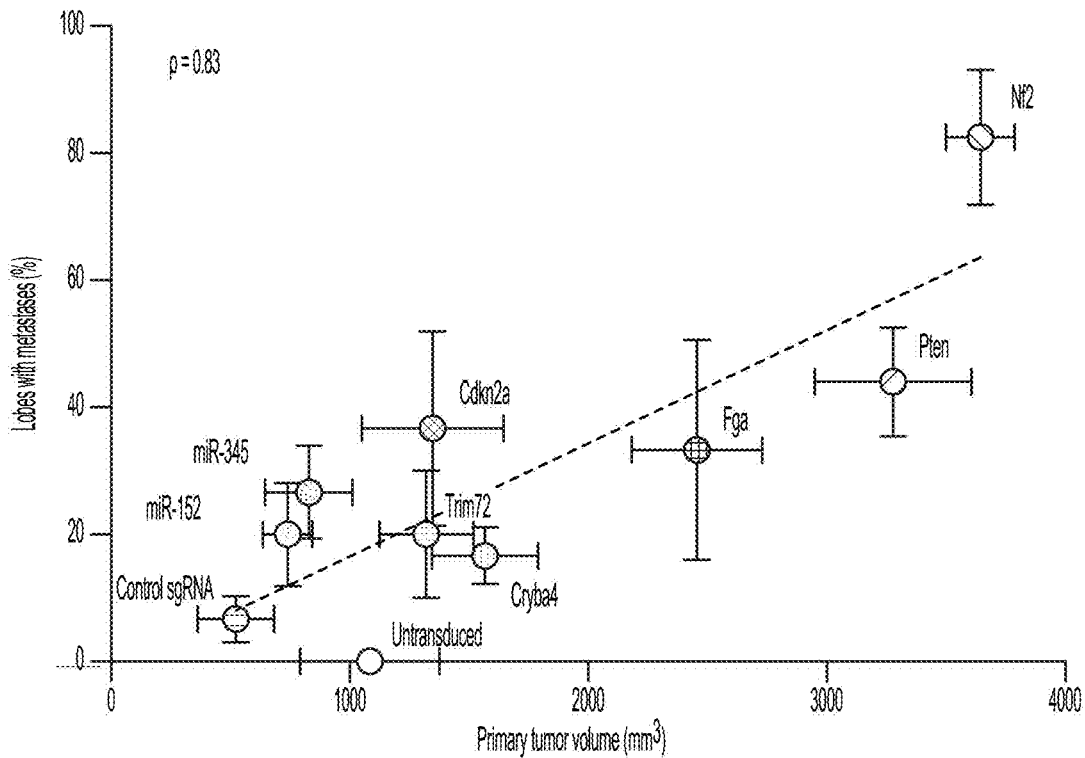

Most genes targeted with single sgRNAs also showed effects in accelerating primary tumor growth compared to controls (FIG. 5E). Nf2 and Pten loss-of-function dramatically enhanced tumor growth (KS test, $p<0.001$) (FIG. 5E); Cdkn2a-, Trim72- and Fga-targeting sgRNAs slightly accelerate primary tumor growth (KS test, $p=0.003-0.01$); Cryba4 has a marginal effect (KS test, $p=0.08$); neither miR-152- nor miR-345-targeting sgRNAs promote primary tumor growth (KS test, $p>0.1$). Overall, for the targets Applicants examined using individual sgRNAs, the rate of development of lung metastases strongly correlates with the terminal volume of the late primary tumor (or average primary tumor growth rate)(correlation, $\rho=0.83$, F-test, $p<0.01$) (FIG. 5F), indicating at a single gene level that mutant cells with a stronger ability to promote primary tumor growth generate metastases faster.

Competitive Dynamics of Top Hits in a Targeted Sub-Library

To better understand the relative metastatic potential of multiple genes from the genome-wide screen, Applicants designed a targeted pooled screen with a much smaller library. This small library (termed validation pool hereafter) contains 624 sgRNAs targeting 53 genes (10 sgRNAs per gene for most genes) plus 100 non-targeting sgRNAs. Applicants also created a size-matched library containing 624 non-targeting sgRNAs (termed control pool hereafter)(FIG. 6A). Lentiviruses from these two pools were used to transduce the Cas9-GFP KPD cells, which were then cultured in vitro for one week, and then transplanted into Nu/Nu mice (FIG. 6A). Both validation pool and control pool transduced cells induced primary tumor growth at a similar rate (FIG. 6B). However, the validation pool had a dramatically increased the rate of lung metastases formation (FIG. 6C).

Figure 14H:
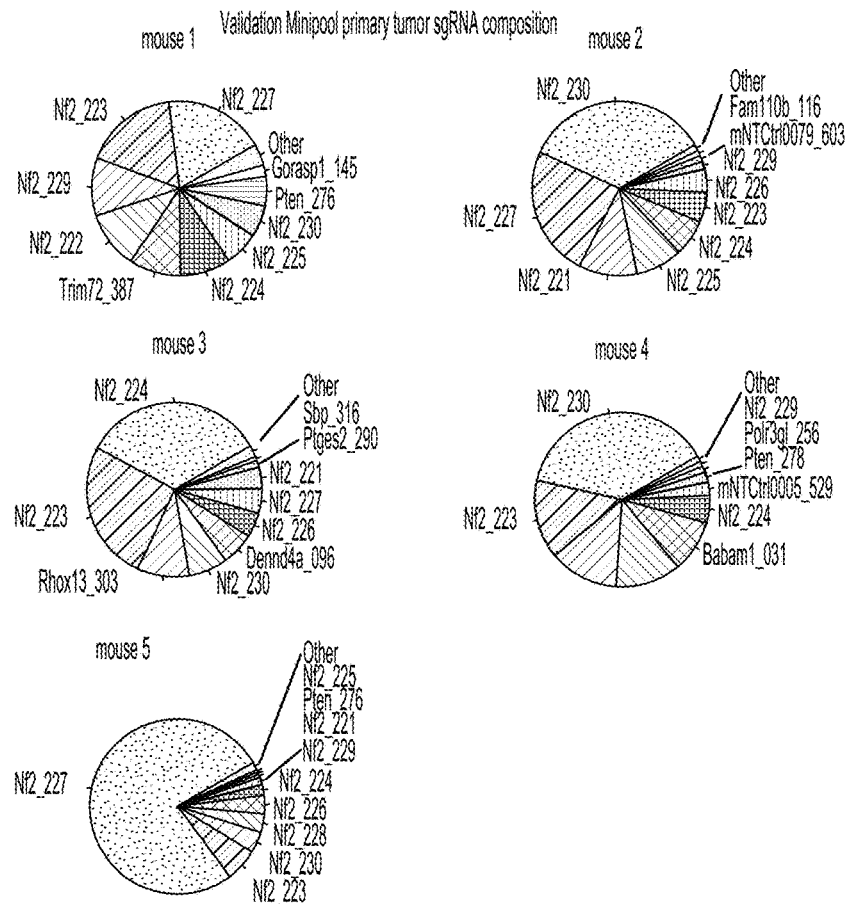
Figure 14I:
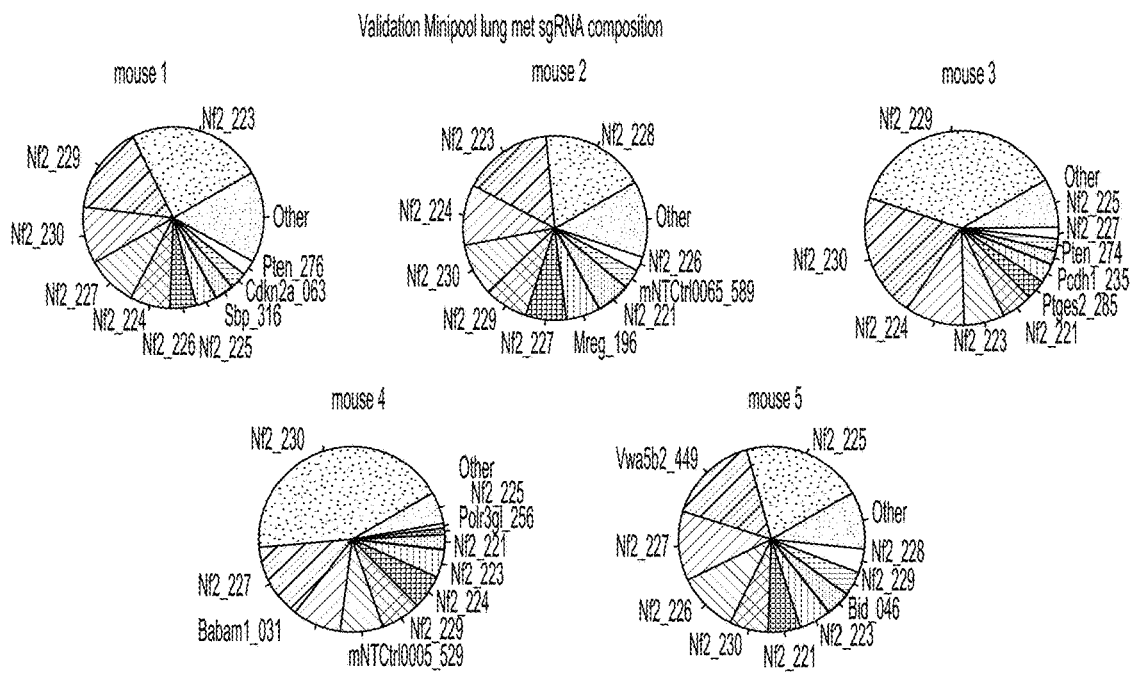

Applicants sequenced the validation pool plasmid library, the transduced cells pre-transplantation, as well as the late stage primary tumors and whole lungs of the animals at 5 weeks post-transplantation. The sgRNA representations correlate strongly between technical replicates of the transduced cell pool, late primary tumor and/or lung metastases (correlation, p=0.55, F-test, p<0.01, n=5) (FIG. 14B). The sgRNA distribution in the cell sample strongly correlated with the plasmid (correlation, p=0.91) (FIG. 14B, 14D). Almost all (99.4%) sgRNAs were recovered in the plasmid and the cell population (FIG. 14C). The sgRNA distributions in lung metastases clustered with each other and the primary tumors, away from plasmid or cell (FIG. 14D). The late primary tumors retained less than half of the sgRNAs, while the metastases in the whole lung only retained a small fraction (2~7%) of all sgRNAs (FIG. 14C). Similar to the case of full library, in the minipool plasmid and the cell samples showed tight distributions of sgRNAs, whereas the late primary tumors and lung metastases contained a largely bi-modal distribution, with the majority being zero and a small fraction of sgRNAs spanning a large range of non-zero read counts (FIG. 6D). Intriguingly, two animals retained relatively high sgRNA diversity in primary tumors (FIG. 6D), likely due to dormant or slowly proliferating cells that remained in low numbers during tumor growth. Similar to the genome-wide screen, there is a large shift in the distribution of sgRNA read counts in the tumor and lung metastases (Kolmogorov-Smirnov (KS) test, $p<10^{-15}$ for pairwise comparisons between the cell, primary tumor and lung metastases, p=0.02 between plasmid and cell) (FIG. 6E). As in the genome-wide library, the sgRNAs detected in the late primary tumors or the lungs of five different mice significantly overlap with each other (FIG. 14E-14F).

Figure 7A:
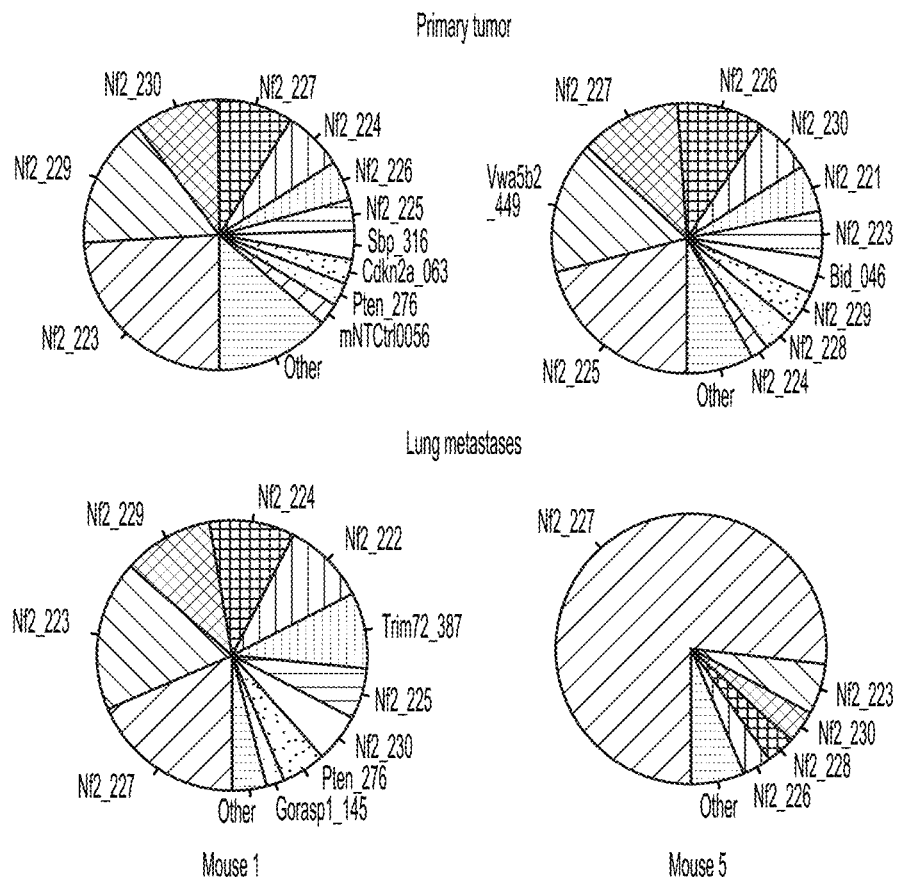
Figure 7B:
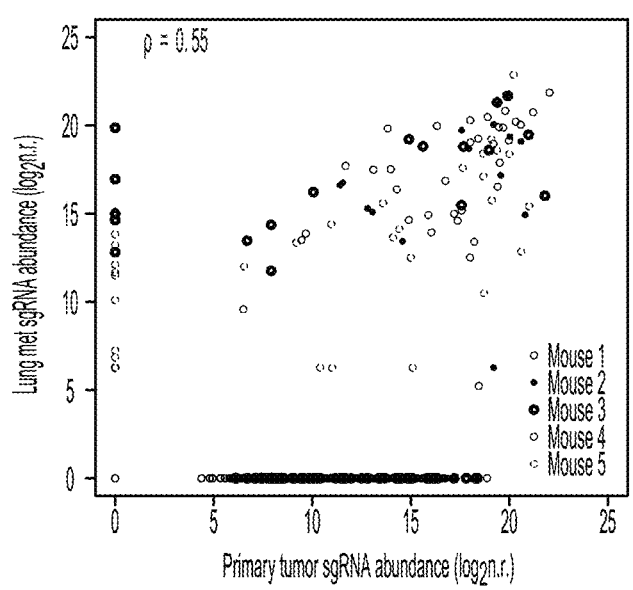
Figure 7C:
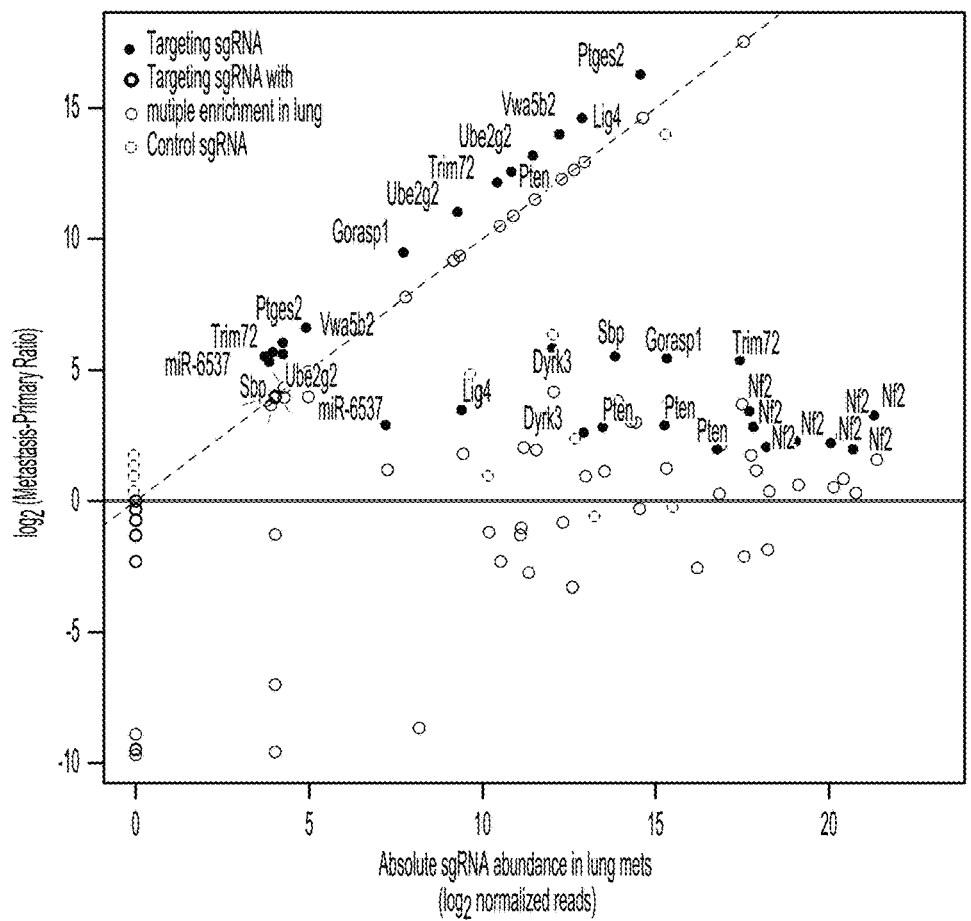
Figure 7D:
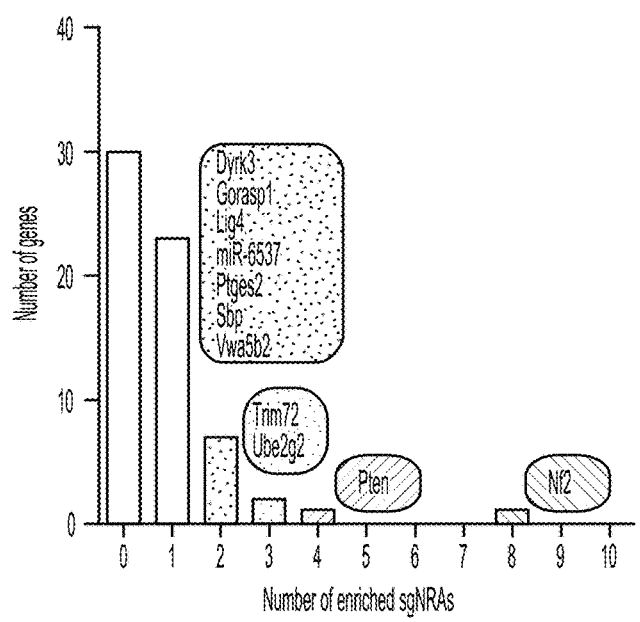

The late stage primary tumors and lung metastases with the validation pool are dominated by a few sgRNAs (FIG. 7A, FIG. 14G-I), suggesting these sgRNAs outcompete the others relatively during tumor growth and metastasis. The gene with the strongest effect is again Nf2, with all ten sgRNAs significantly enriched in both late primary tumors and lung metastases in one or more mice, accounting for 71-98% of the total reads in each mouse (FIG. 7A, FIG. 14G-14I), indicating that Nf2 loss-of-function is the main driver of tumor growth and metastases in this experimental setting. In this small library, the sgRNA read counts are correlated between late stage primary tumors and lung metastases (correlation, p=0.6 on average, F test, p<0.001, n=5) (FIG. 7B). The late stage primary tumors and lung metastases have dozens of sgRNAs targeting genes at moderate to high frequencies (FIG. 7B-7C). Several genes have multiple independent sgRNAs that are enriched in the lung over the primary tumor (MPR>1), such as Nf2 (8 sgRNAs), Pten (4 sgRNAs), Trim72 (3 sgRNAs), Ube2g2 (3 sgRNAs), Ptges2 (2 sgRNAs) and ATP-dependent DNA Ligase IV (Lig4) (2 sgRNAs) (FIG. 7C). Two Cdkn2a sgRNAs were present in both late primary tumors and lung metastases in two mice, but with MPR<1. Fga-, Cryba4-, miR-152- or miR-345-targeting sgRNAs were not found at high frequency in either late primary tumors or lung metastases, which suggests that they are outcompeted by other loss-of-function mutations (such as Nf2), also in agreement with the relatively reduced metastases formation in single sgRNA validation. These results further validated several of the top hits from the primary screen and, in contrast to screen validation using single sgRNAs, provides a higher-throughput method for validating the top candidates. This validation pool also furthers our understanding of the dynamics of multiple competing mutants within a heterogeneous tumor, and indicates that mutants with strong pro-growth effects tend to enhance metastases in this model.

Further Validation with a Tiny Pool

Figure 16A:
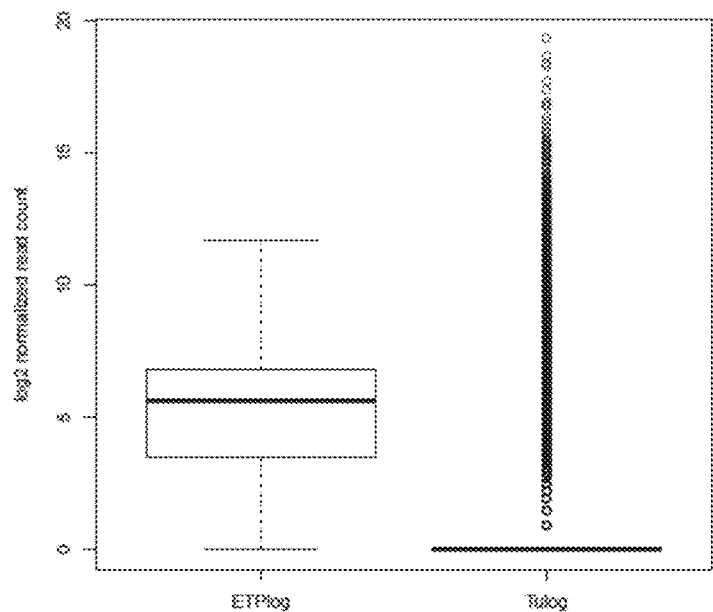
FIG. 16A-16B: Tiny pool sgRNA representation in cell pool, late tumor and lung metastasis.
Figure 16B:
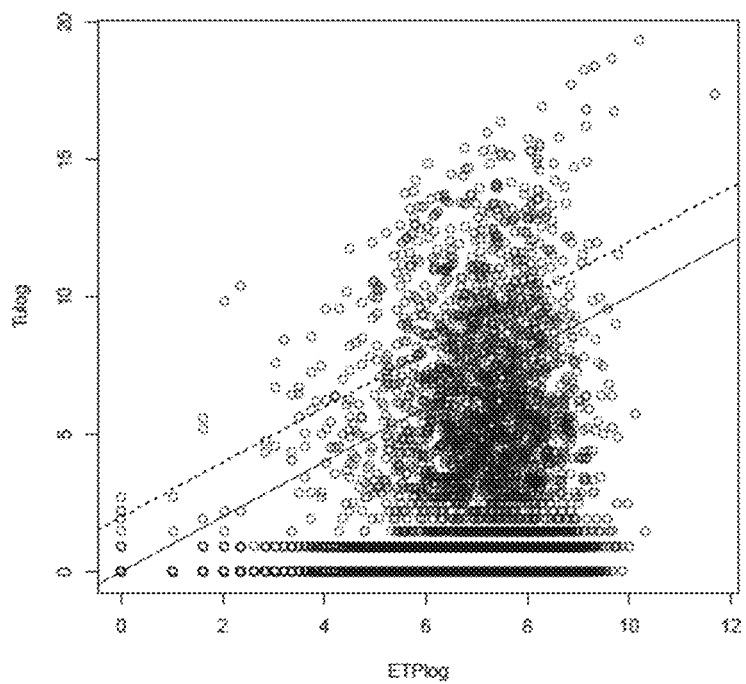

Applicants designed a further targeted pooled screen with an even smaller library. This very small library (termed tiny pool hereafter) contains 23 sgRNAs targeting 6 genes (3 sgRNAs per gene) and 4 non-targeting sgRNAs (Ctrl) (FIG. 16). The six selected genes were Nf2, Pten, Trim72, Cdkn2a, miR-152, and miR-345. Lentiviruses from these pools were used to transduce the Cas9-GFP KPD cells, which were then cultured in vitro for one week, and then transplanted into Nu/Nu mice. Both tiny pool and control pool transduced cells induced primary tumor growth at a similar rate, while non-transduced cells did not induce tumor growth (FIG. 16B). This targeted subpool strategy provides a higher-throughput method for validating the top candidates and assaying competing mutants in parallel.

Generation of a Xenograft Model

The human cell line H23 was transduced with a lentivirus carrying a Cas9 transgene fused to a nuclear localization sequence (NLS) a triple FLAG epitope (3×FLAG), and a green fluorescent protein (GFP). The transduction was performed at a very low multiplicity of infection (MOI<0.01) to ensure that most cells receive only one lentiviral transgene. Clonal cell lines expressing Cas9-GFP were established. A clonal Cas9-H23 cell line was selected for introduction of the genome wide knockout library.

A human genome-scale CRISPR knockout library hGeCKOa was made as described in Shalem et al. 2014 and used to transduce the human Cas9-H23 cell line as described above.

Human H23 cells infected with NLS-Cas9-GFP vector only or NLS-Cas9-GFP and hGeCKO library were injected subcutaneously into the right side flank of Nu/Nu mice at $3 \times 10^7$ cells per mouse.

Figure 17:
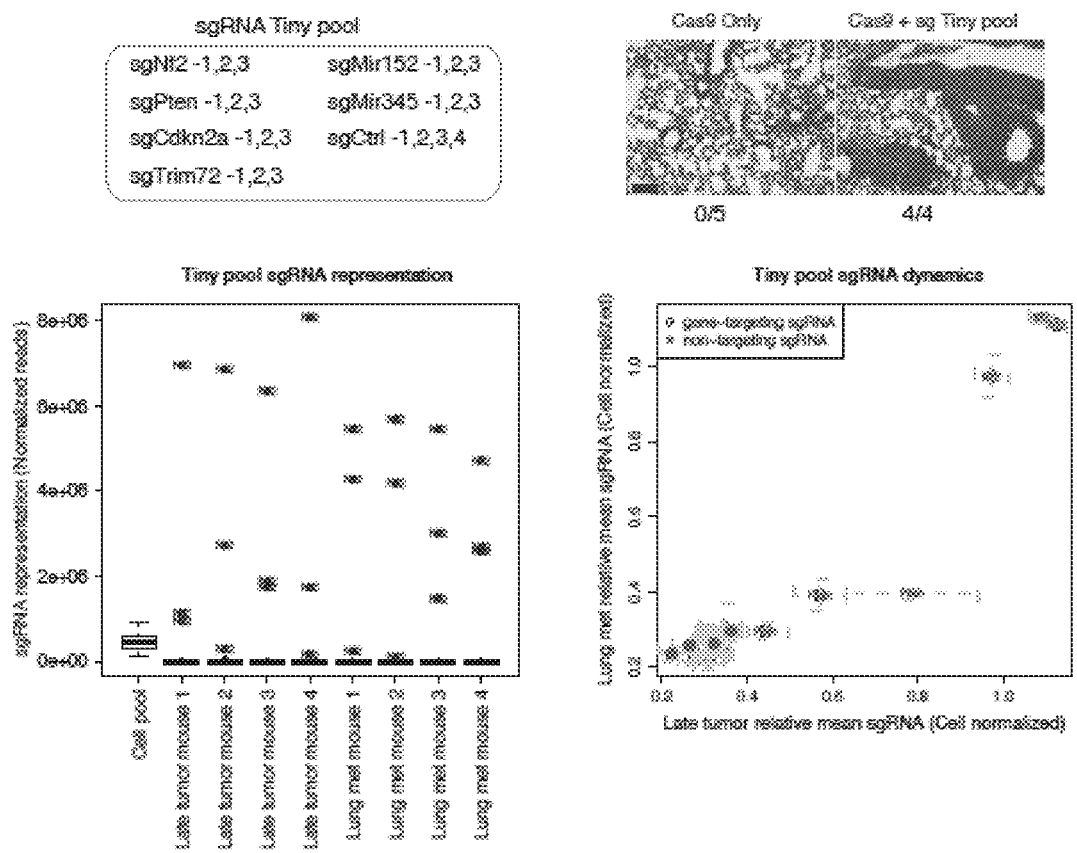
FIG. 17: Boxplot of the sgRNA representation in the human xenograft model. Tu=human cell line H23 mouse xenograft sgRNA representation, ETP=human cell line H23 in vitro culture sgRNA representation, log=log 2 normalized reads.

The in vitro culture sgRNA and mouse xenograft sgRNA representation are provided in FIG. 17.

The invention is further described by the following numbered paragraphs:

1. A method for modeling tumor formation and/or tumor evolution comprising the steps of:
   (a) providing an isolated Cas transgenic eukaryotic cell expressing Cas or capable of inducibly and/or conditionally expressing Cas;
   (b) introducing in said Cas transgenic eukaryotic cell one or more RNA capable of guiding Cas to one or more genetic target locus of a eukaryote; or
   introducing in said Cas transgenic eukaryotic cell one or more polynucleotide encoding one or more RNA capable of guiding Cas to one or more genetic target locus of a eukaryote;
   (c) introducing said Cas transgenic eukaryotic cell after step (b) in a non-human eukaryote;
   (d) analyzing tumor formation and/or tumor evolution in said non-human eukaryote.
2. The method according to numbered paragraph 1, wherein step (c) comprises introducing a plurality of Cas transgenic eukaryotic cells in a non-human eukaryote, each cell of said plurality of Cas transgenic eukaryotic cells comprising a different RNA capable of guiding Cas to a genetic target locus of said eukaryote; or
   each cell of said plurality of Cas transgenic eukaryotic cells comprising a different polynucleotide encoding an RNA capable of guiding Cas to a genetic target locus of said eukaryote.
3. The method according to any of numbered paragraphs 1 to 2, wherein step (d) comprises identifying one or more genes which are involved in tumor formation and/or evolution.

4. The method according to any of numbered paragraphs 1 to 3, wherein step (d) comprises analyzing tumor metastasis.
5. The method according to any of numbered paragraphs 1 to 4, wherein step (d) comprises analyzing gene expression.
6. The method according to any of numbered paragraphs 1 to 5, wherein step (d) comprises analyzing gene expression in said tumor.
7. The method according to any of numbered paragraphs 1 to 5, wherein step (d) comprises identifying one or more of said RNA of step (b) in said tumor.
8. The method according to any of numbered paragraphs 4 to 5, wherein step (d) comprises analyzing gene expression in said tumor metastasis.
9. The method according to any of numbered paragraphs 4 to 5, wherein step (d) comprises identifying one or more of said RNA of step (b) in said tumor metastasis.
10. A method for identifying genes which are involved in tumor formation and/or tumor metastasis, comprising the steps of:
(a) providing an isolated Cas transgenic eukaryotic cell expressing Cas or capable of inducibly and/or conditionally expressing Cas;
(b) introducing in said Cas transgenic eukaryotic cell one or more RNA capable of guiding Cas to one or more genetic target locus of a eukaryote; or
introducing in said Cas transgenic eukaryotic cell one or more polynucleotide encoding one or more RNA capable of guiding Cas to one or more genetic target locus of a eukaryote;
(c) introducing a plurality of said Cas transgenic eukaryotic cell after step (b) in a non-human eukaryote, each cell of said plurality of Cas transgenic eukaryotic cells comprising a different RNA capable of guiding Cas to a genetic target locus, or each cell of said plurality of Cas transgenic eukaryotic cells comprising a different polynucleotide encoding an RNA capable of guiding Cas to a genetic target locus;
(d) identifying genes which are involved in tumor formation and/or tumor metastasis in said non-human eukaryote based on the identification in said tumor or tumor metastasis of one or more of said RNA capable of guiding Cas to one or more genetic target locus.
11. The method according to any of numbered paragraphs 3 to 10, wherein said genes involved in tumor formation, tumor evolution, and/or tumor metastasis are tumor suppressor genes and/or metastasis suppressor genes.
12. The method according to any of numbered paragraphs 1 to 11, wherein said method after step (b) comprises introducing one or more genomic mutations in said Cas transgenic eukaryotic cell.
13. The method according to any of numbered paragraphs 1 to 12, wherein said RNA capable of guiding Cas comprises CRISPR RNA and transactivating (tracr) RNA.
14. The method according to any of numbered paragraphs 1 to 13, wherein said RNA capable of guiding Cas comprises a single guide (sg) RNA.
15. The method according to any of numbered paragraphs 1 to 14, wherein said RNA capable of guiding Cas is introduced in said Cas transgenic eukaryotic cell by means of transduction.
16. The method according to any of numbered paragraphs 1 to 15, wherein said RNA capable of guiding Cas is introduced in said Cas transgenic eukaryotic cell by means of lentiviral transduction.
17. The method according to any of numbered paragraphs 1 to 16, wherein said polynucleotide encoding one or more RNA capable of guiding Cas is capable of constitutively expressing said RNA or alternatively inducibly and/or conditionally expressing said RNA.
18. The method according to any of numbered paragraphs 1 to 17, wherein said Cas transgenic eukaryotic cell of step (a) is a tumor cell.
19. The method according to any of numbered paragraphs 1 to 18, wherein said Cas transgenic eukaryotic cell of step (a) is a non-metastasizing tumor cell.
20. The method according to any of numbered paragraphs 1 to 18, wherein said Cas transgenic eukaryotic cell of step (a) is characterized by oncogenic expression ofKras (KrasG12D), homozygousp53 loss (p53−/−), and/or heterozygous Dicer1 loss (Dicer+/−), preferably all.
21. The method according to any of numbered paragraphs 1 to 20, wherein said Cas comprises a type II Cas.
22. The method according to any of numbered paragraphs 1 to 21, wherein said Cas comprises Cas9.
23. The method according to any of numbered paragraphs 1 to 22, wherein said Cas comprises a Cas originating from *Streptococcus pyogenes, Streptococcus* thermophiles, or *Staphylococcus aureus*.
24. The method according to any of numbered paragraphs 1 to 23, wherein said Cas comprises a mutated Cas having an altered catalytic activity.
25. The method according to any of numbered paragraphs 1 to 24, wherein said Cas comprises a catalytically inactive Cas.
26. The method according to any of numbered paragraphs 1 to 25, wherein said Cas is fused to an enzyme which modifies genomic DNA or genomic DNA architecture.
27. The method according to any of numbered paragraphs 1 to 26, wherein said Cas is fused to a polypeptide which alters gene transcription.
28. The method according to any of numbered paragraphs 1 to 27, wherein said Cas transgenic eukaryotic cell is a cell from an animal.
29. The method according to any of numbered paragraphs 1 to 28, wherein said Cas transgenic eukaryotic cell is a cell from a eukaryote selected from the group consisting of mammal, primate, rodent, mouse, rat, rabbit, canine, dog, cow, bovine, sheep, ovine, goat, pig, fowl, poultry, chicken, fish, insect, and arthropod.
30. The method according to any of numbered paragraphs 1 to 29, wherein said Cas transgenic eukaryotic cell is a mammalian cell, preferably a mouse cell.
31. The method according to any of numbered paragraphs 1 to 30, wherein said eukaryote in step (c) is an animal, preferably a mammal.
32. The method according to any of numbered paragraphs 1 to 31, wherein said eukaryote in step (c) is an immunocompromised animal, preferably an immunocompromised mammal.
33. The method according to any of numbered paragraphs 1 to 32, wherein said eukaryote in step (c) is selected from mammal, primate, rodent, mouse, rat, rabbit, canine, dog, cow, bovine, sheep, ovine, goat, pig, fowl, poultry, chicken, fish, insect, and arthropod.
34. The method according to any of numbered paragraphs 1 to 33, wherein said eukaryote in step (c) is a mouse.

35. The method according to any of numbered paragraphs 1 to 34, wherein step (c) comprises introducing said cells subcutaneously.

36. The method according to any of numbered paragraphs 1 to 35, wherein said tumor is selected from lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdoid tumor, thyroid cancer, and urinary bladder cancer.

37. A tumor sample or a tumor metastasis sample isolated from said non-human eukaryote after introduction of said Cas transgenic eukaryotic cell of step (c) in numbered paragraph 1.

38. The tumor sample or the tumor metastasis sample according to numbered paragraph 37, wherein said tumor is selected from the group consisting of lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdoid tumor, thyroid cancer, and urinary bladder cancer.

39. A cell isolated from said tumor sample or said tumor metastasis sample according to any of numbered paragraphs 37 to 38.

40. A cell line obtained or obtainable from said tumor sample or said tumor metastasis sample according to any of numbered paragraphs 37 to 38.

41. A cell line obtained or obtainable from said cell of numbered paragraph 39.

42. A method for generating a non-human eukaryote model for tumor formation and/or tumor evolution, comprising the steps of:
(a) providing an isolated Cas transgenic eukaryotic cell expressing Cas or capable of inducibly and/or conditionally expressing Cas;
(b) introducing in said Cas transgenic eukaryotic cell one or more RNA capable of guiding Cas to one or more genetic target locus of a eukaryote; or
introducing in said Cas transgenic eukaryotic cell one or more polynucleotide encoding one or more RNA capable of guiding Cas to one or more genetic target locus of a eukaryote;
(c) introducing a plurality of said Cas transgenic eukaryotic cell after step (b) in a non-human eukaryote, each cell of said plurality of Cas transgenic eukaryotic cells comprising a different RNA capable of guiding Cas to a genetic target locus, or each cell of said plurality of Cas transgenic eukaryotic cells comprising a different polynucleotide encoding an RNA capable of guiding Cas to a genetic target locus.

43. A method for generating a non-human eukaryote model for identifying genes involved in formation and/or tumor evolution, comprising the steps of:
(a) providing an isolated Cas transgenic eukaryotic cell expressing Cas or capable of inducibly and/or conditionally expressing Cas;
(b) introducing in said Cas transgenic eukaryotic cell one or more RNA capable of guiding Cas to one or more genetic target locus of a eukaryote; or introducing in said Cas transgenic eukaryotic cell one or more polynucleotide encoding one or more RNA capable of guiding Cas to one or more genetic target locus of a eukaryote;
(c) introducing a plurality of said Cas transgenic eukaryotic cell after step (b) in a non-human eukaryote, each cell of said plurality of Cas transgenic eukaryotic cells comprising a different RNA capable of guiding Cas to a genetic target locus, or each cell of said plurality of Cas transgenic eukaryotic cells comprising a different polynucleotide encoding an RNA capable of guiding Cas to a genetic target locus.

44. A non-human eukaryote obtained or obtainable by the method of numbered paragraph 42 or 43.

45. The non-human eukaryote according to numbered paragraph 44, wherein said eukaryote is an animal, preferably a mammal.

46. The non-human eukaryote according to any of numbered paragraphs 44 to 45, wherein said eukaryote is an immunocompromised animal, preferably an immunocompromised mammal.

47. The non-human eukaryote according to any of numbered paragraphs 44 to 46, wherein said eukaryote is selected from the group consisting of mammal, primate, rodent, mouse, rat, rabbit, canine, dog, cow, bovine, sheep, ovine, goat, pig, fowl, poultry, chicken, fish, insect, and arthropod.

48. The non-human eukaryote according to any of numbered paragraphs 44 to 47, wherein said eukaryote is a mouse.

49. A method for determining whether a compound is capable of suppressing tumor formation and/or tumor evolution comprising the steps of:
(a) providing an animal model according to the method of numbered paragraph 42,
(b) administering said compound to said animal model,
(c) determining whether or not said compound is capable of suppressing tumor formation and/or tumor evolution in said animal model.

50. A kit comprising:
an isolated Cas transgenic eukaryotic cell expressing Cas or capable of inducibly and/or conditionally expressing Cas;
one or more RNA capable of guiding Cas to one or more genetic target locus, or one or more polynucleotide encoding one or more RNA capable of guiding Cas to one or more genetic target locus.

51. The kit according to numbered paragraph 50, further comprising a non-human eukaryote.

52. The kit according to any of numbered paragraphs 50 to 51, further comprising instructions for performing the method according to any of numbered paragraphs 1 to 36.

53. The kit according to any of numbered paragraphs 50 to 52, wherein said one or more RNA capable of guiding Cas to one or more genetic target locus, or one or more polynucleotide encoding one or more RNA capable of guiding Cas to one or more genetic target locus are comprised in a vector, preferably a lentiviral vector.

54. The kit according to any of numbered paragraphs 50 to 53, comprising a plurality of RNAs capable of guiding Cas to a genetic target locus; or a plurality of polynucleotides encoding an RNA capable of guiding Cas to a genetic target locus.

55. The kit according to any of numbered paragraphs 50 to 54, wherein said RNA capable of guiding Cas comprises CRISPR RNA and transactivating (tracr) RNA.

56. The kit according to any of numbered paragraphs 50 to 55, wherein said RNA capable of guiding Cas comprises a single guide (sg) RNA.

57. The kit according to any of numbered paragraphs 50 to 56, wherein said polynucleotide encoding one or more RNA capable of guiding Cas is capable of constitutively expressing said RNA or alternatively inducibly and/or conditionally expressing said RNA.

58. The kit according to any of numbered paragraphs 50 to 57, wherein said Cas transgenic eukaryotic cell is a tumor cell.

59. The kit according to any of numbered paragraphs 50 to 58, wherein said Cas transgenic eukaryotic cell is a non-metastasizing tumor cell.

60. The kit according to any of numbered paragraphs 50 to 59, wherein said Cas is a type II Cas.

61. The kit according to any of numbered paragraphs 50 to 60, wherein said Cas is Cas9.

62. The kit according to any of numbered paragraphs 50 to 61, wherein said Cas is a Cas originating from *Streptococcus pyogenes, Streptococcus* thermophiles, or Staphilococcus *aureus*.

63. The kit according to any of numbered paragraphs 50 to 62, wherein said Cas is a mutated Cas having an altered catalytic activity.

64. The kit according to any of numbered paragraphs 50 to 63, wherein said Cas is a catalytically inactive Cas.

65. The kit according to any of numbered paragraphs 50 to 64, wherein said Cas is fused to an enzyme which modifies genomic DNA or genomic DNA architecture.

66. The kit according to any of numbered paragraphs 50 to 65, wherein said Cas is fused to a polypeptide which alters gene transcription.

67. The kit according to any of numbered paragraphs 50 to 66, wherein said Cas transgenic eukaryotic cell is a cell from an animal.

68. The kit according to any of numbered paragraphs 50 to 67, wherein said Cas transgenic eukaryotic cell is a cell from a eukaryote selected from the group consisting of mammal, primate, rodent, mouse, rat, rabbit, canine, dog, cow, bovine, sheep, ovine, goat, pig, fowl, poultry, chicken, fish, insect, and arthropod.

69. The kit according to any of numbered paragraphs 50 to 68, wherein said Cas transgenic eukaryotic cell is a mammalian cell, preferably a mouse cell.

70. The kit according to any of numbered paragraphs 51 to 69, wherein said eukaryote is an animal, preferably a mammal.

71. The kit according to any of numbered paragraphs 51 to 70, wherein said eukaryote is an immunocompromised animal, preferably an immunocompromised mammal.

72. The kit according to any of numbered paragraphs 51 to 71, wherein said eukaryote is selected from the group consisting of mammal, primate, rodent, mouse, rat, rabbit, canine, dog, cow, bovine, sheep, ovine, goat, pig, fowl, poultry, chicken, fish, insect, and arthropod.

73. The kit according to any of numbered paragraphs 51 to 72, wherein said eukaryote is a mouse.

74. A method for diagnosing tumorigenesis and/or tumor metastasis, comprising the step of genetically analyzing or analyzing expression of one or more genes identified according to the method according to any of numbered paragraphs 10 to 36.

75. A method for prognosing tumorigenesis and/or tumor metastasis, comprising the step of genetically analyzing or analyzing expression of one or more genes identified according to the method according to any of numbered paragraphs 10 to 36.

76. A method for determining the likelihood of developing tumor metastasis, comprising the step of genetically analyzing or analyzing expression of one or more genes identified according to the method according to any of numbered paragraphs 10 to 36.

77. The method according to any of numbered paragraphs 74 to 76, wherein analyzing expression of said one or more genes comprises comparing expression level with a predetermined expression level.

78. The method according to any of numbered paragraphs 74 to 77, wherein said one or more gene is selected from the group consisting of Nf2, Pten, Trim72, Cdkn2a, miR-152, and miR-345.

79. The method according to numbered paragraph 78, wherein said tumor metastasis is lung metastasis.

80. The method according to any of numbered paragraphs 74 to 78, wherein said tumor or tumor metastasis is selected from the group consisting of lung cancer, lung adenocarcinoma, lung squamous cell carcinoma, acute myeloid leukemia, basal cell (skin) carcinoma, bladder cancer, breast cancer, carcinoid cancer, chronic lymphocytic leukemia, colorectal cancer, lymphoma, diffuse large B-cell lymphoma, endometrial cancer, esophageal cancer, esophageal adenocarcinoma, glioblastoma multiforme, glioma, head and neck cancer, kidney cell cancer, medulloblastoma, melanoma, multiple myeloma, nasopharyngeal cancer, neuroblastoma, ovarian cancer; prostate cancer, rhabdoid tumor, thyroid cancer, and urinary bladder cancer.

REFERENCES

Aceto, N., Bardia, A., Miyamoto, D. T., Donaldson, M. C., Wittner, B. S., Spencer, J. A., Yu, M., Pely, A., Engstrom, A., Zhu, H., et al. (2014). Circulating tumor cell clusters are oligoclonal precursors of breast cancer metastasis. Cell 158, 1110-1122.

Bell, C. L., Vandenberghe, L. H., Bell, P., Limberis, M. P., Gao, G. P., Van Vliet, K., Agbandje-McKenna, M., and Wilson, J. M. (2011). The AAV9 receptor and its modification to improve in vivo lung gene transfer in mice. The Journal of clinical investigation 121, 2427-2435. Chen, S., Xue, Y., Wu, X., Le, C., Bhutkar, A., Bell, E. L., Zhang, F., Langer, R., and Sharp, P. A. (2014). Global microRNA depletion suppresses tumor angiogenesis. Genes & development 28, 1054-1067.

Bibikova, M., Beumer, K., Trautman, J. K., and Carroll, D. (2003). Enhancing gene targeting with designed zinc finger nucleases. Science 300, 764.

Cerami, E., Gao, J., Dogrusoz, U., Gross, B. E., Sumer, S. O., Aksoy, B. A., Jacobsen, A., Byrne, C. J., Heuer, M. L., Larsson, E., et al. (2012). The cBio cancer genomics portal: an open platform for exploring multidimensional cancer genomics data. Cancer discovery 2, 401-404.

Chen, S., Xue, Y., Wu, X., Le, C., Bhutkar, A., Bell, E. L., Zhang, F., Langer, R., and Sharp, P. A. (2014). Global microRNA depletion suppresses tumor angiogenesis. Genes & development 28, 1054-1067.

Cheng, Z., Ma, R., Tan, W., and Zhang, L. (2014). MiR-152 suppresses the proliferation and invasion of NSCLC cells by inhibiting FGF2. Experimental & molecular medicine 46, e112.

Chung, J., Issadore, D., Ullal, A., Lee, K., Weissleder, R., and Lee, H. (2013). Rare cell isolation and profiling on a hybrid magnetic/size-sorting chip. Biomicrofluidics 7, 54107.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Deltcheva, E., Chylinski, K., Sharma, C. M., Gonzales, K., Chao, Y., Pirzada, Z. A., Eckert, M. R., Vogel, J., and Charpentier, E. (2011). CRISPR RNA maturation by trans-encoded small RNA and host factor RNase III. Nature 471, 602-607.

Dull, T., Zufferey, R., Kelly, M., Mandel, R. J., Nguyen, M., Trono, D., and Naldini, L. (1998). A third-generation lentivirus vector with a conditional packaging system. Journal of virology 72, 8463-8471.

DuPage, M., Dooley, A. L., and Jacks, T. (2009). Conditional mouse lung cancer models using adenoviral or lentiviral delivery of Cre recombinase. Nature protocols 4, 1064-1072.

Francia, G., Cruz-Munoz, W., Man, S., Xu, P., and Kerbel, R. S. (2011). Mouse models of advanced spontaneous metastasis for experimental therapeutics. Nature reviews Cancer 11, 135-141.

Frese, K. K., and Tuveson, D. A. (2007). Maximizing mouse cancer models. Nature reviews Cancer 7, 645-658.

Garraway, L. A., and Lander, E. S. (2013). Lessons from the cancer genome. Cell 153, 17-37.

Gasiunas, G., Barrangou, R., Horvath, P., and Siksnys, V. (2012). Cas9-crRNA ribonucleoprotein complex mediates specific DNA cleavage for adaptive immunity in bacteria. Proceedings of the National Academy of Sciences of the United States of America 109, E2579-2586.

Gao, J., Aksoy, B. A., Dogrusoz, U., Dresdner, G., Gross, B., Sumer, S. O., Sun, Y., Jacobsen, A., Sinha, R., Larsson, E., et al. (2013). Integrative analysis of complex cancer genomics and clinical profiles using the cBioPortal. Science signaling 6, pl1.

Gilbert, L. A., Horlbeck, M. A., Adamson, B., Villalta, J. E., Chen, Y., Whitehead, E. H., Guimaraes, C., Panning, B., Ploegh, H. L., Bassik, M. C., et al. (2014). Genome-Scale CRISPR-Mediated Control of Gene Repression and Activation. Cell.

Govindan, R., Ding, L., Griffith, M., Subramanian, J., Dees, N. D., Kanchi, K. L., Maher, C. A., Fulton, R., Fulton, L., Wallis, J., et al. (2012). Genomic landscape of non-small cell lung cancer in smokers and never-smokers. Cell 150, 1121-1134.

Halbert, C. L., Allen, J. M., and Miller, A. D. (2002). Efficient mouse airway transduction following recombination between AAV vectors carrying parts of a larger gene. Nature biotechnology 20, 697-701.

Hanahan, D., and Weinberg, R. A. (2011). Hallmarks of cancer: the next generation. Cell 144, 646-674.

Hegi, M. E., Diserens, A. C., Gorlia, T., Hamou, M. F., de Tribolet, N., Weller, M., Kros, J. M., Hainfellner, J. A., Mason, W., Mariani, L., et al. (2005). MGMT gene silencing and benefit from temozolomide in glioblastoma. The New England journal of medicine 352, 997-1003.

Heimann, R., and Hellman, S. (1998). Aging, progression, and phenotype in breast cancer. Journal of clinical oncology: official journal of the American Society of Clinical Oncology 16, 2686-2692.

Herbig, E., Warfield, L., Fish, L., Fishburn, J., Knutson, B. A., Moorefield, B., Pacheco, D., and Hahn, S. (2010). Mechanism of Mediator recruitment by tandem Gcn4 activation domains and three Gal11 activator-binding domains. Molecular and cellular biology 30, 2376-2390.

Herbst, R. S., Heymach, J. V., and Lippman, S. M. (2008). Lung cancer. The New England journal of medicine 359, 1367-1380.

Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nature biotechnology 31, 827-832.

Hsu, P. D., Lander, E. S., and Zhang, F. (2014). Development and applications of CRISPR-Cas9 for genome engineering. Cell 157, 1262-1278.

Huang, S., Holzel, M., Knijnenburg, T., Schlicker, A., Roepman, P., McDermott, U., Garnett, M., Grernrum, W., Sun, C., Prahallad, A., et al. (2012). MED12 controls the response to multiple cancer drugs through regulation of TGF-beta receptor signaling. Cell 151, 937-950.

Ioannidis John, P. A., Castaldi P., Evangelou E. A compendium of genome-wide associations for cancer: critical synopsis and reappraisal. J. Natl Cancer Inst 2010; 102: 846-858.

Iwasaki, M., Homma, S., Hishiya, A., Dolezal, S. J., Reed, J. C., and Takayama, S. (2007). BAG3 regulates motility and adhesion of epithelial cancer cells. Cancer research 67, 10252-10259.

Jasin, M., de Villiers, J., Weber, F., and Schaffner, W. (1985). High frequency of homologous recombination in mammalian cells between endogenous and introduced SV40 genomes. Cell 43, 695-703.

Jackson, E. L., Willis, N., Mercer, K., Bronson, R. T., Crowley, D., Montoya, R., Jacks, T., and Tuveson, D. A. (2001). Analysis of lung tumor initiation and progression using conditional expression of oncogenic K-ras. Genes & development 15, 3243-3248.

Jesien-Lewandowicz, E., Jesionek-Kupnicka, D., Zawlik, I., Szybka, M., Kulczycka-Wojdala, D., Rieske, P., Sieruta, M., Jaskolski, D., Och, W., Skowronski, W., et al. (2009). High incidence of MGMT promoter methylation in primary glioblastomas without correlation with TP53 gene mutations. Cancer genetics and cytogenetics 188, 77-82.

Ji, H., Ramsey, M. R., Hayes, D. N., Fan, C., McNamara, K., Kozlowski, P., Torrice, C., Wu, M. C., Shimamura, T., Perera, S. A., et al. (2007). LKB1 modulates lung cancer differentiation and metastasis. Nature 448, 807-810.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Johnson, L., Mercer, K., Greenbaum, D., Bronson, R. T., Crowley, D., Tuveson, D. A., and Jacks, T. (2001). Somatic activation of the K-ras oncogene causes early onset lung cancer in mice. Nature 410, 1111-1116.

Kaczmarczyk, G., Lewandowski, R., Trautsolt, W., Ziolkowski, A., and Kozielski, J. (2012). Cytological examination of pleural cavity lavage accompanied by the study of gene promoter hypermethylation of p16 and 06-methylguanine-DNA-methyltransferase genes in diagnostics of non-small cell lung cancer metastatic changes into pleura. Contemporary oncology 16, 322-327.

Kaina, B., Christmann, M., Naumann, S., and Roos, W. P. (2007). MGMT: key node in the battle against genotoxicity, carcinogenicity and apoptosis induced by alkylating agents. DNA repair 6, 1079-1099.

Kandoth, C., McLellan, M. D., Vandin, F., Ye, K., Niu, B., Lu, C., Xie, M., Zhang, Q., McMichael, J. F., Wyczalkowski, M. A., et al. (2013). Mutational landscape and significance across 12 major cancer types. Nature 502, 333-339.

Kang, Y., Siegel, P. M., Shu, W., Drobnjak, M., Kakonen, S. M., Cordon-Cardo, C., Guise, T. A., and Massague, J. (2003). A multigenic program mediating breast cancer metastasis to bone. Cancer cell 3, 537-549.

Koboldt, D. C., Zhang, Q., Larson, D. E., Shen, D., McLellan, M. D., Lin, L., Miller, C. A., Mardis, E. R., Ding, L., and Wilson, R. K. (2012). VarScan 2: somatic mutation and copy number alteration discovery in cancer by exome sequencing. Genome research 22, 568-576.

Koike-Yusa, H., Li, Y., Tan, E. P., Velasco-Herrera Mdel, C., and Yusa, K. (2014). Genome-wide recessive genetic screening in mammalian cells with a lentiviral CRISPR-guide RNA library. Nature biotechnology 32, 267-273.

Kumar, M. S., Pester, R. E., Chen, C. Y., Lane, K., Chin, C., Lu, J., Kirsch, D. G., Golub, T. R., and Jacks, T. (2009). Dicer1 functions as a haploinsufficient tumor suppressor. Genes & development 23, 2700-2704.

Langmead, B., Trapnell, C., Pop, M., and Salzberg, S. L. (2009). Ultrafast and memory-efficient alignment of short DNA sequences to the human genome. Genome biology 10, R25.

Lawrence, M. S., Stojanov, P., Polak, P., Kryukov, G. V., Cibulskis, K., Sivachenko, A., Carter, S. L., Stewart, C., Mermel, C. H., Roberts, S. A., et al. (2013). Mutational heterogeneity in cancer and the search for new cancer-associated genes. Nature 499, 214-218.

Lawrence, M. S. Stojanov, P., Mermel, C. H., Robinson, J. T., Garraway, L. A., Golub, T. R, Meyerson, M., Gabriel, S. B., and Lander E. S. Discovery and saturation analysis of cancer genes across 21 tumour types. Nature 23 Jan. 2014; vol 505, 495-355 and supplementary tables 1-6.

Li, H., and Durbin, R. (2010). Fast and accurate long-read alignment with Burrows-Wheeler transform. Bioinformatics 26, 589-595.

Limberis, M. P., and Wilson, J. M. (2006). Adeno-associated virus serotype 9 vectors transduce murine alveolar and nasal epithelia and can be readministered. Proceedings of the National Academy of Sciences of the United States of America 103, 12993-12998.

Mali, P., Yang, L. H., Esvelt, K. M., Aach, J., Guell, M., DiCarlo, J. E., Norville, J. E., and Church, G. M. (2013). RNA-Guided Human Genome Engineering via Cas9. Science 339, 823-826.

Martin, M. (2011). Cutadapt removes adapter sequences from high-throughput sequencing reads. EMBnet 17, 1.

McClatchey, A. I., Saotome, I., Mercer, K., Crowley, D., Gusella, J. F., Bronson, R. T., and Jacks, T. (1998). Mice heterozygous for a mutation at the Nf2 tumor suppressor locus develop a range of highly metastatic tumors. Genes & development 12, 1121-1133.

McFadden, D. G., Papagiannakopoulos, T., Taylor-Weiner, A., Stewart, C., Carter, S. L., Cibulskis, K., Bhutkar, A., McKenna, A., Dooley, A., Vernon, A., et al. (2014). Genetic and clonal dissection of murine small cell lung carcinoma progression by genome sequencing. Cell 156, 1298-1311.

Mitzner, W., Brown, R., and Lee, W. (2001). In vivo measurement of lung volumes in mice. Physiological genomics 4, 215-221.

Molenaar, R. J., Verbaan, D., Lamba, S., Zanon, C., Jeuken, J. W., Boots-Sprenger, S. H., Wesseling, P., Hulsebos, T. J., Troost, D., van Tilborg, A. A., et al. (2014). The combination of IDH1 mutations and MGMT methylation status predicts survival in glioblastoma better than either IDH1 or MGMT alone. Neuro-oncology 16, 1263-1273.

Naba, A., Clauser, K. R., Lamar, J. M., Carr, S. A., and Hynes, R. O. (2014a). Extracellular matrix signatures of human mammary carcinoma identify novel metastasis promoters. eLife 3, e01308.

Naba, A., Clauser, K. R., Whittaker, C. A., Carr, S. A., Tanabe, K. K., and Hynes, R. O. (2014b). Extracellular matrix signatures of human primary metastatic colon cancers and their metastases to liver. BMC cancer 14, 518.

Nguyen, D. X., Chiang, A. C., Zhang, X. H., Kim, J. Y., Kris, M. G., Ladanyi, M., Gerald, W. L., and Massague, J. (2009). WNT/TCF signaling through LEF1 and HOXB9 mediates lung adenocarcinoma metastasis. Cell 138, 51-62.

Nissen, L. J., Cao, R., Hedlund, E. M., Wang, Z., Zhao, X., Wetterskog, D., Funa, K., Brakenhielm, E., and Cao, Y. (2007). Angiogenic factors FGF2 and PDGF-BB synergistically promote murine tumor neovascularization and metastasis. The Journal of clinical investigation 117, 2766-2777.

Park, W. Y., Kim, M. H., Shin, D. H., Lee, J. H., Choi, K. U., Kim, J. Y., Park do, Y., Lee, C. H., and Sol, M. Y. (2012). Ciliated adenocarcinomas of the lung: a tumor of non-terminal respiratory unit origin. Modern pathology: an official journal of the United States and Canadian Academy of Pathology, Inc 25, 1265-1274.

Platt, R. J., Chen, S., Zhou, Y., Yim, M. J., Swiech, L., Kempton, H. R., Dahlman, J. E., Parnas, O., Eisenhaure, T. M., Jovanovic, M., et al. (2014). CRISPR-Cas9 Knockin Mice for Genome Editing and Cancer Modeling. Cell 159, 440-455.

Pylayeva-Gupta, Y., Grabocka, E., and Bar-Sagi, D. (2011). RAS oncogenes: weaving a tumorigenic web. Nature reviews Cancer 11, 761-774.

Sanjana, N. E., Shalem, O., and Zhang, F. (2014). Improved vectors and genome-wide libraries for CRISPR screening. Nature Methods 11, 783-784.

Schiano, C., Casamassimi, A., Rienzo, M., de Nigris, F., Sommese, L., and Napoli, C. (2014). Involvement of Mediator complex in malignancy. Biochimica et biophysica acta 1845, 66-83.

Schneider, C. A., Rasband, W. S., and Eliceiri, K. W. (2012). NIH Image to ImageJ: 25 years of image analysis. Nature methods 9, 671-675.

Shackelford, D. B., and Shaw, R. J. (2009). The LKB1-AMPK pathway: metabolism and growth control in tumour suppression. Nature reviews Cancer 9, 563-575.

Schramek, D., Sendoel, A., Segal, J. P., Beronja, S., Heller, E., Oristian, D., Reva, B., and Fuchs, E. (2014). Direct in vivo RNAi screen unveils myosin IIa as a tumor suppressor of squamous cell carcinomas. Science 343, 309-313.

Shalem, O., Sanjana, N. E., Hartenian, E., Shi, X., Scott, D. A., Mikkelsen, T. S., Heckl, D., Ebert, B. L., Root, D. E., Doench, J. G., et al. (2014). Genome-scale CRISPR-Cas9 knockout screening in human cells. Science 343, 84-87.

Shao, D. D., Xue, W., Krall, E. B., Bhutkar, A., Piccioni, F., Wang, X., Schinzel, A. C., Sood, S., Rosenbluh, J., Kim, J. W., et al. (2014). KRAS and YAP1 converge to regulate EMT and tumor survival. Cell 158, 171-184.

Tang, J. T., Wang, J. L., Du, W., Hong, J., Zhao, S. L., Wang, Y. C., Xiong, H., Chen, H. M., and Fang, J. Y. (2011). MicroRNA 345, a methylation-sensitive microRNA is involved in cell proliferation and invasion in human colorectal cancer. Carcinogenesis 32, 1207-1215.

Tano, K., Shiota, S., Collier, J., Foote, R. S., and Mitra, S. (1990). Isolation and structural characterization of a cDNA clone encoding the human DNA repair protein for 06-alkylguanine. Proceedings of the National Academy of Sciences of the United States of America 87, 686-690.

TCGA-Network (2012). Comprehensive genomic characterization of squamous cell lung cancers. Nature 489(7417): 519-25.

TCGA-Network (2014a). Comprehensive molecular characterization of urothelial bladder carcinoma. Nature 507, 315-322.

TCGA-Network (2014b). Comprehensive molecular profiling of lung adenocarcinoma. Nature Published online 9 Jul. 2014.

Teo, A. K., Oh, H. K., Ali, R. B., and Li, B. F. (2001). The modified human DNA repair enzyme O(6)-methylguanine-DNA methyltransferase is a negative regulator of estrogen receptor-mediated transcription upon alkylation DNA damage. Molecular and cellular biology 21, 7105-7114.

Valastyan, S., and Weinberg, R. A. (2011). Tumor metastasis: molecular insights and evolving paradigms. Cell 147, 275-292.

Valiente, M., Obenauf, A. C., Jin, X., Chen, Q., Zhang, X. H., Lee, D. J., Chaft, J. E., Kris, M. G., Huse, J. T., Brogi, E., et al. (2014). Serpins promote cancer cell survival and vascular co-option in brain metastasis. Cell 156, 1002-1016.

Vanharanta, S., and Massague, J. (2013). Origins of metastatic traits. Cancer cell 24, 410-421.

Waghorne, C., Thomas, M., Lagarde, A., Kerbel, R. S., and Breitman, M. L. (1988). Genetic evidence for progressive selection and overgrowth of primary tumors by metastatic cell subpopulations. Cancer research 48, 6109-6114.

Wang, T., Wei, J. J., Sabatini, D. M., and Lander, E. S. (2014). Genetic Screens in Human Cells Using the CRISPR-Cas9 System. Science 343, 80-84.

Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas-mediated genome engineering. Cell 153, 910-918.

Weinberg, R. A. (2007). The biology of cancer (New York, Garland Science).

Whittaker, S. R., Theurillat, J. P., Van Allen, E., Wagle, N., Hsiao, J., Cowley, G. S., Schadendorf, D., Root, D. E., and Garraway, L. A. (2013). A genome-scale RNA interference screen implicates NF1 loss in resistance to RAF inhibition. Cancer discovery 3, 350-362.

Winslow, M. M., Dayton, T. L., Verhaak, R. G., Kim-Kiselak, C., Snyder, E. L., Feldser, D. M., Hubbard, D. D., DuPage, M. J., Whittaker, C. A., Hoersch, S., et al. (2011). Suppression of lung adenocarcinoma progression by Nkx2-1. Nature 473, 101-104.

Xue, W., Chen, S., Yin, H., Tammela, T., Papagiannakopoulos, T., Joshi, N. S., Cai, W., Yang, G., Bronson, R., Crowley, D. G., et al. (2014). CRISPR-mediated direct mutation of cancer genes in the mouse liver. Nature.

Yokota, J., Nishioka, M., Tani, M., and Kohno, T. (2003). Genetic alterations responsible for metastatic phenotypes of lung cancer cells. Clinical & experimental metastasis 20, 189-193.

Zender, L., Xue, W., Zuber, J., Semighini, C. P., Krasnitz, A., Ma, B., Zender, P., Kubicka, S., Luk, J. M., Schirmacher, P., et al. (2008). An oncogenomics-based in vivo RNAi screen identifies tumor suppressors in liver cancer. Cell 135, 852-864.

What is claimed is:

1. A method for identifying genes implicated in the metastasis of a primary tumor to the lung comprising the steps of:
   a) transducing a population of Cas9 expressing immortalized eukaryote cells with a genome-wide library of guide RNAs to inactivate one or more genetic target loci in each cell by CRISPR-cas9 gene editing;
   b) transplanting the modified, gene-edited cell population into a non-human animal host
   c) isolating guide RNAs enriched in tumors in the lung that have metastasized from primary tumors obtained from the transplanted cell population; and
   d) identifying candidate genes implicated in the metastasis of primary tumor cells to the lung,
   wherein said candidate genes comprise at least one of Nf2, Pten, Cdkn2a, Trim72, Fga, miR-345, and miR-152,
   wherein a loss of function mutation in any one of the candidate genes alone is sufficient to accelerate the rate of metastasis formation to the lung relative to untransduced and nontargeting sgRNA controls, and
   wherein the modified, gene-edited cell population implanted into the non-human animal host does not metastasize to the liver, kidney, or spleen.

2. The method of claim 1, further comprising
   a) transducing a second population of Cas9 expressing immortalized eukaryote cells with guide RNAs targeting the candidate genes identified in step d) using CRISPR-Cas9 gene editing;
   b) implanting the gene-edited cell population into the non-human animal host, and
   c) isolating guide RNAs enriched in tumors in the lung that have metastasized from primary tumors obtained from the transplanted cell population, thereby validating the involvement of the candidate genes in the metastasis to the lung, wherein the modified, gene-edited cell population implanted into the non-human animal host does not metastasize to the liver, kidney, or spleen.

3. The method of claim 1, wherein the gene-edited cell population is implanted subcutaneously.

4. The method of claim 1, wherein the non-human animal host is immunocompromised.

5. The method of claim 1, wherein said candidate genes comprise Nf1 or Pten.

6. The method of claim 1, wherein said candidate genes comprise at least three genes chosen from Nf2, Pten, and any one of Cdkna2a, Trim72, Fga, miR-345, and miR-152.

7. The method of claim 1, wherein said candidate genes comprise at least three genes chosen from Nf2, Pten, any two of Cdkna2a, Trim72, Fga, miR-345, and miR-152.

8. The method of claim 1, wherein said candidate genes comprise Nf2, Pten, Cdkna2a, Trim72, Fga, miR-345, and miR-152.

9. The method of claim 1, wherein said candidate genes further comprise Ube2g2, Ptges2 or ATP-dependent DNA Ligase IV (Lig4).

10. The method of claim 1, wherein, prior to modification by gene editing, the immortalized eukaryote cells comprise a loss-of-function mutation in a tumor suppressor gene and a gain-of-function mutation in a proto-oncogene.

11. The method of claim 10, wherein the tumor suppressor gene comprises a p53−/− and/or Lkb1−/−.

12. The method of claim 10, wherein the proto-oncogene comprises Kras.

13. The method of claim 12, wherein the Kras gain-of-function mutation comprises a KrasG12D/+ oncogenic mutation.

14. The method of claim 1, wherein the unmodified population of immortalized eukaryote cells does not metastasize to the lung.

15. The method of claim 1, wherein the population of immortalized eukaryote cells is obtained from a lung cancer.

16. The method of claim 1, wherein the population of immortalized eukaryote cells is a non-small-cell lung cancer (NSCLC) cell line.

17. The method of claim 1, wherein the immortalized eukaryote cell is a cell from an eukaryote selected from the group consisting of a mammal, a primate, a rodent, a mouse, a rat, a rabbit, a canine, a dog, a cow, a bovine, a sheep, an ovine, a goat and a pig.

18. The method of claim 1, wherein said Cas9 is a Cas9 originating from *Streptococcus pyogenes, Streptococcus thermophiles,* or *Staphylococcus aureus*; a mutated Cas9 having an altered catalytic activity; a catalytically inactive Cas9; or wherein the Cas9 is fused to an enzyme which modifies genomic DNA or genomic DNA architecture or a polypeptide which alters gene transcription.

* * * * *

UNITED STATES PATENT AND TRADEMARK OFFICE
CERTIFICATE OF CORRECTION

PATENT NO. : 12,116,619 B2
APPLICATION NO. : 15/640103
DATED : October 15, 2024
INVENTOR(S) : Sidi Chen et al.

It is certified that error appears in the above-identified patent and that said Letters Patent is hereby corrected as shown below:

On the Title Page

On the page 3, in Column 2, under item (56) "Other Publications", Line 40, delete "lla" and insert -- IIa --.

In the Specification

In Column 5, Line 11, delete "IL," and insert -- II, --.

In Column 15, Line 8, delete "0-" and insert -- β- --.

In Column 37, Line 60, delete "Flepa1 c1" and insert -- Flepa1 cl --.

In Column 38, Line 55, delete "$10^1$" and insert -- $10^3$ --.

In Column 38, Line 55, delete "$10^1$" and insert -- $10^3$ --.

In Column 38, Line 57, delete "$10^1$" and insert -- $10^5$ --.

In Column 44, Line 47, delete "Specficity." and insert -- Specificity. --.

In Column 44, Line 52, delete "Cas9nucleases." and insert -- Cas9 nucleases. --.

In Column 45, Line 58, delete "$srep10^{833}$" and insert -- srep10833 --.

In Column 46, Line 50, delete "E" and insert -- E. --.

In Column 47, Line 64, delete "MFD12" and insert -- MED12 --.

Signed and Sealed this
Tenth Day of June, 2025

Coke Morgan Stewart
*Acting Director of the United States Patent and Trademark Office*

CERTIFICATE OF CORRECTION (continued)
U.S. Pat. No. 12,116,619 B2

In Column 49, Line 62, delete "BCL11A" and insert -- BCL11A --.

In Column 52, Line 9, delete "MMMMMMMMMMNNNNNNNNNNXGGXG" and insert -- MMMMMMMMMNNNNNNNNNNXGGXG --.

In Column 53, Line 9, delete "tatataa" and insert -- ttatttaa --.

In Column 53, Line 18, delete "etagte" and insert -- ctagtc --.

In Column 60, Line 31, delete "hRNPAI" and insert -- hRNPA1 --.

In Column 72, Line 49, delete "Corynebacter" and insert -- Corynebacterium --.

In Column 77, Line 18, delete "Cas f ensequence" and insert -- Cas sequence --.

In Column 101, Line 49, delete "FWYHKMTLVAGC" and insert -- FWYHKMILVAGC --.

In Column 102, Line 45, delete "j.cel." and insert -- j.cell. --.

In Column 107, Line 17, delete "7 s" and insert -- 7s --.

In Column 108, Line 9, delete "E" and insert -- E. --.

In Column 114, Line 3, delete "1-" and insert -- t- --.

In Column 116, Line 12, delete "3.4+" and insert -- 3,4+ --.

In Column 118, Line 37, delete "0.003-0.01);" and insert -- 0.003~0.01); --.

In Column 119, Line 4, delete "p=" and insert -- $\rho=$ --.

In Column 119, Line 6, delete "p=" and insert -- $\rho=$ --.

In Column 119, Line 44, delete "p=" and insert -- $\rho=$ --.

In Column 122, Line 18, delete "ofKras" and insert -- of Kras --.

In Column 122, Line 18, delete "homozygousp53" and insert -- homozygous p53 --.

In Column 128, Line 67, delete "06-" and insert -- O6- --.

In Column 130, Line 58, delete "Ha" and insert -- IIa --.

In Column 131, Line 9, delete "06-" and insert -- O6- --.